(12) United States Patent
Yamashita et al.

(10) Patent No.: US 8,071,600 B2
(45) Date of Patent: Dec. 6, 2011

(54) DERIVATIVES OF 4-PIPERAZIN-1-YL-4-BENZO[B]THIOPHENE SUITABLE FOR THE TREATMENT OF CNS DISORDERS

(75) Inventors: Hiroshi Yamashita, Tokushima (JP); Hideaki Kuroda, Tokushima (JP); Nobuaki Ito, Tokushima (JP); Shin Miyamura, Tokushima (JP); Kunio Oshima, Tokushima (JP); Jun Matsubara, Tokushima (JP); Haruka Takahashi, Tokushima (JP); Tae Fukushima, Tokushima (JP); Satoshi Shimizu, Tokushima (JP); Kazumi Kondo, Tokushima (JP); Yohji Sakurai, Tokushima (JP); Takeshi Kuroda, Tokushima (JP); Shinichi Taira, Tokushima (JP); Motohiro Itotani, Tokushima (JP); Tatsuyoshi Tanaka, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 189 days.

(21) Appl. No.: 11/991,146

(22) PCT Filed: Aug. 31, 2006

(86) PCT No.: PCT/JP2006/317704
§ 371 (c)(1),
(2), (4) Date: Feb. 28, 2008

(87) PCT Pub. No.: WO2007/026959
PCT Pub. Date: Mar. 8, 2007

(65) Prior Publication Data
US 2009/0264404 A1   Oct. 22, 2009

(30) Foreign Application Priority Data
Aug. 31, 2005   (JP) ................. 2005-251055

(51) Int. Cl.
*A61K 31/496* (2006.01)
*A61K 31/55* (2006.01)
*A61K 31/551* (2006.01)
*C07D 333/54* (2006.01)
*C07D 409/12* (2006.01)
*C07D 409/14* (2006.01)
*A61K 31/536* (2006.01)
*A61K 31/5415* (2006.01)
*C07D 407/12* (2006.01)
*C07D 413/12* (2006.01)
*C07D 417/12* (2006.01)

(52) U.S. Cl. ......... 514/252.11; 514/253.11; 514/254.01; 514/252.13; 540/523; 540/524; 540/575; 544/52; 544/92; 544/105; 544/121; 544/287; 544/295; 544/357; 544/361; 544/362; 544/363; 544/364; 544/366; 544/367; 544/368; 544/369; 544/370; 544/371; 544/372; 544/373; 544/376

(58) Field of Classification Search .................. None
See application file for complete search history.

(56) References Cited

U.S. PATENT DOCUMENTS

| 4,234,584 | A | 11/1980 | Lattrell et al. |
| 4,831,031 | A | 5/1989 | Lowe, III et al. |
| 4,883,795 | A | 11/1989 | Lowe, III et al. |
| 2003/0050306 | A1* | 3/2003 | Ruhland et al. ............... 514/218 |
| 2003/0195219 | A1 | 10/2003 | Dutta |

FOREIGN PATENT DOCUMENTS

| EP | 0 367 141 | 5/1990 |
| EP | 0 512 525 | 11/1992 |
| EP | 0 732 332 | 9/1996 |
| EP | 0 934 932 | 8/1999 |
| EP | 1 188 747 | 3/2002 |
| FR | 2 740 134 A1 | 4/1997 |
| FR | 2 761 068 A1 | 9/1998 |
| JP | 56-49361 | 5/1981 |
| WO | WO 91/00863 | 1/1991 |
| WO | WO 96/22290 | 7/1996 |
| WO | WO 98/07703 | 2/1998 |
| WO | WO 00/71517 | 11/2000 |
| WO | WO 02/066469 | 8/2002 |
| WO | WO 2004/026864 A1 | 4/2004 |
| WO | WO 2004/029048 | 4/2004 |
| WO | WO 2005/019215 A1 | 3/2005 |

OTHER PUBLICATIONS

Yagcioglu, Turkish Journal of Psychiatry, vol. 18(4), p. 1-10 (2007).*
Aripiprazole, from Wikipedia, 1 page, retrieved from the Internet at http://en.wikipedia.org/wiki/Aripiprazole on Feb. 1, 2011.*
Tramontina et al. J.Clin.Psychiatry, vol. 70(5),pp. 756-764 (2009) (Abstract provided).*
M. Toru, "Creativity in the Development of the Drug, Aripiprazole: A Novel Partial Dopamine $D_2$ Receptor Agonist for the Treatment of Schizophrenia", Seishin-Igaku, Psychiatry, vol. 46, pp. 855-864, (2004).

(Continued)

*Primary Examiner* — Emily Bernhardt
(74) *Attorney, Agent, or Firm* — Finnegan, Henderson, Farabow, Garrett & Dunner, L.L.P.

(57) ABSTRACT

A heterocyclic compound or a salt thereof represented by the formula (1): where $R^2$ represents a hydrogen atom or a lower alkyl group; A represents a lower alkylene group or lower alkenylene group; and $R^1$ represents an aromatic group or a heterocyclic group. The compound of the present invention has a wide treatment spectrum for mental disorders including central nervous system disorders, no side effects and high safety.

(1)

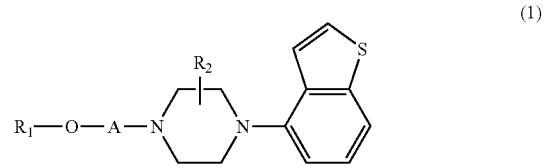

14 Claims, No Drawings

OTHER PUBLICATIONS

Harrison et al., "Aripiprazole: A Review of Its Use in Schizophrenia and Schizoaffective Disorder", ADIS Drug Evaluation, Drugs, vol. 64, No. 15, pp. 1715-1736, (2004).

Pullar et al., "LY367265, An Inhibitor of the 5-Hydroxytryptamine Transporter and 5-Hydroxytryptamine$_{2A}$ Receptor Antagonist : A Comparison With the Antidepressant, Nefazodone", European Journal of Pharmacology, vol. 407, pp. 39-46, (2000).

Meltzer et al, "Serotonin Receptors : Their Key Role in Drugs to Treat Schizophrenia", Progress in Neuro-Psychopharmacology & Biological Psychiatry, vol. 27, pp. 1159-1172, (2003).

Svensson, "α-Adrenoceptor Modulation Hypothesis of Antipsychotic Atypicality", Progress in Neuro-Psychopharmacology & Biological Psychiatry, vol. 27, pp. 1145-1158, (2003).

Oshiro et al., "Novel Antipsychotic Agents With Dopamine Autoreceptor Agonist Properties: Synthesis and Pharmacology of 7-[4-(4-Phenyl-1-Piperazinyl)Butoxy]-3,4-Dihydro-2(1$H$)-Quinolinone Derivatives", J. Med. Chem., vol. 41, pp. 658-667, (1998).

Ishigooka et al., "Trends in the Clinical Development of the Second Generation Antipsychotics", Rinsho-Seishin-Yakuri, Japanese Journal of Clinical Psychopharmacology), vol. 4, pp. 1653-1644, (2001).

Findling et al., "Aripiprazole in Children with Attention-Deficit/Hyperactivity Disorder," *J. Child & Adolesc. Psychopharmacol.*, 18(4):347-54 (2008).

Keck et al., "A Randomized, Double-Blind, Placebo-Controlled 26-Week Trial of Aripiprazole in Recently Manic Patients with Bipolar I Disorder," *J. Clin. Psychiatry*, 67(4):626-37 (2006).

Marcus et al., "A Double-Blind, Randomized, Placebo-Controlled Study of Fixed-Dose Aripiprazole in Children and Adolescents with Autistic Disorder," *J. Am. Acad. Child Adolesc. Psychiatry*, 48(11):1110-19 (2009).

Partial translation of Murasaki et al., "The Prospect of New Pharmacological Treatment Against Psychiatric Disorders", Rinsho-Seishin-Yakuri, (Japanese Journal of Clinical Psychopharmacology), 1:5-22 (1998).

Translation of Kikuchi et al., "Aripiprazole, A Novel Antipsychotic—A Dopamine D$_2$ Partial Agonist", Nou-no-Kagaku, Brain Science, 25:579-583 (2003).

English language abstract of FR 2 740134 A1, (1997).

Search Report and Written Opinion for Singapore Patent Application No. 200905174-9 dated Aug. 3, 2010.

English language Derwent abstract of FR 2 761 068 A1, (1998).

* cited by examiner

DERIVATIVES OF 4-PIPERAZIN-1-YL-4-BENZO[B]THIOPHENE SUITABLE FOR THE TREATMENT OF CNS DISORDERS

CROSS-REFERENCE TO RELATED APPLICATIONS

This application is a national phase application of International Application No. PCT/JP2006/317704, filed Aug. 31, 2006, and claims the priority of Japanese Application No. 2005-251055, filed Aug. 31, 2005, the content of both of which is incorporated herein by reference.

TECHNICAL FIELD

The present invention relates to a novel heterocyclic compound.

BACKGROUND ART

Since causal factor of schizophrenia as well as of bipolar disorder, mood disorders and emotional disorders is heterogeneous, it is desirable that a drug has multiple pharmacological effects so as to develop wide treatment spectrum.

WO2004/026864A1 discloses that a carbostyril derivative represented by the general formula:

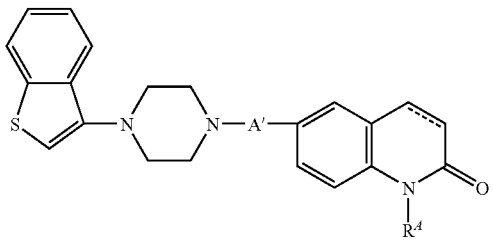

(wherein A' represents —$(CH_2)_mCH_2$—, —$(CH_2)_mO$—, etc.; m represents an integer of 1 to 4; and $R^4$ represents a hydrogen atom, a $C_{1-4}$ alkyl group which may be substituted with 1 to 3 fluorine atoms, etc.) has $D_2$ receptor antagonist activity and serotonin 2A (5-$HT_{2A}$) receptor antagonist activity and it is effective for treatment of schizophrenia and other central nervous system disorders).

However, there is no description in WO2004/026864A1 that carbostyril derivatives described in the document have $D_2$ receptor partial agonist activity, 5-$HT_{2A}$ receptor antagonist activity, $\alpha_1$ receptor antagonist activity and serotonin uptake inhibitory activity together and have a wide treatment spectrum.

WO 2005/019215 A1 discloses the compounds represented by the following formula:

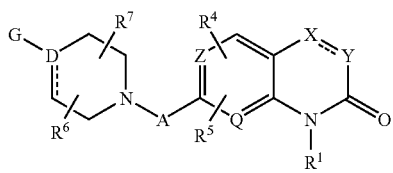

(wherein A is —$(CH_2)_mCH_2$—, —$(CH_2)_mO$— or the like; m is an integer of 2 to 5; D is N, C or the like; Z and Q are independently N, C or CH, provided that at least one of Z and Q is N; X and Y are independently C, N or the like, and the bond between X and Y is a single or double bond; $R^1$ is hydrogen, ($C_1$-$C_3$)alkyl group or the like; $R^4$, $R^5$, $R^1$ and $R^7$ each represents hydrogen, alkyl group or the like; and G represents a group of monocyclic or bicyclic compound), which bind to dopamine $D_2$ receptors. WO 2005/019215 A1 teaches that some compounds disclosed therein have an activity as partial agonists of $D_2$ receptors or an activity as antagonists of $D_2$ receptors, and may be effective for the treatment of schizophrenia and other central nervous system.

However, WO 2005/019215 A1 does not specifically disclose the compounds of the present invention.

DISCLOSURE OF THE INVENTION

An object of the present invention is to provide an antipsychotic drug which has a wider treatment spectrum, less side effects and excellent tolerability and safety as compared with well-known typical and atypical antipsychotic drugs.

The present inventors have conducted intensive studies on the above-described problem and consequently succeeded in synthesizing a novel compound which has dopamine $D_2$ receptor partial agonist activity ($D_2$ receptor partial agonist activity), serotonin 5-$HT_{2A}$ receptor antagonist activity (5-$HT_{2A}$ receptor antagonist activity) and adrenalin $\alpha_1$ receptor antagonist activity ($\alpha_1$ receptor antagonist activity) and further has serotonin uptake inhibitory effect (or serotonin reuptake inhibitory effect) together in addition to these effects. The present invention has been completed based on this finding.

There is provided a heterocyclic compound or a salt thereof represented by the formula (1):

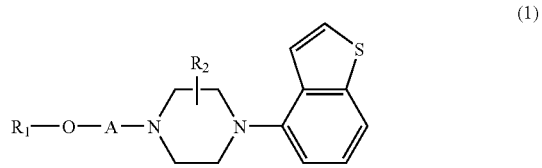

where $R^2$ represents a hydrogen atom or a lower alkyl group;
A represents a lower alkylene group or a lower alkenylene group; and
$R^1$ represents a cyclo C3-C8 alkyl group, an aromatic group or a heterocyclic group selected from the group consisting of (I) to (IV) below:
(I) a cyclo C3-C8 alkyl group;
(II) an aromatic group selected from a phenyl group, a naphthyl group, a dihydroindenyl group and a tetrahydronaphthyl group;
(III) a saturated or unsaturated heteromonocyclic group having 1 to 4 hetero atoms selected from the group consisting of a nitrogen atom, an oxygen atom and a sulfur atom; and
(IV) a benzene fused heterocyclic group that has 1 to 4 hetero atoms selected from the group consisting of a nitrogen atom, an oxygen atom and a sulfur atom and that is selected from the group consisting of (1) a tetrahydroquinoxalinyl group, (2) a tetrahydroquinazolinyl group, (3) a dihydroquinazolinyl group, (4) an indolinyl group, (5) an indolyl group, (6) an isoindolinyl group, (7) a benzimidazolyl group, (8) a dihydrobenzimidazolyl group, (9) a tetrahydrobenzazepinyl group, (10) a tetrahydrobenzodiazepinyl group, (11) a hexahydrobenzazocinyl group, (12) a dihydrobenzoxazinyl group, (13) a dihydrobenzoxazolyl group, (14) a benzisoxazolyl group, (15) a benzoxadiazolyl group, (16) a tetrahydrobenzoxazepinyl group, (17) a dihydrobenzothiazinyl group, (18) a benzothiazolyl group, (19) a benzoxathiolyl group, (20) a chromenyl group, (21) a dihydrobenzofuryl group, (22) a carbazolyl group, (23) a dibenzofuryl group and (24) a quinoxalinyl group.

wherein at least one group selected from the group consisting of the groups (1) to (66) below may be present as a substituent on the cyclo C3-C8 alkyl group, the aromatic group and the heterocyclic group represented by $R^1$:

(1) a lower alkyl group,
(2) a lower alkenyl group,
(3) a halogen substituted lower alkyl group,
(4) a lower alkoxy group,
(5) an aryloxy group,
(6) a lower alkylthio group,
(7) a halogen substituted lower alkoxy group,
(8) a hydroxy group,
(9) a protected hydroxy group,
(10) a hydroxy lower alkyl group,
(11) a protected hydroxy lower alkyl group,
(12) a halogen atom,
(13) a cyano group,
(14) an aryl group,
(15) a nitro group,
(16) an amino group,
(17) an amino group having a group(s) selected from the group consisting of a lower alkyl group, a lower alkanoyl group, a lower alkoxycarbonyl group, a lower alkylsulfonyl group, a carbamoyl group, a lower alkyl carbamoyl group, an amino lower alkanoyl group, a lower alkanoylamino lower alkanoyl group and a lower alkoxy carbonylamino lower alkanoyl group as a substituent,
(18) a lower alkanoyl group,
(19) an arylsulfonyl group that may have a lower alkyl group(s) on the aryl group,
(20) a carboxy group,
(21) a lower alkoxycarbonyl group,
(22) a carboxy lower alkyl group,
(23) a lower alkoxycarbonyl lower alkyl group,
(24) a lower alkanoylamino lower alkanoyl group,
(25) a carboxy lower alkenyl group,
(26) a lower alkoxycarbonyl lower alkenyl group,
(27) a carbamoyl lower alkenyl group that may have a group(s) selected from the group consisting of a lower alkyl group and a halogen substituted lower alkyl group as a substituent,
(28) a carbamoyl group that may have a group(s) selected from the group consisting of the groups (i) to (lxxviii) below as a substituent:

(i) a lower alkyl group,
(ii) a lower alkoxy group,
(iii) a hydroxy lower alkyl group,
(iv) a lower alkoxy lower alkyl group,
(v) an aryloxy lower alkyl group,
(vi) a halogen substituted lower alkyl group,
(vii) an amino lower alkyl group that may have a group(s) selected from the group consisting of a lower alkyl group, a lower alkanoyl group, an aroyl group and a carbamoyl group,
(viii) a cyclo C3-C8 alkyl group that may have a group(s) selected from the group consisting of a lower alkyl group, a hydroxy group, a lower alkoxycarbonyl group and a phenyl lower alkoxy group as a substituent,
(ix) a cyclo C3-C8 alkyl substituted lower alkyl group,
(x) a lower alkenyl group,
(xi) a carbamoyl lower alkyl group that may have a group(s) selected from the group consisting of a lower alkyl group, phenyl group that may have a lower alkyl group(s) and a phenyl group(s) that may have a lower alkoxy group(s) as a substituent,
(xii) a lower alkoxycarbonyl lower alkyl group,
(xiii) a furyl lower alkyl group (that may have a lower alkyl group(s) as a substituent) on the furyl group,
(xiv) a tetrahydrofuryl lower alkyl group,
(xv) a 1,3-dioxolanyl lower alkyl group,
(xvi) a tetrahydropyranyl lower alkyl group,
(xvii) a pyrrolyl lower alkyl group (that may have a lower alkyl group(s) as a substituent on the pyrrolyl group),
(xviii) a lower alkyl group substituted with a dihydropyrazolyl group that may have an oxo group(s),
(xix) a pyrazolyl lower alkyl group (that may have a lower alkyl group(s) as a substituent on the pyrazolyl group),
(xx) an imidazolyl lower alkyl group,
(xxi) a pyridyl lower alkyl group,
(xxii) a pyrazinyl lower alkyl group (that may have a lower alkyl group(s) as a substituent on the pyrazinyl group),
(xxiii) a pyrrolidinyl lower alkyl group (that may have a group(s) selected from the group consisting of an oxo group(s) and a lower alkyl group as a substituent on the pyrrolidinyl group),
(xxiv) a piperidyl lower alkyl group (that may have a group(s) selected from the group consisting of a benzoyl group and a lower alkanoyl group as a substituent on the piperidyl group),
(xxv) a piperazinyl lower alkyl group (that may have a lower alkyl group(s) as a substituent on the piperazinyl group),
(xxvi) a morpholinyl lower alkyl group,
(xxvii) a thienyl lower alkyl group (that may have a lower alkyl group(s) as a substituent on the thienyl group),
(xxviii) a thiazolyl lower alkyl group,
(xxix) a dihydrobenzofuryl lower alkyl group,
(xxx) a benzopyranyl lower alkyl group (that may have an oxo group(s) as a substituent on the benzopyranyl group),
(xxxi) a benzimidazolyl lower alkyl group,
(xxxii) an indolyl lower alkyl group that may have a lower alkoxycarbonyl group(s) on the lower alkyl group),
(xxxiii) an imidazolyl lower alkyl group that has a substituent(s) selected from the group consisting of a carbamoyl group and a lower alkoxycarbonyl group on the lower alkyl group,
(xxxiv) a pyridyl group that may have a group(s) selected from the group consisting of a lower alkyl group, a lower alkoxy group and a lower alkylthio lower alkyl group as a substituent,
(xxxv) a pyrrolidinyl group that may have a group(s) selected from the group consisting of a lower alkyl group, a lower alkoxycarbonyl group, a lower alkanoyl group and an aroyl group as a substituent,
(xxxvi) a piperidyl group that may have a group(s) selected from the group consisting of a lower alkyl group, a lower alkoxycarbonyl group, a lower alkanoyl group and an aroyl group that may have a group(s) selected from the group consisting of a lower alkyl group and a halogen atom as a substituent,
(xxxvii) a tetrahydrofuryl group that may have an oxo group(s),
(xxxviii) a hexahydroazepinyl group that may have an oxo group(s),
(xxxix) a pyrazolyl group that may have a group(s) selected from the group consisting of a lower alkyl group, an aryl group and a furyl group as a substituent,
(xl) a thiazolyl group, (xli) a thiadiazolyl group that may have a lower alkyl group(s), (xlii) an isoxazolyl group that may have a lower alkyl group(s), (xliii) an indazolyl group, (xliv) an indolyl group, (xlv) a tetrahydrobenzothiazolyl group, (xlvi) a tetrahydroquinolyl group that may have a group(s) selected from the group consisting of a lower alkyl group, a lower alkoxy group, a halogen atom and an oxo group as a substituent, (xlvii) a quinolyl group that may have a lower alkyl group(s), (xlviii) a benzodioxolyl lower alkyl group, (xlix) an aryl group that may have a group(s) as a substituent, selected from the group consisting of
a halogen atom; a lower alkyl group; a lower alkoxy group; a halogen substituted lower alkyl group; a halogen substituted lower alkoxy group; a lower alkenyl group; an amino group that may have a group(s) selected from the group consisting of a lower alkanoyl group, a lower alkyl sulfonyl group, a lower alkyl group and an aryl group; a sulfamoyl group; a lower alkylthio group; a lower alkanoyl group; a lower alkoxycarbonyl group; a pyrrolyl group; a lower alkynyl group; a cyano group; a nitro group; an aryloxy group; an aryl lower alkoxy group; a hydroxy group; a hydroxy lower alkyl group; a carbamoyl group that may have a group(s) selected from the group consisting of a lower alkyl group and an aryl group; a pyrazolyl group; a pyrrolidinyl group that may have an oxo group(s); an oxazolyl group; an imidazolyl group that may have a lower alkyl group(s); a dihydrofuryl group that may have an oxo group(s); a thiazolidinyl lower alkyl group that may have an oxo group(s); an imidazolyl lower alkanoyl group and a piperidinylcarbonyl group, (l) a cyano lower alkyl group, (li) a dihydroquinolyl group that may have a group(s) selected from the group consisting of a lower alkyl group and an oxo group, (lii) a halogen substituted lower alkylamino group, (liii) a lower alkylthio lower alkyl group, (liv) an amidino group that may have a lower alkyl group(s), (lv) an amidino lower alkyl group, (lvi) a lower alkenyloxy lower alkyl group, (lvii) an arylamino group that may have a substituent(s) selected from the group consisting of a lower alkyl group, a lower alkoxy group, a halogen substituted lower alkyl group and a halogen substituted lower alkoxy group, on the aryl group, (lviii) an aryl lower alkenyl group, (lix) a pyridylamino group that may have a lower alkyl group(s), (lx) an aryl lower alkyl group (that may have on the aryl group and/or the lower alkyl group a group(s) selected from the group consisting of a halogen atom, a lower alkyl group, a halogen substituted lower alkyl group, a halogen substituted lower alkoxy group, a lower alkoxy group, a carbamoyl group and a lower alkoxycarbonyl group as a substituent), (lxi) a lower alkynyl group, (lxii) an aryloxy lower alkyl group (that may have as a substituent on the aryl group a group(s) selected from the group consisting of a lower alkoxy group; a carbamoyl group that may have a group(s) selected from the group consisting of a lower alkoxy group and a lower alkyl group; and a pyrrolidinyl group that may have an oxo group(s)), (lxiii) an isoxazolidinyl group that may have an oxo group(s), (lxiv) a dihydroindenyl group, (lxv) an aryl lower alkoxy lower alkyl group, (lxvi) a tetrahydropyranyl group, (lxvii) an azetidinyl group that may have a group(s) selected from the group consisting of a lower alkanoyl group and an aroyl group, (lxviii) an azetidinyl lower alkyl group that may have a group(s) selected from the group consisting of a lower alkanoyl group and aroyl group, (lxix) a tetrazolyl group, (lxx) an indolinyl group that may have an oxo group(s), (lxxi) a triazolyl group that may have a group(s) selected from the group consisting of a lower alkyl group and a lower alkylthio group, (lxxii) an imidazolyl group that may have a carbamoyl group(s), (lxxiii) an oxazolyl group that may have a lower alkyl group(s), (lxxiv) an isothiazolyl group that may have a lower alkyl group(s), (lxxv) a benzimidazolyl group, (lxxvi) a dihydrobenzothiazolyl group that may have an oxo group(s), (lxxvii) a thienyl group that may have a lower alkoxycarbonyl group(s), and (lxxviii) an oxazolyl lower alkyl group that may have a lower alkyl group(s)

(29) an amino lower alkyl group that may have a group(s) selected from the group consisting of a lower alkyl group, a halogen substituted lower alkyl group, a lower alkoxycarbonyl group, a lower alkanoyl group, an aryl group, an aryl lower alkyl group, an aroyl group and an amino substituted alkyl group (that may have a lower alkyl group(s) as a substituent on the amino group) on the amino group,

(30) a lower alkyl group substituted with a carbamoyl group that may have a group(s) selected from the group consisting of a lower alkyl group and a halogen substituted lower alkyl group,

(31) a thiocarbamoyl group that may have a lower alkyl group(s),

(32) a sulfamoyl group,

(33) an oxazolidinyl group that may have an oxo group(s),

(34) an imidazolidinyl group that may have a substituent(s) selected from the group consisting of an oxo group and a lower alkyl group,

(35) a pyrrolidinyl group that may have an oxo group(s),

(36) an imidazolyl group,

(37) a triazolyl group,

(38) an isoxazolyl group,

(39) a piperidyl group that may have a substituent(s) selected from the group consisting of a lower alkyl group, a lower alkanoyl group, an arylsulfonyl group, an oxo group, a hydroxy group, and an amino group that may have a group(s) selected from the group consisting of a lower alkyl group, a lower alkanoyl group, a lower alkoxycarbonyl group and a lower alkanoylamino lower alkanoyl group,

(40) a piperidylcarbonyl group that may have a substituent(s) selected from the group consisting of a lower alkyl group, a hydroxy group, a hydroxy lower alkyl group, a lower alkanoyl group, a carboxy lower alkyl group, a lower alkyl carbamoyl lower alkyl group, a carbamoyl group, a lower alkoxy group, a carboxy group, a lower alkoxycarbonyl group, an amino group (on which 1 to 2 groups selected from the group consisting of a lower alkyl group, a lower alkanoyl group, a lower alkoxycarbonyl group and an aroyl group may be present), a piperidyl group (on which a group(s) selected from the group consisting of a lower alkanoyl group, a lower alkoxycarbonyl group and an aroyl group may be present), piperazinyl group (on which a lower alkyl group(s) may be present as a substituent), a 1,4-dioxa-8-azaspiro[4.5]decyl group, a morpholinyl group, a hexahydro-1,4-diazepinyl group (on which a lower alkyl group(s) may be present as a substituent), a pyridyl group, a pyridyloxy group, a pyridyl lower alkoxy group, a tetrahydroquinolyl group (on which an oxo group(s) may be present), a benzodioxolyl group, an aryl lower alkoxy group (that may have a group(s) selected from the group consisting of a halogen atom, a lower alkyl group, a lower alkoxy group and a halogen substituted lower alkoxy group on the aryl group), an aryl group (on which a group(s) selected from the group consisting of a halogen atom, a lower alkoxy group, a hydroxy group may be present), an aryloxy group (that may have on the aryl group a group(s) selected from the group consisting of a cyano group, a halogen atom, a lower alkyl group, a lower alkoxy group and a halogen substituted lower alkyl group), an aryl lower alkyl group (that may have on the aryl group a group(s) selected from the group consisting of a halogen atom, a lower alkyl group, a lower alkoxy group and a halogen substituted lower alkyl group), and an aroyl group (that may have on the aryl group a group(s) selected from the group consisting of a halogen atom and a lower alkoxy group),

(41) a pyrrolidinylcarbonyl group that may have a group as a substituent, selected from the group consisting of a hydroxy lower alkyl group, a carbamoyl group, a hydroxy group, an amino group (that may have on the amino group a group(s) selected from the group consisting of a lower alkyl group, a lower alkanoyl group and an aroyl group), a morpholinyl lower alkyl group, a pyrrolidinyl lower alkyl group, a piperidyl lower alkyl group, a piperazinyl lower alkyl group (that may have a lower alkyl group(s) as a substituent on the piperazinyl group), an amino lower alkyl group (that may have a lower alkyl group(s) as a substituent on the amino group), an aryloxy group (that may have a halogen substituted lower alkoxy group(s) on the aryl group), an aryloxy lower alkyl group (that may have a halogen substituted lower alkoxy group(s) on the aryl group) and a tetrahydroquinolyl group (on which an oxo group(s) may be present),

(42) a piperazinylcarbonyl group that may have a group(s) as a substituent, selected from the group consisting of a lower alkyl group, a cyclo C3-C8 alkyl group, a lower alkanoyl group, a hydroxy lower alkyl group, a lower alkoxy lower alkyl group, a lower alkoxycarbonyl group, an amino lower alkyl group (that may have a lower alkyl group(s) as a substituent on the amino group), a piperidyl lower alkyl group (that may have a lower alkyl group(s) as a substituent on the piperidyl group), a morpholinyl lower alkyl group, a pyrrolidinyl lower alkyl group, a 1,3-dioxolanyl lower alkyl group, a tetrahydrofuryl lower alkyl group, a pyridyl lower alkyl group (that may have a phenyl group(s) as a substituent on the lower alkyl group), an imidazolyl lower alkyl group, a furyl lower alkyl group, a pyrrolidinylcarbonyl lower alkyl group, a piperidyl group that may have a lower alkyl group(s) as a substituent, pyridyl group (that may have on the pyridyl group a group(s) selected from the group consisting of a lower alkyl group, a cyano group and a halogen substituted lower alkyl group as a substituent), a thieno[2,3-b]pyridyl group, an aryl group (on which a group(s) selected from the group consisting of a halogen atom and a lower alkyl group may be present), an aroyl group, a furyl carbonyl group, an aryl lower alkoxycarbonyl group and an oxo group,

(43) a hexahydroazepinylcarbonyl group,

(44) a hexahydro-1,4-diazepinylcarbonyl group that may have a substituent(s) selected from the group consisting of a lower alkyl group and a pyridyl group,

(45) a dihydropyrrolylcarbonyl group that may have a lower alkyl group(s),

(46) a thiomorpholinylcarbonyl group,

(47) a morpholinylcarbonyl group that may have a group(s) selected from the group consisting of a lower alkyl group, a piperidyl lower alkyl group and an aryl group,

(48) a thiazolidinyl carbonyl group that may have an aryl group(s) that may have a group(s) selected from the group consisting of a lower alkoxy group and a cyano group,

(49) an azabicyclo[3.2.2]nonylcarbonyl group,

(50) an 8-azabicyclo[3.2.1]octylcarbonyl group that may have a halogen substituted or unsubstituted aryloxy group(s),

(51) an indolinylcarbonyl group,

(52) a tetrahydroquinolylcarbonyl group,

(53) a tetrahydropyrido[3.4-b]indolylcarbonyl group,

(54) a morpholinyl lower alkyl group,

(55) a piperazinyl lower alkyl group that may have a lower alkyl group(s) on the piperazinyl group,

(56) a morpholinylcarbonyl lower alkyl group,

(57) a piperazinylcarbonyl lower alkyl group that may have a lower alkyl group(s) on the piperazinyl group,

(58) an oxo group,

(59) an amino lower alkoxy group (that may have a lower alkyl group(s) on the amino group),

(60) a lower alkoxy lower alkoxy group,

(61) a piperazinyl group that may have a group(s) selected from the group consisting of an oxo group, a lower alkyl group, a lower alkanoyl group and a lower alkoxycarbonyl group,

(62) a morpholinyl group,

(63) a 1,3,8-triazaspiro[4.5]decanylcarbonyl group that may have a group(s) selected from the group consisting of an oxo group and an aryl group,

(64) a tetrahydropyridylcarbonyl group that may have a pyridyl group(s),

(65) an imidazolidinylcarbonyl group that may have a thioxo group(s), and

(66) a 1,4-dioxa-8-azaspiro[4.5]decanyl group.

The present invention provides a compound represented by the general formula (1), wherein $R^1$ represents a cyclo C5-C6 alkyl group, an aromatic group or a heterocyclic group selected from the group consisting of (I) to (IV) below:

(I) a cyclo C5-C6 alkyl group;

(II) an aromatic group selected from a phenyl group, naphthyl group, dihydroindenyl group and tetrahydronaphthyl group;

(III) a saturated or unsaturated heteromonocyclic group that has 1 to 2 hetero atoms selected from the group consisting of a nitrogen atom, oxygen atom and sulfur atom, and that is selected from the group consisting of a pyrrolidinyl group, piperidyl group, pyrazolyl group, pyridyl group, pyrimidinyl group, pyrazinyl group, isoxazolyl group, thiazolyl group, pyranyl group, and thienyl group; and (IV) a benzene fused heterocyclic group that has 1 to 4 hetero atoms selected from the group consisting of a nitrogen atom, oxygen atom and sulfur atom and that is selected from the group consisting of (1) a tetrahydroquinoxalinyl group, (2) a tetrahydroquinazolinyl group, (3) a dihydroquinazolinyl group, (4) an indolinyl group, (5) an indolyl group, (6) an isoindolinyl group, (7) a benzimidazolinyl group, (8) a dihydrobenzimidazolyl group, (9) a tetrahydrobenzazepinyl group, (10) a tetrahydrobenzodiazepinyl group, (11) a hexahydrobenzazocinyl group, (12) a dihydrobenzoxazinyl group, (13) a dihydrobenzoxazolyl group, (14) a benzisoxazolyl group, (15) a benzoxadiazolyl group, (16) a tetrahydrobenzoxazepinyl group, (17) a dihydrobenzothiazinyl group, (18) a benzothiazolyl group, (19) a benzoxathiolyl group, (20) a chromenyl group, (21) a dihydrobenzofuryl group, (22) a carbazolyl group, (23) a dibenzofuryl group, and (24) a quinoxalinyl group wherein, on the aromatic group and the heterocyclic group represented by $R^1$, 1 to 5 groups selected from the group consisting of the groups (1) to (66) below may be present as a substituent(s):

(1) a lower alkyl group,
(2) a lower alkenyl group,
(3) a halogen substituted lower alkyl group,
(4) a lower alkoxy group,
(5) a phenoxy group,
(6) a lower alkylthio group,
(7) a halogen substituted lower alkoxy group,
(8) a hydroxy group,
(9) a phenyl lower alkoxy group,
(10) a hydroxy lower alkyl group,
(11) a lower alkoxy lower alkyl group,
(12) a halogen atom,
(13) a cyano group,
(14) a phenyl group,
(15) a nitro group,
(16) an amino group,
(17) an amino group having 1 to 2 groups selected from the group consisting of a lower alkyl group, a lower alkanoyl group, a lower alkoxycarbonyl group, a lower alkylsulfonyl group, a carbamoyl group, a lower alkyl carbamoyl group, an amino lower alkanoyl group, a lower alkanoylamino lower alkanoyl group and a lower alkoxycarbonylamino lower alkanoyl group as a substituent(s),
(18) a lower alkanoyl group,
(19) a phenylsulfonyl group that may have a single lower alkyl group on the phenyl group,
(20) a carboxy group,
(21) a lower alkoxycarbonyl group,
(22) a carboxy lower alkyl group,
(23) a lower alkoxycarbonyl lower alkyl group,
(24) a lower alkanoylamino lower alkanoyl group,
(25) a carboxy lower alkenyl group,
(26) a lower alkoxycarbonyl lower alkenyl group,
(27) a carbamoyl lower alkenyl group that may have 1 to 2 groups selected from the group consisting of a lower alkyl group and a lower alkyl group substituted with 1 to 3 halogen atoms as a substituent(s),
(28) a carbamoyl group that may have 1 to 2 groups selected from the group consisting of the groups (i) to (lxxviii) below as a substituent(s):
(i) a lower alkyl group,
(ii) a lower alkoxy group,
(iii) a hydroxy lower alkyl group,
(iv) a lower alkoxy lower alkyl group,
(v) an phenoxy lower alkyl group,
(vi) a halogen substituted lower alkyl group,
(vii) an amino lower alkyl group that may have 1 to 2 groups selected from the group consisting of a lower alkyl group, a lower alkanoyl group, a benzoyl group and a carbamoyl group,
(viii) a cyclo C3-C8 alkyl group that may have 1 to 3 groups selected from the group consisting of a lower alkyl group, a hydroxy group, a lower alkoxycarbonyl group and a phenyl lower alkoxy group as a substituent(s),
(ix) a cyclo C3-C8 alkyl substituted lower alkyl group,
(x) a lower alkenyl group,
(xi) a lower alkyl group having 1 to 2 carbamoyl groups that may have 1 to 2 groups as a substituent(s) selected from the group consisting of a lower alkyl group, a phenyl group that may have a single lower alkyl group and a phenyl group that may have a single lower alkoxy group,
(xii) a lower alkyl group having 1 to 2 lower alkoxy carbonyl groups,
(xiii) a furyl lower alkyl group (that may have 1 to 2 lower alkyl groups as a substituent(s) on the furyl group),
(xiv) a tetrahydrofuryl lower alkyl group,
(xv) a 1,3-dioxolanyl lower alkyl group,
(xvi) a tetrahydropyranyl lower alkyl group,
(xvii) a pyrrolyl lower alkyl group (that may have 1 to 2 lower alkyl groups on the pyrrolyl group as a substituent(s)),
(xviii) a lower alkyl group substituted with a dihydropyrazolyl group that may have a single oxo group,
(xix) a pyrazolyl lower alkyl group (that may have 1 to 3 lower alkyl groups as a substituent(s) on the pyrazolyl group),
(xx) an imidazolyl lower alkyl group,
(xxi) a pyridyl lower alkyl group,
(xxii) a pyrazinyl lower alkyl group (that may have 1 to 3 (preferably 1) lower alkyl groups as a substituent(s) on the pyrazinyl group),
(xxiii) a pyrrolidinyl lower alkyl group (that may have 1 to 2 groups selected from the group consisting of an oxo group and a lower alkyl group as a substituent(s) on the pyrrolidinyl group),
(xxiv) a piperidyl lower alkyl group (that may have 1 to 3 groups selected from the group consisting of a benzoyl group and a lower alkanoyl group as a substituent(s) on the piperidyl group),
(xxv) a piperazinyl lower alkyl group (that may have 1 to 3 lower alkyl groups as a substituent(s) on the piperazinyl group),
(xxvi) a morpholinyl lower alkyl group,
(xxvii) a thienyl-lower alkyl group (that may have 1 to 3 lower alkyl groups as a substituent(s) on the thienyl group),
(xxviii) a thiazolyl lower alkyl group,
(xxix) a dihydrobenzofuryl lower alkyl group,
(xxx) a benzopyranyl lower alkyl group (that may have a single oxo group as a substituent on the benzopyranyl group),
(xxxi) a benzimidazolyl lower alkyl group,
(xxxii) an indolyl lower alkyl group that may have 1 to 3 lower alkoxycarbonyl groups on the lower alkyl group),
(xxxiii) an imidazolyl lower alkyl group that has 1 to 3 substituents selected from the group consisting of a carbamoyl group and a lower alkoxycarbonyl group, on the lower alkyl group,
(xxxiv) a pyridyl group that may have 1 to 3 groups selected from the group consisting of a lower alkyl group, a lower alkoxy group and a lower alkylthio lower alkyl group as a substituent(s),
(xxxv) a pyrrolidinyl group that may have 1 to 3 groups selected from the group consisting of a lower alkyl group, a lower alkoxycarbonyl group, a lower alkanoyl group and a benzoyl group as a substituent (s),
(xxxvi) a piperidyl group that may have 1 to 3 groups selected from the group consisting of a lower alkyl group, a lower alkoxycarbonyl group, a lower alkanoyl group and a benzoyl group (that may have 1 to 3 groups selected from the group consisting of a lower alkyl group and a halogen atom as a substituent(s) on the phenyl group),
(xxxvii) a tetrahydrofuryl group that may have a single oxo group
(xxxviii) a hexahydroazepinyl group that may have a single oxo group,
(xxxix) a pyrazolyl group that may have 1 to 3 groups selected from the group consisting of a lower alkyl group, a phenyl group and a furyl group as a substituent(s),
(xl) a thiazolyl group, (xli) a thiadiazolyl group that may have 1 to 3 lower alkyl groups,
(xlii) an isoxazolyl group that may have 1 to 3 lower alkyl groups,
(xliii) an indazolyl group,
(xliv) an indolyl group,
(xlv) a tetrahydrobenzothiazolyl group,
(xlvi) a tetrahydroquinolyl group that may have 1 to 3 groups selected from the group consisting of a lower alkyl group, a lower alkoxy group, a halogen atom and an oxo group as a substituent(s),
(xlvii) a quinolyl group that may have 1 to 3 lower alkyl groups,
(xlviii) a benzodioxolyl lower alkyl group,
(xlix) a phenyl group or naphthyl group that may have 1 to 3 groups as a substituent(s), selected from the group consisting of
a halogen atom; a lower alkyl group; a lower alkoxy group; a halogen substituted lower alkyl group; a halogen substituted lower alkoxy group; a lower alkenyl group; an amino group that may have 1 to 2 groups selected from the group consisting of a lower alkanoyl group, a lower alkyl sulfonyl group, a lower alkyl group and an aryl group; a sulfamoyl group; a lower alkylthio group; a lower alkanoyl group; a lower alkoxycarbonyl group; pyrrolyl group; a lower alkynyl group; a cyano group; a nitro group; a phenyloxy group; a phenyl lower alkoxy group; a hydroxy group; a hydroxy lower alkyl group; a carbamoyl group that may have 1 to 2 groups selected from the group consisting of a lower alkyl group and a phenyl group; a pyrazolyl group; a pyrrolidinyl group that may have a single oxo group; oxazolyl group; an imidazolyl group that may have 1 to 3 lower alkyl groups; a dihydrofuryl group that may have a single oxo group; thiazolidinyl lower alkyl group that may have two oxo groups; imidazolyl lower alkanoyl group and piperidinylcarbonyl group,
(l) a cyano lower alkyl group,
(li) a dihydroquinolyl group that may have 1 to 3 group(s) selected from the group consisting of a lower alkyl group and oxo group,
(lii) a halogen substituted lower alkylamino group,
(liii) a lower alkylthio lower alkyl group,
(liv) an amidino group that may have a lower alkyl group,
(lv) an amidino lower alkyl group,
(lvi) a lower alkenyloxy lower alkyl group,
(lvii) a phenylamino group that may have 1 to 3 substituents selected from the group consisting of a lower alkyl group, a lower alkoxy group, a halogen substituted lower alkyl group and a halogen substituted lower alkoxy group on the phenyl group,
(lviii) a phenyl lower alkenyl group,
(lix) a pyridylamino group that may have 1 to 3 lower alkyl groups,
(lx) a phenyl lower alkyl group (that may have as a substituent(s) on the phenyl group and/or the lower alkyl group 1 to 3 groups selected from the group consisting of a halogen atom, a lower alkyl group, a halogen substituted lower alkyl group, a halogen substituted lower alkoxy group, a lower alkoxy group, carbamoyl group and a lower alkoxycarbonyl group),
(lxi) a lower alkynyl group,
(lxii) a phenyloxy lower alkyl group (that may have 1 to 3 groups selected from the group consisting of a lower alkoxy group, N-lower alkoxy-N-lower alkylcarbamoyl group and oxopyrrolidinyl group as a substituent(s) on the phenyl group),
(lxiii) an isoxazolidinyl group that may have a single oxo group,
(lxiv) a dihydroindenyl group,
(lxv) a phenyl lower alkoxy lower alkyl group,
(lxvi) a tetrahydropyranyl group,
(lxvii) an azetidinyl group that may have 1 to 3 groups selected from the group consisting of a lower alkanoyl group and benzoyl group,
(lxviii) an azetidinyl lower alkyl group that may have 1 to 3 groups selected from the group consisting of a lower alkanoyl group and benzoyl group,
(lxix) a tetrazolyl group,
(lxx) an indolinyl group that may have a single oxo group,
(lxxi) a triazolyl group that may have 1 to 3 groups selected from the group consisting of a lower alkyl group and a lower alkylthio group,
(lxxii) an imidazolyl group that may have 1 to 3 carbamoyl groups,
(lxxiii) an oxazolyl group that may have 1 to 3 lower alkyl groups,
(lxxiv) an isothiazolyl group that may have 1 to 3 lower alkyl groups,
(lxxv) a benzimidazolyl group,
(lxxvi) a dihydrobenzothiazolyl group that may have a single oxo group,
(lxxvii) a thienyl group that may have 1 to 3 lower alkoxycarbonyl groups, and
(lxxviii) an oxazolyl lower alkyl group that may have 1 to 3 lower alkyl groups,
(29) an amino lower alkyl group that may have 1 to 2 groups selected from the group consisting of a lower alkyl group, a halogen substituted lower alkyl group, a lower alkoxycarbonyl group, a lower alkanoyl group, a phenyl group, a phenyl lower alkyl group, a benzoyl group and an amino substituted alkyl group (that may have 1 to 2 lower alkyl groups as a substituent(s) on the amino group), on the amino group,
(30) a lower alkyl group substituted with a single carbamoyl group that may have 1 to 2 groups selected from the group consisting of a lower alkyl group and a halogen substituted lower alkyl group,
(31) a thiocarbamoyl group that may have 1 to 2 lower alkyl groups,
(32) a sulfamoyl group,
(33) an oxazolidinyl group that may have a single oxo group,
(34) an imidazolidinyl group that may have 1 to 2 substituents selected from the group consisting of an oxo group and a lower alkyl group,
(35) a pyrrolidinyl group that may have a single oxo group,
(36) an imidazolyl group,
(37) a triazolyl group,
(38) an isoxazolyl group,
(39) a piperidyl group that may have 1 to 3 substituents selected from the group consisting of a lower alkyl group, a lower alkanoyl group, a lower alkylphenylsulfonyl group, an oxo group, a hydroxy group, and an amino group that may have 1 to 2 groups selected from the group consisting of a lower alkyl group, a lower alkanoyl group, a lower alkoxycarbonyl group and a lower alkanoylamino lower alkanoyl group,
(40) a piperidylcarbonyl group that may have 1 to 3 substituent(s) selected from the group consisting of a lower alkyl group, a hydroxy group, a hydroxy lower alkyl group, a lower alkanoyl group, a carboxy lower alkyl group, a lower alkyl carbamoyl lower alkyl group, a carbamoyl group, a lower alkoxy group, a carboxy group, a lower alkoxycarbonyl group, an amino group (on which 1 to 2 groups selected from the group consisting of a lower alkyl group, a lower alkanoyl group, a lower alkoxycarbonyl group and a benzoyl group may be present), a piperidyl group (on which 1 to 3 groups selected from the group consisting of a lower alkanoyl group, a lower alkoxycarbonyl group and a benzoyl group may be present), a piperazinyl group (on which 1 to 3 lower alkyl groups may be present as a substituent(s)), a 1,4-dioxa-8-azaspiro[4.5]decyl group, a morpholinyl group, a hexahydro-1,4-diazepynyl group (on which a single lower alkyl group may be present as a substituent), a pyridyl group, a pyridyloxy group, a pyridyl lower alkoxy group, a tetrahydroquinolyl group (on which a single oxo group may be present), a benzodioxolyl group, a phenyl lower alkoxy group (that may have on the phenyl group 1 to 3 groups selected from the group consisting of a halogen atom, a lower alkyl group, a lower alkoxy group and a halogen substituted lower alkoxy group), a phenyl group (on which 1 to 3 groups selected from the group consisting of a halogen atom, a lower alkoxy group and a hydroxy group may be present), phenyloxy group (that may have on the phenyl group 1 to 3 groups selected from the group consisting of a cyano group, a halogen atom, a lower alkyl group, a lower alkoxy group and a halogen substituted lower alkyl group), a phenyl lower alkyl group (on the phenyl group, 1 to 3 groups selected from the group consisting of a halogen atom, a lower alkyl group, a lower alkoxy group and a halogen substituted lower alkyl group may be present), and a benzoyl group (that may have 1 to 3 groups selected from the group consisting of a halogen atom and a lower alkoxy group on the phenyl group),

(41) a pyrrolidinylcarbonyl group that may have 1 to 3 groups as a substituent(s) selected from the group consisting of a hydroxy lower alkyl group, carbamoyl group, a hydroxy group, an amino group (that may have 1 to 2 groups selected from the group consisting of a lower alkyl group, a lower alkanoyl group and a bemzoyl group on the amino group), a morpholinyl lower alkyl group, a pyrrolidinyl lower alkyl group, a piperidyl lower alkyl group, a piperazinyl lower alkyl group (that may have a single lower alkyl group as a substituent on the piperazinyl group), an amino lower alkyl group (that may have 1 to 2 lower alkyl groups may be present as a substituent on the amino group), phenyloxy group (that may have 1 to 3 halogen substituted lower alkoxy groups on the phenyl group), a phenyloxy lower alkyl group (that may have 1 to 3 halogen substituted lower alkoxy groups on the phenyl group) and a tetrahydroquinolyl group (on which an oxo group may be present),

(42) a piperazinylcarbonyl group that may have 1 to 3 groups as a substituent(s) selected from the group consisting of a lower alkyl group, a cyclo C3-C8 alkyl group, a lower alkanoyl group, a hydroxy lower alkyl group, a lower alkoxy lower alkyl group, a lower alkoxycarbonyl group, an amino lower alkyl group (that may have 1 to 2 lower alkyl groups as a substituent(s) on the amino group), a piperidyl lower alkyl group (that may have 1 to 2 lower alkyl groups as a substituent(s) on the piperidyl group), a morpholinyl lower alkyl group, a pyrrolidinyl lower alkyl group, a 1,3-dioxoranyl lower alkyl group, a tetrahydrofuryl lower alkyl group, a pyridyl lower alkyl group (that may have 1 to 2 phenyl groups as a substituent(s) on the lower alkyl group), an imidazolyl lower alkyl group, a furyl lower alkyl group, a pyrrolidinylcarbonyl lower alkyl group, a piperidyl group that may have 1 to 2 lower alkyl groups as a substituent(s)), a pyridyl group (that may have 1 to 3 groups selected from the group consisting of a lower alkyl group, a cyano group and a halogen substituted lower alkyl group as a substituent(s) on the pyridyl group), a thieno[2,3-b]pyridyl group, a phenyl group (on which 1 to 3 groups selected from the group consisting of a halogen atom and a lower alkyl group may be present), a benzoyl group, a furyl carbonyl group, a phenyl lower alkoxycarbonyl group and an oxo group,

(43) a hexahydroazepinylcarbonyl group,

(44) a hexahydro-1,4-diazepinylcarbonyl group that may have 1 to 3 substituents selected from the group consisting of a lower alkyl group and a pyridyl group,

(45) a dihydropyrrolylcarbonyl group that may have 1 to 3 lower alkyl groups,

(46) a thiomorpholinylcarbonyl group,

(47) a morpholinylcarbonyl group that may have 1 to 3 groups selected from the group consisting of a lower alkyl group, a piperidyl lower alkyl group and a phenyl group,

(48) a thiazolidinyl carbonyl group that may have 1 to 3 phenyl groups that may have 1 to 3 groups selected from the group consisting of a lower alkoxy group and a cyano group,

(49) an azabicyclo[3.2.2]nonylcarbonyl group,

(50) an 8-azabicyclo[3.2.1]octylcarbonyl group that may have 1 to 3 halogen substituted or unsubstituted phenyloxy groups,

(51) an indolinylcarbonyl group,

(52) a tetrahydroquinolylcarbonyl group,

(53) a tetrahydropyrido[3.4-b]indolylcarbonyl group,

(54) a morpholinyl lower alkyl group,

(55) a piperazinyl lower alkyl group that may have 1 to 3 lower alkyl groups on the piperazinyl group,

(56) a morpholinylcarbonyl lower alkyl group,

(57) a piperazinylcarbonyl lower alkyl group that may have 1 to 3 lower alkyl groups on the piperazinyl group,

(58) an oxo group,

(59) an amino lower alkoxy group (that may have 1 to 2 lower alkyl groups on the amino group),

(60) a lower alkoxy lower alkoxy group,

(61) a piperazinyl group that may have 1 to 3 groups selected from the group consisting of an oxo group, a lower alkyl group, a lower alkanoyl group and a lower alkoxycarbonyl group,

(62) a morpholinyl group,

(63) a 1,3,8-triazaspiro[4.5]decanylcarbonyl group that may have 1 to 3 groups selected from the group consisting of an oxo group and a phenyl group,

(64) a tetrahydropyridylcarbonyl group that may have 1 to 3 pyridyl groups,

(65) an imidazolidinylcarbonyl group that may have a single thioxo group, and

(66) a 1,4-dioxa-8-azaspiro[4.5]decanyl group.

The present invention provides a compound represented by the general formula (1), wherein A is a lower alkylene group.

The present invention provides a compound represented by the general formula (1), wherein $R^1$ represents a cyclo C5-C6 alkyl group, an aromatic group or a heterocyclic group selected from the group consisting of (I) to (III) shown below:

(I) a cyclo C5-C6 alkyl group;

(II) a phenyl group; and (III) a saturated or unsaturated heteromonocyclic group having 1 to 2 nitrogen atoms selected from the group consisting of a pyrrolidinyl group, a piperidyl group, a pyrazolyl group, a pyridyl group, pyrimidinyl group and a thiazolyl group, and on the cyclo C5-C6 alkyl group, the aromatic group and the heterocyclic group represented by $R^1$, 1 to 5 groups selected from the group consisting of (1) to (66) defined in claim 2 may be present as a substituent(s).

The present invention provides a compound represented by the general formula (1), wherein $R^1$ represents (I) a cyclo C5-C6 alkyl group, and, on the cyclo C5-C6 alkyl group represented by R¹, 1 to 5 groups selected from the group consisting of (1) to (66) defined in claim 2 may be present as a substituent(s).

The present invention provides a compound represented by the general formula (1), wherein R¹ represents (II) a phenyl group, and, on aromatic group represented by R¹, 1 to 5 groups selected from the group consisting of (1) to (66) defined in claim 2 may be present as a substituent(s).

The present invention provides a compound represented by the general formula (1), wherein R¹ represents (III) a saturated or unsaturated heteromonocyclic group having 1 to 2 nitrogen atoms selected from a pyrrolidinyl group, a piperidyl group, pyrazolyl group, a pyridyl group, a pyrimidinyl group and a thiazolyl group, and, on heterocyclic group represented by R¹, 1 to 5 groups selected from the group consisting of (1) to (66) defined in claim 2 may be present as a substituent(s).

The present invention provides a compound represented by the general formula (1), wherein R¹ represents a cyclo C5-C6 alkyl group, an aromatic group or a heterocyclic group selected from the group consisting of (I) to (III) shown below:
 (I) a cyclo C5-C6 alkyl group;
 (II) a phenyl group; and
 (III) a saturated or unsaturated heteromonocyclic group having 1 to 2 nitrogen atoms selected from a pyrrolidinyl group, a piperidyl group, a pyrazolyl group, a pyridyl group, a pyrimidinyl group and a thiazolyl group, and
 on the cyclo C5-C6 alkyl group, aromatic group and heterocyclic group represented by R¹, 1 to 5 groups selected from the group consisting of (1), (4), (10), (17), (18), (21), (28), (29), (30), (33), (34), (35), (36), (39), (61) and (62) shown below may be present as a substituent(s):
 (1) a lower alkyl group,
 (4) a lower alkoxy group,
 (10) a hydroxy lower alkyl group,
 (17) an amino group having 1 to 2 groups selected from the group consisting of a lower alkyl group, a lower alkanoyl group, a lower alkoxycarbonyl group, a lower alkylsulfonyl group, a carbamoyl group, a lower alkyl carbamoyl group, an amino lower alkanoyl group, a lower alkanoylamino lower alkanoyl group and a lower alkoxycarbonylamino lower alkanoyl group, as a substituent(s),
 (18) a lower alkanoyl group,
 (21) a lower alkoxycarbonyl group,
 (28) a carbamoyl group that may have 1 to 2 groups selected from the group consisting of the groups (i), (ii), (iv), (xii) and (xxi) below as a substituent(s):
  (i) a lower alkyl group,
  (ii) a lower alkoxy group,
  (iv) a lower alkoxy lower alkyl group,
  (xii) a lower alkyl group having 1 to 2 lower alkoxy carbonyl groups,
  (xxi) a pyridyl lower alkyl group,
 (29) an amino lower alkyl group that may have, on the amino group, 1 to 2 groups selected from the group consisting of a lower alkyl group, a halogen substituted lower alkyl group, a lower alkoxycarbonyl group, a lower alkanoyl group, a phenyl group, a phenyl lower alkyl group, a benzoyl group and an amino substituted lower alkyl group (which may have 1 to 2 lower alkyl groups may be present as a substituent(s) on the amino group);
 (30) a lower alkyl group substituted with a single carbamoyl group that may have 1 to 2 groups selected from the group consisting of a lower alkyl group and a halogen substituted lower alkyl group,
 (33) an oxazolidinyl group that may have a single oxo group,
 (34) an imidazolidinyl group that may have 1 to 2 substituents selected from the group consisting of an oxo group and a lower alkyl group,
 (35) a pyrrolidinyl group that may have a single oxo group,
 (36) an imidazolyl group,
 (39) a piperidyl group that may have 1 to 3 substituents selected from the group consisting of a lower alkyl group, a lower alkanoyl group, a lower alkyl phenylsulfonyl group, an oxo group, hydroxy group, and an amino group that may have 1 to 2 groups selected from the group consisting of a lower alkyl group, a lower alkanoyl group, a lower alkoxycarbonyl group and a lower alkanoylamino lower alkanoyl group,
 (61) a piperazinyl group that may have 1 to 3 groups selected from the group consisting of an oxo group, a lower alkyl group, a lower alkanoyl group and a lower alkoxycarbonyl group, and
 (62) a morpholinyl group.

The present invention provides a compound represented by the general formula (1), wherein R¹ represents (I) a cyclohexyl group, and, on the cyclo C5-C6 alkyl group represented by R¹, 1 to 3 groups selected from the group consisting of (1), (4), (10), (17), (18), (21), (28), (29), (30), (33), (34), (35), (36), (39), (61) and (62) defined in claim 8 may be present as a substituent(s).

The present invention provides a compound represented by the general formula (1), wherein R¹ represents (II) a phenyl group, and, on the aromatic group represented by R¹, 1 to 3 groups selected from the group consisting of (1), (4), (10), (17), (18) (21), (28), (29), (30), (33), (34), (35), (36), (39), (61) and (62) defined in claim 8 may be present as a substituent(s).

The present invention provides a compound represented by the general formula (1), wherein R¹ represents (II) a phenyl group, and, on the aromatic group represented by R¹, 1 to 3 groups selected from the group consisting of (1), (4), (10), (17), (18), (28), (33), (35), (39) and (61) shown below may be present as a substituent(s).
 (1) a lower alkyl group,
 (4) a lower alkoxy group,
 (10) a hydroxy lower alkyl group,
 (17) an amino group having 1 to 2 groups selected from the group consisting of a lower alkyl group, a amino lower alkanoyl group, a lower alkanoylamino lower alkanoyl group and a lower alkoxy carbonylamino lower alkanoyl group, as a substituent(s),
 (18) a lower alkanoyl group,
 (28) a carbamoyl group having a single lower alkoxy lower alkyl group,
 (33) an oxazolidinyl group that may have a single oxo group,
 (35) a pyrrolidinyl group that may have a single oxo group,
 (39) a piperidyl group, and
 (61) a piperazinyl group that may have 1 to 2 groups selected from the group consisting of an oxo group, a lower alkanoyl group and a lower alkoxycarbonyl group.

The compound according to claim 11, wherein R¹ is a phenyl group having, on the phenyl group, a single lower alkyl group, a single lower alkoxy group and a single amino group having 1 or 2 lower alkyl groups on the amino group;
 a phenyl group having, on the phenyl group, a single lower alkyl group, a single lower alkoxy group and a single carbamoyl group having a single lower alkyl group, which has two lower alkoxy groups on the lower alkyl group;
 a phenyl group having, on the phenyl group, a single hydroxy lower alkyl group, a single lower alkoxy group and a single oxazolidinyl group having a single oxo group on the oxazolidinyl group;

a phenyl group having, on the phenyl group, a single lower alkyl group, a single lower alkoxy group and a single pyrrolidinyl group;

a phenyl group having, on the phenyl group, a single lower alkyl group, a single lower alkoxy group and a single piperidyl group;

a phenyl group having, on the phenyl group, a single lower alkyl group, a single lower alkoxy group and a single piperazyl group having a single lower alkanoyl group on the piperazyl group;

a phenyl group having, on the phenyl group, a single lower alkyl group, a single lower alkoxy group and a single piperazyl group having a single lower alkanoyl group and a single oxo group on the piperazyl group;

a phenyl group having, on the phenyl group, a single lower alkyl group, a single lower alkoxy group and a single piperazyl group having a single lower alkoxycarbonyl group and a single oxo group on the piperazyl group;

a phenyl group having, on the phenyl group, a single lower alkyl group, a single lower alkoxy group and a single N-[(N-lower alkoxy-carbonylamino)lower alkanoyl]amino group;

a phenyl group having, on the phenyl group, a single lower alkyl group, a single lower alkoxy group and a single N-(amino lower alkanoyl)amino group;

a phenyl group having, on the phenyl group, a single lower alkyl group, a single lower alkoxy group and a single N-[(N-lower alkanoyl amino)lower alkanoyl]amino group;

a phenyl group having, on the phenyl group, a single lower alkoxy group, a single lower alkanoyl group and a single piperazyl group having a single lower alkoxycarbonyl group on the piperazyl group; or a phenyl group having, on the phenyl group, a single lower alkoxy group, a single hydroxy lower alkyl group and a single piperazyl group having a single lower alkoxycarbonyl group on the piperazyl group.

The present invention provides a compound represented by the general formula (1), wherein $R^1$ represents a saturated or unsaturated heteromonocyclic group having 1 to 2 nitrogen atoms selected from a piperidyl group, pyrazolyl group and thiazolyl group, and, on the heterocyclic group represented by $R^1$, 1 to 3 groups selected from the group consisting of (1), (4), (10), (17), (18), (21), (28), (29), (30), (33), (34), (35), (36), (39), (61) and (62) defined in claim 8 may be present as a substituent(s).

The present invention provides a compound represented by the general formula (1), wherein $R^1$ represents (III) a saturated or unsaturated heteromonocyclic group having 1 to 2 nitrogen atoms selected from a piperidyl group, pyrazolyl group and thiazolyl group, and, on the heterocyclic group represented by $R^1$, 1 to 3 groups selected from the group consisting of (1), (17) and (28) shown below may be present as a substituent(s).

(1) a lower alkyl group;

(17) an amino group having 1 to 2 groups selected from the group consisting of a lower alkyl group and a lower alkanoyl group, as a substituent(s); and

(28) a carbamoyl group that may have 1 to 2 lower alkyl groups.

The present invention provides a compound represented by the general formula (1), wherein $R^1$ represents a pyrazolyl group having a single lower alkyl group and a single lower alkanoyl amino group;

a pyrazolyl group having a single lower alkyl group and a single N,N-di-lower alkyl amino group;

a piperidyl group having a single N,N-di-lower alkyl carbamoyl group; or a thiazolyl group having a single N,N-di-lower alkyl carbamoyl group.

The present invention provides a pharmaceutical composition comprising a heterocyclic compound of the general formula (1) or a salt thereof according to the present invention, as an active ingredient and a pharmaceutically acceptable carrier.

The present invention provides a pharmaceutical composition according to the present invention can be used as a pharmaceutical composition for treating or preventing central nervous system disorders.

The present invention provides a pharmaceutical composition according to the present invention can be used as a pharmaceutical composition for treating or preventing central nervous system disorders selected from the group consisting of schizophrenia; refractory, intractable or chronic schizophrenia; emotional disturbance; psychotic disorder; mood disorder; bipolar I type disorder; bipolar II type disorder; depression; endogenous; depression; major depression; melancholy and refractory depression; dysthymic disorder; cyclothymic disorder; panic attack; panic disorder; agoraphobia; social phobia; obsessive-compulsive disorder; post-traumatic stress disorder; generalized anxiety disorder; acute stress disorder; hysteria; somatization disorder; conversion disorder; pain disorder; hypochondriasis; factitious disorder; dissociative disorder; sexual dysfunction; sexual desire disorder; sexual arousal disorder; erectile dysfunction; anorexia nervosa; bulimia nervosa; sleep disorder; adjustment disorder; alcohol abuse; alcohol intoxication; drug addiction; stimulant intoxication; narcotism; anhedonia; iatrogenic anhedonia; anhedonia of a psychic or mental cause; anhedonia associated with depression; anhedonia associated with schizophrenia; delirium; cognitive impairment; cognitive impairment associated with Alzheimer's disease, Parkinson's disease and other neurodegenerative diseases; cognitive impairment caused by Alzheimer's disease; Parkinson's disease and associated neurodegenerative diseases; cognitive impairment of schizophrenia; cognitive impairment caused by refractory, intractable or chronic schizophrenia; vomiting; motion sickness; obesity; migraine; pain (ache); mental retardation; autism disorder (autism); Tourette's disorder; tic disorder; attention-deficit/hyperactivity disorder; conduct disorder; and Down's syndrome.

The present invention provides a process for producing a pharmaceutical composition comprising mixing a heterocyclic compound represented by the formula (1) or a salt thereof with a pharmaceutically acceptable carrier.

The present invention provides use of a heterocyclic compound represented by the formula (1) or a salt thereof as a drug.

Specifically provided is of a heterocyclic compound represented by the formula (1) or a salt thereof, as a dopamine $D_2$ receptor partial agonist and/or serotonin 5-$HT_{2A}$ receptor antagonist and/or an adrenaline $\alpha_1$ receptor antagonist and/or a serotonin uptake inhibitor (or a serotonin reuptake inhibitor).

The present invention provides a method for treating or preventing a central nervous system disorder comprising administering a heterocyclic compound of the formula (1) or a salt thereof to human or animal.

The present invention provides a process for producing a heterocyclic compound represented by the formula (1):

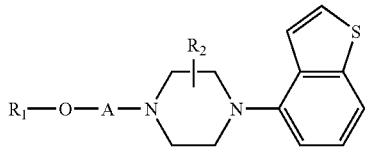

(1)

[wherein $R_1$, $R_2$ and A are the same as defined in claim 1] or a salt thereof, characterized by comprising a reaction of a compound represented by the formula:

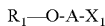

$R_1$—O—A—$X_1$

[wherein $R_1$ and A are the same as defined above, and $X_1$ represents a halogen atom or a group which causes a substitution reaction the same as in a halogen atom] or a salt thereof with a compound represented by the formula:

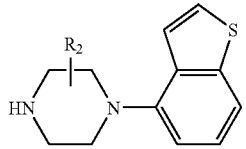

[wherein $R_2$ is the same as defined above] or a salt thereof.

BEST MODE FOR CARRYING OUT THE INVENTION

Specific examples of each of the groups shown in the general formula (1) are as follows.

Specific examples of each of the groups shown in the general formula are as follows.

Examples of the lower alkyl group include a linear or branched alkyl group having 1 to 6 carbon atoms. Specific examples thereof include a methyl group, ethyl group, n-propyl group, isopropyl group, n-butyl group, isobutyl group, tert-butyl group, sec-butyl group, n-pentyl group, 1-ethylpropyl group, isopentyl group, neo-pentyl group, n-hexyl group, 1,2,2-trimethylpropyl group, 3,3-dimethylbutyl group, 2-ethylbutyl group, isohexyl group, and 3-methylpentyl group.

Examples of the lower alkylene group include a linear or branched alkylene group having 1 to 6 carbon atoms. Specific examples thereof include a methylene group, ethylene group, trimethylene group, 2-methyltrimethylene group, 2,2-dimethylethylene group, 2,2-dimethyltrimethylene group, 1-methyltrimethylene group, methylmethylene group, ethylmethylene group, tetramethylene group, pentamethylene group, and hexamethylene group.

Examples of the lower alkenylene group include a linear or branched alkenylene group having 1 to 3 double bonds and 2 to 6 carbon atoms. Specific examples thereof include a vinylene group, 1-propenylene group, 1-methyl-1-propenylene group, 2-methyl-1-propenylene group, 2-propenylene group, 2-butenylene group, 1-butenylene group, 3-butenylene group, 2-pentenylene group, 1-pentenylene group, 3-pentenylene group, 4-pentenylene group, 1,3-butadienylene group, 1,3-pentadienylene group, 2-penten-4-ynylene group, 2-hexenylene group, 1-hexenylene group, 5-hexenylene group, 3-hexenylene group, 4-hexenylene group, 3,3-dimethyl-1-propenylene group, 2-ethyl-1-propenylene group, 1,3,5-hexatrienylene group, 1,3-hexadienylene group, and 1,4-hexadienylene group.

Examples of the lower alkenyl group include a linear or branched alkenyl group having 1 to 3 double bonds and 2 to 6 carbon atoms, including both a trans and cis-configurations. Specific examples thereof include a vinyl group, 1-propenyl group, 2-propenyl group, 1-methyl-1-propenyl group, 2-methyl-1-propenyl group, 2-methyl-2-propenyl group, 2-propenyl group, 2-butenyl group, 1-butenyl group, 3-butenyl group, 2-pentenyl group, 1-pentenyl group, 3-pentenyl group, 4-pentenyl group, 1,3-butadienyl group, 1,3-pentadienyl group, 2-penten-4-yl group, 2-hexenyl group, 1-hexenyl group, 5-hexenyl group, 3-hexenyl group, 4-hexenyl group, 3,3-dimethyl-1-propenyl group, 2-ethyl-1-propenyl group, 1,3,5-hexatrienyl group, 1,3-hexadienyl group, and 1,4-hexadienyl group.

Examples of the halogen atom include a fluorine atom, chlorine atom, bromine atom and iodine atom.

Examples of the halogen substituted lower alkyl group include a lower alkyl group as illustrated above substituted with 1 to 7, more preferably, 1 to 3 halogen atoms. Specific examples thereof include a fluoromethyl group, difluoromethyl group, trifluoromethyl group, chloromethyl group, dichloromethyl group, trichloromethyl group, bromomethyl group, dibromomethyl group, dichlorofluoromethyl group, 2,2-difluoroethyl group, 2,2,2-trifluoroethyl group, pentafluoroethyl group, 2-fluoroethyl group, 2-chloroethyl group, 3,3,3-trifluoropropyl group, heptafluoropropyl group, 2,2,3,3,3-pentafluoropropyl group, heptafluoroisopropyl group, 3-chloropropyl group, 2-chloropropyl group, 3-bromopropyl group, 4,4,4-trifluorobutyl group, 4,4,4,3,3-pentafluorobutyl group, 4-chlorobutyl group, 4-bromobutyl group, 2-chlorobutyl group, 5,5,5-trifluoropentyl group, 5-chloropentyl group, 6,6,6-trifluorohexyl group, 6-chlorohexyl group, and perfluorohexyl group.

Examples of the lower alkoxy group include a linear or branched alkoxy group having 1 to 6 carbon atoms. Specific examples thereof include a methoxy group, ethoxy group, n-propoxy group, isopropoxy group, n-butoxy group, isobutoxy group, tert-butoxy group, sec-butoxy group, n-pentyloxy group, isopentyloxy group, neopentyloxy group, n-hexyloxy group, isohexyloxy group, and 3-methylpentyloxy group.

Examples of the aryl group include a phenyl group, substituted phenyl group, biphenyl group, substituted biphenyl group, naphthyl group, and substituted naphthyl group. Examples of the substituent for an aryl group include a lower alkyl group as illustrated above (preferably a linear or branched lower alkyl group having 1 to 6 carbon atoms), a halogen atom as illustrated above, and an amino group. On the aryl group, 1 to 7, preferably 1 to 5, more preferably, 1 to 2 substituents of at least one type of these may be present. Specific examples of the aryl group may include a phenyl group, (2-, 3-, or 4-)biphenyl group, (1- or 2-)naphthyl group, (2-, 3-, or 4-)methylphenyl group, (2-, 3-, or 4-)ethylphenyl group, (2-, 3-, or 4-)n-propylphenyl group, (2-, 3-, or 4-)n-butylphenyl group, (2-, 3-, or 4-)n-pentylphenyl group, (2-, 3-, or 4-)n-hexylphenyl group, (2-, 3-, or 4-)isobutylphenyl group, (2-, 3-, or 4-)tert-butylphenyl group, (3-, 4-, 5-, 6-, 2'-, 3'-, 4'-, 5'-, or 6'-)methyl-2-biphenyl group, (2-, 4-, 5-, 6-, 2'-, 3'-, 4'-, 5'-, or 6'-)methyl-3-biphenyl group, (2-, 3-, 5-, 6-, 2'-, 3'-, 4'-, 5'-, or 6'-)methyl-4-biphenyl group, (3-, 4-, 5-, 6-, 2'-, 3'-, 4'-, 5'-, or 6'-)ethyl-2-biphenyl group, (2-, 4-, 5-, 6-, 2'-, 3'-, 4'-, 5'-, or 6'-)ethyl-3-biphenyl group, (2-, 3-, 5-, 6-, 2'-, 3'-, 4'-, 5'-, or 6'-)ethyl-4-biphenyl group, (3-, 4-, 5-, 6-, 2'-, 3'-, 4'-, 5'-, or 6'-)n-propyl-2-biphenyl group, (2-, 4-, 5-, 6-, 2'-, 3'-, 4'-, 5'-, or 6'-)n-propyl-3-biphenyl group, (2-, 3-, 5-, 6-, 2'-, 3'-, 4'-, 5'-, or 6'-)n-propyl-4-biphenyl group, (3-, 4-, 5-, 6-, 2'-, 3'-, 4'-, 5'-, or 6'-)n-butyl-2-biphenyl group, (2-, 4-, 5-, 6-, 2'-, 3'-, 4'-, 5'-, or 6'-)n-butyl-3-biphenyl group, (2-, 3-, 5-, 6-, 2'-, 3'-4'-, 5'-, or 6'-)n-butyl-4-biphenyl group, (3-, 4-, 5-, 6-, 2'-, 3'-, 4'-, 5'-, or 6'-)n-pentyl-2-biphenyl group, (2-, 4-, 5-, 6-, 2'-, 3'-, 4'-, 5'-, or 6'-)n-pentyl-3-biphenyl group, (2-, 3-, 5-, 6-, 2'-, 3'-, 4'-, 5'-, or 6'-)n-pentyl-4-biphenyl group, (3-, 4-, 5-6-, 2'-, 3'-, 4'-, 5'-, or 6'-)n-hexyl-2-biphenyl group, (2-, 4-, 5-, 6-, 2'-, 3'-, 4'-, 5'-, or 6'-)n-hexyl-3-biphenyl group, (2-, 3-, 5-, 6-, 2'-, 3'-, 4'-, 5'-, or 6'-)n-hexyl-4-biphenyl group, (3-, 4-, 5-, 6-, 2'-, 3'-, 4'-, 5'-, or 6'-)isobutyl-2-biphenyl group, (2-, 4-, 5-, 6-, 2'-, 3'-, 4'-, 5'-, or 6'-)isobutyl-3-biphenyl group, (2-, 3-, 5-, 6-, 2'-, 3'-, 4'-, 5'-, or 6'-)isobutyl-4-biphenyl group, (3-, 4-, 5-, 6-, 2'-, 3'-, 4'-, 5'-, or 6'-)tert-butyl-2-biphenyl group, (2-, 4-, 5-, 6-, 2'-, 3'-, 4'-, 5'-, or 6'-)tert-butyl-3-biphenyl group, (2-, 3-, 5-, 6-, 2'-, 3'-, 4'-, 5'-, or 6'-)tert-butyl-4-biphenyl group, (2-, 3-, 4-, 5-, 6-, 7-, or 8-)methyl-1-naphthyl group, (1-, 3-, 4-, 5-, 6-, 7-, or 8-)methyl-2-naphthyl group, (2-, 3-, 4-, 5-, 6-, 7-, or 8-)ethyl-1-naphthyl group, (1-, 3-, 4-, 5-, 6-, 7-, or 8-)ethyl-2-naphthyl group, (2-, 3-, 4-, 5-, 6-, 7-, or 8-)n-propyl-1-naphthyl group, (1-, 3-, 4-, 5-, 6-, 7-, or 8-)n-propyl-2-naphthyl group, (2-, 3-, 4-, 5-, 6-, 7-, or 8-)n-butyl-1-naphthyl group, (1-, 3-, 4-, 5-, 6-, 7-, or 8-)n-butyl-2-naphthyl group, (2-, 3-, 4-, 5-, 6-, 7-, or 8-)n-pentyl-1-naphthyl group, (1-, 3-, 4-, 5-, 6-, 7-, or 8-)n-pentyl-2-naphthyl group, (2-, 3-, 4-, 5-, 6-, 7-, or 8-)n-hexyl-1-naphthyl group, (1-, 3-, 4-, 5-, 6-, 7-, or 8-)n -hexyl-2-naphthyl group, (2-, 3-, 4-, 5-, 6-, 7-, or 8-)isobutyl-1-naphthyl group, (1-, 3-, 4-, 5-, 6-, 7-, or 8-)isobutyl-2-naphthyl group, (2-, 3-, 4-, 5-, 6-, 7-, or 8-)tert-butyl-1-naphthyl group, (1-, 3-, 4-, 5-, 6-, 7-, or 8-)tert-butyl-2-naphthyl group, (2-, 3-, or 4-)chlorophenyl group, (2-, 3-, or 4-)fluorophenyl group, (2-, 3-, or 4-)bromophenyl group, (2-, 3-, 4-, 5-, 6-, 7-, or 8-)chloro-1-naphthyl group, (1-, 3-, 4-, 5-, 6-, 7-, or 8-)chloro-2-naphthyl group, (2-, 3-, 4-, 5-, 6-, 7-, or 8-)fluoro-1-naphthyl group, (1-, 3-, 4-, 5-, 6-, 7-, or 8-)fluoro-2-naphthyl group, (2-, 3-, 4-, 5-, 6-, 7-, or 8-)bromo-1-naphthyl group, (1-, 3-, 4-, 5-, 6-, 7-, or 8-)bromo-2-naphthyl group, (2-, 3-, or 4-)aminophenyl group, (2-, 3-, 4-, 5-, 6-, 7-, or 8-)amino-1-naphthyl group, (1-, 3-, 4-, 5-, 6-, 7-, or 8-)amino-2-naphthyl group, 2,3-dimethylphenyl group, 3,4-dimethylphenyl group, 2,4-dimethylphenyl group, 2,5-dimethylphenyl group, 2,6-dimethylphenyl group, 2,4,6-trimethylphenyl group, 3,4,5-trimethylphenyl group, 2,3,4,5-tetraethylphenyl group, pentamethylphenyl group, 2,4-dimethyl-1-naphthyl group, 2,3-dimethyl-1-naphthyl group, 3,4-dimethyl-1-naphthyl group, 3,5,7-triethylnaphthyl group, 3,4,5,7-tetramethyl-1-naphthyl group, 2,3,4,5,7-pentamethyl-1-naphthyl group, 2,3,4,5,6,7-hexaethyl-1-naphthyl group, heptamethyl-1-naphthyl group, 2,3-diaminophenyl group, 2,4,6-triaminophenyl group, and 2-methyl-5-chloro-1-naphthyl group.

Examples of the aryloxy group include a phenyloxy group, substituted phenyloxy group, biphenyloxy group, substituted biphenyloxy group, naphthyloxy group, and substituted naphthyloxy group. Examples of the substituent for an aryloxy group include a lower alkyl group as illustrated above (preferably a linear or branched alkyl group having 1 to 6 carbon atoms), a halogen atom as illustrated above, and an amino group. On the aryl group, 1 to 7, preferably 1 to 5, more preferably, 1 to 2 substituents of at least one type of these may be present. Specific examples of the aryloxy groups include a phenyloxy group, (2-, 3-, or 4-)biphenyloxy group, (1- or 2-)naphthyloxy-group, (2-, 3-, or 4-)methylphenyloxy group, (2-, 3-, or 4-)ethylphenyloxy group, (2-, 3-, or 4-)n-propylphenyloxy group, (2-, 3-, or 4-)n-butylphenyloxy group, (2-, 3-, or 4-)n-pentylphenyloxy group, (2-, 3-, or 4-)n-hexylphenyloxy group, (2-, 3-, or 4-)isobutylphenyloxy group, (2-, 3-, or 4-)tert-butylphenyloxy group, (3-, 4-, 5-, 6-, 2'-, 3'-, 4'-, 5'-, or 6'-)methyl-2-biphenyloxy group, (2-, 4-, 5-, 6-, 2'-, 3'-, 4'-, 5'-, or 6'-)methyl-3-biphenyloxy group, (2-, 3-, 5-, 6-, 2'-, 3'-, 4'-, 5'-, or 6'-)methyl-4-biphenyloxy group, (3-, 4-, 5-, 6-, 2'-, 3'-, 4'-, 5'-, or 6'-)ethyl-2-biphenyloxy group, (2-, 4-, 5-, 6-, 2'-, 3'-, 4'-, 5'-, or 6'-)ethyl-3-biphenyloxy group, (2-, 3-, 5-, 6-, 2'-, 3'-, 4'-, 5'-, or 6'-)ethyl-4-biphenyloxy group, (3-, 4-, 5-, 6-, 2'-, 3'-, 4'-, 5'-, or 6'-)n-propyl-2-biphenyloxy group, (2-4-, 5-, 6-, 2'-, 3'-, 4'-, 5'-, or 6'-)n-propyl-3-biphenyloxy group, (2-, 3-, 5-, 6-, 2'-, 3'-, 4'-, 5'-, or 6'-)n-propyl-4-biphenyloxy group, (3-, 4-, 5-, 6-, 2'-, 3'-, 4'-, 5'-, or 6'-)n-butyl-2-biphenyloxy group, (2-, 4-, 5-, 6-, 2'-, 3'-, 4'-, 5'-, or 6'-)n-butyl-3-biphenyloxy group, (2-, 3-, 5-, 6-, 2'-, 3'-, 4'-, 5'-, or 6'-)n-butyl-4-biphenyloxy group, (3-, 4-, 5-, 6-, 2'-, 3'-, 4'-, 5'-, or 6'-)n-pentyl-2-biphenyloxy group, (2-, 4-, 5-, 6-, 2'-, 3'-, 4'-, 5'-, or 6'-)n-pentyl-3-biphenyloxy group, (2-, 3-, 5-, 6-, 2'-, 3'-, 4'-, 5'-, or 6'-)n-pentyl-4-biphenyloxy group, (3-, 4-, 5-, 6-, 2'-, 3'-, 4'-, 5'-, or 6'-)n-hexyl-2-biphenyloxy group, (2-, 4-, 5-, 6-, 2'-, 3'-, 4'-, 5'-, or 6'-)n-hexyl-3-biphenyloxy group, (2-, 3-, 5-, 6-, 2'-, 3'-, 4'-, 5'-, or 6'-)n-hexyl-4-biphenyloxy group, (3-, 4-, 5-, 6-, 2'-, 3'-, 4'-, 5'-, or 6'-)isobutyl-2-biphenyloxy group, (2-, 4-, 5-, 6-, 2'-, 3'-, 4'-, 5'-, or 6'-)isobutyl-3-biphenyloxy group, (2-, 3-, 5-, 6-, 2'-, 3'-, 4'-, 5'-, or 6'-)isobutyl-4-biphenyloxy group, (3-, 4-, 5-, 6-, 2'-, 3'-, 4'-, 5'-, or 6'-)tert-butyl-2-biphenyloxy group, (2-, 4-, 5-, 6-, 2'-, 3'-, 4'-, 5'-, or 6'-)tert-butyl-3-biphenyloxy group, (2-, 3-, 5-, 6-, 2'-, 3'-, 4'-, 5'-, or 6'-)tert-butyl-4-biphenyloxy group, (2-, 3-, 4-, 5-, 6-, 7-, or 8-)methyl-1-naphthyloxy group, (1-, 3-, 4-, 5-, 6-, 7-, or 8-)methyl-2-naphthyloxy group, (2-, 3-, 4-, 5-, 6-, 7-, or 8-)ethyl-1-naphthyloxy group, (1-, 3-, 4-, 5-, 6-, 7-, or 8-)ethyl-2-naphthyloxy group, (2-, 3-, 4-, 5-, 6-, 7-, or 8-)n-propyl-1-naphthyloxy group, (1-, 3-, 4-, 5-, 6-, 7-, or 8-)n-propyl-2-naphthyloxy group, (2-, 3-, 4-, 5-, 6-, 7-, or 8-)n -butyl-1-naphthyloxy group, (1-, 3-, 4-, 5-, 6-, 7-, or 8-)n-butyl-2-naphthyloxy group, (2-, 3-, 4-, 5-, 6-, 7-, or 8-)n-pentyl-1-naphthyloxy group, (1-, 3-, 4-, 5-, 6-, 7-, or 8-)n-pentyl-2-naphthyloxy group, (2-, 3-, 4-, 5-, 6-, 7-, or 8-)n-hexyl-1-naphthyloxy group, (1-, 3-, 4-, 5-, 6-, 7-, or 8-)n-hexyl-2-naphthyloxy group, (2-, 3-, 4-, 5-, 6-, 7-, or 8-)isobutyl-1-naphthyloxy group, (1-, 3-, 4-, 5-, 6-, 7-, or 8-)isobutyl-2-naphthyloxy group, (2-, 3-, 4-, 5-, 6-, 7-, or 8-)tert-butyl-1-naphthyloxy group, (1-, 3-, 4-, 5-, 6-, 7-, or 8-)tert-butyl-2-naphthyloxy group, (2-, 3-, or 4-)chlorophenyloxy group, (2-, 3-, or 4-)fluorophenyloxy group, (2-, 3-, or 4-)bromophenyloxy group, (2-, 3-, 4-, 5-, 6-, 7-, or 8-)chloro-1-naphthyloxy group, (1-, 3-, 4-, 5-, 6-, 7-, or 8-)chloro-2-naphthyloxy group, (2-, 3-, 4-, 5-, 6-, 7-, or 8-)fluoro-1-naphthyloxy group, (1-, 3-, 4-, 5-, 6-, 7-, or 8-)fluoro-2-naphthyloxy group, (2-, 3-, 4-, 5-, 6-, 7-, or 8-)bromo-1-naphthyloxy group, (1-, 3-, 4-, 5-, 6-, 7-, or 8-)bromo-2-naphthyloxy group, (2-, 3-, or 4-)aminophenyloxy group, (2-, 3-, 4-, 5-, 6-, 7-, or 8-)amino-1-naphthyloxy group, (1-, 3-, 4-, 5-, 6-, 7-, or 8-)amino-2-naphthyloxy group, 2,3-dimethylphenyloxy group, 3,4-dimethylphenyloxy group, 2,4-dimethylphenyloxy group, 2,5-dimethylphenyloxy group, 2,6-dimethylphenyloxy group, 2,4,6-trimethylphenyloxy group, 3,4,5-trimethylphenyloxy group, 2,3,4,5-tetraethylphenyloxy group, pentamethylphenyloxy group, 2,4-dimethyl-1-naphthyloxy group, 2,3-dimethyl-1-naphthyloxy group, 3,4-dimethyl-1-naphthyloxy group, 3,5,7-triethyl-1-naphthyloxy group, 3,4,5,7-tetramethyl-1-naphthyloxy group, 2,3,4,5,7-pentamethyl-1-naphthyloxy group, 2,3,4,5,6,7-hexaethyl-1-naphthyloxy group, heptamethyl-1-naphthyloxy group, 2,3-diaminophenyloxy group, 2,4,6-triaminophenyloxy group, and 2-methyl-5-chloro-1-naphthyloxy group.

Examples of the lower alkylthio group include a linear or branched alkylthio group having 1 to 6 carbon atoms. Specific examples thereof include a methylthio group, ethylthio group, n-propylthio group, isopropylthio group, n-butylthio group, tert-butylthio group, n-pentylthio group, and n-hexylthio group.

Examples of the halogen-substituted lower alkoxy group include a lower alkoxy group as illustrated above substituted with 1 to 7, preferably, 1 to 3 halogen atoms. Specific examples thereof include a fluoromethoxy group, difluoromethoxy group, trifluoromethoxy group, chloromethoxy group, dichloromethoxy group, trichloromethoxy group, bromomethoxy group, dibromomethoxy group, dichlorofluoromethoxy group, 2,2,2-trifluoroethoxy group, pentafluoroethoxy group, 2-chloroethoxy group, 3,3,3-trifluoropropoxy group, heptafluoropropoxy group, heptafluoroisopropoxy group, 3-chloropropoxy group, 2-chloropropoxy group, 3-bromopropoxy group, 4,4,4-trifluorobutoxy group, 4,4,4,3,3-pentafluorobutoxy group, 4-chlorobutoxy group, 4-bromobutoxy group, 2-chlorobutoxy group, 5,5,5-trifluoropentoxy group, 5-chloropentoxy group, 6,6,6-trifluorohexyloxy group, and 6-chlorohexyloxy group.

Examples of the protecting group of a hydroxy group include a linear or branched alkyl group having 1 to 6 carbon atoms, a lower alkanoyl group (preferably a linear or branched alkanoyl group having 1 to 6 carbon atoms), and a phenyl lower alkyl group whose lower alkyl moiety is a linear or branched alkyl group having 1 to 6 carbon atoms.

Examples of the hydroxy group protected include a methoxy group, ethoxy group, n-propoxy group, isopropoxy group, n-butoxy group, isobutoxy group, tert-butoxy group, sec-butoxy group, n-pentyloxy group, isopentyloxy group, neopentyloxy group, n-hexyloxy group, isohexyloxy group, 3-methylpentyloxy group, lower alkanoyloxy group and phenyl lower alkoxy group. Specific examples include a formyloxy group, acetyloxy group, propionyloxy group, butyryloxy group, isobutyryloxy group, pentanoyloxy group, tert-butylcarbonyloxy group, hexanoyloxy group, benzyloxy group, 2-phenylethoxy group, 1-phenylethoxy group, 3-phenylpropoxy group, 4-phenylbutoxy group, 5-phenylpentyloxy group, 6-phenylhexyloxy group, 1,1-dimethyl-2-phenylethoxy group, and 2-methyl-3-phenylpropoxy group.

Examples of the hydroxy lower alkyl group include a lower alkyl group as illustrated above having 1 to 5, preferably 1 to 3 hydroxy groups (preferably a linear or branched alkyl group having 1 to 6 carbon atoms). Specific examples thereof include a hydroxymethyl group, 2-hydroxyethyl group, 1-hydroxyethyl group, 3-hydroxypropyl group, 2,3-dihydroxypropyl group, 4-hydroxybutyl group, 3,4-dihydroxybutyl group, 1,1-dimethyl-2-hydroxyethyl group, 5-hydroxypentyl group, 6-hydroxyhexyl group, 3,3-dimethyl-3-hydroxypropyl group, 2-methyl-3-hydroxypropyl group, 2,3,4-trihydroxybutyl group, and perhydroxyhexyl group.

Example of a protecting group of a hydroxy lower alkyl group include a linear or branched alkyl group having 1 to 6 carbon atoms, a lower alkanoyl group (preferably a linear or branched alkanoyl group having 1 to 6 carbon atoms), and a phenyl lower alkyl group whose lower alkyl moiety is a linear or branched alkyl group having 1 to 6 carbon atoms.

Examples of the hydroxy lower alkyl group protected include a lower alkyl group as illustrated above (preferably a linear or branched alkyl group having 1 to 6 carbon atoms) having 1 to 5, preferably 1 to 3 protected hydroxy groups as illustrated above (preferably a lower alkoxy group, lower alkanoyloxy group or phenyl lower alkoxy group). Specific examples thereof include a methoxymethyl group, 2-methoxyethyl group, 2-ethoxyethyl group, 2-n-propoxyethyl group, 2-isopropoxyethyl group, 2-n-butoxyethyl group, 2-isobutoxyethyl group, 2-tert-butoxyethyl group, 2-sec-butoxyethyl group, 2-n-pentyloxyethyl group, 2-isopentyloxyethyl group, 2-neopentyloxyethyl group, 2-n-hexyloxyethyl group, 2-isohexyloxyethyl group, 2-(3-methylpentyloxy)ethyl group, 2-formyloxyethyl group, 2-acetyloxyethyl group, 2-propionyloxyethyl group, 2-butyryloxyethyl group, 2-isobutyryloxyethyl group, 2-pentanoyloxyethyl group, 2-tert-butylcarbonyloxyethyl group, 2-hexanoyloxyethyl group, 2-benzyloxyethyl group, 2-(2-phenylethoxy)ethyl group, 2-(1-phenylethoxy)ethyl group, 2-(3-phenylpropoxy)ethyl group, 2-(4-phenylbutoxy)ethyl group, 2-(5-phenylpentyloxy)ethyl group, 2-(6-phenylhexyloxy)ethyl group, 2-(1,1-dimethyl-2-phenylethoxy)ethyl group, 2-(2-methyl-3-phenylpropoxy)ethyl group, 3-ethoxypropyl group, 2,3-diethoxypropyl group, 4-ethoxybutyl group, 3,4-diethoxybutyl group, 1,1-dimethyl-2-ethoxyethyl group, 5-ethoxypentyl group, 6-ethoxyhexyl group, 3,3-dimethyl-3-ethoxypropyl group, 2-methyl-3-ethoxypropyl group, and 2,3,4-triethoxybutyl group.

Examples of the lower alkanoyl group include a linear or branched alkanoyl group having 1 to 6 carbon atoms. Specific examples thereof include a formyl group, acetyl group, propionyl group, butyryl group, isobutyryl group, pentanoyl group, tert-butylcarbonyl group, and hexanoyl group.

Examples of the lower alkoxycarbonyl group include a linear or branched alkoxycarbonyl group whose lower alkoxy moiety is one as illustrated above, and preferably having 1 to 6 carbon atoms. Specific examples thereof include a methoxycarbonyl group, ethoxycarbonyl group, n-propoxycarbonyl group, isopropoxycarbonyl group, n-butoxycarbonyl group, isobutoxy carbonyl group, tert-butoxycarbonyl group, sec-butoxycarbonyl group, n-pentyloxycarbonyl group, neopentyloxy group, n-hexyloxycarbonyl group, isohexyloxycarbonyl group, and 3-methylpentyloxycarbonyl group.

Examples of the lower alkylsulfonyl group include a linear or branched alkylsulfonyl group whose lower alkyl moiety is one as illustrated above, and preferably having 1 to 6 carbon atoms. Specific examples thereof include a methylsulfonyl group, ethylsulfonyl group, n-propylsulfonyl group, isopropylsulfonyl group, n-butylsulfonyl group, isobutylsulfonyl group, tert-butylsulfonyl group, sec-butylsulfonyl group, n-pentylsulfonyl group, isopentylsulfonyl group, neopentylsulfonyl group, n-hexylsulfonyl group, isohexylsulfonyl group, and 3-methylpentylsulfonyl group.

Examples of the lower alkylcarbamoyl group include a carbamoyl group having 1 to 2 lower alkyl groups as illustrated above (preferably a linear or branched alkyl group having 1 to 6 carbon atoms) as a substituent(s). Specific examples thereof include a N-methylcarbamoyl group, N,N-dimethylcarbamoyl group, N-ethylcarbamoyl group, N,N-diethylcarbamoyl group, N-n-propylcarbamoyl group, N-n-butylcarbamoyl group, N-n-pentylcarbamoyl group, N-n-hexylcarbamoyl group, N-isobutylcarbamoyl group, N-tert-butylcarbamoyl group, and N,N-di-n-propylcarbamoyl group.

Examples of the aminoalkanoyl group include a lower alkanoyl group as illustrated above (preferably a linear or branched alkanoyl group having 1 to 6 carbon atoms) having 1 to 3 (preferably 1) amino groups. Specific examples thereof include an aminoacetyl group, 3-aminopropionyl group, 4-aminobutyryl group, 3,4-diaminobutyryl group, 3,3-dimethyl-3-aminopropionyl group, 4-aminobutyryl group and 5-aminovaleryl group.

Examples of the lower alkanoyl amino lower alkanoyl group include a lower alkanoyl group as illustrated above (preferably a linear or branched alkanoyl group having 1 to 6 carbon atoms) whose lower alkanoyl moiety has 1 to 3 (preferably 1) lower alkanoylamino groups as illustrated above.

Specific examples thereof include an N-formylaminoacetyl group, N-acetylaminoacetyl group, N-propionylaminoacetyl group, 3-(N-acetylamino)propionyl group, 4-(N-acetylamino)butyryl group, 3,4-di(N-acetylamino)butyryl group, 3,3-dimethyl-3-(N-propinylamino)propionyl group, 4-(N-formylamino)butyryl group, and 5-(N-acetylamino)valeryl group.

Examples of the lower alkoxy carbonylamino lower alkanoyl group include a lower alkanoyl group as illustrated above (preferably a linear or branched alkanoyl group having 1 to 6 carbon atoms) whose lower alkoxycarbonyl moiety has 1 to 3 (preferably 1) lower alkoxy carbonylamino groups as illustrated above. Specific examples thereof include an N-methoxycarbonylaminoacetyl group, N-ethoxycarbonylaminoacetyl group, N-tert-butoxycarbonylaminoacetyl group, 3-(N-methoxycarbonylamino)propionyl group, 4-(N-acetylamino)butyryl group, 3,4-di(N-acetylamino)butyryl group, 3,3-dimethyl-3-(N-propinylamino)propionyl group, 4-(N-formylamino)butyryl group and 5-(N-acetylamino) valeryl group. Examples of the amino group having, as a substituent, a group selected from the group consisting of a lower alkyl group, lower alkanoyl group, lower alkoxycarbonyl group, lower alkylsulfonyl group, carbamoyl group, lower alkylcarbamoyl group, amino lower alkanoyl group, lower alkanoylamino lower alkanoyl group, and lower alkoxycarbonylamino lower alkanoyl group include an amino group having, as a substituent, 1 to 2 groups selected from the group consisting of a lower alkyl group as illustrated above (preferably a linear or branched alkyl group having 1 to 6 carbon atoms);
a lower alkanoyl group as illustrated above (preferably a linear or branched alkanoyl group having 1 to 6 carbon atoms);
a lower alkoxycarbonyl group as illustrated above (preferably a linear or branched alkoxycarbonyl group having 1 to 6 carbon atoms);
a lower alkylsulfonyl group as illustrated above (preferably a linear or branched alkylsulfonyl group having 1 to 6 carbon atoms);
a carbamoyl group;
a lower alkylcarbamoyl group as illustrated above (preferably a carbamoyl group having, as a substituent, 1 to 2 lower alkyl groups as illustrated above (preferably a linear or branched alkyl group having 1 to 6 carbon atoms)); an amino lower alkanoyl group as illustrated above; a lower alkanoylamino lower alkanoyl group as illustrated above; and a lower alkoxycarbonylamino lower alkanoyl group as illustrated above. Specific examples thereof include an amino group, N-methylamino group, N,N-dimethylamino group, N-ethylamino group, N-n-propylamino group, N-isopropylamino group, N-formylamino group, N-acetylamino group, N-tert-butoxycarbonylamino group, N-methoxycarbonylamino group, N-methylsulfonylamino group, N-ethylsulfonylamino group, N-methyl-N-acetylamino group, N-methyl-N-methoxycarbonylamino group, N-[N,N-dimethylcarbamoyl]amino group, N-carbamoylamino group, N-[N-methylcarbamoyl]amino group, N-[N,N-diethylcarbamoyl]amino group, N-[aminoacetyl]amino group, N-[[N-formylamino]acetyl]amino group, N-[[N-acetylamino]acetyl]amino group, N-[[N-methoxycarbonylamino]acetyl]amino group, and N-[[N-tert-butoxycarbonylamino]acetyl]amino group.

Examples of the arylsulfonyl group that may have a lower alkyl group on an aryl group include an arylsulfonyl group whose aryl moiety is phenyl, biphenyl, naphthyl or the like and on which 1 to 7, preferably 1 to 5, more preferably, 1 to 2 linear or branched alkyl groups having 1 to 6 carbon atoms.

Specific examples of the arylsulfonyl group that may have a lower alkyl group on an aryl group include a phenylsulfonyl group, (2-, 3-, or 4-)biphenylsulfonyl group, (1- or 2-)naphthylsulfonyl group, (2-, 3-, or 4-)methylphenylsulfonyl group, (2-, 3-, or 4-)ethylphenylsulfonyl group, (2-, 3-, or 4-)n-propylphenylsulfonyl group, (2-, 3-, or 4-)n-butylphenylsulfonyl group, (2-, 3-, or 4-)n-pentylphenylsulfonyl group, (2-, 3-, or 4-)n-hexylphenylsulfonyl group, (2-, 3-, or 4-)isobutylphenylsulfonyl group, (2-, 3-, or 4-)tert-butylphenylsulfonyl group, (3-, 4-, 5-, 6-, 2'-, 3'-, 4'-, 5'-, or 6'-)methyl-2-biphenylsulfonyl group, (2-, 4-, 5-, 6-, 2'-, 3'-, 4'-, 5'-, or 6'-)methyl-3-biphenylsulfonyl group, (2-, 3-, 5-, 6-, 2'-, 3'-, 4'-, 5'-, or 6'-)methyl-4-biphenylsulfonyl group, (3-, 4-, 5-, 6-, 2'-, 3'-, 4'-, 5'-, or 6'-)ethyl-2-biphenylsulfonyl group, (2-, 4-, 5-, 6-, 2'-, 3'-, 4'-, 5'-, or 6'-)ethyl-3-biphenylsulfonyl group, (2-, 3-, 5-, 6-, 2'-, 3'-, 4'-, 5'-, or 6'-)ethyl-4-biphenylsulfonyl group, (3-, 4-, 5-, 6-, 2'-, 3'-, 4'-, 5'-, or 6'-)n-propyl-2-biphenylsulfonyl group, (2-, 4-, 5-, 6-, 2'-, 3'-, 4'-, 5'-, or 6'-)n-propyl-3-biphenylsulfonyl group, (2-, 3-, 5-, 6-, 2'-, 3'-, 4'-, 5'-, or 6'-)n-propyl-4-biphenylsulfonyl group, (3-, 4-, 5-, 6-, 2'-, 3'-, 4'-, 5'-, or 6'-)n-butyl-2-biphenylsulfonyl group, (2-, 4-, 5-, 6-, 2'-, 3'-, 4'-, 5'-, or 6'-)n-butyl-3-biphenylsulfonyl group, (2-, 3-, 5-, 6-, 2'-, 3'-, 4'-, 5'-, or 6'-)n-butyl-4-biphenylsulfonyl group, (3-, 4-, 5-, 6-, 2'-, 3'-, 4'-, 5'-, or 6'-)n-pentyl-2-biphenylsulfonyl group, (2-, 4-, 5-, 6-, 2'-, 3'-, 4'-, 5'-, or 6'-)n-pentyl-3-biphenylsulfonyl group, (2-, 3-, 5-, 6-, 2'-, 3'-, 4'-, 5'-, or 6'-)n-pentyl-4-biphenylsulfonyl group, (3-, 4-, 5-, 6-, 2'-, 3'-, 4'-, 5'-, or 6'-)n-hexyl-2-biphenylsulfonyl group, (2-, 4-, 5-, 6-, 2'-, 3'-, 4'-, 5'-, or 6'-)n-hexyl-3-biphenylsulfonyl group, (2-, 3-, 5-, 6-, 2'-, 3'-, 4'-, 5'-, or 6'-)n-hexyl-4-biphenylsulfonyl group, (3-, 4-, 5-, 6-, 2'-, 3'-, 4'-, 5'-, or 6'-)isobutyl-2-biphenylsulfonyl group, (2-, 4-, 5-, 6-, 2'-, 3'-, 4'-, 5'-, or 6'-)isobutyl-3-biphenylsulfonyl group, (2-, 3-, 5-, 6-, 2'-, 3'-, 4'-, 5'-, or 6'-)isobutyl-4-biphenylsulfonyl group, (3-, 4-, 5-, 6-, 2'-, 3'-, 4'-, 5'-, or 6'-)tert-butyl-2-biphenylsulfonyl group, (2-, 4-, 5-, 6-, 2'-, 3'-, 4'-, 5'-, or 6'-)tert-butyl-3-biphenylsulfonyl group, (2-, 3-, 5-, 6-, 2'-, 3'-, 4'-, 5'-, or 6'-)tert-butyl-4-biphenylsulfonyl group, (2-, 3-, 4-, 5-, 6-, 7-, or 8-5)methyl-1-naphthylsulfonyl group, (1-, 3-, 4-, 5-, 6-, 7-, or 8-)methyl-2-naphthylsulfonyl group, (2-, 3-, 4-, 5-, 6-, 7-, or 8-)ethyl-1-naphthylsulfonyl group, (1-, 3-, 4-, 5-, 6-, 7-, or 8-)ethyl-2-naphthylsulfonyl group, (2-, 3-, 4-, 5-, 6-, 7-, or 8-)n-propyl-1-naphthylsulfonyl group, (1-, 3-, 4-, 5-, 6-, 7-, or 8-)n-propyl-2-naphthylsulfonyl group, (2-, 3-, 4-, 5-, 6-, 7-, or 8-)n-butyl-1-naphthylsulfonyl group, (1-, 3-, 4-, 5-, 6-, 7-, or 8-)n-butyl-2-naphthylsulfonyl group, (2-, 3-, 4-, 5-, 6-, 7-, or 8-)n-pentyl-1-naphthylsulfonyl group, (1-, 3-, 4-, 5-, 6-, 7-, or 8-)n-pentyl-2-naphthylsulfonyl group, (2-, 3-, 4-, 5-, 6-, 7-, or 8-)n-hexyl-1-naphthylsulfonyl group, (1-, 3-, 4-, 5-, 6-, 7-, or 8-)n-hexyl-2-naphthylsulfonyl group, (2-, 3-, 4-, 5-, 6-, 7-, or 8-)isobutyl-1-naphthylsulfonyl group, (1-, 3-, 4-, 5-, 6-, 7-, or 8-)isobutyl-2-naphthylsulfonyl group, (2-, 3-, 4-, 5-, 6-, 7-, or 8-)tert-butyl-1-naphthylsulfonyl group, (1-, 3-, 4-, 5-, 6-, 7-, or 8-)tert-butyl-2-naphthylsulfonyl group, 2,3-dimethylphenylsulfonyl group, 3,4-dimethylphenylsulfonyl group, 2,4-dimethylphenylsulfonyl group, 2,5-dimethylphenylsulfonyl group, 2,6-dimethylphenylsulfonyl group, 2,4,6-trimethylphenylsulfonyl group, 3,4,5-trimethylphenylsulfonyl group, 2,3,4,5-tetraethylphenylsulfonyl group, pentamethylphenylsulfonyl group, 2,4-dimethyl-1-naphthylsulfonyl group, 2,3-dimethyl-1-naphthylsulfonyl group, 3,4-dimethyl-1-naphthylsulfonyl group, 3,5,7-triethyl-1-naphthylsulfonyl group, 3,4,5,7-tetramethyl-1-naphthylsulfonyl group, 2,3,4,5,7-pentamethyl-1-naphthylsulfonyl group, 2,3,4,5,6,7-hexaethyl-1-naphthylsulfonyl group, and heptamethyl-1-naphthylsulfonyl group.

Examples of a carboxyl lower alkyl group include a lower alkyl group as illustrated above (preferably a linear or branched alkyl group having 1 to 6 carbon atoms) having 1 to 3 (preferably 1) carboxyl groups. Specific examples thereof include carboxymethyl group, 2-carboxyethyl group, 1-carboxyethyl group, 1-carboxy-1-methylethyl group, 3-carboxypropyl group, 2,3-dicarboxypropyl group, 4-carboxybutyl group, 3,4-dicarboxybutyl group, 1,1-dimethyl-2-carboxyethyl group, 5-carboxypentyl group, 6-carboxyhexyl group, 3,3-dimethyl-3-carboxypropyl group, 2-methyl-3-carboxypropyl group, and 2,3,4-tricarboxybutyl group.

Examples of a lower alkoxycarbonyl lower alkyl group include a lower alkyl group as illustrated above (preferably a linear or branched alkyl group having 1 to 6 carbon atoms) having 1 to 3 (preferably 1 to 2) lower alkoxycarbonyl groups as illustrated above (preferably a linear or branched alkoxycarbonyl group having 1 to 6 carbon atoms). Specific examples thereof include a methoxycarbonylmethyl group, ethoxycarbonylmethyl group, 1-methoxycarbonylethyl group, 2-methoxycarbonylethyl group, 2-ethoxycarbonylethyl group, 1-ethoxycarbonylethyl group, 3-methoxycarbonylpropyl group, 3-ethoxycarbonylpropyl group, 4-ethoxycarbonylbutyl group, 5-isopropoxycarbonylpentyl group, 6-n-propoxycarbonylhexyl group, 1,1-dimethyl-2-n-butoxycarbonylethyl group, 1-methyl-1-methoxycarbonylethyl group, 2-methyl-1-methoxycarbonylpropyl group, 2-methyl-3-tert-butoxycarbonylpropyl group, 3-methyl-1-methoxycarbonylbutyl group, diethoxycarbonylmethyl group, 1,2-diethoxycarbonylethyl group, 2-n-pentyloxycarbonylethyl group, and n-hexyloxycarbonylmethyl group.

Examples of the carbamoyl lower alkyl group that may have a group, as a substituent, selected from the group consisting of a lower alkyl group, a phenyl group that may have a lower alkyl group and a phenyl group that may have a lower alkoxy group include a lower alkyl group as illustrated above (preferably a linear or branched alkyl group having 1 to 6 carbon atoms) having 1 to 3 (preferably 1 to 2) carbamoyl groups. The carbamoyl moiety may have 1 to 2 groups selected from the group consisting of a phenyl group that may have 1 to 3 (preferably 1) lower alkyl groups as illustrated above (preferably linear or branched alkyl groups having 1 to 6 carbon atoms) and a phenyl group that may have 1 to 3 (preferably 1) lower alkoxy groups as illustrated above (preferably linear or branched alkoxy groups having 1 to 6 carbon atoms). Specific examples of the carbamoyl lower alkyl group include a carbamoylmethyl group, dicarbamoylmethyl group, 2-carbamoylethyl group, 1-carbamoylethyl group, 1-carbamoyl-2-methylpropyl group, 3-carbamoylpropyl group, 4-carbamoylbutyl group, 5-carbamoylpentyl group, 6-carbamoylhexyl group, 1,1-dimethyl-2-carbamoylethyl group, 2-methyl-3-carbamoylpropyl group, N-methylcarbamoylmethyl group, N,N-dimethylcarbamoylmethyl group, N-methyl-N-ethylcarbamoylmethyl group, N-methylcarbamoylmethyl group, 2-(N-methylcarbamoyl)ethyl group, 2-(N-ethylcarbamoyl)ethyl group, N-phenylcarbamoylmethyl group, N-(2-methoxyphenyl)carbamoylmethyl group, and N-(4-methylphenyl)carbamoylmethyl group.

Examples of the carboxyl lower alkenyl group include a lower alkenyl group as illustrated above having 1 to 3, preferably 1, carboxyl groups and including both trans and cis configurations (preferably a linear or branched alkenyl group having 1 to 3 double bonds and 2 to 6 carbon atoms). Specific examples thereof include a 2-carboxyethenyl group, 3-carboxy-2-propenyl group, 4-carboxy-2-butenyl group, 4-carboxy-3-butenyl group, 4-carboxy-1,3-butadienyl group, 5-carboxy-1,3,5-hexatrienyl group, 5-carboxy-2,4-hexadienyl group, 5-carboxy-3-pentenyl group, and 3-carboxy-1-propenyl group.

Examples of the lower alkoxycarbonyl lower alkenyl group include a lower alkenyl group as illustrated above (preferably a linear or branched alkenyl group having 1 to 3 double bonds and 2 to 6 carbon atoms) having 1 to 3 lower alkoxycarbonyl groups as illustrated above (preferably a linear or branched alkoxycarbonyl group having 1 to 6 carbon atoms) and including both trans and cis configurations. Specific example of the lower alkoxycarbonyl lower alkenyl group include a 2-methoxycarbonylethenyl group, 2-ethoxycarbonylethenyl group, 1-ethoxycarbonylethenyl group, 3-methoxycarbonyl-2-propenyl group, 3-ethoxycarbonyl-2-propenyl group, 4-ethoxycarbonyl-2-butenyl group, 4-ethoxycarbonyl-1,3-buthadienyl group, 5-isopropoxycarbonyl-3-pentenyl group, 6-n-propoxycarbonyl-1,3,5-hexatrienyl group, 1,1-dimethyl-2-n-butoxycarbonylethenyl group, 2-methyl-3-tert-butoxycarbonyl-2-propenyl group, and 2-n-pentyloxycarbonylethenyl group.

Examples of the carbamoyl lower alkenyl group include a lower alkenyl group as illustrated above (preferably a linear or branched alkenyl group having 2 to 6 carbon atoms and 1 to 3 double bonds) having 1 to 3, preferably 1, carbamoyl groups. Specific examples thereof include a 2-carbamoylethenyl group, 3-carbamoyl-2-propenyl group, 4-carbamoyl-2-butenyl group, 4-carbamoyl-3-butenyl group, 4-carbamoyl-1,3-butadienyl group, 5-carbamoyl-1,3,5-hexatrienyl group, 5-carbamoyl-2,4-hexadienyl group, 5-carbamoyl-3-pentenyl group, and 3-carbamoyl-1-propenyl group.

Examples of the carbamoyl lower alkenyl group that may have, as a substituent, a group selected from the group consisting of a lower alkyl group and a halogen-substituted lower alkyl group include a lower alkenyl group as illustrated above (preferably a linear or branched alkenyl group having 1 to 3 double bonds and 2 to 6 carbon atoms) having 1 to 3, preferably 1 carbamoyl group that may have, on the carbamoyl group, 1 to 2 substituents selected from the group consisting of a lower alkyl group as illustrated above (preferably a linear or branched alkyl group having 1 to 6 carbon atoms); and a halogen-substituted lower alkyl group as illustrated above (preferably a linear or branched alkyl group having 1 to 6 carbon atoms having 1 to 7, preferably 1 to 3 substituents of halogen atoms). Specific examples thereof include a 2-carbamoylethenyl group, 2-(N-methylcarbamoyl)ethenyl group, 2-(N-ethylcarbamoyl)ethenyl group, 2-(N,N-dimethylcarbamoyl)ethenyl group, and 2-[N-(2,2,2-trifluoroethyl)carbamoyl]ethenyl group.

Examples of the lower alkoxy lower alkyl group include a lower alkyl group as illustrated above (preferably a linear or branched alkyl group having 1 to 6 carbon atoms) having 1 to 3, preferably 1, lower alkoxy groups as illustrated above (preferably a linear or branched alkoxy group having 1 to 6 carbon atoms). Specific examples thereof include a methoxymethyl group, 2-methoxyethyl group, 1-ethoxyethyl group, 2-ethoxyethyl group, 2-isobutoxyethyl group, 2,2-dimethoxyethyl group, 2-methoxy-1-methylethyl group, 2-methoxy-1-ethylethyl group, 3-methoxypropyl group, 3-ethoxypropyl group, 2-isopropoxyethyl group, 3-isopropoxypropyl group, 3-n-butoxypropyl group, 4-n-propoxybutyl group, 1-methyl-3-isobutoxy propyl group, 1,1-dimethyl-2-n-pentyloxyethyl group, 5-n-hexyloxypentyl group, 6-methoxyhexyl group, 1-ethoxyisopropyl group, and 2-methyl-3-methoxypropyl group.

Examples of the aryloxy lower alkyl group include a lower alkyl group as illustrated above (preferably a linear or branched alkyl group having 1 to 6 carbon atoms) having 1 to 3, preferably 1 aryloxy groups whose aryl moiety is phenyl, biphenyl, naphthyl or the like. Examples of a substituent for an aryl group include a lower alkyl group as illustrated above (preferably a linear or branched alkyl group having 1 to 6 carbon atoms), a halogen atom as illustrated above, and an amino group. One to seven substituents of at least one type of these may be present on an aryl ring. Specific examples of the aryloxy lower alkyl include a phenoxymethyl group, 2-phenoxyethyl group, 2-[(1- or 2-)naphthyloxy]ethyl group, 2-[(2-, 3-, or 4-)methylphenoxy]ethyl group, 2-[(2-, 3-, or 4-)ethylphenoxy]ethyl group, 2-[(2-, 3-, or 4-)n -propylphenoxy]ethyl group, 2-[(2-, 3-, or 4-)n-butylphenoxy]ethyl group, 2-[(2-, 3-, or 4-)n-pentylphenoxy]ethyl group, 2-[(2-, 3-, or 4-)n-hexylphenoxy]ethyl group, 2-[(2-, 3-, or 4-)isobutylphenoxy]ethyl group, 2-[(2-, 3-, or 4-)tert -butylphenoxy]ethyl group, 2-[(2-, 3-, 4-, 5-, 6-, 7-, or 8-)methyl-1-naphthyloxy]ethyl group, 2-[(1-, 3-, 4-, 5-, 6-, 7-, or 8-)methyl-2-naphthyloxy)ethyl group, 2-[(2-, 3-, 4-, 5-, 6-, 7-, or 8-)ethyl-1-naphthyloxy]ethyl group, 2-[(1-, 3-, 4-, 5-, 6-, 7-, or 8-)ethyl-2-naphthyloxy]ethyl group, 2-[(2-, 3-, 4-, 5-, 6-, 7-, or 8-)n-propyl-1-naphthyloxy]ethyl group, 2-[(1-, 3-, 4-, 5-, 6-, 7-, or 8-)n-propyl-2-naphthyloxy]ethyl group, 2-[(2-, 3-, 4-, 5-, 6-, 7-, or 8-)n-butyl-1-naphthyloxy]ethyl group, 2-[(1-, 3-, 4-, 5-, 6-, 7-, or 8-)n-butyl-2-naphthyloxy]ethyl group, 2-[(2-, 3-, 4-, 5-, 6-, 7-, or 8-)n-pentyl-1-naphthyloxy]ethyl group, 2-[(1-, 3-, 4-, 5-, 6-, 7-, or 8-)n-pentyl-2-naphthyloxy]ethyl group, 2-[(2-, 3-, 4-, 5-, 6-, 7-, or 8-)n-hexyl-1-naphthyloxy]ethyl group, 2-[(1-, 3-, 4-, 5-, 6-, 7-, or 8-)n-hexyl-2-naphthyloxy]ethyl group, 2-[(2-, 3-, 4-, 5-, 6-, 7-, or 8-)isobutyl-1-naphthyloxy]ethyl group, 2-[(1-, 3-, 4-, 5-, 6-, 7-, or 8-)isobutyl-2-naphthyloxy]ethyl group, 2-[(2-, 3-, 4-, 5-, 6-, 7-, or 8-)tert-butyl-1-naphthyloxy]ethyl group, 2-[(1-, 3-, 4-, 5-, 6-, 7-, or 8-)tert-butyl-2-naphthyloxy]ethyl group, 2-[(2-, 3-, or 4-)chlorophenoxy]ethyl group, 2-[(2-, 3-, or 4-)fluorophenoxy]ethyl group, 2-[((2-, 3-, or 4-)bromophenoxy]ethyl group, 2-[(2-, 3-, 4-, 5-, 6-, 7-, or 8-)chloro-1-naphthyloxy]ethyl group, 2-[(1-, 3-, 4-, 5-, 6-, 7-, or 8-)chloro-2-naphthyloxy]ethyl group, 2-[(2-, 3-, 4-, 5-, 6-, 7-, or 8-)fluoro-1-naphthyloxy]ethyl group, 2-[(1-, 3-, 4-, 5-, 6-, 7-, or 8-)fluoro-2-naphthyloxy]ethyl group, 2-[(2-, 3-, 4-, 5-, 6-, 7-, or 8-)bromo-1-naphthyloxy]ethyl group, 2-[(1-, 3-, 4-, 5-, 6-, 7-, or 8-)bromo-2-naphthyloxy]ethyl group, 2-[(2-, 3-, or 4-)aminophenoxy]ethyl group, 2-[(2-, 3-, 4-, 5-, 6-, 7-, or 8-)amino-1-naphthyloxy]ethyl group, 2-[(1-, 3-, 4-, 5-, 6-, 7-, or 8-)amino-2-naphthyloxy]ethyl group, 2-(2,3-dimethylphenoxy)ethyl group, 2-(3,4-dimethylphenoxy)ethyl group, 2-(2,4-dimethylphenoxy)ethyl group, 2-(2,5-dimethylphenoxy)ethyl group, 2-(2,6-dimethylphenoxy)ethyl group, 2-(2,4,6-trimethylphenoxy)ethyl group, 2-(3,4,5-trimethylphenoxy)ethyl group, 2-(2,3,4,5-tetraethylphenoxy)ethyl group, 2-(pentamethylphenoxy)ethyl group, 2-(2,4-dimethyl-1-naphthyloxy)ethyl group, 2-(2,3-dimethyl-1-naphthyloxy)ethyl group, 2-(3,4-dimethyl-1-naphthyloxy)ethyl group, 2-(3,5,7-triethyl-1-naphthyloxy)ethyl group, 2-(3,4,5,7-tetramethyl-1-naphthyloxy)ethyl group, 2-(2,3,4,5,7-pentamethyl-1-naphthyloxy)ethyl group, 2-(2,3,4,5,6,7-hexaethyl-1-naphthyloxy)ethyl group, 2-(heptamethyl-1-naphthyloxy)ethyl group, 2-(2,3-diaminophenoxy)ethyl group, 2-(2,4,6-triaminophenoxy)ethyl group, 2-(2-methyl-5-chloro-1-naphthyl)ethyl group, 3-phenoxypropyl group, 2,3-diphenoxypropyl group, 4-phenoxybutyl group, 3,4-diphenoxybutyl group, 1,1-dimethyl-2-phenoxyethyl group, 5-phenoxypentyl group, 6-phenoxyhexyl group, 3,3-dimethyl-3-phenoxypropyl group, 2-methyl-3-phenoxypropyl group, and 2,3,4-triphenoxybutyl group, 3-[(1- or 2-)naphthyloxy]propyl group, 2,3-di[(1- or 2-)naphthyloxy]propyl group, 4-[(1- or 2-)naphthyloxy]butyl group, 3,4-di[(1- or 2-)naphthyloxy]butyl group, 1,1-dimethyl-2-[(1- or 2-)naphthyloxy]ethyl group, 5-[(1- or 2-)naphthyloxy]pentyl group, 6-[(1- or 2-)naphthyloxy]hexyl group, 3,3-dimethyl-3-[(1- or 2-)naphthyloxy]propyl group, 2-methyl-3-[(1- or 2-)naphthyloxy]propyl group, and 2,3,4-tri[(1- or 2-)naphthyloxy]butyl group.

Examples of the amino lower alkyl group that may have a group selected from the group consisting of
a lower alkyl group, lower alkanoyl group, aroyl group and carbamoyl group include
a lower alkyl group as illustrated above (preferably a linear or branched alkyl group having 1 to 6 carbon atoms) having 1 to 5 (preferably 1) amino groups that may have 1 to 2 groups selected from the group consisting of a lower alkyl group as illustrated above (preferably a linear or branched alkyl group having 1 to 6 carbon atoms), lower alkanoyl group as illustrated above (preferably a linear or branched alkanoyl group having 1 to 6 carbon atoms), aroyl group as illustrated above (preferably benzoyl group) as illustrated above and carbamoyl group. Specific examples of the amino lower alkyl group include an aminomethyl group, 2-aminoethyl group, 1-aminoethyl group, 3-aminopropyl group, 4-aminobutyl group, 5-aminopentyl group, 6-aminohexyl group, 1,1-dimethyl-2-aminoethyl group, 2-methyl-3-aminopropyl group, N,N-dimethylaminomethyl group, N-methyl-N-ethylaminomethyl group, N-methylaminomethyl group, 2-(N-methylamino)ethyl group, 1-methyl-2-(N,N-dimethylamino)ethyl group, 1-methyl-2-(N,N-diethylamino)ethyl group, 2-(N,N-dimethylamino)ethyl group, 2-(N,N-diethylamino)ethyl group, 2-(N,N-diisopropylamino)ethyl group, 3-(N,N-dimethylamino)propyl group, 3-(N,N-diethylamino)propyl group, 2-(N-acetylamino)ethyl group, 2-(N-methyl-N-acetylamino)ethyl group, 2-(N-methyl-N-n-butyrylamino)ethyl group, 2-(N-methyl-N-benzoylamino)ethyl group, and 2-(N-carbamoylamino)ethyl group.

Examples of the cyclo C3-C8 alkyl group include a cyclopropyl group, cyclobutyl group, cyclopentyl group, cyclohexyl group, cycloheptyl group, and cyclooctyl group.

Examples of the cyclo C3-C8 alkyl group that may have a group, as a substituent, selected from the group consisting of a lower alkyl group, hydroxy group, lower alkoxy carbonyl group and phenyl lower alkoxy group include a cyclo C3-C8 alkyl group that may have 1 to 3 (preferably 1) groups, as a substituent(s), selected from the group consisting of
a lower alkyl group as illustrated above (preferably a linear or branched alkyl group having 1 to 6 carbon atoms);
a hydroxy group;
a lower alkoxy carbonyl group as illustrated above (preferably a linear or branched alkoxycarbonyl group having 1 to 6 carbon atoms); and
a lower alkoxy group (preferably a linear or branched alkoxy group having 1 to 6 carbon atoms) having 1 to 3 (preferably 1) phenyl groups. Specific examples thereof include a cyclopropyl group, cyclobutyl group, cyclopentyl group, cyclohexyl group, cycloheptyl group, cyclooctyl group, 1-methylcyclopropyl group, 1-methylcyclopentyl group, 1-methylcyclohexyl group, 2-methylcyclohexyl group, 4-hydroxycyclohexyl group, 4-methoxycarbonylcyclohexyl group, 2-benzyloxypentyl group, and 2-benzyloxyhexyl group.

Example of the cyclo C3-C8 alkyl substituted lower alkyl group include a lower alkyl group as illustrated above (preferably a linear or branched alkyl group having 1 to 6 carbon atoms) having 1 to 3, preferably 1 cyclo C3-C8 alkyl group as illustrated above. Specific examples thereof include a cyclopropylmethyl group, cyclohexylmethyl group, 2-cyclopropylethyl group, 1-cyclobutylethyl group, cyclopentylmethyl group, 3-cyclopentylpropyl group, 4-cyclohexylbutyl group, 5-cycloheptylpentyl group, 6-cyclooctylhexyl group, 1,1-dimethyl-2-cyclohexylethyl group, and 2-methyl-3-cyclopropylpropyl group.

Examples of the furyl lower alkyl group (that may have a substituent of a lower alkyl group on the furyl group) include a lower alkyl group as illustrated above (preferably a linear or branched alkyl group having 1 to 6 carbon atoms) having 1 to 2 (preferably 1) furyl groups on which 1 to 3 (preferably 1 to 2) lower alkyl groups as illustrated above (preferably a linear or branched alkyl group having 1 to 6 carbon atoms) may be present as a substituent. Specific examples thereof include a [(2- or 3-)furyl]methyl group, 2-[(2- or 3-)furyl]ethyl group, 1-[(2- or 3-)furyl]ethyl group, 3-[(2- or 3-)furyl]propyl group, 4-[(2- or 3-)furyl]butyl group, 5-[(2- or 3-)furyl]pentyl group, 6-[(2- or 3-)furyl]hexyl group, 1,1-dimethyl-2-[(2- or 3-)furyl]ethyl group, 2-methyl-3-[(2- or 3-)furyl]propyl group, [5-ethyl-(2-, 3-, or 4-)furyl]methyl group, [5-methyl-(2-, 3-, or 4-)furyl]methyl group, [2-n-propyl-(3-, 4-, or 5-)furyl]methyl group, [3-tert-butyl-(2-, 4-, or 5-)furyl]methyl group, [4-n-pentyl-(2-, 3-, or 5-)furyl]methyl group, [2-n-hexyl-(3-, 4-, or 5-)furyl]methyl group, [2,5-dimethyl-(3- or 4-)furyl]methyl group, [2,5-diethyl-(3- or 4-)furyl]methyl group, and [2,4,5-triethyl-3-furyl]methyl group.

Examples of the tetrahydrofuryl lower alkyl group include a lower alkyl group as illustrated above (preferably a linear or branched alkyl group having 1 to 6 carbon atoms) having 1 to 2 (preferably 1) tetrahydrofuryl groups. Specific examples thereof include a (2- or 3-)(2,3,4,5-tetrahydrofuryl)methyl group, 2-[(2- or 3-)(2,3,4,5-tetrahydrofuryl)]ethyl group, 1-[(2- or 3-)(2,3,4,5-tetrahydrofuryl)]ethyl group, 3-[(2- or 3-)(2,3,4,5-tetrahydrofuryl)]propyl group, 2,3-di[(2- or 3-)(2,3,4,5-tetrahydrofuryl)]propyl group, 4-[(2- or 3-)(2,3,4,5-tetrahydrofuryl)]butyl group, 3,4-di[(2- or 3-)(2,3,4,5-tetrahydrofuryl)]butyl group, 1,1-dimethyl-2-[(2- or 3-)(2,3,4,5-tetrahydrofuryl)]ethyl group, 5-[(2- or 3-)(2,3,4,5-tetrahydrofuryl)]pentyl group, 6-[(2- or 3-)(2,3,4,5-tetrahydrofuryl)]hexyl group, 3,3-dimethyl-3-[(2- or 3-)(2,3,4,5-tetrahydrofuryl)]propyl group, 2-methyl-3-[(2- or 3-)(2,3,4,5-tetrahydrofuryl)]propyl group, and 2,3,4-tri[(2- or 3-) (2,3,4,5-tetrahydrofuryl)]butyl group.

Examples of a 1,3-dioxolanyl lower alkyl group include a lower alkyl group as illustrated above (preferably a linear or branched alkyl group having 1 to 6 carbon atoms) having 1 to 2 (preferably 1) 1,3-dioxolanyl groups. Specific examples thereof include a [(2- or 4-)1,3-dioxolanyl]methyl group, 2-[(2- or 4-)1,3-dioxolanyl]ethyl group, 1-[(2- or 4-)1,3-dioxolanyl]ethyl group, 3-[(2- or 4-)1,3-dioxolanyl]propyl group, 4-[(2- or 4-)1,3-dioxolanyl]butyl group, 1,1-dimethyl-2-[(2- or 4-)1,3-dioxolanyl]ethyl group, 5-[(2- or 4-)1,3-dioxolanyl]pentyl group, 6-[(2- or 4-)1,3-dioxolanyl]hexyl group, 1-[(2- or 4-)1,3-dioxolanyl]isopropyl group, and 2-methyl-3-[(1-, 2-, or 4-)imidazolyl]propyl group.

Examples of the tetrahydropyranyl lower alkyl group include a lower alkyl group as illustrated above (preferably a linear or branched alkyl group having 1 to 6 carbon atoms) having 1 to 2 (preferably 1) tetrahydropyranyl groups. Specific examples thereof include a [(2-, 3-, or 4-)tetrahydropyranyl]methyl group, 2-[(2-, 3-, or 4-)tetrahydropyranyl]ethyl group, 1-[(2-, 3-, or 4-)tetrahydropyranyl]ethyl group, 3-[(2-, 3-, or 4-)tetrahydropyranyl]propyl group, 4-[(2-, 3-, or 4-)tetrahydropyranyl]butyl group, 1,1-dimethyl-2-[(2-, 3-, or 4-)tetrahydropyranyl]ethyl group, 5-[(2-, 3-, or 4-)tetrahydropyranyl]pentyl group, 6-[(2-, 3-, or 4-)tetrahydropyranyl]hexyl group, 1-[(2-, 3-, or 4-)tetrahydropyranyl]isopropyl group, and 2-methyl-3-[(2-, 3-, or 4-)tetrahydropyranyl]propyl group.

Examples of the pyrrolyl lower alkyl group (that may have a substituent of a lower alkyl group on the pyrrolyl group) include a lower alkyl group as illustrated above (preferably a linear or branched alkyl group having 1 to 6 carbon atoms) having 1 to 2 (preferably 1) pyrrolyl groups on which 1 to 3 (preferably 1 to 2) lower alkyl groups as illustrated above (preferably a linear or branched alkyl group having 1 to 6 carbon atoms) may be present as a substituent(s). Specific examples thereof include a [(1-, 2-, or 3-)pyrrolyl]methyl group, 2-[(1-, 2-, or 3-)pyrrolyl]ethyl group, 1-[(1-, 2-, or 3-)pyrrolyl]ethyl group, 3-[(1-, 2-, or 3-)pyrrolyl]propyl group, 4-[(1-, 2-, or 3-)pyrrolyl]butyl group, 1,1-dimethyl-2-[(1-, 2-, or 3-)pyrrolyl]ethyl group, 5-[(1-, 2-, or 3-)pyrrolyl]pentyl group, 6-[(1-, 2-, or 3-)pyrrolyl]hexyl group, 1-[(1-, 2-, or 3-)pyrrolyl]isopropyl group, 2-methyl-3-[(1-, 2-, or 3-)pyrrolyl]propyl group, [1-methyl-(2- or 3-)pyrrolyl]methyl group, [1-ethyl-(2- or 3-)pyrrolyl]methyl group, [1-n-propyl-(2- or 3-)pyrrolyl]methyl group, [1-n-butyl-(2- or 3-)pyrrolyl]methyl group, [1-n-pentyl-(2- or 3-)pyrrolyl]methyl group, [1-n-hexyl-(2- or 3-)pyrrolyl]methyl group, 2-[5-methyl-(1-, 2-, 3-, or 4-)pyrrolyl]ethyl group, 1-[1-ethyl-(2- or 3-)pyrrolyl]ethyl group, 3-[1-ethyl-(2- or 3-)pyrrolyl]propyl group, 4-[1-n-propyl-(2- or 3-)pyrrolyl]butyl group, 5-[1-n-butyl-(2- or 3-)pyrrolyl]pentyl group, 6-[1-n-pentyl-(2- or 3-)pyrrolyl]hexyl group, [1,5-dimethyl-(2-, 3-, or 4-)pyrrolyl]methyl group, [1,3,5-trimethyl-2-pyrrolyl]methyl group, and [1,2,4-trimethyl-3-pyrrolyl]methyl group.

Examples of the lower alkyl group substituted with a dihydropyrazolyl group that may have an oxo group include a lower alkyl group as illustrated above (preferably a linear or branched alkyl group having 1 to 6 carbon atoms) having a 2,3-dihydropyrazolyl group or 4,5-dihydropyrazolyl group as a dihydropyrazolyl group, on which an oxo group may be present. Specific examples thereof include a 3-(2,3- or 4,5-)dihydropyrazolylmethyl group, 2-[4-(2,3- or 4,5-)dihydropyrazolyl]ethyl group, 1-[5-(2,3- or 4,5-)dihydropyrazolyl]ethyl group, 3-[3-(2,3- or 4,5-)dihydropyrazolyl]propyl group, 4-[4-(2,3- or 4,5-)dihydropyrazolyl]butyl group, 5-[1-(2,3- or 4,5-)dihydropyrazolyl]pentyl group, 6-[5-(2,3- or 4,5-)dihydropyrazolyl]hexyl group, 2-methyl-3-[1-(2,3- or 4,5-)dihydropyrazolyl]propyl group, 1,1-dimethyl-2-[3-(2,3- or 4,5-)dihydropyrazolyl]ethyl group, 5-oxo-4-(4,5-dihydropyrazolyl)methyl group, 2-[5-oxo-4-(4,5-dihydropyrazolyl)]ethyl group, and 3-[5-oxo-4-(4,5-dihydropyrazolyl)]propyl group.

Examples of the pyrazolyl lower alkyl group (that may have a substituent of a lower alkyl group on the pyrazolyl group) include a lower alkyl group as illustrated above (preferably a linear or branched alkyl group having 1 to 6 carbon atoms) having 1 to 2 (preferably 1) pyrazolyl groups, on which 1 to 3 (preferably 1 to 2) lower alkyl groups as illustrated above (preferably a linear or branched alkyl group having 1 to 6 carbon atoms) may be present as a substituent(s). Specific examples thereof include a 3-pyrazolylmethyl group, 2-(4-pyrazolyl)ethyl group, 2-(1-pyrazolyl)ethyl group, 1-(5-pyrazolyl)ethyl group, 3-(3-pyrazolyl)propyl group, 4-(4-pyrazolyl)butyl group, 5-(1-pyrazolyl)pentyl group, 6-(5-pyrazolyl)hexyl group, 2-methyl-3-(1-pyrazolyl)propyl group, 1,1-dimethyl-2-(3-pyrazolyl)ethyl group, 1-methyl-3-pyrazolylmethyl group, 1-ethyl-3-pyrazolylmethyl group, 1-n-propyl-3-pyrazolylmethyl group, 1-n-butyl-3-pyrazolylmethyl group, 1-n-pentyl-3-pyrazolylmethyl group, 1-methyl-4-pyrazolylmethyl group, 5-methyl-3-pyrazolylmethyl group, 1-ethyl-4-pyrazolylmethyl group, 1-n-propyl-4-pyrazolylmethyl group, 1-n-butyl-4-pyrazolylmethyl group, 1-n-hexyl-4-pyrazolylmethyl group, 3-methyl-1-pyrazolylmethyl group, 3-ethyl-1-pyrazolylmethyl group, 3-n-propyl-1-pyrazolylmethyl group, 3-n-butyl-1-pyrazolylmethyl group, 1,5-dimethyl-3-pyrazolylmethyl group, 3,5-dimethyl-4-pyrazolylmethyl group, 3,4-dimethyl-1-pyrazolylmethyl group, 1,3-dimethyl-5-pyrazolylmethyl group, 3,4-diethyl-1-pyrazolylmethyl group, 3,4-di-n-propyl-1-pyrazolylmethyl group, 3,4-di-n-butyl-1-pyrazolylmethyl group, 1,3,5-trimethyl-4-pyrazolylmethyl group, 3,4,5-trimethyl-1-pyrazolylmethyl group, 3,4,5-triethyl-1-pyrazolylmethyl group, 3,4,5-tri-n-propyl-1-pyrazolylmethyl group, 3,4,5-tri-n-butyl-1-pyrazolylmethyl group, 1-methyl-5-pyrazolylmethyl group, 1-ethyl-5-pyrazolylmethyl group, 1-n-propyl-5-pyrazolylmethyl group, 1-n-butyl-5-pyrazolylmethyl group, 2-(3-pyrazolyl)ethyl group, 3-(3-pyrazolyl)propyl group, 4-(3-pyrazolyl)butyl group, 5-(3-pyrazolyl)pentyl group, 6-(3-pyrazolyl)hexyl group, 2-(1-(4-chlorophenyl)-3-pyrazolyl)ethyl group, 3-(1-methyl-3-pyrazolyl)propyl group, 3-(3-methyl-4-pyrazolyl)propyl group, 3-(5-methyl-4-pyrazolyl)propyl group, 3-(1,5-dimethyl-3-pyrazolyl)propyl group, 3-(1-ethyl-3-pyrazolyl)propyl group, 3-(1-n-propyl-3-pyrazolyl)propyl group, 3-(1-n-butyl-3-pyrazolyl)propyl group, 4-(1-methyl-3-pyrazolyl) butyl group, 4-(1-ethyl-3-pyrazolyl)butyl group, 4-(1-n-propyl-3-pyrazolyl)butyl group, 4-(1-n-butyl-3-pyrazolyl) butyl group, 5-(1-methyl-3-pyrazolyl)pentyl group, 5-(1-ethyl-3-pyrazolyl)pentyl group, 5-(1-n-propyl-3-pyrazolyl) pentyl group, 5-(1-n-butyl-3-pyrazolyl)pentyl group, 6-(1-methyl-3-pyrazolyl)hexyl group, 6-(1-ethyl-3-pyrazolyl) hexyl group, 6-(1-n-propyl-3-pyrazolyl)hexyl group, and 6-[1-(3-butyl)-3-pyrazolyl]hexyl group.

Examples of the imidazolyl lower alkyl group include a lower alkyl group as illustrated above (preferably a linear or branched alkyl group having 1 to 6 carbon atoms) having 1 to 2 (preferably 1) imidazolyl groups. Specific examples thereof include a [(1-, 2-, 4- or 5-)imidazolyl]methyl group, 2-[(1-, 2-, 4- or 5-)imidazolyl]ethyl group, 1-[(1-, 2-, 4- or 5-)imidazolyl]ethyl group, 3-[(1-, 2-, 4- or 5-)imidazolyl]propyl group, 4-[(1-, 2-, 4- or 5-)imidazolyl]butyl group, 1,1-dimethyl-2-[(1-, 2-, 4- or 5-)imidazolyl]ethyl group, 5-[(1-, 2-, 4- or 5-)imidazolyl]pentyl group, 6-[(1-, 2-, 4- or 5-)imidazolyl] hexyl group, 1-[(1-, 2-, 4- or 5-)imidazolyl]isopropyl group, and 2-methyl-3-[(1-, 2-, 4- or 5-)imidazolyl]propyl group.

Examples of the pyridyl lower alkyl group include a lower alkyl group as illustrated above (preferably a linear or branched alkyl group having 1 to 6 carbon atoms) having 1 to 2 (preferably 1) pyridyl groups. Specific examples thereof include a (2-, 3- or 4-)pyridylmethyl group, 2-[(2-, 3- or 4-)pyridyl]methyl group, 1-[(2-, 3- or 4-)pyridyl]ethyl group, 3-[(2-, 3- or 4-)pyridyl]propyl group, 4-[(2-, 3- or 4-)pyridyl] butyl group, 1,1-dimethyl-2-[(2-, 3- or 4-)pyridyl]ethyl group, 5-[(2-, 3- or 4-)pyridyl]pentyl group, 6-[(2-, 3- or 4-)pyridyl]hexyl group, 1-[(2-, 3or 4-)pyridyl]isopropyl group, 2-methyl-3-[(2-, 3- or 4-)pyridyl]propyl group.

Examples of the pyrazinyl lower alkyl group (a lower alkyl group may be present as a substituent on the pyrazinyl group) include a lower alkyl group as illustrated above (preferably a linear or branched alkyl group having 1 to 6 carbon atoms) having 1 to 2 (preferably 1) pyrazinyl groups on which 1 to 3 (preferably 1) lower alkyl groups as illustrated above (preferably a linear or branched alkyl group having 1 to 6 carbon atoms) may be present as a substituent(s). Specific examples thereof include a 2-pyrazinylmethyl group, 2-(2-pyrazinyl) ethyl group, 1-(2-pyrazinyl)ethyl group, 3-(2-pyrazinyl)propyl group, 4-(2-pyrazinyl)butyl group, 5-(2-pyrazinyl)pentyl group, 6-(2-pyrazinyl)hexyl group, 3-methyl-3-(2-pyrazinyl) propyl group, 1,1-dimethyl-2-(2-pyrazinyl)ethyl group, 3-methyl-2-pyrazinylmethyl group, 3-ethyl-2-pyrazinylmethyl group, 3-n-propyl-2-pyrazinylmethyl group, 3-n-butyl-2-pyrazinylmethyl group, 3-n-pentyl-2-pyrazinylmethyl group, 5-methyl-2-pyrazinylmethyl group, 5-ethyl-2-pyrazinylmethyl group, 5-n-propyl-2-pyrazinylmethyl group, 5-n-butyl-2-pyrazinylmethyl group, 6-methyl-2-pyrazinylmethyl group, 6-ethyl-2-pyrazinylmethyl group, 6-n-propyl-2-pyrazinylmethyl group, 6-n-butyl-2-pyrazinylmethyl group, 3,5-dimethyl-2-pyrazinylmethyl group, 3,5-diethyl-2-pyrazinylmethyl group, 3,5-di-n-propyl-2-pyrazinylmethyl group, 3,5-di-n-butyl-2-pyrazinylmethyl group, 2-(5-methyl-2-pyrazinyl)ethyl group, 2-(5-ethyl-2-pyrazinyl)ethyl group, 2-(5-n-propyl-2-pyrazinyl)ethyl group, 2-(5-n-butyl-2-pyrazinyl)ethyl group, 3-(5-methyl-2-pyrazinyl)propyl group, 3-(5-ethyl-2-pyrazinyl)propyl group, 3-(5-n-propyl-2-pyrazinyl)propyl group, 3-(5-n-butyl-2-pyrazinyl)propyl group, 4-(5-methyl-2-pyrazinyl)butyl group, 4-(5-ethyl-2-pyrazinyl)butyl group, 4-(5-n-propyl-2-pyrazinyl)butyl group, 4-(5-n-butyl-2-pyrazinyl)butyl group, 5-(5-methyl-2-pyrazinyl)pentyl group, 5-(5-ethyl-2-pyrazinyl)pentyl group, 5-(5-n-propyl-2-pyrazinyl)pentyl group, 5-(5-n-butyl-2-pyrazinyl)pentyl group, 6-(5-methyl-2-pyrazinyl)hexyl group, 6-(5-ethyl-2-pyrazinyl)hexyl group, 6-(5-n-propyl-2-pyrazinyl)hexyl group, and 6-(5-n-butyl-2-pyrazinyl)hexyl group.

Examples of the pyrrolidinyl lower alkyl group (a group selected from the group consisting of an oxo group and a lower alkyl group may be present as a substituent on the pyrrolidinyl group) include a lower alkyl group as illustrated above (preferably a linear or branched alkyl group having 1 to 6 carbon atoms) having 1 to 2 (preferably 1) pyrrolidinyl groups, on which 1 to 3 (preferably 1) groups selected from the group consisting of an oxo group and a lower alkyl group as illustrated above (preferably a linear or branched alkyl group having 1 to 6 carbon atoms) may be present as a substituent(s). Specific examples thereof include a [(1-, 2-, or 3-)pyrrolidinyl]methyl group, 2-[(1-, 2-, or 3-)pyrrolidinyl] ethyl group, 1-[(1-, 2-, or 3-)pyrrolidinyl]ethyl group, 3-[(1-, 2-, or 3-)pyrrolidinyl]propyl group, 4-[(1-, 2-, or 3-)pyrrolidinyl]butyl group, 5-[(1-, 2-, or 3-)pyrrolidinyl]pentyl group, 6-[(1-, 2-, or 3-)pyrrolidinyl]hexyl group, 1-methyl-2-[(1-, 2-, or 3-)pyrrolidinyl]ethyl group, 1,1-dimethyl-2-[(1-, 2-, or 3-)pyrrolidinyl]ethyl group, 2-methyl-3-[(1-, 2-, or 3-)pyrrolidinyl)propyl group, 1-methyl-(2- or 3-)pyrrolidinylmethyl group, 1-ethyl-(2- or 3-)pyrrolidinylmethyl group, 1-n-propyl-(2- or 3-)pyrrolidinylmethyl group, 1-n-butyl-(2- or 3-)pyrrolidinylmethyl group, 1-n-pentyl-(2- or 3-)pyrrolidinylmethyl group, 1-n-hexyl-(2- or 3-)pyrrolidinylmethyl group, 2-methyl-1-pyrrolidinylmethyl group, 2-ethyl-1-pyrrolidinylmethyl group, 2-n-propyl-1-pyrrolidinylmethyl group, 2-n-butyl-1-pyrrolidinylmethyl group, 2-n-pentyl-1-pyrrolidinylmethyl group, 2-n-hexyl-1-pyrrolidinylmethyl group, 3-methyl-2-pyrrolidinylmethyl group, 3-ethyl-2-pyrrolidinylmethyl group, 3-n-propyl-2-pyrrolidinylmethyl group, 3-n-butyl-2-pyrrolidinylmethyl group, 1,5-dimethyl-(2- or 3-)pyrrolidinylmethyl group, 1,5-di-ethyl-(2- or 3-)pyrrolidinylmethyl group, 1,5-di-n-propyl-(2- or 3-)pyrrolidinylmethyl group, 1,5-di-n-butyl-(2- or 3-)pyrrolidinylmethyl group, 1,4,5-triethyl-(2- or 3-)pyrrolidinylmethyl group, 1,4,5-tri-n-propyl-(2- or 3-)pyrrolidinylmethyl group, 1,4,5-tri-n-butyl-(2- or 3-)pyrrolidinylmethyl group, 3-[2-oxo-(1-pyrrolidinyl)propyl]group, 3-[5-oxo-(2-, 3-, or 4-)pyrrolidinyl] propyl group, and 3-[1-methyl-5-oxo-(2-, 3-, or 4-)pyrrolidinyl]propyl group.

Examples of the piperidyl lower alkyl group (that may have as a substituent on the piperidyl group, a group selected from the group consisting of a benzoyl group and a lower alkanoyl group) include a lower alkyl group as illustrated above (preferably a linear or branched alkyl group having 1 to 6 carbon atoms) having 1 to 2 (preferably 1) piperidyl groups having 1 to 3 (preferably 1) groups, as a substituent(s), selected from the group consisting of a benzoyl group and a lower alkanoyl group as illustrated above (preferably a linear or branched alkyl group having 1 to 6 carbon atoms) on the piperidyl group(s). Specific examples thereof include a (1-, 2-, 3-, or 4-)piperidylmethyl group, 2-[(1-, 2-, 3-, or 4-)piperidyl]ethyl group, 2-[1-benzoyl-(2-, 3-, or 4-)piperidyl]ethyl group, 2-[1-acetyl-(2-, 3-, or 4-)piperidyl]ethyl group, 2-[1-butyryl-(2-, 3-, or 4-)piperidyl]ethyl group, 1-[(1-, 2-, 3-, or 4-)piperidyl]ethyl group, 3-[(1-, 2-, 3-, or 4-)piperidyl]propyl group, 4-[(1-, 2-, 3-, or 4-)piperidyl]butyl group, 1,1-dimethyl-2-[(1-, 2-, 3-, or 4-)piperidyl]ethyl group, 5-[(1-, 2-, 3-, or 4-)piperidyl]pentyl group, 6-[(1-, 2-, 3-, or 4-)piperidyl]hexyl group, 1-[(1-, 2-, 3-, or 4-)piperidyl]isopropyl group, and 2-methyl-3-[(1-, 2-, 3-, or 4-)piperidyl]propyl group.

Examples of the piperazinyl lower alkyl group (that may have a lower alkyl group as a substituent on the piperazinyl group) include a lower alkyl group as illustrated above (preferably a linear or branched alkyl group having 1 to 6 carbon atoms) having 1 to 2 (preferably 1) piperazinyl groups, on which 1 to 3 (preferably 1) lower alkyl groups as illustrated above (preferably a linear or branched alkyl group having 1 to 6 carbon atoms) may be present as a substituent(s). Specific examples thereof include a 1-piperazinylmethyl group, 2-piperazinylmethyl group, 2-(1-piperazinyl)ethyl group, 2-(2-piperazinyl)ethyl group, 1-(1-piperazinyl)ethyl group, 1-(2-piperazinyl)ethyl group, 3-(1-piperazinyl)propyl group, 3-(2-piperazinyl)propyl group, 4-(1-piperazinyl)butyl group, 4-(2-piperazinyl)butyl group, 2-(4-ethyl-2-piperazinyl)ethyl group, 1-(4-n-propyl-2-piperazinyl)ethyl group, 2-(4-n-butyl-2-piperazinyl)ethyl group, 2-(4-n-pentyl-2-piperazinyl)ethyl group, 1-(4-n-hexyl-2-piperazinyl)ethyl group, 2-(5-methyl-2-piperazinyl)ethyl group, 1-(5-ethyl-2-piperazinyl)ethyl group, 2-(5-n-propyl-2-piperazinyl)ethyl group, 1-(5-n-butyl-2-piperazinyl)ethyl group, 2-(5-n-pentyl-2-piperazinyl)ethyl group, 1-(5-n-hexyl-2-piperazinyl)ethyl group, 2-(6-methyl-2-piperazinyl)ethyl group, 1-(6-ethyl-2-piperazinyl)ethyl group, 2-(6-n-propyl-2-piperazinyl)ethyl group, 1-(6-n-butyl-2-piperazinyl)ethyl group, 2-(6-n-pentyl-2-piperazinyl)ethyl group, 2-(6-n-hexyl-2-piperazinyl)ethyl group, 3-(2-methyl-1-piperazinyl)propyl group, 3-(2-ethyl-1-piperazinyl)propyl group, 3-(2-n-propyl-1-piperazinyl)propyl group, 3-(2-n-butyl-1-piperazinyl)propyl group, 3-(2-n-pentyl-1-piperazinyl)propyl group, 3-(2-n-hexyl-1-piperazinyl)propyl group, 3-(3-methyl-1-piperazinyl)propyl group, 3-(3-ethyl-1-piperazinyl)propyl group, 3-(3-n-propyl-1-piperazinyl)propyl group, 3-(3-n-butyl-1-piperazinyl)propyl group, 3-(3-n-pentyl-1-piperazinyl)propyl group, 3-(3-n-hexyl-1-piperazinyl)propyl group, 3-(4-methyl-1-piperazinyl)propyl group, 3-(4-ethyl-1-piperazinyl)propyl group, 3-(4-n-propyl-1-piperazinyl)propyl group, 3-(4-n-butyl-1-piperazinyl)propyl group, 3-(4-n-pentyl-1-piperazinyl)propyl group, 6-(5-n-butyl-2-piperazinyl)hexyl group, 6-(5-n-pentyl-2-piperazinyl)hexyl group, 6-(5-n-hexyl-2-piperazinyl)hexyl group, 6-(6-methyl-2-piperazinyl)hexyl group, 6-(6-ethyl-2-piperazinyl)hexyl group, 6-(6-n-propyl-2-piperazinyl)hexyl group, 6-(6-n-butyl-2-piperazinyl)hexyl group, 6-(6-n-pentyl-2-piperazinyl)hexyl group, 6-(6-n-hexyl-2-piperazinyl)hexyl group, 2,3-dimethyl-1-piperazinylmethyl group, 3,3-dimethyl-1-piperazinylmethyl group, and 2-(1,3,4-trimethyl-2-piperazinyl)ethyl group.

Examples of the morpholinyl lower alkyl group include a lower alkyl group as illustrated above (preferably a linear or branched alkyl group having 1 to 6 carbon atoms) having 1 to 2 (preferably 1) morpholinyl groups. Specific examples thereof include a 2-morpholinylmethyl group, 3-morpholinylmethyl group, 4-morpholinylmethyl group, 2-(2-morpholinyl)ethyl group, 2-(3-morpholinyl)ethyl group, 2-(4-morpholinyl)ethyl group, 1-(2-morpholinyl)ethyl group, 1-(3-morpholinyl)ethyl group, 1-(4-morpholinyl)ethyl group, 3-(2-morpholinyl)propyl group, 3-(3-morpholinyl)propyl group, 3-(4-morpholinyl)propyl group, 4-(2-morpholinyl)butyl group, 4-(3-morpholinyl)butyl group, 4-(4-morpholinyl)butyl group, 5-(2-morpholinyl)pentyl group, 5-(3-morpholinyl)pentyl group, 5-(4-morpholinyl)pentyl group, 6-(2-morpholinyl)hexyl group, 6-(3-morpholinyl)hexyl group, 6-(4-morpholinyl)hexyl group, 3-methyl-3-(2-morpholinyl)propyl group, 3-methyl-3-(3-morpholinyl)propyl group, 3-methyl-3-(4-morpholinyl)propyl group, 1,1-dimethyl-2-(2-morpholinyl)ethyl group, 1,1-dimethyl-2-(3-morpholinyl)ethyl group, and 1,1-dimethyl-2-(4-morpholinyl)ethyl group.

Example of a thienyl lower alkyl group (that may have a lower alkyl group as a substituent on the thienyl group) include a lower alkyl group as illustrated above (preferably a linear or branched alkyl group having 1 to 6 carbon atoms) having 1 to 2 (preferably 1) thienyl groups, on which 1 to 3 (preferably 1) lower alkyl groups as illustrated above (preferably a linear or branched alkyl group having 1 to 6 carbon atoms) may be present as a substituent(s). Specific examples thereof include a (2- or 3-)thienylmethyl group, 2-[(2- or 3-)thienyl]ethyl group, 1-[(2- or 3-)thienyl]ethyl group, 3-[(2- or 3-)thienyl]propyl group, 4-[(2- or 3-)thienyl]butyl group, 5-[(2- or 3-)thienyl]pentyl group, 6-[(2- or 3-)thienyl]hexyl group, 1,1-dimethyl-2-[(2- or 3-)thienyl]ethyl group, 2-methyl-3-[(2- or 3-)thienyl]propyl group, 3-methyl-(2-, 4-, or 5-)-thienylmethyl group, [5-methyl-(2,3- or 4-)thienyl]methyl group, [4-ethyl-(2- or 3-)thienyl]methyl group, [5-n-propyl-(2,3- or 4-)thienyl]methyl group, [3-n-butyl-(2-, 4-, or 5-)-thienyl]]methyl group, [4,5-dimethyl-(2- or 3-)thienyl]methyl group, (3,4,5-trimethyl-2-thienyl)methyl group, 2-[3-methyl-(2-, 4-, or 5-)-thienyl]ethyl group, 1-[4-n-pentyl-(2- or 3-)thienyl]ethyl group, 3-[3-hexyl-2-thienyl]propyl group, 4-[4,5-dimethyl-(2- or 3-)thienyl]butyl group, 5-(2,4,5-trimethyl-3-thienyl)pentyl group, and 6-[5-ethyl-(2-, 3-, or 4-)thienyl]hexyl group.

Examples of the thiazolyl group include a (2-, 4- or 5-)thiazolyl group.

Examples of the thiazolyl lower alkyl group include a lower alkyl group as illustrated above (preferably a linear or branched alkyl group having 1 to 6 carbon atoms) having 1 to 2 (preferably 1) thiazolyl groups. Specific examples thereof include a (2-, 4-, or 5-)thiazolylmethyl group, 2-[(2-, 4-, or 5-)thiazolyl)ethyl group, 1-[(2-, 4-, or 5-)thiazolyl]ethyl group, 3-[(2-, 4-, or 5-)thiazolyl]propyl group, 4-[(2-, 4-, or 5-)thiazolyl]butyl group, 5-[(2-, 4-, or 5-)thiazolyl)]pentyl group, 6-[(2-, 4-, or 5-)thiazolyl)]hexyl group, 1,1-dimethyl-2-[(2-, 4-, or 5-)thiazolyl]ethyl group, and [2-methyl-3-[(2-, 4-, or 5-)thiazolyl]propyl group.

Examples of the dihydrobenzofuryl group include a 2,3-dihydro-(2-, 3-, 4-, 5-, 6- or 7-)benzofuryl group.

Examples of the dihydrobenzofuryl lower alkyl group include a lower alkyl group as illustrated above (preferably a linear or branched alkyl group having 1 to 6 carbon atoms) having 1 to 2 (preferably 1) dihydrobenzofuryl groups. Specific examples thereof include a 2,3-dihydro-4-benzofurylmethyl group, 2-(2,3-dihydro-4-benzofuryl)ethyl group, 3-(2,3-dihydro-4-benzofuryl)propyl group, 4-(2,3-dihydro-4-benzofuryl)butyl group, 5-(2,3-dihydro-4-benzofuryl)pentyl group, 6-(2,3-dihydro-4-benzofuryl)hexyl group, 2,3-dihydro-5-benzofurylmethyl group, 2-(2,3-dihydro-5-benzofuryl)ethyl group, 3-(2,3-dihydro-5-benzofuryl)propyl group, 4-(2,3-dihydro-5-benzofuryl)butyl group, 2,3-dihydro-6-benzofurylmethyl group, 2-(2,3-dihydro-6-benzofuryl)ethyl group, 3-(2,3-dihydro-6-benzofuryl)propyl group, 4-(2,3-dihydro-6-benzofuryl)butyl group, 5-(2,3-dihydro-6-benzofuryl)pentyl group, 2,3-dihydro-7-benzofurylmethyl group, 2,3-dihydro-7-benzofurylethyl group, 3-(2,3-dihydro-7-benzofuryl)propyl group, 4-(2,3-dihydro-7-benzofuryl)butyl group, and 6-(2,3-dihydro-7-benzofuryl)hexyl group.

Examples of the benzopyranyl lower alkyl group (that may have an oxo group as a substituent on the benzopyranyl group) include a lower alkyl group as illustrated above (preferably a linear or branched alkyl group having 1 to 6 carbon atoms) having 1 to 2 (preferably 1) benzopyranyl groups on which an oxo group may be present as a substituent. Specific examples thereof include a (4H-1-benzopyran-2-yl)methyl group, 2-(4H-1-benzopyran-2-yl)ethyl group, 3-(4H-1-benzopyran-2-yl)propyl group, 4-(4H-1-benzopyran-2-yl)butyl group, 5-(4H-1-benzopyran-2-yl)pentyl group, 6-(4H-1-benzopyran-2-yl)hexyl group, (4H-1-benzopyran-3-yl)methyl group, 2-(4H-1-benzopyran-3-yl)ethyl group, 3-(4H-1-benzopyran-3-yl)propyl group, 4-(4H-1-benzopyran-3-yl)butyl group, 5-(4H-1-benzopyran-3-yl)pentyl group, 6-(4H-1-benzopyran-3-yl)hexyl group, (4H-1-benzopyran-4-yl)methyl group, 2-(4H-1-benzopyran-4-yl)ethyl group, 3-(4H-1-benzopyran-4-yl)propyl group, 4-(4H-1-benzopyran-4-yl)butyl group, 5-(4H-1-benzopyran-4-yl)pentyl group, 6-(4H-1-benzopyran-4-yl)hexyl group, (2H-1-benzopyran-2-yl)methyl group, 2-(2H-1-benzopyran-2-yl)ethyl group, 3-(2H-1-benzopyran-2-yl)propyl group, 4-(2H-1-benzopyran-2-yl)butyl group, 5-(2H-1-benzopyran-2-yl)pentyl group, 6-(2H-1-benzopyran-2-yl)hexyl group, (2H-1-benzopyran-3-yl)methyl group, 2-(2H-1-benzopyran-3-yl)ethyl group, 3-(2H-1-benzopyran-3-yl)propyl group, 4-(2H-1-benzopyran-3-yl)butyl group, 5-(2H-1-benzopyran-3-yl)pentyl group, 6-(2H-1-benzopyran-3-yl)hexyl group, (2H-1-benzopyran-4-yl)methyl group, 2-(2H-1-benzopyran-4-yl)ethyl group, 3-(2H-1-benzopyran-4-yl)propyl group, 4-(2H-1-benzopyran-4-yl)butyl group, 5-(2H-1-benzopyran-4-yl)pentyl group, 6-(2H-1-benzopyran-4-yl)hexyl group, (1H-2-benzopyran-1-yl)methyl group, 2-(1H-2-benzopyran-1-yl)ethyl group, 3-(1H-2-benzopyran-1-yl)propyl group, 4-(1H-2-benzopyran-1-yl)butyl group, 5-(1H-2-benzopyran-1-yl)pentyl group, 6-(1H-2-benzopyran-1-yl)hexyl group, (1H-2-benzopyran-3-yl)methyl group, 2-(1H-2-benzopyran-3-yl)ethyl group, 3-(1H-2-benzopyran-3-yl)propyl group, 4-(1H-2-benzopyran-3-yl)butyl group, 5-(1H-2-benzopyran-3-yl)pentyl group, 6-(1H-2-benzopyran-3-yl)hexyl group, (1H-2-benzopyran-3-yl)methyl group, 2-(1H-2-benzopyran-4-yl)ethyl group, 3-(1H-2-benzopyran-4-yl)propyl group, 4-(1H-2-benzopyran-4-yl)butyl group, 5-(1H-2-benzopyran-4-yl)pentyl group, 6-(1H-2-benzopyran-4-yl)hexyl group, (4-oxo-4H-1-benzopyran-2-yl)methyl group, 2-(4-oxo-4H-1-benzopyran-2-yl)ethyl group, 3-(4-oxo-4H-1-benzopyran-2-yl)propyl group, 4-(4-oxo-4H-1-benzopyran-2-yl)butyl group, 5-(4-oxo-4H-1-benzopyran-2-yl)pentyl group, 6-(4-oxo-4H-1-benzopyran-2-yl)hexyl group, (4-oxo-4H-1-benzopyran-3-yl)methyl group, 2-(4-oxo-4H-1-benzopyran-3-yl)ethyl group, 3-(4-oxo-4H-1-benzopyran-3-yl)propyl group, 4-(4-oxo-4H-1-benzopyran-3-yl)butyl group, 5-(4-oxo-4H-1-benzopyran-3-yl)pentyl group, 6-(4-oxo-4H-1-benzopyran-3-yl)hexyl group, (4-oxo-4H-1-benzopyran-4-yl)methyl group, (2-oxo-2H-1-benzopyran-3-yl)methyl group, 2-(2-oxo-2H-1-benzopyran-3-yl)ethyl group, 3-(2-oxo-2H-1-benzopyran-3-yl)propyl group, 4-(2-oxo-2H-1-benzopyran-3-yl)butyl group, 5-(2-oxo-2H-1-benzopyran-3-yl)pentyl group, 6-(2-oxo-2H-1-benzopyran-3-yl)hexyl group, (2-oxo-2H-1-benzopyran-4-yl)methyl group, 2-(2-oxo-2H-1-benzopyran-4-yl)ethyl group, 3-(2-oxo-2H-1-benzopyran-4-yl)propyl group, 4-(2-oxo-2H-1-benzopyran-4-yl)butyl group, 5-(2-oxo-2H-1-benzopyran-4-yl)pentyl group, 6-(2-oxo-2H-1-benzopyran-4-yl)hexyl group, (1-oxo-1H-2-benzopyran-3-yl)methyl group, 2-(1-oxo-1H-2-benzopyran-3-yl)ethyl group, 3-(1-oxo-1H-2-benzopyran-3-yl)propyl group, 4-(1-oxo-1H-2-benzopyran-3-yl)butyl group, 5-(1-oxo-1H-2-benzopyran-3-yl)pentyl group, 6-(1-oxo-1H-2-benzopyran-3-yl)hexyl group, (1-oxo-1H-2-benzopyran-4-yl)methyl group, 2-(1-oxo-1H-2-benzopyran-4-yl)ethyl group, 3-(1-oxo-1H-2-benzopyran-4-yl)propyl group, 4-(1-oxo-1H-2-benzopyran-4-yl)butyl group, 5-(1-oxo-1H-2-benzopyran-4-yl)pentyl group, and 6-(1-oxo-1H-2-benzopyran-4-yl)hexyl group.

Examples of the benzimidazolyl lower alkyl group include a lower alkyl group as illustrated above (preferably a linear or branched alkyl group having 1 to 6 carbon atoms) having 1 to 2 (preferably 1) benzimidazolyl groups. Specific examples thereof include a 1-benzimidazolylmethyl group, 2-(1-benzimidazolyl)ethyl group, 3-(1-benzimidazolyl)propyl group, 4-(1-benzimidazolyl)butyl group, 5-(1-benzimidazolyl)pentyl group, 6-(1-benzimidazolyl)hexyl group, 2-benzimidazolylmethyl group, 2-(2-benzimidazolyl)ethyl group, 3-(2-benzimidazolyl)propyl group, 4-(2-benzimidazolyl)butyl group, 5-(2-benzimidazolyl)pentyl group, and 6-(2-benzimidazolyl)hexyl group.

Examples of the indolyl lower alkyl group that may have a lower alkoxycarbonyl group on the lower alkyl group include a lower alkyl group (preferably a linear or branched alkyl group having 1 to 6 carbon atoms) as illustrated above that may have 1 to 3 (preferably 1) lower alkoxycarbonyl groups as illustrated above (preferably linear or branched alkoxycarbonyl groups having 1 to 6 carbon atoms) that may have 1 to 2 (preferably 1) indolyl groups. Specific examples thereof include an indol(-1-, -2-, -3-, -4-, -5-, -6-, or -7-)ylmethyl group, 2-indol(-1-, -2-, -3-, -4-, -5-, -6-, or -7-)ylethyl group, 3-indol(-1-, -2-, -3-, -4-, -5-, -6-, or -7-)ylpropyl group, 4-indol(-1-, -2-, -3-, -4-, -5-, -6-, or -7-)ylbutyl group, 5-indol(-1-, -2-, -3-, -4-, -5-, -6-, or -7-)ylpentyl group, 6-indol(-1-, -2-, -3-, -4-, -5-, -6-, or -7-)ylhexyl group, 3-methyl-3-indol(-1-, -2-, -3-, -4-, -5-, -6-, or -7-)ylpropyl group, 1,1-dimethyl-2-indol(-1-, -2-, -3-, -4-, -5-, -6-, or -7-)ylethyl group, and 1-methoxycarbonyl-2-indol(-1-, -2-, -3-, -4-, -5-, -6-, or -7-)ylethyl group.

Examples of the imidazolyl lower alkyl group having an substituent selected from the group consisting of a carbamoyl group and a lower alkoxycarbonyl group on the lower alkyl group include an imidazolyl lower alkyl group having a 1 to 3, preferably 1, substituents selected from the group consisting of a carbamoyl group and a lower alkoxycarbonyl group as illustrated above on the alkyl group whose lower alkyl moiety is the same as that illustrated above, preferably a linear or branched alkyl group having 1 to 6 carbon atoms. Specific examples thereof include a carbamoyl-[(1-, 2-, 4-, or 5-)imidazolyl]methyl group, methoxycarbonyl-[(1-, 2-, 4-, or 5-)imidazolyl]methyl group, ethoxycarbonyl-[(1-, 2-, 4-, or 5-)imidazolyl]methyl group, n-butoxycarbonyl-[(1-, 2-, 4-, or 5-)imidazolyl]methyl group, isobutoxycarbonyl-[(1-, 2-, 4-, or 5-)imidazolyl]methyl group, tert-butoxycarbonyl-[(1-, 2-, 4-, or 5-)imidazolyl]methyl group, sec-butoxycarbonyl-[(1-, 2-, 4-, or 5-)imidazolyl]methyl group, n-pentyloxycarbonyl-[(1-, 2-, 4-, or 5-)imidazolyl]methyl group, neopentyloxy-[(1-, 2-, 4-, or 5-)imidazolyl]methyl group, n-hexyloxycarbonyl-[(1-, 2-, 4-, or 5-)imidazolyl]methyl group, isohexyloxycarbonyl-[(1-, 2-, 4-, or 5-)imidazolyl]methyl group, 3-methylpentyloxycarbonyl-[(1-, 2-, 4-, or 5-)imidazolyl]methyl group, 1-carbamoyl-2-[(1-, 2-, 4-, or 5-)imidazolyl]ethyl group, 1-methoxycarbonyl-2-[(1-, 2-, 4-, or 5-)imidazolyl]ethyl group, 1,1-dimethoxycarbonyl-2-[(1-, 2-, 4-, or 5-)imidazolyl]ethyl group, 1,1-dicarbamoyl-2-[(1-, 2-, 4-, or 5-)imidazolyl]ethyl group, 2-carbamoyl-1-[(1-, 2-, 4-, or 5-)imidazolyl]ethyl group, 2-methoxycarbonyl-3-[(1-, 2-, 4-, or 5-)imidazolyl]propyl group, 2-carbamoyl-4-[(1-, 2-, 4-, or 5-)imidazolyl]butyl group, 1-methyl-1-carbamoylmethyl-2-[(1-, 2-, 4-, or 5-)imidazolyl]ethyl group, 2-methoxycarbonyl-5-[(1-, 2-, 4-, or 5-)imidazolyl]pentyl group, 3-carbamoyl-6-[(1-, 2-, 4-, or 5-)imidazolyl]hexyl group, 2-methoxycarbonyl-1-[(1-, 2-, 4-, or 5-)imidazolyl]isopropyl group, and 2-carbamoylmethyl-3-[(1-, 2-, 4-, or 5-)imidazolyl]propyl group.

Examples of the pyridyl group that may have a group selected from the group consisting of a lower alkyl group, lower alkoxy group, and lower alkylthio lower alkyl group, as a substituent include a pyridyl group that may have 1 to 4 (preferably 1) groups, as a substituent(s), which are selected from the group consisting of a lower alkyl group as illustrated above (preferably a linear or branched alkyl group having 1 to 6 carbon atoms), a lower alkoxy group as illustrated above preferably a linear or branched alkoxy group having 1 to 6 carbon atoms), and a lower alkylthio lower alkyl group in which the two lower alkyl moieties each are composed of a lower alkyl group as illustrated above (preferably a linear or branched alkyl group having 1 to 6 carbon atoms). Specific examples thereof include a 2-pyridyl group, 3-pyridyl group, 4-pyridyl group, 4-methyl-2-pyridyl group, 5-methyl-2-pyridyl group, 5-ethyl-3-pyridyl group, 2-n-propyl-3-pyridyl group, 4-n-butyl-2-pyridyl group, 4-tert-butyl-2-pyridyl group, 5-n-pentyl-3-pyridyl group, 4-n-hexyl-2-pyridyl group, 4-methoxy-2-pyridyl group, 5-methoxy-2-pyridyl group, 2-methylthiomethyl-3-pyridyl group, 5-ethylthiomethyl-2-pyridyl group, 4-n-propylthiomethyl-2-pyridyl group, 3-n-butylthiomethyl-2-pyridyl group, 5-n-pentylthiomethyl-3-pyridyl group, 4-n-hexylthiomethyl-3-pyridyl group, 2-(2-methylthioethyl)-3-pyridyl group, 2-(3-methylthiopropyl)-4-pyridyl group, 3-(4-methylthiobutyl)-4-pyridyl group, 4-(6-methylthiopentyl)-2-pyridyl group, 4-(6-methylthiohexyl)-2-pyridyl group, 3,4-dimethyl-2-pyridyl group, 2,4,6-triethyl-3-pyridyl group, 2,3,5,6-tetramethyl-4-pyridyl group, and 2-methyl-3-methylthiomethyl-4-pyridyl group.

Examples of the pyrrolidinyl group that may have a group selected from the group consisting of a lower alkyl group, lower alkoxycarbonyl group, lower alkanoyl group, and aroyl group as a substituent include a pyrrolidinyl group that may have 1 to 3, preferably 1 group, as a substituent(s), which is selected from the group consisting of a lower alkyl group as illustrated above (preferably a linear or branched alkyl group having 1 to 6 carbon atoms), a lower alkoxycarbonyl group as illustrated above (preferably a linear or branched alkoxycarbonyl group having 1 to 6 carbon atoms) a lower alkanoyl group as described above (preferably a linear or branched alkanoyl group having 1 to 6 carbon atoms), and an aroyl group (preferably a benzoyl group). Specific examples thereof include a pyrrolidin-1-yl group, pyrrolidin-2-yl group, pyrrolidin-3-yl group, 1-methylpyrrolidin-3-yl group, 2-ethylpyrrolidin-3-yl group, 3-n-propylpyrrolidin-3-yl group, 4-n-butylpyrrolidin-3-yl group, 1-tert-butylpyrrolidin-3-yl group, 5-n-pentylpyrrolidin-3-yl group, 1-n-hexylpyrrolidin-2-yl group, 2-methoxycarbonyl-2-yl group, 3-ethoxycarbonylpyrrolidin-2-yl group, 1-tert-butoxycarbonylpyrrolidin-3-yl group, 4-propoxycarbonylpyrrolidin-2-yl group, 5-butoxycarbonylpyrrolidin-2-yl group, 1-pentoxycarbonyl-2-yl group, 2-hexyloxycarbonylpyrrolidin-2-yl group, 1,3-dimethoxycarbonylpyrrolidin-2-yl group, 3,4,5-triethylpyrrolidin-2-yl group, 2,3,4,5-tetramethylpyrrolidin-1-yl group, 2,4-dimethoxycarbonylpyrrolidin-1-yl group, 3,4,5-triethoxycarbonylpyrrolidin-1-yl group, 2-methyl-4-methoxycarbonylpyrrolidin-1-yl group, 1-benzoylpyrrolidin-3-yl group, 1-acetylpyrrolidin-3-yl group, and 1-butyrylpyrrolidin-3-yl group.

Examples of the piperidyl group that may have a group as a substituent selected from the group consisting of a lower alkyl group, a lower alkoxycarbonyl group, a lower alkanoyl group, and an aroyl group that may have a group selected from the group consisting of a lower alkyl group and a halogen atom include a piperidyl group that may have 1 to 5 (preferably 1 to 4) groups, as a substituent(s), which are selected from the group consisting of
a lower alkyl group as illustrated above (preferably a linear or branched alkyl group having 1 to 6 carbon atoms);
a lower alkoxy group as illustrated above (preferably a linear or branched alkoxy group having 1 to 6 carbon atoms);
a lower alkanoyl group as illustrated above (preferably a linear or branched alkanoyl group having 1 to 6 carbon atoms); and
an aroyl group that may have 1 to 3 groups (preferably 1 group) selected from the group consisting of a lower alkyl group as illustrated above and a halogen atom as illustrated above (preferably a benzoyl group). Specific examples thereof include a 1-piperidyl group, 2-piperidyl group, 3-piperidyl group, 4-piperidyl group, 1-methyl-4-piperidyl group, 2-ethyl-4-piperidyl group, 3-n-propyl-4-piperidyl group, 4-n-butyl-4-piperidyl group, 1-n-pentyl-4-piperidyl group, 2-n-hexyl-4-piperidyl group, 1-methoxycarbonyl-4-piperidyl group, 1-ethoxycarbonyl-4-piperidyl group, 4-n-propoxycarbonyl-4-piperidyl group, 5-n-butoxycarbonyl-4-piperidyl group, 1-tert-butoxycarbonyl-4-piperidyl group, 1-formyl-4-piperidyl group, 1-acetyl-4-piperidyl group, 1-butyryl-4-piperidyl group, 1-butyryl-3-piperidyl group, 2-propionyl-4-piperidyl group, 3-butyryl-4-piperidyl group, 4-isobutyryl-4-piperidyl group, 1-n-pentanoyl-4-piperidyl group, 2-tert-butylcarbonyl-4-piperidyl group, 3-n-hexanoyl-4-piperidyl group, 1-benzoyl-4-piperidyl group, 1-benzoyl-3-piperidyl group, 1-(2-, 3-, or 4-chlorobenzoyl)-4-piperidyl group, 1-(2-, 3-, or 4-fluorobenzoyl)-4-piperidyl group, 1-(2-, 3-, or 4-methylbenzoyl)-4-piperidyl group, 2,6-dimethyl-4-piperidyl group, 2,4,6-trimethyl-3-piperidyl group, 2,2,6,6-tetramethyl-4-piperidyl group, and 2,2,4,4,6-pentamethyl-3-piperidyl group.

Examples of the tetrahydrofuryl group that may have an oxo group include a 2-tetrahydrofuryl group, 3-tetrahydrofuryl group, 3-oxo-2-tetrahydrofuryl group, 4-oxo-2-tetrahydrofuryl group, 5-oxo-2-tetrahydrofuryl group, 2-oxo-3-tetrahydrofuryl group, 4-oxo-3-tetrahydrofuryl group, and 5-oxo-4-tetrahydrofuryl group.

Examples of the hexahydroazepinyl group that may have an oxo group include 2-hexahydroazepinyl group, 3-hexahydroazepinyl group, 4-hexahydroazepinyl group, 2-oxo-3-hexahydroazepinyl group, 3-oxo-2-hexahydroazepinyl group, 4-oxo-2-hexahydroazepinyl group, 5-oxo-2-hexahydroazepinyl group, and 6-oxo-2-hexahydroazepinyl group.

Examples of the pyrazolyl group that may have a group selected from the group consisting of a lower alkyl group, aryl group, and furyl group as a substituent include a pyrazolyl group that may have 1 to 3 (preferably 1 to 2) groups, as a substituent(s), which are selected from the group consisting of a lower alkyl group as illustrated above (preferably a linear or branched alkyl group having 1 to 6 carbon atoms);

an aryl group as illustrated above; and a furyl group. Specific examples thereof include a 1-pyrazolyl group, 3-pyrazolyl group, 4-pyrazolyl group, 1-methyl-5-pyrazolyl group, 1-ethyl-5-pyrazolyl group, 3-n-propyl-5-pyrazolyl group, 4-n-butyl-5-pyrazolyl group, 1-tert-butyl-4-pyrazolyl group, 1-n-pentyl-4-pyrazolyl group, 3-n-hexyl-4-pyrazolyl group, 3-phenyl-5-pyrazolyl group, 1-(2-naphthyl)-3-pyrazolyl group, 4-(2-methylphenyl)-3-pyrazolyl group, 5-(3-ethylphenyl)-3-pyrazolyl group, 1-(4-n-propylphenyl)-4-pyrazolyl group, 3-(2-n-butylphenyl)-4-pyrazolyl group, 5-(3-n-pentylphenyl)-4-pyrazolyl group, 1-(4-n-hexylphenyl)-5-pyrazolyl group, 3-(2-isobutylphenyl)-5-pyrazolyl group, 4-(3-tert-butylphenyl)-5-pyrazolyl group, 3-(2-chlorophenyl)-1-pyrazolyl group, 4-(3-fluorophenyl)-1-pyrazolyl group, 5-(4-bromophenyl)-1-pyrazolyl group, 1-(2-aminophenyl)-3-pyrazolyl group, 4-(2,3-dimethylphenyl)-3-pyrazolyl group, 5-(3,4,5-trimethylphenyl)-3-pyrazolyl group, 1-(2,3-diaminophenyl)-4-pyrazolyl group, 3-(2-furyl)-5-pyrazolyl group, 1,3-dimethyl-5-pyrazolyl group, 1,3,4-triethyl-5-pyrazolyl group, 1,3,5-trimethyl-4-pyrazolyl group, and 1-methyl-3-phenyl-5-pyrazolyl group.

Examples of the thiadiazolyl group include a 1,2,3-thiadiazolyl group, 1,2,4-thiadiazolyl group, 1,2,5-thiadiazolyl group or 1,3,4-thiadiazolyl group.

Examples of the thiadiazolyl group that may have a lower alkyl group include a thiadiazolyl group as illustrated above that may have 1 to 3, preferably 1, lower alkyl groups as illustrated above (preferably a linear or branched alkyl group having 1 to 6 carbon atoms). Specific examples thereof include a 4- or 5-(1,2,3-thiadiazolyl) group, 3- or 5-(1,2,4-thiadiazolyl) group, 3-(1,2,5-thiadiazolyl) group, 2-(1,3,4-thiadiazolyl) group, 5-methyl-1,3,4-thiadiazol-2-yl group, 4-ethyl-1,2,3-thiadiazol-5-yl group, 5-n-propyl-1,2,4-thiadiazol-3-yl group, 5-n-butyl-1,3,4-thiadiazol-2-yl group, 4-tert-butyl-1,2,3-thiadiazol-5-yl group, 5-n-pentyl-1,2,4-thiadiazol-3-yl group, and 5-n-hexyl-1,3,4-thiadiazol-2-yl group.

Examples of an isoxazolyl group that may have a lower alkyl group include an isoxazolyl group that may have 1 to 2 lower alkyl group as illustrated above (preferably a linear or branched alkyl group having 1 to 6 carbon atoms). Specific examples thereof include a 3-isoxazolyl group, 4-isoxazolyl group, 5-isoxazolyl group, 3-methyl-5-isoxazolyl group, 4-ethyl-5-isoxazolyl group, 4-n-propyl-3-isoxazolyl group, 5-methyl-3-isoxazolyl group, 5-n-butyl-3-isoxazolyl group, 3-tert-butyl-4-isoxazolyl group, 5-n-pentyl-4-isoxazolyl group, 3-n-hexyl-5-isoxazolyl group, and 3,4-dimethyl-5-isoxazolyl group.

Examples of the indazolyl group include a (1-, 3-, 4-, 5-, 6- or 7-)indazolyl group.

Examples of the tetrahydrobenzothiazolyl group include a (2-, 4-, 5-, 6-, or 7-) (4,5,6,7-tetrahydrobenzothiazolyl) group.

Examples of the tetrahydroquinolyl group include a (1-, 2-, 4-, 5-, 6- or -8)(1,2,3,4-tetrahydroquinolyl) group.

Example of a tetrahydroquinolyl group that may have a group selected from the group consisting of a lower alkyl group, lower alkoxy group, halogen atom and oxo group as a substituent include a tetrahydroquinolyl group as illustrated above that may have 1 to 3 (preferably 1 to 2) groups, as a substituent(s), which are selected from the group consisting of a lower alkyl group as illustrated above (preferably a linear or branched alkyl group having 1 to 6 carbon atoms);

a lower alkoxy group as illustrated above (preferably a linear or branched alkoxy group having 1 to 6 carbon atoms); a halogen atom; and an oxo group. Specific examples thereof include a 1-(1,2,3,4-tetrahydroquinolyl) group, 2-(1,2,3,4-tetrahydroquinolyl) group, 3-(1,2,3,4-tetrahydroquinolyl) group, 4-(1,2,3,4-tetrahydroquinolyl) group, 5-(1,2,3,4-tetrahydroquinolyl) group, 6-(1,2,3,4-tetrahydroquinolyl) group, 7-(1,2,3,4-tetrahydroquinolyl) group, 8-(1,2,3,4-tetrahydroquinolyl) group, 2-methyl-3-(1,2,3,4-tetrahydroquinolyl) group, 3-ethyl-2-(1,2,3,4-tetrahydroquinolyl) group, 4-n-propyl-2-(1,2,3,4-tetrahydroquinolyl) group, 5-n-butyl-3-(1,2,3,4-tetrahydroquinolyl) group, 6-tert-butyl-3-(1,2,3,4-tetrahydroquinolyl) group, 7-n-pentyl-2-(1,2,3,4-tetrahydroquinolyl) group, 8-n-hexyl-2-(1,2,3,4-tetrahydroquinolyl) group, 2-methoxy-4-(1,2,3,4-tetrahydroquinolyl) group, 3-ethoxy-4-(1,2,3,4-tetrahydroquinolyl) group, 4-propoxy-5-(1,2,3,4-tetrahydroquinolyl) group, 5-butoxy-6-(1,2,3,4-tetrahydroquinolyl) group, 6-pentoxy-7-(1,2,3,4-tetrahydroquinolyl) group, 7-hexyloxy-8-(1,2,3,4-tetrahydroquinolyl) group, 4-oxo-3-(1,2,3,4-tetrahydroquinolyl) group, 2-oxo-(1-, 3-, 4-, 5-, 6-, 7-, or 8-)-(1,2,3,4-tetrahydroquinolyl) group, 2-oxo-8-methyl-(3-, 4-, 5-, 6-, or 7-)-(1,2,3,4-tetrahydroquinolyl) group, 2-oxo-8-methoxy-3-(1,2,3,4-tetrahydroquinolyl) group, 2-oxo-5-methoxy-(1-, 3-, 4-, 6-, 7-, or 8-)-(1,2,3,4-tetrahydroquinolyl) group, 2-oxo-8-fluoro-(3-, 4-, 5-, 6-, or 7-)-(1,2,3,4-tetrahydroquinolyl) group, and 2-oxo-6,8-dimethyl-3-(1,2,3,4-tetrahydroquinolyl) group.

Examples of the quinolyl group include a 2-quinolyl group, 3-quinolyl group, 4-quinolyl group, 5-quinolyl group, 6-quinolyl group, 7-quinolyl group, and 8-quinolyl group. Examples of the quinolyl group that may have a lower alkyl group include a quinolyl group that may have 1 to 2 lower alkyl groups as illustrated above (preferably linear or branched alkyl groups having 1 to 6 carbon atoms). Specific examples thereof include a 2-, 3-, 4-, 5-, 6-, 7- or 8-quinolyl group, 2-methyl-6-quinolyl group, 4-ethyl-5-quinolyl group, 4-n-propyl-3-quinolyl group, 5-methyl-3-quinolyl group, 5-n-butyl-3-quinolyl group, 3-tert-butyl-4-quinolyl group, 5-n-pentyll-4-quinolyl group, 3-n-hexyl-5-quinolyl group and 3,4-dimethyl-5-quinolyl group.

Examples of the benzodioxolyl lower alkyl group include a lower alkyl group as illustrated above (preferably a linear or branched alkyl group having 1 to 6 carbon atoms) having 1 to 2 (preferably 1) benzodioxolyl groups. Specific examples thereof include a 2-, 4- or 5-(1,3-benzodioxolyl)methyl group, 2-(2-, 4- or 5-)(1,3-benzodioxolyl)ethyl group and 3-(2-, 4- or 5-)(1,3-benzodioxolyl) propyl group.

Examples of the aryl group that may have a group selected from the group consisting of a halogen atom; a lower alkyl group; a lower alkoxy group; a halogen substituted lower alkyl group; a halogen substituted lower alkoxy group; a lower alkenyl group; an amino group that may have a group selected from the group consisting of a lower alkylsulfonyl group, lower alkyl group, and aryl group; a sulfamoyl group; a lower alkylthio group; a lower alkanoyl group; a lower alkoxycarbonyl group; a pyrrolyl group; lower alkynyl group; cyano group, nitro group; aryloxy group; aryl lower alkoxy group; hydroxy group; hydroxy lower alkyl group; carbamoyl group that may have a group selected from the group consisting of a lower alkyl group and an aryl group; pyrazolyl group; pyrrolidinyl group that may have an oxo group; oxazolyl group; imidazolyl group that may have a lower alkyl group; dihydrofuryl group that may have an oxo group; thiazolidinyl lower alkyl group that may have an oxo group; imidazolyl lower alkanoyl group; and piperidinylcarbonyl group include an aryl group as illustrated above that may have 1 to 7, preferably 1 to 5, more preferably, 1 to 2 groups, as a substituent(s), which are selected from the group consisting of a halogen atom as illustrated above;

a lower alkyl group as illustrated above (preferably a linear or branched alkyl group having 1 to 6 carbon atoms);

a lower alkoxy group as illustrated above (preferably a linear or branched alkoxy group having 1 to 6 carbon atoms);

a halogen substituted lower alkyl group as illustrated above (preferably a linear or branched alkyl group having 1 to 6 carbon atoms substituted with 1 to 7 halogen atoms);

a halogen substituted lower alkoxy group as illustrated above (preferably a linear or branched alkoxy group having 1 to 6 carbon atoms substituted with 1 to 7 halogen atoms);

a lower alkenyl group as illustrated above (preferably a linear or branched alkenyl group having 1 to 3 double bonds and 2 to 6 carbon atoms (including both trans and cis configurations));

an amino group having 1 to 2 lower alkanoyl groups as illustrated above, lower alkyl groups as illustrated above, and aryl groups as illustrated above;

a sulfamoyl group;

a lower alkylthio group whose lower alkyl moiety is a lower alkyl group as illustrated above (preferably a linear or branched alkyl group having 1 to 6 carbon atoms);

a lower alkanoyl group as illustrated above (preferably a linear or branched alkanoyl group having 1 to 6 carbon atoms);

a lower alkoxycarbonyl group as illustrated above (preferably a linear or branched alkoxycarbonyl group having 1 to 6 carbon atoms); a pyrrolyl group; an alkynyl group as illustrated below; cyano group; nitro group; aryloxy group whose aryl moiety is as illustrated above; aryl lower alkoxy group whose aryl moiety and lower alkoxy moiety are as illustrated above; hydroxy group; a hydroxy lower alkyl group whose lower alkyl moiety is as illustrated above; a carbamoyl group that may have 1 to 2 groups selected from the group consisting of a lower alkyl group as illustrated above and aryl group as illustrated above; pyrazolyl group; pyrrolidinyl group that may have 1 to 2 (preferably 1) oxo groups; oxazolyl group; imidazolyl group that may have 1 to 3 (preferably 1 to 2) lower alkyl groups as illustrated above; dihydrofuryl group that may have 1 to 2 (preferably 1) oxo groups; thiazolidinyl group that may have 1 to 2 (preferably 1) oxo groups and having an lower alkyl moiety as illustrated above; imidazolyl lower alkanoyl group whose alkanoyl moiety is as illustrated above and piperidinylcarbonyl group. Specific examples thereof include a phenyl group, 1-naphthyl group, 2-naphthyl group, (2-, 3-, or 4-)biphenyl group, (2-, 3-, or 4-)chlorophenyl group, (2-, 3-, or 4-)fluorophenyl group, (2-, 3-, or 4-)bromophenyl group, (2-, 3-, or 4-)methylphenyl group, (2-, 3-, 4-, 5-, 6-, 7-, or 8-)ethyl-1-naphthyl group, (2-, 3-, or 4-)n-propylphenyl group, (2-, 3-, or 4-)n-butylphenyl group, (2-, 3-, or 4-)n-pentylphenyl group, (2-, 3-, 4-, 5-, 6-, 7-, or 8-)n-hexyl-1-naphthyl group, (2-, 3-, or 4-)isobutylphenyl group, (2-, 3-, 4-, 5-, 6-, 7-, or 8-)tert-butyl-1-naphthyl group, (2-, 3-, or 4-)methoxyphenyl group, (2-, 3-, 4-, 5-, 6-, 7-, or 8-)ethoxy-1-naphthyl group, (2-, 3-, or 4-)n-propoxyphenyl group, (2-, 3-, 4-, 5-, 6-, 7-, or 8-)isopropoxy-1-naphthyl group, (2-, 3-, or 4-)n-butoxyphenyl group, (1-, 3-, 4-, 5-, 6-, 7-, or 8-)isobutoxy-2-naphthyl group, (2-, 3-, or 4-)tert-butoxyphenyl group, (2-, 3-, 4-, 5-, 6-, 7-, or 8-)sec-butoxy-1-naphthyl group, (2-, 3-, or 4-)n-pentyloxyphenyl group, (2-, 3-, 4-, 5-, 6-, 7-, or 8-)isopentyloxy-1-naphthyl group, (2-, 3-, or 4-)neopentyloxyphenyl group, (1-, 3-, 4-, 5-, 6-, 7-, or 8-)n-hexyloxy-2-naphthyl group, (2-, 3-, or 4-)isohexyloxyphenyl group, (2-, 3-, 4-, 5-, 6-, 7-, or 8-)(3-methylpentyloxy)-1-naphthyl group, (2-, 3-, or 4-)chloromethylphenyl group, (2-, 3-, or 4-)trifluoromethylphenyl group, (2-, 3-, 4-, 5-, 6-, 7-, or 8-)fluoroethyl-1-naphthyl group, (2-, 3-, or 4-)(3-bromopropyl)phenyl group, (2-, 3-, or 4-)(4-chlorobutyl)phenyl group, (2-, 3-, or 4-)(5-fluoropentyl)phenyl group, (2-, 3-, 4-, 5-, 6-, 7-, or 8-)(6-bromohexyl)-1-naphthyl group, (2-, 3-, or 4-)(1,1-dimethyl-2-chloroethyl)phenyl group, (1-, 3-, 4-, 5-, 6-, 7-, or 8-)(2-methyl-3-fluoropropyl)-2-naphthyl group, (2-, 3-, or 4-)chloromethoxyphenyl group, (2-, 3-, 4-, 5-, 6-, 7-, or 8-)(2-fluoroethoxy)-1-naphthyl group, (2-, 3-, or 4-)(3-bromopropoxy)phenyl group, (2-, 3-, or 4-)(4-chlorobutoxy)phenyl group, (2-, 3-, or 4-)(5-fluoropentyloxy)phenyl group, (2-, 3-, or 4-)trifluoromethoxyphenyl group, 4-(6-bromohexyloxy)-1-naphthyl group, (2-, 3-, or 4-)(1,1-dimethyl-2-chloroethoxy)phenyl group, 7-(2-methyl-3-fluoropropoxy)-2-naphthyl group, 2-vinylphenyl group, 2-(1-methylvinyl)phenyl group, 2-(1-propenyl)-1-naphthyl group, (2-, 3-, or 4-)(1-methyl-1-propenyl)phenyl group, 3-(2-methyl-1-propenyl)-1-naphthyl group, (2-, 3-, or 4-)(1-propenyl)phenyl group, (2-, 3-, or 4-)(2-propenyl)phenyl group, 4-(2-butenyl)-1-naphthyl group, (2-, 3-, or 4-)(1-butenyl)phenyl group, 5-(3-butenyl)-1-naphthyl group, (2-, 3-, or 4-)(2-pentenyl)phenyl group, 6-(1-pentenyl)-1-naphthyl group, (2-, 3-, or 4-)(3-pentenyl)phenyl group, 7-(4-pentenyl)-1-naphthyl group, (2-, 3-, or 4-)(1,3-butadienyl)phenyl group, 8-(1,3-pentadienyl)-1-naphthyl group, (2-, 3-, or 4-)(2-penten-4-ynyl)phenyl group, 1-(2-hexenyl)-2-naphthyl group, 4-(1-hexenyl)phenyl group, a 3-(5-hexenyl)-2-naphthyl group, (2-, 3-, or 4-)(3-hexenyl) group, 4-(4-hexenyl)-2-naphthyl group, (2-, 3-, or 4-)(3,3-dimethyl-1-propenyl)phenyl group, 5-(2-ethyl-1-propenyl)-2-naphthyl group, 4-(1,3,5-hexatrienyl)phenyl group, 6-(1,3-hexadienyl)-2-naphthyl group, (2-, 3-, or 4-)(1,4-hexadienyl)phenyl group, (2-, 3-, or 4-)(N-formylamino)phenyl group, (2-, 3-, or 4-)(N-acetylamino)phenyl group, 7-(N-acetylamino)-2-naphthyl group, (2-, 3-, or 4-)(N-propionylamino)phenyl group, 8-(N-butyrylamino)-2-naphthyl group, (2-, 3-, or 4-)(N-isobutyrylamino)phenyl group, 2-(N-pentanoylamino)-1-naphthyl group, (2-, 3-, or 4-)(N-tert-butylcarbonylamino)phenyl group, 3-(N-hexanoylamino)-1-naphthyl group, (2-, 3-, or 4-)(N,N-diformylamino)phenyl group, 4-(N,N-diacetylamino)-1-naphthyl group, (2-, 3-, or 4-)(N,N-dimethylamino)phenyl group, (2-, 3-, or 4-)(N-phenylamino)phenyl group, (2-, 3-, or 4-)sulfamoylphenyl group, 5-sulfamoyl-1-naphthyl group, (2-, 3-, or 4-)methylthiophenyl group, 6-ethylthio-1-naphthyl group, (2-, 3-, or 4-)n-propylthiophenyl group, 7-isopropylthio-1-naphthyl group, (2-, 3-, or 4-)n-butylthiophenyl group, 8-tert-butylthio-1-naphthyl group, (2-, 3-, or 4-)n-pentylthiophenyl group, 1-n-hexylthio-2-naphthyl group, (2-, 3-, or 4-)(N-methyl(sulfonylamino)phenyl group, (2-, 3-, or 4-)formylphenyl group, (2-, 3-, or 4-)acetylphenyl group, (2-, 3-, or 4-)butyrylphenyl group, 3-acetyl-2-naphthyl group, (2-, 3-, or 4-)propionylphenyl group, 4-butyryl-2-naphthyl group, (2-, 3-, or 4-)isobutyrylphenyl group, 5-pentanoyl-2-naphthyl group, (2-, 3-, or 4-)cyanophenyl group, (2-, 3-, or 4-)methoxycarbonylphenyl group, (2-, 3-, or 4-)tert-butylcarbonylphenyl group, 6-hexanoyl-2-naphthyl group, (2-, 3-, or 4-)ethoxycarbonylphenyl group, 7-ethoxycarbonyl-2-naphthyl group, (2-, 3-, or 4-)n-propoxycarbonylphenyl group, 8-isopropoxycarbonyl-2-naphthyl group, (2-, 3-, or 4-)n-butoxycarbonylphenyl group, 2-isobutoxycarbonyl-1-naphthyl group, (2-, 3-, or 4-)tert-butoxycarbonylphenyl group, 3-sec-butoxycarbonyl-1-naphthyl group, (2-, 3-, or 4-)n-pentyloxycarbonylphenyl group, 4-neopentyloxy-1-naphthyl group, (2-, 3-, or 4-)n-hexyloxycarbonylphenyl group, 5-isohexyloxycarbonyl-1-naphthyl group, (2-, 3-, or 4-)(3-methylpentyloxycarbonyl)phenyl group, 6-(1-pyrrolyl)-1-naphthyl group, (2-, 3-, or 4-)(1-pyrrolyl)phenyl group, (2-, 3-, or 4-)ethynylphenyl group, (2-, 3-, or 4-)(N-methylcarbamoyl)phenyl group, (2-, 3-, or 4-)(N-phenylcarbamoyl)phenyl group, (2-, 3-, or 4-)(2-hydroxyethyl)phenyl group, (2-, 3-, or 4-)phenoxyphenyl group, (2-, 3-, or 4-)nitrophenyl group, (2-, 3-, or 4-)benzyloxyphenyl group, (2-, 3-, or 4-)hydroxyphenyl group, (2-, 3-, or 4-)(2-oxo-2,5-dihydrofuran-4-yl)phenyl group, (2-, 3-, or 4-)(1-imidazolylacetyl)phenyl group, (2-, 3-, or 4-)(2,4-dioxothiazolidin-5-ylmethyl)phenyl group, (2-, 3-, or 4-)[(1-, 2-, 3-, or 4-)piperidylcarbonyl]phenyl group, (2-, 3-, or 4-)[(1-, 3-, 4-, or 5-)pyrazolyl]phenyl group, (2-, 3-, or 4-)[2-oxo-(1- or 3-)pyrrolidinyl]phenyl group, (2-, 3-, or 4-)[(2-, 4-, or 5-)oxazolyl]phenyl group, (2-, 3-, or 4-)(2-ethyl-4-methylimidazol-1-yl)phenyl group, (2-, 3-, or 4-)biphenyl group, 2,3-dimethoxyphenyl group, 2,4-dimethoxyphenyl group, 2,5-dimethoxyphenyl group, 2,6-dimethoxyphenyl group, 3,4-dimethoxyphenyl group, 3,5-dimethoxyphenyl group, 2,3-dichlorophenyl group, 2,4-dichlorophenyl group, 3,4-dichlorophenyl group, 2-methoxy-5-chlorophenyl group, 2-methoxy-5-methylphenyl group, 2-methoxy-5-acetylaminophenyl group, 2-vinyl-4-methylphenyl group, 2-vinyl-5-ethylphenyl group, 2,6-disulfamoylphenyl group, 2,4,6-trimethoxyphenyl group, 3,4,5-triethoxyphenyl group, 2-vinyl-3,4,5-triethylphenyl group, pentamethoxyphenyl group, 2-vinylnaphthyl group, 2,3-dimethoxy-1-naphthyl group, 3,4-diethoxyphenyl group, 2-methoxy-5-methoxycarbonylphenyl group, 3,5-dimethoxycarbonylphenyl group, 3-chloro-4-hydroxyphenyl group, 2-chloro-5-(N-acetylamino)phenyl group, 2-chloro-5-cyanophenyl group, 2-chloro-5-carbamoylphenyl group, 2-methoxy-5-(N-acetylamino)phenyl group, 2-chloro-5-ethoxycarbonylphenyl group, 3,5,7-triethoxy-1-naphthyl group, 3,4,5,7-tetramethyl-1-naphthyl group, 2,3,4,5-tetramethyl-7-(N-pentaacetylamino)-1-naphthyl group, 2,3,4,5,6,7-hexaethoxy-1-naphthyl group, and heptamethoxy-1-naphthyl group.

Examples of the cyano lower alkyl group include a lower alkyl group as illustrated above (preferably a linear or branched alkyl group having 1 to 6 carbon atoms) having a single cyano group. Specific examples thereof include a cyanomethyl group, 2-cyanoethyl group, 1-cyanoethyl group, 3-cyanopropyl group, 4-cyanobutyl group, 1,1-dimethyl-2-cyanoethyl group, 5-cyanopentyl group, 6-cyanohexyl group, 1-cyanoisopropyl group, and 2-methyl-3-cyanopropyl group.

Examples of the lower alkanoylamino lower alkyl group include a lower alkyl group as illustrated above (preferably a linear or branched alkyl group having 1 to 6 carbon atoms) having 1 to 3, preferably 1, amino groups which has 1 to 2 lower alkanoyl groups as illustrated above (preferably a linear or branched alkanoyl group having 1 to 6 carbon atoms). Specific examples thereof include a 2-(N-formylamino)ethyl group, 2-(N-acetylamino)ethyl group, 2-(N-propionylamino)ethyl group, 2-(N-butyrylamino)ethyl group, 2-(N-isobutyrylamino)ethyl group, 2-(N-pentanoylamino)ethyl group, 2-(N-tert-butylcarbonylamino)ethyl group, 2-(N-hexanoylamino)ethyl group, N-acetylaminomethyl group, 1-(N-acetylamino)ethyl group, 3-(N-acetylamino)propyl group, 4-(N-acetylamino)butyl group, 5-(N-acetylamino)pentyl group, 6-(N-acetylamino)hexyl group, 1,1-dimethyl-2-(N-acetylamino)ethyl group, 2-methyl-3-(N-acetylamino)propyl group, and 2-(N,N-diacetylamino)ethyl group.

Examples of a halogen substituted lower alkylamino group include an amino group having 1 to 2 (preferably 1) halogen substituted lower alkyl groups as illustrated above (preferably a linear or branched halogen substituted alkyl group having 1 to 6 carbon atoms with 1 to 7 (preferably 1 to 3) halogen atoms). Specific examples thereof include an N-fluoromethylamino group, N-difluoromethylamino group, N-trifluoromethylamino group, N-chloromethylamino group, N-dichloromethylamino group, N-trichloromethylamino group, N-bromomethylaminogroup, N-dibromomethylamino group, N-dichlorofluoromethylamino group, N-2,2,2-trifluoroethylamino group, N-pentafluoroethylamino group, N-2-chloroethylamino group, N-3,3,3-trifluoropropylamino group, N-heptafluoropropylamino group, N-heptafluoroisopropylamino group, N-3-chloropropylamino group, N-2-chloropropylamino group, N-3-bromopropylamino group, N-4,4,4-trifluorobutylamino group, N-4,4,4,3,3-pentafluorobutylamino group, N-4-chlorobutylamino group, N-4-bromobutylamino group, N-2-chlorobutylamino group, N-5,5,5-trifluoropentylamino group, N-5-chloropentylamino group, N-6,6,6-trifluorohexylamino group, N-6-chlorohexylamino group, N-(1,1-dimethyl-2-chloroethyl)amino group, N-(2-methyl-3-fluoropropyl)amino group, and N,N-di(fluoromethyl)amino group.

Examples of the lower alkylthio lower alkyl group include a lower alkyl group as illustrated above (preferably a linear or branched alkyl group having 1 to 6 carbon atoms) having 1 to 3 lower alkylthio groups whose alkyl moiety is a lower alkyl group as illustrated above (preferably a linear or branched alkyl group having 1 to 6 carbon atoms). Specific examples thereof include a 2-methylthioethyl group, 2-ethylthioethyl group, 2-n-propylthioethyl group, 2-n-butylthioethyl group, 2-tert-butylthioethyl group, 2-n-pentylthioethyl group, 2-n-hexylthioethyl group, methylthiomethyl group, 1-methylthioethyl group, 3-methylthiopropyl group, 4-methylthiobutyl group, 5-methylthiopentyl group, 6-methylthiohexyl group, 1,1-dimethyl-2-methylthioethyl group, 2-methyl-3-methylthiopropyl group, 2,2-diethylthioethyl group, and 2,2,2-triethylthioethyl group.

Examples of the amidino group that may have a lower alkyl group include an amidino group that may have 1 to 2 lower alkyl groups as illustrated above (preferably a linear or branched alkyl group having 1 to 6 carbon atoms). Specific examples thereof include an amidino group, N-methylamidino group, N-ethylamidino group, N-n-propylamidino group, N-n-butylamidino group, N-n-pentylamidino group, N-n-hexylamidino group, N-isopropylamidino group, N-tert-butylamidino group, N,N-dimethylamidino group, N,N'-dimethylamidino group, and N-methyl-N'-ethyl-amidino group.

Examples of the amidino lower alkyl group include a lower alkyl group as illustrated above (preferably a linear or branched alkyl group having 1 to 6 carbon atoms) having 1 to 3 amidino groups. Specific examples thereof include an amidinomethyl group, 2-amidinoethyl group, 3-amidinopropyl group, 4-amidinobutyl group, 5-amidinopropyl group, 6-amidinohexyl group, 1-amidinoethyl group, 1,1-dimethyl-2-amidinoethyl group, 2-methyl-3-amidinopropyl group, 2,2-diamidinoethyl group, and 2,2,2-triamidinoethyl group.

Examples of the lower alkenyloxy group include a lower alkenyloxy group whose lower alkenyl moiety is one as illustrated above (preferably a linear or branched alkenyloxy group having 1 to 3 double bonds and 2 to 6 carbon atoms). Specific examples thereof include a vinyloxy group, 1-propenyloxy group, 1-methyl-1-propenyloxy group, 2-methyl-1-propenyloxy group, 2-propenyloxy group, 2-butenyloxy group, 1-butenyloxy group, 3-butenyloxy group, 2-pentenyloxy group, 1-pentenyloxy group, 3-pentenyloxy group, 4-pentenyloxy group, 1,3-butadienyloxy group, 1,3-pentadienyloxy group, 2-penten-4-ynyloxy group, 2-hexenyloxy group, 1-hexenyloxy group, 5-hexenyloxy group, 3-hexenyloxy group, 4-hexenyloxy group, 3,3-dimethyl-1-propenyloxy group, 2-ethyl-1-propenyloxy group, 1,3,5-hexatrienyloxy group, 1,3-hexadienyloxy group, and 1,4-hexadienyloxy group.

Examples of the lower alkenyloxy lower alkyl group include a lower alkyl group as illustrated above (preferably a linear or branched alkyl group having 1 to 6 carbon atoms) having 1 to 3 lower alkenyloxy groups whose lower alkenyloxy moiety is a lower alkenyloxy group as illustrated above (preferably a linear or branched alkenyl group having 2 to 6 carbon atoms and 1 to 3 double bonds). Specific examples thereof include a vinyloxymethyl group, 2-vinyloxyethyl group, 2-(1-propenyloxy)ethyl group, 2-(1-methyl-1-propenyloxy)ethyl group, 2-(2-methyl-1-propenyloxy)ethyl group, 2-(2-propenyloxy)ethyl group, 2-(2-butenyloxy)ethyl group, 2-(1-butenyloxy)ethyl group, 2-(3-butenyloxy)ethyl group, 2-(2-pentenyloxy)ethyl group, 2-(1-pentenyloxy)ethyl group, 2-(3-pentenyloxy)ethyl group, 2-(4-pentenyloxy)ethyl group, 2-(1,3-butadienyloxy)ethyl group, 2-(1,3-pentadienyloxy)ethyl group, 2-(2-penten-4-ynyloxy)ethyl group, 2-(2-hexenyloxy)ethyl group, 2-(1-hexenyloxy)ethyl group, 2-(5-hexenyloxy)ethyl group, 2-(3-hexenyloxy)ethyl group, 2-(4-hexenyloxy)ethyl group, 2-(3,3-dimethyl-1-propenyloxy)ethyl group, 2-(2-ethyl-1-propenyloxy)ethyl group, 2-(1,3,5-hexatrienyloxy)ethyl group, 2-(1,3-hexadienyloxy)ethyl group, 2-(1,4-hexadienyloxy)ethyl group, 3-vinyloxypropyl group, 4-vinyloxybutyl group, 5-vinyloxypropyl group, 6-vinyloxyhexyl group, 1-vinyloxyethyl group, 1,1-dimethyl-2-vinyloxyethyl group, 2-methyl-3-vinyloxypropyl group, 2,2-divinyloxyethyl group, and 2,2,2-trivinyloxyethyl group.

Examples of the arylamino group that may have a substituent selected from the group consisting of a lower alkyl group, lower alkoxy group, halogen substituted lower alkyl group, and halogen substituted lower alkoxy group on the aryl group include an amino group having 1 to 2 aryl groups as illustrated above that may have 1 to 7, preferably 1 to 5, more preferably 1 to 2 substituents, on the aryl group, which are selected from the group consisting of a lower alkyl group as illustrated above (preferably a linear or branched alkyl group having 1 to 6 carbon atoms);

a lower alkoxy group as illustrated above (preferably a linear or branched alkoxy group having 1 to 6 carbon atoms);

a halogen substituted alkyl group as illustrated above (preferably a linear or branched alkyl group having 1 to 6 carbon atoms with 1 to 7, preferably 1 to 3 halogen atoms); and halogen substituted lower alkoxy group as illustrated above (preferably a linear or branched alkoxy group having 1 to 6 carbon atoms with 1 to 7, preferably 1 to 3 halogen atoms). Specific examples thereof include an N-phenylamino group, N-2-naphthylamino group, N-(2-methylphenyl) amino group, N-(3-ethyl-1-naphthyl)amino group, N-(4-n-propylphenyl)amino group, N-(2-n-butyl-1-phenyl) amino group, N-(3-n-pentylphenyl)amino group, N-(4-n-hexyl-1-naphthyl)amino group, N-(2-isobutylphenyl) amino group, N-(3-tert-butyl-1-naphthyl)amino group, N-(2-methoxyphenyl)amino group, N-(3-ethoxy-1-naphthyl)amino group, N-(4-n-propoxyphenyl)amino group, N-(3-isopropoxy-1-naphthyl)amino group, N-(n-butoxyphenyl)amino group, N-(1-isobutoxy-2-naphthyl)amino group, N-(tert-butoxyphenyl)amino group, N-(5-sec-butoxy-1-naphthyl)amino group, N-(n-pentyloxyphenyl) amino group, N-(5-isopentyloxy-1-naphthyl)amino group, N-(1-neopentyloxyphenyl)amino group, N-(6-n-hexyloxy-2-naphthyl)amino group, N-(isohexyloxyphenyl) amino group, N-(3-methylpentyloxy-1-naphthyl)amino group, N-(2-trifluoromethylphenyl)amino group, N-(4-trifluoromethylphenyl)amino group, N-(2-chloromethylphenyl)amino group, N-[3-(2-fluoroethyl)-1-naphthyl]amino group, N-[4-(3-bromopropyl)phenyl]amino group, N-[2-(4-chlorobutyl)-1-phenyl]amino group, N-[3-(5-fluoropentyl)phenyl]amino group, N-[4-(6-bromohexyl)-1-naphthyl]amino group, N-[2-(1,1-dimethyl-2-chloroethyl)phenyl]amino group, N-[7-(2-methyl-3-fluoropropyl)-2-naphthyl]amino group, N-(2-chloromethoxyphenyl) amino group, N-(4-trifluoromethoxyphenyl)amino group, N-(3-(2-fluoroethoxy)-1-naphthyl)amino group, N-[4-(3-bromopropoxy)phenyl]amino group, N-[2-(4-chlorobutoxy)-1-phenyl]amino group, N-[3-(5-fluoropentyloxy) phenyl]amino group, N-[4-(6-bromohexyloxy)-1-naphthyl]amino group, N-[2-(1,1-dimethyl-2-chloroethoxy)phenyl]amino group, N-[7-(2-methyl-3-fluoropropoxy)-2-naphthyl]amino group, N-(2-chloromethoxyphenyl)amino group, N-[3-(2-fluoroethoxy)-1-naphthyl]amino group, N-[4-(3-bromopropoxy)phenyl]amino group, N-[2-(4-chlorobutoxy)-1-phenyl]amino group, N-[3-(5-fluoropentyloxy)phenyl]amino group, N-[4-(6-bromohexyloxy)-1-naphthyl]amino group, N-[2-(1,1-dimethyl-2-chloroethoxy)phenyl]amino group, N-[7-(2-methyl-3-fluoropropoxy)-2-naphthyl]amino group, and N,N-diphenylamino group.

Examples of the aryl lower alkenyl group include a lower alkenyl group as illustrated above having an aryl group as illustrated above (preferably a linear or branched alkenyl group having 1 to 3 aryl groups and 1 to 6 carbon atoms). Specific examples thereof include a 2-phenylethenyl group, 3-phenyl-2-propenyl group, 3-[(1- or 2-)naphthyl]-2-propenyl group, 4-[(2-, 3-, or 4-)methylphenyl]-2-butenyl group, 4-[(2-, 3-, or 4-)ethylphenyl]-3-butenyl group, 4-[(2-, 3-, or 4-)n-propylphenyl]-1,3-butadienyl group, 5-[(2-, 3-, or 4-)n-butylphenyl]-1,3,5-hexatrienyl group, 5-[(2-, 3-, or 4-)n-pentylphenyl]-2,4-hexadienyl group, 5-[(2-, 3-, or 4-)n-hexylphenyl]-3-pentenyl group, 3-[(2-, 3-, or 4-)isobutylphenyl]-2-propenyl group, 2-[(2-, 3-, or 4-)tert-butylphenyl]phenyl group, 3-[(2-, 3-, 4-, 5-, 6-, 7-, or 8-)methyl-1-naphthyl]-2-propenyl group, 4-[(1-, 3-, 4-, 5-, 6-, 7-, or 8-)methyl-2-naphthyl]-2-butenyl group, 4-[(2-, 3-, 4-, 5-, 6-, 7-, or 8-)ethyl-1-naphthyl]-3-butenyl group, 4-[(1-, 3-, 4-, 5-, 6-, 7-, or 8-)ethyl-2-naphthyl]-1,3-butadienyl group, 5-[(2-, 3-, 4-, 5-, 6-, 7-, or 8-)n-propyl-1-naphthyl]-1,3,5-hexatrienyl group, 5-[(1-, 3-, 4-, 5-, -6-, 7-, or 8-)n-propyl-2-naphthyl]-2,4-hexadienyl group, 5-[(2-, 3-, 4-, 5-, 6-, 7-, or 8-)n-butyl-1-naphthyl]-3-pentenyl group, 3-[(1-, 3-, 4-, 5-, 6-, 7-, or 8-)n-butyl-2-naphthyl]-2-propenyl group, 2-[(2-, 3-, 4-, 5-, 6-, 7-, or 8-)n-pentyl-1-naphthyl]ethenyl group, 3-[(1-, 3-, 4-, 5-, 6-, 7-, or 8-)n-pentyl-2-naphthyl]-2-propenyl group, 4-[(2-, 3-, 4-, 5-, 6-, 7-, or 8-)n-hexyl-1-naphthyl]-2-butenyl group, 4-[(1-, 3-, 4-, 5-, 6-, 7-, or 8-)n-hexyl-2-naphthyl]-3-butenyl group, 4-[(2-, 3-, 4-, 5-, 6-, 7-, or 8-)isobutyl-1-naphthyl]-1,3-butadienyl group, 5-[(1-, 3-, 4-, 5-, 6-, 7-, or 8-)isobutyl-2-naphthyl]-1,3,5-hexatrienyl group, 5-[(2-, 3-, 4-, 5-, 6-, 7-, or 8-)tert-butyl-1-naphthyl]-2,4-hexadienyl group, 5-[(1-, 3-, 4-, 5-, 6-, 7-, or 8-)tert-butyl-2-naphthyl]-1,3,5-hexatrienyl group, 5-[(2-, 3-, or 4-)chlorophenyl group, (2-, 3-, or 4-)fluorophenyl]-2,4-hexadienyl group, 5-[(2-, 3-, or 4-)bromophenyl]-3-pentenyl group, 3-[(2-, 3-, 4-, 5-, 6-, 7-, or 8-)chloro-1-naphthyl]-2-propenyl group, 2-[(1-, 3-, 4-, 5-, 6-, 7-, or 8-)chloro-2-naphthyl]ethenyl group, 3-[(2-, 3-, 4-, 5-, 6-, 7-, or 8-)fluoro-1-naphthyl]-2-propenyl group, 4-[(1-, 3-, 4-, 5-, 6-, 7-, or 8-)fluoro-2-naphthyl]-2-butenyl group, 4-[(2-, 3-, 4-, 5-, 6-, 7-, or 8-)bromo-1-naphthyl]-3-butenyl group, 4-[(1-, 3-, 4-, 5-, 6-, 7-, or 8-)bromo-2-naphthyl]-1,3-butadienyl group, 5-[(2-, 3-, or 4-)aminophenyl]-1,3,5-hexatrienyl group, 5-[(2-, 3-, 4-, 5-, 6-, 7-, or 8-)amino-1-naphthyl]-2,4-hexadienyl group, 5-[(1-, 3-, 4-, 5-, 6-, 7-, or 8-)amino-2-naphthyl]-3-pentenyl group, 3-(2,3-dimethylphenyl)-2-propenyl group, 2-(3,4-dimethylphenyl)vinyl group, 3-(2,4-dimethylphenyl)-2-propenyl group, 4-(2,5-dimethylphenyl)-2-butenyl group, 4-(2,6-dimethylphenyl)-3-butenyl group, 4-(2,4,6-trimethylphenyl)-1,3-butadienyl group, 5-(3,4,5-trimethylphenyl)-1,3,5-hexatrienyl group, 5-(2,3,4,5-tetraethylphenyl)-2,4-hexadienyl group, 5-(pentamethylphenyl)-3-pentenyl group, 3-(2-methylnaphthyl)-2-propenyl group, 2-(2,3-dimethylnaphthyl)ethenyl group, 3-(3,4-dimethylphenyl)-2-propenyl group, 4-(3,5,7-triethylnaphthyl)-2-butenyl group, 4-(3,4,5,7-tetramethylnaphthyl)-3-butenyl group, 4-(2,3,4,5,7-pentamethylnaphthyl)-1,3-butadienyl group, 5-(2,3,4,5,6,7-hexaethylnaphthyl)-1,3,5-hexatrienyl group, 5-(heptamethylnaphthyl)-2,4-hexadienyl group, 5-(2,3-diaminophenyl)-3-pentenyl group, 3-(2,4,6-triaminophenyl)-2-propenyl group, and 2-(2-methyl-5-chloronaphthyl)ethenyl group.

Examples of the pyridylamino group that may have a lower alkyl group include a pyridylamino group that may have 1 to 3, preferably 1 to 2 lower alkyl groups as illustrated above (preferably a linear or branched alkyl group having 1 to 6 carbon atoms), on the pyridyl group and/or amino group. Specific examples thereof include an N-(2-, 3-, or 4-)pyridylamino group, N-3-methyl-2-pyridylamino group, N-(4-methyl-2-pyridyl)amino group, N-(5-methyl-2-pyridyl)amino group, N-(6-methyl-2-pyridyl)amino group, N-(2-methyl-3-pyridyl)amino group, N-(4-methyl-3-pyridyl)amino group, N-(5-methyl-3-pyridyl)amino group, N-(6-methyl-3-pyridyl)amino group, N-(2-methyl-4-pyridyl)amino group, N-(3-methyl-4-pyridyl)amino group, N-(3-ethyl-2-pyridyl)amino group, N-(4-n-propyl-2-pyridyl)amino group, N-(5-n-propyl-2-pyridyl)amino group, N-(2-n-butyl-3-pyridyl)amino group, N-(4-n-pentyl-3-pyridyl)amino group, N-(5-n-hexyl-3-pyridyl)amino group, N-(2-isopropyl-4-pyridyl)amino group, N-(3-tert-butyl-4-pyridyl)amino group, N-(3-methyl-2-pyridyl)-N-methyl-amino group, and N-(2,4-diethyl-3-pyridyl)-N-methyl-amino group.

Examples of the aryl lower alkyl group (that may have a group selected from the group consisting of halogen atom, lower alkyl group, halogen substituted alkyl group, halogen substituted lower alkoxy group, lower alkoxy group, carbamoyl group, and lower alkoxycarbonyl group, as a substituent, on the aryl group and/or the lower alkyl group) include a lower alkyl group as illustrated above (preferably a linear or branched alkyl group having 1 to 6 carbon atoms) having 1 to 3 (preferably 1) aryl groups as illustrated above. Note that, on the aryl group and/or the alkyl moiety, there may be 1 to 7, preferably 1 to 5, more preferably, 1 to 2 substituents selected from the group consisting of a halogen atom as illustrated above;
a lower alkyl group as illustrated above (preferably a linear or branched alkyl group having 1 to 6 carbon atoms);
a halogen substituted lower alkyl group as illustrated above (preferably a linear or branched alkyl group having 1 to 6 carbon atoms substituted with 1 to 7 halogen atoms);
a lower alkoxy group as illustrated above (preferably a linear or branched alkoxy group having 1 to 6 carbon atoms substituted with 1 to 7 halogen atoms);
a lower alkoxy group as illustrated above (preferably a linear or branched alkoxy group having 1 to 6 carbon atoms);
a carbamoyl group; and
a lower alkoxy-carbonyl group as illustrated above (preferably a linear or branched alkoxycarbonyl group having 1 to 6 carbon atoms). Specific examples of the aryl lower alkyl group (that may have a substituent selected from the group consisting of a halogen atom, lower alkyl group, halogen substituted lower alkyl group, halogen substituted lower alkoxy group, lower alkoxy group, carbamoyl group and lower alkoxycarbonyl group, on the aryl group and/or the lower alkyl group) include a benzyl group, 1-phenylethyl group, 2-phenylethyl group, 1-methyl-1-phenylethyl group, 1,1-dimethyl-2-phenylethyl group, 1,1-dimethyl-3-phenylpropyl group, (2-, 3-, or 4-)fluorobenzyl group, 2-[(2-, 3-, or 4-)fluorophenyl]ethyl group, 1-[(2-, 3-, or 4-)fluorophenyl]ethyl group, 1-[(2-, 3-, or 4-)fluorophenyl]propyl group, 2-[(2,6- or 3,5-)difluorophenyl]ethyl group, 1-(3,5-difluorophenyl)ethyl group, 1-(3,5-difluorophenyl)propyl group, (2-, 3-, or 4-)chlorobenzyl group, 2-[(2-, 3-, or 4-)chlorophenyl]ethyl group, 2-(3,4-dichlorophenyl)ethyl group, 1-(3-chlorophenyl)butyl group, 1-(4-chlorophenyl)butyl group, (2-, 3-, or 4-)trifluoromethylphenylbenzyl group, 1-[(2-, 3-, or 4-)trifluoromethylphenyl]ethyl group, 1-[(2-, 3-, or 54-)trifluoromethylphenyl]propyl group, (2-, 3-, or 4-)methylbenzyl group, 2-[(2- 3-, or 4-)methylphenyl]ethyl group, (2-, 3-, or 4-)trifluoromethoxybenzyl group, 1-[(2-, 3-, or 4-)trifluoromethylphenyl]ethyl group, (2-, 3-, or 4-)methoxybenzyl group, 2-[(2-, 3-, or 4-)methylphenyl]ethyl group, 1-[(2-, 3-, or 4-)methoxyphenyl]propyl group, (2-, 3-, or 4-)ethoxybenzyl group, (3,4- or 3,5-)dimethoxybenzyl group, (3,4- or 3,5-)di(n-butoxy)benzyl group, 2-[(3,5- or 3,4-)dimethoxyphenyl]ethyl group, 2-(2-ethoxyphenyl)ethyl group, 1-(4-methoxyphenyl)butyl group, 1-phenyl-1-methoxycarbonylmethyl group, 1-carbamoyl-2-phenylethyl group, 1-methoxycarbonyl-2-phenylethyl group, 2-methoxycarbonyl-2-phenylethyl group, 2-phenyl-2-hydroxyethyl group, 2-(4-hydroxyphenyl)-1-methoxycarbonylethyl group, 3-chloro-4-difluoromethoxyphenylmethyl group, and naphthylmethyl group.

Examples of the lower alkynyl group include a linear or branched alkynyl group having 2 to 6 carbon atoms. Specific examples thereof include an ethynyl group, 2-propynyl group, 2-butynyl group, 3-butynyl group, 1-methyl-2-propynyl group, 2-pentynyl group, and 2-hexynyl group.

Examples of the aryloxy lower alkyl group (on the aryl group, a group selected from the group consisting of a lower alkoxy group; a carbamoyl group that may have a group selected from the group consisting of a lower alkoxy group and a lower alkyl group; and a pyrrolidinyl group that may have an oxo group, may be present, include an aryl lower alkyl group (preferably a linear or branched alkyl group having 1 to 6 carbon atoms) whose aryl moiety and lower alkyl group are as illustrated above. On the aryl group herein, 1 to 5 (preferably 1 to 2) groups selected from the group consisting of a lower alkoxy group as illustrated above; a carbamoyl group that may have 1 to 2 groups selected from the group consisting of a lower alkoxy group as illustrated above and a lower alkyl group as illustrated above; and oxo group may be present as a substituent(s). Specific examples thereof include a 2-[(2-, 3- or 4-)methoxyphenoxy]ethyl group, 2-[(2-, 3- or 4-)carbamoylphenoxy]ethyl group, 2-[(2-, 3- or 4-)(N-methyl-N-ethoxycarbamoyl)phenoxy]ethyl group and 2-[(2-, 3- or 4-)(2-oxo-1-pyrrolidinyl)phenoxy]ethyl group.

Examples of the isoxazolidinyl group that may have an oxo group include an isoxazolidinyl group that may have 1 to 2 (preferably 1) oxo groups. Specific examples thereof include a 3-oxoisooxazolidin-4- or 5-yl group and 3,5-dioxoisoxazolidin-4-yl group.

Examples of the dihydroindenyl group include a (1-, 2-, 4- or 5-)-1,2-dihydroindenyl group.

Examples of the aryl lower alkoxy lower alkyl group include an aryl lower alkoxy lower alkyl group whose aryl moiety, lower alkoxy moiety and lower alkyl group moiety are as illustrated above. Specific examples thereof include a benzyloxymethyl group, 2-benzyloxyethyl group and 2-benzyloxybutyl group.

Examples of the azetidinyl group that may have a group selected from the group consisting of a lower alkanoyl group and an aroyl group include an azetidinyl group that may have a 1 to 3 (preferably 1) groups selected from a lower alkanoyl group as illustrated above and an aroyl group as illustrated above. Specific examples thereof include a 2- or 3-azetinyl group, 1-acetyl-(2- or 3-)azetidinyl group, 1-butyryl-(2- or 3-)azetidinyl group and 1-benzoyl-(2- or 3-)azetidinyl group.

Examples of the azetidinyl lower alkyl group that may have a group selected from the group consisting of a lower alkanoyl group and an aroyl group include an azetidinyl lower alkyl group that may have 1 to 3 (preferable 1) groups selected from the group consisting of a lower alkanoyl group as illustrated above and an aroyl group as illustrated above and have a lower alkyl moiety as illustrated above. Specific examples thereof include a 2- or 3-azetidinylmethyl group, 2-(2- or 3-azetidinyl)ethyl group, 1-acetyl-(2- or 3-)azetidinylmethyl group, 1-butyryl-(2- or 3-)azetidinylmethyl group, 1-benzoyl-(2- or 3-)azetidinylmethyl group, 2-[1-acetyl-(2- or 3-)azetidinyl]ethyl group, 2-[1-butyryl-(2- or 3-)azetidinyl] ethyl group and 2-[1-benzoyl-(2- or 3-)azetidinyl]ethyl group.

Examples of the tetrazolyl group include a (1- or 5-)tetrazolyl group.

Examples of the indolinyl group that may have an oxo group include an indolinyl group that may have 1 to 2 (preferably 1) oxo groups. Specific examples thereof include a (1-, 3-, 5-, 6-, 7- or 8-)indolinyl group, 2-oxo-(1-, 3-, 5-, 6-, 7- or 8-)indolinyl group and 2,3-dioxo-(1-, 5-, 6-, 7- or 8-)indolinyl group.

Examples of the triazolyl group include a 1,2,4,-trizolyl group and a 1,3,5,-trizolyl group.

Examples of the triazolyl group that may have a group selected from the group consisting of a lower alkyl group and a lower alkylthio group include a triazolyl group as illustrated above that may have 1 to 3 (more preferably 1 to 2) groups selected from the group consisting of a lower alkyl group as illustrated above and a lower alkylthio group as illustrated above. Specific examples thereof include a (1-, 3- or 5-)-1,2,4-triazolyl group, (1-, 2- or 5-)-1,3,5-triazolyl group, 1-methyl-5-methylthio-1,2,4-triazol-3-yl group and 1-methyl-5-methylthio-1,2,3-triazol-2-yl group.

Examples of the imidazolyl group that may have a carbamoyl group include an imidazolyl group that may have 1 to 2 (preferably 1) carbamoyl groups. Specific examples thereof include a (1-, 2-, 4- or 5-)imidazolyl group and a 4-carbamoyl-(1,2- or 5-)imidazolyl group.

Examples of the oxazolyl group that may have a lower alkyl group include an oxazolyl group that may have 1 to 2 (preferably 1) lower alkyl groups as illustrated above. Specific examples thereof include a (2-, 3- or 4-)oxazolyl group and a 4-methyl-(2- or 3-)oxazolyl group.

Examples of the isothiazolyl group that may have a lower alkyl group include an isothiazolyl group that may have 1 to 2 (preferably 1) lower alkyl groups as illustrated above. Specific examples thereof include a (3-, 4- or 5-)isothiazolyl group and a (3- or 4-)methyl-2-isothiazolyl group.

Examples of the dihydrobenzothiazolyl group include a (1-, 2-, 4-, 5-, 6- or 7-)2,3-dihydrobenzothiazolyl group.

Examples of the dihydrobenzothiazolyl group that may have an oxo group include a dihydrobenzothiazolyl group that may have a single oxo group. Specific examples thereof include a (1-, 2-, 5-, 6-, 7- or 8-)2,3-dihydrobenzothiazolyl group and a 2-oxo-(1-, 5-, 6-, 7- or 8-)2,3-dihydrobenzothiazolyl group.

Examples of the thienyl group that may have a lower alkoxycarbonyl group include a thienyl group that may have 1 to 2 (preferably 1) lower alkoxycarbonyl groups as illustrated above. Specific examples thereof include a (2- or 3-)thienyl group and a 3-methoxycarbonyl-2-thienyl group.

Examples of the oxazolyl lower alkyl group that may have a lower alkyl group include an oxazolyl lower alkyl group as illustrated above, whose alkyl group as illustrated above, having 1 to 3 (more preferably 1 to 2) lower alkyl groups as illustrated above on the oxazole ring. Specific examples thereof include a (2-, 4- or 5-)oxazolylmethyl group, 2-(2-, 4- or 5-)oxazolylmethyl group, [2-methyl-(4- or 5-)oxazolyl] methyl group and (2,5-dimethyl-4-oxazolyl)methyl group.

Examples of the amino lower alkyl group that may have a group, on the amino group, which is selected from the group consisting of a lower alkyl group, halogen substituted lower alkyl group, lower alkoxycarbonyl group, lower alkanoyl group, aryl group, aryl lower alkyl group, aroyl group, and amino substituted alkyl group (on the amino group of the amino substituted alkyl group, a lower alkyl group may be present as a substituent) include a lower alkyl group as illustrated above (preferably a linear or branched alkyl group having 1 to 6 carbon atoms) having 1 to 5, preferable 1 to 3, more preferably 1, amino groups. Note that, on the amino group, 1 to 2 substituents may be present which are selected from the group consisting of a lower alkyl group as illustrated above (preferably a linear or branched alkyl group having 1 to 6 carbon atoms);

a halogen substituted lower alkyl group as illustrated above (preferably a linear or branched alkyl group having 1 to 6 carbon atoms with 1 to 13, preferably 1 to 7, more preferably 1 to 3 halogen atoms);

a lower alkoxy-carbonyl group as illustrated above (preferably a linear or branched alkoxycarbonyl group having 1 to 6 carbon atoms);

a lower alkanoyl group as illustrated above (preferably a linear or branched alkanoyl group having 1 to 6 carbon atoms);

an aryl group as illustrated above;

an aryl lower alkyl group as illustrated above;

an aroyl group as illustrated above; and a lower alkyl group as illustrated above (preferably a linear or branched alkyl group having 1 to 6 carbon atoms) having 1 to 5, preferably 1 to 3, more preferably 1, amino groups (1 to 2 lower alkyl groups as illustrated above (preferably a linear or branched alkyl group having 1 to 6 carbon atoms) may be present on the amino group, as a substituent(s)). Specific examples of the amino lower alkyl group that may have, on the amino group, a group selected from the group consisting of a lower alkyl group, halogen substituted lower alkyl group, lower alkoxycarbonyl group, lower alkanoyl group, aryl group, aryl lower alkyl group, aroyl group, and amino substituted alkyl group ((on the amino group of the amino substituted alkyl group, a lower alkyl group may be present as a substituent) include an N-methylaminomethyl group, N-ethylaminomethyl group, N-n-propylaminomethyl group, N,N-dimethylaminomethyl group, N,N-diethylaminomethyl group, N-methyl-N-n-propylaminomethyl group, N-methyl-N-ethylaminomethyl group, N-(2,2,2-trifluoroethyl)aminomethyl group, N-methyl-N-benzylaminomethyl group, N-phenylaminomethyl group, N-methyl-N-phenylaminomethyl group, N-formylaminomethyl group, N-methyl-N-acetylaminomethyl group, N-methyl-N-propionylaminomethyl group, N-(2-(N,N-diethylamino)ethyl)aminomethyl group, N-methyl-N-benzoylaminomethyl group, N-methylaminoethyl group, N-ethylaminoethyl group, N-(2,2,2-trifluoroethyl)aminoethyl group, N,N-dimethylaminoethyl group, N,N-diethylaminoethyl group, N-methyl-N-acetylaminoethyl group, N-methyl-N-benzoylaminoethyl group, N-methyl-N-propionylaminoethyl group, N-methyl-N-benzylaminoethyl group, and N-methyl-N-tert-butoxycarbonylaminoethyl group.

Examples of the lower alkyl group substituted with a carbamoyl group that may have a group selected from the group consisting of a lower alkyl group and a halogen substituted lower alkyl group include a lower alkyl group as illustrated above (preferably a linear or branched alkyl group having 1 to 6 carbon atoms) and substituted with 1 to 3 (preferably 1) carbamoyl groups that may have 1 to 2 groups selected from the group consisting of a lower alkyl group as illustrated above (preferably a linear or branched alkyl group having 1 to 6 carbon atoms); and a halogen substituted lower alkyl group as illustrated above (preferably a linear or branched alkyl group having 1 to 6 carbon atoms and 1 to 13, preferably 1 to 7, more preferably 1 to 3 halogen atoms). Specific examples thereof include a carbamoylmethyl group, 2-carbamoylethyl group, 1-carbamoylethyl group, 3-carbamoylpropyl group, 4-carbamoylbutyl group, 5-carbamoylpentyl group, 6-carbamoylhexyl group, 1,1-dimethyl-2-carbamoylethyl group, 2-methyl-3-carbamoylpropyl group, 1,2-dicarbamoylethyl group, 2,2-dicarbamoylethyl group, 1,2,3-tricarbamoylpropyl group, N-methylcarbamoylmethyl group, N-ethylcarbamoylmethyl group, 2-(N-n-propylcarbamoyl)ethyl group, 3-(N-n-butylcarbamoyl)propyl group, 4-(N-isobutylcarbamoyl)butyl group, 5-(N-tert-butylcarbamoyl)pentyl group, 6-(N-pentylcarbamoyl)hexyl group, N,N-dimethylcarbamoylmethyl group, N,N-diethylcarbamoylmethyl group, 2-(N-2-fluoroethylcarbamoyl)ethyl group, 3-(N-2-chloroethylcarbamoyl)propyl group, 4-(N-2-bromoethylcarbamoyl)butyl group, 2-(N-2,2-dichloroethylcarbamoyl)ethyl group, N-2,2,2-trifluoroethylcarbamoylmethyl group, and N-heptafluoropropylcarbamoylmethyl group.

Examples of the thiocarbamoyl group that may have a lower alkyl group include a thiocarbamoyl group that may have 1 to 2 lower alkyl groups as illustrated above (preferably a linear or branched alkyl group having 1 to 6 carbon atoms). Specific examples thereof include a thiocarbamoyl group, N-methyl-thiocarbamoyl group, N-ethyl-thiocarbamoyl group, N-n-propyl-thiocarbamoyl group, N-n-butyl-thiocarbamoyl group, N-n-pentyl-thiocarbamoyl group, N-n-hexyl-thiocarbamoyl group, N-isobutyl-thiocarbamoyl group, N-tert-butyl-thiocarbamoyl group, N,N-dimethyl-thiocarbamoyl group, and N-methyl-N-ethyl-thiocarbamoyl group.

Examples of the oxazolidinyl group that may have an oxo group include an oxazolidinyl group that may have 1 to 2 (preferably 1) oxo groups. Specific examples thereof include an oxazolidin-3-yl group, oxazolidin-4-yl group, oxazolidin-5-yl group, 2-oxo-oxazolidin-4-yl group, 2-oxo-oxazolidin-3-yl group, and 2-oxo-oxazolidin-5-yl group.

Examples of the imidazolidinyl group that may have a substituent selected from the group consisting of an oxo group and a lower alkyl group include an imidazolidinyl group that may have 1 to 3, preferably 1 to 2 substituents selected from the group consisting of oxo group and a lower alkyl group as illustrated above (preferably a linear or branched alkyl group having 1 to 6 carbon atoms). Specific examples thereof include an imidazolidin-1-yl group, imidazolidin-2-yl group, imidazolidin-4-yl group, 2-oxo-imidazolidin-1-yl group, 4-oxo-imidazolidin-1-yl group, 5-oxo-imidazolidin-1-yl group, 4-oxo-imidazolidin-2-yl group, 2-oxo-imidazolidin-4-yl group, 2-methyl-imidazolidin-1-yl group, 4-ethyl-imidazolidin-1-yl group, 5-n-propyl-imidazolidin-1-yl group, 4-n-butyl-imidazolidin-2-yl group, 2-n-pentyl-imidazolidin-4-yl group, 2-n-hexyl-imidazolidin-1-yl group, 4-isobutyl-imidazolidin-2-yl group, 2-tert-butyl-imidazolidin-4-yl group, 2-oxo-3-methyl-imidazolidin-1-yl group, and 2-oxo-3,4-dimethyl-imidazolidin-1-yl group.

Examples of the pyrrolidinyl group that may have an oxo group include a pyrrolidinyl group that may have 1 to 2 (preferably 1) oxo groups. Specific examples thereof include a (1-, 2- or 3-)pyrrolidinyl group, (2- or 3-)oxo-1-pyrrolidinyl group, (3-, 4- or 5-)oxo-2-pyrrolidinyl group, and (2-, 4- or 5-)oxo-3-pyrrolidinyl group.

Examples of the imidazolyl group include a (1-, 2-, 4- or -5)imidazolyl group.

Examples of the isoxazolyl group include a (3-, 4- or 5-)isoxazolyl group.

Examples of the arylsulfonyl group include an arylsulfonyl group whose aryl moiety is phenyl, biphenyl, substituted biphenyl, substituted phenyl, naphthyl and substituted naphthyl, and which may have, on the aryl moiety, 1 to 7, preferably 1 to 5, more preferably 1 to 2 linear or branched alkyl groups having 1 to 6 carbon atoms. Examples of the substituent such as phenyl, biphenyl and naphthyl include a linear or branched alkyl group having 1 to 6 carbon atoms, a halogen atom, an amino group and the like. One to seven, preferably 1 to 5, more preferably 1 to 2 substituents of at least one type of these may be present on the phenyl, biphenyl, naphthyl ring and the like. Specific Examples of the arylsulfonyl group that may have a lower alkyl group on the aryl group include a phenylsulfonyl group, (2-, 3-, or 4-)biphenylsulfonyl group, (1- or 2-)naphthylsulfonyl group, (2-, 3-, or 4-)methylphenylsulfonyl group, (2-, 3-, or 4-)ethylphenylsulfonyl group, (2-, 3-, or 4-)n-propylphenylsulfonyl group, (2-, 3-, or 4-)n-butylphenylsulfonyl group, (2-, 3-, or 4-)n-pentylphenylsulfonyl group, (2-, 3-, or 4-)n-hexylphenylsulfonyl group, (2-, 3-, or 4-)isobutylphenylsulfonyl group, (2-, 3-, or 4-)tert-butylphenylsulfonyl group, (3-, 4-, 5-, 6-, 2'-, 3'-, 4'-, 5'-, or 6'-)methyl-2-biphenylsulfonyl group, (2-, 4-, 5-, 6-, 2'-, 3'-, 4'-, 5'-, or 6'-)methyl-3-biphenylsulfonyl group, (2-, 3-, 5-, 6-, 2'-, 3'-, 4'-, 5'-, or 6'-)methyl-4-biphenylsulfonyl group, (3-, 4-, 5-, 6-, 2'-, 3'-, 4'-, 5'-, or 6'-)ethyl-2-biphenylsulfonyl group, (2-, 4-, 5-, 6-, 2'-, 3'-, 4'-, 5'-, or 6'-)ethyl-3-biphenylsulfonyl group, (2-, 3-, 5-, 6-, 2'-, 3'-, 4'-, 5'-, or 6'-)ethyl-4-biphenylsulfonyl group, (3-, 4-, 5-, 6-, 2'-, 3'-, 4'-, 5'-, or 6'-)n-propyl-2-biphenylsulfonyl group, (2-, 4-, 5-, 6-, 2'-, 3'-, 4'-, 5'-, or 6'-)n-propyl-3-biphenylsulfonyl group, (2-, 3-, 5-, 6-, 2'-, 3'-, 4'-, 5'-, or 6'-)n-propyl-4-biphenylsulfonyl group, (3-, 4-, 5-, 6-, 2'-, 3'-, 4'-, 5'-, or 6'-)n-butyl-2-biphenylsulfonyl group, (2-, 4-, 5-, 6-, 2'-, 3'-, 4'-, 5'-, or 6'-)n-butyl-3-biphenylsulfonyl group, (2-, 3-, 5-, 6-, 2'-, 3'-, 4'-, 5'-, or 6'-)n-butyl-4-biphenylsulfonyl group, (3-, 4-, 5-, 6-, 2'-, 3'-, 4'-, 5'-, or 6'-)n-pentyl-2-biphenylsulfonyl group, (2-, 4-, 5-, 6-, 2'-, 3'-, 4'-, 5'-, or 6'-)n-pentyl-3-biphenylsulfonyl group, (2-, 3-, 5-, 6-, 2'-, 3'-, 4'-, 5'-, or 6'-)n-pentyl-4-biphenylsulfonyl group, (3-, 4-, 5-, 6-, 2'-, 3'-, 4'-, 5'-, or 6'-)n-hexyl-2-biphenylsulfonyl group, (2-, 4-, 5-, 6-, 2'-, 3'-, 4'-, 5'-, or 6'-)n-hexyl-3-biphenylsulfonyl group, (2-, 3-, 5-, 6-, 2'-, 3'-, 4'-, 5'-, or 6'-)n-hexyl-4-biphenylsulfonyl group, (3-, 4-, 5-, 6-, 2'-, 3'-, 4'-, 5'-, or 6'-)isobutyl-2-biphenylsulfonyl group, (2-, 4-, 5-, 6-, 2'-, 3'-, 4'-, 5'-, or 6'-)isobutyl-3-biphenylsulfonyl group, (2-, 3-, 5-, 6-, 2'-, 3'-, 4'-, 5'-, or 6'-)isobutyl-4-biphenylsulfonyl group, (3-, 4-, 5-, 6-, 2'-, 3'-, 4'-, 5'-, or 6'-)tert-butyl-2-biphenylsulfonyl group, (2-, 4-, 5-, 6-, 2'-, 3'-, 4'-, 5'-, or 6'-)tert-butyl-3-biphenylsulfonyl group, (2-, 3-, 5-, 6-, 2'-, 3'-, 4'-, 5'-, or 6'-)tert-butyl-4-biphenylsulfonyl group, (2-, 3-, 4-, 5-, 6-, 7-, or 8-)methyl-1-naphthylsulfonyl group, (1-, 3-, 4-, 5-, 6-, 7-, or 8-)methyl-2-naphthylsulfonyl group, (2-, 3-, 4-, 5-, 6-, 7-, or 8-)ethyl-1-naphthylsulfonyl group, (1-, 3-, 4-, 5-, 6-, 7-, or 8-)ethyl-2-naphthylsulfonyl group, (2-, 3-, 4-, 5-, 6-, 7-, or 8-)n-propyl-1-naphthylsulfonyl group, (1-, 3-, 4-, 5-, 6-, 7-, or 8-)n-propyl-2-naphthylsulfonyl group, (2-, 3-, 4-, 5-, 6-, 7-, or 8-)n-butyl-1-naphthylsulfonyl group, (1-, 3-, 4-, 5-, 6-, 7-, or 8-)n-butyl-2-naphthylsulfonyl group, (2-, 3-, 4-, 5-, 6-, 7-, or 8-)n-pentyl-1-naphthylsulfonyl group, (1-, 3-, 4-, 5-, 6-, 7-, or 8-)n-pentyl-2-naphthylsulfonyl group, (2-, 3-, 4-, 5-, 6-, 7-, or 8-)n-hexyl-1-naphthylsulfonyl group, (1-, 3-, 4-, 5-, 6-, 7-, or 8-)n-hexyl-2-naphthylsulfonyl group, (2-, 3-, 4-, 5-, 6-, 7-, or 8-)isobutyl-1-naphthylsulfonyl group, (1-, 3-, 4-, 5-, 6-, 7-, or 8-)isobutyl-2-naphthylsulfonyl group, (2-, 3-, 4-, 5-, 6-, 7-, or 8-)tert-butyl-1-naphthylsulfonyl group, (1-, 3-, 4-, 5-, 6-, 7-, or 8-)tert-butyl-2-naphthylsulfonyl group, (2-, 3-, or 4-)chlorophenylsulfonyl group, (2-, 3-, or 4-)fluorophenylsulfonyl group, (2-, 3-, or 4-)bromophenylsulfonyl group, (2-, 3-, 4-, 5-, 6-, 7-, or 8-)chloro-1-naphthylsulfonyl group, (1-, 3-, 4-, 5-, 6-, 7-, or 8-)chloro-2-naphthylsulfonyl group, (2-, 3-, 4-, 5-, 6-, 7-, or 8-)fluoro-1-naphthylsulfonyl group, (1-, 3-, 4-, 5-, 6-, 7-, or 8-)fluoro-2-naphthylsulfonyl group, (2-, 3-, 4-, 5-, 6-, 7-, or 8-)bromo-1-naphthylsulfonyl group, (1-, 3-, 4-, 5-, 6-, 7-, or 8-)bromo-2-naphthylsulfonyl group, (2-, 3-, or 4-)aminophenylsulfonyl group, (2-, 3-, 4-, 5-, 6-, 7-, or 8-)amino-1-naphthylsulfonyl group, (1-, 3-, 4-, 5-, 6-, 7-, or 8-)amino-2-naphthylsulfonyl group, 2,3-dimethylphenylsulfonyl group, 3,4-dimethylphenylsulfonyl group, 2,4-dimethylphenylsulfonyl group, 2,5-dimethylphenylsulfonyl group, 2,6-dimethylphenylsulfonyl group, 2,4,6-trimethylphenylsulfonyl group, 3,4,5-trimethylphenylsulfonyl group, 2,3,4,5-tetraethylphenylsulfonyl group, pentamethylphenylsulfonyl group, 2-methylnaphthylsulfonyl group, 2,3-dimethylnaphthylsulfonyl group, 3,4-dimethylphenylsulfonyl group, 3,5,7-triethylnaphthylsulfonyl group, 3,4,5,7-tetramethylnaphthylsulfonyl group, 2,3,4,5,7-pentamethylnaphthylsulfonyl group, 2,3,4,5,6,7-hexaethylnaphthylsulfonyl group, heptamethylnaphthylsulfonyl group, 2,3-diaminophenylsulfonyl group, 2,4,6-triaminophenylsulfonyl group, and 2-methyl-5-chloronaphthylsulfonyl group.

Examples of the piperidyl group that may have a substituent selected from the group consisting of a lower alkyl group; lower alkanoyl group; arylsulfonyl group; oxo group; hydroxy group and amino group that may have a group selected from the group consisting of a lower alkyl group, lower alkanoyl group, lower alkoxycarbonyl group and lower alkanoylamino lower alkanoyl group include a piperidyl group that may have 1 to 5, preferably 1 to 3, more preferably 1 substituent selected from the group consisting of a lower alkyl group as illustrated above (preferably a linear or branched alkyl group having 1 to 6 carbon atoms);

a lower alkanoyl group as illustrated above (preferably a linear or branched alkanoyl group having 1 to 6 carbon atoms); and an arylsulfonyl group as illustrated above; an oxo group; a hydroxy group; and an amino group that may have 1 to 2 groups selected from the group consisting of a lower alkyl group as illustrated above, lower alkanoyl group as illustrated above, lower alkoxycarbonyl group as illustrated above and lower alkanoyl amino lower alkanoyl group as illustrated above. Specific examples thereof include a (1-, 2-, 3-, or 4-)piperidyl group, 1-methyl-4-piperidyl group, 2-ethyl-4-piperidyl group, 3-n-propyl-4-piperidyl group, 4-isopropyl-4-piperidyl group, 2-n-butyl-1-piperidyl group, 3-isobutyl-1-piperidyl group, 4-tert-butyl-1-piperidyl group, 1-sec-butyl-2-piperidyl group, 2-n-pentyl-2-piperidyl group, 3-(1-ethylpropyl)-2-piperidyl group, 4-iso-pentyl-2-piperidyl group, 5-neopentyl-2-piperidyl group, 6-n-hexyl-2-piperidyl group, 1-(1,2,2-trimethylpropyl)-3-piperidyl group, 2-(3,3-dimethylbutyl)-3-piperidyl group, 3-(2-ethylbutyl)-3-piperidyl group, 4-isohexyl-3-piperidyl group, 5-(3-methylpentyl group)-3-piperidyl group, 6-formyl-3-piperidyl group, 1-acetyl-4-piperidyl group, 2-propionyl-4-piperidyl group, 3-butyryl-4-piperidyl group, 4-isobutyryl-4-piperidyl group, 2-pentanoyl-1-piperidyl group, 3-tert-butylcarbonyl-1-piperidyl group, 4-hexanoyl-1-piperidyl group, 1-phenylsulfonyl-2-piperidyl group, 2-(2-biphenylsulfonyl)-2-piperidyl group, 3-(1-naphthylsulfonyl)-2-piperidyl group, 1-tosyl-4-piperidyl group, 4-(4-ethylphenylsulfonyl)-2-piperidyl group, 5-(2-n-propylphenylsulfonyl)-2-piperidyl group, 6-(3-n-butylphenylsulfonyl)-2-piperidyl group, 1-(4-n-pentylphenylsulfonyl)-3-piperidyl group, 2-(2-n-hexylphenylsulfonyl)-3-piperidyl group, 3-(3-isobutylphenylsulfonyl)-3-piperidyl group, 4-(4-tert-butylphenylsulfonyl)-3-piperidyl group, 5-(2-chlorophenylsulfonyl)-3-piperidyl group, 6-(4-fluorophenylsulfonyl)-3-piperidyl group, 1-(3-bromophenylsulfonyl)-4-piperidyl group, 2-(2-aminophenylsulfonyl)-4-piperidyl group, 3-(2,3-dimethylphenylsulfonyl)-4-piperidyl group, 4-(3,4,5-trimethylphenylsulfonyl)-4-piperidyl group, 2-(2,3-diaminophenylsulfonyl)-1-piperidyl group, 4-oxo-1-piperidyl group, 2-oxo-3-piperidyl group, 4-hydroxy-1-piperidyl group, 2-hydroxy-3-piperidyl group, 4-amino-1-piperidyl group, 2-amino-4-piperidyl group, 4-methylamino-1-piperidyl group, 2-methylamino-4-piperidyl group, 4-ethylamino-1-piperidyl group, 2-ethylamino-4-piperidyl group, 2-dimethylamino-4-piperidyl group, 4-diethylamino-1-piperidyl group, 4-formylamino-1-piperidyl group, 4-acetylamino-1-piperidyl group, 4-(N-methyl-N-acetylamino)-1-piperidyl group, 4-(N-methyl-N-methoxycarbonylamino)-1-piperidyl group, 4-(N-methyl-N-tert-butoxycarbonylamino)-1-piperidyl group, 4-[N-methyl-N-(N-acetylamino)acetylamino]-1-piperidyl group.

Examples of the piperidylcarbonyl group that may have a substituent selected from the group consisting of a lower alkyl group, hydroxy group, hydroxy lower alkyl group, lower alkanoyl group, carboxy lower alkyl group, lower alkyl carbamoyl lower alkyl group, carbamoyl group, lower alkoxy group, carboxy group, lower alkoxycarbonyl group, amino group (on which 1 to 2 groups selected from the group consisting of a lower alkyl group, lower alkanoyl group, lower alkoxycarbonyl group and aroyl group may be present), piperidyl group (on which a group selected from the group consisting of a lower alkanoyl group, lower alkoxycarbonyl group and aroyl group may be present), piperazinyl group (on which a lower alkyl group may be present as a substituent), 1,4-dioxa-8-azasprio[4.5]decyl group, morpholinyl group, hexahydro-1,4-diazepinyl group (on which a lower alkyl group may be present as a substituent), pyridyl group, pyridyloxy group, pyridyl lower alkoxy group, tetrahydroquinolyl group (on which an oxo group may be present), benzodioxolyl group, aryl lower alkoxy group (that may have on the aryl group a group selected from the group consisting of a halogen atom, lower alkyl group, lower alkoxy group and halogen substituted lower alkoxy group), aryl group (on which a group selected from the group consisting of a halogen atom, lower alkoxy group and hydroxy group may be present), aryloxy group (that may have on the aryl group a group selected from the group consisting of a cyano group, halogen atom, lower alkyl group, lower alkoxy group and halogen substituted lower alkyl group), aryl lower alkyl group (that may have on the aryl group a group selected from the group consisting of a halogen atom, lower alkyl group, lower alkoxy group and halogen substituted lower alkyl group) and aroyl group (that may have on the aryl group a group selected from the group consisting of a halogen atom and a lower alkoxy group) include a piperidylcarbonyl group that may have 1 to 3 (preferably 1) substituents, on the piperidyl group, selected from the group consisting of a lower alkyl group as illustrated above (preferably a linear or branched alkyl group having 1 to 6 carbon atoms);

a hydroxy group;

a hydroxy lower alkyl group as illustrated above (preferably a linear or branched alkyl group having 1 to 6 carbon atoms and having 1 to 3 hydroxy groups);

a lower alkanoyl group as illustrated above;

a carboxy lower alkyl group as illustrated above having a lower alkyl moiety as illustrated above;

a linear or branched alkyl group having 1 to 6 carbon atoms and substituted with a carbamoyl group having 1 to 2 lower alkyl groups as illustrated above (preferably linear or branched alkyl groups having 1 to 6 carbon atoms);

a carbamoyl group;

a lower alkoxy group as illustrated above (preferably a linear or branched alkoxy group having 1 to 6 carbon atoms);

a carboxy group;

a lower alkoxycarbonyl group as illustrated above (preferably a linear or branched alkoxycarbonyl group having 1 to 6 carbon atoms), an amino group (on which 1 to 2 groups selected from the group consisting of a lower alkyl group as illustrated above, a lower alkanoyl group as illustrated above, lower alkoxycarbonyl group as illustrated above and aroyl group as illustrated above may be present);

a piperidyl group (on which 1 to 3 groups (preferably 1) selected from the group consisting of a lower alkanoyl group as illustrated above, lower alkoxycarbonyl group as illustrated above and aroyl group as illustrated above may be present);

a piperazinyl group (on which 1 to 3 lower alkyl groups as illustrated above (preferably linear or branched alkyl groups having 1 to 6 carbon atoms) may be present as a substituent (s));

a 1,4-dioxa-8-azasprio[4.5]decyl group;

a morpholinyl group;

a hexahydro-1,4-diazepinyl group (on which 1 to 3 lower alkyl groups as illustrated above (preferably linear or branched alkyl groups having 1 to 6 carbon atoms) may be present as a substituent(s));

a pyridyl group;

a pyridyloxy group;

a pyridyl lower alkoxy group having a lower alkoxy moiety as illustrated above;

a tetrahydroquinolyl group (on which 1 to 2 (preferably 1) oxo groups may be present);

a benzodioxolyl group (preferably benzo[1.3]dioxolyl group);

an aryl lower alkoxy group having an aryl moiety and lower alkoxy moiety as illustrated above (that may have on the aryl group 1 to 3 (preferably 1 to 2) groups selected from the group consisting of a halogen atom as illustrated above, lower alkyl group as illustrated above, lower alkoxy group as illustrated above and halogen substituted lower alkoxy group as illustrated above);

an aryl group as illustrated above (that may have on the aryl group 1 to 3 (preferably 1 to 2) groups selected from the group consisting of a halogen atom as illustrated above, lower alkoxy group as illustrated above and hydroxy group);

an aryloxy group having an aryl moiety as illustrated above (that may have on the aryl group 1 to 3 (preferably 1 to 2) groups selected from the group consisting of a cyano group, halogen atom, lower alkyl group as illustrated above, lower alkoxy group as illustrated above and halogen substituted lower alkyl group as illustrated above);

an aryl lower alkyl group having an aryl moiety and lower alkyl moiety as illustrated above (that may have on the aryl group 1 to 3 (preferably 1 to 2) groups selected from the group consisting of a halogen atom, lower alkyl group, lower alkoxy group and halogen substituted lower alkyl group); and an aroyl group as illustrated above (that may have on the aryl group 1 to 3 (preferably 1 to 2) groups selected from the group consisting of a halogen atom as illustrated above and a lower alkoxy group as illustrated above). Specific examples thereof include a (1-, 2-, 3-, or 4-)piperidylcarbonyl group, (1-, 2-, 3-, or 4-)ethyl-4-piperidylcarbonyl group, (2-, 3-, or 4-)methyl-1-piperidylcarbonyl group, (1-, 2-, 3-, 4-, 5-, or 6-)methyl-2-piperidylcarbonyl group, (1-, 2-, 3-, 4-, 5-, or 6-)methyl-3-piperidylcarbonyl group, (1-, 2-, 3-, or 4-)methyl-4-piperidylcarbonyl group, (2-, 3-, or 4-)hydroxy-1-piperidylcarbonyl group, (1-, 2-, 3-, 4-, 5-, or 6-)hydroxy-2-piperidylcarbonyl group, (1-, 2-, 3-, 4-, 5-, or 6-)hydroxy-3-piperidylcarbonyl group, (1-, 2-, 3-, or 4-)hydroxy-4-piperidylcarbonyl group, (2-, 3-, or 4-)hydroxymethyl-1-piperidylcarbonyl group, (1-, 2-, 3-, 4-, 5-, or 6-)hydroxymethyl-2-piperidylcarbonyl group, (1-, 2-, 3-, 4-, 5-, or 6-)hydroxymethyl-3-piperidylcarbonyl group, (1-, 2-, 3-, or 4-)hydroxymethyl-4-piperidylcarbonyl group, (1-, 2-, 3-, or 4-)(2-hydroxyethyl)-4-piperidylcarbonyl group, (2-, 3-, or 4-)(N-ethyl-carbamoylmethyl)-1-piperidylcarbonyl group, (1-, 2-, 3-, 4-, 5-, or 6-)(N-ethyl-carbamoylmethyl)-2-piperidylcarbonyl group, (1-, 2-, 3-, 4-, 5-, or 6-)(N-ethyl-carbamoylmethyl)-3-piperidylcarbonyl group, (1-, 2-, 3-, or 4-)N-ethyl-carbamoylmethyl-4-piperidylcarbonyl group, (2-, 3-, or 4-)carbamoyl-1-piperidylcarbonyl group, (1-, 2-, 3-, 4-, 5-, or 6-)carbamoyl-2-piperidylcarbonyl group, (1-, 2-, 3-, 4-, 5-, or 6-)carbamoyl-3-piperidylcarbonyl group, (1-, 2-, 3-, or 4-)carbamoyl-4-piperidylcarbonyl group, (2-, 3-, or 4-)carboxy-1-piperidylcarbonyl group, (2-, 3-, or 4-)carboxymethyl-1-piperidylcarbonyl group, (2-, 3-, or 4-)ethoxycarbonyl-1-piperidylcarbonyl group, (2-, 3-, or 4-)methoxy-1-piperidylcarbonyl group, (1-, 2-, 3-, 4-, 5-, or 6-)methoxy-2-piperidylcarbonyl group, (1-, 2-, 3-, 4-, 5-, or 6-)methoxy-3-piperidylcarbonyl group, (1-, 2-, 3-, or 4-)methoxy-4-piperidylcarbonyl group, (2-, 3-, or 4-)methoxycarbonyl-1-piperidylcarbonyl group, (1-, 2-, 3-, 4-, 5-, or 6-)methoxycarbonyl-2-piperidylcarbonyl group, (1-, 2-, 3-, 4-, 5-, or 6-)methoxycarbonyl-3-piperidylcarbonyl group, (1-, 2-, 3-, or 4-)methoxycarbonyl-4-piperidylcarbonyl group, (2-, 3-, or 4-)ethoxycarbonyl-1-piperidylcarbonyl group, (1-, 2-, 3-, 4-, 5-, or 6-)ethoxycarbonyl-2-piperidylcarbonyl group, (1-, 2-, 3-, 4-, 5-, or 6-)ethoxycarbonyl-3-piperidylcarbonyl group, (1-, 2-, 3-, or 4-)ethoxycarbonyl-4-piperidylcarbonyl group, (2-, 3-, or 4-)acetylamino-1-piperidylcarbonyl group, (1-, 2-, 3-, 4-, 5-, or 6-)acetylamino-2-piperidylcarbonyl group, (1-, 2-, 3-, 4-, 5-, or 6-)acetylamino-3-piperidylcarbonyl group, (1-, 2-, 3-, or 4-)acetylamino-4-piperidylcarbonyl group, (2-, 3-, or 4-)tert-butoxycarbonylamino-1-piperidylcarbonyl group, (1-, 2-, 3-, 4-, 5-, or 6-)tert-butoxycarbonylamino-2-piperidylcarbonyl group, (1-, 2-, 3-, 4-, 5-, or 6-)tert-butoxycarbonylamino-3-piperidylcarbonyl group, (1-, 2-, 3-, or 4-)tert-butoxycarbonylamino-4-piperidylcarbonyl group, (2-, 3-, or 4-)butyrylamino-1-piperidylcarbonyl group, (2-, 3-, or 4-)benzoylamino-1-piperidylcarbonyl group, (2-, 3-, or 4-)(N-methyl-N-acetylamino)-1-piperidylcarbonyl group, (2-, 3-, or 4-)(N-methyl-N-butyrylamino)-1-piperidylcarbonyl group, (2-, 3-, or 4-)(N-methyl-N-tert-butoxycarbonylamino)-1-piperidylcarbonyl group, (2-, 3-, or 4-)(N-methyl-N-benzoylamino)-1-piperidylcarbonyl group, (2-, 3-, or 4-)[(1-, 2-, 3-, or 4-)piperidyl]-1-piperidylcarbonyl group, (1-, 2-, 3-, 4-, 5-, or 6-)[(1-, 2-, 3-, or 4-)piperidyl]-2-piperidylcarbonyl group, (1-, 2-, 3-, 4-, 5-, or 6-)[(1-, 2-, 3-, or 4-)piperidyl]-3-piperidylcarbonyl group, (1-, 2-, 3-, or 4-)[(1-, 2-, 3-, or 4-)piperidyl]-4-piperidylcarbonyl group, (2-, 3-, or 4-)[1-acetyl-(2-, 3-, or 4-)piperidyl]-1-piperidylcarbonyl group, (2-, 3-, or 4-)[1-butyryl-(2-, 3-, or 4-)piperidyl]-1-piperidylcarbonyl group, (2-, 3-, or 4-)[1-tert-butoxycarbonyl-(2-, 3-, or 4-)piperidyl]-1-piperidylcarbonyl group, (2-, 3-, or 4-)[1-benzoyl-(2-, 3-, or 4-)piperidyl]-1-piperidylcarbonyl group, (2-, 3-, or 4-)(1-piperazinyl)-1-piperidylcarbonyl group, (2-, 3-, or 4-)[1-(3,14-dimethylpiperazinyl)]-1-piperidylcarbonyl group, (1-, 2-, 3-, 4-, 5-, or 6-)[1-(3,4-dimethylpiperazinyl)]-2-piperidylcarbonyl group, (1-, 2-, 3-, 4-, 5-, or 6-)[1-(3,4-dimethylpiperazinyl)]-3-piperidylcarbonyl group, (1-, 2-, 3-, or 4-)[1-(3,4-dimethylpiperazinyl)]-4-piperidylcarbonyl group, (2-, 3-, or 4-)[1-(4-methylpiperazinyl)]-1-piperidylcarbonyl group, (1-, 3-, or 4-)[1-(4-methylpiperazinyl)]-2-piperidylcarbonyl group, (1-, 2-, or 4-)[1-(4-methylpiperazinyl)]-3-piperidylcarbonyl group, (1-, 2-, or 3-)[1-(4-methylpiperazinyl)]-4-piperidylcarbonyl group, (2-, 3-, or 4-)[(2-, 3-, or 4-)morpholinyl]-1-piperidylcarbonyl group, (1-, 3-, or 4-)[(2-, 3-, or 4-)morpholinyl]-2-piperidylcarbonyl group, (1-, 2-, 4-, 5-, or 6-)[(2-, 3-, or 4-)morpholinyl]-3-piperidylcarbonyl group, (1-, 2-, or 3-)[(2-, 3-, or 4-)morpholinyl]-4-piperidylcarbonyl group, (1-, 2-, 3-, 4-, 5-, 6-, or 7-)(4-methyl-hexahydro-1,4-diazepinyl)-1-piperidylcarbonyl group, (1-, 2-, 3-, 4-, 5-, or 6-)(4-methyl-hexahydro-1,4-diazepinyl)-2-piperidylcarbonyl group, (1-, 2-, 3-, 4-, 5-, or 6-)(4-methyl-hexahydro-1,4-diazepinyl)-3-piperidylcarbonyl group, (1-, 2-, 3-, or 4-)(4-methyl-hexahydro-1,4-diazepinyl)-4-piperidylcarbonyl group, (2-, 3-, or 4-)(1,4-dioxa-8-azaspiro[4.5]dec-8-yl)-1-piperidylcarbonyl group, (1-, 2-, 3-, 4-, 5-, or 6-)(1,4-dioxa-8-azaspiro[4.5]dec-8-yl)-2-piperidylcarbonyl group, (1-, 2-, 3-, 4-, 5-, or 6-)(1,4-dioxa-8-azaspiro[4.5]dec-8-yl)-3-piperidylcarbonyl group, (1-, 2-, 3-, or 4-)(1,4-dioxa-8-azaspiro[4.5]dec-8-yl)-4-piperidylcarbonyl group, (2-, 3-, or 4-)[(2-, 4-, or 5-)benzo[1.3]dioxolyl]-1-piperidylcarbonyl group, (2-, 3-, or 4-)[2-oxo-(1-, 3-, 4-, 5-, 6-, 7-, or 8-)-1,2,3,4-tetrahydroquinolyl]-1-piperidylcarbonyl group, 4-[2-oxo-(1-, 3-, 4-, 5-, 6-, 7-, or 8-)-1,2,3,4-tetrahydroquinolyl]-(2- or 3-methyl)-1-piperidylcarbonyl group, (2-, 3-, or 4-)[(2-, 3-, or 4-)pyridyl]-1-piperidylcarbonyl group, (2-, 3-, or 4-)[(2-, 3-, or 4-)pyridyloxy]-1-piperidylcarbonyl group, (2-, 3-, or 4-)[(2-, 3-, or 4-)pyridylmethoxy]-1-piperidylcarbonyl group, (2-, 3-, or 4-)[(2-, 3-, or 4-)fluorobenzyloxy]-1-piperidylcarbonyl group, (2-, 3-, or 4-)[(2-, 3-, or 4-)chlorobenzyloxy]-1-piperidylcarbonyl group, (2-, 3-, or 4-)[(2-, 3-, or 4-)bromobenzyloxy]-1-piperidylcatbonyl group, (2-, 3-, or 4-)[(2-, 3-, or 4-)methylbenzyloxy]-1-piperidylcarbonyl group, (2-, 3-, or 4-)[(2-, 3-, or 4-)trifluoromethoxybenzyloxy]-1-piperidylcarbonyl group, (2-, 3-, or 4-)(3,4-dichlorobenzyloxy)-1-piperidylcarbonyl group, (2-, 3-, or 4-)(3,4-dimethoxybenzyloxy)-1-piperidylcarbonyl group, (2-, 3-, or 4-)(3-chloro-4-methoxybenzyloxy)-1-piperidylcarbonyl group, (2-, 3-, or 4-)[(2-, 3-, or 4-)fluorophenoxy]-1-piperidylcarbonyl group, (2-, 3-, or 4-)[(2-, 3-, or 4-)chlorophenoxy]-1-piperidylcarbonyl group; (2-, 3-, or 4-)[(2-, 3-, or 4-)cyanophenoxy]-1-piperidylcarbonyl group, (2-, 3-, or 4-)[(2-, 3-, or 4-)methoxyphenoxy]-1-piperidylcarbonyl group, (2-, 3-, or 4-)[(2-, 3-, or 4-)methylphenoxy]-1-piperidylcarbonyl group, (2-, 3-, or 4-)[(2-, 3-, or 4-)trifluoromethoxyphenoxy]-1-piperidylcarbonyl group, (2-, 3-, or 4-)phenyl-1-piperidylcarbonyl group, 4-hydroxy-(2-, 3-, or 4-)phenyl-1-piperidylcarbonyl group, (2-, 3-, or 4-)[(2-, 3-, or 4-)chlorophenyl]-1-piperidylcarbonyl group, (2-, 3-, or 4-)[(2-, 3-, or 4-)methoxyphenyl]-1-piperidylcarbonyl group, (2-, 3-, or 4-)[(2-, 3-, or 4-)hydroxyphenoxy]-1-piperidylcarbonyl group, 4-hydroxy-(2-, 3-, or 4-)phenyl-1-piperidylcarbonyl group, 4-ethoxycarbonyl-(2-, 3-, or 4-)phenyl-1-piperidylcarbonyl group, 4-hydroxy-(2-, 3-, or 4-)[(2-, 3-, or 4-)chlorophenyl]-1-piperidylcarbonyl group, (2-, 3-, or 4-)benzyl-1-piperidylcarbonyl group, (2-, 3-, or 4-)[(2-, 3-, or 4-)chlorobenzyl]-1-piperidylcarbonyl group, (2-, 3-, or 4-)[(2-, 3-, or 4-)methylbenzyl]-1-piperidylcarbonyl group, (2-, 3-, or 4-)[(2-, 3-, or 4-)methoxybenzyl]-1-piperidylcarbonyl group, (2-, 3-, or 4-)[(2-, 3-, or 4-)trifluoromethoxybenzyl]-1-piperidylcarbonyl group, 4-hydroxy-(2-, 3-, or 4-)benzyl-1-piperidylcarbonyl group, (2-, 3-, or 4-)[(2-, 3-, or 4-)chlorobenzoyl]-1-piperidylcarbonyl group, (2-, 3-, or 4-)[(2-, 3-, or 4-)methoxybenzoyl]-1-piperidylcarbonyl group, (2-, 3-, or 4-)[(2-, 3-, or 4-)fluorobenzoyl]-1-piperidylcarbonyl group, and (2-, 3-, or 4-)[(2-, 3-, or 4-)trifluoromethoxybenzyl]-1-piperidylcarbonyl group.

Examples of the pyrrolidinylcarbonyl group that may have a substituent selected from the group consisting of a hydroxy lower alkyl group, carbamoyl group, hydroxy group, amino group (that may have a group selected from the group consisting of a lower alkyl group, lower alkanoyl group, and aroyl group thereon) morpholinyl lower alkyl group, pyrrolidinyl lower alkyl group, piperidyl lower alkyl group, piperazinyl lower alkyl group (that may have a lower alkyl group thereon as a substituent), amino lower alkyl group (that may have a lower alkyl group thereon as a substituent) and aryl oxy group (that may have on the aryl group a halogen substituted lower alkoxy group), aryloxy lower alkyl group (on the aryl group, a halogen substituted lower alkoxy group may be present) and a tetrahydroquinolyl-group (on which an oxo group may be present) include a pyrrolidinylcarbonyl group that may have 1 to 3 (preferably 1) substituents, on the pyrrolidinyl group, which are selected from the group consisting of a lower alkyl group as illustrated above having 1 to 3 hydroxy groups (preferably a linear or branched alkyl group having 1 to 6 carbon atoms);

a carbamoyl group;

a hydroxy group;

an amino group (that may have 1 to 2 groups selected from the group consisting of a lower alkyl group as illustrated above, a lower alkanoyl group as illustrated above, and an aroyl group as illustrated above);

a morpholinyl lower alkyl group whose lower alkyl moiety is one as illustrated above, preferably a linear or branched alkyl group having 1 to 6 carbon atoms;

a pyrrolidinyl lower alkyl group whose lower alkyl moiety is one as illustrated above, preferably a linear or branched alkyl group having 1 to 6 carbon atoms;

a piperidyl lower alkyl group whose lower alkyl moiety is one as illustrated above, preferably a linear or branched alkyl group having 1 to 6 carbon atoms;

a piperazinyl lower alkyl group whose lower alkyl moiety is one as illustrated above preferably a linear or branched alkyl group having 1 to 6 carbon atoms (1 to 3 (preferably 1) lower alkyl groups as illustrated above (preferably a linear or branched alkyl group having 1 to 6 carbon atoms) may be present on the piperazinyl group, as a substituent(s));

an amino lower alkyl group whose lower alkyl moiety is one as illustrated above, preferably a linear or branched alkyl group having 1 to 6 carbon atoms (1 to 2 lower alkyl groups as illustrated above (preferably a linear or branched alkyl group having 1 to 6 carbon atoms) may be present on the amino group, as a substituent(s)), aryloxy group having an aryl moiety as illustrated above (which may have on the aryl group, 1 to 3 (preferably 1) halogen substituted lower alkoxy groups), aryloxy lower alkyl group having an aryl moiety and lower alkyl moiety as illustrated above (which may have on the aryl group, 1 to 3 (preferably 1) halogen substituted lower alkoxy groups) and a tetrahydroquinolyl group (on which a single oxo group may be present). Specific examples thereof include a (1-, 2-, or 3-)pyrrolidinylcarbonyl group, (2- or 3-)hydroxymethyl-1-pyrrolidinylcarbonyl group, (1-, 2-, 3-, 4-, or 5-)hydroxymethyl-2-pyrrolidinylcarbonyl group, (1-, 2-, 3-, 4-, or 5-)hydroxymethyl-3-pyrrolidinylcarbonyl group, (2- or 3-)carbamoyl-1-pyrrolidinylcarbonyl group, (1-, 2-, 3-, 4-, or 5-)carbamoyl-2-pyrrolidinylcarbonyl group, (1-, 2-, 3-, 4-, or 5-)carbamoyl-3-pyrrolidinylcarbonyl group, (2- or 3-)hydroxy-1-pyrrolidinylcarbonyl group, (1-, 2-, 3-, 4-, or 5-)hydroxy-2-pyrrolidinylcarbonyl group, (1-, 2-, 3-, 4-, or 5-)hydroxy-3-pyrrolidinylcarbonyl group, (2- or 3-)amino-1-pyrrolidinylcarbonyl group, (2- or 3-)acetamido-1-pyrrolidinylcarbonyl group, (1-, 2-, 3-, 4-, or 5-)acetamido-2-pyrrolidinylcarbonyl group, (1-, 2-, 3-, 4-, or 5-)acetamido-3-pyrrolidinylcarbonyl group, (1-, 2-, 3-, 4-, or 5-)butyrylamino-3-pyrrolidinylcarbonyl group, (1-, 2-, 3-, 4-, or 5-)(N-methyl-N-acetylamino)-3-pyrrolidinylcarbonyl group, (1-, 2-, 3-, 4-, or 5-)(N-methyl-N-butyrylamino)-3-pyrrolidinylcarbonyl group, (1-, 2-, 3-, 4-, or 5-)benzoylamino-3-pyrrolidinylcarbonyl group, (1-, 2-, 3-, 4-, or 5-)(N-methyl-N-benzoylamino)-3-pyrrolidinylcarbonyl group, (2- or 3-)[(2-, 3-, or 4-)morpholinylmethyl]-1-pyrrolidinylcarbonyl group, (1-, 2-, 3-, 4-, or 5-)[(2-, 3-, or 4-)morpholinylmethyl]-2-pyrrolidinylcarbonyl group, (1-, 2-, 3-, 4-, or 5-)[(2-, 3-, or 4-)morpholinylmethyl]-3-pyrrolidinylcarbonyl group, (2- or 3-)[(1-, 2-, or 3-)pyrrolidinylmethyl]-1-pyrrolidinylcarbonyl group, (1-, 2-, 3-, 4-, or 5-)[(1-, 2-, or 3-)pyrrolidinylmethyl]]-2-pyrrolidinylcarbonyl group, (1-, 2-, 3-, 4-, or 5-)[(1-, 2-, or 3-)pyrrolidinylmethyl]]-3-pyrrolidinylcarbonyl group, (2- or 3-)[(1-, 2-, 3-, or 4-)piperidylmethyl]]-1-pyrrolidinylcarbonyl group, (1-, 2-, 3-, 4-, or 5-)[(1-, 2-, 3-, or 4-)piperidylmethyl]]-2-pyrrolidinylcarbonyl group, (1-, 2-, 3-, 4-, or 5-)[(1-, 2-, 3-, or 4-)piperidylmethyl)]-3-pyrrolidinylcarbonyl group, (2- or 3-)(4-methyl-1-piperazinylmethyl)-1-pyrrolidinylcarbonyl group, (1-, 2-, 3-, 4-, or 5-)(4-methyl-1-piperazinylmethyl)-2-pyrrolidinylcarbonyl group, (1-, 2-, 3-, 4-, or 5-)(4-methyl-1-piperazinylmethyl)-3-pyrrolidinylcarbonyl group, (2- or 3-)N,N-dimethylaminomethyl-1-pyrrolidinylcarbonyl group, (1-, 2-, 3-, or 5-)N,N-dimethylaminomethyl-2-pyrrolidinylcarbonyl group, (1-, 2-, 3-, 4-, or 5-)N,N-dimethylaminomethyl-3-pyrrolidinylcarbonyl group, (2- or 3-)N,N-diethylaminomethyl-1-pyrrolidinylcarbonyl group, (1-, 2-, 3-, 4-, or 5-)N,N-diethylaminomethyl-2-pyrrolidinylcarbonyl group, (1-, 2-, 3-, 4-, or 5-)N,N-diethylaminomethyl-3-pyrrolidinylcarbonyl group, (1-, 2-, 3-, 4-, or 5-)(4-trifluoromethoxyphenoxymethyl)-3-pyrrolidinylcarbonyl group, (1-, 2-, 3-, 4-, or 5-)(4-trifluoromethoxyphehoxy)-3-pyrrolidinylcarbonyl group, and (1-, 3-, 4-, 5-, 6-, 7-, or 8-)(2-oxy-1,2,3,4-tetrahydroquinolyl)-3-pyrrolidinylcarbonyl group.

Examples of a piperazinylcarbonyl group that may have a substituent selected from the group consisting of a lower alkyl group, cyclo C3-C8 alkyl group, lower alkanoyl group, hydroxy lower alkyl group, lower alkoxy lower alkyl group, lower alkoxycarbonyl group, amino lower alkyl group (a lower alkyl group may be present on the amino group, as a substituent), piperidyl lower alkyl group (a lower alkyl group may be present on the piperidyl group, as a substituent), morpholinyl lower alkyl group, pyrrolidinyl lower alkyl group, 1,3-dioxolanyl lower alkyl group, tetrahydrofuryl lower alkyl group, pyridyl lower alkyl group (a phenyl group may be present on the lower alkyl group as a substituent), imidazolyl lower alkyl group, furyl lower alkyl group, pyrrolidinyl carbonyl lower alkyl group, piperidyl group that may have a lower alkyl group as a substituent, pyridyl group (a substituent selected from the group consisting of a lower alkyl group, cyano group, and halogen substituted lower alkyl group may be present on the pyridyl group, as a substituent), thieno[2,3-c]pyridyl group aryl group (on which a group selected from the group consisting of a halogen atom and a lower alkyl group may be present), aroyl group, furyl lower alkyl group, aryl lower alkoxycarbonyl group and oxo group, include a piperazinylcarbonyl group that may have 1 to 3 (preferably 1) substituents, on the piperazinyl group, which are selected from the group consisting of a lower alkyl group as illustrated above (preferably a linear or branched alkyl group having 1 to 6 carbon atoms);

a cyclo C3-C8 alkyl group as illustrated above;

a lower alkanoyl group as illustrated above (preferably a linear or branched alkanoyl group having 1 to 6 carbon atoms);

a hydroxy lower alkyl group as illustrated above (preferably a linear or branched alkyl group having 1 to 6 carbon atoms with 1 to 3 hydroxy groups);

a lower alkoxy lower alkyl group as illustrated above (preferably a linear or branched alkyl group having 1 to 6 carbon atoms and 1 to 3 lower alkoxy groups as illustrated above (preferably a linear or branched alkoxy group having 1 to 6 carbon atoms));

a lower alkoxycarbonyl group as illustrated above (preferably a linear or branched alkoxycarbonyl group having 1 to 6 carbon atoms);

an amino lower alkyl group whose lower alkyl moiety is one as illustrated above, preferably a linear or branched alkyl group having 1 to 6 carbon atoms (1 to 2 lower alkyl groups as illustrated above (preferably a linear or branched alkyl group having 1 to 6 carbon atoms) may be present on the amino group, as substituent(s));

a piperidyl lower alkyl group whose lower alkyl moiety is one as illustrated above, preferably a linear or branched alkyl group having 1 to 6 carbon atoms (1 to 3 lower alkyl groups as illustrated above (preferably a linear or branched alkyl group having 1 to 6 carbon atoms) may be present on the piperidyl group as a substituent(s));

a morpholinyl lower alkyl group whose alkyl moiety is one as illustrated above, preferably a linear or branched alkyl group having 1 to 6 carbon atoms;

a pyrrolidinyl lower alkyl group whose alkyl moiety is one as illustrated above preferably a linear or branched alkyl group having 1 to 6 carbon atoms;
a 1,3 dioxolanyl lower alkyl group whose lower alkyl moiety is one as illustrated above, preferably a linear or branched alkyl group having 1 to 6 carbon atoms;
a tetrahydrofuryl lower alkyl group whose lower alkyl moiety is one as illustrated above, preferably a linear or branched alkyl group having 1 to 6 carbon atoms;
a pyridyl lower alkyl group whose lower alkyl moiety is one as illustrated above, preferably a linear or branched alkyl group having 1 to 6 carbon atoms (1 to 3 phenyl groups may be present on the alkyl group, as a substituent(s));
an imidazolyl lower alkyl group, whose lower alkyl moiety is one as illustrated above, preferably a linear or branched alkyl group having 1 to 6 carbon atoms;
a furyl lower alkyl group, whose lower alkyl moiety is one as illustrated above, preferably a linear or branched alkyl group having 1 to 6 carbon atoms;
a pyrrolidinyl carbonyl lower alkyl group, whose lower alkyl moiety is one as illustrated above, preferably a linear or branched alkyl group having 1 to 6 carbon atoms;
a piperidyl group that may have 1 to 3 lower alkyl groups as illustrated above (preferably a linear or branched alkyl group having 1 to 6 carbon atoms);
a pyridyl group (1 to 3 groups (preferably 1) selected from the group consisting of a lower alkyl group as illustrated above (preferably a linear or branched alkyl group having 1 to 6 carbon atoms), cyano group, and halogen substituted lower alkyl group as illustrated above (preferably a linear or branched alkyl group having 1 to 6 carbon atoms substituted with 1 to 7 halogen atoms) may be present on the pyridyl group); a tieno[2,3-c]pyridyl group; aryl group as illustrated above (which may have on the aryl group 1 to 3 (preferably 1) groups selected from the group consisting of a halogen atom and a lower alkyl group), aroyl group as illustrated above, furyl lower alkyl group having a lower alkyl moiety as illustrated above, aryl lower alkoxy carbonyl group having an aryl moiety and lower alkoxy carbonyl moiety as illustrated above and oxo group. Specific examples thereof include a (1- or 2-)piperazinylcarbonyl group, (2-, 3-, or 4-)methyl-1-piperazinylcarbonyl group, (1-, 2-, 3-, 4-, 5-, or 6-)methyl-2-piperazinylcarbonyl group, (2-, 3-, or 4-)ethyl-1-piperazinylcarbonyl group, (1-, 2-, 3-, 4-, 5-, or 6-)ethyl-2-piperazinylcarbonyl group, (2-, 3-, or 4-)n-propyl-1-piperazinylcarbonyl group, (1-, 2-, 3-, 4-, 5-, or 6-)n-propyl-2-piperazinylcarbonyl group, (2-, 3-, or 4-)n-butyl-1-piperazinylcarbonyl group, (1-, 2-, 3-, 4-, 5-, or 6-)n-butyl-2-piperazinylcarbonyl group, (2-, 3-, or 4-) [(1-ethyl-n-propyl)]-1-piperazinylcarbonyl group, (1-, 2-, 3-, 4-, 5-, or 6-)[(1-ethyl-n-propyl)]-2-piperazinylcarbonyl group, (2-, 3-, or 4-)isopropyl-1-piperazinylcarbonyl group, (1-, 2-, 3-, 4-, 5-, or 6-)isopropyl-2-piperazinylcarbonyl group, (2-, 3-, or 4-)tert-butyl-1-piperazinylcarbonyl group, (1-, 2-, 3-, 4-, 5-, or 6-)tert-butyl-2-piperazinylcarbonyl group, (2-, 3-, or 4-)n-hexyl-1-piperazinylcarbonyl group, (1-, 2-, 3-, 4-, 5-, or 6-)n-hexyl-2-piperazinylcarbonyl group, (2-, 3-, or 4-)cyclopentyl-1-piperazinylcarbonyl group, (1-, 2-, 3-, 4-, 5-, or 6-)cyclopentyl-2-piperazinylcarbonyl group, (2-, 3-, or 4-)cycloheptyl-1-piperazinylcarbonyl group, (1-, 2-, 3-, 4-, 5-, or 6-)cycloheptyl-2-piperazinylcarbonyl group, (2-, 3-, or 4-)acetyl-1-piperazinylcarbonyl group, (2-, 3-, or 4-)butyryl-1-piperazinyl carbonyl group, (1-, 2-, 3-, 4-, 5-, or 6-)acetyl-2-piperazinylcarbonyl group, (2-, 3-, or 4-)(2-hydroxyethyl)-1-piperazinylcarbonyl group, (1-, 2-, 3-, 4-, 5-, or 6-)(2-hydroxyethyl)-2-piperazinylcarbonyl group, (2-, 3-, or 4-) (2-methoxyethyl)-1-piperazinylcarbonyl group, (1-, 2-, 3-, 4-, 5-, or 6-)(2-methoxyethyl)-2-piperazinylcarbonyl group, (2-, 3-, or 4-) (3-methoxypropyl)-1-piperazinylcarbonyl group, (1-, -2-, 3-, 4-, 5-, or 6-)(3-methoxypropyl)-2-piperazinylcarbonyl group, (2-, 3-, or 4-)(4-methoxybutyl)-1-piperazinylcarbonyl group, (1-, 2-, 3-, 4-, 5-, or 6-)(4-methoxybutyl)-2-piperazinylcarbonyl group, (2-, 3-, or 4-)ethoxycarbonyl-1-piperazinylcarbonyl group, (1-, 2-, 3-, 4-, 5-, or 6-)ethoxycarbonyl-2-piperazinylcarbonyl group, (2-, 3-, or 4-)tert-butoxycarbonyl-1-piperazinylcarbonyl group, (1-, 2-, 3-, 4-, 5-, or 6-)tert-butoxycarbonyl-2-piperazinylcarbonyl group, (2-, 3-, or 4-)methoxycarbonyl-1-piperazinylcarbonyl group, (1-, 2-, 3-, 4-, 5-, or 6-)methoxycarbonyl-2-piperazinylcarbonyl group, (2-, 3-, or 4-)[3-(N,N-dimethylamino)propyl]-1-piperazinylcarbonyl group, (1-, 2-, 3-, 4-, 5-, or 6-)[3-(N,N-dimethylamino)propyl]-2-piperazinylcarbonyl group, (2-, 3-, or 4-)[2-(N,N-dimethylamino)ethyl]-1-piperazinylcarbonyl group, (1-, 2-, 3-, 4-, 5-, or 6-)(2-(N,N-dimethylamino)ethyl)-2-piperazinylcarbonyl group, (2-, 3-, or 4-)(2-(1-piperidyl)ethyl)-1-piperazinylcarbonyl group, (1-, 2-, 3-, 4-, 5-, or 6-)(2-(1-piperidyl)ethyl)-2-piperazinylcarbonyl group, (2-, 3-, or 4-)[(1-methyl-3-piperidyl)methyl]-1-piperazinylcarbonyl group, (1-, 2-, 3-, 4-, 5-, or 6-)[(1-methyl-3-piperidyl)methyl]-2-piperazinylcarbonyl group, (2-, 3-, or 4-)((1-methyl-4-piperidyl)methyl]-1-piperazinylcarbonyl group, (1-, 2-, 3-, 4-, 5-, or 6-)[(1-methyl-4-piperidyl)methyl]-2-piperazinylcarbonyl group, (2-, 3-, or 4-) [2-(4-morpholinyl)ethyl]-1-piperazinylcarbonyl group, (1-, 2-, 3-, 4-, 5-, or 6-)[2-(4-morpholinyl)ethyl]-2-piperazinylcarbonyl group, (2-, 3-, or 4-)[2-(1-pyrrolidinyl)ethyl]-1-piperazinylcarbonyl group, (1-, 2-, 3-, 4-, 5-, or 6-)[2-(1-pyrrolidinyl)ethyl]-2-piperazinylcarbonyl group, (2-, 3-, or 4-)[2-(1,3-dioxolanyl)methyl]-1-piperazinylcarbonyl group, (1-, 2-, 3-, 4-, 5-, or 6-)[2-(1,3-dioxolanyl)methyl]-2-piperazinylcarbonyl group, (2-, 3-, or 4-){2-[2-(1,3-dioxolanyl)]ethyl}-1-piperazinylcarbonyl group, (1-, 2-, 3-, 4-, 5-, or 6-){2-[2-(1,3-dioxolanyl)]ethyl}-2-piperazinylcarbonyl group, (2-, 3-, or 4-)(2-tetrahydrofurylmethyl)-1-piperazinylcarbonyl group, (1-, 2-, 3-, 4-, 5-, or 6-)(2-tetrahydrofurylmethyl)-2-piperazinylcarbonyl group, (2-, 3-, or 4-)(2-pyridylmethyl)-1-piperazinylcarbonyl group, (1-, 2-, 3-, 4-, 5-, or 6-)(2-pyridylmethyl)-2-piperazinylcarbonyl group, (2-, 3-, or 4-)(3-pyridylmethyl)-1-piperazinylcarbonyl group, (1-, 2-, 3-, 4-, 5-, or 6-)(3-pyridylmethyl)-2-piperazinylcarbonyl group, (2-, 3-, or 4-)(4-pyridylmethyl)-1-piperazinylcarbonyl group, (1-, 2-, 3-, 4-, 5-, or 6-)(4-pyridylmethyl)-2-piperazinylcarbonyl group, (2-, 3-, or 4-)[2-(4-pyridyl)ethyl]-1-piperazinylcarbonyl group, (1-, 2-, 3-, 4-, 5-, or 6-)[2-(4-pyridyl)ethyl]-2-piperazinylcarbonyl group, (2-, 3-, or 4-)[2-(2-pyridyl)ethyl]-1-piperazinylcarbonyl group, (1-, 2-, 3-, 4-, 5-, or 6-)[2-(2-pyridyl)ethyl]-2-piperazinylcarbonyl group, (2-, 3-, or 4-)[2-phenyl-2-(4-pyridyl)ethyl]-1-piperazinylcarbonyl group, (1-, 2-, 3-, 4-, 5-, or 6-)[2-phenyl-2-(4-pyridyl)ethyl]-2-piperazinylcarbonyl group, (2-, 3-, or 4-)[2-(1-imidazolyl)ethyl]-1-piperazinylcarbonyl group, (1-, 2-, 3-, 4-, 5-, or 6-)[2-(1-imidazolyl)ethyl]-2-piperazinylcarbonyl group, (2-, 3-, or 4-)(3-furylmethyl)-1-piperazinylcarbonyl group, (1-, 2-, 3-, 4-, 5-, or 6-)(3-furylmethyl)-2-piperazinylcarbonyl group, (2-, 3-, or 4-)(1-pyrrolidinylcarbonylmethyl)-1-piperazinylcarbonyl group, (1-, 2-, 3-, 4-, 5-, or 6-)(1-pyrrolidinylcarbonylmethyl)-2-piperazinylcarbonyl group, (2-, 3-, or 4-)(1-methyl-4-piperidyl)-1-piperazinylcarbonyl group, (1-, 2-, 3-, 4-, 5-, or 6-)(1-methyl-4-piperidyl)-2-piperazinylcarbonyl group, (2-, 3-, or 4-)[(2-, 3-, or 4-)pyridyl]-1- piperazinylcarbonyl group, (1-, 2-, 3-, 4-, 5-, or 6-)(2-, 3-, or 4-pyridyl)-2-piperazinylcarbonyl group, (2-, 3-, or 4-) (3-cyano-2-pyridyl)-1-piperazinylcarbonyl group, (1-, 2-, 3-, 4-, 5-, or 6-)(3-cyano-2-pyridyl)-2-piperazinylcarbonyl group, (2-3-, or 4-){4-methyl-2-pyridyl}-1-piperazinylcarbonyl group, (1-, 2-, 3-, 4-, 5-, or 6-)(4-methyl-2-pyridyl)-2-piperazinylcarbonyl group, (2-, 3-, or 4-)(3-methyl-2-pyridyl)-1-piperazinylcarbonyl group, (1-, 2-, 3-, 4-, 5-, or 6-)(3-methyl-2-pyridyl)-2-piperazinylcarbonyl group, (2-, 3-, or 4-)(3-trifluoromethyl-2-pyridyl)-1-piperazinylcarbonyl group, (1-, 2-, 3-, 4-, 5-, or 6-) (3-trifluoromethyl-2-pyridyl)-2-piperazinylcarbonyl group, (2-, 3-, or 4-)[(2-, 3-, 4-, 5-, or 6-)thieno[2,3-c]pyridyl]-1-piperazinylcarbonyl group, (1-, 2-, 3-, 4-, 5-, or 6-)[(2-, 3-, 4-, 5-, or 6-)thieno[2,3-c]pyridyl]-2-piperazinylcarbonyl group, (2-, 3-, or 4-)phenyl-1-piperazinylcarbonyl group, (2-, 3-, or 4-)[(2-, 3-, or 4-)chlorophenyl]-1-piperazinylcarbonyl group, (2-, 3-, or 4-)[(2-, 3-, or 4-)methylphenyl]-1-piperazinylcarbonyl group, 3-oxo-(2- or 4-)phenyl-1-piperazinylcarbonyl group, (2-, 3-, or 4-)benzolyl-1-piperazinylcarbonyl group, (2-, 3-, or 4-)[(2- or 3-)furylcarbonyl]-1-piperazinylcarbonyl group, and (2-, 3-, or 4-)benzyloxycarbonyl-1-piperazinylcarbonyl group.

Example of a hexahydroazepinylcarbonyl group include a (1-, 2-, 3- or 4-)hexahydroazepinylcarbonyl group.

Example of a hexahydro-1,4-diazepinylcarbonyl group that may have a substituent selected from the group consisting of a lower alkyl group and a pyridyl group include a hexahydro-1,4-diazepinylcarbonyl group that may have 1 to 3, preferably 1, substituents selected from the group consisting of a lower alkyl group as illustrated above (preferably a linear or branched alkyl group having 1 to 6 carbon atoms) and a pyridyl group. Specific examples thereof include a (hexahydro-1,4-diazepin-(1-, 2-, 5- or 6-)yl)carbonyl group, (4-methyl-hexahydro-1,4-diazepin-1-yl)carbonyl group, and (4-(4-pyridyl)-methyl-hexahydro-1,4-diazepin-1-yl)carbonyl group.

Example of a dihydropyrrolylcarbonyl group include a 2,3-dihydropyrrolylcarbonyl group and a 2,5-dihydropyrrolylcarbonyl group.

Examples of the dihydropyrrolylcarbonyl group that may have a lower alkyl group include a dihydropyrrolylcarbonyl group as illustrated above that may have 1 to 4, preferably 1 to 2 lower alkyl groups as illustrated above (preferably a linear or branched alkyl group having 1 to 6 carbon atoms). Specific examples thereof include a (1-, 2- or 3-)(2,5-dihydropyrrolylcarbonyl) group, 2,5-dimethyl-1-(2,5-dihydropyrrolylcarbonyl) group, and 2,5-dimethyl-1-(2,3-dihydropyrrolylcarbonyl) group.

Examples of the thiomorpholinylcarbonyl group include a (2-, 3- or 4-)thiomorpholinylcarbonyl group.

Examples of the morpholinylcarbonyl group that may have a group selected from the group consisting of a lower alkyl group, and piperidyl lower alkyl group, and aryl group include a morpholinylcarbonyl group that may have 1 to 5 groups, more preferably 1 to 2 groups selected from the group consisting of a lower alkyl group as illustrated above (preferably a linear or branched alkyl group having 1 to 6 carbon atoms) (on which 1 to 3 (preferably 1) piperidyl groups may be present as substituent(s)) an aryl group as described above. Specific examples thereof include a (2-, 3- or 4-)morpholinylcarbonyl group, 2,6-dimethyl-4-morpholinylcarbonyl group, 2-(1-piperidylmethyl)-4-morpholinylcarbonyl group, and 2-phenyl-4-morpholinylcarbonyl group.

Examples of the thiazolidinylcarbonyl group include a (2-, 3-, 4- or 5-) thiazolidinylcarbonyl group.

Examples of the thiazolidinylcarbonyl group that may have an aryl group that may have a group selected from the group consisting of a lower alkoxy group and a cyano group include a thiazolidinylcarbonyl group that may have 1 to 3 (preferably 1) aryl groups that may have 1 to 3 (preferably 1) groups selected from the group consisting of a lower alkoxy group and a cyano group as illustrated above. Specific examples thereof include a (2-, 3-, 4- or 5-)thiazolidinylcarbonyl group, (2-, 4- or 5-)[(2-, 3- or 4-)methoxyphenyl]-3-thiazolidinylcarbonyl group and (2-, 4- or 5-)[(2-, 3- or 4-)cyanophenyl]-3-thiazolidinylcarbonyl group.

Examples of the azabicyclo[3.2.2]nonylcarbonyl group include a 1-azabicyclo[3.2.2]non-(2-, 3-, 5-, or 6-)ylcarbonyl group, 2-azabicyclo[3.2.2]non-(1-, 2-, 3-, 4-, 5-, 6- or 7-)ylcarbonyl group, 3-azabicyclo[3.2.2]non-(1-, 2-, 3-, or 6-)ylcarbonyl group, and 6-azabicyclo[3.2.2]non-(1-, 2-, 3-, 4-, 5-, 6-, 7-, 8- or 9-)ylcarbonyl group.

Examples of the azabicyclo[3.2.1]octylcarbonyl group that may have a halogen substituted or unsubstituted aryloxy group include an azabicyclo[3.2.1]octylcarbonyl group that may have 1 to 2 (preferably 1) halogen substituted aryl groups as illustrated above (preferably an aryl group that may be substituted with 1 to 3, preferably 1 halogen atom), or an azabicyclo[3.2.1]octylcarbonyl group that may have 1 to 2 (preferably 1) unsubstituted aryl groups as illustrated above. Specific examples thereof include a 1-azabicyclo[3.2.1]oct-(2-, 3-, 4-, 5-, 6-, 7-, or 8-)ylcarbonyl group, 2-azabicyclo[3.2.1]oct-(1-, 2-, 3-, 4-, 5-, 6-, 7-, or 8-)ylcarbonyl group, 3-azabicyclo[3.2.1]oct-(1-, 2-, 3-, 6-, or 8-)ylcarbonyl group, 6-azabicyclo[3.2.1]oct-(1-, 2-, 3-, 4-, 5-, 6-, 7-, or 8-)ylcarbonyl group, 8-azabicyclo[3.2.1]oct-(1-, 2-, 3-, 6-, or 8-)ylcarbonyl group, 3-(phenyloxy)-1-azabicyclo[3.2.1]oct-2-ylcarbonyl group, 3-(2-biphenyloxy)-1-azabicyclo[3.2.1]oct-3-ylcarbonyl group, 3-(1-naphthyloxy)-1-azabicyclo[3.2.1]oct-4-ylcarbonyl group, 3-(3-methylphenyloxy)-1-azabicyclo[3.2.1]oct-5-ylcarbonyl group, 3-(4-ethylphenyloxy)-1-azabicyclo[3.2.1]oct-6-ylcarbonyl group, 3-(2-n-propylphenyloxy)-1-azabicyclo[3.2.1]oct-7-ylcarbonyl group, 3-(3-n-butylphenyloxy)-1-azabicyclo[3.2.1]oct-8-ylcarbonyl group, 3-(4-n-pentylphenyloxy)-2-azabicyclo[3.2.1]oct-1-ylcarbonyl group, 3-(2-n-hexylphenyloxy)-2-azabicyclo[3.2.1]oct-2-ylcarbonyl group, 3-(3-isobutylphenyloxy)-2-azabicyclo[3.2.1]oct-3-ylcarbonyl group, 3-(4-tert-butylphenyloxy)-2-azabicyclo[3.2.1]oct-4-ylcarbonyl group, 3-(2-chlorophenyloxy)-2-azabicyclo[3.2.1]oct-5-ylcarbonyl group, 3-(3-fluorophenyloxy)-8-aza-bicyclo[3.2.1]oct-8-ylcarbonyl group, 3-(3-bromophenyloxy)-2-azabicyclo[3.2.1]oct-6-ylcarbonyl group, 3-(2-aminophenyloxy)-2-azabicyclo[3.2.1]oct-7-ylcarbonyl group, 3-(2,3-dimethylphenyloxy)-2-azabicyclo[3.2.1]oct-8-ylcarbonyl group, 3-(3,4,5-trimethylphenyloxy)-8-azabicyclo[3.2.1]oct-1-ylcarbonyl group, and 3-(2,3-diaminophenyloxy)-8-azabicyclo[3.2.1]oct-2-ylcarbonyl group.

Examples of the indolinylcarbonyl group include a (1-, 2-, 3-, 4-, 5-, 6-, or 7-)indolinylcarbonyl group.

Examples of the tetrahydropyrido[3.4-b]indolylcarbonyl group include a (1-, 2-, 3-, 4-, 5-, 6-, 7-, 8- or 9-)(2-, 3-, 4-, 9-tetrahydropyrido[3.4-b]indolylcarbonyl) group.

Examples of the piperazinyl lower alkyl group that may have a lower alkyl group on the piperazinyl group include a piperazinyl lower alkyl group whose lower alkyl moiety is a lower alkyl group as illustrated above (preferably a linear or branched alkyl group having 1 to 6 carbon atoms) and 1 to 7, preferably 1 to 5, more preferably 1, lower alkyl groups as illustrated above (preferably a linear or branched alkyl group having 1 to 6 carbon atoms) may be present on the piperazinyl group. Specific examples thereof include a (1- or 2-)piperazinylmethyl group, 2-[(1- or 2-)piperazinyl]ethyl group, 1-[(1- or 2-)piperazinyl]ethyl group, 3-[(1- or 2-)piperazinyl]propyl group, 4-[(1- or 2-)piperazinyl]butyl group, 5-[(1- or 2-)piperazinyl]pentyl group, 6-[(1- or 2-)piperazinyl]hexyl group, 1,1-dimethyl-2-[(1- or 2-)piperazinyl]ethyl group, 2-methyl-3-[(1- or 2-)piperazinyl]propyl group, 4-methyl-1-piperazinylmethyl group, 2-(4-methyl-2-piperazinyl)ethyl group, 3-(2-ethyl-1-piperazinyl)propyl group, 4-(3-n-propyl-1-piperazinyl)butyl group, 5-(4-n-butyl-1-piperazinyl)pentyl group, 6-(1-n-pentyl-2-piperazinyl)hexyl group, 2-n-hexyl-2-piperazinylmethyl group, 2-(3-isobutyl-2-piperazinyl)ethyl group, and 3-(4-tert-butyl-2-piperazinyl)propyl group.

Examples of the morpholinylcarbonyl lower alkyl group include a morpholinylcarbonyl lower alkyl group whose lower alkyl moiety is a lower alkyl group as illustrated above (preferably a linear or branched alkyl group having 1 to 6 carbon atoms). Specific examples thereof include a 2-morpholinylcarbonylmethyl group, 3-morpholinylcarbonylmethyl group, 4-morpholinylcarbonylmethyl group, 2-(2-morpholinylcarbonyl)ethyl group, 2-(3-morpholinylcarbonyl)ethyl group, 2-(4-morpholinylcarbonyl)ethyl group, 1-(2-morpholinylcarbonyl)ethyl group, 1-(3-morpholinylcarbonyl)ethyl group, 1-(4-morpholinylcarbonyl)ethyl group, 3-(2-morpholinylcarbonyl)propyl group, 3-(3-morpholinylcarbonyl)propyl group, 3-(4-morpholinylcarbonyl)propyl group, 4-(2-morpholinylcarbonyl)butyl group, 4-(3-morpholinylcarbonyl)butyl group, 4-(4-morpholinylcarbonyl)butyl group, 5-(2-morpholinylcarbonyl)pentyl group, 5-(3-morpholinylcarbonyl)pentyl group, 5-(4-morpholinylcarbonyl)pentyl group, 6-(2-morpholinylcarbonyl)hexyl group, 6-(3-morpholinylcarbonyl)hexyl group, 6-(4-morpholinylcarbonyl)hexyl group, 3-methyl-3-(2-morpholinylcarbonyl)propyl group, 3-methyl-3-(3-morpholinylcarbonyl)propyl group, 3-methyl-3-(4-morpholinylcarbonyl)propyl group, 1,1-dimethyl-2-(2-morpholinylcarbonyl)ethyl group, 1,1-dimethyl-2-(3-morpholinylcarbonyl)ethyl group, and 1,1-dimethyl-2-(4-morpholinylcarbonyl)ethyl group.

Examples of the piperazinylcarbonyl lower alkyl group that may have a lower alkyl group on the piperazinyl group include a piperazinylcarbonyl lower alkyl group whose lower alkyl moiety is a lower alkyl group as illustrated above (preferably a linear or branched alkyl group having 1 to 6 carbon atoms) and which may have 1 to 7, preferably 1 to 5, more preferably 1, lower alkyl groups as illustrated above (preferably a linear or branched alkyl group having 1 to 6 carbon atoms) on the piperazinyl group. Specific examples thereof include a (1- or 2-)piperazinylcarbonylmethyl group, 2-[(1- or 2-)piperazinylcarbonyl]ethyl group, 1-[(1- or 2-)piperazinylcarbonyl]ethyl group, 3-[(1- or 2-)piperazinylcarbonyl]propyl group, 4-[(1- or 2-)piperazinylcarbonyl]butyl group, 5-[(1- or 2-)piperazinylcarbonyl]pentyl group, 6-[(1- or 2-)piperazinylcarbonyl]hexyl group, 1,1-dimethyl-2-[1- or 2-)piperazinylcarbonyl]ethyl group, 2-methyl-3-[(1- or 2-)piperazinylcarbonyl]propyl group, 4-methyl-1-piperazinylcarbonylmethyl group, 2-(4-methyl-2-piperazinylcarbonyl)ethyl group, 3-(2-ethyl-1-piperazinylcarbonyl)propyl group, 4-(3-n-propyl-1-piperazinylcarbonyl)butyl group, 5-(4-n-butyl-1-piperazinylcarbonyl)pentyl group, 6-(1-n-pentyl-2-piperazinylcarbonyl)hexyl group, 2-n-hexyl-2-piperazinylcarbonylmethyl group, 2-(3-isobutyl-2-piperazinylcarbonyl)ethyl group, and 3-(4-tert-butyl-2-piperazinylcarbonyl)propyl group.

Examples of the amino lower alkoxy group (on the amino group, a lower alkyl group may be present) include a lower alkoxy group as illustrated above (preferably a linear or branched alkoxy group having 1 to 6 carbon atoms) having 1 to 5 (preferably 1) amino groups that may have 1 to 2 lower alkyl groups as illustrated above. Specific examples thereof include an amino methoxy group, 2-amino ethoxy group, 1-aminoethoxy group, 3-aminopropoxy group, 4-aminobutoxy group, 5-aminopentoxy group, 6-aminohexyloxy group, 1,1-dimethyl-2-aminoethoxy group, N,N-dimethylaminomethoxy group, N-methyl-N-ethylaminomethoxy group, N-methylaminomethoxy group, 2-(N-methylamino)ethoxy group, 2-(N,N-dimethylamino)ethoxy group, 2-(N,N-diethylamino)ethoxy group, 2-(N,N-diisopropylamino)ethoxy group and 3-(N,N-dimethylamino)propoxy group.

Examples of the lower alkoxy lower alkoxy group include a lower alkoxy lower alkoxy group having a lower alkoxy moiety as illustrated above. Specific examples thereof include a methoxymethoxy group, 2-methoxyethoxy group, 1-ethoxyethoxy group, 2-ethoxyethoxy group, 2-isobutoxyethoxy group, 2,2-dimethtoxyethoxy group and 2-methoxy-1-methylethoxy group.

Examples of the piperazinyl group that may have a group selected from the group consisting of an oxo group, lower alkyl group, lower alkanoyl group and lower alkoxy carbonyl group include a piperazinyl group that may have a group 1 to 3 (1 to 2) groups selected from the group consisting of an oxo group, lower alkyl group as illustrated above, lower alkanoyl group as illustrated above and lower alkoxy carbonyl group as illustrated above. Specific examples thereof include a (1- or 2-)piperazinyl group, (2-, 3- or 4-)methyl-1-piperazinyl group, (1-, 2-, 3-, 4-, 5- or 6-)methyl-2-piperazinyl group, (2-, 3- or 4-)ethyl-1-piperazinyl group, (1-, 2-, 3-, 4-, 5- or 6-)ethyl-2-piperazinyl group, (2-, 3- or 4-)n-propyl-1-piperazinyl group, (1-, 2-, 3-, 4-, 5- or 6-)n-propyl-2-piperazinyl group, (2-, 3- or 4-)formyl-1-piperazinyl group, (2-, 3- or 4-)acetyl-1-piperazinyl group, (2-, 3- or 4-)propionyl-1-piperazinyl group, (1-, 2-, 3-, 4-, 5- or 6-)propionyl-2-piperazinyl group, (2-, 3- or 4-)butyryl-1-piperazinyl group, (1-, 2-, 3-, 4-, 5- or 6-)butyryl-2-piperazinyl group, (2-, 3- or 4-)methoxycarbonyl-1-piperazinyl group, (2-, 3- or 4-)ethoxycarbonyl-1-piperazinyl group, (2-, 3- or 4-)tert-butoxycarbonyl-1-piperazinyl group, (2- or 3-)oxo-1-piperazinyl group, 2-oxo-(3-, 4-, 5- or 6-)acetyl-1-piperazinyl group, 2-oxo-(3-, 4-, 5- or 6-)butyryl-1-piperazinyl group, 2-oxo-(3-, 4-, 5- or 6-)methoxycarbonyl-1-piperazinyl group and 2-oxo-(3-, 4-, 5- or 6-)methoxycarbonyl-1-piperazinyl group.

Examples of the 1,3,8-triazaspiro[4.5]decanylcarbonyl group that may have a group selected from the group consisting of an oxo group and an aryl group include a 1,3,8-triazaspiro[4.5]decanylcarbonyl group that may have 1 to 3 (1 to 2) groups selected from the group consisting of an oxo group and an aryl group as illustrated above. Specific examples thereof include a 1,3,8-triazaspiro[4.5]decanyl-(1, 2, 3, 4 or 8-)ylcarbonyl group, 1-phenyl-1,3,8-triazaspiro[4.5]decanyl-8-ylcarbonyl group and 1-phenyl-4-oxo-1,3,8-triazaspiro[4.5]decanyl-8-ylcarbonyl group.

Examples of the tetrahydropyridyl group include a (1-, 2-, 3-, 4-, 5- or 6-)-1,2,3,4-tetrahydropyridyl group and (1-, 2-, 3-, 4-, 5- or 6-)-1,2,3,6-tetrahydropyridyl group.

Examples of the tetrahydropyridylcarbonyl group that may have a pyridyl group include a tetrahydropyridylcarbonyl group as illustrated above that may have 1 to 3 (preferably 1) pyridyl groups. Specific examples thereof include a (2-, 3- or -4)pyridyl-1,2,3,6-tetrahydropyridyl-1-ylcarbonyl group.

Examples of the imidazolidinylcarbonyl group that may have a thioxo group include an imidazolidinylcarbonyl group that may have 1 to 2 (preferably 1) thioxo groups. Specific examples thereof include a 2-thioxo-1-imidazolidinylcarbonyl group.

Examples of the tetrahydronaphthyl group include a (1- or 2-)-1,2,3,4-tetrahydronaphthyl group.

Examples of the saturated or unsaturated heteromonocyclic group having 1 to 4 heteroatoms selected from the group consisting of a nitrogen atom, oxygen atom and sulfur atom include a heteromonocyclic groups represented by (1) to (9) below.

(1) a saturated 3 to 8 (preferably 5 to 6) membered heteromonocyclic group having 1 to 4 (preferably 1 to 2) nitrogen atoms (for example, pyrrolidinyl group, imidazolidinyl group, piperidyl group, hexahydropyrimidinyl group, piperazinyl group, azepanyl group and azocanyl group);

(2) an unsaturated 3 to 8 (preferably 5 to 6) membered heteromonocyclic group having 1 to 4 (preferably 1 to 3) nitrogen atoms, for example, a pyrrolyl group, dihydropyrrolyl group such as 1H-2,5-dihydropyrolyl group, imidazolyl group (such as 1H-imidazolyl group), dihydroimidazolyl group (such as 1H-2,3-dihydroimidazolyl group), triazolyl group (such as 4H-1,2,4-trizaolyl group, 1H-1,2,3-trizaolyl group, and 2H-1,2,3-trizaolyl group), dihydrotriazolyl group (such as 1H-4,5-dihydro-1,2,4-triazolyl group), pyrazolyl group, pyridyl group, dihydropyridyl group (such as 1,2-dihydropyridyl group), pyrimidinyl group, dihydropyrimidinyl group (such as 1,6-dihydropyrimidinyl group), pyrazinyl group, dihydropyrazinyl group (such as 1,2-dihydropyrazinyl), pyridazinyl group, and tetrazolyl group (such as 1H-tetrazolyl group and 2H-tetrazolyl group);

(3) an unsaturated 3 to 8 (preferably 5 to 6) membered heteromonocyclic group having 1 to 2 (preferably 1) oxygen atoms and 1 to 3 (preferably 1 to 2) nitrogen atoms, for example, an oxazolyl group, isoxazolyl group, oxadiazolyl group (such as 1,2,4-oxadiazolyl group, 1,3,4-oxadiazolyl group and 1,2,5-oxadiazolyl group) and a saturated 3 to 8 (preferably 5 to 6 membered heteromonocyclic group having 1 to 2 (preferably 1) oxygen atoms and 1 to 3 (preferably 1 to 2) nitrogen atoms, for example an oxazolidinyl group, isoxazolidinyl group and morpholinyl group;

(4) an unsaturated 3 to 8 (preferably 5) membered heteromonocyclic group having 1 to 2 sulfur atoms and 1 to 3 nitrogen atoms, for example, a thiazolyl group, dihydrothiazolyl group (such as 2,3-dihydrothiazolyl group), isothiazolyl group, thiadiazolyl group (such as, 1,2,3-thiadiazolyl group, 1,2,4-thiadiazolyl group, 1,3,4-thiadiazolyl group, and 1,2,5-thiadiazolyl group) and dihydrothiazinyl group.

(5) a saturated 3 to 8 (preferably 5 to 6) membered heteromonocyclic group having 1 to 2 sulfur atoms and 1 to 3 nitrogen atoms, for example, a thiazolidinyl group;

(6) a saturated 3 to 8 (preferably 5 to 6) membered heteromonocyclic group having 1 to 2 oxygen atom, for example, a tetrahydrofuryl group and a tetrahydropyranyl group;

(7) an unsaturated 3 to 8 (preferably 5 to 6) membered heteromonocyclic group having 1 to 2 oxygen atoms, for example, a pyranyl group (such as 2H-pyranyl group);

(8) a saturated 3 to 8 (preferably 5 to 6) membered heteromonocyclic group having 1 to 2 sulfur atoms, for example, a tetrahydrothiofuryl group and a tetrahydrothiopyranyl group; and (9) an unsaturated 3 to 8 (preferably 5 to 6) membered heteromonocyclic group having 1 to 2 sulfur atoms, for example, a thienyl group and a thiopyranyl group (such as 2H-thiopyranyl).

Of them, mention may be preferably made of a saturated or unsaturated heteromonocyclic group having a 1 to 2 hetero atoms selected from a nitrogen atom, oxygen atom and sulfur atom and selected from the group consisting of a pyrrolidinyl group, piperidyl group, pyrazolyl group, pyridyl group, pyrimidinyl group, pyrazinyl group, isoxazolyl group, thiazolyl group, pyranyl group and thienyl group; and further preferably made of a saturated or unsaturated heteromonocyclic group having a 1 to 2 nitrogen atoms and selected from the group a pyrrolidinyl group, piperidyl group, pyrazolyl group, pyridyl group, pyrimidinyl group and thiazolyl group.

Examples of the tetrahydroquinoxalinyl group include a (1-, 2-, 5- or 6-)-1,2,3,4-tetrahydroquinoxalinyl group and (1-, 2-, 5- or 6-)-5,6,7,8-tetrahydroquinoxalinyl group.

Examples of the tetrahydroquinazolinyl group include a (1-, 2-, 3-, 4-, 5-, 6-, 7- or 8-)-1,2,3,4-tetrahydroquinazolinyl group and (1-, 2-, 3-, 4-, 5-, 6-, 7- or 8-)-5,6,7,8-tetrahydroquinazolinyl group.

Examples of the dihydroquinazolinyl group include a (1-, 2-, 3-, 4-, 5-, 6-, 7- or 8-)-3,4-dihydroquinazolinyl group and (1-, 2-, 3-, 4-, 5-, 6-, 7- or 8-)-1,2-dihydroquinazolinyl group.

Examples of the dihydrobenzimidazolyl group include a (1-, 2-, 4- or 5-)-2,3-dihydro-1H-benzimidazolyl group.

Examples of the tetrahydrobenzazepinyl group include a (1-, 2-, 3-, 4-, 5-, 6-, 7-, 8- or 9-)-2,3,4,5-tetrahydro-1H-benzo[b]azepinyl group and (1-, 2-, 3-, 4-, 5-, 6-, 7-, 8- or 9-)-2,3,4,5-tetrahydro-1H-benzo[c]azepinyl group.

Examples of the tetrahydrobenzodiazepinyl group include a (1-, 2-, 3-, 4-, 5-, 6-, 7-, 8- or 9-)-2,3,4,5-tetrahydro-1H-benzo[b][1.4]diazepinyl group and (1-, 2-, 3-, 4-, 5-, 6-, 7-, 8- or 9-)-2,3,4,5-tetrahydro-1H-benzo[e][1.4]diazepinyl group.

Examples of the hexahydrobenzazocinyl group include a (1-, 2-, 3-, 4-, 5-, 6-, 7-, 8-, 9-, or 10-)-1,2,3,4,5,6-tetrahydrobenzo[b]azocinyl group and (1-, 2-, 3-, 4-, 5-, 6-, 7-, 8-, 9- or 10-)-1,2,3,4,5,6-hexahydrobenzo (cazocinyl group.

Examples of the dihydrobenzoxazinyl group include a (2-, 3-, 4-, 5-, 6-, 7- or 8-)-3,4-dihydro-2H-benzo[b][1.4]oxazinyl group and (1-, 2-, 4-, 5-, 6-, 7- or 8-)-2,4-dihydro-1H-benzo[d][1.3]oxazinyl group.

Examples of the dihydrobenzoxazolyl group include a (2-, 3-, 4-, 5-, 6- or 7-)-2,3-dihydrobenzoxazolyl group.

Examples of the benzisoxazolyl group include a (3-, 4-, 5-, 6- or 7-)-benzo[d]-isoxazolyl group and (3-, 4-, 5-, 6- or 7-)-benzo[c]-isoxazolyl group.

Examples of the benzoxadiazolyl group include a (4- or 5-)-benzo[c][1.2.5]oxadiazolyl group.

Examples of the tetrahydrobenzoxazepinyl group include a (2-, 3-, 4-, 5-, 6-, 7-, 8- or 9-)-2,3,4,5-tetrahydrobenzo[b][1.4]oxazepinyl group, (1-, 3-, 4-, 5-, 6-, 7-, 8- or 9-)-1,3,4,5-tetrahydrobenzo[e][1.3]oxazepinyl group and (2-, 3-, 4-, 5-, 6-, 7-, 8- or 9-)-2,3,4,5-tetrahydrobenzo[f][1.4]oxazepinyl group.

Examples of the dihydrobenzothiazinyl group include a (2-, 3-, 4-, 5-, 6-, 7- or 8-)-3,4-dihydro-2H-benzo[b][1.4]thiazinyl group and (2-, 3-, 4-, 5-, 6-, 7- or 8-)-3,4-dihydro-2H-benzo[e][1.3]thiazinyl group.

Examples of the benzoxathiolyl group include a (2-, 4-, 5-, 6- or 7-)-benzo[d][1.3]oxathiolyl group, (3-, 4-, 5-, 6- or 7-)-3H-benzo[c][1.2]oxathiolyl group and (3-, 4-, 5-, 6- or 7-)-3H-benzo[d][1.2]oxathiolyl group.

Examples of the dihydrobenzofuryl group include a (2-, 3-, 4-, 5-, 6- or 7-)-2,3-dihydrobenzofuryl group.

A heterocyclic compound (hereinafter referred to as a compound (1)) represented by the general formula (1) can be produced by various kinds of methods, for example, a method shown in the following reaction formula-1 or reaction formula 2.

Reaction formula-1

[Formula 4]

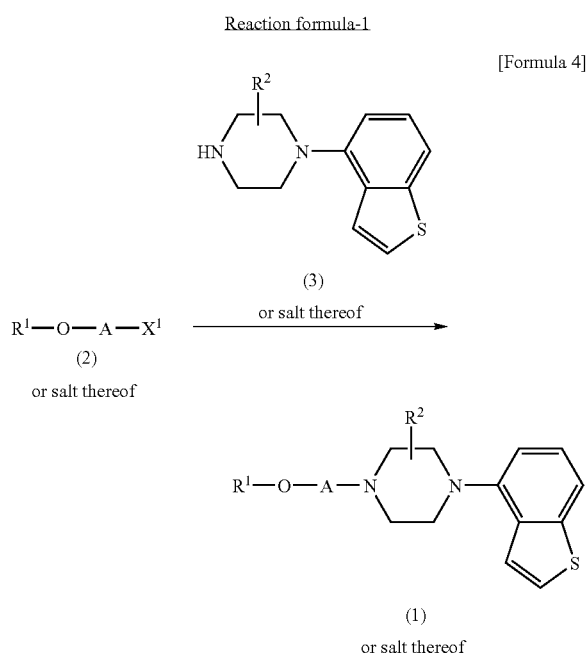

wherein $R^1$, $R^2$ and A are the same as defined above; and $X^1$ is a halogen atom or a group mediating the same substitution reaction as in a halogen atom.

Examples of the group mediating the same substitution reaction as in a halogen atom include a lower alkanesulfonyloxy group, arylsulfonyloxy group, and aralkylsulfonyloxy group.

A halogen atom represented by $X^1$ in the general formula (2) is a fluorine atom, chlorine atom, bromine atom and iodine atom.

Specific examples of the lower alkanesulfonyloxy group represented by $X^1$ include a linear or branched alkanesulfonyloxy group having 1 to 6 carbon atoms such as a methanesulfonyloxy group ethanesulfonyloxy group, isopropanesulfonyloxy group, n-propanesulfonyloxy group, n-butanesulfonyloxy group, tert-butanesulfonyloxy group, n-pentanesulfonyloxy group, and n-hexanesulfonyloxy group.

Specific examples of the arylsulfonyloxy group represented by $X^1$ include a phenylsulfonyloxy group and naphthylsulfonyloxy group that may have 1 to 3 substituents selected from the group consisting of a linear or branched alkyl group having 1 to 6 carbon atoms, a linear or branched alkoxy group having 1 to 6 carbon atoms, a nitro group, and a halogen atom, on the phenyl ring. Specific examples of the phenylsulfonyloxy group that may have a substituent include a phenylsulfonyloxy group, 4-methylphenylsulfonyloxy group, 2-methylphenylsulfonyloxy group, 4-nitrophenylsulfonyloxy group, 4-methoxyphenylsulfonyloxy group, 2-nitrophenylsulfonyloxy group, and 3-chlorophenylsulfonyloxy group. Specific examples of the naphthylsulfonyloxy group include α-naphthylsulfonyloxy group and β-naphthylsulfonyloxy group.

Examples of the aralkylsulfonyloxy group represented by $X^1$ include a linear or branched alkylsulfonyloxy group having 1 to 6 carbon atoms and substituted with a phenyl group; and
a linear or branched alkylsulfonyloxy group having 1 to 6 carbon atoms and substituted with a naphthyl group; both of which may have 1 to 3 substituents selected from the group consisting of a linear or branched alkyl group having 1 to 6 carbon atoms, a linear or branched alkoxy group having 1 to 6 carbon atoms, a nitro group and a halogen atom, on the phenyl ring. Specific examples of the alkylsulfonyloxy group substituted with a phenyl group as mentioned above include a benzylsulfonyloxy group, 2-phenylethylsulfonyloxy group, 4-phenylbutylsulfonyloxy group, 2-methylbenzylsulfonyloxy group, 4-methoxybenzylsulfonyloxy group, 4-nitrobenzylsulfonyloxy group, and 3-chlorobenzylsulfonyloxy group. Specific examples of the alkylsulfonyloxy group substituted with a naphthyl group include an α-naphthylmethylsulfonyloxy group and β-naphthylmethylsulfonyloxy group.

The compound (1) can be produced by reacting a compound (hereinafter referred to as a compound (2)) represented by the general formula (2) and a compound (hereinafter referred to as a compound (3)) represented by the general formula (3).

This reaction is generally performed in a conventional solvent that may not negatively affect the reaction, such as water; an alcohol based solvent such as methanol, ethanol, isopropanol, n-butanol, trifluoroethanol, and ethylene glycol; a ketone based solvent such as acetone and methylethyl ketone; an ether based solvent such as tetrahydrofuran, dioxane, diethyl ether, and diglyme; an ester based solvent such as methyl acetate and ethyl acetate; a non-proton polar solvent such as acetonitrile, N,N-dimethylformamide, and dimethylsulfoxide; a halogenated hydrocarbon based solvent such as methylene chloride and ethylene chloride; or other organic solvents. Furthermore, the reaction can be performed in a solution mixture of these conventional solvents. The reaction is generally performed in the presence of an inorganic base such as an alkali metal (e.g., sodium and potassium), an alkaline metal hydrogen carbonate (e.g., lithium hydrogen carbonate, sodium hydrogen carbonate, and potassium hydrogen carbonate), alkali metal hydroxide (e.g., lithium hydroxide, sodium hydroxide, potassium hydroxide, and cesium hydroxide), alkali metal carbonate (e.g., lithium carbonate, sodium carbonate, potassium carbonate, and cesium carbonate), alkali metal lower alkoxide (e.g., sodium methoxide and sodium ethoxide), and a hydride (e.g., sodium hydride and potassium hydride); or in the presence of an organic base such as a trialkylamine (e.g., trimethylamine, triethylamine, N-ethyl diisopropylamine), pyridine, quinoline, piperidine, imidazole, picoline, dimethylaminopyridine, dimethylaniline, N-methylmorpholine, 1,5-diazabicyclo[4.3.0]non-5-ene (DBN), 1,4-diazabicyclo[2.2.2]octane (DABCO), and 1,8-diazabicyclo[5.4.0]undecene-7 (DBU). When these bases take liquid form, they can be used as solvents.

These basic compounds may be used alone or in a mixture of two types or more.

A basic compound may be used in a molar amount, which is generally 0.5 to 10 times, preferably 0.5 to 6 times as large as that of the compound (2).

The reaction mentioned above may be performed, if necessary, with the addition of an alkaline metal iodide serving as an accelerator, such as potassium iodide and sodium iodide.

The ratio of a compound (2) to a compound (3) used in the reaction formula-1 may be at least about 0.5 times mole, preferably about 0.5-5 times by mole.

The reaction temperature is not particularly limited and may be generally performed under cool or heating conditions and preferably performed at a temperature from near room temperature to about 150° C. for 1 to 30 hours.

The compound (2) serving as a starting material for a compound according to the present invention include a novel compound and can be produced by various methods, for example, a method represented by the following reaction formula-3.

The compound (3) serving as a starting material for a compound according to the present invention is a known compound or a compound that can be easily produced from a known compound.

A salt of a compound (2) in place of the compound (2) and a salt of a compound (3) in place of the compound (3) may be used. The salts of compounds (2) and (3) include acid-addition salts. These acid addition salts may be prepared by reacting a pharmaceutically acceptable acid with a compound (2) or (3). Examples of the acid used herein include inorganic acids such as sulfuric acid, nitric acid, hydrochloric acid, phosphoric acid, and hydrobromic acid; sulfonic acids such as p-toluene sulfonic acid, methane sulfonic acid, and ethane sulfonic acid; and organic acids such as acetic acid, oxalic acid, maleic acid, fumaric acid, malic acid, tartaric acid, citric acid, succinic acid, and benzoic acid.

Of the compounds (2), a compound having an acidic group can easily produce a salt by reacting with a pharmaceutically acceptable basic compound. Examples of such a basic compound include metal hydroxides such as sodium hydroxide, potassium hydroxide, lithium hydroxide, and calcium hydroxide; alkali metal carbonates or bicarbonates such as sodium carbonate, sodium hydrogen carbonate, potassium hydrogen carbonate; and alkali metal alcoholates such as sodium methylate and potassium ethylate.

Reaction formula-2

[Formula 5]

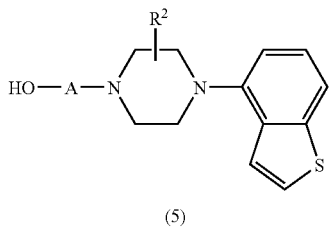

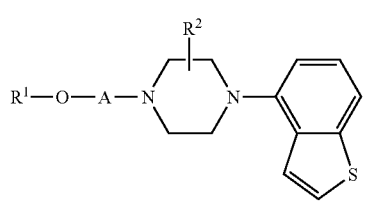

wherein $R^1$, $R^2$ and A are the same as defined above; and $X^2$ is a hydroxy group, halogen atom or a group mediating the same substitution reaction as in a halogen atom.

Examples of the halogen atom represented by $X^2$ and the group mediating the same substitution reaction as in a halogen atom in connection with the general formula (4) are the same as mentioned above.

The compound (1) can be produced by reacting a compound (hereinafter referred to as a compound (4)) represented by the general formula (4) and a compound (hereinafter referred to as a "compound (5)") represented by the general formula (5).

The reaction can be performed under the similar conditions as in reaction formula-1.

In the case of a compound (4) in which $X^2$ is a hydroxy group, the reaction can be performed in an appropriate solvent in the presence of an appropriate condensing agent.

This reaction is generally performed in a conventional solvent that may not negatively affect the reaction, such as water; an alcohol based solvent such as methanol, ethanol, isopropanol, n-butanol, trifluoroethanol, and ethylene glycol; a ketone based solvent such as acetone and methylethyl ketone; an ether based solvent such as tetrahydrofuran, dioxane, diethyl ether, and diglyme; an ester based solvent such as methyl acetate and ethyl acetate; a non-proton polar solvent such as acetonitrile, N,N-dimethylformamide, and dimethylsulfoxide; a halogenated hydrocarbon based solvent such as methylene chloride and ethylene chloride; or other organic solvents. Furthermore, as a solvent to be used herein, a solution mixture of these conventional solvents may be mentioned.

As the condensing agent, a mixture of an azocarboxylate such as diethyl azodicarboxylate and a phosphine compound such as triphenylphosphine may be mentioned.

The amount of the condensing agent used herein is generally at least equimolar, preferably equimolar to twice as large as that of a compound (4).

The ratio of a compound (4) to a compound (5) used in the reaction formula-2 may be generally at least equimole preferably about 2 times by mole.

The reaction temperature is not particularly limited and may generally be performed under cool or heating conditions, and preferably performed at a temperature from 0° C. to about 150° C. for 1 to 10 hours.

The compound (4) serving as a starting material for a compound according to the present invention is a known compound or a compound that can be easily produced from a known compound.

The compound (5) serving as a starting material for a compound according to the present invention include a novel compound and a compound that can be produced by various methods, for example, a method represented by the following reaction formula-4 or -5.

A salt of a compound (4) in place of the compound (4) and a salt of a compound (5) in place of the compound (5) may be used. As a preferable salt of a compound (4), the same salt as shown in a compound (2) may be mentioned. As a preferable salt of a compound (5), the same salt as shown in a compound (3) may be mentioned.

Reaction formula-3

[Formula 6]

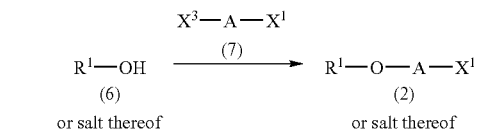

wherein $R^1$, $X^1$ and A are the same as defined above; and $X^3$ is a halogen atom or a group mediating the same substitution reaction as in a halogen atom.

Examples of the halogen atom represented by $X^3$ and the group mediating the same substitution reaction as in a halogen atom in connection with the general formula (7) are the same as mentioned above.

The compound (2) can be produced by reacting a compound (hereinafter referred to as a compound (6)) represented by the general formula (6) and a compound (hereinafter referred to as a compound (7)) represented by the general formula (7).

The reaction can be performed under the similar conditions as in reaction formula-1.

The compounds (6) and (7) serving as starting materials for a compound according to the present invention are known compounds or compounds that can be easily produced from known compounds.

In place of a compound (6), a salt of the compound (6) may be used. As a preferable salt of a compound (6), the same salt as shown in a compound (2) may be mentioned.

Reaction formula-4

[Formula 7]

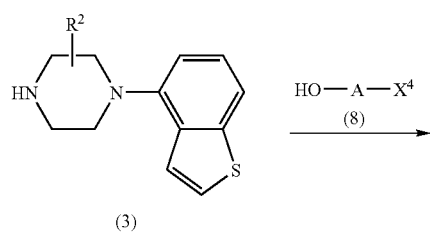

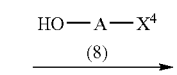

(3)
or salt thereof

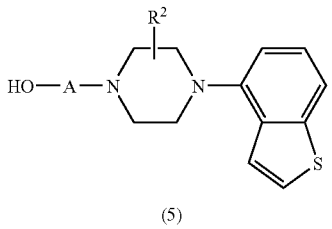

(5)
or salt thereof wherein $R^2$ and A are the same as defined above; and $X^4$ is a halogen atom or a group mediating the same substitution reaction as in a halogen atom.

Examples of the halogen atom represented by $X^4$ and the group mediating the same substitution reaction as in a halogen atom in connection with the general formula (8) are the same as mentioned above.

The compound (5) can be produced by reacting a compound (3) and a compound (hereinafter referred to as a compound (8)) represented by the general formula (8).

The reaction can be performed under the similar conditions as in reaction formula-1.

The compound (8) serving as a starting material for a compound according to the present invention is a known compound or a compound that can be easily produced from a known compound.

In place of a compound (3), a salt of the compound (3) may be used. As a preferable salt of a compound (3), the same salts as above may be mentioned.

Reaction formula-5

[Formula 8]

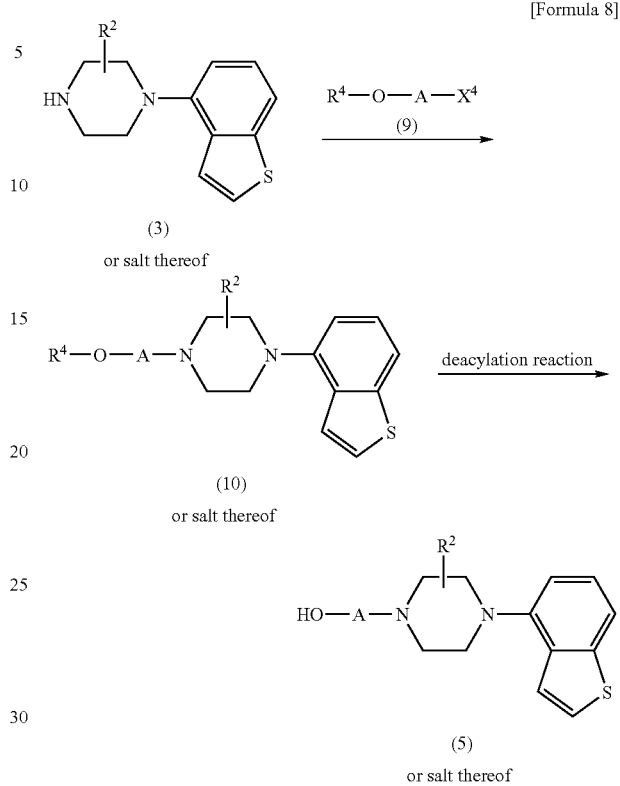

wherein $R^2$ and A are the same as defined above; $R^4$ is a lower alkanoyl group; and $X^4$ is a halogen atom or a group mediating the same substitution reaction as in a halogen atom.

Examples of the lower alkanoyl group represented by $R^4$ in the general formulas (9) and (10) are the same as mentioned above.

Furthermore, examples of the halogen atom represented by $X^4$ and the group mediating the same substitution reaction as in a halogen atom in connection with the general formula (9) are the same as mentioned above.

A compound (hereinafter referred to as a compound (10)) represented by the general formula (10) can be produced by reacting a compound (3) and a compound (9).

The reaction can be performed under the similar conditions as in reaction formula-1.

The compound (9) serving as a starting material for a compound according to the present invention is a known compound or a compound that can be easily produced from a known compound.

In place of a compound (3), a salt of the compound (3) may be used. As a preferable salt of a compound (3), the same salts as above may be mentioned.

Subsequently, the compound (10) is subjected to a reaction for removing an acyl group to produce a compound (5).

As a preferable method of the reaction, a conventional reaction such as hydrolysis may be mentioned. The hydrolysis reaction may be preferably performed in the presence of a base or an acid including Lewis acid. Examples of the preferable base include inorganic salts such as an alkali metal (e.g., sodium and potassium), an alkaline metal hydrogen carbonate (e.g., lithium hydrogen carbonate, sodium hydrogen carbonate, and potassium hydrogen carbonate), an alkali metal hydroxide (e.g., lithium hydroxide, sodium hydroxide, potassium hydroxide, and cesium hydroxide), an alkali metal carbonate (e.g., lithium carbonate, sodium carbonate, potassium carbonate, and cesium carbonate), an alkali metal lower alkoxide (e.g., sodium methoxide and sodium ethoxide), and hydrides (e.g., sodium hydride and potassium hydride); and organic bases such as a trialkylamine (e.g., trimethylamine, triethylamine, and N-ethyl diisopropylamine), pyridine, quinoline, piperidine, imidazole, picoline, dimethylaminopyridine, dimethylaniline, N-methylmorpholine, DBN, DABCO, and DBU. As a preferable acid, mention can be made of organic acids (such as formic acid, acetic acid, propionic acid, trichloroacetic acid, trifluoroacetic acid) and inorganic acids (such as hydrochloric acid, hydrobromic acid, sulfuric acid, hydrogen chloride, and hydrogen bromide). The removal reaction using a Lewis acid such as a trihaloacetic acid (e.g., trichloroacetic acid and trifluoroacetic acid) may be preferably performed in the presence of a cation-trapping agent (e.g., anisole and phenol).

This reaction is generally performed in a conventional solvent that may not negatively affect the reaction, such as water; an alcohol based solvent such as methanol, ethanol, isopropanol, n-butanol, trifluoroethanol, and ethylene glycol; a ketone based solvent such as acetone and methylethyl ketone; an ether based solvent such as tetrahydrofuran, dioxane, diethyl ether, and diglyme; an ester based solvent such as methyl acetate and ethyl acetate; a non-proton polar solvent such as acetonitrile, N,N-dimethylformamide, and dimethylsulfoxide; a halogenated hydrocarbon based solvent such as methylene chloride and ethylene chloride; or other organic solvents. Furthermore, the reaction may be performed in a solution mixture of these conventional solvents. Of them, ethanol is preferable. The reaction temperature is not particularly limited and may generally be performed under cool or heating conditions, and preferably performed at near room temperature to near a boiling point of the solvent to be used for 0.5 to 75 hours.

In place of a compound (10), a salt of the compound (10) may be used. As a preferable salt of a compound (10), the same salt as shown in a compound (3) may be mentioned.

Furthermore, a compound (hereinafter referred to as a compound (5a)) where A of the compound (5) represents —CH$_2$A"- where A" represents a C1 to C5 alkylene group can be produced by a method represented by the following reaction formula-6.

Reaction formula-6

[Formula 9]

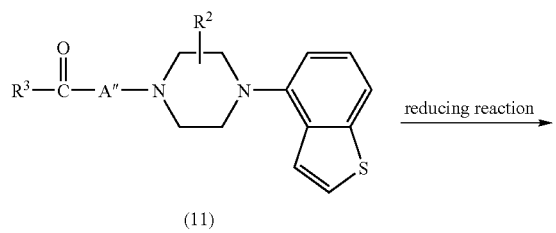

(11)
or salt thereof

↓ reducing reaction

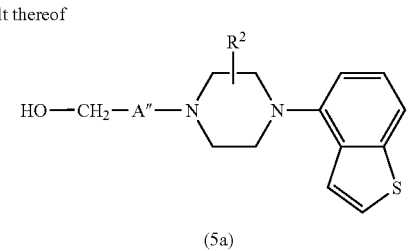

(5a)
or salt thereof wherein R$^2$ is the same as defined above; and R$^3$ is a lower alkoxy group. A" represents a C1 to C5 alkylene group. The lower alkoxy group represented by R$^3$ in the general formula (11) is the same as defined above.

Examples of the C1 to C5 alkylene group represented by A" in the general formulas (11) and (5a) include a linear or branched alkylene group having 1 to carbon atoms such as methylene, ethylene, methyl methylene, trimethylene, tetramethylene, 1-methyl trimethylene, 2-methyl trimethylene, 3-methyl tetramethylene, pentamethylene, and 2,2-dimethyl trimethylene.

The compound (5a) can be produced by subjecting a compound (hereinafter referred to as a compound (11)) represented by the general formula (11) to a reducing reaction.

The reaction can be performed by the method shown in Reference Example 6 or a similar method thereof. The reaction also can be performed by a conventional method using a reducing agent.

As a preferable reducing agent, mention may be made of a hydride (such as lithium aluminum hydride, sodium borohydride, lithium borohydride, diborane, and sodium cyanoborohydride).

This reaction is generally performed in a conventional solvent that may not negatively affect the reaction, such as an alcohol based solvent such as methanol, ethanol, isopropanol, n-butanol, trifluoroethanol, and ethylene glycol; a ketone based solvent such as acetone and methylethyl ketone; an ether based solvent such as tetrahydrofuran, dioxane, diethyl ether, and diglyme; an ester based solvent such as methyl acetate and ethyl acetate; a non-proton polar solvent such as acetonitrile, N,N-dimethylformamide, and dimethylsulfoxide; a halogenated hydrocarbon based solvent such as methylene chloride and ethylene chloride; or other organic solvents. Furthermore, the reaction may be performed in a solution mixture of these conventional solvents. The reaction temperature is not particularly limited and may generally be performed under cool or heating conditions, and preferably performed at near room temperature to near a boiling point of the solvent to be used for 0.5 to 75 hours.

The compound (11) serving as a starting material for a compound according to the present invention is a known compound or a compound that can be easily produced from a known compound.

In place of a compound (11), a salt of the compound (11) may be used. As a preferable salt of a compound (11), the same salt as shown in a compound (2) may be mentioned.

Furthermore, a compound (hereinafter referred to as a compound (11a)) where A" of the compound (11) represents "—(CH$_2$)$_2$—" can be produced by a method represented by the following reaction formula-7.

Reaction formula-7

[Formula 10]

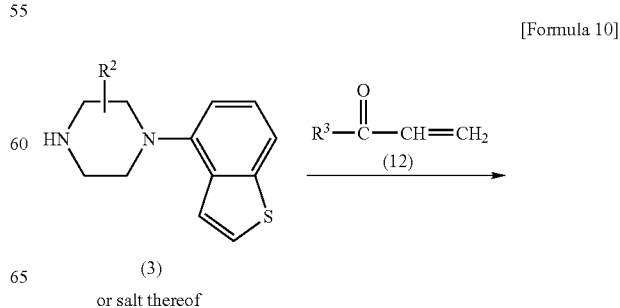

(3)
or salt thereof

-continued

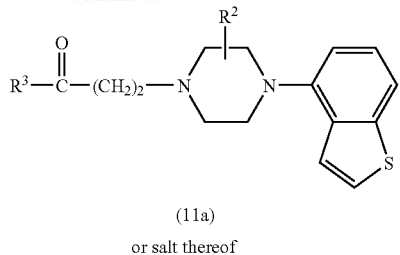

(11a)

or salt thereof where $R^2$ and $R^3$ are the same as defined above.

The compound (11a) can be produced by reacting a compound (3) and a compound (hereinafter referred to as a compound (12)) represented by the general formula (12).

The reaction can be performed by the method shown in Reference Example 5 or a similar method thereof. This reaction is generally performed in a conventional solvent that may not negatively affect the reaction, such as water, an alcohol based solvent such as methanol, ethanol, isopropanol, n-butanol, trifluoroethanol, and ethylene glycol; a ketone based solvent such as acetone and methylethyl ketone; an ether based solvent such as tetrahydrofuran, dioxane, diethyl ether, and diglyme; an ester based solvent such as methyl acetate and ethyl acetate; a non-proton polar solvent such as acetonitrile, N,N-dimethylformamide, and dimethylsulfoxide; a halogenated hydrocarbon based solvent such as methylene chloride and ethylene chloride; or other organic solvents. Furthermore, the reaction may be performed in a solution mixture of these conventional solvents. The reaction temperature is not particularly limited and may generally be performed under cool or heating conditions, and preferably performed at near room temperature to near a boiling point of the solvent to be used for 0.5 to 75 hours.

The compound (12) serving as a starting material for a compound according to the present invention is a known compound or a compound that can be easily produced from a known compound.

A salt of a compound (3) in place of the compound (3) and a salt of a compound (12) in place of the compound (12) may be used. As a preferable salt of a compound (3), the same salt as shown above may be mentioned. As a preferable salt of a compound (12), the same salt as shown in a compound (2) may be mentioned.

The object compound obtained by each of the above reaction formula may form a suitable salt. Such suitable salts include the preferable salts of compound (1) exemplified below.

The preferable salts of compound (1) are pharmacologically acceptable salts and examples include metal salts such as alkali metal salts (for example, sodium salt potassium salt, etc.), alkaline earth metal salts (for example, calcium salt, magnesium salt, etc.), salts of inorganic bases such as ammonium salt, alkaline metal carbonates (for example, lithium carbonate, potassium carbonate, sodium carbonate, cesium carbonate, etc.), alkaline metal hydrogen carbonates (for example, lithium hydrogen carbonate, sodium hydrogen carbonate, potassium bicarbonate, etc.), alkali metal hydroxides (for example, lithium hydroxide, sodium hydroxide, potassium hydroxide, cesium hydroxide, etc.); for example, salts of organic bases such as tri(lower)alkylamine (for example, trimethylamine, triethylamine, N-ethyldiisopropylamine), pyridine, quinoline, piperidine, imidazole, picoline, dimethylaminopyridine, dimethylaniline, N-(lower)alkyl-morpholine (for example, N-methylmorpholine), 1,5-diazabicyclo[4.3.0]nonene-5 (DBN), 1,8-diazabicyclo[5.4.0]undecene-7 (DBU), 1,4-diazabicyclo[2.2.2]octane (DABCO); salts of inorganic acids such as hydrochloride, hydrobromide, hydroiodide, sulfate, nitrate, phosphate; salts of organic acids such as formate, acetate, propionate, oxalate, malonate, succinate, fumarate, maleate, lactate, malate, citrate, tartrate, carbonate, picrate, methanesulfonate, ethanesulfonate, p-toluenesulfonate, glutamate.

In addition, compounds in the form in which solvate (for example, hydrate, ethanolate, etc.) was added to the starting compounds and object compound shown in each of the reaction formulae are included in each of the general formulas. As a preferable solvate, hydrate can be mentioned.

Each of the object compounds obtained by each of the general formulas can be isolated and purified from the reaction mixture by, for example, subjecting the reaction mixture to isolation operation such as filtration, concentration and extraction after cooling to separate a crude reaction product followed by conventional purification operation such as column chromatography or recrystallization.

The compound represented by the general formula (1) of the present invention naturally encompasses isomers such as geometrical isomer, stereoisomer and enantiomer.

A compound and a salt thereof represented by the general formula (1) may be used in the form of general pharmaceutical preparation. The preparation may be prepared by use of a diluent or an excipient such as a filler, extending agent, binder, humectant, disintegrator, surfactant, and lubricant. As a pharmaceutical preparation, various forms can be selected depending upon the therapeutic purpose. Typical forms thereof include a tablet, pill, powder, liquid, suspension, emulsion, granule, encapsulate, suppository, and injection (liquid, suspension).

In forming a tablet, a wide variety of types of carriers conventionally known in the art may be used. Examples of the carrier that may be used include an excipient such as lactose, saccharose, sodium chloride, glucose, urea, starch, calcium carbonate, kaolin, crystalline cellulose, and silicate; a binder such as water, ethanol, propanol, simple syrup, glucose solution, starch solution, gelatine solution, carboxymethylcellulose, shellac, methyl cellulose, potassium phosphate, and polyvinylpyrrolidine; a disintegrator such as dried starch, sodium alginate, powdered agar, powdered laminaran, sodium hydrogen carbonate, calcium carbonate, polyoxyethylene sorbitan fatty acid ester, sodium lauryl sulfate, stearic acid monoglyceride, starch, and lactose; a disintegration suppressant such as saccharose, stearin, cocoa butter, and hydrogenated oil; a sorbefacient such as quaternary ammonium base and sodium lauryl sulfate; a humectant such as glycerin and starch; an adsorbing agent such as starch, lactose, kaolin, bentonite, and colloidal silica; and a lubricant such as refined talc, stearate, powdered boric acid, and polyethylene glycol.

Furthermore, if necessary, a tablet may be coated with a general film. Examples of such a coated tablet include a sugar-coated tablet, gelatine encapsulated tablet, enteric-coated tablet, film coated tablet or double-layer tablet, and multi-layer tablet.

In forming a pill, a wide variety of types of carriers conventionally known in the art may be used. Examples of the carrier that may be used include an excipient such as glucose, lactose, starch, cacao butter, hardened vegetable oil, kaolin and talc; a binder such as powdered gum Arabic, powdered tragacanth, gelatine and ethanol; and a disintegrator such as laminaran and agar.

In forming a suppository, a wide variety of types of carriers conventionally known in the art may be used. Examples of the carrier that may be used include polyethylene glycol, cacao butter, higher alcohol, esters of a higher alcohol, gelatine, and semisynthetic glyceride.

A capsule is usually prepared by mixing an active ingredient compound with a carrier as illustrated above in accordance with a conventional method and filling the mixture in a hard gelatine capsule or a soft capsule.

In preparing an injection, a liquid agent, emulsion and suspension are preferably sterilized and isotonic with blood. When they are prepared into an injection, any diluent can be used as long as it is conventionally used as a diluent in the art. Examples of the diluent that may be used include water, ethyl alcohol, macrogol, propylene glycol, ethoxylated isostearyl alcohol, polyoxylated isostearyl alcohol, polyoxyethylene sorbitan fatty acid esters.

Note that, in this case, a pharmaceutical preparation may contain a salt, glucose or glycerin in a sufficient amount to prepare an isotonic solution. Alternatively, a general auxiliary solubilizer, buffer, soothing agent may be added. Furthermore, a pigment, preservative, aroma, flavor, sweetening agent and other medicinal substances may be added to a pharmaceutical preparation, if necessary.

The amount of a compound of the general formula (1) and a salt thereof to be contained in a pharmaceutical preparation according to the present invent is not particularly limited and appropriately selected from the wide range; however generally about 1 to 70 wt %, preferably about 1 to 30 wt % in a preparation composition.

A method of administrating a pharmaceutical preparation according to the present invention is not limited and administered by a method in accordance with the form of a preparation, the age, gender and other conditions of a patient, and severity of a disease. For example, in the case of a tablet, pill, liquid agent, suspension, emulsion, granule and capsule, it is perorally administered. In addition, in the case of an injection, it is intravenously administered by itself or by mixing with a general replenisher such as glucose and amino acids, and, if necessary, it is solely administered intramuscularly, intracutaneously, subcutaneously or intraperitoneally. In the case of a suppository, it is administered into the rectum.

The dose of a pharmaceutical preparation according to the present invention is appropriately selected depending upon the dosage regimen (direction for use), age, gender and other conditions of a patient, and severity of a disease, etc.; however, the dose of an active ingredient compound may be generally and preferably set at about 0.1 to 10 mg/weight (kg) per day. It is desirable that an active ingredient compound be contained in the range of about 1 to 200 mg per dosage unit of a preparation.

Advantages of the Invention

A compound according to the present invention has a $D_2$ receptor partial agonist effect, 5-$HT_{2A}$ receptor antagonist effect and serotonin uptake inhibitory effect.

The $D_2$ receptor partial agonist effect refers to an action which decelerates dopaminergic (DA) neurotransmission when it is enhanced, whereas accelerates dopaminergic (DA) neurotransmission when it is lowered. In this manner, the $D_2$ receptor partial agonist acts as a dopamine system stabilizer, which stabilizes DA neurotransmission into a normal state. By virtue of this effect, the compound of the present invention produces an excellent clinical improvement effect on symptoms caused by abnormal DA neurotransmission (acceleration or deceleration) without developing side effects. As the excellent clinical improvement effect, mention may be made of, effects of improving positive and negative symptoms, cognitive impairment and depressive symptom (see Michio Toru, Psychiatry, Vol. 46, page 855-864 (2004); Tetsuro Kikuchi and Hirose Takeshi, Brain Science, vol. 25, page 579-583 (2004); and Harrison, T. S. and Perry, C. M.: Drugs 64: 1715-1736, 2004).

5-$HT_{2A}$ receptor antagonist effect refers to an action which reduces extrapyramidal side effects and develops a superior clinical response and more specifically effectively works for improving negative symptoms, cognitive impairment, depressive symptom, and insomnia (see Jun Ishigooka and Ken Inada: Japanese Journal of Clinical Psychopharmacology, vol. 4, page 1653-1664 (2001); Mitsukuni Murasaki: Japanese Journal of Clinical Psychopharmacology, vol. 1, page 5-22 (1998), and Meltzer, H. Y. et al.: Prog. Neuro-Psychopharmacol. Biol. Psychiatry 27: 1159-1172, 2003).

The serotonin uptake inhibitory effect is, for example, effective in improving depressive symptoms (see Mitsukuni Murasaki: Japanese Journal of Clinical Psychopharmacology, vol. 1, page 5-22 (1998)).

The compound of the present invention is excellent in all these three effects or significantly excellent in one or two effects of them.

In addition, some of the compounds according to the present invention has an $\alpha_1$ receptor antagonist effect in addition to the effects mentioned above. The $\alpha_1$ receptor antagonist effect is effective in improving positive symptoms of schizophrenia (see Svensson, T. H.: Prog. Neuro-Psychopharmacol. Biol. Psychiatry 27: 1145-1158, 2003)

Therefore, a compound of the present invention has a wide treatment spectrum for schizophrenia and other central nervous system disorder and possesses a superior clinical response.

Accordingly, a compound of the present invention is extremely effective for improving various kinds of disorders of the central nervous system such as schizophrenia; refractory, intractable or chronic schizophrenia; emotional disturbance; psychotic disorder; mood disorder; bipolar disorder (for example, bipolar Type-I disorder and bipolar Type-II disorder); depression, endogenous depression, major depression; melancholy and refractory depression; dysthymic disorder; cyclothymic disorder; anxiety disorder (for example, panic attack, panic disorder, agoraphobia, social phobia, obsessive-compulsive disorder, post-traumatic stress disorder, generalized anxiety disorder, and acute stress disorder); somatoform disorder (for example, hysteria, somatization disorder, conversion disorder, pain disorder, and hypochondriasis), factitious disorder; dissociative disorder; sexual disorder (for example, sexual dysfunction, sexual desire disorder, sexual arousal disorder, and erectile dysfunction); eating disorder (for example, anorexia nervosa and bulimia nervosa); sleep disorder; adjustment disorder; substance-related disorder (for example, alcohol abuse; alcohol intoxication; drug addiction, stimulant intoxication, and narcotism); anhedonia (for example, iatrogenic anhedonia, anhedonia of a psychic or mental cause, anhedonia associated with depression, and anhedonia associated with schizophrenia); delirium; cognitive impairment; cognitive impairment associated with Alzheimer's disease, Parkinson's disease and other neurodegenerative diseases; cognitive impairment caused by Alzheimer's disease; Parkinson's disease and associated neurodegenerative diseases; cognitive impairment of schizophrenia; cognitive impairment caused by refractory, intractable or chronic schizophrenia; vomiting; motion sickness; obesity; migraine; pain (ache); mental retardation; autism disorder (autism); Tourette's disorder; tic disorder; attention-deficit/hyperactivity disorder; conduct disorder; and Down's syndrome.

Furthermore, a compound of the present invention has few side effects, and excellent in tolerability and safety.

The starting compounds used in each of the above reaction formula may be suitable salt, the object compound obtained by each of the reaction may form a suitable salt. Such suitable salts include the preferable salts of compound (1) exemplified below.

The preferable salts of compound (1) are pharmacologically acceptable salts and examples include metal salts such as alkali metal salts (for example, sodium salt potassium salt, etc.), alkaline earth metal salts (for example, calcium salt, magnesium salt, etc.), salts of inorganic bases such as ammonium salt, alkaline metal carbonates (for example, lithium carbonate, potassium carbonate, sodium carbonate, cesium carbonate, etc.), alkaline metal hydrogen carbonates (for example, lithium hydrogen carbonate, sodium hydrogen carbonate, potassium bicarbonate, etc.), alkali metal hydroxides (for example, lithium hydroxide, sodium hydroxide, potassium hydroxide, cesium hydroxide, etc.); for example, salts of organic bases such as tri(lower)alkylamine (for example, trimethylamine, triethylamine, N-ethyldiisopropylamine), pyridine, quinoline, piperidine, imidazole, picoline, dimethylaminopyridine, dimethylaniline, N-(lower)alkyl-morpholine (for example, N-methylmorpholine), 1,5-diazabicyclo[4.3.0]nonene-5 (DBN), 1,8-diazabicyclo[5.4.0]undecene-7 (DBU), 1,4-diazabicyclo[2.2.2]octane (DABCO); salts of inorganic acids such as hydrochloride, hydrobromide, hydroiodide, sulfate, nitrate, phosphate; salts of organic acids such as formate, acetate, propionate, oxalate, malonate, succinate, fumarate, maleate, lactate, malate, citrate, tartrate, carbonate, picrate, methanesulfonate, ethanesulfonate, p-toluenesulfonate, glutamate.

In addition, compounds in the form in which solvate (for example, hydrate, ethanolate, etc.) was added to the starting compounds and object compound shown in each of the reaction formulae are included in each of the general formulas. As a preferable solvate, hydrate can be mentioned.

Each of the object compounds obtained by each of the general formulas can be isolated and purified from the reaction mixture by, for example, subjecting the reaction mixture to isolation operation such as filtration, concentration and extraction after cooling to separate a crude reaction product followed by conventional purification operation such as column chromatography or recrystallization.

The compound represented by the general formula (1) of the present invention naturally encompasses isomers such as geometrical isomer, stereoisomer and enantiomer.

The compound of the general formula (1) and a salt thereof can be used in a common form of pharmaceutical preparation. The pharmaceutical preparation is prepared by using usually used diluent or excipient such as filler, extending agent, binder, humectant, disintegrating agent, surfactant and lubricant. As for this pharmaceutical preparation, various forms can be selected depending on the purpose of treatment, and typical examples include a tablet, pill, powder, solution, suspension, emulsion, granule, capsule, suppository, and injection (solution, suspension).

For shaping in tablet form, various materials conventionally well known as carrier in the art can be widely used. As examples, excipient such as lactose, saccharose, sodium chloride, glucose, urea, starch, calcium carbonate, kaolin, crystalline cellulose, silicate; binder such as water, ethanol, propanol, simple syrup, glucose solution, starch liquid, gelatine solution, carboxymethylcellulose, shellac, methylcellulose, potassium phosphate, polyvinylpyrrolidone; disintegrating agent such as dried starch, sodium alginate, agar powder, laminaran powder, sodium hydrogen carbonate, calcium carbonate, polyoxyethylene sorbitan fatty acid ester, sodium lauryl sulfate, stearic acid monoglyceride, starch, lactose; disintegration preventing agent such as saccharose, stearin, cacao butter, hydrogenated oil; sorbefacient such as quaternary ammonium base, sodium lauryl sulfate; moisturizing agent such as glycerine, starch; absorbing agent such as starch, lactose, kaolin, bentonite, colloidal silica; lubricant such as purified talc, stearate, borate powder, polyethylene glycol can be used, for example. Furthermore, the tablet may be a tablet provided with conventional coating as required, for example, sugar-coated tablet, gelatine encapsulated tablet, enteric coating tablet, film coated tablet or double tablet, multilayer tablet.

For shaping in pill form, various materials conventionally well known as carrier in the art can be widely used. As examples, excipient such as glucose, lactose, starch, cacao butter, hydrogenated vegetable oil, kaolin, talc; binder such as powdered gum arabic, powdered tragacanth, gelatine, ethanol; disintegrating agent such as laminaran, agar can be used, for example.

For shaping in suppository form, various materials conventionally well known as carrier can be widely used. Examples thereof include polyethylene glycol, cacao butter, higher alcohol, esters of higher alcohol, gelatine, semisynthesized glyceride, for example.

A capsule is usually prepared according to a conventional method by mixing active ingredient compounds with various carrier exemplified above and filling them into a hard gelatin capsule, a soft capsule or the like.

When prepared as injection liquid, it is preferable that solution, emulsion and suspension are sterilized and isotonic to the blood and for forming in these modes, any of those conventionally used in the art as diluent can be used, and, for example, water, ethyl alcohol, macrogol, propylene glycol, ethoxylated isostearyl alcohol, polyoxylated isostearyl alcohol, polyoxyethylene sorbitan fatty acid ester, etc. can be used.

The pharmaceutical preparation may contain common salt, glucose or glycerine in an amount sufficient to prepare an isotonic solution in this case, and conventional solubilizer, buffer, soothing agent may be also added. Pigment, preservative, aromatic, flavor, sweetening and other pharmaceuticals may be further contained as required.

The amount of a compound of the general formula (1) or a salt thereof to be contained in the pharmaceutical preparation of the present invention is not particularly limited but usually about 1 to 70% by weight in the preparation composition is suitable and preferably about 1 to 30% by weight.

There is not limitation in particular in the way of administration of the pharmaceutical preparation of the present invention and may be administered by a method in accordance with specific form of the preparation, age, sex and the other conditions of a patient, severity of disease, etc. For example, in the case of tablet, pill, solution, suspension, emulsion, granule and capsule, it is orally administered. In the case of injection, it is intravenously administered alone or in a mixture with conventional replacement fluid such as glucose and amino acids, and if necessary, and the preparation alone may be also administered intramuscularly, intracutaneously, subcutaneously or interperitoneally. It is administered in rectum in the case of suppository.

Applied dose of the pharmaceutical preparation of the present invention is appropriately selected in accordance with dosage regimen, age, sex and the other conditions of a patient, severity of disease, etc., but it is suitable that the amount of the active ingredient compound is usually about 0.1 to 10 mg per 1 kg of body weight per day. In addition, it is desirable that the active ingredient compound is contained in the preparation of a dosage unit form in the range of about 1 to 200 mg.

The compound of the present invention has $D_2$ receptor partial agonist effect, $5\text{-}HT_{2A}$ receptor antagonist effect and serotonin uptake inhibitory effect (or serotonin uptake inhibitory effect).

The $D_2$ receptor partial agonist effect suppresses dopaminergic (DA) neurotransmission when it is enhanced, and accelerates the DA neurotransmission when it is lowered and thus has a function to stabilize the DA neurotransmission to a normal state (dopamine system stabilizer). According to this function, excellent clinically improving effect on the conditions based on the DA abnormal neurotransmission (enhancement and lowering), for example, improving effect on positive and negative symptoms, improving effect on cognitive impairment, improving effect on depressive symptom, etc. are developed without developing side effects (See Michio Toru: Seishin-Igaku (Psychiatry), Vol. 46, pp. 855-864 (2004), Tetsuro Kikuchi and Tsuyoshi Hirose Nou-no-Kagaku (Brain Science), Vol. 25, pp. 579-583 (2003) and Harrison, T. S. and Perry, C. M.: Drugs 64: 1715-1736, 2004).

$5\text{-}HT_{2A}$ receptor antagonist effect reduces extrapyramidal side effects, develops superior clinical effects, and is effective for improvement of negative symptoms, improvement of cognitive impairment, improvement of depression condition, improvement of insomnia, for example (See Jun Ishigooka and Ken Inada: Rinsho-Seishin-Yakuri (Japanese Journal of Clinical Psychopharmacology), Vol. 4, pp. 1653-1664 (2001), Mitsukuni Murasaki Rinsho-Seishin-Yakuri (Japanese Journal of Clinical Psychopharmacology), Vol. 1, pp. 5-22 (1998), Puller, I. A. et al., Eur. J. Pharmacol., 407:39-46, 2000, and Meltzer, H. Y. et al, Prog. Neuro-Psychopharmacol. Biol. Psychiatry 27: 1159-1172, 2003).

Serotonin uptake inhibitory effect (or serotonin reuptake inhibitory effect) is effective for improving depressive symptoms, for example (See Mitsukuni Murasaki: Rinsho-Seishin-Yakuri (Japanese Journal of Clinical Psychopharmacology), Vol. 1, pp. 5-22 (1998)).

The compounds of the present invention are excellent in all of these three effects, or remarkably excellent in one or two of these effects.

In addition, some of the compounds of the present invention have $\alpha_1$ receptor antagonist effect in addition to the above-described effects. The $\alpha_1$ receptor antagonist effect is effective for improving positive symptoms of schizophrenia (See Svensson, T. H.: Prog. Neuro-Psychopharmacol. Biol. Psychiatry 27: 1145-1158, 2003).

Therefore, the compounds of the present invention have a wide treatment spectrum for and excellent clinical effect on schizophrenia and other central nervous system disorders.

Accordingly, the compounds of the present invention are extremely effective for the treatment or prevention of central nervous system disorders including the group consisting of schizophrenia; refractory, intractable or chronic schizophrenia; emotional disturbance; psychotic disorder; mood disorder; bipolar disorder (for example, bipolar I type disorder and bipolar II type disorder); depression; endogenous depression; major depression; melancholy and refractory depression; dysthymic disorder; cyclothymic disorder; anxiety disorder (for example, panic attack, panic disorder, agoraphobia, social phobia, obsessive-compulsive disorder, post-traumatic stress disorder, generalized anxiety disorder, acute stress disorder, etc.); somatoform disorder (for example, hysteria, somatization disorder, conversion disorder, pain disorder, hypochondriasis, etc.); factitious disorder; dissociative disorder; sexual disorder (for example, sexual dysfunction, sexual desire disorder, sexual arousal disorder, erectile dysfunction, etc.); eating disorder (for example, anorexia nervosa, bulimia nervosa, etc.); sleep disorder; adjustment disorder; substance-related disorder (for example, alcohol abuse, alcohol intoxication, drug addiction, stimulant intoxication, narcotism, etc.); anhedonia (for example, iatrogenic anhedonia, anhedonia of a psychic or mental cause, anhedonia associated with depression, anhedonia associated with schizophrenia, etc.); delirium; cognitive impairment; cognitive impairment associated with Alzheimer's disease, Parkinson's disease, and other neurodegenerative diseases; cognitive impairment caused by Alzheimer's disease, Parkinson's disease and associated neurodegenerative diseases; cognitive impairment of schizophrenia; cognitive impairment caused by refractory, intractable or chronic schizophrenia; vomiting; motion sickness; obesity; migraine; pain (ache); mental retardation; autism disorder (autism); Tourette's disorder; tic disorder; attention-deficit/hyperactivity disorder; conduct disorder; and Down's syndrome.

Furthermore, the compounds of the present invention have little or no side effects and they are excellent in safety and tolerability.

A preferable example of a desired compound (1) is as follows:

[Formula 1]

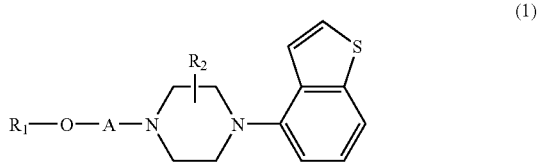

(1)

where $R^2$ represents a hydrogen atom or a lower alkyl group;
A represents a lower alkylene group or a lower alkenylene group (preferably a lower alkylene group); and
$R^1$ represents a cyclo C3-C8 alkyl group, an aromatic group or a heterocyclic group selected from the group consisting of (I) to (IV) below:

(I) a cyclo C3-C8 alkyl group (more preferably a cyclohexyl group);

(II) an aromatic group selected from a phenyl group, naphthyl group, dihydroindenyl group and tetrahydronaphthyl group (more preferably a phenyl group);

(III) a saturated or unsaturated heteromonocyclic group having 1 to 4 hetero atoms selected from the group consisting of a nitrogen atom, oxygen atom and sulfur atom and selected from the group consisting of a pyrrolidinyl group, imidazolidinyl group, piperidyl group, hexahydropyrimidinyl group, piperazinyl group, azepanyl group, azocanyl group, pyrrolyl group, dihydropyrrolyl group, imidazolyl group, dihydroimidazolyl group, triazolyl group, dihydrotriazolyl group, pyrazolyl group, pyridyl, dihydropyridyl group, pyrimidinyl group, dihydropyrimidinyl group, pyrazinyl group, dihydropyrazinyl group, pyridazinyl group, tetrazolyl group, oxazolyl group, isoxazolyl group, oxadiazolyl group, oxazolidinyl group, isoxazolidinyl group, morpholinyl group, thiazolyl group, dihydrothiazolyl group, isothiazolyl group, thiadiazolyl group, dihydrothiazinyl group, thiazolidinyl group, tetrahydrofuryl group, tetrahydropyranyl group, pyranyl group, tetrahydrothiofuryl group, tetrahydrothiopyranyl group, thienyl group and thiopyranyl group (more preferably, a saturated or unsaturated heteromonocyclic group having 1 to 2 hetero atoms selected from the group consisting of a nitrogen atom, an oxygen atom and a sulfur atom and selected from the group consisting of a pyrrolidinyl group, a piperidyl group, a pyrazolyl group, a pyridyl group, a pyrimidinyl group, a pyrazinyl group, an isoxazolyl group, a thiazolyl group, a pyranyl group and a thienyl group; and more preferably, a saturated or unsaturated heteromonocyclic group having 1 to 2 nitrogen atoms selected from the group consisting of a pyrrolidinyl group, a piperidyl group, a pyrazolyl group, a pyridyl group, a pyrimidinyl group and a thiazolyl group; and (IV) a benzene fused heterocyclic group that has 1 to 4 hetero atoms selected from the group consisting of a nitrogen atom, oxygen atom and sulfur atom and that is selected from the group consisting of (1) a tetrahydroquinoxalinyl group, (2) a tetrahydroquinazolinyl group, (3) a dihydroquinazolinyl group, (4) an indolinyl group, (5) an indolyl group, (6) an isoindolinyl group, (7) a benzimidazolyl group, (8) a dihydrobenzimidazolyl group, (9) a tetrahydrobenzazepinyl group, (10) a tetrahydrobenzodiazepinyl group, (11) a hexahydrobenzazocinyl group, (12) a dihydrobenzoxazinyl group, (13) a dihydrobenzoxazolyl group, (14) a benzisoxazolyl group, (15) a benzoxadiazolyl group, (16) a tetrahydrobenzoxazepinyl group, (17) a dihydrobenzothiazinyl group, (18) a benzothiazolyl group, (19) a benzoxathiolyl group, (20) a chromenyl group, (21) a dihydrobenzofuryl group, (22) a carbazolyl group, (23) a dibenzofuryl group and (24) a quinoxalinyl group wherein, on the cyclo C3-C8 alkyl group, the aromatic group and the heterocyclic group represented by $R^1$, 1 to 5 (more preferably 1 to 3) groups selected from the group consisting of the groups (1) to (66) below may be present as a substituent:

(1) a lower alkyl group,
(2) a lower alkenyl group,
(3) a halogen substituted lower alkyl group,
(4) a lower alkoxy group,
(5) a phenoxy group,
(6) a lower alkylthio group,
(7) a halogen substituted lower alkoxy group,
(8) a hydroxy group,
(9) a phenyl lower alkoxy group,
(10) a hydroxy lower alkyl group,
(11) a lower alkoxy lower alkyl group,
(12) a halogen atom,
(13) a cyano group,
(14) a phenyl aryl group,
(15) a nitro group,
(16) an amino group,
(17) an amino group having 1 to 2 groups selected from the group consisting of a lower alkyl group; a lower alkanoyl group, a lower alkoxycarbonyl group, a lower alkylsulfonyl group, a carbamoyl group, a lower alkyl carbamoyl group, an amino lower alkanoyl group, a lower alkanoylamino lower alkanoyl group and a lower alkoxycarbonylamino lower alkanoyl group as a substituent(s) (more preferably an N-lower alkylamino group, N,N-di lower alkylamino group, N-lower alkanoylamino group, N-lower alkoxycarbonylamino group, N-lower alkylsulfonylamino group, N-lower alkyl-N-lower alkanoylamino group, N-lower alkyl-N-lower alkoxycarbonylamino group, N-[carbamoyl]amino group, N-[N-lower alkylcarbamoyl]amino group, N-[N,N-di lower alkylcarbamoyl]amino group, N-[amino lower alkanoyl] amino group, N-[[N-lower alkanoylamino] lower alkanoyl] amino group, or N-[[N-lower alkoxycarbonylamino] lower alkanoyl]amino group),
(18) a lower alkanoyl group,
(19) a phenyl sulfonyl group that may have a lower alkyl group on the phenyl group (more preferably a lower alkylphenylsulfonyl group),
(20) a carboxy group,
(21) a lower alkoxycarbonyl group,
(22) a carboxy lower alkyl group,
(23) a lower alkoxycarbonyl lower alkyl group,
(24) a lower alkanoylamino lower alkanoyl group,
(25) a carboxy lower alkenyl group,
(26) a lower alkoxycarbonyl lower alkenyl group,
(27) a carbamoyl lower alkenyl group that may have as a substituent(s) 1 to 2 groups selected from the group consisting of a lower alkyl group and a lower alkyl group substituted with 1 to 3 halogen atoms (more preferably a carbamoyl lower alkenyl group, an N-lower alkylcarbamoyl lower alkenyl group, an N,N-di lower alkylcarbamoyl lower alkenyl group or N-[a lower alkyl substituted with 1 to 3 halogen atoms] carbamoyl lower alkenyl),
(28) a carbamoyl group that may have 1 to 2 groups selected from the group consisting of the groups (i) to (lxxviii) below as a substituent(s):

(i) a lower alkyl group,
(ii) a lower alkoxy group,
(iii) a hydroxy lower alkyl group,
(iv) a lower alkoxy lower alkyl group,
(v) an phenyloxy lower alkyl group,
(vi) a halogen substituted lower alkyl group,
(vii) an amino lower alkyl group that may have 1 to 2 groups selected from the group consisting of a lower alkyl group, a lower alkanoyl group, a benzoyl group and a carbamoyl group (more preferably an N,N-di lower alkylamino lower alkyl group, an N-lower alkanoylamino lower alkyl group, an N-lower alkyl-N-lower alkanoylamino lower alkyl group, an N-lower alkyl-N-benzoylamino lower alkyl group, or an N-carbamoylamino lower alkyl group)
(viii) a cyclo C3-C8 alkyl group that may have 1 to 3 groups (preferably 1 to 2 groups, and more preferably 1 group) selected from the group consisting of a lower alkyl group, a hydroxy group, a lower alkoxycarbonyl group and a phenyl lower alkoxy group as a substituent,
(ix) a cyclo C3-C8 alkyl substituted lower alkyl group,
(x) a lower alkenyl group,
(xi) a lower alkyl group having 1 to 2 carbamoyl groups which may have 1 to 2 groups (preferably 1 group) selected from the group consisting of a lower alkyl group, a phenyl group that may have a single lower alkyl group and a phenyl group that may have a single lower alkoxy group as a substituent(s) (more preferably a carbamoyl lower alkyl group, a dicarbamoyl lower alkyl group, an N-lower alkylcarbamoyl lower alkyl group, an N,N-di lower alkylcarbamoyl lower alkyl group, an N-[lower alkylphenyl]carbamoyl lower alkyl group, or an N-[lower alkoxyphenyl]carbamoyl lower alkyl group),
(xii) a lower alkyl group having 1 to 2 lower alkoxycarbonyl groups,
(xiii) a furyl lower alkyl group (that may have 1 to 2 lower alkyl groups as a substituent(s) on the furyl group),
(xiv) a tetrahydrofuryl lower alkyl group,
(xv) a 1,3-dioxolanyl lower alkyl group,
(xvi) a tetrahydropyranyl lower alkyl group,
(xvii) a pyrrolyl lower alkyl group (that may have 1 to 2 lower alkyl groups as a substituent(s) on the pyrrolyl group),
(xviii) a dihydropyrazolyl lower alkyl group that may have a single oxo group,
(xix) a pyrazolyl lower alkyl group (that may have 1 to 3 lower alkyl groups as a substituent(s) on the pyrazolyl group),
(xx) an imidazolyl lower alkyl group, (xxi) a pyridyl lower alkyl group, (xxii) a pyrazinyl lower alkyl group (that may have 1 to 3 (preferably 1) lower alkyl groups as a substituent on the pyrazinyl group), (xxiii) a pyrrolidinyl lower alkyl group (that may have 1 to 2 groups selected from the group consisting of an oxo group and a lower alkyl group as a substituent(s) on the pyrrolidinyl group), (xxiv) a piperidyl lower alkyl group (that may have 1 to 3 groups (preferably 1 group) selected from the group consisting of a benzoyl group and a lower alkanoyl group as a substituent(s) on the piperidyl group), (xxv) a piperazinyl lower alkyl group (that may have 1 to 3 (preferably 1) lower alkyl groups as a substituent(s) on the piperazinyl group), (xxvi) a morpholinyl lower alkyl group, (xxvii) a thienyl lower alkyl group (that may have 1 to 3 (preferably 1) lower alkyl group as a substituent(s) on the thienyl group), (xxviii) a thiazolyl lower alkyl group, (xxix) a dihydrobenzofuryl lower alkyl group, (xxx) a benzopyranyl lower alkyl group (that may have a single oxo group as a substituent on the benzopyranyl group), (xxxi) a benzimidazolyl lower alkyl group, (xxxii) an indolyl lower alkyl group that may have 1 to 3 (preferably 1) lower alkoxycarbonyl groups on the lower alkyl group), (xxxiii) an imidazolyl lower alkyl group that has 1 to 3 substituents (preferably 1 substituent) selected from the group consisting of a carbamoyl group and a lower alkoxycarbonyl group on the lower alkyl group, (xxxiv) a pyridyl group that may have 1 to 3 groups (preferably 1 group) selected from the group consisting of a lower alkyl group, a lower alkoxy group and a lower alkylthio lower alkyl group as a substituent(s), (xxxv) a pyrrolidinyl group that may have 1 to 3 groups (preferably 1 group) selected from the group consisting of a lower alkyl group, a lower alkoxycarbonyl group, a lower alkanoyl group and a benzoyl group as a substituent, (xxxvi) a piperidyl group that may have 1 to 3 groups (preferably 1 group) selected from the group consisting of a lower alkyl group, a lower alkoxycarbonyl group, a lower alkanoyl group and a benzoyl group that may have 1 to 3 groups (preferably 1 group) selected from the group consisting of a lower alkyl group and a halogen atom on the phenyl group, (xxxvii) a tetrahydrofuryl group that may have a single oxo group, (xxxviii) a hexahydroazepinyl group that may have a single oxo group, (xxxix) a pyrazolyl group that may have 1 to 3 groups (preferably 1 group) selected from the group consisting of a lower alkyl group, a phenyl group and a furyl group as a substituent, (xl) a thiazolyl group, (xli) a thiadiazolyl group that may have 1 to 3 (preferably 1) lower alkyl groups, (xlii) an isoxazolyl group that may have 1 to 3 (preferably 1 to 2) lower alkyl groups, (xliii) an indazolyl group, (xliv) an indolyl group, (xlv) a tetrahydrobenzothiazolyl group, (xlvi) a tetrahydroquinolyl group that may have 1 to 3 (preferably 1 to 2) groups selected from the group consisting of a lower alkyl group, a lower alkoxy group, a halogen atom and an oxo group as a substituent, (xlvii) a quinolyl group that may have 1 to 3 (preferably 1) lower alkyl groups, (xlviii) a benzodioxolyl lower alkyl group, (xlix) a phenyl group or naphthyl group that may have 1 to 3 groups as a substituent(s), selected from the group consisting of
a halogen atom; a lower alkyl group; a lower alkoxy group; a halogen substituted lower alkyl group; a halogen substituted lower alkoxy group; a lower alkenyl group; an amino group that may have 1 to 2 groups selected from the group consisting of a lower alkanoyl group, a lower alkyl sulfonyl group, a lower alkyl group and an aryl group; a sulfamoyl group; a lower alkylthio group; a lower alkanoyl group; a lower alkoxycarbonyl group; a pyrrolyl group; a lower alkynyl group; a cyano group; a nitro group; a phenyloxy group; a phenyl lower alkoxy group; a hydroxy group; a hydroxy lower alkyl group; a carbamoyl group that may have a group selected from the group consisting of a lower alkyl group and a phenyl group; a pyrazolyl group; a pyrrolidinyl group that may have a single oxo group; an oxazolyl group; an imidazolyl group that may have 1 to 3 (preferably 1 to 2) lower alkyl groups; a dihydrofuryl group that may have a single oxo group; a thiazolidinyl lower alkyl group that may have two oxo groups; an imidazolyl lower alkanoyl group and a piperidinylcarbonyl group, (l) a cyano lower alkyl group, (li) a dihydroquinolyl group that may have 1 to 3 (more preferably 1 to 2) groups selected from the group consisting of a lower alkyl group and an oxo group, (lii) a halogen substituted lower alkylamino group, (liii) a lower alkylthio lower alkyl group, (liv) an amidino group that may have 1 to 2 lower alkyl groups, (lv) an amidino lower alkyl group, (lvi) a lower alkenyloxy lower alkyl group, (lvii) a phenyl amino group that may have 1 to 3 substituents (more preferably 1 substituent) selected from the group consisting of a lower alkyl group, a lower alkoxy group, a halogen substituted lower alkyl group and a halogen substituted lower alkoxy group on the phenyl group, (lviii) a phenyl lower alkenyl group, (lix) a pyridylamino group that may have 1 to 3 (more preferably 1 to 2) lower alkyl groups (more preferably N-lower alkyl-N-[lower alkylpyridyl]amino group), (lx) a phenyl lower alkyl group (that may have 1 to 3 groups (more preferably 1 to 2 groups) selected from the group consisting of a halogen atom, a lower alkyl group, a halogen substituted lower alkyl group, a halogen substituted lower alkoxy group, a lower alkoxy group, a carbamoyl group and a lower alkoxycarbonyl group as a substituent on the phenyl group and/or the lower alkyl group), (lxi) a lower alkynyl group, (lxii) a phenyloxy lower alkyl group (that may have as a substituent(s) on the phenyl group 1 to 3 groups (preferably 1 group) selected from the group consisting of a lower alkoxy group, an N-lower alkoxy-N-lower alkylcarbamoyl group and an oxopyrrolidinyl group), (lxiii) an isoxazolidinyl group that may have a single oxo group, (lxiv) a dihydroindenyl group, (lxv) a phenyl lower alkoxy lower alkyl group, (lxvi) a tetrahydropyranyl group, (lxvii) an azetidinyl group that may have 1 to 3 groups (more preferably 1 group) selected from the group consisting of a lower alkanoyl group and a benzoyl group, (lxviii) an azetidinyl lower alkyl group that may have 1 to 3 groups (more preferably 1 group) selected from the group consisting of a lower alkanoyl group and a benzoyl group, (lxix) a tetrazolyl group, (lxx) an indolinyl group that may have a single oxo group, (lxxi) a triazolyl group that may have 1 to 3 groups (more preferably 1 to 2 groups) selected from the group consisting of a lower alkyl group and a lower alkylthio group, (lxxii) an imidazolyl group that may have 1 to 3 (more preferably 1) carbamoyl groups, (lxxiii) an oxazolyl group that may have 1 to 3 (more preferably 1) lower alkyl groups, (lxxiv) an isothiazolyl group that may have 1 to 3 (more preferably 1) lower alkyl groups, (lxxv) a benzimidazolyl group, (lxxvi) a dihydrobenzothiazolyl group that may have a single oxo group, (lxxvii) a thienyl group that may have 1 to 3 (more preferably 1) lower alkoxycarbonyl groups, and (lxxviii) an oxazolyl lower alkyl group that may have 1 to 3 (more preferably 1 to 2) lower alkyl groups

(29) an amino lower alkyl group that may have 1 to 2 groups selected from the group consisting of a lower alkyl group, a halogen substituted lower alkyl group, a lower alkoxycarbonyl group, a lower alkanoyl group, a phenyl group, a phenyl lower alkyl group, a benzoyl group and an amino substituted alkyl group (that may have 1 to 2 (more preferably 2) lower alkyl groups as a substituent(s) on the amino group) on the amino group,

(30) a lower alkyl group substituted with a single carbamoyl group that may have 1 to 2 groups selected from the group consisting of a lower alkyl group and a halogen substituted lower alkyl group,

(31) a thiocarbamoyl group that may have 1 to 2 (more preferably 1) lower alkyl group,

(32) a sulfamoyl group,

(33) an oxazolidinyl group that may have a single oxo group (more preferably an oxazolidinyl group substituted with a single oxo group),

(34) an imidazolidinyl group that may have 1 to 2 substituents selected from the group consisting of an oxo group and a lower alkyl group,

(35) a pyrrolidinyl group that may have a single oxo group,

(36) an imidazolyl group,

(37) a triazolyl group,

(38) an isoxazolyl group,

(39) a piperidyl group that may have 1 to 3 (more preferably 1 to 2, and still more preferably 1) substituents selected from the group consisting of a lower alkyl group, a lower alkanoyl group, a lower alkylphenylsulfonyl group, an oxo group, a hydroxy group, and amino group that may have 1 to 2 groups selected from the group consisting of a lower alkyl group, a lower alkanoyl group, a lower alkoxycarbonyl group and lower alkanoylamino lower alkanoyl group (more preferably a piperidyl group that may have 1 to 3 (more preferably 1 to 2, and still more preferably 1) substituents selected from the group consisting of a lower alkyl group, a lower alkanoyl group, a lower alkylphenylsulfonyl group, an oxo group, a hydroxy group, an amino group, an N-lower alkylamino group, an N,N-di lower alkylamino group, an N-lower alkanoylamino group, an N-lower alkyl-N-lower alkoxycarbonylamino group, an N-lower alkyl-N-lower alkanoylamino group, and an N-lower alkanoylamino lower alkanoylamino group),

(40) a piperidylcarbonyl group that may have 1 to 3 (more preferably 1 to 2) substituents selected from the group consisting of a lower alkyl group, a hydroxy group, a hydroxy lower alkyl group, a lower alkanoyl group, a carboxy lower alkyl group, a lower alkyl carbamoyl lower alkyl group, a carbamoyl group, a lower alkoxy group, a carboxy group, a lower alkoxycarbonyl group, an amino group (on which 1 to 2 groups selected from the group consisting of a lower alkyl group, a lower alkanoyl group, a lower alkoxycarbonyl group and a benzoyl group may be present), a piperidyl group (on which 1 to 3 groups (more preferably 1 group) selected from the group consisting of a lower alkanoyl group, a lower alkoxycarbonyl group and a benzoyl group may be present), a piperazinyl group (on which 1 to 3 (more preferably 1 to 2) lower alkyl groups may be present as a substituent), a 1,4-dioxa-8-azaspiro[4.5]decyl group, a morpholinyl group, a hexahydro-1,4-diazepinyl group (on which a single lower alkyl group may be present as a substituent), pyridyl group, pyridyloxy group, pyridyl lower alkoxy group, tetrahydroquinolyl group (on which a single oxo group may be present), benzodioxolyl group, phenyl lower alkoxy group (that may have 1 to 3 groups (more preferably 1 to 2 groups) selected from the group consisting of a halogen atom, a lower alkyl group, a lower alkoxy group and a halogen substituted lower alkoxy group on the phenyl group), phenyl group (on which 1 to 3 groups (preferably 1 to 2 groups) selected from the group consisting of a halogen atom, a lower alkoxy group and a hydroxy group may be present), a phenyloxy group (that may have on the phenyl group 1 to 3 groups (preferably 1 to 2 groups) selected from the group consisting of a cyano group, a halogen atom, a lower alkyl group, a lower alkoxy group and a halogen substituted lower alkyl group), a phenyl lower alkyl group (that may have on the phenyl group 1 to 3 groups (more preferably 1 to 2 groups) selected from the group consisting of a halogen atom, a lower alkyl group, a lower alkoxy group and a halogen substituted lower alkyl group), and a benzoyl group (that may have on the phenyl group 1 to 3 groups (more preferably 1 to 2 groups) selected from the group consisting of a halogen atom and a lower alkoxy group),

(41) a pyrrolidinylcarbonyl group that may have 1 to 3 (more preferably 1) groups as a substituent, selected from the group consisting of a hydroxy lower alkyl group, a carbamoyl group, a hydroxy group, an amino group (that may have on the amino group 1 to 2 groups selected from the group consisting of a lower alkyl group, a lower alkanoyl group and a benzoyl group), morpholinyl lower alkyl group, a pyrrolidinyl lower alkyl group, a piperidyl lower alkyl group, a piperazinyl lower alkyl group (that may have a single lower alkyl group as a substituent on the piperazinyl group), an amino lower alkyl group (that may have 1 to 2 lower alkyl groups as a substituent on the amino group), phenyloxy group (that may have 1 to 3 (more preferably 1) halogen substituted lower alkoxy groups on the phenyl group), a phenyloxy lower alkyl group (that may have 1 to 3 (more preferably 1) halogen substituted lower alkoxy groups on the phenyl group) and a tetrahydroquinolyl group (on which an oxo group may be present),

(42) a piperazinylcarbonyl group that may have 1 to 3 groups (more preferably 1 to 2 groups), as a substituent, selected from the group consisting of a lower alkyl group, a cyclo C3-C8 alkyl group, a lower alkanoyl group, a hydroxy lower alkyl group, a lower alkoxy lower alkyl group, a lower alkoxycarbonyl group, an amino lower alkyl group (that may have 1 to 2 lower alkyl groups as a substituent on the amino group), piperidyl lower alkyl group (that may have 1 to 2 (more preferably 1) lower alkyl groups as a substituent(s) on the piperidyl group), a morpholinyl lower alkyl group, a pyrrolidinyl lower alkyl group, a 1,3-dioxolanyl lower alkyl group, a tetrahydrofuryl lower alkyl group, a pyridyl lower alkyl group (that may have 1 to 2 (more preferably 1) phenyl groups as a substituent(s) on the lower alkyl group), an imidazolyl lower alkyl group, a furyl lower alkyl group, a pyrrolidinylcarbonyl lower alkyl group, a piperidyl group that may have 1 to 2 (more preferably 1) lower alkyl groups as a substituent(s), a pyridyl group (that may have on the pyridyl group 1 to 3 groups (more preferably 1 group) selected from the group consisting of a lower alkyl group, a cyano group and a halogen substituted lower alkyl group as a substituent), a thieno[2,3-b]pyridyl group, a phenyl group (on which 1 to 3 groups (more preferably 1 group) selected from the group consisting of a halogen atom and a lower alkyl group may be present), a benzoyl group, a furyl carbonyl group, a phenyl lower alkoxycarbonyl group and an oxo group,

(43) a hexahydroazepinylcarbonyl group,

(44) a hexahydro-1,4-diazepinylcarbonyl group that may have 1 to 3 substituents (more preferably 1 substituent) selected from the group consisting of a lower alkyl group and a pyridyl group,

(45) a dihydropyrrolylcarbonyl group that may have 1 to 3 (more preferably 1 to 2) lower alkyl groups,

(46) a thiomorpholinylcarbonyl group,

(47) a morpholinylcarbonyl group that may have 1 to 3 groups (more preferably 1 group) selected from the group consisting of a lower alkyl group, a piperidyl lower alkyl group and a phenyl group,

(48) a thiazolidinyl carbonyl group that may have 1 to 3 (more preferably 1) phenyl groups that may have 1 to 3 groups (more preferably 1 group) selected from the group consisting of a lower alkoxy group and a cyano group,

(49) an azabicyclo[3.2.2]nonylcarbonyl group,

(50) an 8-azabicyclo[3.2.1]octylcarbonyl group that may have 1 to 3 (more preferably 1) halogen substituted or unsubstituted phenyloxy groups,

(51) an indolinylcarbonyl group,

(52) a tetrahydroquinolylcarbonyl group,

(53) a tetrahydropyrido[3.4-b]indolylcarbonyl group,

(54) a morpholinyl lower alkyl group,

(55) a piperazinyl lower alkyl group that may have 1 to 3 (more preferably 1) lower alkyl groups on the piperazinyl group,

(56) a morpholinylcarbonyl lower alkyl group,

(57) a piperazinylcarbonyl lower alkyl group that may have 1 to 3 (more preferably 1) lower alkyl groups on the piperazinyl group,

(58) an oxo group,

(59) an amino lower alkoxy-group (that may have 1 to 2 (more preferably 2) lower alkyl groups on the amino group),

(60) a lower alkoxy lower alkoxy group,

(61) a piperazinyl group that may have 1 to 3 groups (more preferably 1 to 2 groups) selected from the group consisting of an oxo group, a lower alkyl group, a lower alkanoyl group and a lower alkoxycarbonyl group (more preferably, a piperazinyl group substituted with a single oxo group, a piperazinyl group substituted with a single lower alkyl group, a piperazinyl group substituted with a single lower alkanoyl group, a piperazinyl group substituted with a single oxo group and a single lower alkanoyl group, and a piperazinyl group substituted with a single oxo group and a single lower alkoxy carbonyl group),

(62) a morpholinyl group,

(63) a 1,3,8-triazaspiro[4.5]decanylcarbonyl group that may have 1 to 3 groups (more preferably 1 to 2 groups) selected from the group consisting of an oxo group and a phenyl group,

(64) a tetrahydropyridylcarbonyl group that may have 1 to 3 (more preferably 1) pyridyl groups,

(65) an imidazolidinylcarbonyl group that may have one thioxo group, and

(66) a 1,4-dioxa-8-azaspiro[4.5]decanyl group.

In the general formula (1), $R^1$ is preferably a cyclohexyl group, phenyl group, pyrrolidinyl group, piperidyl group, pyrazolyl group, pyridyl group, pyrimidinyl group, or thiazolyl group. The ring of each groups is preferably substituted with 1 to 3 groups selected from the group consisting of:

(1) a lower alkyl group, (4) a lower alkoxy group,

(10) a hydroxy lower alkyl group,

(17) an amino group having 1 to 2 groups selected from the group consisting of a lower alkyl group, a lower alkanoyl group, a lower alkoxy carbonyl group, a lower alkyl sulfonyl group, a carbamoyl group, a lower alkyl carbamoyl group, an amino lower alkanoyl group, a lower alkanoylamino lower alkanoyl group and a lower alkoxycarbonylamino lower alkanoyl group as a substituent (s),

(21) a lower alkoxycarbonyl group,

(28) a carbamoyl group that may have 1 to 2 substituents selected from the group consisting of the groups (i), (ii), (iv), (xii) and (xxi) below:

(i) a lower alkyl group, (ii) a lower alkoxy group, (iv) a lower alkoxy lower alkyl group, (xii) a lower alkyl group having 1 to 2 lower alkylcarbonyl groups, (xxi) a pyridyl lower alkyl group,

(29) an amino lower alkyl group that may have 1 to 2 groups selected from the group consisting of a lower alkyl group, a halogen substituted lower alkyl group, a lower alkoxycarbonyl group, a lower alkanoyl group, a phenyl group, a phenyl lower alkyl group, a benzoyl group and an amino substituted alkyl group (that may have 1 to 2 lower alkyl groups as a substituent(s) on the amino group) on the amino group,

(30) a lower alkyl group substituted with a single carbamoyl group that may have 1 to 2 groups selected from the group consisting of a lower alkyl group and a halogen substituted lower alkyl group,

(33) an oxazolidinyl group that may have a single oxo group,

(34) an imidazolidinyl group that may have 1 to 2 substituents selected from the group consisting of an oxo group and a lower alkyl group,

(35) a pyrrolidinyl group that may have a single oxo group,

(36) an imidazolyl group,

(39) a piperidyl group that may have a single substituent selected from the group consisting of a lower alkyl group, a lower alkanoyl group, a lower alkyl phenylsulfonyl group, an oxo group, a hydroxy group, an amino group, an N-lower alkylamino group, an N-N di-lower alkyl amino group, an N-lower alkanoylamino group, an N-lower alkyl-N-lower alkoxycarbonylamino group, an N-lower alkyl-N-lower alkanoylamino group, and an N-lower alkanoylamino lower alkanoylamino group,

(61) a piperazinyl group that may have 1 to 2 groups selected from the group consisting of an oxo group, a lower alkyl group, a lower alkanoyl group and a lower alkoxy carbonyl group, and

(62) a morpholinyl group.

EXAMPLE

Hereinbelow, the present invention will be further made clear with reference to Reference Examples, Examples and Pharmacological Experimental Examples and Preparation Examples.

Reference Example 1

Synthesis of 1-benzo[b]thiophen-4-yl-piperazine hydrochloride

A mixture consisting of 14.4 g of 4-bromobenzo[b]thiophene, 29.8 g of piperazine anhydride, 9.3 g of sodium t-butoxide, 0.65 g of (R)-(+)-2,2'-bis(diphenylphosphino)-1,1'-binaphthyl (BINAP), 0.63 g of tris (dibenzylideneacetone) dipalladium (0) and 250 ml of toluene was refluxed with heating for one hour under a nitrogen atmosphere. Water was poured to the reaction solution, which was then extracted with ethyl acetate, washed with water and dried over magnesium sulfate. The solvent was evaporated under reduced pressure. The obtained residue was purified by silica gel column chromatography (dichloromethane:methanol:25% ammonia water=100:10:1), to obtain 9.5 g of 1-benzo[b]thiophen-4-yl-piperazine in the form of yellow oil.

Then, 3.7 ml of concentrated hydrochloric acid was added to a methanol solution of 9.5 g of 1-benzo[b]thiophen-4-yl-piperazine, and the solvent was evaporated under reduced pressure. Ethyl acetate was added to the obtained residue and precipitated crystals were obtained by filtration. Recrystallization was performed from methanol to obtain 1-benzo[b]thiophen-4-yl-piperazine hydrochloride as colorless needle-like crystals.

Melting point 276-280° C.

$^1$H-NMR (DMSO-d$_6$) δppm: 3.25-3.35 (8H, m), 6.94 (1H, d, J=7.6 Hz), 7.30 (1H, dd, J=7.8 Hz, J=7.8 Hz), 7.51 (1H, d, J=5.5 Hz), 7.68 (1H, d, J=8.1 Hz), 7.73 (1H, d, J=5.5 Hz), 9.35 (2H, brs).

Reference Example 2

Synthesis of tert-butyl 4-benzo[b]thiophen-4-yl-3-methylpiperazin-1-carboxylate The titled compound was obtained using tert-butyl 3-methylpiperazin-1-carboxylate and 4-bromobenzo[b]thiophene in the same manner as in Reference Example 1.

$^1$H-NMR (CDCl$_3$) δppm: 1.85-1.95 (3H, m, 1.50 (9H, s, 2.8-2.9 (1H, m), 3.15-3.35 (2H, m), 3.4-3.5 (1H, m), 3.5-3.65 (1H, m), 3.65-3.7 (1H, m), 3.7-3.9 (1H, m), 6.98 (1H, d, J=7.5 Hz), 7.29 (1H, dd, J=8 Hz, J=8 Hz), 7.38 (1H, d, J=5.5 Hz), 7.61 (1H, d, J=8 Hz).

Reference Example 3

Synthesis of 1-benzo[b]thiophen-4-yl-2-methylpiperazine dihydrochloride

Trifluoroacetic acid (6 ml) was added to a solution of 1.22 g (3.7 mmol) of tert-butyl 4-benzo[b]thiophen-4-yl-3-methylpiperazin-1-carboxylate in a dichloromethane solution (12 ml) and the mixture was stirred at room temperature for one hour. The reaction mixture was concentrated under reduced pressure, and a 5% aqueous potassium carbonate solution was added to the residue and the resulting mixture was extracted with dichloromethane. The extraction solution with dichloromethane was dried over magnesium sulfate and thereafter concentrated under reduced pressure. To the residue obtained, concentrated hydrochloric acid (0.6 ml) and methanol (10 ml) were added and the resulting mixture was concentrated under reduced pressure. The obtained residue was subjected to recrystallization from acetonitrile to obtain 1-benzo[b]thiophen-4-yl-2-methylpiperazine dihydrochloride (0.98 g) as light brown powder.

$^1$H-NMR (DMSO-d$_6$) δppm: 0.92 (3H, d, J=6.5 Hz), 2.8-3.6 (6H, m), 3.6-4.0 (1H, m), 5.3-6.8 (1H, m), 7.20 (1H, br), 7.38 (1H, dd, J=8 Hz, J=8 Hz), 7.5-8.0 (3H, m), 9.4-10.1 (2H, m).

Reference Example 4

Synthesis of 1-benzo[b]thiophen-4-yl-3-methylpiperazine dihydrochloride

The titled compound was obtained using 2-methylpiperazine and 4-bromobenzo[b]thiophene in the same manner as in Reference Example 1.

$^1$H-NMR (DMSO-d$_6$) δppm: 1.34 (3H, d, J=6.5 Hz), 2.85-2.95 (1H, m), 3.05-3.15 (1H, m), 3.2-3.6 (6H, m), 6.97 (1H, d, J=7.5 Hz), 7.31 (1H, dd, J=8 Hz, J=8 Hz), 7.54 (1H, d, J=5.5 Hz), 7.69 (1H, d, J=8 Hz), 7.75 (1H, d, J=5.5 Hz), 9.2-9.3 (1H, m), 9.64 (1H, br).

Reference Example 5

Synthesis of ethyl 3-(4-benzo[b]thiophen-4-yl-piperazin-1-yl)propionate 5.05 g (19.8 mmol) of 1-benzo[b]thiophen-4-yl-piperazine hydrochloride was added to an aqueous solution of sodium hydroxide, and the mixture was extracted with dichloromethane. The extraction solution was dried over magnesium sulfate and concentrated under reduced pressure. The obtained residue was dissolved in 50 ml of ethanol and ethyl acrylate (2.44 ml, 21.8 mmol) was added thereto, and then the reaction mixture was refluxed with heating for 4 hours. The reaction solution was cooled to room temperature and concentrated under reduced pressure. Diisopropyl ether was added to the residue and insoluble matter precipitated was obtained by filtration, washed with diisopropyl ether, and dried to obtain ethyl 3-(4-benzo[b]thiophen-4-yl-piperazin-1-yl)propionate (5.26 g) as white powder.

$^1$H-NMR (CDCl$_3$) δppm: 1.28 (3H, t, J=7.0 Hz), 2.50-2.63 (2H, m), 2.67-2.87 (6H, m), 3.11-3.24 (4H, m), 4.17 (2H, q, J=7.0 Hz), 6.89 (1H, d, J=7.8 Hz), 7.27 (1H, t, J=7.8 Hz), 7.37-7.42 (2H, m), 7.55 (1H, d, J=7.8 Hz).

Reference Example 6

Synthesis of 3-(4-benzo[b]thiophen-4-yl-piperazin-1-yl)propan-1-ol

Lithium aluminum hydride (1.18 g, 24.8 mmol) was added to a solution of 5.26 g (16.5 mmol) of ethyl 3-(4-benzo[b]thiophen-4-yl-piperazin-1-yl)propionate in a tetrahydrofuran (THF) solution (55 ml) under ice cooling, and the mixture was stirred at room temperature for 4 hours. To the reaction solution, water (1.2 ml), 15% aqueous sodium hydroxide solution (1.2 ml), and water (3.6 ml) were added in this order and the mixture was stirred at room temperature. Insoluble matter was removed by filtration, and the filtrate was concentrated under reduced pressure. The obtained residue was purified by silica gel column chromatography (n-hexane:ethyl acetate=3:2→ethyl acetate) and concentrated to dryness under reduced pressure to obtain 3-(4-benzo[b]thiophen-4-yl-piperazin-1-yl)propan-1-ol (0.23 g) as white powder.

¹H-NMR (CDCl₃) δppm: 1.75-1.85 (2H, m), 2.74 (2H, t, J=5.8 Hz), 2.75-2.85 (4H, m), 3.15-3.25 (4H, m), 3.85 (2H, t, J=5.3 Hz), 5.19 (1H, brs), 6.88 (1H, d, J=7.6 Hz), 7.27 (1H, dd, J=7.9 Hz, J=7.8 Hz), 7.39 (2H, s), 7.56 (1H, d, J=8.0 Hz).

Reference Example 7

Synthesis of 4-(4-benzo[b]thiophen-4-yl-piperazin-1-yl)butyl acetate 1.0 g (3.9 mmol) of 1-benzo[b]thiophen-4-yl-piperazine hydrochloride was suspended in 20 ml of dimethylformamide (DMF), and potassium carbonate (1.3 g, 9.4 mmol) and 4-bromobutyl acetate (0.7 ml, 4.8 mmol) were added thereto. The reaction mixture was stirred at 80° C. for 6 hours, cooled to room temperature, and water was added thereto, and extracted with ethyl acetate. The organic phase was washed with water, dried over sodium sulfate, and concentrated under reduced pressure. The obtained residue was purified by silica gel column chromatography (dichloromethane:methanol=30:1), and concentrated to dryness under reduced pressure to obtain 4-(4-benzo[b]thiophen-4-yl-piperazin-1-yl)butyl acetate (0.72 g) as light yellow oil.

¹H-NMR (CDCl₃) δppm: 1.60-1.73 (4H, m), 2.07 (3H, s), 2.47 (2H, t, J=7.2 Hz), 2.60-2.72 (4H, m), 3.17-3.22 (4H, m), 4.11 (2H, t, J=6.3 Hz), 6.90 (1H, d, J=7.6 Hz), 7.27 (1H, dd, J=7.6 Hz, J=8.0 Hz), 7.37-7.42 (2H, m), 7.55 (1H, d, J=8.0 Hz).

Reference Example 8

Synthesis of 4-(4-benzo[b]thiophen-4-yl-piperazin-1-yl)butan-1-ol

Potassium carbonate (3.87 g, 28 mmol) was added to a solution of 7.76 g (23.3 mmol) of 4-(4-benzo[b]thiophen-4-yl-piperazin-1-yl)butyl acetate in 90% methanol solution (150 ml). The solution mixture was stirred at room temperature for 2 hours. Water was added to the reaction solution, which was then extracted with dichloromethane. The extraction solution was dried over sodium sulfate and concentrated under reduced pressure. The residue was purified by basic silica gel column chromatography (n-hexane:ethyl acetate=2:1→1:1), and concentrated under reduced pressure to obtain 4-(4-benzo[b]thiophen-4-yl-piperazin-1-yl)butan-1-ol (6.65 g) as colorless oil.

¹H-NMR (CDCl₃) δppm: 1.60-1.74 (4H, m), 2.50-2.55 (2H, m), 2.70-2.80 (4H, m), 3.20-3.30 (4H, m), 3.60-3.63 (2H, m), 6.2 (1H, brs), 6.90 (1H, d, J=7.6 Hz), 7.27 (1H, dd, J=7.6 Hz, J=8.0 Hz), 7.39 (1H, s), 7.56 (1H, d, J=8.0 Hz).

Reference Example 9

Synthesis of 1-benzo[b]thiophen-4-yl-4-(3-chloropropyl)piperazine 3.56 g (12.9 mmol) of 3-(4-benzo[b]thiophen-4-yl-piperazin-1-yl)propan-1-ol was suspended in 30 ml of dichloromethane, and carbon tetrachloride (30 ml) and triphenyl phosphine (4.06 g, 15.5 mmol) were added thereto. The mixture was refluxed with heating for 3 hours. The reaction solution was cooled to room temperature, then methanol and dichloromethane were added thereto to homogenize the mixture. Silica gel (30 g) was added to the solution, and the solvent was evaporated under reduced pressure. The obtained residue was loaded on silica gel column (300 g) and extracted with a solvent mixture of n-hexane:ethyl acetate=2:1. The extraction solution was concentrated under reduced pressure to obtain 1-benzo[b]thiophen-4-yl-4-(3-chloropropyl)piperazine (2.36 g) as colorless oil.

¹H-NMR (CDCl₃) δppm: 1.95-2.10 (2H, m), 2.60 (2H, t, J=7.2 Hz), 2.65-2.75 (4H, m), 3.15-3.25 (4H, m), 3.65 (2H, t, J=6.6 Hz), 6.89 (1H, dd, J=7.6 Hz, J=0.7 Hz), 7.27 (1H, dd, J=7.9 Hz, J=7.8 Hz), 7.38 (1H, d, J=5.6 Hz), 7.41 (1H, d, J=5.7 Hz), 7.55 (1H, d, J=8.0 Hz).

Reference Example 10

Synthesis of methyl 4-hydroxythiophene-2-carboxylate

Thionyl chloride (1.6 ml) was added dropwise to a methanol solution (20 ml) of 4-hydroxythiophene-2-carboxylic acid (1.1 g, 7.6 mmol) under ice cooling. The solution mixture was refluxed with heating for 5 hours. The reaction solution was cooled to room temperature, poured into ice water and extracted with ethyl acetate. The extraction solution with ethyl acetate was dried over magnesium sulfate and concentrated under reduced pressure. The residue was purified by silica gel column chromatography (n-hexane:ethyl acetate=4:1) and concentrated/dried under reduced pressure to obtain methyl 4-hydroxythiophene-2-carboxylate (0.7 g) as white powder.

¹H-NMR (CDCl₃) δppm: 3.90 (3H, s), 5.50-6.60 (1H, br), 6.64 (1H, d, J=1.9 Hz), 7.43 (1H, d, J=1.8 Hz).

Reference Example 11

Synthesis of ethyl 6-hydroxypyrimidine-4-carboxylate

The titled compound was obtained using 6-hydroxypyrimidine-4-carboxylic acid in the same manner as in Reference Example 10.

¹H-NMR (CDCl₃) δppm: 1.29 (3H, t, J=7.0 Hz), 4.29 (2H, q, J=7.0 Hz), 6.87 (1H, d, J=1.0 Hz), 8.27 (1H, d, J=1.0 Hz), 10.54 (1H, br).

Reference Example 12

Synthesis of methyl 5-hydroxy-1-methyl-1H-pyrazole-3-carboxylate

A diethyl ether solution (35 ml) of dimethyl acetylenedicarboxylate (5.0 g, 35 mmol) was cooled with a freezing medium (salt & ice). To this solution, a diethyl ether solution (15 ml) of methyl hydrazine (0.63 ml, 35 mmol) was added dropwise while maintaining the temperature at 0° C. or less. After completion of dropwise addition, the solution was stirred at 0° C. for one hour. The insoluble matter precipitated was obtained by filtration and washed with diethyl ether. The filter cake was heated to 130° C. for 30 minutes and cooled to room temperature. Methanol was added to the cake, which was concentrated under reduced pressure. Ethyl acetate was added to the obtained residue and the residue was concentrated under reduced pressure. Ethyl acetate was added to the residue and the insoluble matter precipitated was obtained by filtration, washed with ethyl acetate, and dried to obtain methyl 5-hydroxy-1-methyl-1H-pyrazole-3-carboxylate (3.26 g) as light yellow powder.

¹H-NMR (DMSO-d₆) δppm: 3.58 (3H, s), 3.73 (3H, s), 5.77 (1H, s), 11.41 (1H, br).

Reference Example 13

Synthesis of
6-chloro-N-(2,2,2-trifluoroethyl)nicotine amide

Triethylamine (1.03 ml, 7.4 mmol) and isobutyl chloroformate (0.76 ml, 5.5 mmol) were added to an acetonitrile solution (12 ml) of 6-chloronicotinic acid (0.58 g, 3.6 mmol) under ice cooling and the mixture was stirred at 0° C. for 30 minutes. To the solution mixture, 2,2,2-trifluoroethyl amine (0.88 ml, 11.2 mmol) was added and the mixture was stirred at room temperature for 10 minutes. Water was added to the reaction solution, which was then extracted with ethyl acetate. The extraction solution with ethyl acetate was dried over magnesium sulfate, and concentrated under reduced pressure. The residue was purified by basic silica gel column chromatography (n-hexane:ethyl acetate=5:1→1:1). The purified product was concentrated under reduced pressure and diisopropyl ether and n-hexane were added. The insoluble matter precipitated was obtained by filtration and dried to obtain 6-chloro-N-(2,2,2-trifluoroethyl)nicotine amide (0.58 g) as light yellow powder.
$^1$H-NMR (CDCl$_3$) δppm: 4.15 (2H, dq, J=6.5 Hz, 9.0 Hz), 6.35 (1H, br), 7.46 (1H, dd, J=0.7 Hz, J=8.5 Hz), 8.11 (1H, dd, J=2.5 Hz, J=8.5 Hz), 8.77 (1H, dd, J=0.7 Hz, J=2.5 Hz).

Reference Example 14

Synthesis of N-(2,2,2-trifluoroethyl)-4-chloropyridine-2-carboxamide 1-hydroxybenzotriazole (0.53 g, 3.5 mmol), 1-(3-dimethylaminopropyl)-3-ethylcarbodiimide hydrochloride (WSC) (0.67 g, 3.5 mmol) and 2,2,2-trifluoroethyl amine (0.51 ml, 6.35 mmol) were added to a dichloromethane solution (5 ml) of 4-chloropyridine-2-carboxylic acid (0.5 g, 3.17 mmol) and the mixture was stirred at room temperature for one hour. Water was added to the reaction solution, which was then extracted with ethyl acetate. The extraction solution with ethyl acetate was dried over magnesium sulfate and concentrated under reduced pressure. The residue was purified by silica gel column chromatography (n-hexane:ethyl acetate=11:1→5:1). The purified product was concentrated to dryness under reduced pressure to obtain N-(2,2,2-trifluoroethyl)-4-chloropyridine-2-carboxamide (435 mg) as white powder.
$^1$H-NMR (CDCl$_3$) δppm: 4.13 (2H, dq, J=6.8 Hz, 9.0 Hz), 7.49 (1H, dd, J=2.1 Hz, J=5.3 Hz), 8.22 (1H, dd, J=0.4 Hz, J=2.1 Hz), 8.30 (1H, br), 8.49 (1H, dd, J=0.4 Hz, J=5.3 Hz).

Reference Example 15

Synthesis of 2-chlorothiazole-4-carboxamide 1-hydroxybenzotriazole (0.56 g, 3.7 mmol), 1-(3-dimethylaminopropyl)-3-ethylcarbodiimide hydrochloride (WSC) (0.7 g, 3.7 mmol) and ammonia water (28%, 0.5 ml)) were added to a dichloromethane solution (10 ml) of 2-chlorothiazole-4-carboxylic acid (0.5 g, 3.06 mmol) and the mixture was stirred at room temperature for 46 hours. Water was added to the reaction solution, which was then extracted with ethyl acetate. The extraction solution with ethyl acetate was dried over magnesium sulfate and concentrated under reduced pressure. The residue was purified by silica gel column chromatography (n-hexane:ethyl acetate=3:5→ethyl acetate). The purified product was concentrated to dryness under reduced pressure to obtain 2-chlorothiazole-4-carboxamide (475 mg) as white powder.
$^1$H-NMR (CDCl$_3$) δppm: 5.70 (1H, br), 7.01 (1H, br), 8.06 (1H, s).

Reference Example 16

Synthesis of
N-methyl-2-chlorothiazole-5-carboxamide

The titled compound was obtained using 2-chlorothiazole-5-carboxylic acid in the same manner as in Reference Example 13.
$^1$H-NMR (CDCl$_3$) δppm: 3.00 (3H, d, J=4.9 Hz), 5.92 (1H, br), 7.84 (1H, br).

Reference Example 17

Synthesis of
6-methoxy-2,2-dimethyl-4H-benzo[1,4]oxazin-3-one

5% palladium carbon (1.5 g) were added to an ethanol solution (250 ml) of ethyl 2-(4-methoxy-2-nitrophenoxy)-2-methylpropionate (14.6 g, 51.6 mmol) to perform catalytic reduction at room temperature. The catalyst was removed by filtration and the filtrate was concentrated under reduced pressure. Water was added to the obtained residue, which was then extracted with ethyl acetate. The extraction solution was dried over magnesium sulfate, and concentrated under reduced pressure. The obtained residue was purified by silica gel column chromatography (n-hexane:ethyl acetate=9:1). The purified product was concentrated to dryness under reduced pressure to obtain 6-methoxy-2,2-dimethyl-4H-benzo[1,4]oxazin-3-one (7.0 g) as white powder.
$^1$H-NMR (CDCl$_3$) δppm: 1.53 (6H, s), 3.78 (3H, s), 6.40 (1H, d, J=2.8 Hz), 6.52 (1H, dd, J=2.8 Hz, J=8.8 Hz), 6.88 (1H, d, J=8.7 Hz), 8.66 (1H, brs).

Reference Example 18

Synthesis of
6-hydroxy-2,2-dimethyl-4H-benzo[1,4]oxazin-3-one

A dichloromethane solution (36 ml) of 2M boron tribromide was added dropwise to a dichloromethane solution of 6-methoxy-2,2-dimethyl-4H-benzo[1,4]oxazin-3-one (5.0 g, 26 mmol) under ice cooling and the mixture was stirred overnight. Water was added to the reaction solution to decompose the reagents excessively present. The reaction solution was washed with water, dried over magnesium sulfate and concentrated under reduced pressure. The obtained residue was purified by silica gel column chromatography (n-hexane: ethyl acetate=2:1). The purified product was concentrated to dryness under reduced pressure to obtain 6-hydroxy-2,2-dimethyl-4H-benzo[1,4]oxazin-3-one (4.02 g) as white powder.
$^1$H-NMR (DMSO-d$_6$) δppm: 1.34 (6H, s), 6.25-6.40 (2H, m), 6.70 (1H, d, J=8.5 Hz), 9.09 (1H, s), 10.41 (1H, brs).

Reference Example 19

Synthesis of
6-hydroxy-2-methyl-4H-benzo[1,4]oxazin-3-one

The titled compound was obtained using 6-methoxy-2-methyl-4H-benzo[1,4]oxazin-3-one in the same manner as in Reference Example 18.
White Powder
$^1$H-NMR (DMSO-d$_6$) δppm: 1.34 (3H, d, J=6.8 Hz), 4.46 (1H, q, J=6.8 Hz), 6.23-6.27 (1H, m), 6.33 (1H, d, J=2.7 Hz), 6.70 (1H, d, J=8.6 Hz), 9.11 (1H, s), 10.44 (1H, brs).

Reference Example 20

Synthesis of 4-(4-methoxyphenyl)-1-(toluene-4-sulfonyl)piperidine p-Toluenesulfonyl chloride (4.39 g, 23 mmol) was added to a pyridine solution (30 ml) of 4-(4-methoxyphenyl)piperidine (4.0 g, 21 mmol) and the mixture was stirred at room temperature overnight. Water was added to the solution mixture, which was then extracted with ethyl acetate. The organic phase was washed with hydrochloric acid and water, dried over magnesium sulfate and concentrated under reduced pressure. The obtained residue was purified by silica gel column chromatography (n-hexane:ethyl acetate=1:1). The purified product was concentrated to dryness under reduced pressure to obtain 4-(4-methoxyphenyl)-1-(toluene-4-sulfonyl)piperidine (4.8 g) as white powder.

$^1$H-NMR (CDCl$_3$) δppm: 1.60-1.90 (4H, m), 2.30-2.40 (3H, m), 2.46 (3H, s), 3.78 (3H, s), 3.90-3.95 (2H, m), 6.84 (2H, dd, J=1.9, J=6.8 Hz), 7.07 (2H, dd, J=1.9, J=6.8 Hz), 7.35 (2H, d, J=8.2 Hz), 7.68 (2H, d, J=8.2 Hz).

Reference Example 21

Synthesis of 4-(4-hydroxyphenyl)-1-(toluene-4-sulfonyl)piperidine

The titled compound was obtained using 4-(4-methoxyphenyl)-1-(toluene-4-sulfonyl)piperidine in the same manner as in Reference Example 18.
Brown Powder $^1$H-NMR (CDCl$_3$) δppm: 1.60-1.90 (4H, m), 2.30-2.50 (3H, m), 2.45 (3H, s), 3.90-3.95 (2H, m), 6.67 (1H, brs), 6.80 (2H, dd, J=1.9, J=6.8 Hz), 7.02 (2H, dd, J=1.8, J=6.9 Hz), 7.35 (2H, d, J=8.1 Hz), 7.68 (2H, d, J=8.1 Hz).

Reference Example 22

Synthesis of 4-bromo-2-hydroxymethyl-6-methoxyphenol

Sodium borohydride (0.28 g, 6.9 mmol) was added to a THF solution (30 ml) of 5-bromo-2-hydroxy-3-methoxybenzaldehyde (3.2 g 13.8 mmol) under ice cooling and the mixture was stirred at 0° C. for 2 hours. Acetic acid was added to the reaction solution to set pH at 3. 10% hydrochloric acid was added to the reaction mixture, which was then extracted with ethyl acetate. The extracted material was dried over magnesium sulfate and concentrated under reduced pressure. The obtained residue was purified by silica gel column chromatography (n-hexane:ethyl acetate=5:1→1:1) and concentrated to dryness under reduced pressure to obtain 4-bromo-2-hydroxymethyl-6-methoxyphenol (3.23 g) as light yellow oil.

$^1$H-NMR (CDCl$_3$) δppm: 3.88 (3H, s), 4.71 (2H, s), 6.94 (1H, d, J=2.0 Hz), 7.03 (1H, d, J=2.0 Hz).

Reference Example 23

Synthesis of 5-bromo-3-methoxy-2-methoxymethoxybenzaldehyde

Ethyldiisopropylamine (3.01 ml, 17.1 mmol) and methoxymethylchloride (1.5 ml, 15.7 mmol) were added to a dichloromethane solution (30 ml) of 5-bromo-2-hydroxy-3-methoxybenzaldehyde (3.3 g, 14.3 mmol) under ice cooling, and the mixture was stirred at room temperature for 2 hours. The reaction solution was washed with water, dried over magnesium sulfate, and concentrated under reduced pressure. The obtained residue was purified by silica gel column chromatography (n-hexane:ethyl acetate=3:1→11:9). The purified product was concentrated to dryness under reduced pressure to obtain 5-bromo-3-methoxy-2-methoxymethoxybenzaldehyde (4.2 g) as light yellow solid.

$^1$H-NMR (CDCl$_3$) δppm: 3.56 (3H, s), 3.89 (3H, s), 5.21 (2H, s), 7.23 (1H, d, J=2.5 Hz), 7.56 (1H, d, J=2.5 Hz), 10.39 (1H, s).

Reference Example 24

Synthesis of 3-methoxy-2-methoxymethoxy-5-(2-oxo-oxazolidin-3-yl)benzaldehyde 2-oxazolidinone (0.38 g, 4.36 mmol), dipalladium tris(dibenzylideneacetone) (0.17 g, 0.18 mmol), 9,9-dimethyl-4,5-bis(diphenylphosphino)xanthene (XANTPHOS)(0.32 g, 0.55 mmol) and cesium carbonate (1.66 g, 5.1 mmol) were added to a dioxane solution (20 ml) of 5-bromo-3-methoxy-2-methoxymethoxybenzaldehyde (1.0 g, 3.6 mmol) and the mixture was stirred at 100° C. for 24 hours under an argon atmosphere. The reaction solution was cooled to room temperature and ethyl acetate was added thereto. The mixture was filtrated by cerite. The filtrate was washed with water, dried over magnesium sulfate and concentrated under reduced pressure. The obtained residue was purified by silica gel column chromatography (n-hexane:ethyl acetate 4:1→1:1). The purified product was concentrated under reduced pressure. Ethyl acetate and diisopropyl ether were added to the residue. The insoluble matter thus purified was obtained by filtration and dried to obtain 3-methoxy-2-methoxymethoxy-5-(2-oxo-oxazolidin-3-yl)benzaldehyde (0.5 g) as white powder.

$^1$H-NMR (CDCl$_3$) δppm: 3.57 (3H, s), 3.93 (3H, s), 4.06-4.12 (2H, m), 4.48-4.54 (2H, m), 5.21 (2H, s), 6.96 (1H, d, J=2.5 Hz), 8.18 (1H, d, J=2.5 Hz), 10.45 (1H, s).

Reference Example 25

Synthesis of 3-(3-methoxy-4-methoxymethoxy-5-methylphenyl)oxazolidin-2-one

3-Methoxy-2-methoxymethoxy-5-(2-oxo-oxazolidin-3-yl)benzaldehyde (0.5 g, 1.79 mmol) was dissolved in a solvent mixture of acetic acid (5 ml) and ethanol (5 ml) and 10% palladium carbon (0.05 g) was added thereto to perform catalytic reduction at 1 atm at 50° C. for 4 hours. The reaction mixture was cooled to room temperature and filtrated by cerite. The filtrate was concentrated under reduced pressure. The residue was dissolved in acetic acid (10 ml) and 10% palladium carbon (0.05 g) was added thereto to perform catalytic reduction at 1 atm at 50° C. for 6 hours. The solvent was removed under reduced pressure to obtain 3-(3-methoxy-4-methoxymethoxy-5-methylphenyl)oxazolidin-2-one as a crude product, which was subjected to the next reaction as it was.

$^1$H-NMR (CDCl$_3$) δppm: 2.32 (3H, s), 3.56 (3H, s), 3.85 (3H, s), 3.98-4.06 (2H, m), 4.43-4.50 (2H, m), 5.05 (2H, s), 6.61 (1H, d, J=2.3 Hz), 7.36 (1H, d, J=2.3 Hz).

Reference Example 26

Synthesis of 3-(4-hydroxy-3-methoxy-5-methylphenyl)oxazolidin-2-one

10% hydrochloric acid (5 ml) was added to a methanol solution (5 ml) of 3-(3-methoxy-4-methoxymethoxy-5-methylphenyl)oxazolidin-2-one (0.48 g, 1.79 mmol) and the mixture was stirred at 50° C. for 10 minutes. Water was added to the reaction solution, which was extracted with ethyl acetate. The extracted material was dried over magnesium sulfate, and thereafter concentrated to dryness under reduced pressure to obtain 3-(4-hydroxy-3-methoxy-5-methylphenyl)oxazolidin-2-one (434 mg) as a light yellow powder.

$^1$H-NMR (CDCl$_3$) δppm: 2.26 (3H, s), 3.90 (3H, s), 4.02 (2H, dd, J=7.0 Hz, J=8.5 Hz), 4.46 (2H, dd, J=7.0 Hz, J=8.5 Hz), 5.55 (1H, br), 6.56 (1H, d, J=2.5 Hz), 7.31 (1H, d, J=2.5 Hz).

Reference Example 27

Synthesis of 1-(8-methoxy-2,2-dimethyl-4H-benzo[1,3]dioxin-6-yl)pyrrolidin-2-one The titled compound was obtained using 6-bromo-8-methoxy-2,2-dimethyl-4H-benzo[1,3]dioxin and 2-pyrrolidone in the same manner as in Reference Example 25.

$^1$H-NMR (CDCl$_3$) δppm: 1.59 (6H, s), 2.09-2.21 (2H, m), 2.60 (2H, t, J=8.3 Hz), 3.82 (2H, t, J=7.0 Hz), 3.88 (3H, s), 4.83 (2H, s), 6.67 (1H, d, J=2.5 Hz), 7.24 (1H, d, J=2.5 Hz).

Reference Example 28

Synthesis of 1-(4-hydroxy-3-hydroxymethyl-5-methoxyphenyl)pyrrolidin-2-one

10% hydrochloric acid (4 ml) was added to a THF solution (7 ml) of 1-(8-methoxy-2,2-dimethyl-4H-benzo[1,3]dioxin-6-yl)pyrrolidin-2-one (0.36 g, 1.3 mmol) and the mixture was stirred at room temperature for 17 hours. Water was added to the reaction solution, which was then extracted with dichloromethane. The extracted material was dried over magnesium sulfate, concentrated under reduced pressure and purified by silica gel column chromatography (dichloromethane:methanol:=300:1→30:1). The purified product was concentrated to dryness under reduced pressure to obtain 1-(4-hydroxy-3-hydroxymethyl-5-methoxyphenyl)pyrrolidin-2-one (0.31 g) as light brown powder.

$^1$H-NMR (CDCl$_3$) δppm: 2.05-2.28 (3H, m), 2.26 (2H, t, J=7.5 Hz), 3.84 (2H, t, J=7.0 Hz), 3.91 (3H, s), 4.74 (2H, s), 5.90 (1H, br), 6.78 (1H, d, J=2.5 Hz), 7.52 (1H, d, J=2.5 Hz).

Reference Example 29

Synthesis of 3-methoxy-2-methoxymethoxy-5-(2-oxopyrrolidin-1-yl)benzaldehyde

The titled compound was obtained using 5-bromo-3-methoxy-2-methoxymethoxybenzaldehyde and 2-pyrrolidone in the same manner as Reference Example 25.

$^1$H-NMR (CDCl$_3$) δppm: 2.11-2.24 (2H, m), 2.63 (2H, t, J=8.3 Hz), 3.56 (3H, s), 3.89 (2H, t, J=7.0 Hz), 3.92 (3H, s), 5.21 (2H, s), 7.08 (1H, d, J=2.5 Hz), 8.28 (1H, d, J=2.5 Hz), 10.46 (1H, s).

Reference Example 30

Synthesis of 1-(4-hydroxy-3-methoxy-5-methylphenyl)pyrrolidin-2-one 3-methoxy-2-methoxymethoxy-5-(2-oxopyrrolidin-1-yl)benzaldehyde (0.72 g, 2.56 mmol) was dissolved in a solvent mixture of acetic acid (5 ml) and ethanol (7 ml) and 10% palladium carbon (70 mg) was added thereto to perform catalytic reduction at 50° C. for 10 hours. The reaction solution was cooled to room temperature and filtrated by cerite. The filtered cake was concentrated under reduced pressure. The residue thus obtained was dissolved in dichloromethane (15 ml) and trifluoroacetic acid (2.0 ml, 25.6 mmol) and triethylsilane (2.0 ml, 12.8 mmol) were added thereto under ice cooling. The mixture was stirred at room temperature for 16 hours. The mixture was concentrated under reduced pressure and the residue was purified by silica gel column chromatography (n-hexane:ethyl acetate=5:1→ethyl acetate). The purified product was concentrated under reduced pressure to obtain 1-(4-hydroxy-3-methoxy-5-methylphenyl)pyrrolidin-2-one (0.41 g) as light yellow oil.

$^1$H-NMR (CDCl$_3$) δppm: 2.17-2.25 (5H, m), 2.72 (2H, t, J=8.3 Hz), 3.88 (2H, t, J=7.0 Hz), 3.89 (3H, s), 6.66 (1H, d, J=2.5 Hz), 7.15 (1H, d, J=2.5 Hz).

Reference Example 31

Synthesis of 3,4-diacetoxy-5-methylbenzaldehyde

Acetic anhydride (1.2 ml, 12 mmol) was added to a pyridine solution (4 ml) of 3,4-dihydroxy-5-methylbenzaldehyde (0.72 g, 4.7 mmol) and the mixture was stirred at 0° C. for one hour. 10% hydrochloric acid was added to the reaction solution, which was extracted with ethyl acetate. The organic phase was washed with an aqueous sodium hydrogen carbonate solution, dried over magnesium sulfate and concentrated under reduced pressure. The obtained residue was purified by silica gel column chromatography (n-hexane:ethyl acetate=5:1→3:1). The purified product was concentrated under reduced pressure to obtain 3,4-diacetoxy-5-methylbenzaldehyde (0.98 g) as light yellow oil.

$^1$H-NMR (CDCl$_3$) δppm: 2.29 (3H, s), 2.32 (3H, s), 2.35 (3H, s), 7.58 (1H, d, J=1.6 Hz), 7.67 (1H, d, J=1.6 Hz), 9.93 (1H, s).

Reference Example 32

Synthesis of 7-hydroxy-1,4-dihydrobenzo[d][1,3]oxazin-2-one

The titled compound was obtained using 7-methoxymethoxy-1,4-dihydrobenzo[d][1,3]oxazin-2-one in the same manner as in Reference Example 26.
White Powder $^1$H-NMR (DMSO-d$_6$) δppm: 5.14 (2H, s), 6.35 (1H, d, J=2.2 Hz), 6.39 (1H, dd, J=8.1, J=2.2 Hz), 6.97 (1H, d, J=8.1 Hz), 9.98 (1H, br-s).

Reference Example 33

Synthesis of 7-methoxy-3,4-dihydro-1H-quinazolin-2-one 2-aminomethyl-5-methoxyaniline (1.2 g. 7.9 mmol) and carbonyl diimidazole (1.53 g, 9.5 mmol) were added to THF (100 ml) and the mixture was stirred at room temperature overnight. The insoluble matter precipitated was obtained by filtration, washed with dichloromethane and water, dried to obtain 7-methoxy-3,4-dihydro-1H-quinazolin-2-one (1.11 g) as white powder.

$^1$H-NMR (DMSO-d$_6$) δppm: 3.68 (3H, s), 4.23 (2H, s), 6.35 (1H, d, J=2.5 Hz), 6.42 (1H, dd, J=8.3 Hz, J=2.5 Hz), 6.96 (1H, d, J=8.3 Hz), 8.90 (1H, brs).

Reference Example 34

Synthesis of 7-hydroxy-3,4-dihydro-1H-quinazolin-2-one

The titled compound was obtained using 7-methoxy-3,4-dihydro-1H-quinazolin-2-one in the same manner as in Reference Example 18.
Light Brown Powder
$^1$H-NMR (DMSO-d$_6$) δppm: 4.18 (2H, brs), 6.75-6.85 (1H, m), 7.01 (1H, dd, J=2.0 Hz, J=9.0 Hz), 8.07 (1H, d, J=9.0 Hz), 8.87 (1H, brs), 9.48 (1H, brs), 13.21 (1H, brs).

Reference Example 35

Synthesis of methyl 5-(3-chloropropoxy)-1-methyl-1H-pyrazole-3-carboxylate

Cesium carbonate (2.08 g, 6.4 mmol) and 1-bromo-3-chloropropane (1.6 ml) were added to a DMF solution (5 ml) of methyl 5-hydroxy-1-methyl-1H-pyrazole-3-carboxylate (0.83 g, 5.3 mmol) and the mixture was stirred at room temperature for 21 hours. Water was added to the reaction solution, which was then extracted with ethyl acetate. The organic phase was washed with water and dried over magnesium sulfate. The reaction solution was concentrated under reduced pressure. The residue was purified by silica gel column chromatography (n-hexane:ethyl acetate=100:1→4:1). The purified product was concentrated to dryness under reduced pressure to obtain methyl 5-(3-chloropropoxy)-1-methyl-1H-pyrazole-3-carboxylate (1.17 g) as white solid.
$^1$H-NMR (CDCl$_3$) δppm: 2.21-2.32 (2H, m), 3.72 (2H, t, J=6.3 Hz), 3.72 (2H, s), 3.91 (3H, s), 4.24 (2H, t, J=5.8 Hz), 6.10 (1H, s).

Reference Example 36

Synthesis of 7-(3-chloropropoxy)-2H-1,4-benzoxazin-3(4H)-one

The titled compound was obtained using 7-hydroxy-2H-1,4-benzoxazin-3(4H)-one and 1-bromo-3-chloropropane in the same manner as in Reference Example 35.
Light brown needle-like crystal (ethanol-n-hexane)
Melting point: 119-120° C.
The compounds listed in the following Tables 1 to 12 were produced using appropriate starting substances in the same manners as in Reference Examples 1 to 36.

TABLE 1

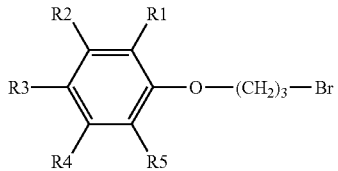

| Reference Example | R1 | R2 | R3 | R4 | R5 | NMR |
|---|---|---|---|---|---|---|
| 37 | —H | —H | —CONHC$_2$H$_5$ | —H | —H | $^1$H-NMR (CDCl$_3$) δ ppm: 1.25 (3 H, t, J = 7.5 Hz), 2.29-2.39 (2 H, m), 3.43-3.54 (2 H, m), 3.61 (2 H, t, J = 6.3 Hz), 4.15 (2 H, t, J = 5.8 Hz), 5.99 (1 H, br), 6.89-6.95 (2 H, m), 7.70-7.75 (2 H, m) |
| 38 | —H | —H | —CONHC$_3$H$_7$ | —H | —H | $^1$H-NMR (CDCl$_3$) δ ppm: 0.99 (3 H, t, J = 7.5 Hz), 1.57-1.68 (2 H, m), 2.23-2.36 (2 H, m), 3.37-3.45 (2 H, m), 3.61 (2 H, t, J = 6.3 Hz), 3.75 (2 H, t, J = 6.3 Hz) 4.12-4.18 (2 H, m), 6.02 (1 H, br), 6.71-6.95 (2 H, m), 7.71-7.75 (2 H, m) |

TABLE 2

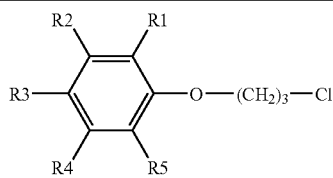

| Reference Example | R1 | R2 | R3 | R4 | R5 | NMR |
|---|---|---|---|---|---|---|
| 39 | —H | —H | —NO$_2$ | —H | —F | $^1$H-NMR (CDCl$_3$) δ ppm: 2.20-2.45 (2 H, m), 3.70-3.80 (2 H, m), 4.30-4.35 (2 H, m), 7.07 (1 H, dd, J = 8.2, 8.9 Hz), 8.00 (1 H, dd, J = 2.7, 10.7 Hz), 8.07 (1 H, dd, J = 0.9, 9.0 Hz), |
| 40 | —H | —H | —NH$_2$ | —H | —H | $^1$H-NMR (CDCl$_3$) δ ppm: 2.14-2.24 (2 H, m), 3.26 (2 H, br), 3.73 (2 H, t, J = 6.3 Hz), 4.04 (2 H, t, J = 5.8 Hz), 6.61-5.67 (2 H, m), 6.72-6.78 (2 H, m) |

TABLE 2-continued

Structure: R1, R2, R3, R4, R5 substituted benzene with —O—(CH₂)₃—Cl

| Reference Example | R1 | R2 | R3 | R4 | R5 | NMR |
|---|---|---|---|---|---|---|
| 41 | —H | —H | —NHCO₂CH₃ | —H | —H | ¹H-NMR (CDCl₃) δ ppm: 2.15-2.25 (2 H, m), 3.74 (2 H, t, J = 6.3 Hz), 3.76 (3 H, s), 4.09 (2 H, t, J = 5.8 Hz), 6.42 (1 H, br), 6.85 (2 H, dd, J = 2.5, 6.8 Hz), 7.21-7.33 (2 H, m) |
| 42 | —H | —H | —CH₂CON(C₂H₅)₂ | —H | —H | 1 H-NMR (CDCl₃) δ ppm: 1.07-1.14 (6 H, m), 2.17-2.30 (2 H, m), 3.26-3.42 (4 H, m), 3.63 (2 H, s), 3.74 (2 H, t, J = 6.3 Hz), 4.09 (2 H, t, J = 5.8 Hz), 6.83-6.88 (2 H, m), 7.14-7.19 (2 H, m) |
| 43 | —H | —H | —H | —NHCO₂CH₃ | —H | ¹H-NMR (CDCl₃) δ ppm: 2.28-2.37 (2 H, m), 3.74 (2 H, t, J = 6.5 Hz), 3.77 (3 H, s), 4.11 (2 H, t, J = 6.0 Hz), 6.50-6.67 (2 H, m), 6.83 (1 H, dd, J = 1.5 Hz, 7.8 Hz), 7.16-7.22 (2 H, m) |
| 44 | —H | —H | —NHSO₂C₂H₅ | —H | —H | ¹H-NMR (CDCl₃) δ ppm 1.37 (3 H, t, J = 7.4 Hz), 2.15-2.30 (2 H, m), 3.07 (2 H, q, J = 7.4 Hz), 3.75 (2 H, t, J = 8.3 Hz), 4.10 (2 H, t, J = 5.8 Hz), 8.41 (1 H, brs), 6.88 (2 H, dt, J = 8.9, 3.4 Hz), 7.19 (2 H, dt, J = 8.9, 3.4 Hz), |
| 45 | —H | —H | —NH₂ | —H | —OCH₃ | ¹H-NMR (CDCl₃) δ ppm: 2.15-2.30 (2 H, m), 3.20-3.70 (2 H, br), 3.75-3.95 (2 H, m), 3.83 (3 H, s), 4.07 (2 H, t, J = 3 Hz), 6.24 (1 H, dd, J = 2.6, 8.4 Hz), 6.33 (1 H, d, J = 2.7 Hz), 6.77 (1 H, d, J = 8.4 Hz), |
| 46 | —H | —H | —NHCO₂CH₃ | —H | —OCH₃ | ¹H-NMR (CDCl₃) δ ppm: 2.20-2.30 (2 H, m), 3.77 (3 H, s), 3.86 (3 H, s), 4.13 (2 H, t, J = 6.0 Hz), 6.55 (1 H, brs), 6.73 (1 H, dd, J = 2.4, 8.6 Hz), 6.84 (1 H, d, J = 8.6 Hz), 7.20 (1 H, brs), |
| 47 | —H | —H | —CONHC₂H₅ | —H | —H | ¹H-NMR (CDCl₃) δ ppm: 1.23 (3 H, t, J = 7.3 Hz), 2.20-2.30 (2 H, m), 3.40-3.50 (2 H, m), 3.74 (2 H, t, J = 6.3 Hz), 4.14 (2 H, t, J = 5.8 Hz), 6.13 (1 H, brs), 6.85-6.95 (2 H, m), 7.70-7.75 (2 H, m), |
| 48 | —H | —H | —NHCON(CH₃)₂ | —H | —H | ¹H-NMR (CDCl₃) δ ppm: 2.15-2.25 (2 H, m), 3.02 (6 H, s), 3.74 (2 H, t, J = 6.4 Hz), 4.08 (2 H, t, J = 5.9 Hz), 6.20 (1 H, brs), 6.84 (2 H, dd, J = 2.0, 6.8 Hz), 7.26 (2 H, dd, J = 2.1, 8.8 Hz), |
| 49 | —H | —H | —CO₂C₂H₅ | —H | —Cl | ¹H-NMR (CDCl₃) δ ppm: 1.39 (3 H, t, J = 7.0 Hz), 2.27-2.37 (2 H, m), 3.81 (2 H, t, J = 6.8 Hz), 4.25 (2 H, t, J = 6.3 Hz), 4.36 (2 H, q, J = 7.0 Hz), 6.96 (1 H, d, J = 8.5 Hz), 7.93 (1 H, dd, J = 2.0 Hz, 8.5 Hz), 8.06 (1 H, d, J = 2.0 Hz) |

TABLE 3

Structure: R1, R2, R3, R4, R5 substituted benzene with —O—(CH₂)₃—Cl

| Reference Example | R1 | R2 | R3 | R4 | R5 | NMR |
|---|---|---|---|---|---|---|
| 50 | —H | —H | —CH₂CO₂C₂H₅ | —H | —Cl | ¹H-NMR (CDCl₃) δ ppm: 1.26 (3 H, t, J = 7.0 Hz), 2.23-2.33 (2 H, m), 3.52 (2 H, s), 3.80 (2 H, t, J = 6.3 Hz), 4.15 (2 H, q, J = 7.0 Hz), 6.90 (1 H, d, J = 8.3 Hz), 7.13 (1 H, dd, J = 2.0 Hz, 8.3 Hz), 7.30 (1 H, d, J = 2.0 Hz) |

TABLE 3-continued

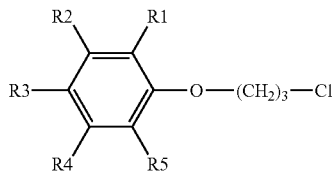

| Reference Example | R1 | R2 | R3 | R4 | R5 | NMR |
|---|---|---|---|---|---|---|
| 51 | —H | —H | —CH$_2$CONHCH$_3$ | —H | —H | $^1$H-NMR (CDCl$_3$) δ ppm: 2.19-2.29 (2 H, m), 2.76 (3 H, d, J = 4.8 Hz), 3.52 (2 H, s), 3.76 (2 H, t, J = 6.3 Hz), 4.12 (2 H, t, J = 5.8 Hz), 5.35 (1 H, br), 6.86-6.92 (2 H, m), 7.13-7.18 (2 H, m) |
| 52 | —H | —H | —CH$_2$CH$_2$NHCH$_3$ | —H | —H | $^1$H-NMR (CDCl$_3$) δ ppm: 2.18-2.27 (2 H, m), 2.43 (2 H, s), 2.72-2.83 (4 H, m), 3.71 (3 H, s), 3.75 (4 H, t, J = 5.3 Hz), 4.09 (2 H, t, J = 5.8 Hz), 6.83-6.86 (2 H, m), 7.10-7.14 (2 H, m) |
| 53 | —H | —H | —(CH$_2$)$_2$N(CH$_3$)CO$_2$C(CH$_3$)$_3$ | —H | —H | $^1$H-NMR (CDCl$_3$) δ ppm: 1.42 (9 H, s), 2.17-2.27 (2 H, m), 2.67-2.86 (5 H, m), 3.35-3.41 (2 H, m), 3.74 (2 H, t, J = 6.3 Hz), 4.09 (2 H, t, J = 5.8 Hz), 6.83 (2 H, d, J = 8.5 Hz), 7.00-7.16 (2 H, m) |
| 54 | —H | —H | —NH$_2$ | —H | —F | $^1$H-NMR (CDCl$_3$) δ ppm: 2.15-2.25 (2 H, m), 3.54 (2 H, brs), 3.76 (2 H, t, J = 6.4 Hz), 4.05-4.15 (2 H, m), 6.35-6.40 (1 H, m), 6.46 (1 H, dd, J = 0.9, 12.6 Hz), 6.82 (1 H, dd, J = 8.5, 8.5 Hz), |
| 55 | —H | —H | —NHCO$_2$CH$_3$ | —H | —F | $^1$H-NMR (CDCl$_3$) δ ppm: 2.20-2.30 (2 H, m), 3.77 (2 H, t, J = 6.5 Hz), 3.77 (3 H, s), 4.10-4.20 (2 H, m), 6.57 (1 H, brs), 6.85-7.00 (2 H, m), 7.25-7.30 (1 H, m), |
| 56 | —H | —H | —CH$_2$CO$_2$C$_2$H$_5$ | —H | —F | $^1$H-NMR (CDCl$_3$) δ ppm: 1.26 (3 H, t, J = 7.0 Hz), 2.21-2.30 (2 H, m), 3.5382 H, s), 3.77 (2 H, t, J = 6.3 Hz), 4.11-4.20 (4 H, m), 6.89-7.06 (3 H, m) |
| 57 | —H | —H | —CO$_2$C$_2$H$_5$ | —H | —Br | $^1$H-NMR (CDCl$_3$) δ ppm: 1.39 (3 H, t, J = 7.0 Hz), 2.27-2.37 (2 H, m), 3.82 (2 H, t, J = 6.3 Hz), 4.24 (2 H, t, J = 5.8 Hz), 4.35 (2 H, q, J = 7.0 Hz), 6.92 (1 H, d, J = 8.5 Hz), 7.98 (1 H, dd, J = 2.0 Hz, 8.5 Hz), 8.23 (1 H, d, J = 2.0 Hz) |
| 58 | —H | —H | —CHO | —OCH$_3$ | —H | $^1$H-NMR (CDCl$_3$) δ ppm: 2.23-2.34 (2 H, m), 3.76 (2 H, t, J = 6.3 Hz), 3.91 (3 H, s), 4.20 (2 H, t, J = 5.8 Hz), 6.46 (1 H, d, J = 2.0 Hz), 6.56 (1 H, dd, J = 2.0 Hz, 8.3 Hz), 7.81 (1 H, d, J = 8.3 Hz), 10.29 (1 H, s) |
| 59 | —H | —H | —CO$_2$C$_2$H$_5$ | —H | —NO$_2$ | $^1$H-NMR (CDCl$_3$) δ ppm: 1.41 (3 H, t, J = 7.0 Hz), 2.25-2.40 (2 H, m), 3.81 (2 H, t, J = 6.3 Hz), 4.32-4.44 (4 H, m), 7.15 (1 H, d, J = 8.8 Hz), 8.22 (1 H, dd, J = 2.0 Hz, 8.8 Hz), 8.52 (1 H, d, J = 2.0 Hz) |

TABLE 4

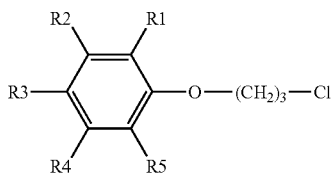

| Reference Example | R1 | R2 | R3 | R4 | R5 | NMR |
|---|---|---|---|---|---|---|
| 60 | —H | —H | —CONHC$_2$H$_5$ | —H | —NO$_2$ | $^1$H-NMR (CDCl$_3$) δ ppm 1.26 (3 H, t, J = 7.3 Hz), 2.25-2.35 (2 H, m), 3.45-3.55 (2 H, m), 3.80 (2 H, t, J = 6.1 Hz), 4.30-4.35 (2 H, m), 6.34 (1 H, brs), 7.15 (1 H, d, J = 8.8 Hz), 8.04 (1 H, dd, J = 2.3, 8.8 Hz), 8.25 (1 H, d, J = 2.3 Hz), |

TABLE 4-continued

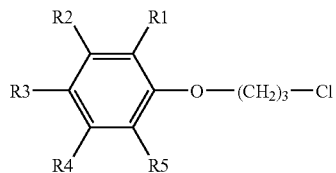

| Reference Example | R1 | R2 | R3 | R4 | R5 | NMR |
|---|---|---|---|---|---|---|
| 61 | —H | —H | —CONH$_2$ | —OCH$_3$ | —H | $^1$H-NMR (CDCl$_3$) δ ppm: 2.21-2.35 (2 H, m), 3.75 (2 H, t, J = 6.3 Hz), 3.95 (3 H, s), 4.18 (2 H, t, J = 5.8 Hz), 5.67 (1 H, br), 6.51 (1 H, d, J = 2.5 Hz), 6.61 (1 H, dd, J = 2.5 Hz, 8.8 Hz), 7.59 (1 H, br), 8.18 (1 H, d, J = 8.8 Hz) |
| 62 | —H | —H | —CONHCH$_3$ | —OCH$_3$ | —H | $^1$H-NMR (CDCl$_3$) δ ppm: 2.20-2.30 (2 H, m), 2.99 (3 H, d, J = 5.0 Hz), 3.75 (2 H, t, J = 6.3 Hz), 3.94 (3 H, s), 4.17 (2 H, t, J = 6.0 Hz), 6.49 (1 H, d, J = 2.5 Hz), 6.60 (1 H, dd, J = 2.5 Hz, 8.8 Hz), 7.70 (1 H, br), 8.19 (1 H, d, J = 8.8 Hz) |
| 63 | —H | —H | —CONHC$_2$H$_5$ | —OCH$_3$ | —H | $^1$H-NMR (CDCl$_3$) δ ppm: 1.23 (3 H, t, J = 7.3 Hz), 2.20-2.30 (2 H, m), 3.43-3.54 (2 H, m), 3.75 (2 H, t, J = 6.3 Hz), 3.94 (3 H, s), 4.17 (2 H, t, J = 6.3 Hz), 6.49 (1 H, d, J = 2.5 Hz), 6.60 (1 H, dd, J = 2.5 Hz, 8.8 Hz), 7.70 (1 H, br), 8.18 (1 H, d, J = 8.8 Hz) |
| 64 | —H | —H | —CONHCH$_2$CF$_3$ | —OCH$_3$ | —H | $^1$H-NMR (CDCl$_3$) δ ppm: 2.21-2.31 (2 H, m), 3.75 (2 H, t, J = 6.3 Hz), 3.98 (3 H, s), 4.07-4.21 (4 H, m), 6.51 (1 H, d, J = 2.5 Hz), 6.62 (1 H, dd, J = 2.5 Hz, 8.8 Hz), 8.09 (1 H, br), 8.18 (1 H, d, J = 8.8 Hz) |
| 65 | —H | —H | —CH=CHCO$_2$C$_2$H$_5$ | —H | —H | $^1$H-NMR (CDCl$_3$) δ ppm: 1.33 (3 H, t, J = 7.0 Hz), 2.20-2.30 (2 H, m), 3.75 (2 H, t, J = 6.3 Hz), 4.15 (2 H, t, J = 5.8 Hz), 4.25 (2 H, q, J = 7.0 Hz), 6.31 (1 H, d, J = 16.0 Hz), 6.88-6.93 (2 H, m), 7.44-7.50 (2 H, m), 7.64 (1 H, d, J = 16.0 Hz) |
| 66 | —F | —H | —H | —CO$_2$C$_2$H$_5$ | —H | $^1$H-NMR (CDCl$_3$) δ ppm: 1.40 (3 H, t, J = 7.0 Hz), 2.25-2.34 (2 H, m), 3.78 (2 H, t, J = 6.3 Hz), 4.25 (2 H, t, J = 5.8 Hz), 4.37 (2 H, q, J = 7.0 Hz), 7.08-7.15 (1 H, m), 7.62-7.70 (2 H, m) |
| 67 | —H | —H | —CO$_2$H | —CH$_3$ | —H | $^1$H-NMR (CDCl$_3$) δ ppm: 2.21-2.31 (2 H, m), 2.64 (3 H, s), 3.75 (2 H, t, J = 6.3 Hz), 4.18 (2 H, t, J = 5.8 Hz), 6.77-6.81 (2 H, m), 8.06 (1 H, d, J = 9.5 Hz), 11.00 (1 H, br) |
| 68 | —Cl | —H | —H | —CO$_2$C$_2$H$_5$ | —H | $^1$H-NMR (CDCl$_3$) δ ppm: 1.40 (3 H, t, J = 7.0 Hz), 2.25-2.37 (2 H, m), 3.82 (2 H, t, J = 6.3 Hz), 4.25 (2 H, t, J = 5.8 Hz), 4.38 (2 H, q, J = 7.0 Hz), 7.42 (1 H, d, J = 8.5 Hz), 7.58-7.62 (2 H, m) |
| 69 | —CH$_3$ | —H | —H | —CO$_2$C$_2$H$_5$ | —H | $^1$H-NMR (CDCl$_3$) δ ppm: 1.39 (3 H, t, J = 7.0 Hz), 2.24-2.34 (2 H, m), 2.26 (3 H, s), 3.78 (2 H, t, J = 6.3 Hz), 4.19 (2 H, t, J = 5.8 Hz), 4.37 (2 H, q, J = 7.0 Hz), 7.19 (1 H, d, J = 7.8 Hz), 7.49 (1 H, d, J = 1.5 Hz), 7.57 (1 H, dd, J = 1.5 Hz, 7.8 Hz) |

TABLE 5

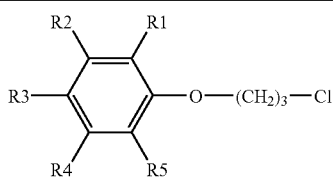

| Reference Example | R1 | R2 | R3 | R4 | R5 | NMR |
|---|---|---|---|---|---|---|
| 70 | —H | —H | —CONH$_2$ | —CH$_3$ | —H | $^1$H-NMR (CDCl$_3$) δ ppm: 2.19-2.29 (2 H, m), 2.51 (3 H, s), 3.75 (2 H, t, J = 6.3 Hz), 4.14 (2 H, t, J = 6.3 Hz), 6.53 (2 H, br), 6.71 (2 H, m), 7.45 (1 H, d, J = 8.3 Hz) |

TABLE 5-continued

[Structure: benzene ring with R1, R2, R3, R4, R5 substituents and O—(CH2)3—Cl group]

| Reference Example | R1 | R2 | R3 | R4 | R5 | NMR |
|---|---|---|---|---|---|---|
| 71 | —H | —H | —CONHCH$_3$ | —CH$_3$ | —H | $^1$H-NMR (CDCl$_3$) δ ppm: 2.18-2.28 (2 H, m), 2.45 (3 H, s), 2.98 (3 H, d, J = 4.9 Hz), 3.74 (2 H, t, J = 6.3 Hz), 4.12 (2 H, t, J = 5.8 Hz), 5.72 (1 H, br), 6.68-6.75 (2 H, m), 7.32 (1 H, d, J = 8.3 Hz) |
| 72 | —H | —H | —CONHC$_2$H$_5$ | —CH$_3$ | —H | $^1$H-NMR (CDCl$_3$) δ ppm: 1.24 (3 H, t, J = 7.3 Hz), 2.19-2.28 (2 H, m), 2.45 (3 H, s), 3.41-3.52 (2 H, m), 3.74 (2 H, t, J = 6.3 Hz), 4.12 (2 H, t, J = 6.0 Hz), 5.68 (1 H, br), 6.68-6.75 (2 H, m), 7.32 (1 H, d, J = 8.3 Hz) |
| 73 | —CH$_3$ | —H | —CO$_2$C$_2$H$_5$ | —H | —CH$_3$ | $^1$H-NMR (CDCl$_3$) δ ppm: 1.38 (3 H, t, J = 7.0 Hz), 2.21-2.28 (2 H, m), 2.31 (6 H, s), 3.84 (2 H, t, J = 6.3 Hz), 3.93 (2 H, t, J = 5.8 Hz), 4.35 (2 H, t, J = 7.0 Hz), 7.72 (2 H, s) |
| 74 | —H | —CO$_2$C$_2$H$_5$ | —H | —H | —OCH$_3$ | $^1$H-NMR (CDCl$_3$) δ ppm: 1.39 (3 H, t, J = 7.1 Hz), 2.26-2.36 (2 H, m), 3.78 (2 H, t, J = 6.3 Hz), 3.91 (3 H, s), 4.22 (2 H, t, J = 5.8 Hz), 4.36 (2 H, q, J = 7.1 Hz), 6.89 (1 H, d, J = 8.3 Hz), 7.58 (1 H, d, J = 2.0 Hz), 7.70 (1 H, d, J = 8.3 Hz) |
| 75 | —OCH$_3$ | —H | —CO$_2$C$_2$H$_5$ | —H | —OCH$_3$ | $^1$H-NMR (CDCl$_3$) δ ppm: 1.40 (3 H, t, J = 7.0 Hz), 2.13-2.23 (2 H, m), 3.85 (2 H, t, J = 6.3 Hz), 3.90 (6 H, s), 4.17 (2 H, t, J = 5.8 Hz), 4.38 (2 H, q, J = 7.0 Hz), 7.30 (2 H, s) |
| 76 | —CH$_3$ | —H | —CHO | —H | —OCH$_3$ | $^1$H-NMR (CDCl$_3$) δ ppm 2.17-2.29 (2 H, m), 2.34 (3 H, s), 3.83 (2 H, t, J = 6.3 Hz), 3.91 (3 H, s), 4.18 (2 H, t, J = 5.8 Hz), 7.31 (1 H, s), 9.85 (1 H, s) |
| 77 | —CH$_3$ | —H | —CO$_2$H | —H | —OCH$_3$ | $^1$H-NMR (CDCl$_3$) δ ppm: 2.18-2.28 (2 H, m), 2.32 (6 H, s), 3.83 (2 H, t, J = 6.3 Hz), 3.90 (3 H, s), 4.16 (2 H, t, J = 5.8 Hz), 7.50 (1 H, d, J = 2.0 Hz), 7.60 (1 H, d, J = 2.0 Hz) |
| 78 | —CH$_3$ | —H | —CONH$_2$ | —H | —OCH$_3$ | $^1$H-NMR (CDCl$_3$) δ ppm: 2.17-2.27 (2 H, m), 2.30 (3 H, s), 3.83 (2 H, t, J = 6.3 Hz), 3.89 (3 H, s), 4.12 (2 H, t, J = 5.8 Hz), 5.24-6.26 (2 H, br), 7.15 (1 H, d, J = 2.0 Hz), 7.32 (1 H, d, J = 2.0 Hz) |
| 79 | —CH$_3$ | —H | —CONHCH$_3$ | —H | —OCH$_3$ | $^1$H-NMR (CDCl$_3$) δ ppm: 2.17-2.26 (2 H, m), 2.29 (3 H, s), 3.00 (3 H, d, J = 5.0 Hz), 3.83 (2 H, t, J = 6.3 Hz), 3.88 (3 H, s), 4.10 (2 H, t, J = 5.8 Hz), 6.06 (1 H, br), 7.08 (1 H, d, J = 1.9 Hz), 7.28 (1 H, d, J = 1.9 Hz) |

TABLE 6

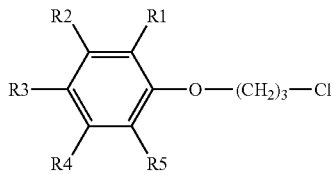

| Reference Example | R1 | R2 | R3 | R4 | R5 | NMR |
|---|---|---|---|---|---|---|
| 80 | —CH₃ | —H | —CONHC₂H₅ | —H | —OCH₃ | ¹H-NMR (CDCl₃) δ ppm: 1.25 (3 H, t, J = 7.3 Hz), 2.17-2.26 (2 H, m), 2.30 (3 H, s), 3.43-3.54 (2 H, m), 3.83 (2 H, t, J = 6.3 Hz), 3.89 (3 H, s), 4.10 (2 H, t, J = 5.8 Hz), 6.02 (1 H, br), 7.07 (1 H, d, J = 2.0 Hz), 7.28 (1 H, d, J = 2.0 Hz) |
| 81 | —CH₃ | —H | —NHCO₂C(CH₃)₃ | —H | —OCH₃ | ¹H-NMR (CDCl₃) δ ppm: 1.51 (9 H, s), 2.14-2.26 (2 H, m), 2.23 (3 H, s), 3.82 (2 H, t, J = 6.3 Hz), 3.83 (3 H, s), 3.99 (2 H, t, J = 5.8 Hz), 6.34 (1 H, br), 6.59 (1 H, d, J = 2.5 Hz), 7.01 (1 H, d, J = 2.5 Hz) |
| 82 | —CH₃ | —H | —NHCO₂CH₃ | —H | —OCH₃ | ¹H-NMR (COCl₃) δ ppm 2.17-2.29 (2 H, m), 2.30 (3 H, s), 3.83 (2 H, t, J = 6.3 Hz), 3.89 (6 H, s), 4.13 (2 H, t, J = 5.8 Hz), 7.44 (1 H, d, J = 2.0 Hz), 7.51 (1 H, d, J = 2.0 Hz) |
| 83 | —CH₃ | —H | —CO₂CH₃ | —H | —OCH₃ | ¹H-NMR (CDCl₃) δ ppm: 2.15-2.30 (2 H, m), 2.29 (3 H, s), 3.75-3.90 (2 H, m), 3.88 (3 H, s), 3.89 (3 H, s), 4.13 (2 H, t, J = 5.9 Hz), 7.43 (1 H, d, J = 1.8 Hz), 7.50 (1 H, d, J = 1.4 Hz), |
| 84 | —CH₃ | —H | —NH₂ | —H | —OCH₃ | ¹H-NMR (CDCl₃) δ ppm: 2.14-2.22 (2 H, m), 2.19 (3 H, s), 3.47 (2 H, br), 3.82 (2 H, t, J = 5.3 Hz), 3.95 (2 H, t, J = 4.8 Hz), 6.09-8.13 (2 H, m) |
| 85 | —CH₃ | —H | —NHCOCH₃ | —H | —OCH₃ | ¹H-NMR (CDCl₃) δ ppm: 2.11-2.28 (2 H, m), 2.15 (3 H, s), 2.24 (3 H, s), 3.82 (2 H, t, J = 6.3 Hz), 3.83 (3 H, s), 4.01 (2 H, t, J = 5.8 Hz), 6.66 (1 H, d, J = 2.1 Hz), 7.02 (1 H, br), 7.23 (1 H, d, J = 2.1 Hz) |
| 86 | —CH₃ | —H | —CHO | —H | —OCOCH₃ | ¹H-NMR (CDCl₃) δ ppm: 2.17-2.27 (2 H, m), 2.37 (6 H, s), 3.79 (2 H, t, J = 5.6 Hz), 4.11 (2 H, t, J = 5.8 Hz), 7.46 (1 H, d, J = 2.0 Hz), 7.62 (1 H, d, J = 2.0 Hz), 9.88 (1 H, s) |
| 87 | —CH₃ | —H | —CO₂H | —H | —OCOCH₃ | ¹H-NMR (CDCl₃) δ ppm: 2.16-2.26 (2 H, m), 2.35 (3 H, s), 2.36 (3 H, s), 3.79 (2 H, t, J = 6.3 Hz), 4.09 (2 H, t, J = 5.8 Hz), 7.67 (1 H, d, J = 2.0 Hz), 7.84 (1 H, d, J = 2.0 Hz) |
| 88 | —OH | —H | —CONHCH₃ | —H | —CH₃ | ¹H-NMR (CDCl₃) δ ppm: 2.21-2.35 (2 H, m), 2.32 (3 H, s), 2.99 (3 H, d, J = 4.9 Hz), 3.85 (2 H, t, J = 6.3 Hz), 4.05 (2 H, t, J = 5.8 Hz), 5.90 (1 H, br), 6.02 (1 H, br), 7.15 (1 H, d, J = 1.8 Hz), 7.20 (1 H, d, J = 2.0 Hz) |
| 89 | —CH₃ | —H | —CONHCH₃ | —H | —OC₂H₅ | ¹H-NMR (CDCl₃) δ ppm: 1.46 (3 H, t, J = 7.0 Hz), 2.17-2.27 (2 H, m), 2.28 (3 H, s), 2.99 (3 H, d, J = 5.0 Hz), 3.83 (2 H, t, J = 6.3 Hz), 4.06-4.15 (4 H, m), 6.04 (1 H, br), 7.07 (1 H, d, J = 1.8 Hz), 7.25 (1 H, d, J = 1.8 Hz) |
| 90 | —H | —H | —CO₂H | —OCH₃ | —H | ¹H-NMR (CDCl₃) δ ppm: 2.22-2.32 (2 H, m), 3.75 (2 H, t, J = 6.3 Hz), 4.05 (3 H, s), 4.21 (2 H, t, J = 5.8 Hz), 6.55 (1 H, d, J = 2.5 Hz), 6.66 (1 H, d, J = 8.8 Hz), 8.14 (1 H, d, J = 8.8 Hz), 10.43 (1 H, br) |

TABLE 7

Structure: Benzene ring with R1, R2, R3, R4, R5 substituents and O—(CH₂)₃—Cl group

| Reference Example | R1 | R2 | R3 | R4 | R5 | NMR |
|---|---|---|---|---|---|---|
| 91 | —H | —H | 1-methylimidazol-2-yl (N-methylimidazole) | —H | —H | $^1$H-NMR (CDCl$_3$) δ ppm: 2.2-2.3 (2 H, m), 3.77 (2 H, t, J = 6.3 Hz), 4.16 (2 H, t, J = 5.8 Hz), 7.00 (2 H, dd, J = 2.2, 6.7 Hz), 7.15-7.25 (2 H, m), 7.25-7.35 (2 H, m), 7.76 (1 H, s), |
| 92 | —H | —H | 1-methyl-1,2,4-triazol-3-yl | —H | —H | $^1$H-NMR (CDCl$_3$) δ ppm: 2.26 (2 H, t, J = 6.1 Hz), 3.75 (2 H, t, J = 6.3 Hz), 4.15 (2 H, t, J = 5.7 Hz), 7.00 (1 H, dd, J = 2.1, 6.9 Hz), 7.56 (1 H, dd, J = 2.2, 7.1 Hz), 8.07 (1 H, s), 8.45 (1 H, s). |
| 93 | —H | —H | 4-methyl-1-(p-tolylsulfonyl)piperidinyl | —H | —H | $^1$H-NMR (CDCl$_3$) δ ppm: 1.70-1.90 (4 H, m), 2.10-2.40 (3 H, m), 2.45 (3 H, s), 3.55-3.75 (2 H, m), 3.90-3.95 (2 H, m), 4.05-4.15 (2 H, m), 6.84 (2 H, dd, J = 1.9, 6.8 Hz), 7.06 (2 H, dd, J = 1.8, 6.9 Hz), 7.34 (2 H, d, J = 8.0 Hz), 7.68 (2 H, d, J = 8.2 Hz). |
| 94 | —CH$_3$ | —H | 3-methyl-2-oxo-oxazolidin-yl | —H | —OCH$_3$ | $^1$H-NMR (CDCl$_3$) δ ppm: 2.16-2.25 (2 H, m), 2.28 (3 H, s), 3.83 (2 H, t, J = 6.3 Hz), 3.86 (3 H, s), 3.99-4.06 (4 H, m), 4.46 (2 H, dd, J = 6.3 Hz, 8.8 Hz), 6.61 (1 H, d, J = 2.5 Hz), 7.33 (1 H, d, J = 2.5 Hz) |
| 95 | —OCH$_3$ | —H | 1-methyl-2-oxo-pyrrolidin-yl | —H | —CH$_2$OH | $^1$H-NMR (CDCl$_3$) δ ppm: 2.09-2.28 (2 H, m), 2.61 (2 H, t, J = 7.8 Hz), 3.79-3.87 (4 H, m), 3.88 (3 H, s), 4.13 (2 H, t, J = 5.5 Hz), 4.71 (2 H, d, J = 5.8 Hz), 6.85 (1 H, d, J = 2.5 Hz), 7.59 (1 H, d, J = 2.5 Hz) |
| 96 | —CH$_3$ | —H | 1-methyl-2-oxo-pyrrolidin-yl | —H | —OCH$_3$ | $^1$H-NMR (CDCl$_3$) δ ppm: 2.05-2.25 (4 H, m), 2.27 (3 H, s), 2.60 (2 H, t, J = 8.3 Hz), 3.79-3.89 (42 H, m), 3.86 (3 H, s), 8.71 (1 H, d, J = 2.5 Hz), 7.37 (1 H, d, J = 2.5 Hz) |

TABLE 8

Structure: Benzene ring with R1, R2, R3, R4, R5 substituents and O—(CH₂)₄—Cl group

| Reference Example | R1 | R2 | R3 | R4 | R5 | NMR |
|---|---|---|---|---|---|---|
| 97 | —H | —H | —H | —NO$_2$ | —H | $^1$H-NMR (CDCl$_3$) δ ppm: 1.93-2.11 (4 H, m), 3.59-3.70 (2 H, m), 4.00-4.13 (2 H, m), 7.20-7.24 (1 H, m), 7.43 (1 H, t, J = 8.0 Hz), 7.72 (1 H, t, J-2.3 Hz), 7.80-7.84 (1 H, m) |
| 98 | —H | —H | —H | —CN | —H | $^1$H-NMR (CDCl$_3$) δ ppm 1.96-2.00 (4 H, m), 3.60-3.65 (2 H, m), 3.99-4.14 (2 H, m), 7.10-7.14 (2 H, m), 7.22-7.26 (1 H, m), 7.34-7.40 (1 H, m) |

TABLE 9

R1—O—(CH2)3—Cl

| Reference Example | R1 | NMR |
|---|---|---|
| 99 | methyl 4-methylthiophene-2-carboxylate group | ¹H-NMR (CDCl₃) δ ppm: 2.15-2.30 (2H, m), 3.72 (2H, t, J = 6.3 Hz), 3.87 (3H, s), 4.05-4.15 (2H, m), 8.55 (1H, d, J = 1.8 Hz), 7.42 (1H, d, J = 1.8 Hz). |
| 100 | methyl 3-methylisoxazole-5-carboxylate group | ¹H-NMR (CDCl₃) δ ppm: 2.21-2.31 (2H, m), 3.70 (2H, t, J = 6.3 Hz), 3.95 (3H, s), 4.46 (2H, t, J = 6.0 Hz), 6.54 (1H, s) |
| 101 | methyl 1,5-dimethylpyrazole-3-carboxylate group | ¹H-NMR (CDCl₃) δ ppm: 2.21-2.32 (2H, m), 3.72 (2H, t., J = 6.3 Hz), 3.72 (2H, s), 3.91 (3H, s), 4.24 (2H, t, J = 5.8 Hz), 6.10 (1H, s) |
| 102 | ethyl 1-ethyl-5-methylpyrazole-3-carboxylate group | ¹H-NMR (CDCl₃) δ ppm: 1.39 (3H, t, J = 7.0 Hz), 1.39 (3H, t, J = 7.3 Hz), 2.22-2.32 (2H, m), 3.71 (2H, t,, J = 6.3 Hz), 4.10 (2H, q, J = 7.3 Hz), 4.24 (2H, t, J = 5.8 Hz), 4.39 (2H, q, J = 7.0 Hz), 6.08 (1H, s) |
| 103 | 2-methylpyridine N-oxide-5-yl group | ¹H-NMR (CDCl₃) δ ppm: 2.20-2.29 (2H, m), 2.46 (3H, s), 3.72 (2H, t, J = 6.3 Hz), 4.12 (2H, t, J = 5.8 Hz), 6.84 (1H, dd, J = 2.5 Hz, 6.6 Hz), 7.13 (1H, d, J = 8.8 Hz), 8.07 (1H, d, J = 2.5 Hz) |
| 104 | 6-(acetoxymethyl)pyridin-3-yl group | ¹H-NMR (CDCl₃) δ ppm: 2.13 (3H, s), 2.21-2.31 (2H, m), 3.76 (2H, t, J = 6.3 Hz), 4.18 (2H, t, J = 5.8 Hz), 5.17 (2H, s), 7.19-7.32 (2H, m), 8.30 (1H, d, J = 2.5 Hz) |
| 105 | 6-formylpyridin-3-yl group | ¹H-NMR (CDCl₃) δ ppm: 2.27-2.36 (2H, m), 3.77 (2H, t, J = 6.0 Hz), 4.28 (2H, t, J = 6.8 Hz), 7.33 (1H, dd, J = 2.5 Hz, 6.5 Hz), 7.97 (1H, dd, J = 2.5 Hz, 8.5 Hz), 8.44 (1H, d, J = 2.5 Hz), 10.00 (1H, s) |
| 106 | 6-(N-ethylcarbamoyl)pyridin-3-yl group | ¹H-NMR (CDCl₃) δ ppm: 1.26 (3H, t, J = 7.3 Hz), 2.24-2.34 (2H, m), 3.55 (2H, dq, J = 6.0 Hz, 7.3 Hz), 3.77 (2H, t, J = 6.3 Hz), 4.22 (2H, t, J = 5.8 Hz), 7.29 (1H, dd, J = 2.3 Hz, 8.8 Hz), 7.83 (1H, br), 6.18 (1H, d, J = 8.8 Hz), 8.20 (1H, d, J = 2.3 Hz) |
| 107 | 6-carbamoylpyridin-3-yl group | ¹H-NMR (CDCl₃) δ ppm: 2.25-2.34 (2H, m), 3.77 (2H, t,, J = 6.3 Hz), 4.23 (2H, t, J = 5.8 Hz), 5.48 (1H, br), 7.31 (1H, dd, J = 2.3 Hz, 8.8 Hz), 7.68 (1H, br), 8.16 (1H, d, J = 8.8 Hz), 8.23 (1H, d, J = 2.3 Hz) |

TABLE 9-continued

R1—O—(CH2)3—Cl

| Reference Example | R1 | NMR |
|---|---|---|
| 108 | [pyrazine with CH3 ester and methyl substituent] | ¹H-NMR (CDCl₃) δ ppm: 2.24-2.34 (2H, m), 3.73 (2H, t,, J = 6.3 Hz), 4.00 (3H, s), 4.58 (2H, t, J = 6.0 Hz), 8.28 (1H, d, J = 1.3 Hz), 8.87 (1H, d, J = 1.3 Hz) |

TABLE 10

R1—O—(CH2)3—Cl

| Reference Example | R1 | NMR |
|---|---|---|
| 109 | [pyrimidine with ethyl ester] | ¹H-NMR (CDCl₃) δ ppm: 1.44 (3H, t, J = 7.0 Hz), 2.22-2.31 (2H, m), 3.72 (2H, t, J = 6.3 Hz), 4.48 (2H, q, J = 7.0 Hz), 4.59 (2H, t, J = 6.0 Hz), 7.44 (1H, d, J = 1.0 Hz), 8.90 (1H, d, J = 1.0 Hz) |
| 110 | [indanone] | ¹H-NMR (CDCl₃) δ ppm: 2.20-2.30 (2H, m), 2.70-2.75 (2H, m), 3.07 (2H, t, J = 5.8 Hz), 3.74 (2H, t, J = 6.4 Hz), 7.15-7.20 (2H, m), 7.37 (1H, d, J = 8.2 Hz). |
| 111 | [oxindole] | ¹H-NMR (DMSO-d₆) δ ppm: 2.1-2.2 (2H, m), 3.37 (2H, s), 3.78 (2H, t, J = 6.5 Hz), 4.04 (2H, t, J = 6 Hz), 6.40 (1H, d, J = 2.5 Hz), 6.49 (1H, dd, J = 2.5, 8 Hz), 7.08 (1H, d, J = 8 Hz), 10.33 (1H, bs). |
| 112 | [isoindolinone] | ¹H-NMR (CDCl₃) δ ppm: 2.27 (2H, t, J = 6.1 Hz), 3.76 (2H, t, J = 6.3 Hz), 4.19 (2H, t, J = 5.7 Hz), 4.41 (2H, s), 6.96 (1H, s), 7.01 (1H, dd, J = 2.2, 6.5 Hz), 7.17 (1H, brs), 7.77 (1H, d, J = 8.4 Hz). |
| 113 | [isoindolinone isomer] | ¹H-NMR (CDCl₃) δ ppm: 2.27 (2H, t, J = 6.1 Hz), 3.76 (2H, t, J = 6.3 Hz), 4.19 (2H, t, J = 5.7 Hz), 4.40 (2H, s), 6.50-6.60 (1H, br), 7.15 (1H, dd, J = 2.3, 8.5 Hz), 7.35-7.40 (2H, m). |
| 114 | [N-methyl benzimidazolone] | ¹H-NMR (CDCl₃) δ ppm: 2.20-2.35 (2H, m), 3.39 (3H, s), 3.75-3.80 (2H, m), 4.05-4.15 (2H, m), 6.55-6.65 (2H, m), 6.98 (1H, d, J = 7.5 Hz), 9.92 (1H, brs). |
| 115 | [N-methyl benzimidazole] | ¹H-NMR (CDCl₃) δ ppm: 2.28 (2H, t, J = 6.0 Hz), 3.75-3.80 (5H, m), 4.18 (2H, t, J = 5.7 Hz), 6.85 (1H, d, J = 2.1 Hz), 6.90-6.95 (1H, m), 7.66 (1H, d, J = 8.8 Hz), 7.76 (1H, s). |
| 116 | [N-methyl benzimidazole isomer] | ¹H-NMR (CDCl₃) δ ppm: 2.20-2.30 (2H, m), 3.78 (2H, t, J = 6.9 Hz), 3.82 (3H, s), 4.16 (2H, t, J = 5.8 Hz), 6.97 (1H, dd, J = 2.3, 8.8 Hz), 7.25-7.30 (2H, m), 7.81 (1H, s). |

TABLE 10-continued

R1—O—(CH2)3—Cl

| Reference Example | R1 | NMR |
|---|---|---|
| 117 | [8-methyl-2H-benzo[b][1,4]oxazin-3(4H)-one] | $^1$H-NMR (CDCl$_3$) δ ppm: 2.20-2.35 (2H, m), 3.77 (2H, t, J = 6.2 Hz), 4.19 (2H, t, J = 6.0 Hz), 4.66 (2H, s), 6.47 (1H, dd, J = 7.9, 1.2 Hz), 6.67 (1H, dd, J = 8.3, 1.1 Hz), 6.90 (1H, dd, J = 8.2, 8.1 Hz), 8.29 (1H, brs). |
| 118 | [6-methylquinazolin-4(3H)-one] | $^1$H-NMR (CDCl$_3$) δ ppm: 2.24 (2H, tt, J = 6.2 Hz), 3.70 (2H, t, J = 6.4 Hz), 3.77 (3H, s), 4.45 (2H, t, J = 6.1 Hz), 6.70 (1H, d, J = 8.9 Hz), 6.98 (1H, dd, J = 8.9, 3.0 Hz), 7.35 (1H, d, J = 3.0 Hz) |

TABLE 11

R1—O—(CH2)3—Cl

| Reference Example | R1 | NMR |
|---|---|---|
| 119 | [3-methyl-6-methylquinazolin-4(3H)-one] | $^1$H-NMR (CDCl$_3$) δ ppm: 2.30 (2H, tt, J = 6.1, 6.1 Hz), 3.60 (3H, s), 3.77 (2H, t, J = 6.3 Hz), 4.25 (2H, t, J = 5.8 Hz), 7.34 (1H, dd, J = 8.9, 2.9 Hz), 7.65 (1H, d, J = 8.9 Hz), 7.68 (1H, d, J = 2.9 Hz), 7.96 (1H, s) |
| 120 | [7-methyl-3,4-dihydronaphthalen-1(2H)-one] | $^1$H-NMR (CDCl$_3$) δ ppm: 2.12 (2H, tt, J = 6.3, 6.3 Hz), 2.24 (2H, tt, J = 6.1, 6.1 Hz), 2.62 (2H, t, J = 6.5 Hz), 2.902 (2H, t, J = 6.1 Hz), 3.74 (2H, t, J = 6.3 Hz), 4.15 (2H, t, J = 5.8 Hz), 7.05 (1H, dd, J = 8.4, 2.8 Hz), 7.17 (1H, d, J = 8.4 Hz), 7.52 (1H, d, J = 2.8 Hz). |
| 121 | [1,6-dimethyl-1H-indol-5-yl] | $^1$H-NMR (CDCl$_3$) δ ppm: 2.25 (2H, tt, J = 6.1, 6.1 Hz), 3.76 (3H, s), 3.78 (2H, t, J = 6.4 Hz), 4.15 (2H, t, J = 5.8 Hz), 6.39 (1H, t, J = 3.0 Hz), 6.88 (1H, dd, J = 8.8, 2.4 Hz), 7.02 (1H, d, J = 3.0 Hz), 7.10 (1H, d, J = 2.3 Hz), 7.21 (1H, d, J = 8.8 Hz) |

TABLE 12

R1—O—(CH2)4—Cl

| Reference Example | R1 | NMR |
|---|---|---|
| 122 | [pyridin-2-yl] | $^1$H-NMR (CDCl$_3$) δ ppm: 1.85-2.05 (4H, m), 3.62 (2H, t, J = 6.3 Hz), 4.33 (2H, t, J = 6.3 Hz), 6.72 (1H, d, J = 8.3 Hz), 6.85 (1H, dt, J = 0.8, 5.1 Hz), 7.56 (1H, dt, J = 2.0, 8.4 Hz), 8.14 (1H, dd, J = 5.1, 1.4 Hz). |
| 123 | [pyridin-4-yl] | $^1$H-NMR (CDCl$_3$) δ ppm: 1.95-2.05 (4H, m), 3.62 (2H, t, J = 6.2 Hz), 4.05 (2H, t, J = 5.8 Hz), 6.80 (2H, dd, J = 4.8, 1.6 Hz), 8.43 (2H, dd, J = 4.9, 1.5 Hz). |
| 124 | [6-methylindolin-2-one] | $^1$H-NMR (DMSO-d$_6$) δ ppm: 1.75-1.9 (4H, m), 3.36 (2H, s), 3.70 (2H, t, J = 6.5 Hz), 3.96 (2H, t, J = 6 Hz), 6.38 (1H, d, J = 2 Hz), 6.48 (1H, dd, J = 2.5, 8 Hz), 7.07 (1H, d, J = 8 Hz), 10.32 (1H, bs). |

TABLE 12-continued

R1—O—(CH2)4—Cl

| Reference Example | R1 | NMR |
|---|---|---|
| 125 | [structure: 7-methyl-2H-benzo[e][1,3]oxazin-2-one] | $^1$H-NMR (CDCl$_3$) δ ppm: 1.91-2.00 (4H, m), 3.62 (2H, t, J = 6.2 Hz), 3.98 (2H, t, J = 5.6 Hz), 5.26 (2H, s), 6.36 (1H, d, J = 2.3 Hz), 6.57 (1H, dd, J = 8.4, 2.3 Hz), 7.00 (1H, d, J = 8.4 Hz), 8.08 (1H, br-s). |
| 126 | [structure: 8-methyl-2H-benzo[b][1,4]oxazin-3(4H)-one] | $^1$H-NMR (CDCl$_3$) δ ppm: 1.95-2.04 (4H, m), 3.61-3.65 (2H, m), 4.06-4.09 (2H, m), 4.66 (2H, s), 6.46 (1H, d, J = 8.0 Hz), 6.63 (1H, d, J = 8.3 Hz), 6.89 (1H, dd, J = 8.0, 8.3 Hz), 8.41 (1H, br). |
| 127 | [structure: 8-methyl-2H-benzo[b][1,4]oxazin-3(4H)-one isomer] | $^1$H-NMR (CDCl$_3$) δ ppm: 1.80-2.00 (4H, m), 3.77 (2H, t, J = 6.4 Hz), 4.24 (2H, t, J = 5.8 Hz), 4.63 (2H, s), 6.55-6.70 (2H, m), 6.90 (1H, dd, J = 8.4, 8.4 Hz), 8.00 (1H, brs). |
| 128 | [structure: 2,2-dimethyl-6-substituted-2H-benzo[b][1,4]oxazin-3(4H)-one] | $^1$H-NMR (CDCl$_3$) δ ppm: 1.52 (6H, s), 1.90-2.10 (4H, m), 3.63 (2H, t, J = 6.3 Hz), 3.95 (2H, t, J = 5.8 Hz), 6.38 (1H, d, J = 2.8 Hz), 6.50 (1H, dd, J = 2.8, 8.7 Hz), 6.86 (1H, d, J = 8.8 Hz), 8.57 (1H, brs). |
| 129 | [structure: 2-methyl-2H-benzo[b][1,4]oxazin-3(4H)-one] | $^1$H-HMR (CDCl$_3$) δ ppm: 1.56 (3H, d, J = 6.8 Hz), 1.85-2.10 (4H, m), 3.61 (2H, t, J = 6.2 Hz), 3.94 (2H, t, J = 5.8 Hz), 4.59 (1H, q, J = 6.8 Hz), 6.38 (1H, d, J = 2.8 Hz), 6.49 (1H, dd, J = 2.8, 8.7 Hz), 5.88 (1H, d, J = 8.7 Hz), 8.60 (1H, brs). |
| 130 | [structure: 3,4-dihydroquinazolin-2(1H)-one derivative] | $^1$H-NMR (DMSO-d$_6$) δ ppm: 1.81-2.10 (4H, m), 3.54-3.70 (2H, m), 3.89-4.03 (2H, m), 4.47 (2H, brs), 5.02 (1H, brs), 6.22 (1H, d, J = 2.4 Hz), 6.49 (1H, dd, J = 8.3, 2.4 Hz), 6.86-7.00 (2H, m). |

Example 1

Synthesis of methyl 5-[3-(4-benzo[b]thiophen-4-yl-piperazin-1-yl)propoxy]-1-methyl-1H-pyrazole-3-carboxylate Methyl 5-(3-chloropropoxy)-1-methyl-1H-pyrazole-3-carboxylate (1.17 g, 5.0 mmol), 1-benzo[b]thiophen-4-yl piperazine hydrochloride (1.35 g, 5.3 mmol), potassium carbonate (1.74, 12.6 mmol) and sodium iodide (0.75 g, 5.0 mmol) were added to DMF (12 ml), and the mixture was stirred at 80° C. for 3 hours. The reaction solution was cooled to room temperature and water was added thereto, and then, extracted with ethyl acetate. The organic phase was washed with water and dried over magnesium sulfate. The reaction solution was concentrated under reduced pressure and the residue was purified by silica gel column chromatography (n-hexane:ethyl acetate=7:3→dichloromethane:methanol=100:3). The purified product was concentrated under reduced pressure to obtain a light yellow oily substance (1.97 g). The oily substance was allowed to stand still at room temperature to obtain a solid substance, which was washed with diisopropyl ether and dried to obtain methyl 5-[3-(4-benzo[b]thiophen-4-yl-piperazin-1-yl)propoxy]-1-methyl-1H-pyrazole-3-carboxylate (1.49 g).

Melting point: 109.0-110.5° C.

MS 414 (M$^+$)

Example 2

Synthesis of 5-[3-(4-benzo[b]thiophen-4-yl-piperazin-1-yl)propoxy]-1-methyl-1H-pyrazole-3-carboxylic acid A 6N aqueous sodium hydroxide solution (2 ml) was added to an ethanol solution (10 ml) of methyl 5-[3-(4-benzo[b]thiophen-4-yl-piperazin-1-yl)propoxy]-1-methyl-1H-pyrazole-3-carboxylate (1.62 g, 3.9 mmol) and the mixture was stirred at room temperature for 4 days. Then, 6N hydrochloric acid (2 ml) was added to the reaction solution under ice cooling and the solution mixture was stirred. Dichloromethane was added to the reaction solution and the precipitate was obtained by filtration. The filtrate was separated and the organic phase was concentrated under reduced pressure. The filter cake and the residue were combined, washed with water and dried to obtain 5-[3-(4-benzo[b]thiophen-4-yl-piperazin-1-yl)propoxy]-1-methyl-1H-pyrazole-3-carboxylic acid (1.53 g) as white powder.

Melting point: 114.5-118.0° C.

Example 3

Synthesis of N-methyl-5-[3-(4-benzo[b]thiophen-4-yl-piperazin-1-yl)]propoxy]-1-methyl-1H-pyrazole-3-carboxamide hydrochloride A DMF solution of 5-[3-(4-benzo[b]thiophen-4-yl-piperazin-1-yl)propoxy]-1-methyl-1H-pyrazole-3-carboxylic acid (0.3 g, 0.75 mmol) was cooled on ice and triethylamine (0.73 ml, 5.2 mmol), methylamine hydrochloride (0.3 g, 4.5 mmol) and diethylphosphorocyanidate (DEPC)(0.25 ml, 1.4 mmol) were added thereto, and then, the mixture was stirred at room temperature for 24 hours. To the reaction solution, triethylamine (0.73 ml, 5.2 mmol), methylamine hydrochloride (0.3 g, 4.5 mmol) and DEPC (0.25 ml, 1.4 mmol) were added and the mixture was stirred at room temperature for 4 days. Water was added to the reaction solution, which was then extracted with ethyl acetate. The extracted material was washed with water and dried over magnesium sulfate. The solution was concentrated under reduced pressure and the residue was purified by basic silica gel column chromatography (n-hexane:ethyl acetate=5:1→ethyl acetate). The purified product was concentrated under reduced pressure and the residue was dissolved in ethyl acetate and a solution of 4N-hydrochloric acid/ethyl acetate was added thereto. The insoluble matter precipitated was obtained by filtration and dried to obtain N-methyl-5-[3-(4-benzo[b]thiophen-4-yl-piperazin-1-yl)propoxy]-1-methyl-1H-pyrazole-3-carboxamide hydrochloride (0.24 g) as white powder.
Melting point: 228.0-232.5° C. (dec)

Example 4

Synthesis of 5-[3-(4-benzo[b]thiophen-4-yl-piperazin-1-yl)propoxy]-1-methyl-1H-pyrazole-3-carboxamide The titled compound was obtained using 5-[3-(4-benzo[b]thiophen-4-yl-piperazin-1-yl)propoxy]-1-methyl-1H-pyrazole-3-carboxylic acid and ammonium chloride in the same manner as in Example 3.
White Powder (ethyl acetate-diisopropyl ether)
Melting point: 186.5-188.5° C.

Example 5

Synthesis of 4-[3-4-benzo[b]thiophen-4-yl-piperazin-1-yl)propoxy]-3-methoxy-5,N-dimethylbenzamide The titled compound was obtained using 4-(3-chloropropoxy)-3-methoxy-5,N-dimethylbenzamide and 1-benzo[b]thiophen-4-yl-piperazine hydrochloride in the same manner as in Example 1.
White Powder (ethyl acetate-methanol)
Melting point: 141.5-142.5° C.

Example 6

Synthesis of N-methyl-2-[3-(4-benzo[b]thiophen-4-yl-piperazin-1-yl)propoxy]thiazole-4-carboxamide hydrochloride Sodium hydride (55%, oily, 90 mg, 2.2 mmol) was added to a DMF solution (2 ml) of 3-(4-benzo[b]thiophen-4-yl-piperazin-1-yl)propanol (0.2 g, 0.7 mmol) and N-methyl-2-chlorothiazole-4-carboxamide (0.26 g, 1.45 mmol) under ice cooling and the solution was stirred at 80° C. for 1.5 hours. After the reaction solution was cooled to room temperature and water was added thereto, it was extracted with ethyl acetate. The extraction solution with ethyl acetate was washed with water, dried over magnesium sulfate and concentrated under reduced pressure. The obtained residue was purified by silica gel column chromatography (dichloromethane:ethyl acetate=5:1→ethyl acetate). After the purified product was concentrated under reduced pressure, the residue was dissolved in ethyl acetate. A solution of 4N-hydrochloric acid/ethyl acetate was added to the solution and the insoluble matter precipitated was obtained by filtration and dried to obtain N-methyl-2-[3-(4-benzo[b]thiophen-4-yl-piperazin-1-yl)propoxy]thiazole-4-carboxamide hydrochloride (0.24 g) as light yellow powder.
Melting point: 199.5-202.5° C.

Example 7

Synthesis of 2-[3-(4-benzo[b]thiophen-4-yl-piperazin-1-yl)propoxy]thiazole-4-carboxamide The titled compound was obtained using 3-(4-benzo[b]thiophen-4-yl-piperazin-1-yl)propanol (0.2 g, 0.7 mmol) and 2-chlorothiazole-4-carboxamide in the same manner as in Example 6.
White Powder (ethyl acetate-diisopropyl ether)
Melting point: 139.5-140.5° C.

Example 8

Synthesis of {4-[3-(4-benzo[b]thiophen-4-yl-piperazin-1-yl)propoxy]-3-methoxy-5-methylphenyl}-carbamic acid tert-butyl ester The titled compound was obtained using [4-(3-chloropropoxy)-3-methoxy-5-methylphenyl]-carbamic acid tert-butyl ester and 1-benzo[b]thiophen-4-yl-piperazine hydrochloride in the same manner as in Example 1.
Light Brown Oily Substance
$^1$H-NMR (CDCl$_3$) δppm: 1.51 (9H, s), 1.95-2.10 (2H, m), 2.24 (3H, s), 2.66-2.81 (6H, m), 3.14-3.31 (2H, m), 3.84 (3H, s), 3.95 (2H, t, J=6.3 Hz), 6.36 (1H, br), 6.60 (1H, d, J=2.5 Hz), 6.87-6.92 (1H, m), 7.01 (1H, d, J=2.0 Hz), 7.24-7.31 (1H, m), 7.37-7.44 (2H, m), 7.55 (1H, d, J=8.0 Hz)
MS 511 (M$^+$).

Example 9

Synthesis of 4-[3-(4-benzo[b]thiophen-4-yl-piperazin-1-yl)-propoxy]-3-methoxy-5-methylaniline 6N-hydrochloric acid (3 ml) was added to a methanol solution (10 ml) of {4-[3-(4-benzo[b]thiophen-4-yl-piperazin-1-yl)propoxy]-3-methoxy-5-methylphenyl}-carbamic acid tert-butyl ester (2.18 g, 4.3 mmol) and the mixture was stirred at room temperature overnight. After stirred at 60° C. for 15 minutes, the mixture was cooled to room temperature and a 6N aqueous sodium hydroxide solution was added thereto to neutralize it. Dichloromethane was added to the reaction mixture, and the substance extracted with dichloromethane was dried over magnesium sulfate and concentrated under reduced pressure. The obtained residue was purified by silica gel column chromatography (n-hexane:ethyl acetate=3:2→ethyl acetate). The purified product was concentrated to dryness under reduced pressure to obtain 4-[3-

(4-benzo[b]thiophen-4-yl-piperazin-1-yl)propoxy]-3-methoxy-5-methylaniline (1.26 g) as light yellow solid
Melting point: 155.0-158.0° C.
MS 411 (M⁺)

Example 10

Synthesis of N-{4-[3-(4-benzo[b]thiophen-4-yl-piperazin-1-yl)propoxy]-3-methoxy-5-methylphenyl}formamide hydrochloride 4-[3-(4-benzo[b]thiophen-4-yl-piperazin-1-yl)propoxy]-3-methoxy-5-methylaniline (0.9 g, 2.2 mmol) was added to ethyl formate (10 ml) and refluxed with heating for 33 hours. After the reaction solution was cooled to room temperature, it was concentrated under reduced pressure. The obtained residue was purified by basic silica gel column chromatography (n-hexane:ethyl acetate=5:1→ethyl acetate). The purified product was concentrated under reduced pressure and a solution of 4N-hydrochloric acid/ethyl acetate was added to an ethyl acetate solution of the residue. The insoluble matter precipitated was obtained by filtration to obtain N-{4-[3-(4-benzo[b]thiophen-4-yl-piperazin-1-yl)propoxy]-3-methoxy-5-methylphenyl}formamide hydrochloride (0.3 g) as white powder.
Melting point: 247.5-253.0° C. (dec)

Example 11

Synthesis of N-methyl-4-[3-(4-benzo[b]thiophen-4-yl-piperazin-1-yl)propoxy]-3-methoxy-5-methylaniline hydrochloride A 6N aqueous sodium hydrochloride solution was added to N-(4-[3-(4-benzo[b]thiophen-4-yl-piperazin-1-yl)propoxy]-3-methoxy-5-methylphenyl formamide hydrochloride (0.23 g, 0.48 mmol) and the solution mixture was extracted with dichloromethane. The extraction solution with dichloromethane was dried over magnesium sulfate and concentrated under reduced pressure. The obtained residue was dissolved in a tetrahydrofuran (THF) solution (5 ml) and lithium aluminum hydride (30 mg, 0.71 mmol) was added thereto under ice cooling and refluxed with heating for 15 minutes. The reaction solution was cooled on ice, and water (0.03 ml), 15% aqueous sodium hydroxide solution (0.03 ml), and water (0.09 ml) were added to the reaction mixture in this order and stirred. Insoluble matter was removed by filtration, and the filtrate was concentrated under reduced pressure. The obtained residue was purified by basic silica gel column chromatography (n-hexane:ethyl acetate=5:1→3:1) and concentrated under reduced pressure. A solution of 4N-hydrochloric acid/ethyl acetate was added to an ethyl acetate solution of the residue, and the insoluble matter precipitated was obtained by filtration to obtain N-methyl-4-[3-(4-benzo[b]thiophen-4-yl-piperazin-1-yl)propoxy]-3-methoxy-5-methylaniline hydrochloride (63 mg) as white powder.
Melting point: 239.5-244.0° C. (dec)

Example 12

Synthesis of 3-{4-[3-(4-benzo[b]thiophen-4-yl-piperazin-1-yl)propoxy]-3-methoxy-5-methylphenyl}oxazolidin-2-one hydrochloride The titled compound was obtained using 3-[4-(3-chloropropoxy)-3-methoxy-5-methylphenyl]oxazolidin-2-one and 1-benzo[b]thiophen-4-yl-piperazine hydrochloride in the same manner as in Example 1.
White Powder (ethanol)
Melting point: 247.5-251.0° C. (dec)

Example 13

Synthesis of N-{4-[3-(4-benzo[b]thiophen-4-yl-piperazin-1-yl)propoxy]-3-methoxy-5-methylphenyl}acetamide The titled compound was obtained using N-[4-(3-chloropropoxy)-3-methoxy-5-methylphenyl]acetamide and 1-benzo[b]thiophen-4-yl-piperazine hydrochloride in the same manner as in Example 1.
White Powder (ethyl acetate-diisopropyl ether)
Melting point: 121.5-122.0° C.

Example 14

Synthesis of N-{4-[3-(4-benzo[b]thiophen-4-yl-piperazin-1-yl)propoxy]-3-methoxy-5-methylphenyl}-N-methylacetamide hydrochloride Sodium hydride (55%, oily, 0.06 g, 1.3 mmol) was added to a DMF solution (5 ml) of N-{4-[3-(4-benzo[b]thiophen-4-yl-piperazin-1-yl)propoxy]-3-methoxy-5-methylphenyl}acetamide (0.45 g, 0.99 mmol) under ice cooling and the mixture was stirred at 0° C. for 15 minutes. Methyl iodide (0.07 ml, 1.1 mmol) was added to the reaction solution and the solution was stirred at 0° C. for one hour. Further, sodium hydride (55% oily, 0.06 g, 1.3 mmol) and methyl iodide (0.07 ml, 1.1 mmol) were added to the reaction solution and the solution mixture was stirred at 0° C. for 2 hours. Water was added to the reaction solution and extraction was performed with ethyl acetate. The extracted material was washed with water, and dried over magnesium sulfate. The reaction solution was concentrated under reduced pressure and the residue was purified by basic silica gel column chromatography (n-hexane:ethyl acetate=5:1→ethyl acetate). After the purified product was concentrated under reduced pressure, a solution of 4N-hydrochloric acid/ethyl acetate was added to an ethyl acetate solution of the residue. The insoluble matter precipitated was obtained by filtration to obtain N-{4-[3-(4-benzo[b]thiophen-4-yl-piperazin-1-yl)propoxy]-3-methoxy-5-methylphenyl}-N-methylacetamide hydrochloride (325 mg).
Melting point: 230.0-234.0° C. (dec)

Example 15

Synthesis of 4-[3-(4-benzo[b]thiophen-4-yl-piperazin-1-yl)propoxy]-N,N-dimethyl-3-methoxy-5-methylaniline hydrochloride Formalin (37%, 0.29 ml, 3.9 mmol) and sodium cyanoborohydride (0.21 g, 3.1 mmol) were added to a methanol solution (6 ml) of 4-[3-(4-benzo[b]thiophen-4-yl-piperazin-1-yl)propoxy]-3-methoxy-5-methylaniline (0.32 g, 0.78 mmol) under ice cooling and the mixture was stirred at 0° C. for 15 minutes. To the reaction solution, acetic acid (0.18 ml, 3.1 mmol) was added and the mixture was stirred at room temperature for one hour. An aqueous potassium carbonate solution was added to the reaction solution under ice cooling, and extraction was performed with ethyl acetate. The extracted material was dried over magnesium sulfate. The reaction solution was concentrated under reduced pressure, and the residue was purified by basic silica gel column chromatography (n-hexane:ethyl acetate 11:1→3:1). The purified product was concentrated under reduced pressure. A solution of 4N-hydrochloric acid and ethyl acetate was added to an ethyl acetate solution of the residue and the insoluble matter precipitated was obtained by filtration to obtain 4-[3-(4-benzo[b]thiophen-4-yl-piperazin-1-yl)propoxy]-N,N-dimethyl-3-methoxy-5-methylaniline hydrochloride (137 mg) as white powder.
Melting point: 234.5-240.5° C. (dec)

Example 16

Synthesis of methyl {4-[3-(4-benzo[b]thiophen-4-yl-piperazin-1-yl)propoxy]-3-methoxy-5-methylphenyl}carbamate hydrochloride The titled compound was obtained using methyl 4-(3-chloropropoxy)-3-methoxy-5-methylphenyl]carbamate and 1-benzo[b]thiophen-4-yl-piperazine hydrochloride in the same manner as in Example 1.
White Powder (ethyl acetate)
Melting point: 230.0-235.5° C.

Example 17

Synthesis of methyl N-methyl-{4-[3-(4-benzo[b]thiophen-4-yl-piperazin-1-yl)propoxy]-3-methoxy-5-methylphenyl}carbamate hydrochloride The titled compound was obtained using methyl {4-[3-(4-benzo[b]thiophen-4-yl-piperazin-1-yl)propoxy]-3-methoxy-5-methylphenyl}carbamate hydrochloride and methyl iodide in the same manner as in Example 14.
White Powder (ethyl acetate)
Melting point: 228.0-233.5° C.

Example 18

Synthesis of 6-[3-(4-benzo[b]thiophen-4-yl-piperazin-1-yl)propoxy]-3,4-dihydro-2H-benzo[1,4]oxazine hydrochloride Lithium aluminum hydride (86 mg, 2.3 mmol) was suspended in THF (20 ml). To this solution, a THF solution (10 ml) of 6-[3-(4-benzo[b]thiophen-4-yl-piperazin-1-yl)propoxy]-3,4-dihydro-2H-benzo[1,4]oxazin-3-one (0.8 g, 1.9 mmol) was added dropwise under an argon atmosphere. After completion of dropwise addition, the solution mixture was refluxed with heating for one hour. Water (0.1 ml), 15% aqueous sodium hydroxide solution (0.1 ml), and water (0.3 ml) were added to the reaction mixture under ice cooling and stirred. Insoluble matter was removed by cerite filtration, and the filtrate was concentrated under reduced pressure. The obtained residue was purified by silica gel column chromatography (dichloromethane:methanol=1:0→20:1) and concentrated under reduced pressure. The residue was dissolved in ethyl acetate (10 ml) and a solution (0.34 ml) of 1N-hydrochloric acid/ethanol was added thereto and the mixture was stirred at room temperature for 15 minutes. The insoluble matter precipitated was obtained by filtration, washed with ethyl acetate, and dried to obtain 6-[3-(4-benzo[b]thiophen-4-yl-piperazin-1-yl)propoxy]-3,4-dihydro-2H-benzo[1,4]oxazine hydrochloride (0.11 g) as white solid.
Melting point 207.9-208.8° C.

Example 19

Synthesis of 7-[3-(4-benzo[b]thiophen-4-yl-piperazin-1-yl)propoxy]-3,4-dihydro-2H-benzo[1,4]oxazine hydrochloride The titled compound was obtained using 7-[3-(4-benzo[b]thiophen-4-yl-piperazin-1-yl)propoxy]-3,4-dihydro-2H-benzo[1,4]oxazin-3-one in the same manner as in Example 18.
Light Brown Solid (ethyl acetate)
Melting point: 214.0-215.9° C.

Example 20

Synthesis of 7-[3-(4-benzo[b]thiophen-4-yl-piperazin-1-yl)propoxy]-4-methyl-3,4-dihydro-2H-benzo[1,4]oxazine hydrochloride Formalin (37%, 0.22 ml, 2.7 mmol) and MP-cyanoborohydride (2.41 mmol/g, 1.12 g, 2.7 mmol) were added to a methanol solution (15 ml) of 7-[3-(4-benzo[b]thiophen-4-yl-piperazin-1-yl)propoxy]-3,4-dihydro-2H-benzo[1,4]oxazine (0.30 g, 0.67 mmol) and the mixture was stirred at room temperature overnight. The insoluble matter was removed by filtration and the filtrate was concentrated under reduced pressure. The obtained residue was purified by silica gel column chromatography (dichloromethane:methanol=1:0→50:1). The purified product was concentrated under reduced pressure and the residue was dissolved in ethyl acetate (15 ml) and a solution (0.64 ml) of 1N-hydrochloric acid/ethanol was added thereto. The mixture was stirred at room temperature for 15 minutes. The insoluble matter precipitated was obtained by filtration, washed with ethyl acetate, and dried to obtain 7-[3-(4-benzo[b]thiophen-4-yl-piperazin-1-yl)propoxy]-4-methyl-3,4-dihydro-2H-benzo[1,4]oxazine hydrochloride (0.23 g) as light brown solid.
Melting point; 248.1-249.6° C.

Example 21

Synthesis of 6-[3-(4-benzo[b]thiophen-4-yl-piperazin-1-yl)propoxy]-3-methyl-1,2,3,4-tetrahydroquinazolin-4-ol hydrochloride and 6-[3-(4-benzo[b]thiophen-4-yl-piperazin-1-yl)propoxy]-3-methyl-1,2,3,4-tetrahydroquinazoline hydrochloride A THF solution (20 ml) of 6-[3-(4-benzo[b]thiophen-4-yl-piperazin-1-yl)propoxy]-3-methylquinazoline (0.25 g, 0.58 mmol) was cooled on ice. To this solution, a THF solution (5 ml) of lithium aluminum hydride (26 mg, 0.69 mmol) was added dropwise under an argon atmosphere. After completion of dropwise addition, the solution was stirred at room temperature for 20 minutes and refluxed with heating for one hour. Water (0.03 ml), 15% aqueous sodium hydroxide solution (0.03 ml), and water (0.1 ml) were added to the reaction solution under ice cooling and stirred. Insoluble matter was removed by cerite filtration, and the filtrate was concentrated under reduced pressure. The obtained residue was purified by silica gel column chromatography (dichloromethane:methanol=1:0→25:1). The purified product was concentrated under reduced pressure and the residue was dissolved in ethyl acetate (5 ml). To this, a solution (0.189 ml) of 1N-hydrochloric acid/ethanol was added and the mixture was stirred at room temperature for 15 minutes. The insoluble matter precipitated was obtained by filtration, washed with ethyl acetate, and dried to obtain 6-[3-(4-benzo[b]thiophen-4-ylpiperazin-1-yl)propoxy]-3-methyl-1,2,3,4-tetrahydroquinazolin-4-ol hydrochloride (87 mg) as white solid.

MS: 438 (M+).

An eluting solution of dichloromethane/methanol (10:1) was passed through the column of the silica gel column chromatography. The obtained eluate was concentrated under reduced pressure and then the residue was dissolved in ethyl acetate (5 ml). To this, a solution (0.226 ml) of 1N-hydrochloric acid/ethanol was added and the mixture was stirred at room temperature for 15 minutes. The insoluble matter precipitated was obtained by filtration, washed with ethyl acetate, and dried to obtain 6-[3-(4-benzo[b]thiophen-4-yl-piperazin-1-yl)propoxy]-3-methyl-1,2,3,4-tetrahydroquinazoline hydrochloride (49 mg) as white solid.

Melting point: 203.1-204.4° C.

Example 22

Synthesis of 5-[3-(4-benzo[b]thiophen-4-yl-piperazin-1-yl)propoxy]-2,3-dihydro-1H-indole hydrochloride Triethylsilane (1.14 ml, 7.14 mmol) was added to a trifluoroacetic acid solution (5 ml) of 5-[3-(4-benzo[b]thiophen-4-yl-piperazin-1-yl)propoxy]-1H-indole (228 mg, 0.71 mmol) and the mixture was stirred at 50° C. for 2 hours. The mixture was concentrated under reduced pressure. The residue was dissolved in dichloromethane, neutralized by a saturated aqueous solution of sodium hydrogen carbonate and separated. The organic phase was washed with a saturated aqueous solution of sodium hydrogen carbonate, water and a saturated saline solution in this order and concentrated under reduced pressure. The obtained residue was purified by basic silica gel column chromatography (n-hexane:ethyl acetate=5: 1→1:1). The purified product was concentrated under reduced pressure and the residue was added to ethyl acetate (5 ml) and a solution of 1N-hydrochloric acid/ethanol (0.10 ml) was added thereto and the mixture was stirred at room temperature for 15 minutes. The insoluble matter precipitated was obtained by filtration, washed with ethyl acetate, and dried to obtain 5-[3-(4-benzo[b]thiophen-4-yl-piperazin-1-yl)propoxy]-2,3-dihydro-1H-indole hydrochloride (32 mg) as white solid.

Melting point: 222.4-223.9° C.

Compounds listed in the following Tables 13 to were produced using appropriate starting substances in the same manners as in Reference Examples 1 to 36 or Examples 1 to 22 and 3094 to 3110.

In the following Tables, compounds with the physical properties, such as crystalline form, m.p. (melting point), salt, $^1$H-NMR and MS (mass spectrum), were prepared actually.

TABLE 13

R1—O—(CH₂)₃—N(piperazine)N—(benzo[b]thiophen-4-yl)

| Example | R1 | Crystal form (Recrystalization solvent) | Melting point (° C.) | Salt |
|---|---|---|---|---|
| 23 | 3-methylpyridine | White solid (Ethanol) | 225-228 | Trihydrochloride |
| 24 | 4-methylpyridine | White needle-form crystal (Ethanol/ethyl acetate) | 165.0-167.0 | Hydrochloride |
| 25 | 2-methylpyridine | White solid (Ethanol) | 204-206 | Hydrochloride |
| 26 | H₃C-NH-C(=O)-(6-methylpyridin-3-yl) | White powder (Ethyl acetate) | 201.5-207.5 | Hydrochloride |
| 27 | H₃C-NH-C(=O)-(6-methylpyridin-3-yl) | White powder (Ethyl acetate/ isopropyl ether) | 132.5-133.5 | — |

TABLE 13-continued

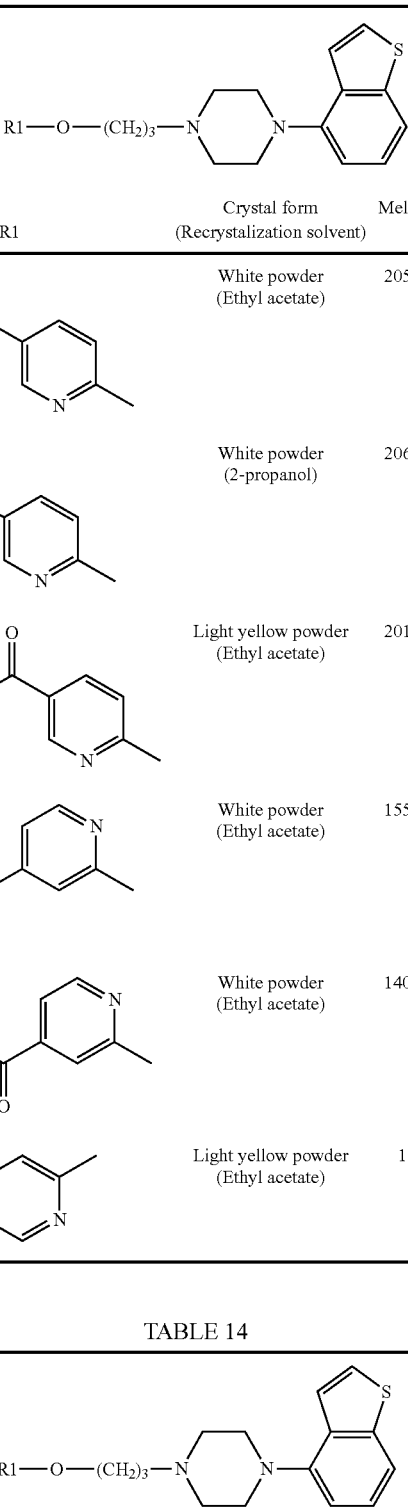

| Example | R1 | Crystal form (Recrystalization solvent) | Melting point (° C.) | Salt |
|---|---|---|---|---|
| 28 | 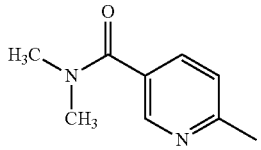 | White powder (Ethyl acetate) | 205.5-208.0 | Hydrochloride |
| 29 | 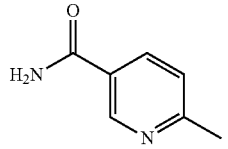 | White powder (2-propanol) | 206.5-208.0 | — |
| 30 | 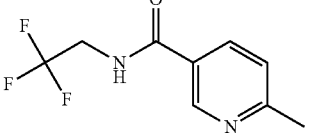 | Light yellow powder (Ethyl acetate) | 201.5-204.0 | Hydrochloride |
| 31 | 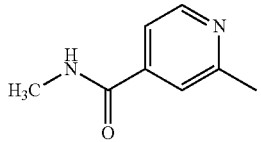 | White powder (Ethyl acetate) | 155.5-162.0 | Hydrochloride |
| 32 | 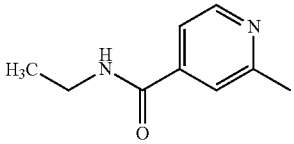 | White powder (Ethyl acetate) | 140.0-141.5 | Hydrochloride |
| 33 | 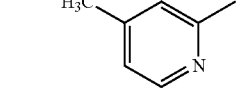 | Light yellow powder (Ethyl acetate) | 192-194 | dihydrochloride |

TABLE 14

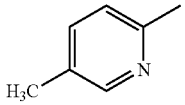

| Example | R1 | Crystal form (Recrystallization solvent) | Melting Point (° C.) | Salt |
|---|---|---|---|---|
| 34 | | Light yellow powder (Ethanol) | 201-203 | Dihydrochloride |

TABLE 14-continued

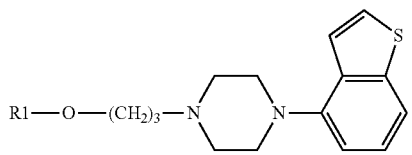

| Example | R1 | Crystal form (Recrystallization solvent) | Melting Point (° C.) | Salt |
|---|---|---|---|---|
| 35 | (2,6-dimethylpyridin-3-yl) | White powder (Ethanol) | 201-203 | Hydrochloride |
| 36 | (2,3-dimethylpyridin-4-yl) | White powder (Ethanol) | 214.0-215.0 | Hydrochloride |
| 37 | (N-ethyl-5-methylpyridine-2-carboxamide) | White powder (Ethyl acetate/ isopropyl ether) | 131.5-132.0 | — |
| 38 | (5-methylpyridine-2-carboxamide) | White powder (Ethyl acetate) | 193.0-194.0 | — |
| 39 | (N,5-dimethylpyridine-2-carboxamide) | White powder (Ethyl acetate/ isopropyl ether) | 128.0-129.5 | — |
| 40 | (2,5-dimethylpyridin-3-yl) | White powder (Ethanol) | 234.0-236.0 | Hydrochloride |
| 41 | (methyl 5-methylnicotinate) | Light yellow powder (Ethyl acetate) | 224.0-226.0 | Dihydrochloride |
| 42 | (5-methylnicotinic acid) | White powder (water) | 230.0 (dec) | Hydrochloride |
| 43 | (5-methylnicotinamide) | White powder (Ethyl acetate/ isopropyl ether) | 171.0-174.5 | — |

TABLE 15

R1—O—(CH₂)₃—[piperazine]—[benzothiophene]

| Example | R1 | Crystal form (Recrystallization solvent) | Melting point (° C.) | Salt |
|---|---|---|---|---|
| 44 | 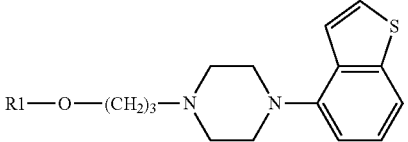 | Light yellow powder (Ethyl acetate) | 166.0 (dec) | Dihydrochloride |
| 45 | 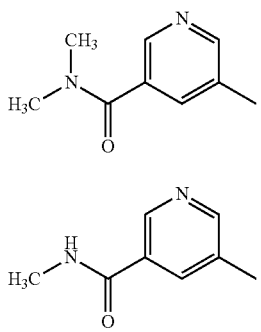 | Light yellow powder (Ethyl acetate) | 198.5-204.0 | Dihydrochloride |
| 46 | 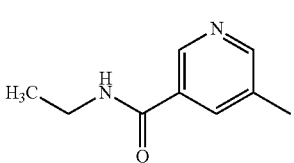 | White powder (Ethyl acetate) | 211.5-214.5 | Dihydrochloride |
| 47 | 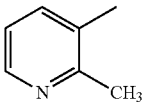 | White powder (Ethanol) | 241.0-243.0 | Hydrochloride |
| 48 | 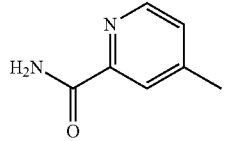 | White powder (Ethyl acetate/ isopropyl ether) | 150.0-150.5 | — |
| 49 | 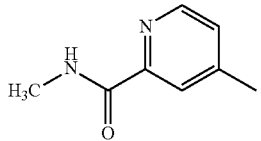 | White powder (Ethyl acetate) | 199.0-200.5 | Dihydrochloride |
| 50 | 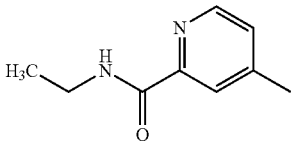 | White powder (Ethyl acetate) | 206.0-208.5 | Hydrochloride |
| 51 | 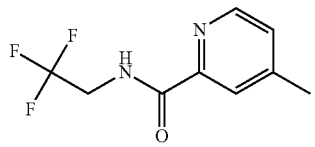 | White powder (Ethyl acetate) | 208.0-213.0 | Hydrochloride |
| 52 | 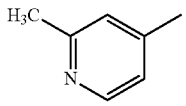 | White powder (Ethanol) | 157-159 | Hydrochloride |

TABLE 15-continued

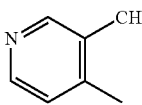

| Example | R1 | Crystal form (Recrystallization solvent) | Melting point (° C.) | Salt |
|---|---|---|---|---|
| 53 | 3-methyl-4-methylpyridin-yl | White powder (Ethanol) | 197.0-199.0 | Dihydrochloride |

TABLE 16

R1—O—(CH₂)₃—N(piperazine)N-benzothiophen-4-yl

| Example | R1 | Crystal form (Recrystallization solvent) | Melting point (° C.) | Salt |
|---|---|---|---|---|
| 54 | 2-methylpyrimidin-yl | White powder (Ethanol) | 205-207 | Hydrochloride |
| 55 | N-methyl-2-methylpyrimidine-4-carboxamide | White powder (Ethyl acetate) | 178.0-182.5 | Hydrochloride |
| 56 | 2-chloro-6-methylpyrimidin-4-yl | Light yellow powder (ethyl acetate) | 191.5-195.5 | Hydrochloride |
| 57 | 2-cyano-6-methylpyrimidin-4-yl | Light yellow powder (Ethyl acetate/ isopropyl ether) | 112.0-115.5 | — |
| 58 | N-methyl-6-methylpyrimidine-4-carboxamide | White powder (Methanol) | 205.0-209.5 | Hydrochloride |
| 59 | 6-methylpyrimidine-4-carboxamide | White powder (Ethyl acetate/ isopropyl ether) | 149.5-151.0 | — |
| 60 | methyl 5-methylpyrazine-2-carboxylate | Light yellow powder (Ethyl acetate/ isopropyl ether) | 114.5-115.5 | — |

TABLE 16-continued

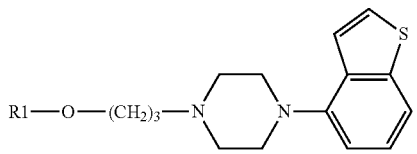

| Example | R1 | Crystal form (Recrystallization solvent) | Melting point (° C.) | Salt |
|---|---|---|---|---|
| 61 | 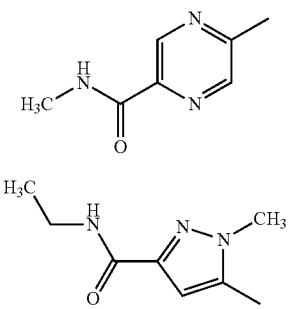 | White powder (Methanol) | 116.5-118.0 | — |
| 62 | 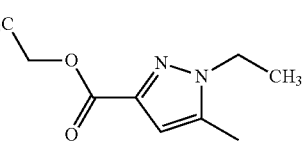 | White powder (Ethyl acetate) | 210.5-214.5 | Hydrochloride |
| 63 | 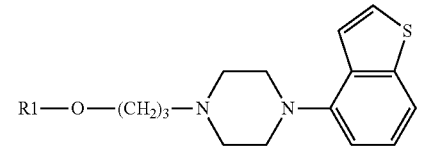 | Light yellow powder (Ethyl acetate/ isopropyl ether) | 109.0-110.0 | — |

TABLE 17

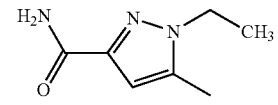

| Example | R1 | Crystal form (Recrystallization solvent) | Melting point (° C.) | Salt |
|---|---|---|---|---|
| 64 | 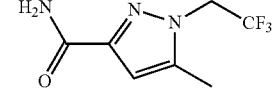 | White powder (Ethanol/water) | 129.0-131.0 | — |
| 65 | 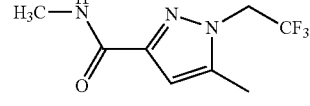 | White powder (Ethyl acetate) | 247.5 (dec) | Hydrochloride |
| 66 | 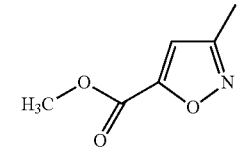 | White powder (Ethyl acetate) | 231.0-234.0 | Hydrochloride |
| 67 |  | White powder (Ethyl acetate) | 245.5 (dec) | Hydrochloride |
| 68 |  | White powder (Ethyl acetate) | 199.5-201.5 | Hydrochloride |

TABLE 17-continued

R1—O—(CH2)3—[piperazine]—[benzothiophen-4-yl]

| Example | R1 | Crystal form (Recrystallization solvent) | Melting point (° C.) | Salt |
|---|---|---|---|---|
| 69 | 3-methyl-5-carboxyisoxazole (HO-C(=O)-isoxazole-CH3) | White powder (Ethanol/water) | 252.5-255.0 (dec) | — |
| 70 | N-methyl-3-methylisoxazole-5-carboxamide | White powder (Ethyl acetate/ isopropyl ether) | 131.5-132.5 | — |
| 71 | 3-methylisoxazole-5-carboxamide (H2N-C(=O)-) | White powder (Ethyl acetate/ isopropyl ether) | 167.5-169.0 | — |
| 72 | N-ethyl-3-methylisoxazole-5-carboxamide | White powder (Ethyl acetate) | 219.5-222.5 (dec) | Hydrochloride |
| 73 | N-ethyl-2-methylthiazole-4-carboxamide | Light yellow powder (Ethyl acetate) | 151.0-153.5 | Hydrochloride |
| 74 | N-methyl-2-methylthiazole-4-carboxamide | White powder (Ethyl acetate/ isopropyl ether) | 138.5-140.0 | — |

TABLE 18

R1—O—(CH2)3—[piperazine]—[benzothiophen-4-yl]

| Example | R1 | NMR | Salt |
|---|---|---|---|
| 75 | N,N-dimethylthiophene-2-carboxamide with methyl | $^1$H-NMR (DMSO-d$_6$) δ ppm: 2.10-2.30 (2H, m), 2.80-3.90 (16H, m). 4.09 (2H, t, J = 5.9 Hz), 6.88 (1H, d, J = 1.5 Hz), 6.96 (1H, d, J = 7.6 Hz), 7.17 (1H, d, J = 1.4 Hz), 7.31 (1H, dd, J = 7.8, 7.8 Hz), 7.48 (1H, d, J = 5.6 Hz), 7.70 (1H, d, J = 8.1 Hz), 7.76 (1H, d, J = 5.6 Hz), 10.68 (1H, brs). | Hydrochloride |

TABLE 18-continued

R1—O—(CH₂)₃—N(piperazine)N—(benzothiophen-4-yl)

| Example | R1 | NMR | Salt |
|---|---|---|---|
| 76 | H₃C-NH-C(O)-(4-methylthiophen-2-yl) | ¹H-NMR (CDCl₃) δ ppm: 1.95-2.10 (2H, m), 2.62 (2H, t, J = 7.0 Hz), 2.65-2.80 (4H, m), 2.98 (3H, d, J = 4.9 Hz), 3.15-3.25 (4H, m), 4.05 (2H, t, J = 6.3 Hz), 5.94 (1H, brs), 6.43 (1H, d, J = 1.8 Hz), 6.90 (1H, dd, J = 1.4, 7.6 Hz), 7.15 (1H, d, J = 1.7 Hz), 7.20-7.35 (1H, m), 7.35-7.45 (2H, m), 7.55 (1H, d, J = 8.1 Hz). | — |
| 77 | H₃C-CH₂-NH-C(O)-(4-methylthiophen-2-yl) | ¹H-NMR (CDCl₃) δ ppm: 1.23 (3H, t, J = 7.3 Hz), 1.95-2.05 (2H, m), 2.61 (2H, t, J = 7.3 Hz), 2.65-2.80 (4H, m), 3.10-3.30 (4H, m), 3.40-3.55 (2H, m), 4.04 (2H, t, J = 6.3 Hz), 6.01 (1H, brs), 6.43 (1H, d, J = 1.6 Hz), 6.90 (1H, d, J = 7.6 Hz), 7.16 (1H, d, J = 1.7 Hz), 7.27 (1H, dd, J = 7.8, 7.8 Hz), 7.35-7.45 (2H, m), 7.55 (1H, d, J = 8.1 Hz). | — |
| 78 | H₂N-C(O)-(4-methylthiophen-2-yl) | ¹H-NMR (CDCl₃) δ ppm: 1.95-2.10 (2H, m), 2.63 (2H, t, J = 7.3 Hz), 2.70-2.80 (4H, m), 3.15-3.25 (4H, m), 4.06 (2H, t, J = 6.3 Hz), 5.74 (2H, brs), 6.51 (1H, d, J = 1.7 Hz), 6.90 (1H, dd, J = 0.5, 7.6 Hz), 7.19 (1H, d, J = 1.7 Hz), 7.28 (1H, dd, J = 7.8, 7.8 Hz), 7.35-7.45 (2H, m), 7.56 (1H, d, J = 8.0 Hz). | — |

TABLE 19

R1—O—(CH₂)₃—N(piperazine)N—(benzothiophen-4-yl)

| Example | R1 | Crystal form (Recrystallization solvent) | Melting point (°C.) | Salt |
|---|---|---|---|---|
| 79 | 1,4-dimethyl-4-methyl-2-oxopyrrolidin-1-yl (3,3-dimethyl-5-oxopyrrolidin-1-yl) | White powder (Ethyl acetate/ether) | 183-186 | Hydrochloride |

TABLE 20

R1—O—(CH₂)₄—N(piperazine)N—(benzothiophen-4-yl)

| Example | R1 | Crystal form (Recrystallization solvent) | Melting point (°C.) | Salt |
|---|---|---|---|---|
| 80 | pyridin-4-yl | White powder (Ethanol/ethyl acetate) | 183.0-185.0 | Dihydrochloride |

TABLE 20-continued

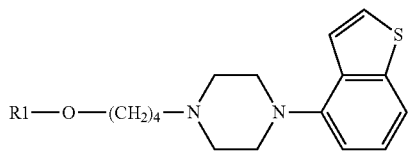

| Example | R1 | Crystal form (Recrystallization solvent) | Melting point (° C.) | Salt |
|---|---|---|---|---|
| 81 | 3-methylpyridine | White powder (Ethanol/ethyl acetate) | 205.0-207.0 | Hydrochloride |
| 82 | 2-methylpyridine | White powder (Ethanol/ethyl acetate) | 197.0-199.0 | Hydrochloride |
| 83 | N-methyl 6-methylnicotinamide | White powder (Ethyl acetate) | 166.5-168.0 | Hydrochloride |
| 84 | N,N-dimethyl 6-methylnicotinamide | White powder (Ethyl acetate) | 196.0-201.0 | Hydrochloride |
| 85 | N-ethyl 6-methylnicotinamide | White powder (Ethyl acetate) | 175.0-176.0 | Hydrochloride |
| 86 | 6-methylnicotinamide | White powder (Ethyl acetate/ isopropyl ether) | 150.0-154.5 | — |
| 87 | N-(2,2,2-trifluoroethyl) 6-methylnicotinamide | White powder (Ethyl acetate) | 172.0-175.0 | Hydrochloride |
| 88 | 1,4,4-trimethyl-2-oxopyrrolidine | White Powder (Ethyl acetate/ether) | 201-205 | Hydrochloride |

TABLE 21

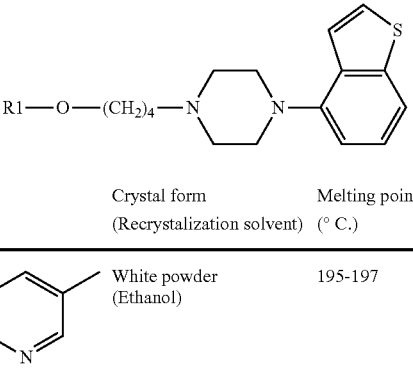

| Example | R1 | Crystal form (Recrystalization solvent) | Melting point (° C.) | Salt |
|---|---|---|---|---|
| 89 | 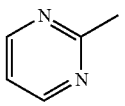 | White powder (Ethanol) | 195-197 | Hydrochloride |
| 90 | 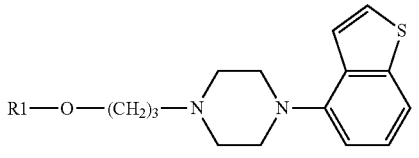 | White powder (Ethanol) | 190-192 | Hydrochloride |

TABLE 22

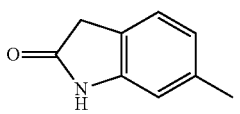

| Example | R1 | Crystal form (Recrystalization solvent) | Melting point (° C.) | Salt |
|---|---|---|---|---|
| 91 | 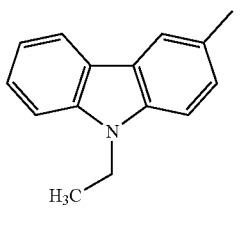 | White powder (Ethyl acetate) | 149-150 | — |
| 92 | 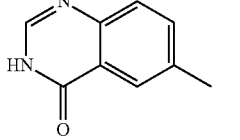 | Light pink powder (Ethanol) | 161-163 | — |
| 93 | 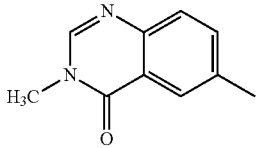 | White solid (Ethyl acetate) | 226.8-229.0 | Hydrochloride |
| 94 | | White solid (Ethyl acetate) | 213.1-218.5 | — |
| 95 | | White solid (Ethyl acetate) | 252.9-254.3 | Hydrochloride |

TABLE 22-continued

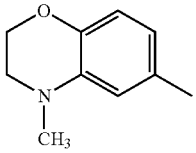

| Example | R1 | Crystal form (Recrystalization solvent) | Melting point (° C.) | Salt |
|---|---|---|---|---|
| 96 | 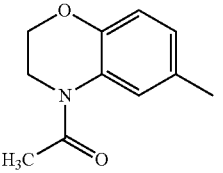 | White solid (Ethyl acetate) | 238.7-239.9 | Hydrochloride |
| 97 | 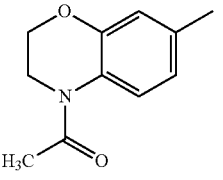 | White solid (Ethyl acetate) | 238.9-240.7 | Hydrochloride |
| 98 | 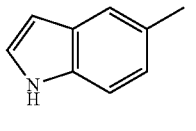 | Light brown solid (Ethyl acetate) | 218.4-220.4 | Hydrochloride |

TABLE 23

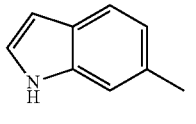

| Example | R1 | Crystal form (Recrystalization solvent) | Melting point (° C.) | Salt |
|---|---|---|---|---|
| 99 | 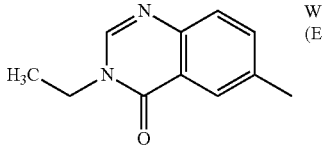 | White solid (Ethyl acetate) | 267.0-271.0 | Hydrochloride |
| 100 | | White solid (Ethyl acetate/ hexane) | 143.8-145.2 | — |
| 101 | | White solid (Ethyl acetate) | 250.6-252.1 | Hydrochloride |

TABLE 23-continued
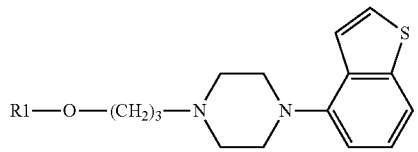
| Example | R1 | Crystal form (Recrystalization solvent) | Melting point (° C.) | Salt |
|---|---|---|---|---|
| 102 | | White solid (Ethyl acetate) | 233.3-235.2 | Hydrochloride |
| 103 | | White solid (Ethanol/ ethyl acetate) | 251.1-253.6 | Hydrochloride |
| 104 | | White solid (Ethyl acetate) | 249.8-252.3 | Hydrochloride |
| 105 | | White solid (Ethyl acetate) | 255.1-256.6 | Hydrochloride |
| 106 | | White solid (Ethyl acetate) | 207.9-208.7 | Hydrochloride |
| 107 | | White solid (Ethyl acetate) | 214.5-216.8 | Hydrochloride |

TABLE 24

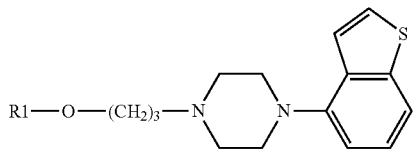

| Example | R1 | NMR | Salt |
|---|---|---|---|
| 108 | (5-methyl-2H-benzo[b][1,4]oxazin-3(4H)-one) | $^1$H-NMR (CDCl$_3$) δ ppm: 2.04-2.13 (2H, m), 2.65 (2H, t, J = 7.2 Hz), 2.73 (4H, br), 3.19 (4H, br), 4.15 (2H, t, J = 6.6 Hz), 4.67 (2H, s), 6.42 (1H, dd, J = 1.3, 8.0 Hz), 6.69 (1H, dd, J = 1.3, 8.3 Hz), 6.87-6.92 (2H, m), 7.25-7.30 (1H, m), 7.35-7.42 (2H, m), 7.55 (1H, d, J = 8.0 Hz), 7.84 (1H, br) | — |
| 109 | (6-methyl-2H-benzo[b][1,4]oxazin-3(4H)-one) | $^1$H-NMR (DMSO-d$_6$) δ ppm: 1.80-2.00 (2H, m), 2.45-2.55 (2H, m), 2.55-2.65 (4H, br), 3.00-3.10 (4H, br), 3.93 (2H, t, J = 6.3 Hz), 4.47 (2H, s), 6.45-6.55 (2H, m), 6.80-6.90 (2H, m), 7.26 (1H, t, J = 7.8 Hz), 7.38 (1H, d, J = 5.5 Hz), 7.60 (1H, d, J = 8.0 Hz), 7.67 (1H, d, J = 5.5 Hz), 10.59 (1H, s) | — |
| 110 | (8-methyl-2H-benzo[b][1,4]oxazin-3(4H)-one) | $^1$H-NMR (CDCl$_3$) δ ppm: 2.06 (2H, quint, J = 6.5 Hz), 2.66 (2H, t, J = 6.9 Hz), 2.70-2.80 (4H, m), 3.20-3.25 (4H, m), 4.12 (2H, t, J = 6.1 Hz), 4.60 (2H, s), 6.55-6.70 (2H, m), 6.88 (1H, d, J = 8.3 Hz), 6.91 (1H, d, J = 8.3 Hz), 7.20-7.30 (1H, m), 7.35-7.45 (2H, m), 7.55 (1H, d, J = 8.1 Hz), 8.43 (1H, brs) | — |
| 111 | (5-methylbenzo[d]oxazol-2(3H)-one) | $^1$H-NMR (DMSO-d$_6$) δ ppm: 1.80-1.90 (2H, m), 2.41 (2H, t, J = 6.6 Hz) 2.50-2.55 (4H, m), 2.95-3.00 (4H, m), 3.83 (2H, t, J = 6.7 Hz), 6.47 (1H, dd, J = 2.4, 8.6 Hz), 6.70 (1H, d, J = 2.4 Hz), 6.85 (1H, d, J = 7.5 Hz), 7.09 (1H, d, J = 8.6 Hz), 7.27 (1H, dd, J = 7.9, 7.9 Hz), 7.36 (1H, d, J = 5.6 Hz), 7.60 (1H, d, J = 8.0 Hz), 7.67 (1H, d, J = 5.6 Hz), 9.46 (1H, brs). | — |
| 112 | (5-methyl-1H-benzo[d]imidazol-2(3H)-one) | $^1$H-NMR (DMSO-d$_6$) δ ppm: 1.88 (2H, t, J = 6.8 Hz), 2.50-2.55 (2H, m), 2.60 (4H, brs), 3.06 (4H, brs), 3.95 (2H, t, J = 6.4 Hz), 6.45-6.55 (2H, m), 6.78 (1H, d, J = 9.1 Hz), 6.88 (1H, d, J = 7.7 Hz), 7.26 (1H, dd, J = 7.8, 7.8 Hz), 7.39 (1H, d, J = 5.6 Hz), 7.55-7.70 (2H, m), 10.35 (1H, brs), 10.49 (1H, brs). | — |

TABLE 25

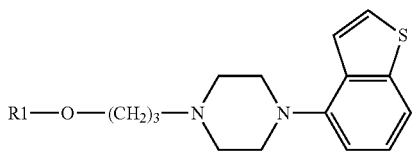

| Example | R1 | NMR | Salt |
|---|---|---|---|
| 113 | (1,5-dimethyl-1H-benzo[d]imidazol-2(3H)-one) | $^1$H-NMR (DMSO-d$_6$) δ ppm: 2.20-2.30 (2H, m), 2.45-2.55 (2H, m), 3.00-3.80 (11H, m), 4.06 (2H, t, J = 5.9 Hz), 6.60-6.70 (2H, m), 6.90-7.00 (2H, m), 7.33 (1H, dd, J = 7.9, 7.9 Hz), 7.50 (1H, d, J = 5.5 Hz), 7.71 (1H, d, J = 8.0 Hz), 7.78 (1H, d, J = 5.5 Hz), 10.67 (1H, brs), 10.81 (1H, brs). | Dihydrochloride |

TABLE 25-continued

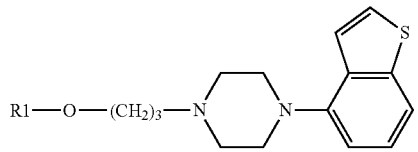

| Example | R1 | NMR | Salt |
|---|---|---|---|
| 114 | H₃C–N, C=O, N–CH₃ benzimidazolone (5-methyl) | ¹H-NMR (CDCl₃) δ ppm: 2.00-2.10 (4H, m), 2.70-2.85 (6H, m), 3.20-3.25 (4H, m), 3.40 (6H, s), 4.097 (2H, t, J = 6.3 Hz), 6.61 (1H, d, J = 2.2 Hz), 6.68 (1H, dd, J = 2.3, 8.4 Hz), 6.85 (1H, d, J = 8.5 Hz), 6.92 (1H, d, J = 7.6 Hz), 7.25-7.35 (1H, m), 7.35-7.45 (2H, m), 7.57 (1H, d, J = 8.0 Hz). | — |
| 115 | 4-methyl-7-coumarinyl | ¹H-NMR (DMSO-d₆) δ ppm: 2.25-2.35 (2H, m), 2.40 (3H, s), 3.20-3.70 (10H, m), 4.22 (2H, t, J = 5.9 Hz), 6.22 (1H, s), 6.95-7.05 (3H, m), 7.31 (1H, dd, J = 7.9, 7.9 Hz), 7.49 (1H, d, J = 5.5 Hz), 7.65-7.80 (3H, m), 10.93 (1H, brs). | Hydrochloride |
| 116 | H₃C–N, C=O, NH benzimidazolone (5-methyl) | ¹H-NMR (CDCl₃) δ ppm: 2.00-2.10 (2H, m), 2.60-2.70 (2H, m), 2.75 (4H, brs), 3.21 (4H, brs), 3.39 (3H, s), 4.05-4.15 (2H, m), 6.55-6.70 (2H, m), 6.90 (1H, d, J = 7.6 Hz), 6.96 (1H, d, J = 8.5 Hz), 7.25-7.30 (1HH, m), 7.35-7.45 (2H, m), 7.55 (1H, d, J = 8.1 Hz), 9.12 (1H, brs) | — |

TABLE 25-1

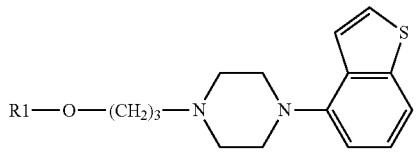

| Example | R1 | NMR | Salt |
|---|---|---|---|
| 117 | 1-methyl-5-benzimidazolyl | ¹H-NMR (CDCl₃) δ ppm: 2.10 (2H, t, J = 7.3 Hz), 2.70 (2H, t, J = 7.4 Hz), 2.77 (4H, brs), 3.22 (4H, brs), 3.80 (3H, s), 4.14 (2H, t, J = 6.3 Hz), 6.85-7.00 (3H, m), 7.25-7.35 (1H, m), 7.35-7.45 (2H, m), 7.56 (1H, d, J = 8.1 Hz), 7.68 (1H, d, J = 8.8 Hz), 7.77 (1H, s). | — |
| 118 | isoindolin-1-one (5-methyl) | ¹H-NMR (CDCl₃) δ ppm: 2.07 (2H, t, J = 7.0 Hz), 2.65 (2H, t, J = 7.2 Hz), 2.74 (4H, brs), 3.20 (4H, brs), 4.13 (2H, t, J = 6.3 Hz), 4.40 (2H, s), 6.38 (1H, brs), 6.90 (1H, d, J = 7.6 Hz), 6.97 (1H, s), 7.02 (1H, dd, J = 2.1, 8.4 Hz), 7.25-7.30 (1H, m), 7.35-7.45 (2H, m), 7.55 (1H, d, J = 8.1 Hz), 7.78 (1H, d, J = 8.4 Hz). | — |
| 119 | N-methyl-isoindolin-1-one (5-methyl) | ¹H-NMR (CDCl₃) δ ppm: 2.07 (2H, t, J = 7.0 Hz), 2.66 (2H, t, J = 5.7 Hz), 2.74 (4H, brs), 3.17 (3H, s), 3.20 (4H, brs), 4.12 (2H, t, J = 6.3 Hz), 4.31 (2H, s), 6.90 (1H, d, J = 7.6 Hz), 6.90-7.00 (2H, m), 7.25-7.30 (1H, m), 7.39 (1H, d, J = 5.5 Hz), 7.41 (1H, d, J = 5.5 Hz), 7.55 (1H, d, J = 8.1 Hz), 7.74 (1H, d, J = 8.4 Hz) | — |

TABLE 25-2

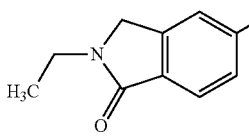

| Example | R1 | Crystal form (Recrystalization solvent) | Melting point (° C.) | Salt |
|---|---|---|---|---|
| 120 | (2-ethyl-isoindolin-1-one-5-yl) | White powder (Methanol) | 242-246 | Hydrochloride |

TABLE 25-3

R1—O—(CH$_2$)$_3$—N(piperazine)N—(benzothiophen-4-yl)

| Example | R1 | NMR | Salt |
|---|---|---|---|
| 121 | 1-methyl-5-benzimidazolyl | $^1$H-NMR (CDCl$_3$) δ ppm: 2.08 (2H, t, J = 7.3 Hz), 2.69 (2H, t, J = 7.4 Hz), 2.76 (4H, brs), 3.21 (4H, brs), 3.82 (3H, s), 4.13 (2H, t, J = 6.3 Hz), 6.91 (1H, d, J = 6.3 Hz), 6.99 (1H, dd, J = 2.3, 8.7 Hz), 7.25-7.35 (3H, m), 7.39 (1H, d, J = 5.6 Hz), 7.43 (1H, d, J = 5.5 Hz), 7.55 (1H, d, J = 8.0 Hz), 7.81 (1H, s). | — |
| 122 | 6-methyl-isoindolin-1-one-5-yl (NH) | $^1$H-NMR (CDCl$_3$) δ ppm: 2.00-2.10 (2H, m), 2.65 (2H, t, J = 7.3 Hz), 2.74 (4H, brs), 3.21 (4H, brs), 4.13 (2H, t, J = 6.4 Hz), 4.40 (2H, s), 6.84 (1H, brs), 6.91 (1H, d, J = 7.5 Hz), 7.16 (1H, dd, J = 2.3, 8.3 Hz), 7.25-7.30 (1H, m), 7.35-7.45 (4H, m), 7.55 (1H, d, J = 8.0 Hz). | — |
| 123 | 2-methyl-isoindolin-1-one-6-yl | $^1$H-NMR (CDCl$_3$) δ ppm: 2.06 (2H, t, J = 7.2 Hz), 2.65 (2H, t, J = 7.3 Hz), 2.74 (4H, brs), 3.20 (7H, brs), 4.12 (2H, t, J = 6.4 Hz), 4.31 (2H, s), 6.91 (1H, d, J = 7.7 Hz), 7.10 (1H, dd, J = 2.4, 8.3 Hz), 7.25-7.35 (2H, m), 7.35 (1H, d, J = 2.3 Hz), 7.39 (1H, d, J = 5.5 Hz), 7.42 (1H, d, J = 5.5 Hz), 7.55 (1H, d, J = 8.0 Hz). | — |
| 124 | 2-ethyl-isoindolin-1-one-6-yl | $^1$H-NMR (DMSO-d$_6$) δ ppm: 1.15 (3H, t, J = 7.3 Hz), 2.20-2.30 (2H, m), 3.15-3.30 (2H, m), 3.30-3.40 (4H, m), 3.45-3.70 (6H, m), 4.16 (2H, t, J = 5.8 Hz), 4.39 (2H, s), 6.97 (1H, d, J = 7.6 Hz), 7.10-7.25 (2H, m), 7.31 (1H, dd, J = 7.9, 7.9 Hz), 7.45-7.55 (2H, m), 7.69 (1H, d, J = 8.1 Hz), 7.76 (1H, d, J = 5.6 Hz), 10.74 (1H, brs). | Hydrochloride |
| 125 | 6-methyl-indanon-1-on-5-yl | $^1$H-NMR (DMSO-d$_6$) δ ppm: 2.20-2.30 (2H, m), 2.64 (2H, t, J = 5.8 Hz), 3.01 (2H, t, J = 5.5 Hz), 3.20-3.40 (6H, m), 3.53 (2H, d, J = 12.3 Hz), 3.64 (2H, t, J = 11.2 Hz), 4.15 (2H, t, J = 6.0 Hz), 6.95 (1H, d, J = 7.7 Hz), 7.13 (1H, d, J = 2.4 Hz), 7.25-7.35 (2H, m), 7.45-7.55 (2H, m), 7.69 (1H, d, J = 8.0 Hz), 7.75 (1H, d, J = 5.6 Hz), 11.12 (1H, brs). | Hydrochloride |

TABLE 26

R1—O—(CH₂)₂—N(piperazine)N—(benzothiophen-4-yl)

| Example | R1 | Crystal form (Recrystalization solvent) | Melting point (° C.) | Salt |
|---|---|---|---|---|
| 126 | 6-methyl-2-oxoindolin-5-yl | Red-brown powder (Acetonitrile) | 191-193 | — |

TABLE 27

R1—O—(CH₂)₄—N(piperazine)N—(benzothiophen-4-yl)

| Example | R1 | Crystal form (Recrystalization solvent) | Melting point (° C.) | Salt |
|---|---|---|---|---|
| 127 | 6-methyl-2-oxoindolin-5-yl | Red-brown powder (Ethanol) | 215-217 | Hydrochloride |
| 128 | 5-methyl-1H-indol-6-yl | White solid (Ethyl acetate) | 209.2-210.9 | Hydrochloride |
| 129 | 7-methyl-1-oxo-tetralin-6-yl | White solid (Ethanol/ethyl acetate) | 242.0-244.9 | Hydrochloride |
| 130 | 6-methyl-3-oxo-3,4-dihydro-2H-benzo[b][1,4]oxazin-7-yl | White powder (Ethanol) | 211-213 | Hydrochloride |
| 131 | 7-methyl-3-oxo-3,4-dihydro-2H-benzo[b][1,4]oxazin-6-yl | Light purple powder (Ethyl acetate) | 180-182 | — |
| 132 | 8-methyl-3-oxo-3,4-dihydro-2H-benzo[b][1,4]oxazin-5-yl | Light pink powder (Ethanol) | 170.2-171.9 | — |
| 133 | 7-methyl-2-oxo-2H-benzo[d][1,3]oxazin-6-yl | White powder (Ethanol/ethyl acetate) | 253-258 (dec) | Hydrochloride |

TABLE 27-continued

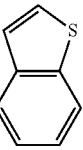

| Example | R1 | Crystal form (Recrystalization solvent) | Melting point (° C.) | Salt |
|---|---|---|---|---|
| 134 | 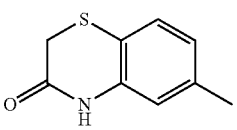 | White powder (2-propanol) | 213.7-220.6 | Hydrochloride |
| 135 | 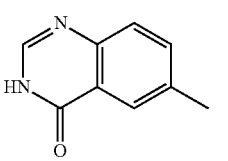 | White solid (Ethyl acetate) | 152.6-155.3 | Hydrochloride |
| 136 | 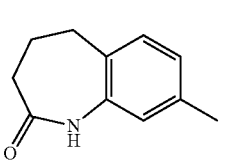 | White powder (Ethanol/ethyl acetate) | 226-228 | Hydrochloride |

TABLE 28

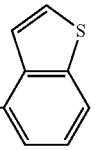

| Example | R1 | Crystal form (Recrystalization solvent) | Melting point (° C.) | Salt |
|---|---|---|---|---|
| 137 | 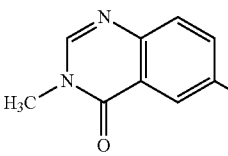 | White solid (Ethyl acetate) | 238.8-241.8 | Hydrochloride |
| 138 | 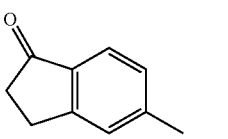 | White powder (Ethyl acetate/ether) | 198-201 | Hydrochloride |
| 139 | 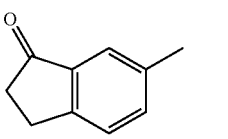 | White powder (Ethyl acetate/ether) | 206-209 | Hydrochloride |
| 140 | 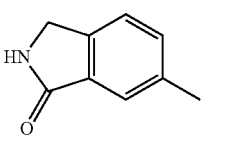 | White powder (Ethyl acetate/ether) | 157-161 | — |

TABLE 29

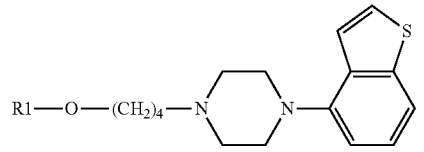

| Example | R1 | NMR | Salt |
|---|---|---|---|
| 141 | 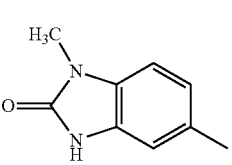 | ¹H-NMR (DMSO-d₆) δ ppm: 1.75-1.85 (2H, m), 1.90-1.95 (2H, m), 3.05 (3H, s), 3.15-3.35 (6H, m), 3.55-3.65 (4H, m), 4.08 (2H, t, J = 6.1 Hz), 4.36 (2H, s), 6.95 (1H, d, J = 7.7 Hz), 7.10-7.20 (2H, m), 7.30 (1H, dd, J = 7.9, 7.9 Hz), 7.45-7.50 (2H, m), 7.69 (1H, d, J = 8.1 Hz), 7.75 (1H, d, J = 5.5 Hz), 10.75 (1H, brs). | Dihydrochloride |
| 142 | 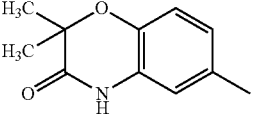 | ¹H-NMR (DMSO-d₆) δ ppm: 1.70-1.80 (2H, m), 1.85-2.00 (2H, m), 3.22 (3H, s), 3.15-3.35 (6H, m), 3.45-3.60 (4H, m), 3.95 (2H, t, J = 6.1 Hz), 6.60-6.65 (2H, m), 6.90-7.00 (2H, m), 7.30 (1H, dd, J = 7.9, 7.9 Hz), 7.45-7.50 (1H, m), 7.68 (1H, d, J = 8.0 Hz), 7.75 (1H, d, J = 5.5 Hz), 10.82 (1H, s), 11.31 (1H, brs). | Hydrochloride |
| 143 | 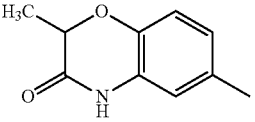 | ¹H-NMR (CDCl₃) δ ppm: 1.52 (6H, s), 1.60-1.90 (4H, m), 2.53 (2H, t, J = 7.3 Hz), 2.70-2.80 (4H, m), 3.10-3.30 (4H, m), 3.97 (2H, t, J = 6.0 Hz), 6.37 (1H, d, J = 2.7 Hz), 6.53 (1H, dd, J = 2.7, 8.8 Hz), 6.85-6.95 (2H, m), 7.25-7.35 (2H, m), 7.35-7.45 (2H, m), 7.56 (1H, d, J = 8.0 Hz), 8.06 (1H, s) | — |
| 144 | 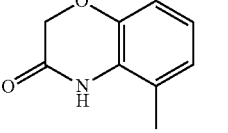 | ¹H-NMR (DMSO-d₆) δ ppm: 1.37 (3H, d, J = 6.7 Hz), 1.50-1.80 (4H, m), 2.41 (2H, t, J = 6.9 Hz), 2.55-2.65 (4H, br), 3.90 (2H, t, J = 6.2 Hz), 4.51 (1H, q, J = 6.7 Hz), 6.45-6.50 (2H, m), 6.80-6.90 (2H, m), 7.25 (1H, t, J = 7.8 Hz), 7.38 (1H, d, J = 8.0 Hz), 7.59 (1H, d, J = 8.0 Hz), 7.67 (1H, d, J = 5.5 Hz), 10.53 (1H, s) | — |
| 145 | 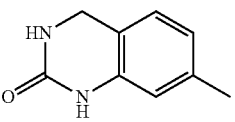 | ¹H-NMR (CDCl₃) δ ppm: 1.65-1.95 (4H, m), 2.53 (2H, t, J = 7.3 Hz), 2.70-2.75 (4H, m), 3.15-3.25 (4H, m), 4.08 (2H, t, J = 6.3 Hz), 4.61 (2H, s), 6.57 (1H, d, J = 8.3 Hz), 6.61 (1H, d, J = 8.3 Hz), 6.85-6.95 (2H, m), 7.20-7.35 (1H, m), 7.35-7.45 (2H, m), 7.55 (1H, d, J = 8.0 Hz), 7.80 (1H, brs) | — |
| 146 | 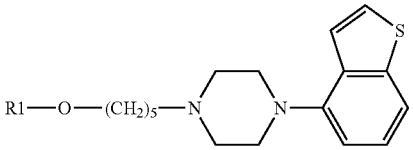 | ¹H-NMR (CDCl₃) δ ppm: 1.60-1.88 (4H, m), 2.51 (2H, t, J = 7.5 Hz), 2.63-2.77 (4H, m), 3.13-3.25 (4H, m), 3.95 (2H, t, J = 6.3 Hz), 4.46 (2H, s), 5.28 (1H, brs), 6.25 (1H, d, J = 2.4 Hz), 6.50 (1H, dd, J = 8.4, 2.4 Hz), 6.90 (1H, d, J = 7.7 Hz), 6.92 (1H, d, J = 8.4 Hz), 7.27 (1H, dd, J = 7.8, 8.0 Hz), 7.38 (1H, d, J = 5.5 Hz), 7.41 (1H, d, J = 5.5 Hz), 7.51 (1H, brs), 7.54 (1H, d, J = 8.0 Hz). | — |

TABLE 30

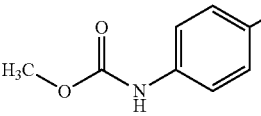

| Example | R1 | Crystal form (Recrystalization solvent) | Melting point (° C.) | Salt |
|---|---|---|---|---|
| 147 | | White powder (Ethyl acetate) | 143-144 | — |
| 148 | | Light yellow powder (Ethyl acetate/ isopropyl ether) | 112.5-114.5 | — |

TABLE 30-continued

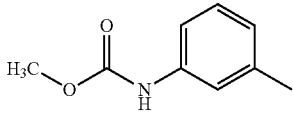

| Example | R1 | Crystal form (Recrystalization solvent) | Melting point (° C.) | Salt |
|---|---|---|---|---|
| 149 | H3C-O-C(=O)-NH-(3-methylphenyl) | White powder (Ethyl acetate) | 208.0-211.5 | Hydrochloride |

TABLE 31

R1—O—(CH2)5—N(piperazine)N—(benzothiophen-4-yl)

| Example | R1 | NMR | Salt |
|---|---|---|---|
| 150 | 8-methyl-2H-benzo[b][1,4]oxazin-3(4H)-one | $^1$H-NMR (DMSO-d$_6$) δ ppm: 1.40-1.67 (2H, m), 1.73-1.90 (4H, m), 3.13-3.30 (6H, m), 3.52-3.62 (4H, m), 3.96-4.01 (2H, m), 4.54 (2H, s), 6.50 (1H, d, J = 7.7 Hz), 6.67 (1H, d, J = 7.3 Hz), 6.83-6.88 (1H, m), 6.96 (1H, d, J = 7.7 Hz), 7.28-7.34 (1H, m), 7.48 (1H, d, J = 5.6 Hz), 7.70 (1H, d, J = 8.1 Hz), 7.76 (1H, d, J = 5.6 Hz), 10.42 (1H, br), 10.67 (1H, br) | Hydrochloride |
| 151 | 6-methyl-2H-benzo[b][1,4]oxazin-3(4H)-one | $^1$H-NMR (DMSO-d$_6$) δ ppm: 1.40-1.60 (4H, m), 1.60-1.80 (2H, m), 2.35-2.45 (2H, m), 2.55-2.65 (4H, br), 3.90 (2H, t, J = 6.4 Hz), 4.49 (2H, s), 6.45-6.55 (2H, m), 6.80-6.95 (2H, m), 7.28 (1H, t, J = 7.8 Hz), 7.40 (1H, d, J = 5.6 Hz), 7.62 (1H, d, J = 8.0 Hz), 7.69 (1H, d, J = 5.5 Hz), 10.61 (1H, s) | — |
| 152 | 5-methyl-2H-benzo[b][1,4]oxazin-3(4H)-one | $^1$H-NMR (CDCl$_3$) δ ppm: 1.45-1.70 (4H, m), 1.80-1.90 (2H, m), 2.45-2.55 (2H, m), 2.65-2.75 (4H, m), 3.15-3.25 (4H, m), 4.05 (2H, t, J = 6.3 Hz), 4.61 (2H, s), 6.50-6.65 (2H, m), 6.85-6.95 (2H, m), 7.20-7.35 (1H, m), 7.35-7.45 (2H, m), 7.55 (1H, d, J = 8.0 Hz), 7.80 (1H, brs) | — |

TABLE 32

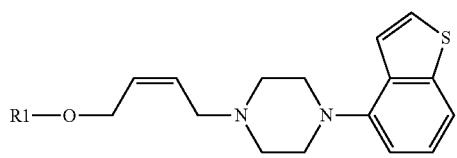

| Example | R1 | NMR | Salt |
|---|---|---|---|
| 153 | 6-methyl-2H-benzo[b][1,4]oxazin-3(4H)-one | $^1$H-NMR (CDCl$_3$) δ ppm: 2.73 (4H, m), 3.19-3.20 (6H, m), 4.56 (2H, s), 4.54-4.62 (2H, m), 5.76-5.92 (2H, m), 6.38 (1H, d, J = 2.7 Hz), 6.54 (1H, dd, J = 8.8, 2.7 Hz), 6.89-6.92 (2H, m), 7.25 (1H, m), 7.39-7.41 (2H, m), 7.53-7.56 (2H, m) | — |

TABLE 33

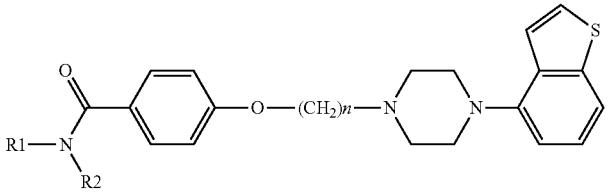

| Example | R1 | R2 | n | Crystal form (Recrystallization solvent) | Melting point (° C.) | Salt |
|---|---|---|---|---|---|---|
| 154 | —H | —$C_2H_5$ | 3 | White powder (Ethyl acetate) | 218.5-222.0 (dec) | Hydrochloride |
| 155 | —H | —$C_3H_7$ | 3 | Light yellow powder (Ethyl acetate/isopropyl ether) | 127.0-128.5 | — |
| 156 | —H | —$CH_3$ | 3 | Light yellow powder (Ethyl acetate/isopropyl ether) | 151.0-154.5 | — |
| 157 | —$CH_3$ | —$CH_3$ | 3 | White powder (Ethyl acetate) | 206.5-211.5 | Hydrochloride |
| 158 | —$C_2H_5$ | —$C_2H_5$ | 3 | White powder (Ethyl acetate) | 205.5-209.0 | Hydrochloride |
| 159 | —H | —$CH_2CF_3$ | 3 | White powder (Ethyl acetate) | 217.0 (dec) | Hydrochloride |
| 160 | —H | —$CH_2CH_2N(C_2H_5)_2$ | 3 | White powder (Ethyl acetate) | 229.5-232.5 | Dihydrochloride |
| 161 | —H | —$CH_2CH_2OCH_3$ | 3 | White powder (Ethyl acetate) | 218.5-221.0 | Hydrochloride |
| 162 | —H | -cyclo-$C_2H_5$ | 3 | White powder (Ethyl acetate/isopropyl ether) | 165.5-167.0 | — |
| 163 | —H | —$CH(CH_3)_2$ | 3 | White powder (Ethyl acetate/isopropyl ether) | 131.5-132.5 | — |
| 164 | —H | —H | 3 | White powder (Dichloromethane) | 186.0-191.0 | — |
| 165 | —H | —$(CH_2)_5OH$ | 3 | White solid (Ethanol) | 202-203 | Hydrochloride |
| 166 | —H | 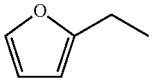 | 3 | Light brown solid (Ethanol) | 215-216 | Hydrochloride |
| 167 | —H | —$C_2H_5$ | 4 | White powder (Ethyl acetate) | 198.0-199.5 | Hydrochloride |
| 168 | —H | —$CH_2CF_3$ | 4 | White powder (Ethyl acetate) | 194.5-196.0 | Hydrochloride |
| 169 | —H | —H | 4 | White powder (2-propanol) | 150.0-151.5 | — |
| 170 | —H | —$CH_3$ | 4 | White powder (Ethyl acetate) | 154.0-156.0 | — |
| 171 | —$CH_3$ | —$CH_3$ | 4 | White powder (Ethyl acetate) | 226.0 (dec) | Hydrochloride |

TABLE 34

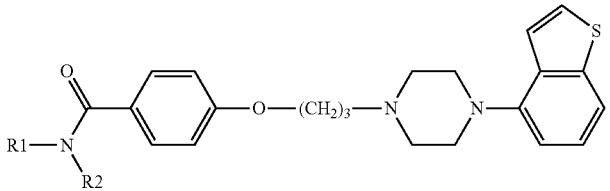

| Example | R1 | R2 | NMR | Salt |
|---|---|---|---|---|
| 172 | —H | —$CH_2CH_2OH$ | $^1$H-NMR (DMSO-$d_6$) δ ppm: 2.1-2.2 (2H, m), 3.1-3.8 (14H, m), 4.17 (2H, t, J = 5.7 Hz), 4.6-4.8 (1H, br), 6.9-7.1 (3H, m), 7.33 (1H, dd, J = 7.9, 8.1 Hz), 7.51 (1H, d, J = 5.5 Hz), 7.72 (1H, d, J = 8.1 Hz), 7.78 (1H, d, J = 5.5 Hz), 7.86 (2H, d, J = 8.8 Hz), 8.2-8.3 (1H, br), 10.2-10.4 (1H, br). | Hydrochloride |

TABLE 35

| Example | R1 | R2 | R3 | R4 | R5 | R6 | Crystal form (Recrystallization solvent) | Melting point (° C.) | Salt |
|---|---|---|---|---|---|---|---|---|---|
| 173 | —H | —H | —H | —OCH$_3$ | —CH$_3$ | —CH$_3$ | White powder (Ethyl acetate) | 199.0-204.0 | Hydrochloride |
| 174 | —OCH$_3$ | —H | —H | —H | —C$_2$H$_5$ | —H | White powder (Ethyl acetate/isopropyl ether) | 162.0-163.0 | — |
| 175 | —Cl | —H | —H | —H | —H | —H | White powder (Ethyl acetate/isopropyl ether) | 154.0-155.5 | — |
| 176 | —Cl | —H | —H | —H | —CH$_3$ | —H | White powder (Ethyl acetate/isopropyl ether) | 145.0-148.0 | — |
| 177 | —H | —H | —H | —Cl | —CH$_3$ | —CH$_3$ | White powder (Ethyl acetate) | 213.0 (dec) | Hydrochloride |
| 178 | —H | —H | —H | —Cl | —C$_2$H$_5$ | —H | White powder (Ethyl acetate) | 211.0 (dec) | Hydrochloride |
| 179 | —Cl | —H | —H | —H | —CH$_2$CF$_3$ | —H | White powder (Ethyl acetate/isopropyl ether) | 128.5-131.0 | — |
| 180 | —F | —H | —H | —H | —H | —H | White powder (Ethyl acetate/isopropyl ether) | 153.5-156.0 | — |

TABLE 36

| Example | R1 | R2 | R3 | R4 | R5 | R6 | Crystal form (Recrystallization solvent) | Melting point (° C.) | Salt |
|---|---|---|---|---|---|---|---|---|---|
| 181 | —H | —H | —H | —F | —CH$_3$ | —H | White powder (Ethyl acetate) | 232.0 (dec) | Hydrochloride |
| 182 | —H | —H | —H | —F | —CH$_3$ | —CH$_3$ | White powder (Ethyl acetate) | 198.0-202.0 | Hydrochloride |
| 183 | —H | —H | —H | —F | —C$_2$H$_5$ | —H | White powder (Ethyl acetate) | 210.5-213.0 | Hydrochloride |
| 184 | —F | —H | —H | —H | —CH$_2$CF$_3$ | —H | Light yellow powder (Ethyl acetate/isopropyl ether) | 176.5-179.5 | — |
| 185 | —CH$_3$ | —H | —H | —H | —H | —H | White powder (2-propanol) | 178.5-180.0 | — |
| 186 | —CH$_3$ | —H | —H | —H | —CH$_3$ | —H | White powder (2-propanol) | 156.5-158.0 | — |
| 187 | —H | —H | —H | —CH$_3$ | —CH$_3$ | —CH$_3$ | White powder (Ethyl acetate) | 220.0-222.0 (dec) | Hydrochloride |
| 188 | —CH$_3$ | —H | —H | —H | —C$_2$H$_5$ | —H | White powder (2-propanol) | 140.5-143.0 | — |
| 189 | —CH$_3$ | —H | —H | —H | —CH$_2$CF$_3$ | —H | White powder (2-propanol) | 154.5-157.0 | — |
| 190 | —OCH$_3$ | —H | —H | —H | —H | —H | White powder (2-propanol) | 162.0-163.5 | — |

TABLE 37

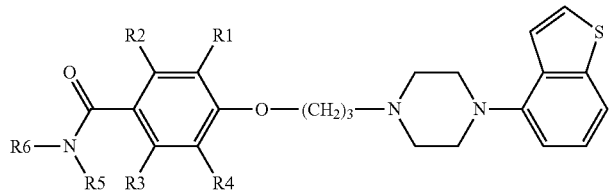

| Example | R1 | R2 | R3 | R4 | R5 | R6 | Crystal form (Recrystallization solvent) | Melting point (° C.) | Salt |
|---|---|---|---|---|---|---|---|---|---|
| 191 | —OCH₃ | —H | —H | —H | —CH₃ | —H | White powder (2-propanol) | 160.5-162.0 | — |
| 192 | —OCH₃ | —H | —H | —H | —CH₂CF₃ | —H | Light yellow powder (2-propanol) | 144.5-146.0 | — |
| 193 | —Cl | —H | —H | —H | —CH₂CH₂OCH₃ | —H | White powder | 120-122 | — |
| 194 | —H | —H | —H | —F | —CH₂CH₂OCH₃ | —H | White powder (Ethanol/ethyl acetate) | 215.0-217.0 | Hydrochloride |
| 195 | —CH₃ | —H | —H | —H | —CH₂CH₂OCH₃ | —H | White powder (Ethanol/hexane) | 120.0-121.0 | — |
| 196 | —H | —H | —H | —OCH₃ | —CH₂CH₂OCH₃ | —H | White powder (Ethanol/ethyl acetate) | 194-196 | Hydrochloride |
| 197 | —Br | —H | —H | —H | —H | —H | White powder (Ethyl acetate/isopropyl ether) | 152.5-154.0 | — |
| 198 | —Br | —H | —H | —H | —CH₃ | —H | White powder (Ethyl acetate/isopropyl ether) | 148.0-150.0 | — |
| 199 | —H | —H | —H | —Br | —CH₃ | —CH₃ | White powder (Ethyl acetate) | 225.0 (dec) | Hydrochloride |
| 200 | —H | —H | —H | —Br | —C₂H₅ | —H | Light yellow powder (Ethyl acetate) | 214.5-220.5 (dec) | Hydrochloride |

TABLE 38

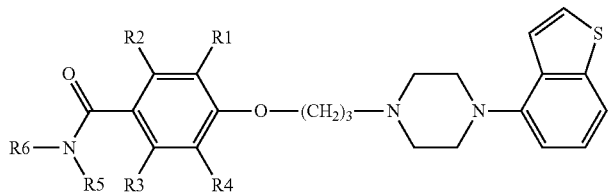

| Example | R1 | R2 | R3 | R4 | R5 | R6 | Crystal form (Recrystallization solvent) | Melting point (° C.) | Salt |
|---|---|---|---|---|---|---|---|---|---|
| 201 | —H | —H | —H | —Br | —CH₂CF₃ | —H | White powder (Ethyl acetate/isopropyl ether) | 230.0-234.5 | Hydrochloride |
| 202 | —CN | —H | —H | —H | —H | —H | White powder (Ethyl acetate) | 182.0-185.0 | — |
| 203 | —CN | —H | —H | —H | —CH₃ | —H | White powder (2-propanol) | 177.5-181.5 | — |
| 204 | —H | —H | —H | —CN | —CH₃ | —CH₃ | White powder (Ethyl acetate) | 213.5-214.0 | Hydrochloride |
| 205 | —CN | —H | —H | —H | —C₂H₅ | —H | White powder (2-propanol) | 162.5-166.0 | — |
| 206 | —H | —H | —H | —CN | —CH₂CF₃ | —H | White powder (Ethyl acetate) | 217.0-222.0 | Hydrochloride |
| 207 | —H | —Cl | —H | —H | —H | —H | White powder (95% 2-propanol) | 133.5-135.5 | — |
| 208 | —H | —Cl | —H | —H | —CH₃ | —H | White powder (95% 2-propanol) | 137.0-139.0 | — |
| 209 | —H | —H | —Cl | —H | —CH₃ | —CH₃ | White powder (Ethyl acetate) | 236.0 (dec) | Hydrochloride |
| 210 | —H | —H | —Cl | —H | —C₂H₅ | —H | White powder (Ethyl acetate) | 223.0-224.0 | Hydrochloride |

TABLE 39

| Example | R1 | R2 | R3 | R4 | R5 | R6 | Crystal form (Recrystallization solvent) | Melting point (° C.) | Salt |
|---|---|---|---|---|---|---|---|---|---|
| 211 | —H | —H | —Cl | —H | —CH₂CF₃ | —H | White powder (Ethyl acetate) | 210.5-216.0 | Hydrochloride |
| 212 | —H | —H | —CF₃ | —H | —C₂H₅ | —H | White powder (Ethyl acetate) | 212.0-219.5 | Hydrochloride |
| 213 | —H | —CF₃ | —H | —H | —H | —H | White powder (Dichloromethane/isopropyl ether) | 139.5-141.0 | Hydrochloride |
| 214 | —H | —H | —CF₃ | —H | —CH₃ | —H | White powder (Ethyl acetate) | 214.0-218.5 | Hydrochloride |
| 215 | —H | —H | —CF₃ | —H | —CH₃ | —CH₃ | White powder (Ethyl acetate) | 252.5 (dec) | Hydrochloride |
| 216 | —H | —H | —CF₃ | —H | —CH₂CF₃ | —H | White powder (Ethyl acetate) | 216.0-218.5 | Hydrochloride |
| 217 | —H | —OCH₃ | —H | —H | —H | —H | White powder (2-propanol) | 173.5-178.5 | — |

TABLE 39-1

| Example | R1 | R2 | R3 | R4 | R5 | R6 | NMR | Salt |
|---|---|---|---|---|---|---|---|---|
| 218 | —N(CH₃)₂ | —H | —H | —H | —C₂H₅ | —H | $^1$H-NMR (CDCl₃) δ ppm: 1.20-1.30 (3H, m), 2.10-2.20 (2H, m), 2.69 (2H, t, J = 7.3 Hz), 2.70-2.75 (4H, m), 2.85 (6H, s), 3.20-3.25 (4H, m), 3.45-3.55 (2H, m), 4.10-4.20 (2H, m), 6.00 (1H, brs), 6.85-6.95 (2H, m), 7.25-7.30 (3H, m), 7.35-7.45 (2H, m), 7.58 (1H, d, J = 8.1 Hz). | — |
| 219 | —NHCOCH₃ | —H | —H | —H | —C₂H₅ | —H | $^1$H-NMR (CDCl₃) δ ppm: 1.20-1.30 (3H, m), 2.05-2.15 (2H, m), 2.25 (3H, s), 2.65 (2H, t, J = 7.1 Hz), 2.70-2.80 (4H, m), 3.20-3.25 (4H, m), 3.40-3.55 (2H, m), 4.21 (2H, t, J = 6.4 Hz), 6.22 (1H, brs), 6.91 (1H, d, J = 7.7 Hz), 6.98 (1H, d, J = 8.6 Hz), 7.25-7.30 (1H, m), 7.35-7.45 (2H, m), 7.56 (1H, d, J = 8.0 Hz), 7.71 (1H, d, J = 8.5 Hz), 7.82 (1H, brs), 8.70 (1H, s). | — |

TABLE 40

| Example | R1 | R2 | R3 | R4 | R5 | R6 | Crystal form (Recrystallization solvent) | Melting point (° C.) | Salt |
|---|---|---|---|---|---|---|---|---|---|
| 220 | —H | —H | —OCH₃ | —H | —CH₃ | —H | White powder (2-propanol) | 221.5-223.0 | Hydrochloride |
| 221 | —H | —H | —OCH₃ | —H | —CH₃ | —CH₃ | White powder (Ethyl acetate) | 207.5-215.0 | Hydrochloride |
| 222 | —H | —H | —OCH₃ | —H | —C₂H₅ | —H | White powder (Ethyl acetate) | 197.0-202.0 | Hydrochloride |
| 223 | —H | —H | —OCH₃ | —H | —CH₂CF₃ | —H | White powder (Ethyl acetate) | 219.0-227.0 | Hydrochloride |

TABLE 40-continued

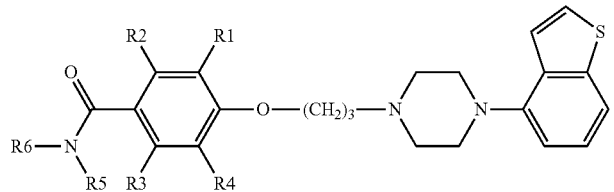

| Example | R1 | R2 | R3 | R4 | R5 | R6 | Crystal form (Recrystallization solvent) | Melting point (° C.) | Salt |
|---|---|---|---|---|---|---|---|---|---|
| 224 | —NO₂ | —H | —H | —H | —H | —H | Light yellow powder (Ethyl acetate/isopropyl ether) | 157.5-161.0 | — |
| 225 | —NO₂ | —H | —H | —H | —CH₃ | —H | Light yellow powder (Ethyl acetate/isopropyl ether) | 157.5-161.5 | — |
| 226 | —H | —H | —H | —NO₂ | —CH₂CF₃ | —H | Light yellow powder (Ethyl acetate) | 217.5-219.5 (dec) | Hydrochloride |
| 227 | —CF₃ | —H | —H | —H | —H | —H | White powder (95% 2-propanol) | 163.5-165.5 | — |
| 228 | —NH₂ | —H | —H | —H | —H | —H | White powder (Ethyl acetate/isopropyl ether) | 172.5-173.0 | — |
| 229 | —CF₃ | —H | —H | —H | —CH₃ | —H | White powder (95% 2-propanol) | 158.5-162.0 | — |
| 230 | —CF₃ | —H | —H | —H | —C₂H₅ | —H | White powder (95% 2-propanol) | 146.5-148.5 | — |

TABLE 41

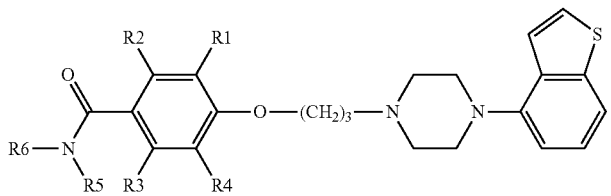

| Example | R1 | R2 | R3 | R4 | R5 | R6 | Crystal form (Recrystallization solvent) | Melting point (° C.) | Salt |
|---|---|---|---|---|---|---|---|---|---|
| 231 | —CF₃ | —H | —H | —H | —CH₂CF₃ | —H | White powder (95% 2-propanol) | 144.5-150.0 | — |
| 232 | —NH₂ | —H | —H | —H | —CH₃ | —H | White powder (Ethyl acetate/isopropyl ether) | 124.0-125.5 | — |
| 233 | —N(CH₃)₂ | —H | —H | —H | —H | —H | White powder (Ethyl acetate/isopropyl ether) | 143.0-145.0 | — |
| 234 | —H | —H | —H | —N(CH₃)₂ | —CH₃ | —H | White powder (Ethyl acetate) | 219.0-223.0 | Hydrochloride |
| 235 | —NH₂ | —H | —H | —H | —CH₂CF₃ | —H | White powder (Ethyl acetate/isopropyl ether) | 125.0-126.0 | — |
| 236 | —N(CH₃)₂ | —H | —H | —H | —CH₂CF₃ | —H | White powder (Ethyl acetate/isopropyl ether) | 147.5-148.5 | — |
| 237 | —H | —CH₃ | —H | —H | —H | —H | White powder (95% 2-propanol) | 150.5-152.5 | — |
| 238 | —H | —CH₃ | —H | —H | —CH₃ | —H | White powder (95% 2-propanol) | 138.0-139.0 | — |
| 239 | —H | —CH₃ | —H | —H | —C₂H₅ | —H | White powder (95% 2-propanol) | 137.5-139.0 | — |
| 240 | —CH₃ | —H | —H | —CH₃ | —H | —H | White powder (95% 2-propanol) | 167.0-168.0 | — |

TABLE 42

| Example | R1 | R2 | R3 | R4 | R5 | R6 | Crystal form (Recrystallization solvent) | Melting point (° C.) | Salt |
|---|---|---|---|---|---|---|---|---|---|
| 241 | —CH₃ | —H | —H | —CH₃ | —CH₃ | —H | White powder (95% 2-propanol) | 152.5-154.5 | — |
| 242 | —CH₃ | —H | —H | —CH₃ | —C₂H₅ | —H | White powder (95% 2-propanol) | 184.0-185.5 | — |
| 243 | —OCH₃ | —H | —H | —OCH₃ | —H | —H | White powder (Ethyl acetate/isopropyl ether) | 147.5-148.0 | — |
| 244 | —OCH₃ | —H | —H | —OCH₃ | —CH₃ | —H | White powder (Ethyl acetate) | 233.0-237.5 (dec) | Hydrochloride |
| 245 | —OCH₃ | —H | —H | —OCH₃ | —C₂H₅ | —H | White powder (Ethyl acetate/isopropyl ether) | 145.5-147.5 | — |
| 246 | —OC₂H₅ | —H | —H | —CH₃ | —CH₃ | —H | White powder (Ethanol/ethyl acetate) | 186.5-188.0 | Hydrochloride |
| 247 | —CH₂CH=CH₂ | —H | —H | —OCH₃ | —H | —H | (Ethyl acetate/isopropyl ether) | 126.0-130.0 | — |
| 248 | —C₃H₇ | —H | —H | —OCH₃ | —H | —H | (Ethyl acetate/isopropyl ether) | 137.5-140.0 | — |
| 249 | —OCH₃ | —H | —H | —CH₂CH=CH₂ | —CH₃ | —H | White powder (Ethyl acetate) | 180.5-186.0 | Hydrochloride |
| 250 | —OCH₃ | —H | —H | —C₃H₇ | —CH₃ | —H | White powder (Ethyl acetate) | 186.5-192.0 | Hydrochloride |

TABLE 43

| Example | R1 | R2 | R3 | R4 | R5 | R6 | Crystal form (Recrystallization solvent) | Melting point (° C.) | Salt |
|---|---|---|---|---|---|---|---|---|---|
| 251 | —CH₃ | —H | —H | —OCH₃ | —H | —H | White powder (Ethyl acetate/isopropyl ether) | 156.0-157.0 | — |
| 252 | —CH₃ | —H | —H | —OCH₃ | —CH₃ | —H | White powder (Ethyl acetate/methanol) | 141.5-142.5 | — |
| 253 | —OCH₃ | —H | —H | —CH₃ | —C₂H₅ | —H | White powder (Ethyl acetate) | 220.5-224.5 | Hydrochloride |
| 254 | —OCH₃ | —H | —H | —CH₃ | —CH₃ | —OCH₃ | White powder (Ethyl acetate) | 223.0-227.5 | Hydrochloride |

TABLE 44

| Example | R1 | R2 | R3 | R4 | R5 | R6 | NMR | Salt |
|---|---|---|---|---|---|---|---|---|
| 255 | —H | —H | —H | —NO₂ | —C₂H₅ | —H | ¹H-NMR (CDCl₃) δ ppm: 1.28 (3H, t, J = 7.3 Hz), 2.05-2.15 (2H, m), 2.68 (2H, t, J = 7.0 Hz), 2.73 (4H, brs), 3.19 (4H, brs), 3.45-3.55 (2H, m), 4.29 (2H, t, J = 8.2 Hz), 6.14 (1H, brs), 6.90 (1H, d, J = 7.6 Hz), 7.18 (1H, d, J = 8.8 Hz), 7.25-7.30 (1H, m), 7.35-7.45 (2H, m), 7.55 (1H, d, J = 8.1 Hz), 8.04 (1H, dd, J = 2.3, 8.8 Hz), 8.23 (1H, d, J = 2.2 Hz). | — |

TABLE 45

| Example | R1 | R2 | R3 | R4 | R5 | Crystal form (Recrystallization solvent) | Melting point (° C.) | Salt |
|---|---|---|---|---|---|---|---|---|
| 256 | —H | —H | —H | —H | morpholine | White powder (Ethyl acetate) | 234.5-238.0 | Hydrochloride |
| 257 | —H | —H | —H | —H | 4-methylpiperazine | White powder (Ethyl acetate) | 244.0 (dec) | Dihydrochloride |
| 258 | —H | —H | —H | —Cl | morpholine | White powder (Ethyl acetate) | 218.5-222.0 | Hydrochloride |
| 259 | —H | —H | —H | —Cl | 4-methylpiperazine | White powder (Ethyl acetate) | 255.0 (dec) | Dihydrochloride |
| 260 | —H | —H | —H | —F | morpholine | White powder (Ethyl acetate) | 224.5-227.5 (dec) | Hydrochloride |
| 261 | —H | —H | —H | —F | 4-methylpiperazine | White powder (Ethyl acetate) | 255.0 (dec) | Dihydrochloride |
| 262 | —H | —H | —H | —CH$_3$ | morpholine | White powder (Ethyl acetate) | 236.0 (dec) | Hydrochloride |
| 263 | —H | —H | —H | —CH$_3$ | 4-methylpiperazine | White powder (Ethyl acetate) | 255.5 (dec) | Dihydrochloride |
| 264 | —H | —H | —H | —OCH$_3$ | morpholine | White powder (Ethyl acetate) | 226.0-228.0 (dec) | Hydrochloride |
| 265 | —H | —H | —H | —OCH$_3$ | 4-methylpiperazine | White powder (Ethyl acetate) | 232.0 (dec) | Dihydrochloride |

TABLE 46

| Example | R1 | R2 | R3 | R4 | R5 | R6 | Crystal form (Recrystallization solvent) | Melting point (° C.) | Salt |
|---|---|---|---|---|---|---|---|---|---|
| 266 | —H | —H | —H | —H | —H | —H | Light yellow powder (Ethyl acetate/isopropyl ether) | 158.0-160.0 | — |
| 267 | —H | —H | —H | —H | —H | —CH$_3$ | Light yellow powder (Ethyl acetate) | 183.0-186.0 | Hydrochloride |
| 268 | —H | —H | —H | —H | —CH$_3$ | —CH$_3$ | Light yellow powder (Ethyl acetate) | 158.0-161.5 | Hydrochloride |

TABLE 46-continued

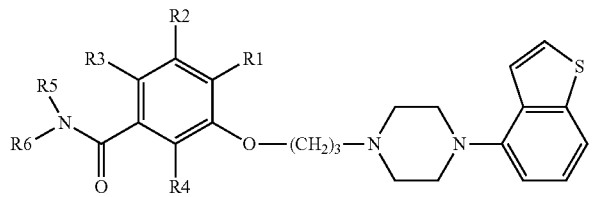

| Example | R1 | R2 | R3 | R4 | R5 | R6 | Crystal form (Recrystallization solvent) | Melting point (° C.) | Salt |
|---|---|---|---|---|---|---|---|---|---|
| 269 | —H | —H | —H | —H | —H | —$C_2H_5$ | Light yellow powder (Ethyl acetate) | 168.5-173.0 | Hydrochloride |
| 270 | —H | —H | —H | —H | —H | —$CH_2CF_3$ | Light yellow powder (Ethyl acetate/isopropyl ether) | 187.5-189.0 | Hydrochloride |
| 271 | —F | —H | —H | —H | —H | —H | White powder (Ethyl acetate/isopropyl ether) | 156.5-159.0 | — |
| 272 | —F | —H | —H | —H | —H | —$CH_3$ | White powder (Ethyl acetate/isopropyl ether) | 214.5-218.0 | Hydrochloride |
| 273 | —F | —H | —H | —H | —H | —$C_2H_5$ | White powder (Ethyl acetate) | 211.0-218.0 | Hydrochloride |
| 274 | —Cl | —H | —H | —H | —H | —H | White powder (Ethyl acetate/isopropyl ether) | 139.0-140.5 | — |
| 275 | —Cl | —H | —H | —H | —H | —$CH_3$ | White powder (Ethyl acetate) | 218.5-222.5 | Hydrochloride |
| 276 | —Cl | —H | —H | —H | —H | —$C_2H_5$ | White powder (Ethyl acetate) | 247.0 (dec) | Hydrochloride |
| 277 | —$CH_3$ | —H | —H | —H | —H | —H | White powder (Ethyl acetate/isopropyl ether) | 129.5-130.0 | — |
| 278 | —$CH_3$ | —H | —H | —H | —H | —$CH_3$ | White powder (Ethyl acetate/isopropyl ether) | 148.5-151.0 | — |
| 279 | —$CH_3$ | —H | —H | —H | —H | —$C_2H_5$ | White powder (Ethyl acetate/isopropyl ether) | 133.0-134.5 | — |
| 280 | —$OCH_3$ | —H | —H | —H | —H | —H | White powder (Ethyl acetate) | 155.5-160.0 | — |
| 281 | —$OCH_3$ | —H | —H | —H | —H | —$CH_3$ | White powder (Ethyl acetate) | 163.5-165.0 | Hydrochloride |

TABLE 47

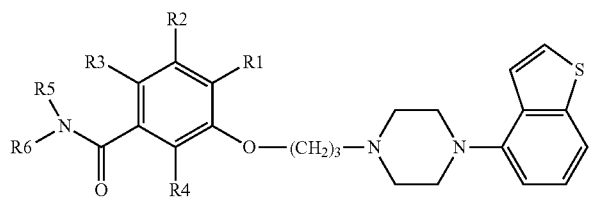

| Example | R1 | R2 | R3 | R4 | R5 | R6 | Crystal form (Recrystallization solvent) | Melting point (° C.) | Salt |
|---|---|---|---|---|---|---|---|---|---|
| 282 | —$OCH_3$ | —H | —H | —H | —H | —$C_2H_5$ | White powder (Ethyl acetate) | 187.0-188.5 | Hydrochloride |
| 283 | —$OCH_3$ | —$OCH_3$ | —H | —H | —H | —H | White powder (Ethyl acetate/isopropyl ether) | 132.0-134.0 | — |
| 284 | —$OCH_3$ | —$OCH_3$ | —H | —H | —H | —$CH_3$ | White powder (Ethyl acetate) | 201.0-206.0 | Hydrochloride |
| 285 | —$OCH_3$ | —$OCH_3$ | —H | —H | —H | —$C_2H_5$ | White powder (Ethyl acetate/isopropyl ether) | 156.0-158.5 | — |

TABLE 48

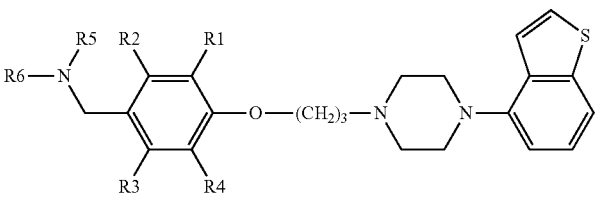

| Example | R1 | R2 | R3 | R4 | R5 | R6 | Crystal form (Recrystallization solvent) | Melting point (° C.) | Salt |
|---|---|---|---|---|---|---|---|---|---|
| 286 | —H | —H | —H | —H | —$C_2H_5$ | —H | Light yellow powder (Ethyl acetate) | 228.0-241.0 (dec) | Dihydrochloride |
| 287 | —H | —H | —H | —H | —$C_3H_7$ | —H | White powder (Ethyl acetate) | 232.0-236.0 (dec) | Dihydrochloride |
| 288 | —H | —H | —H | —H | —$C_3H_7$ | —$CH_3$ | White powder (Ethyl acetate) | 210.0-222.0 (dec) | Dihydrochloride |
| 289 | —H | —H | —H | —H | —$CH_3$ | —H | White powder (Ethyl acetate) | 235.5 (dec) | Dihydrochloride |
| 290 | —H | —H | —H | —H | —$CH_3$ | —$CH_3$ | White powder (Ethyl acetate) | 257.5 (dec) | Dihydrochloride |
| 291 | —H | —H | —H | —H | —$C_2H_5$ | —$C_2H_5$ | White powder (Ethyl acetate) | 232.0 (dec) | Dihydrochloride |
| 292 | —H | —H | —H | —H | —$CH_2CF_3$ | —H | White powder (Ethyl acetate) | 238.5-240.5 (dec) | Dihydrochloride |
| 293 | —H | —H | —H | —H | —$CH_2CH_2N(C_2H_5)_2$ | —H | White powder (Ethyl acetate) | 209.5 (dec) | Triydrochloride |
| 294 | —H | —H | —H | —H | —H | —H | Light yellow powder (Ethyl acetate) | 245.5 (dec) | Dihydrochloride |
| 295 | —H | —H | —H | —H | —CHO | —H | White powder (Ethyl acetate) | 207.5-213.0 | Hydrochloride |
| 296 | —H | —H | —H | —H | —$COCH_3$ | —$CH_3$ | White powder (Ethyl acetate) | 196.5-201.0 | Hydrochloride |
| 297 | —H | —H | —H | —H | —$COC_2H_5$ | —$CH_3$ | White powder (Ethyl acetate) | 194.5-198.0 | Hydrochloride |
| 298 | —H | —H | —H | —H | —$COC_6H_5$ | —$CH_3$ | White powder (Ethyl acetate) | 192.5-195.5 | Hydrochloride |
| 299 | —H | —H | —H | —H | —$CH_2C_6H_5$ | —$CH_3$ | White powder (Ethyl acetate) | 236.5 (dec) | Dihydrochloride |
| 300 | —H | —H | —H | —H | —$C_6H_5$ | —H | White powder (Ethyl acetate) | 191.0-193.5 | Dihydrochloride |
| 301 | —$OCH_3$ | —H | —H | —H | —$CH_3$ | —$CH_3$ | White powder | 101.0-103.0 | — |

TABLE 48-continued

| Example | R1 | R2 | R3 | R4 | R5 | R6 | Crystal form (Recrystallization solvent) | Melting point (° C.) | Salt |
|---|---|---|---|---|---|---|---|---|---|
| 302 | —H | —H | —H | —H | —C₆H₅ | —CH₃ | White powder (Ethyl acetate) (Ethyl acetate/isopropyl ether) | 207.5-214.5 | Trihydrochloride |
| 303 | —H | —H | —H | —Cl | —CH₃ | —CH₃ | White powder (Ethyl acetate) | 259.0 (dec) | Dihydrochloride |
| 304 | —H | —H | —H | —F | —CH₃ | —CH₃ | White powder (Ethyl acetate) | 247.0 (dec) | Dihydrochloride |
| 305 | —H | —H | —H | —F | —CH₃ | —H | White powder (Ethyl acetate) | 237.0 (dec) | Dihydrochloride |
| 306 | —H | —H | —H | —F | —CH₃ | —COCH₃ | White powder (Ethyl acetate) | 196.0-199.0 | Hydrochloride |

TABLE 49

| Example | R1 | R2 | R3 | R4 | R5 | R6 | Crystal form (Recrystallization solvent) | Melting point (° C.) | Salt |
|---|---|---|---|---|---|---|---|---|---|
| 307 | —H | —H | —H | —CH₃ | —CH₃ | —C₂H₅ | White powder (Ethyl acetate) | 256.5 (dec) | Dihydrochloride |
| 308 | —H | —H | —H | —CH₃ | —CH₃ | —H | White powder (Ethyl acetate) | 254.5 (dec) | Dihydrochloride |
| 309 | —H | —H | —H | —CH₃ | —CH₃ | —CH₃ | White powder (Ethyl acetate) | 277.5 (dec) | Dihydrochloride |
| 310 | —H | —H | —H | —CH₃ | —COCH₃ | —CH₃ | White powder (Ethyl acetate) | 230.0-232.0 (dec) | Hydrochloride |
| 311 | —OCH₃ | —H | —H | —H | —CH₃ | —H | White powder (Ethyl acetate) | 239.5 (dec) | Dihydrochloride |
| 312 | —H | —H | —H | —OCH₃ | —CH₃ | —COCH₃ | White powder (Ethyl acetate) | 206.0-211.5 | Hydrochloride |

TABLE 50

| Example | R1 | R2 | R3 | R4 | R5 | Crystal form (Recrystallization solvent) | Melting point (° C.) | Salt |
|---|---|---|---|---|---|---|---|---|
| 313 | —H | —H | —H | —H | morpholinyl | White powder (Ethyl acetate) | 243.5 (dec) | Dihydrochloride |
| 314 | —H | —H | —H | —H | 4-methylpiperazinyl | White powder (Ethyl acetate) | 261.5 (dec) | Dihydrochloride |
| 315 | —H | —H | —H | —Cl | morpholinyl | White powder (Ethyl acetate) | 249.0 (dec) | Dihydrochloride |
| 316 | —H | —H | —H | —Cl | 4-methylpiperazinyl | White powder (Ethyl acetate) | 253.5 (dec) | Trihydrochloride |

TABLE 50-continued

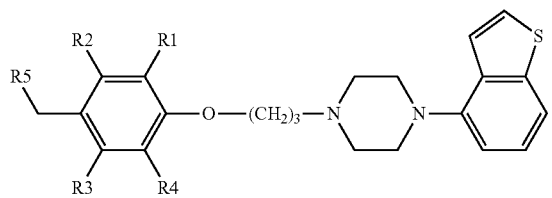

| Example | R1 | R2 | R3 | R4 | R5 | Crystal form (Recrystallization solvent) | Melting point (° C.) | Salt |
|---|---|---|---|---|---|---|---|---|
| 317 | —H | —H | —H | —F | (morpholinomethyl) | White powder (Ethyl acetate) | 252.0 (dec) | Dihydrochloride |
| 318 | —H | —H | —H | —CH₃ | (morpholinomethyl) | White powder (Ethyl acetate) | 242.0 (dec) | Dihydrochloride |

TABLE 51

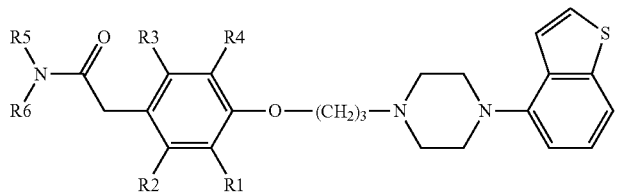

| Example | R1 | R2 | R3 | R4 | R5 | R6 | Crystal form (Recrystallization solvent) | Melting point (° C.) | Salt |
|---|---|---|---|---|---|---|---|---|---|
| 319 | —H | —H | —H | —H | —C$_2$H$_5$ | —C$_2$H$_5$ | Light yellow powder (Ethyl acetate) | 179.0-183.5 | Hydrochloride |
| 320 | —H | —H | —H | —H | —H | —H | White powder (Ethyl acetate/water) | 150.0-154.5 | — |
| 321 | —H | —H | —H | —H | —H | —CH$_3$ | White powder (Ethyl acetate) | 198.0-207.0 | Hydrochloride |
| 322 | —H | —H | —H | —H | —CH$_3$ | —CH$_3$ | White powder (Ethyl acetate/isopropyl ether) | 128.0-129.5 | — |
| 323 | —H | —H | —H | —H | —H | —C$_2$H$_5$ | White powder (Ethyl acetate/isopropyl ether) | 112.5-113.5 | — |
| 324 | —H | —H | —H | —H | —H | —CH$_2$CF$_3$ | White powder (Ethyl acetate/isopropyl ether) | 126.0-127.0 | — |
| 325 | —Cl | —H | —H | —H | —H | —H | White powder (2-propanol) | 161.5-166.0 | — |
| 326 | —H | —H | —H | —Cl | —H | —CH$_3$ | White powder (Ethyl acetate) | 194.5-197.0 | Hydrochloride |
| 327 | —H | —H | —H | —Cl | —CH$_3$ | —CH$_3$ | White powder (Ethyl acetate) | 197.5-201.0 | Hydrochloride |
| 328 | —H | —H | —H | —Cl | —H | —C$_2$H$_5$ | White powder (Ethyl acetate) | 227.5 (dec) | Hydrochloride |
| 329 | —H | —H | —H | —Cl | —H | —CH$_2$CF$_3$ | (Ethyl acetate) | 204.0-206.0 | Hydrochloride |
| 330 | —OCH$_3$ | —H | —H | —H | —H | —H | White powder (Ethyl acetate/isopropyl ether) | 129.0-130.0 | — |
| 331 | —H | —H | —H | —OCH$_3$ | —H | —CH$_3$ | White powder (Ethyl acetate) | 176.0-178.5 | Hydrochloride |
| 332 | —H | —H | —H | —OCH$_3$ | —CH$_3$ | —CH$_3$ | White powder (Ethyl acetate) | 188.5-192.0 | Hydrochloride |
| 333 | —H | —H | —H | —OCH$_3$ | —H | —C$_2$H$_5$ | White powder (Ethyl acetate) | 178.0-184.0 | Hydrochloride |
| 334 | —H | —H | —H | —OCH$_3$ | —H | —CH$_2$CF$_3$ | Light yellow powder (Ethyl acetate) | 187.5-192.0 | Hydrochloride |

TABLE 52

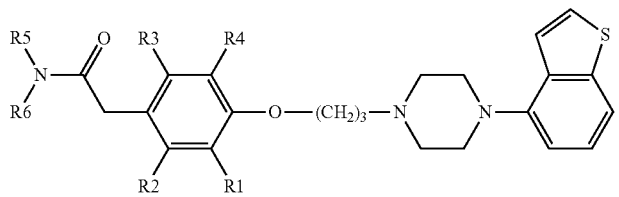

| Example | R1 | R2 | R3 | R4 | R5 | R6 | Crystal form (Recrystallization solvent) | Melting point (° C.) | Salt |
|---|---|---|---|---|---|---|---|---|---|
| 335 | —F | —H | —H | —H | —H | —H | White powder (2-propanol) | 146.5-150.0 | — |
| 336 | —H | —H | —H | —F | —H | —CH$_3$ | White powder (Ethyl acetate) | 191.0-193.0 | Hydrochloride |
| 337 | —H | —H | —H | —F | —CH$_3$ | —CH$_3$ | White powder (Ethyl acetate) | 192.5-197.0 | Hydrochloride |
| 338 | —H | —H | —H | —F | —H | —C$_2$H$_5$ | White powder (Ethyl acetate) | 216.0-220.5 | Hydrochloride |
| 339 | —H | —H | —H | —F | —H | —CH$_2$CF$_3$ | Light yellow powder (Ethyl acetate) | 197.0-202.0 | Hydrochloride |
| 340 | —H | —H | —H | —H | —H | —H | White powder (Ethyl acetate/isopropyl ether) | 149.5-150.5 | — |

TABLE 53

| Example | R1 | R2 | R3 | R4 | R5 | Crystal form (Recrystallization solvent) | Melting point (° C.) | Salt |
|---|---|---|---|---|---|---|---|---|
| 341 | —H | —H | —H | —H | (N-methylmorpholinyl group) | White powder (Ethyl acetate/isopropyl ether) | 130.5-131.5 | — |
| 342 | —H | —H | —H | —H | (4-methylpiperazin-1-yl group) | White powder (Ethyl acetate) | 227.5 (dec) | Dihydrochloride |

TABLE 54

| Example | R1 | R2 | R3 | R4 | R5 | Crystal form (Recrystallization solvent) | Melting point (° C.) | Salt |
|---|---|---|---|---|---|---|---|---|
| 343 | —H | —H | —NHCOCH₃ | —H | —H | White powder (Ethanol) | 283.0-285.0 | Hydrochloride |
| 344 | —H | —H | —NHCO₂CH₃ | —H | —H | Light yellow powder (Ethyl acetate/isopropyl ether) | 149.5-150.5 | — |
| 345 | —H | —H | —NHSO₂C₂H₅ | —H | —H | Light yellow powder (Ethanol/ethyl acetate) | 174-176 | Dihydrochloride |
| 346 | —H | —H | —NHC₂H₅ | —H | —H | White powder (Ethyl acetate) | 225 (dec) | Hydrochloride |
| 347 | —H | —H | —N(CH₃)CO₂CH₃ | —H | —H | White powder (Ethyl acetate) | 196.0-202.0 | Hydrochloride |
| 348 | —H | —H | —N(CH₃)COCH₃ | —H | —H | White powder (Ethanol) | 246-247 | Hydrochloride |
| 349 | —H | —H | —NH₂ | —H | —H | White powder (Ethanol containing water) | 266-271 (dec) | Hydrochloride |
| 350 | —H | —H | —NHCH₃ | —H | —H | White powder (Ethanol) | 264-266 | Dihydrochloride |
| 351 | —H | —H | —N(CH₃)₂ | —H | —H | White powder (Ethanol) | 269-270 | Dihydrochloride |
| 352 | —CH₃ | —H | —NH₂ | —H | —OCH₃ | Light yellow solid (Ethyl acetate) | 155.0-158.0 | — |
| 353 | —OCH₃ | —H | —NHCON(CH₃)₂ | —H | —CH₃ | White powder (Ethyl acetate) | 206.0-210.0 | Hydrochloride |
| 354 | —OCH₃ | —H | —NHCHO | —H | —CH₃ | White powder (Ethyl acetate) | 247.5-253.0 (dec) | Hydrochloride |
| 355 | —OCH₃ | —H | —NHCO₂CH₃ | —H | —CH₃ | White powder (Ethyl acetate) | 230.0-235.5 | Hydrochloride |

TABLE 55

Structure: R1, R2, R3, R4, R5 substituted phenyl-O-(CH2)3-piperazine-benzothiophene

| Example | R1 | R2 | R3 | R4 | R5 | Crystal form (Recrystallization solvent) | Melting point (° C.) | Salt |
|---|---|---|---|---|---|---|---|---|
| 356 | —H | —H | 3-methyl-2-oxoimidazolidin-1-yl (HN-C(=O)-N(CH3)-CH2-CH2-) | —H | —H | White powder (Ethyl acetate/2-propanol) | 154.5-156.5 | — |
| 357 | —H | —H | 1,3-dimethyl-2-oxoimidazolidin-1-yl (H3C-N-C(=O)-N(CH3)-CH2-CH2-) | —H | —H | White powder (2-propanol) | 141.0-144.5 | — |
| 358 | —OCH3 | —H | 3-methyl-2-oxooxazolidin-1-yl (O-C(=O)-N(CH3)-CH2-CH2-) | —H | —CH3 | White powder (Ethanol) | 247.5-251.0 (dec) | Hydrochloride |
| 359 | —CH2OH | —H | 1-methyl-2-oxopyrrolidin-3-yl | —H | —OCH3 | White powder (Ethanol) | 144.0-145.0 | Hydrochloride |

TABLE 56

Structure: R1, R2, R3, R4, R5 substituted phenyl-O-(CH2)3-piperazine-benzothiophene

| Example | R1 | R2 | R3 | R4 | R5 | NMR | Salt |
|---|---|---|---|---|---|---|---|
| 360 | —H | —H | —NHCH(CH3)2 | —H | —H | $^1$H-NMR (DMSO-d$_6$) δ ppm: 1.24 (6H, d, J = 6.5 Hz), 2.2-2.4 (2H, m), 3.15-3.8 (12H, m), 4.15 (2H, t, J = 6 Hz), 6.99 (1H, d, J = 7.5 Hz), 7.11 (2H, d, J = 9 Hz), 7.33 (1H, dd, J = 8, 8 Hz), 7.4-7.55 (3H, m), 7.71 (1H, d, J = 8 Hz), 7.78 (1H, d, J = 5.5 Hz), 10.87 (3H, br). | Trihydrochloride |
| 361 | —OCH3 | —H | —NHCO2CH3 | —H | —H | $^1$H-NMR (CDCl3) δ ppm: 2.00-2.15 (2H, m), 2.60-2.70 (2H, m), 2.73 (4H, brs), 3.20 (4H, brs), 3.77 (3H, s), 3.88 (3H, s), 4.10 (2H, t, J = 6.6 Hz), 8.52 (1H, brs), 8.74 (1H, dd, J = 2.5, 8.8 Hz), 6.87 (1H, d, J = 8.6 Hz), 6.90 (1H, d, J = 7.7 Hz), 7.19 (1H, brs), 7.28 (1H, dd, J = 7.8, 7.8 Hz), 7.35-7.45 (2H, m), 7.55 (1H, d, J = 7.8 Hz). | — |
| 362 | —H | —H | —NHCON(CH3)2 | —H | —H | $^1$H-NMR (DMSO-d$_6$) δ ppm: 2.20-2.30 (2H, m), 2.91 (6H, s), 3.20-3.40 (6H, m), 3.55 (2H, d, J = 12.4 Hz), 3.65 (2H, d, J = 11.4 Hz), 4.05 (2H, t, J = 6.0 Hz), 6.88 (2H, d, J = 9.0 Hz), 6.98 (1H, d, J = 7.6 Hz), 7.30-7.40 (3H, m), 7.50 (1H, d, J = 5.5 Hz), 7.71 (1H, d, J = 8.1 Hz), 7.78 (1H, d, J = 5.5 Hz), 8.16 (1H, brs), 11.05 (1H, brs). | Dihydrochloride |
| 363 | —F | —H | —NHCO2CH3 | —H | —H | $^1$H-NMR (DMSO-d$_6$) δ ppm: 2.24 (2H, brs), 3.10-3.25 (2H, m), 3.30-3.50 (4H, m), 3.50-3.60 (2H, m), 3.66 (3H, s), 3.65-3.70 (2H, m), 4.13 (2H, t, J = 5.9 Hz), 6.98 (1H, d, J = 7.6 Hz), 7.10-7.20 (2H, m), 7.32 (1H, dd, J = 7.9, 7.9 Hz), 7.40 (1H, d, J = 13.3 Hz), 7.50 (1H, d, J = 5.5 Hz), 7.71 (1H, d, J = 8.1 Hz), 7.77 (1H, d, J = 5.5 Hz), 9.69 (1H, brs), 10.56 (1H, brs). | Hydrochloride |

TABLE 56-1

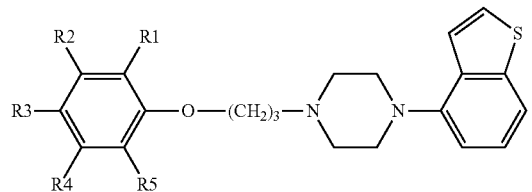

| Example | R1 | R2 | R3 | R4 | R5 | NMR | Salt |
|---|---|---|---|---|---|---|---|
| 364 | —H | —H | —NHCONH$_2$ | —H | —H | $^1$H-NMR (CDCl$_3$) δ ppm: 1.95-2.10 (2H, m), 2.64 (2H, t, J = 7.3 Hz), 2.70-2.75 (4H, m), 3.15-3.20 (4H, m), 4.03 (2H, t, J = 6.3 Hz), 4.83 (2H, brs), 6.83 (1H, brs), 6.85-6.95 (3H, m), 7.20 (2H, d, J = 8.6 Hz), 7.25-7.30 (1H, m), 7.35-7.45 (2H, m), 7.55 (1H, d, J = 8.1 Hz). | — |
| 365 | —H | —H | —NHCON(C$_2$H$_5$)$_2$ | —H | —H | $^1$H-NMR (DMSO-d$_6$) δ ppm: 1.08 (6H, t, J = 7.0 Hz), 2.15-2.30 (2H, m), 3.20-3.45 (10H, m), 3.54 (2H, d, J = 12 Hz), 3.64 (2H, d, J = 12 Hz), 4.03 (2H, t, J = 5.9 Hz), 6.84 (2H, d, J = 8.9 Hz), 6.97 (1H, d, J = 7.7 Hz), 7.25-7.40 (3H, m), 7.49 (1H, d, J = 5.6 Hz), 7.70 (1H, d, J = 8.1 Hz), 7.76 (1H, d, J = 5.6 Hz), 8.01 (1H, s), 10.95 (1H, s). | Dihydrochloride |
| 366 | —H | —H | N-methylimidazolyl | —H | —H | $^1$H-NMR (DMSO-d$_6$) δ ppm: 2.05-2.10 (2H, m), 2.67 (2H, t, J = 7.3 Hz), 2.76 (4H, brs), 3.22 (4H, brs), 4.11 (2H, t, J = 6.3 Hz), 6.91 (1H, d, J = 7.6 Hz), 7.01 (2H, d, J = 8.9 Hz), 7.20 (2H, d, J = 9.6 Hz), 7.25-7.35 (3H, m), 7.35-7.45 (2H, m), 7.56 (1H, d, J = 8.0 Hz), 7.77 (1H, s). | — |
| 367 | —H | —H | N-methyltriazolyl | —H | —H | $^1$H-NMR (CDCl$_3$) δ ppm: 2.05-2.15 (2H, m), 2.67 (2H, t, J = 7.2 Hz), 2.75 (4H, brs), 3.21 (4H, brs), 4.12 (2H, t, J = 6.3 Hz), 6.91 (1H, d, J = 7.6 Hz), 7.00-7.05 (2H, m), 7.25-7.30 (1H, m), 7.35-7.45 (2H, m), 7.50-7.60 (3H, m), 8.08 (1H, s), 8.45 (1H, s). | — |

TABLE 57

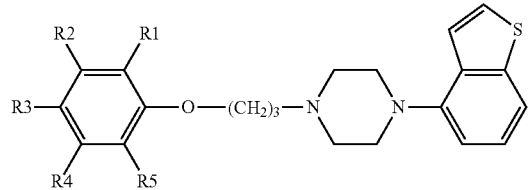

| Example | R1 | R2 | R3 | R4 | R5 | Crystal form (Recrystallization solvent) | Melting point (° C.) | Salt |
|---|---|---|---|---|---|---|---|---|
| 368 | —H | —H | —CH$_2$CH$_2$N(C$_2$H$_5$)$_2$ | —H | —H | White powder (Ethyl acetate) | 224.0-232.0 (dec) | Dihydrochloride |
| 369 | —H | —H | —H | —NHCO$_2$CH$_3$ | —H | White powder (Ethyl acetate) | 178.0-181.0 (dec) | Hydrochloride |
| 370 | —H | —H | —CN | —H | —H | Light yellow powder (Ethyl acetate/isopropyl ether) | 105.5-107.0 | — |
| 371 | —H | —H | —CO$_2$H | —H | —H | White powder (Hydrochloric acid/acetic acid) | 263.0 (dec) | Hydrochloride |
| 372 | —H | —H | —CO$_2$CH$_3$ | —H | —OCH$_3$ | White powder (Ethyl acetate) | 242.0 (dec) | Hydrochloride |
| 373 | —H | —H | —Br | —H | —H | White powder (Ethyl acetate/isopropyl ether) | 119.0-120.0 | — |
| 374 | —OCH$_3$ | —H | —CO$_2$H | —H | —H | White powder (Water) | 121.0-124.5 | — |
| 375 | —Cl | —H | —CO$_2$C$_2$H$_5$ | —H | —H | Light yellow powder (Ethanol/isopropyl ether) | 122.0-123.5 | — |
| 376 | —H | —H | —CH$_2$CO$_2$CH$_3$ | —H | —H | White powder (Ethyl acetate) | 213.5-221.5 (dec) | Hydrochloride |
| 377 | —H | —H | —CO$_2$C$_2$H$_5$ | —H | —F | White powder (Ethyl acetate) | 231.5-233.5 | Hydrochloride |

TABLE 58

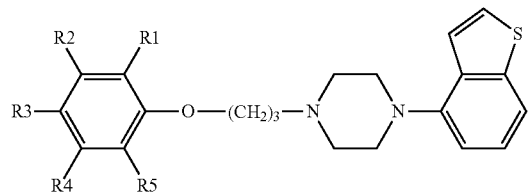

| Example | R1 | R2 | R3 | R4 | R5 | Crystal form (Recrystallization solvent) | Melting point (° C.) | Salt |
|---|---|---|---|---|---|---|---|---|
| 378 | —H | —H | —CO$_2$H | —H | —Cl | White powder (Hydrochloric acid/acetic acid) | 273.0 (dec) | Hydrochloride |
| 379 | —H | —H | —CH$_2$CO$_2$H | —H | —H | White powder (Hydrochloric acid/acetic acid) | 217.0-222.0 | Hydrochloride |
| 380 | —H | —H | —CO$_2$H | —H | —F | White powder (Hydrochloric acid/acetic acid) | 267.0 (dec) | Hydrochloride |
| 381 | —H | —H | —CH$_2$CH$_2$NHCH$_3$ | —H | —H | White powder (Ethyl acetate) | 258.0 (dec) | Dihydrochloride |
| 382 | —H | —H | —CH$_2$CH$_2$N(CH$_3$)$_2$ | —H | —H | White powder (Ethyl acetate) | 238.5 (dec) | Dihydrochloride |
| 383 | —H | —H | —CH$_2$CH$_2$N(CH$_3$)COCH$_3$ | —H | —H | White powder (Ethyl acetate) | 215.0-217.0 | Hydrochloride |
| 384 | —H | —H | —CH$_2$CH$_2$N(CH$_3$)COC$_2$H$_5$ | —H | —H | White powder (Ethyl acetate) | 211.0-217.0 | Hydrochloride |
| 385 | —H | —H | —CH$_2$CH$_2$N(CH$_3$)COC$_6$H$_5$ | —H | —H | White powder (Ethyl acetate) | 210.5-212.0 | Hydrochloride |
| 386 | —H | —H | —CH$_2$CH$_2$N(CH$_3$)CH$_2$C$_6$H$_5$ | —H | —H | White powder (Ethyl acetate) | 196.0-202.0 (dec) | Dihydrochloride |
| 387 | —H | —H | —CH$_2$CH$_2$NHC$_2$H$_5$ | —H | —H | White powder (Ethyl acetate/isopropyl ether) | 230.0 (dec) | Dihydrochloride |

TABLE 59

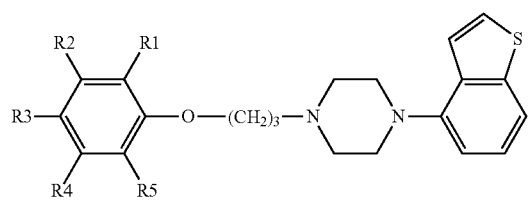

| Example | R1 | R2 | R3 | R4 | R5 | Crystal form (Recrystallization solvent) | Melting point (° C.) | Salt |
|---|---|---|---|---|---|---|---|---|
| 388 | —H | —H | —CH$_2$CH$_2$NHCH$_2$CF$_3$ | —H | —H | White powder (Ethyl acetate) | 223.0 (dec) | Dihydrochloride |
| 389 | —H | —H | —CH$_2$CO$_2$C$_2$H$_5$ | —H | —Cl | White powder (Ethyl acetate) | 225.0-228.5 | Hydrochloride |
| 390 | —H | —H | —CH$_2$CO$_2$H | —H | —Cl | White powder (Hydrochloric acid/acetic acid) | 208.0-209.5 | Hydrochloride |
| 391 | —H | —H | —CH$_2$CO$_2$C$_2$H$_5$ | —H | —OCH$_3$ | White powder (Ethyl acetate) | 205.5-213.5 | Hydrochloride |
| 392 | —CH$_3$ | —H | —CN | —H | —H | Light yellow powder (Ethyl acetate/isopropyl ether) | 105.5-106.0 | — |
| 393 | —H | —H | —CH$_2$CO$_2$H | —H | —OCH$_3$ | White powder (Hydrochloric acid/acetic acid) | 198.5-201.0 | Hydrochloride |
| 394 | —H | —H | —SO$_2$NH$_2$ | —H | —H | White powder (Ethanol) | 199.0-203.0 | — |
| 395 | —H | —H | —CO$_2$H | —H | —CH$_3$ | White powder (Hydrochloric acid/acetic acid) | 280.0 (dec) | Hydrochloride |
| 396 | —H | —H | —CH$_2$CO$_2$C$_2$H$_5$ | —H | —F | White powder (Ethyl acetate) | 220.5-224.0 | Hydrochloride |
| 397 | —H | —H | —CH$_2$CO$_2$H | —H | —F | White powder (Hydrochloric acid/acetic acid) | 181.5-184.5 | Hydrochloride |

TABLE 60

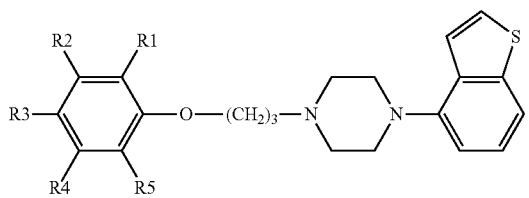

| Example | R1 | R2 | R3 | R4 | R5 | Crystal form (Recrystallization solvent) | Melting point (° C.) | Salt |
|---|---|---|---|---|---|---|---|---|
| 398 | —H | —H | —CN | —OCH₃ | —H | White powder (Ethyl acetate) | 238.0 (dec) | Hydrochloride |
| 399 | —H | —H | —CO₂C₂H₅ | —H | —Br | White powder (Ethyl acetate) | 237.5-242.5 (dec) | Hydrochloride |
| 400 | —H | —CN | —H | —H | —H | White powder (Ethyl acetate) | 217.5-221.0 (dec) | Hydrochloride |
| 401 | —H | —H | —CO₂H | —H | —Br | White powder (Hydrochloric acid/acetic acid) | 271.0 (dec) | Hydrochloride |
| 402 | —H | —H | —H | —CO₂H | —H | White powder (Hydrochloric acid/acetic acid) | 242.5-244.5 | Hydrochloride |
| 403 | —H | —H | —H | —H | —CN | White powder (Ethyl acetate) | 221.5-226.0 | Hydrochloride |
| 404 | —CN | —H | —CO₂C₂H₅ | —H | —H | White powder (Ethyl acetate/isopropyl ether) | 128.5-130.0 | — |
| 405 | —H | —H | —CO₂H | —H | —CN | White powder (Dichloromethane/water) | 271.0 (dec) | Hydrochloride |
| 406 | —CONHC₂H₅ | —H | —H | —H | —H | White powder (Ethyl acetate) | 220.0-227.5 | Hydrochloride |
| 407 | —H | —H | —CO₂C₂H₅ | —CF₃ | —H | White powder (Ethyl acetate) | 224.5-232.0 | Hydrochloride |

TABLE 61

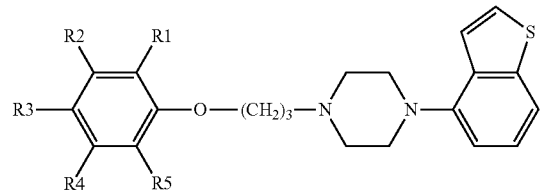

| Example | R1 | R2 | R3 | R4 | R5 | Crystal form (Recrystallization solvent) | Melting point (° C.) | Salt |
|---|---|---|---|---|---|---|---|---|
| 408 | —H | —H | —CO₂C₂H₅ | —Cl | —H | White powder (Ethyl acetate) | 216.5-219.0 | Hydrochloride |
| 409 | —H | —H | —CO₂H | —Cl | —H | White powder (Ethyl acetate) | 259.0 (dec) | Hydrochloride |
| 410 | —H | —OCH₃ | —CHO | —H | —H | White powder (Ethyl acetate 2-propanol) | 118.0-119.5 | — |
| 411 | —H | —H | —CO₂H | —CF₃ | —H | White powder (Water) | 240.0 (dec) | Hydrochloride |
| 412 | —H | —H | —CN | —CH₃ | —H | White powder (Ethyl acetate) | 230.0-237.0 | Hydrochloride |
| 413 | —NO₂ | —H | —CO₂C₂H₅ | —H | —H | Light yellow powder (Ethyl acetate/isopropyl ether) | 113.0-114.0 | — |
| 414 | —H | —H | —CHO | —H | —H | White powder (Ethyl acetate) | 102.5-105.5 | — |
| 415 | —H | —H | —CO₂H | —H | —NO₂ | White powder (Hydrochloric acid/acetic acid) | 259.0 (dec) | Dihydrochloride |
| 416 | —H | —H | —CH=CHCO₂H | —H | —H | White powder (Hydrochloric acid/water) | 265.0 (dec) | Hydrochloride |
| 417 | —H | —H | —CO₂C₂H₅ | —H | —CF₃ | White powder (Ethyl acetate) | 211.5-221.0 | Hydrochloride |

TABLE 62

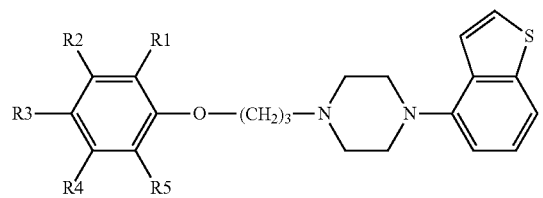

| Example | R1 | R2 | R3 | R4 | R5 | Crystal form (Recrystallization solvent) | Melting point (° C.) | Salt |
|---|---|---|---|---|---|---|---|---|
| 418 | —H | —H | —CO$_2$H | —H | —CF$_3$ | White powder (Ethyl acetate) | 269.0 (dec) | Hydrochloride |
| 419 | —H | —CH$_2$CO$_2$C$_2$H$_5$ | —H | —H | —H | White powder (Ethyl acetate) | 206.0-208.0 | Hydrochloride |
| 420 | —H | —H | —CH=CHCONH$_2$ | —H | —H | White powder (Ethyl acetate) | 210.5-215.0 | — |
| 421 | —H | —CH$_2$CO$_2$H | —H | —H | —H | Light brown powder (Ethyl acetate) | 255.0 (dec) | Hydrochloride |
| 422 | —H | —H | —CH=CHCONHCH$_3$ | —H | —H | White powder (95%-2-propanol) | 165.5-169.0 | — |
| 423 | —H | —H | —CH=CHCON(CH$_3$)$_2$ | —H | —H | White powder (95%-2-propanol) | 130.5-131.5 | — |
| 424 | —H | —H | —CH=CHCONHC$_2$H$_5$ | —H | —H | White powder (95%-2-propanol) | 158.0-159.0 | — |
| 425 | —H | —H | —CH=CHCONHCH$_2$CF$_3$ | —H | —H | White powder (95%-2-propanol) | 177.5-180.0 | — |
| 426 | —H | —H | —(CH$_2$)$_2$CO$_2$C$_2$H$_5$ | —H | —H | White powder (Ethyl acetate) | 235.0-237.5 | Hydrochloride |
| 427 | —F | —H | —H | —CO$_2$C$_2$H$_5$ | —H | White powder (Ethyl acetate) | 218.5-224.0 | Hydrochloride |

TABLE 63

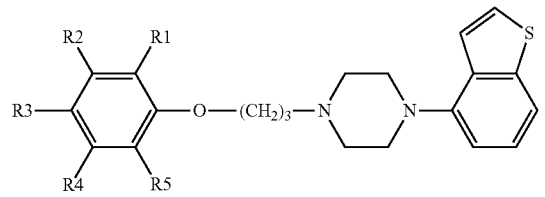

| Example | R1 | R2 | R3 | R4 | R5 | Crystal form (Recrystallization solvent) | Melting point (° C.) | Salt |
|---|---|---|---|---|---|---|---|---|
| 428 | —H | —H | —CH$_2$CH$_2$CO$_2$H | —H | —H | White powder (Hydrochloric acid/acetic acid) | 240.0 (dec) | Hydrochloride |
| 429 | —F | —H | —H | —CO$_2$H | —H | White powder (Hydrochloric acid/acetic acid) | 260.0 (dec) | Hydrochloride |
| 430 | —Cl | —H | —H | —CO$_2$C$_2$H$_5$ | —H | White powder (Ethyl acetate) | 241.0-245.0 | Hydrochloride |
| 431 | —Cl | —H | —H | —CO$_2$H | —H | White powder (Hydrochloric acid/acetic acid) | 268.0 (dec) | Hydrochloride |
| 432 | —CH$_3$ | —H | —H | —CO$_2$C$_2$H$_5$ | —H | White powder (Ethyl acetate) | 238.0-242.0 (dec) | Hydrochloride |
| 433 | —CH$_3$ | —H | —CO$_2$C$_2$H$_5$ | —H | —CH$_3$ | White powder (isopropyl ether) | 106.0-108.0 | — |
| 434 | —CH$_3$ | —H | —H | —CO$_2$H | —H | White powder (Hydrochloric acid/acetic acid) | 256.5 (dec) | Hydrochloride |
| 435 | —CH$_3$ | —H | —CO$_2$H | —H | —CH$_3$ | White powder (Water) | 252.5 (dec) | Hydrochloride |
| 436 | —OCH$_3$ | —OCH$_3$ | —H | —CO$_2$C$_2$H$_5$ | —H | White powder (Ethyl acetate) | 225.0-234.0 | Hydrochloride |
| 437 | —H | —H | —C(CH$_3$)$_2$CO$_2$CH$_3$ | —H | —H | White powder (Ethyl acetate) | 222.0-226.5 | Hydrochloride |

TABLE 64

| Example | R1 | R2 | R3 | R4 | R5 | Crystal form (Recrystallization solvent) | Melting point (° C.) | Salt |
|---|---|---|---|---|---|---|---|---|
| 438 | —OCH$_3$ | —H | —H | —CO$_2$C$_2$H$_5$ | —H | White powder (Ethyl acetate) | 208.0-213.5 | Hydrochloride |
| 439 | —H | —H | —C(CH$_3$)$_2$CO$_2$H | —H | —H | White powder (Hydrochloric acid/acetic acid) | 257.5 (dec) | Hydrochloride |
| 440 | —H | —H | —CH$_2$CH$_2$CONH$_2$ | —H | —H | Light yellow powder (95%-2-propanol) | 167.5-170.0 | — |
| 441 | —H | —H | —CH$_2$CH$_2$CONHCH$_3$ | —H | —H | White powder (95%-2-propanol) | 128.0-132.0 | — |
| 442 | —OCH$_3$ | —H | —H | —CO$_2$H | —H | White powder (Hydrochloric acid/water) | 250.0 (dec) | Hydrochloride |
| 443 | —H | —H | —CH$_2$CH$_2$CONHC$_2$H$_5$ | —H | —H | White powder (95%-2-propanol) | 130.5-132.0 | Hydrochloride |
| 444 | —H | —CH$_2$CONH$_2$ | —H | —H | —H | White powder (Ethyl acetate/isopropyl ether) | 132.5-134.0 | Hydrochloride |
| 445 | —H | —H | —H | —CH$_2$CONHCH$_3$ | —H | White powder (Ethyl acetate) | 173.5-175.0 | Hydrochloride |
| 446 | —OCH$_3$ | —OCH$_3$ | —H | —CO$_2$H | —H | White powder (Water) | 154.0-155.5 | Hydrochloride |
| 447 | —OCH$_3$ | —H | —CO$_2$C$_2$H$_5$ | —H | —OCH$_3$ | White powder (Ethyl acetate) | 239.0-242.0 (dec) | Hydrochloride |

TABLE 65

| Example | R1 | R2 | R3 | R4 | R5 | Crystal form (Recrystallization solvent) | Melting point (° C.) | Salt |
|---|---|---|---|---|---|---|---|---|
| 448 | —OCH$_3$ | —H | —CO$_2$H | —H | —OCH$_3$ | White powder (Water) | 191.0-196.0 | — |
| 449 | —H | —H | —CSNHC$_2$H$_5$ | —H | —H | Light yellow powder (Ethyl acetate/THF) | 193.0-196.5 | Dihydrochloride |
| 450 | —OCH$_3$ | —H | —COCH$_3$ | —H | —CH$_3$ | White powder (Ethyl acetate) | 243.0 (dec) | Hydrochloride |
| 451 | —CH$_2$CH=CH$_2$ | —H | —CO$_2$H | —H | —OCH$_3$ | White powder (Water) | 97.0-102.0 | — |
| 452 | —C$_3$H$_7$ | —H | —CO$_2$H | —H | —OCH$_3$ | White powder (Water) | 145.5-150.5 | — |

TABLE 66

| Example | R1 | R2 | R3 | R4 | R5 | Crystal form (Recrystallization solvent) | Melting point (° C.) | Salt |
|---|---|---|---|---|---|---|---|---|
| 453 | —H | —H | (morpholine-N-propyl group) | —H | —H | White powder (Ethyl acetate/isopropyl ether) | 112.5-113.5 | — |
| 454 | —H | —H | (4-methylpiperazine-N-propyl group) | —H | —H | White powder (Ethyl acetate/isopropyl ether) | 112.0-113.0 | — |

TABLE 67

| Example | R1 | R2 | R3 | R4 | R5 | NMR | Salt |
|---|---|---|---|---|---|---|---|
| 455 | —H | —H | —F | —H | —H | | Hydrochloride |
| 456 | —H | —H | —H | —H | —H | $^1$H-NMR (DMSO-d$_6$) δ ppm: 2.15-2.30 (2H, m), 3.10-3.25 (2H, m), 3.25-3.60 (4H, m), 3.55-3.75 (4H, m), 4.10 (2H, t, J = 6.0 Hz), 6.90-7.10 (4H, m), 7.25-7.40 (3H, m), 7.51 (1H, d, J = 5.6 Hz), 7.72 (1H, d, J = 8.3 Hz), 7.78 (1H, d, J = 5.5 Hz), 10.12 (1H, brs). | Hydrochloride |

| Example | R1 | R2 | R3 | R4 | R5 | Crystal form (Recrystallization solvent) | Melting point (° C.) | Salt |
|---|---|---|---|---|---|---|---|---|
| 457 | —H | —H | —H | —H | —NHCOCH$_3$ | Colorless needle-form crystal (Ethanol) | 243.7-244.8 | — |

TABLE 67-1

| Example | R1 | R2 | R3 | R4 | R5 | NMR | Salt |
|---|---|---|---|---|---|---|---|
| 458 | —H | —H | —COCH$_3$ | —H | —OCH$_3$ | $^1$H-NMR (DMSO-d$_6$) δ ppm : 2.20-2.40 (2H, m), 2.53 (3H, s), 3.20-3.70 (10H, m), 3.83 (3H, s), 4.19 (2H, t, J = 5.8 Hz), 6.96 (1H, d, J = 7.5 Hz), 7.10 (1H, d, | Hydrochloride |

TABLE 67-1-continued

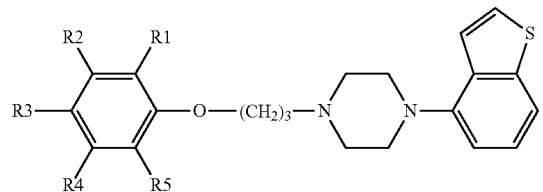

| Example | R1 | R2 | R3 | R4 | R5 | NMR | Salt |
|---|---|---|---|---|---|---|---|
| | | | | | | J = 8.5 Hz), 7.31 (1H, t, J = 7.8 Hz), 7.45-7.50 (2H, m), 7.62 (1H, dd, J = 2.0, 8.4 Hz), 7.69 (1H, d, J = 8.0 Hz), 7.76 (1H, d, J = 5.5 Hz), 11.14 (1H, brs). | |
| 459 | —OCH₃ | —H | —H | —H | —OCH₃ | | Hydrochloride |
| 460 | —H | —H | HN⟨piperidine⟩-CH₃ | —H | —H | ¹H-NMR (CDCl₃) δ ppm: 1.95-2.10 (6H, m), 2.60-2.75 (7H, m), 2.96 (2H, t, J = 11.3 Hz), 3.21 (4H, brs), 3.55 (2H, d, J = 12.4 Hz), 4.06 (2H, t, J = 6.2 Hz), 6.80-6.95 (3H, m), 7.17 (2H, d, J = 8.5 Hz), 7.25-7.35 (1H, m), 7.40 (1H, d, J = 5.5 Hz), 7.43 (1H, d, J = 5.6 Hz), 7.57 (1H, d, J = 8.1 Hz). | — |
| 461 | —H | —H | H₃C-C(O)-N⟨piperidine⟩-CH₃ | —H | —H | ¹H-NMR (CDCl₃) δ ppm: 1.55-1.65 (2H, m), 1.80-1.95 (2H, m), 2.00-2.10 (2H, m), 2.13 (3H, s), 2.55-2.75 (7H, m), 3.10-3.20 (6H, m), 3.93 (1H, d, J = 13.7 Hz), 4.05 (2H, t, J = 6.4 Hz), 4.78 (1H, d, J = 13.3 Hz), 6.85-6.95 (3H, m), 7.11 (2H, d, J = 8.6 Hz), 7.25-7.30 (1H, m), 7.39 (1H, d, J = 5.6 Hz), 7.42 (1H, d, J = 5.5 Hz), 7.55 (1H, d, J = 8.1 Hz). | — |
| 462 | —H | —H | H₃C-N⟨piperidine⟩-CH₃ | —H | —H | ¹H-NMR (CDCl₃) δ ppm: 1.75-1.85 (4H, m), 2.00-2.10 (4H, m), 2.32 (3H, s), 2.35-2.45 (1H, m), 2.63 (2H, t, J = 7.4 Hz), 2.73 (4H, brs), 2.96 (2H, d, J = 11.5 Hz), 3.20 (4H, brs), 4.04 (2H, t, J = 6.3 Hz), 6.85-6.95 (3H, m), 7.14 (2H, d, J = 8.6 Hz), 7.25-7.30 (1H, m), 7.35-7.45 (2H, m), 7.55 (1H, d, J = 8.1 Hz). | — |

TABLE 68

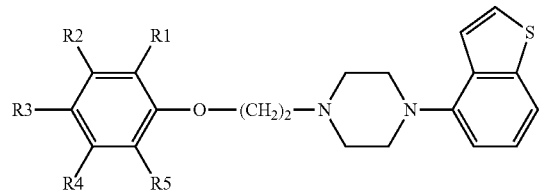

| Example | R1 | R2 | R3 | R4 | R5 | NMR | Salt |
|---|---|---|---|---|---|---|---|
| 463 | —H | —H | —F | —H | —H | ¹H-NMR (DMSO-d₆) δ ppm: 3.10-3.25 (2H, m), 3.40-3.75 (8H, m), 4.40-4.45 (2H, m), 6.98 (1H, d, J = 7.7 Hz), 7.00-7.25 (4H, m), 7.33 (1H, dd, J = 7.9, 7.8 Hz), 7.50 (1H, d, J = 5.6 Hz), 7.71 (1H, d, J = 8.0 Hz), 7.78 (1H, d, J = 5.5 Hz), 10.37 (1H, brs). | Hydrochloride |
| 464 | —H | —H | —H | —H | —H | ¹H-NMR (DMSO-d₆) δ ppm: 3.10-3.35 (2H, m), 3.40-3.80 (8H, m), 4.48 (2H, t, J = 4.8 Hz), 6.95-7.10 (4H, m), 7.25-7.40 (3H, m), 7.51 (1H, d, J = 5.5 Hz), 7.71 (1H, d, J = 8.1 Hz), 7.77 (1H, d, J = 5.5 Hz), 10.80-11.20 (1H, br). | Hydrochloride |

TABLE 69

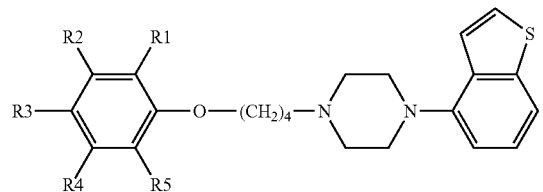

| Example | R1 | R2 | R3 | R4 | R5 | NMR | Salt |
|---|---|---|---|---|---|---|---|
| 465 | —H | —H | —H | —H | —H | ¹H-NMR (DMSO-d₆) δ ppm: 1.70-2.00 (4H, m), 3.10-3.40 (8H, m), 3.50-3.80 (4H, m), 4.03 (2H, t, J = 5.9 Hz), 6.90-7.00 (5H, m), 7.25-7.40 (3H, m), 7.50 (1H, d, J = 5.6 Hz), 7.71 (1H, d, J = 8.0 Hz), 7.77 (1H, d, J = 5.5 Hz), 10.59 (1H, brs) | Hydrochloride |
| 466 | —H | —H | —F | —H | —H | ¹H-NMR (DMSO-d₆) δ ppm: 1.75-1.95 (4H, m), 3.10-3.50 (8H, m), 3.50-3.65 (4H, m), 4.00 (2H, t, J = 5.9 Hz), 8.90-7.00 (3H, m), 7.00-7.20 (2H, m), 7.32 (1H, dd, J = 7.9, 7.8 Hz), 7.50 (1H, d, J = 5.5 Hz), 7.71 (1H, d, J = 8.0 Hz), 7.77 (1H, d, J = 5.5 Hz), 10.40-10.60 (1H, br). | Hydrochloride |
| 467 | —H | —H | —COCH₃ | —H | —OCH₃ | ¹H-NMR (DMSO-d₆) δ ppm: 1.80-1.95 (4H, m), 2.52 (3H, s), 3.20-3.35 (6H, m), 3.50-3.65 (4H, m), 3.83 (3H, s), 4.00-4.15 (2H, m), 6.95 (1H, d, J = 7.5 Hz), 7.08 (1H, d, J = 8.5 Hz), 7.30 (1H, dd, J = 7.8, 7.8 Hz), 7.40-7.50 (2H, m), 7.61 (1H, dd, J = 1.9, 8.4 Hz), 7.69 (1H, d, J = 8.1 Hz), 7.75 (1H, d, J = 5.6 Hz), 11.0 (1H, brs). | Hydrochloride |

TABLE 69-1

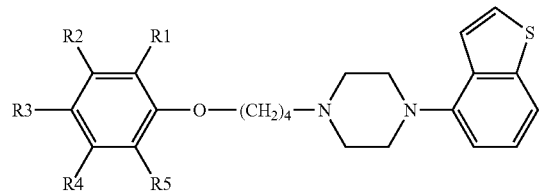

| Example | R1 | R2 | R3 | R4 | R5 | Crystal form (Recrystallization solvent) | Melting point (° C.) | Salt |
|---|---|---|---|---|---|---|---|---|
| 468 | —H | —H | —NHCO₂CH₃ | —H | —H | White powder (Ethyl acetate) | 241.0 (dec) | Hydrochloride |
| 469 | —H | —H | —H | —NHCO₂CH₃ | —H | White powder (Ethyl acetate) | 203.0-209.5 | Hydrochloride |
| 470 | —H | —H | —CN | —H | —H | White powder (Ethyl acetate) | 220.0-223.0 (dec) | Hydrochloride |
| 471 | —H | —H | —CO₂H | —H | —H | White powder (Hydrochloric acid/acetic acid) | 247.5-250.0 (dec) | Hydrochloride |
| 472 | —H | —CN | —H | —H | —H | White powder (Ethyl acetate) | 196.0-198.5 | Hydrochloride |
| 473 | —H | —H | —H | —CO₂H | —H | White powder (Ethyl acetate) | 255.5-258.5 | Hydrochloride |
| 474 | —CN | —H | —H | —H | —H | White powder (Ethyl acetate) | 187.5-188.5 | Hydrochloride |
| 475 | —H | —H | —H | —CONHCH₂CF₃ | —H | White powder (Ethyl acetate/2-propanol) | 137.0 (dec) | Hydrochloride |
| 476 | —H | —H | —H | —CONHC₂H₅ | —H | Light yellow powder (Ethyl acetate/2-propanol) | 130.0-135.0 | Hydrochloride |
| 477 | —H | —H | —H | —H | —CO₂H | White powder (Dichloromethane/water) | 192.0-197.0 | Hydrochloride |
| 478 | —H | —CONH₂ | —H | —H | —H | Light yellow powder (2-propanol) | 148.0-151.0 | — |

TABLE 69-2

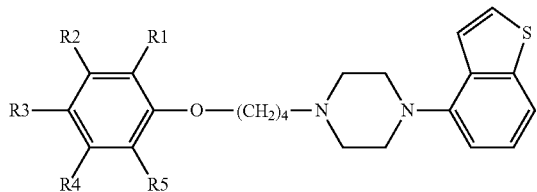

| Example | R1 | R2 | R3 | R4 | R5 | Crystal form (Recrystallization solvent) | Melting point (° C.) | Salt |
|---|---|---|---|---|---|---|---|---|
| 479 | —H | —H | —H | —CONHCH₃ | —H | Light yellow powder (Ethyl acetate) | 234.0-239.0 | Hydrochloride |
| 480 | —H | —H | —H | —CON(CH₃)₂ | —H | Light yellow powder (Ethyl acetate) | 135.0-141.5 | Hydrochloride |
| 481 | —H | —H | —H | —H | —CONHC₂H₅ | White powder (Ethyl acetate) | 209.5-213.0 | Hydrochloride |

TABLE 70

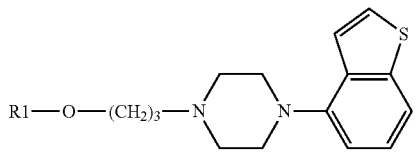

| Example | R1 | NMR | Salt |
|---|---|---|---|
| 482 | (methyl 4-methylthiophene-2-carboxylate group) | ¹H-NMR (CDCl₃) δ ppm: 2.00-2.10 (2H, m), 2.63 (2H, t, J = 7.3 Hz), 2.70-2.80 (4H, m), 3.15-3.25 (4H, m), 3.89 (3H, s), 4.00-4.10 (2H, m), 6.57 (1H, d, J = 1.9 Hz), 6.91 (1H, d, J = 7.6 Hz), 7.20-7.35 (2H, m), 7.35-7.50 (3H, m), 7.56 (1H, d, J = 8.0 Hz). | — |
| 483 | (ethyl 6-methylpyrimidine-4-carboxylate group) | ¹H-NMR (CDCl₃) δ ppm: 1.44 (3H, t, 7.0 Hz), 2.01-2.12 (2H, m), 2.63 (2H, t, J = 7.5 Hz), 2.67-2.81 (4H, m), 3.12-3.29 (4H, m), 4.44-4.55 (4H, m), 6.90 (1H, d, J = 7.5 Hz), 7.27 (1H, dd, J = 5.5 Hz, 7.5 Hz), 7.40 (2H, dd, J = 5.5 Hz, 8.0 Hz), 7.44 (1H, d, J = 1.0 Hz), 7.55 (1H, d, J = 8.0 Hz), 8.90 (1H, d, J = 1.0 Hz) | — |
| 484 | (5-methyl-1-(2,2,2-trifluoroethyl)-1H-pyrazole-3-carboxylic acid group) | ¹H-NMR (DMSO-d₆) δ ppm: 1.83-2.00 (2H, m), 2.59-2.70 (4H, m), 3.00-3.15 (4H, m), 3.17 (1H, d, J = 4.5 Hz), 3.31 (1H, d, J = 4.5 Hz), 4.15 (2H, t, J = 6.0 Hz), 4.77 (2H, q, J = 8.8 Hz), 6.90 (1H, d, J = 7.3 Hz), 7.27 (1H, t, J = 7.8 Hz), 7.40 (1H, d, J = 5.5 Hz), 7.61 (1H, d, J = 8.0 Hz), 7.69 (1H, d, J = 5.5 Hz). | — |

TABLE 71

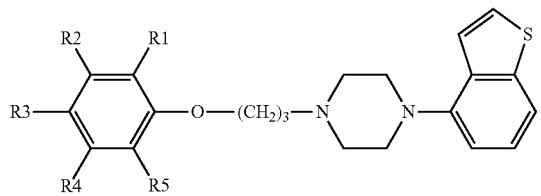

| Example | R1 | R2 | R3 | R4 | R5 | NMR | Salt |
|---|---|---|---|---|---|---|---|
| 485 | —H | —H | —(CH₂)₂N(CH₃)CO₂C(CH₃)₃ | —H | —H | ¹H-NMR (CDCl₃) δ ppm: 1.43 (9H, s), 1.97-2.07 (2H, m), 2.64 (2H, t, J = 7.5 Hz), 2.69-1.87 (6H, m), 2.81 (3H, s), 3.15-3.27 (4H, m), 3.38 (2H, t, | — |

TABLE 71-continued

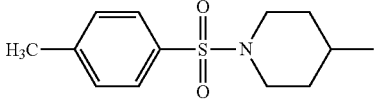

| Example | R1 | R2 | R3 | R4 | R5 | NMR | Salt |
|---|---|---|---|---|---|---|---|
| | | | | | | J = 7.5 Hz), 4.04 (2H, t, J = 6.3 Hz), 6.83-6.92 (3H, m), 7.02-7.15 (2H, m), 7.28 (1H, t, J = 7.8 Hz), 7.37-7.43 (2H, m), 7.55 (1H, d, J = 8.0 Hz) | |
| 486 | —H | —H | 4-methyl-1-(toluene-4-sulfonyl)piperidine | —H | —H | $^1$H-NMR (CDCl$_3$) δ ppm: 1.60-2.10 (6H, m), 2.30-2.40 (2H, m), 2.47 (3H, s), 2.60-2.70 (1H, m), 2.74 (4H, br), 2.85-3.00 (2H, m), 3.20 (4H, br), 3.90-4.10 (4H, m), 6.85-6.95 (2H, m), 7.07 (1H, d, J = 8.6 Hz), 7.25-7.45 (3H, m), 7.56 (1H, d, J = 8.0 Hz), 7.69 (2H, d, J = 4.2 Hz). | — |
| 487 | —H | —H | —H | —H | —CO$_2$H | $^1$H-NMR (DMSO-d$_6$) δ ppm: 2.20-2.43 (2H, m), 3.17-3.77 (10H, m), 4.30 (2H, t, J = 6.0 Hz), 6.90-7.20 (2H, m), 7.30-7.40 (2H, m), 7.50-7.63 (1H, m), 7.70-7.79 (4H, m), 11.00 (1H, br), 12.71 (1H, br). | — |
| 488 | —OCH$_3$ | —H | —CO$_2$CH$_3$ | —H | —CH$_3$ | $^1$H-NMR (CDCl$_3$) δ ppm: 1.95-2.10 (2H, m), 2.31 (3H, s), 2.60-2.80 (6H, m), 3.10-3.30 (4H, m), 3.89 (6H, s), 4.10 (2H, t, J = 6.4 Hz), 6.90 (1H, dd, J = 0.5, 7.6 Hz), 7.27 (1H, dd, J = 7.8, 7.8 Hz), 7.35-7.45 (3H, m), 7.50-7.60 (2H, m). | — |
| 489 | —OCH$_3$ | —H | —CO$_2$H | —H | —CH$_3$ | $^1$H-NMR (DMSO-d$_6$) δ ppm: 1.90-2.05 (2H, m), 2.26 (3H, s), 2.55-3.30 (10H, m), 3.85 (3H, s), 4.03 (2H, t, J = 6.1 Hz), 6.93 (1H, d, J = 7.6 Hz), 7.29 (1H, dd, J = 7.8, 7.8 Hz), 7.35-7.50 (3H, m), 7.65 (1H, d, J = 8.0 Hz), 7.72 (1H, d, J = 5.5 Hz), 11.50-13.50 (1H, br). | — |

TABLE 71-1

| Example | R1 | R2 | R3 | R4 | R5 | NMR | Salt |
|---|---|---|---|---|---|---|---|
| 490 | —CH$_2$CH=CH$_2$ | —H | —CO$_2$CH$_3$ | —H | —OCH$_3$ | $^1$H-NMR (CDCl$_3$) δ ppm: 1.98-2.09 (2H, m), 2.70-2.83 (6H, m), 3.13-3.30 (4H, m), 3.45 (2H, d, J = 6.5 Hz), 3.89 (3H, s), 4.10 (2H, t, J = 6.4 Hz), 5.04-5.11 (2H, m), 5.91-6.09 (1H, m), 6.90 (1H, d, J = 7.5 Hz), 7.24-7.31 (1H, m), 7.38-7.44 (2H, m), 7.47-7.57 (3H, m). | — |
| 491 | —C$_3$H$_7$ | —H | —CO$_2$CH$_3$ | —H | —OCH$_3$ | $^1$H-NMR (CDCl$_3$) δ ppm: 0.97 (3H, t, J = 7.3 Hz), 1.52-1.74 (2H, m), 1.93-2.13 (2H, m), 2.57-2.85 (6H, m), 3.07-3.30 (4H, m), 3.89 (6H, s), 4.09 (2H, t, J = 6.3 Hz), 6.90 (1H, d, J = 7.5 Hz), 7.24-7.31 (1H, m), 7.38-7.45 (3H, m), 7.52-7.57 (2H, m). | — |

TABLE 72

Structure: R1—(CH₂)n—N(piperazine with H₃C substituent)—N-benzothiophene

| Example | R1 | Crystal form (Recrystallization solvent) | Melting point (°C.) | Salt |
|---|---|---|---|---|
| 492 | H₃C-O-C(=O)-NH-C₆H₄-O-CH₃ (methyl 4-methoxyphenylcarbamate) | 3 White powder (Ethyl acetate) | 129.0-138.5 | Hydrochloride |
| 493 | H₃C-CH₂-NH-C(=O)-C₆H₄-O-CH₃ (N-ethyl-4-methoxybenzamide) | 3 White powder (Ethyl acetate) | 130.0-136.0 | Hydrochloride |
| 494 | H₃C-CH₂-NH-C(=O)-C₆H₂(CH₃)(OCH₃)(OCH₃) (N-ethyl-3-methyl-4,5-dimethoxybenzamide) | 3 White powder | — | Fumarate |
| 495 | 6-methoxy-3-oxo-3,4-dihydro-2H-benzo[1,4]oxazine | 4 White powder (Acetonitrile) | 154-156 | Dihydrochloride |

TABLE 73

Structure: R1—(CH₂)n—N(piperazine with CH₃ substituent)—N-benzothiophene

| Example | R1 | Crystal form (Recrystallization solvent) | Melting point (°C.) | Salt |
|---|---|---|---|---|
| 496 | H₃C-CH₂-NH-C(=O)-C₆H₄-O-CH₃ (N-ethyl-4-methoxybenzamide) | 3 White powder (Ethyl acetate) | 151.5-156.5 | Hydrochloride |
| 497 | 6-methoxy-3-oxo-3,4-dihydro-2H-benzo[1,4]oxazine | 4 White powder (Ethanol/ ethyl acetate) | 220-225 | Dihydrochloride |

TABLE 74

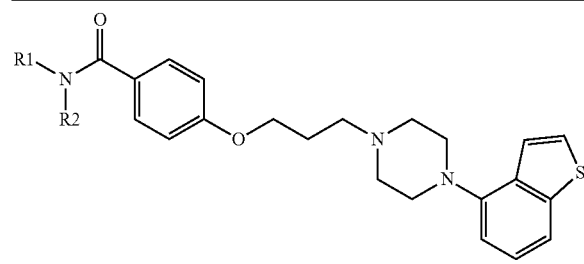

| Example | R1 | R2 | MS (M + 1) |
|---|---|---|---|
| 498 | —H | -cyclo-$C_6H_{11}$ | 478 |
| 499 | —$CH_2CH(CH_3)_2$ | —$CH_2CH(CH_3)_2$ | 508 |
| 500 | —$CH_2CH_2OH$ | —$CH_2CH_2OH$ | 484 |
| 501 | —$CH_3$ | —$CH_2CH_2N(CH_3)_2$ | 481 |
| 502 | —$CH_2CH_2OCH_3$ | —$CH_2CH_2OCH_3$ | 512 |
| 503 | —$C_3H_7$ | —$CH_2$-cyclo-$C_3H_5$ | 492 |
| 504 | —$CH_2CH=CH_2$ | -cyclo-$C_6H_9$ | 504 |
| 505 | —$C_2H_5$ | —$C_2H_5$ | 452 |
| 506 | —H | —$C_4H_9$ | 452 |
| 507 | —H | —$C(CH_3)_3$ | 452 |
| 508 | —H | -cyclo-$C_7H_{13}$ | 492 |
| 509 | —$C_2H_5$ | -cyclo-$C_6H_{11}$ | 506 |
| 510 | —$C_2H_5$ | —$CH(CH_3)_2$ | 466 |
| 511 | —H | —$CH_2CH(CH_3)_2$ | 452 |
| 512 | —H | —$CH_2CH_2OCH_3$ | 454 |
| 513 | —H | —$CH_2CH_2OC_2H_5$ | 468 |
| 514 | —H | —$(CH_2)_3OC_2H_5$ | 482 |
| 515 | —H | -1-$CH_3$-CYCLOHEXYL | 492 |
| 516 | —H | —$CH_2$-cyclo-$C_3H_5$ | 450 |
| 517 | —H | —$CH_2$-cyclo-$C_6H_{11}$ | 492 |
| 518 | —H | —$CH_2CO_2CH_3$ | 468 |
| 519 | —H | —$CH_2CONH_2$ | 453 |
| 520 | —$CH_3$ | —$CH_2CO_2CH_3$ | 482 |
| 521 | —H | —$CH_2CCH$ | 434 |
| 522 | —$CH_3$ | —$CH(CH_3)_2$ | 452 |
| 523 | —H | —$(CH_2)_2CH(CH_3)_2$ | 466 |
| 524 | —H | —$CH(CH_3)C(CH_3)_3$ | 480 |
| 525 | —H | —$CH_2CH_2N(CH_3)_2$ | 467 |
| 526 | —$CH_3$ | —$CH_2$-cyclo-$C_3H_5$ | 464 |
| 527 | —H | —$CH_2CF_3$ | 478 |
| 528 | —$CH_3$ | -cyclo-$C_6H_{11}$ | 492 |
| 529 | —$C_2H_5$ | —$CH_2CH_2OH$ | 468 |
| 530 | —$CH_2CH_2OH$ | -cyclo-$C_6H_{11}$ | 522 |
| 531 | —H | -cyclo-$C_5H_9$ | 464 |
| 532 | —H | -3-PYRIDYL | 473 |
| 533 | —H | -4-PYRIDYL | 473 |
| 534 | —$CH_2CH_2OH$ | —$C_6H_5$ | 516 |

TABLE 75

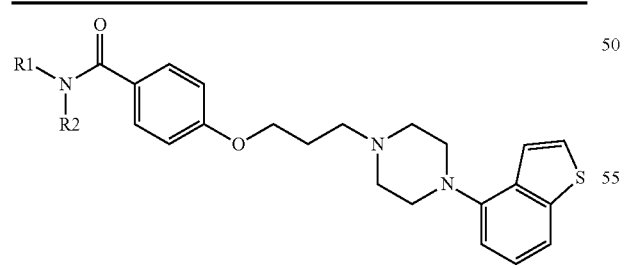

| Example | R1 | R2 | MS (M + 1) |
|---|---|---|---|
| 535 | —H | —$C_6H_5$ | 435 |
| 536 | —H | —$CH_2CH_2C(CH_3)_3$ | 468 |
| 537 | —H | —$CH(C_2H_5)_2$ | 449 |
| 538 | —H | —$CH_2CN$ | 566 |
| 539 | —H | —$(CH_2)_3OCH_3$ | 523 |
| 540 | —H | —$CH_2CH_2CN$ | 523 |
| 541 | —$(CH_2)_3N(CH_3)_2$ | —$(CH_2)_3N(CH_3)_2$ | 481 |

TABLE 75-continued

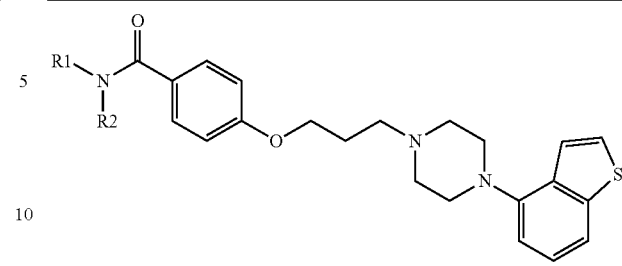

| Example | R1 | R2 | MS (M + 1) |
|---|---|---|---|
| 542 | —$CH_3$ | —$(CH_2)_3N(C_2H_5)_2$ | 482 |
| 543 | —$C_2H_5$ | —$(CH_2)_2N(C_2H_5)_2$ | 523 |
| 544 | —H | —$(CH_2)_2NHCOCH_3$ | 481 |
| 545 | —H | —$(CH_2)_5OH$ | 495 |
| 546 | —H | —$(CH_2)_2N(i-Pr)_2$ | 524 |
| 547 | —H | —$(CH_2)_3N(CH_3)_2$ | 524 |
| 548 | —H | —$(CH_2)_2N(C_2H_5)_2$ | 563 |
| 549 | —$CH_3$ | —$(CH_2)_3CO_2C_2H_5$ | 509 |
| 550 | —H | —$(CH_2)_4CO_2C_2H_5$ | 493 |
| 551 | -cyclo-$C_5H_9$ | —$(CH_2)_2N(C_2H_5)_2$ | 528 |
| 552 | —$CH_3$ | —$(CH_2)_2N(C_2H_5)_2$ | 484 |
| 553 | —H | —$NHCH_2CF_3$ | 496 |
| 554 | —H | —$CH_2CF_2CF_3$ | 482 |
| 555 | —H | —$CH_2CH(OCH_3)_2$ | 442 |
| 556 | —H | —$(CH_2)_3OCH(CH_3)_2$ | 467 |
| 557 | —H | —$(CH_2)_2OCH(CH_3)_2$ | 470 |
| 558 | —H | —$CH_2CH_2F$ | 435 |
| 559 | —H | —$CH_2CONHCH_3$ | 468 |
| 560 | —H | —$CH_2CH_2SCH_3$ | 449 |

TABLE 76

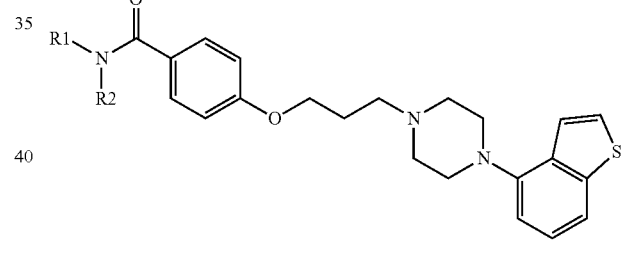

| Example | R1 | R2 | MS (M + 1) |
|---|---|---|---|
| 561 | —H | $CO_2Me$, i-Pr | 510 |
| 562 | —H | $CO_2Me$, i-Pr | 524 |
| 563 | —H | $C(O)NH_2$, i-Pr | 495 |
| 564 | —H | $CO_2Et$, $H_3C$ | 496 |
| 565 | —H | $CO_2Me$, $H_3C$ | 482 |

TABLE 76-continued

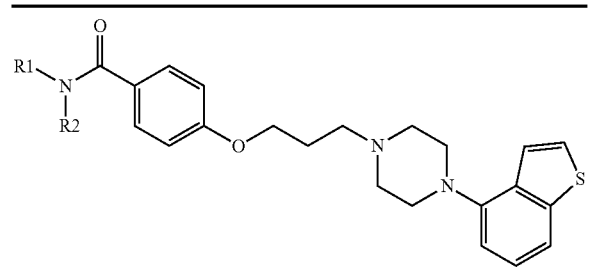

| Example | R1 | R2 | MS (M + 1) |
|---|---|---|---|
| 566 | —H | (S)-CH(CH3)C(O)NH2 | 467 |
| 567 | —H | C(=NH)N(CH3)2 with CH3 | 466 |
| 568 | —H | CH(C2H5)2 CH2CH3 | 480 |
| 569 | —H | CH(CO2Et)CH2CO2Et with CH3 | 568 |
| 570 | —H | CH(CO2Et)2 with iPr | 554 |

TABLE 77

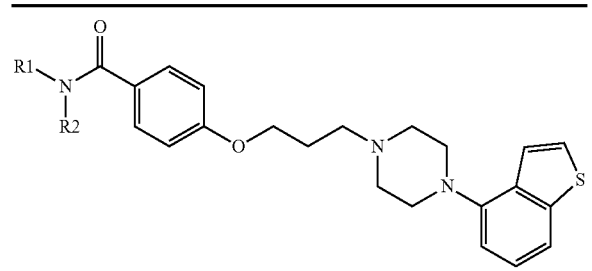

| Example | R1 | R2 | MS (M + 1) |
|---|---|---|---|
| 571 | —H | CH(CH3)(CONH2) with H2NOC | 496 |
| 572 | —H | CH2CH(CH3)CH2OCH3 | 482 |
| 573 | —H | CH(CH3)CH2OCH3 | 468 |

TABLE 77-continued

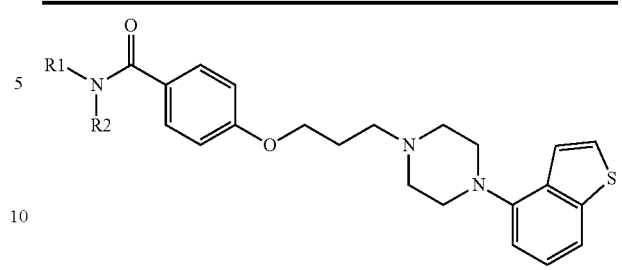

| Example | R1 | R2 | MS (M + 1) |
|---|---|---|---|
| 574 | —H | CH(OH)CH2CH3 with CH2OH | 470 |
| 575 | —H | C(CH3)(=CH2)CH2CH3 | 450 |
| 576 | —H | CH2N(C2H5)2 with CH(CH3)CH3 | 509 |
| 577 | —H | CH2N(CH3)2 with CH2CH(CH3)2 | 481 |
| 578 | —H | cyclopropyl-CH3 | 450 |
| 579 | —H | 1-methylcyclopentyl | 478 |

TABLE 78

| Example | R1 | R2 | MS (M + 1) |
|---|---|---|---|
| 580 | —H | 4-hydroxy-methylcyclohexyl | 494 |
| 581 | —H | 2-methylcyclohexyl | 492 |

TABLE 78-continued
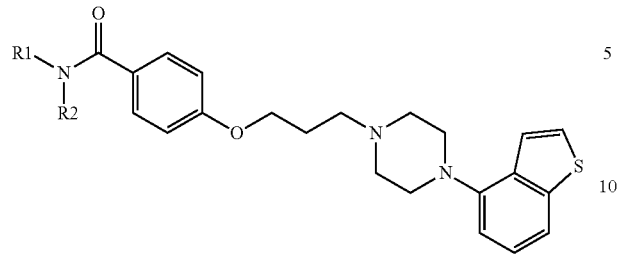
| Example | R1 | R2 | MS (M + 1) |
|---|---|---|---|
| 582 | —H | 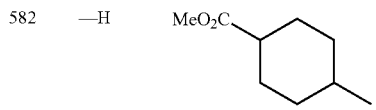 | 536 |
| 583 | —CH₃ | 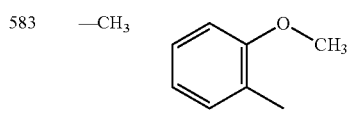 | 516 |
| 584 | —CH₃ | 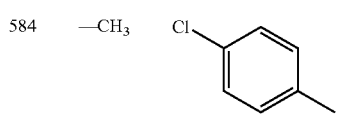 | 520 |
| 585 | —H | 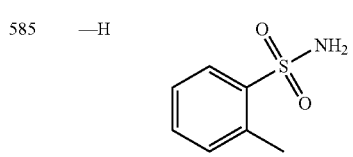 | 551 |
| 586 | —H | 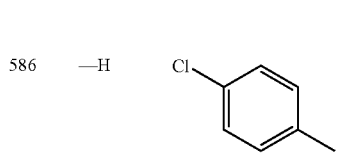 | 506 |
| 587 | —H | 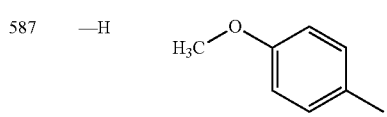 | 502 |
| 588 | —H | 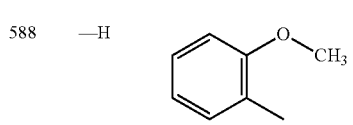 | 502 |
| 589 | —H | 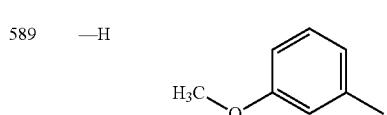 | 502 |
TABLE 79
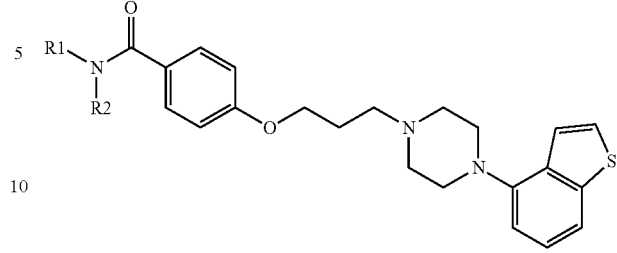
| Example | R1 | R2 | MS (M + 1) |
|---|---|---|---|
| 590 | —H | 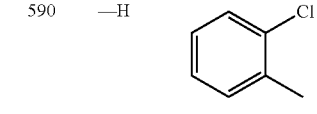 | 506 |
| 591 | —H | 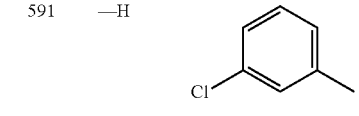 | 506 |
| 592 | —H | 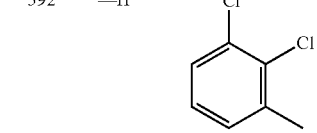 | 540 |
| 593 | —H | 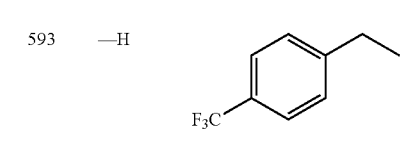 | 554 |
| 594 | —H | 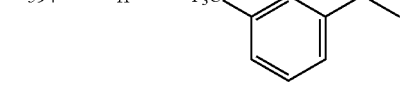 | 554 |
| 595 | —H | 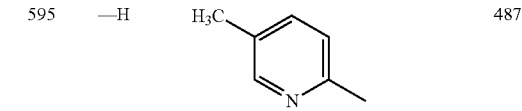 | 487 |
| 596 | —H |  | 533 |
| 597 | —CH₃ | 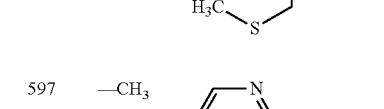 | 515 |
| 598 | —H | 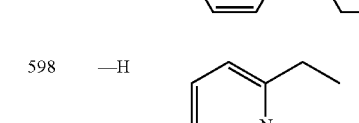 | 487 |

223

TABLE 80

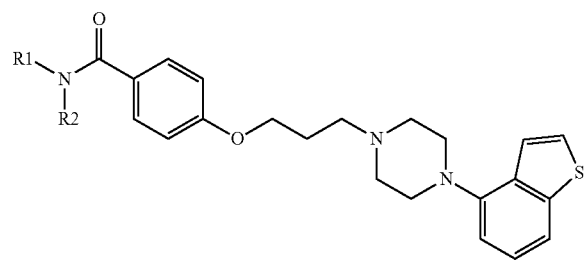

| Example | R1 | R2 | MS (M + 1) |
|---|---|---|---|
| 599 | —H | 3-ethylpyridin-yl | 487 |
| 600 | —H | 4-ethylpyridin-yl | 487 |
| 601 | —C₂H₅ | 2-propylpyridin-yl | 529 |
| 602 | —C₂H₅ | 4-ethylpyridin-yl | 515 |
| 603 | —H | 2-propylpyridin-yl | 501 |
| 604 | —H | 3-propylpyridin-yl | 501 |
| 605 | —H | 4-propylpyridin-yl | 501 |
| 606 | —CH₃ | 1,4-dimethylpiperidinyl | 507 |
| 607 | —CH₃ | 1-acetyl-4-methylpiperidinyl | 535 |
| 608 | —H | 2,2,6,6-tetramethylpiperidin-4-yl | 535 |

224

TABLE 81

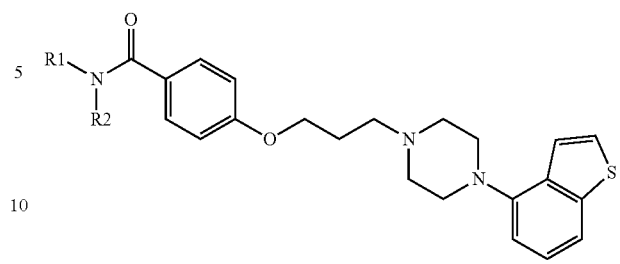

| Example | R1 | R2 | MS (M + 1) |
|---|---|---|---|
| 609 | —H | 1-(ethoxycarbonyl)-4-methylpiperidin-4-yl | 551 |
| 610 | —H | 1-Boc-4-methylpiperidin-4-yl | 579 |
| 611 | —H | 4-methylpiperidin-4-yl | 479 |
| 612 | —H | 1,4-dimethylpiperidin-4-yl | 493 |
| 613 | —H | 1-propylpiperidin-4-yl | 507 |
| 614 | —H | 1-Boc-3-methylpyrrolidin-3-yl | 565 |
| 615 | —H | 3-methylpyrrolidin-3-yl | 465 |
| 616 | —H | 1,3-dimethylpyrrolidin-3-yl | 479 |
| 617 | —H | 1-propylpyrrolidin-3-yl | 493 |
| 618 | —H | 1-butylpyrrolidin-3-yl | 507 |

TABLE 82
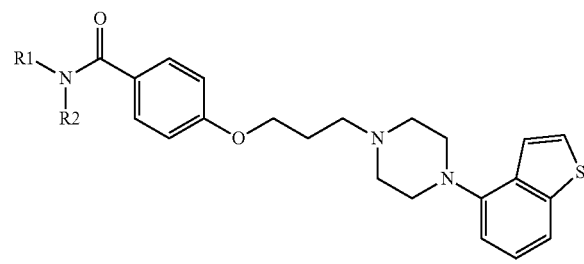
| Example | R1 | R2 | MS (M + 1) |
|---|---|---|---|
| 619 | —H | 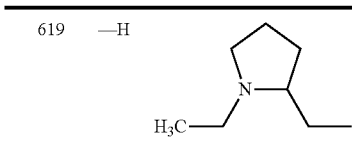 | 507 |
| 620 | —H | 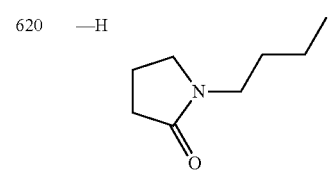 | 521 |
| 621 | —H | 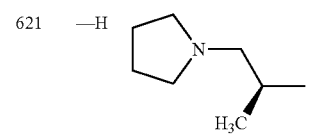 | 507 |
| 622 | —H | 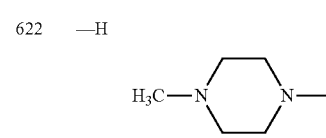 | 538 |
| 623 | —H | 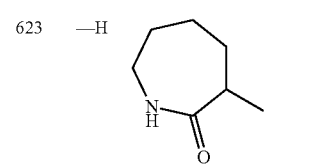 | 507 |
| 624 | —H | 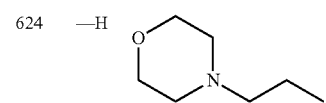 | 509 |
| 625 | —H | | 523 |
| 626 | —H | | 476 |
| 627 | —H | | 490 |
| 628 | —H | | 504 |
TABLE 83
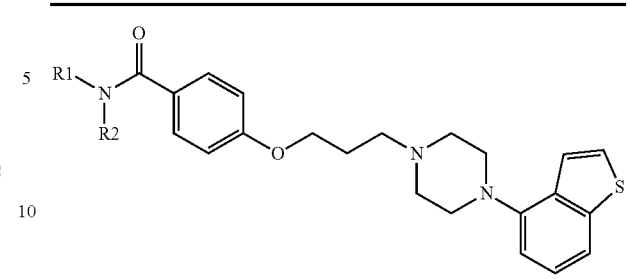
| Example | R1 | R2 | MS (M + 1) |
|---|---|---|---|
| 629 | —H | 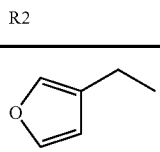 | 476 |
| 630 | —H | 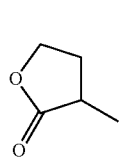 | 480 |
| 631 | —H | 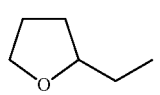 | 480 |
| 632 | —$C_2H_5$ | 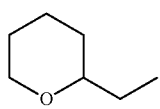 | 522 |
| 633 | —H | 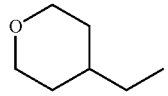 | 494 |
| 634 | —H | 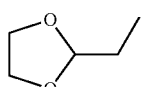 | 482 |
| 635 | —H | 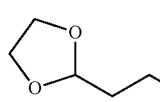 | 496 |
| 636 | —H | 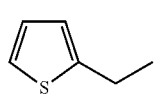 | 492 |
| 637 | —H | 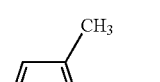 | 506 |
| 638 | —H | 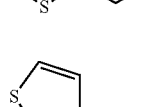 | 492 |

TABLE 84

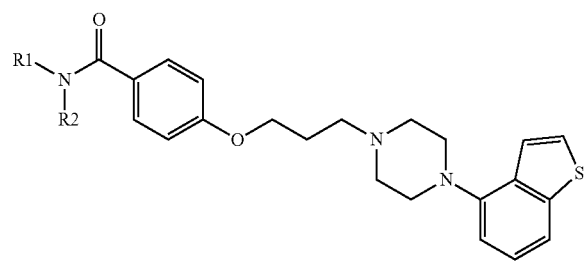

| Example | R1 | R2 | MS (M + 1) |
|---|---|---|---|
| 639 | —H | 2-propylthiophene | 506 |
| 640 | —H | 1-methyl-2-ethylpyrrole | 489 |
| 641 | —H | 1,5-dimethyl-2-ethylpyrrole | 503 |
| 642 | —H | 1-propylpyrrole | 489 |
| 643 | —H | 1,5-dimethyl-3-pyrazole (H3C at 3, H3C at 1) | 490 |
| 644 | —H | 3-phenyl-5-methyl-1H-pyrazole | 538 |
| 645 | —H | 3-(furan-2-yl)-5-methyl-1H-pyrazole | 528 |
| 646 | —H | 1,3,5-trimethyl-4-ethylpyrazole | 518 |
| 647 | —H | 3-methyl-4-butyl-1H-pyrazole | 518 |

TABLE 84-continued

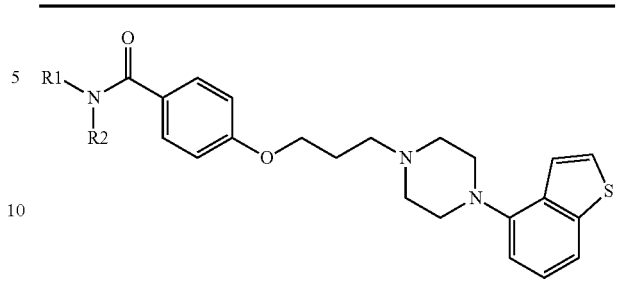

| Example | R1 | R2 | MS (M + 1) |
|---|---|---|---|
| 648 | —H | 1,5-dimethyl-3-ethylpyrazole | 504 |

TABLE 85

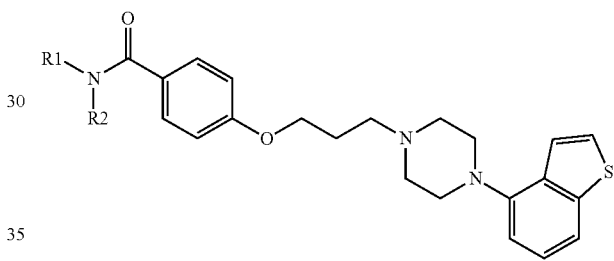

| Example | R1 | R2 | MS (M + 1) |
|---|---|---|---|
| 649 | —H | 4-butyl-5-oxo-4,5-dihydro-1H-pyrazole | 520 |
| 650 | —H | 1-butylimidazole | 504 |
| 651 | —H | 2-methyl-3-(1H-imidazol-5-yl)propanamide | 533 |
| 652 | —H | 4-propyl-1H-imidazole | 490 |
| 653 | —H | 2-methylthiazole | 479 |

TABLE 85-continued
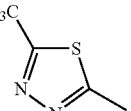
| Example | R1 | R2 | MS (M + 1) |
|---|---|---|---|
| 654 | —H | 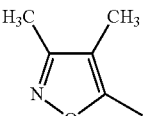 | 494 |
| 655 | —H | 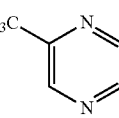 | 491 |
| 656 | —H | 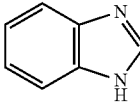 | 502 |
| 657 | —H | 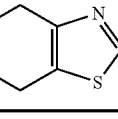 | 526 |
| 658 | —H | 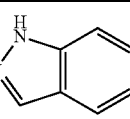 | 533 |
TABLE 86
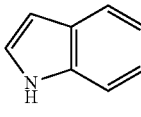
| Example | R1 | R2 | MS (M + 1) |
|---|---|---|---|
| 659 | —H | 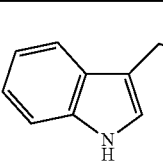 | 512 |
| 660 | —H | 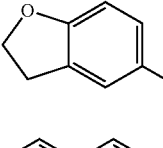 | 511 |
TABLE 86-continued
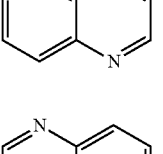
| Example | R1 | R2 | MS (M + 1) |
|---|---|---|---|
| 661 | —H | 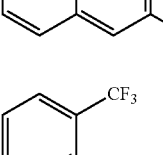 | 539 |
| 662 | —H | 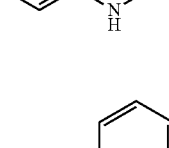 | 528 |
| 663 | —H | 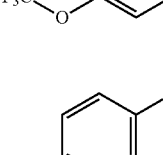 | 523 |
| 664 | —H | 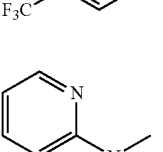 | 523 |
| 665 | —H | 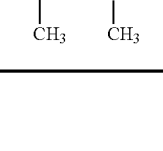 | 555 |
| 666 | —H | | 571 |
| 667 | —H | | 555 |
| 668 | —H | | 570 |

TABLE 87

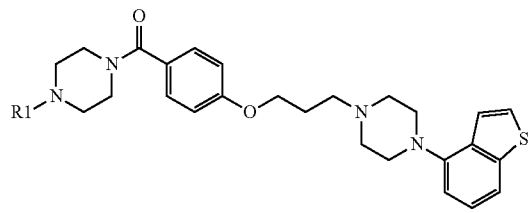

| Example | R1 | MS (M + 1) |
|---|---|---|
| 669 | —H | 465 |
| 670 | —C$_4$H$_9$ | 521 |
| 671 | —CH(C$_2$H$_5$)$_2$ | 535 |
| 672 | —CH(CH$_3$)$_2$ | 507 |
| 673 | —C(CH$_3$)$_3$ | 535 |
| 674 | —C$_3$H$_7$ | 507 |
| 675 | —C$_2$H$_5$ | 493 |
| 676 | —C$_6$H$_{13}$ | 549 |
| 677 | -cyclo-C$_5$H$_9$ | 533 |
| 678 | -cyclo-C$_7$H$_{13}$ | 561 |
| 679 | —CH$_2$CH$_2$OH | 509 |
| 680 | —CH$_2$CH$_2$OCH$_3$ | 523 |
| 681 | —(CH$_2$)$_3$OCH$_3$ | 537 |
| 682 | —(CH$_2$)$_4$OCH$_3$ | 551 |
| 683 | —CO$_2$C$_2$H$_5$ | 537 |
| 684 | —CO$_2$C(CH$_3$)$_3$ | 565 |
| 685 | —COCH$_3$ | 507 |
| 686 | —(CH$_2$)$_3$N(CH$_3$)$_2$ | 550 |
| 687 | —CH$_2$CH$_2$N(CH$_3$)$_2$ | 536 |

TABLE 88

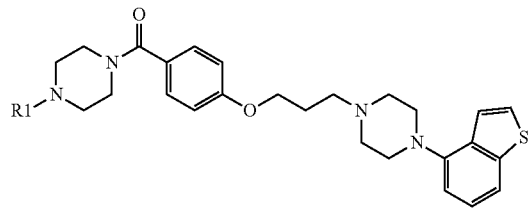

| Example | R1 | MS (M + 1) |
|---|---|---|
| 688 | (N-propylpiperidine) | 576 |
| 689 | (N-propylmorpholine) | 578 |
| 690 | (N-propylpyrrolidine) | 562 |
| 691 | (1,3-dioxolan-2-yl ethyl) | 551 |
| 692 | (1,3-dioxolan-2-yl propyl) | 565 |
| 693 | (tetrahydrofuran-2-yl ethyl) | 549 |

TABLE 88-continued

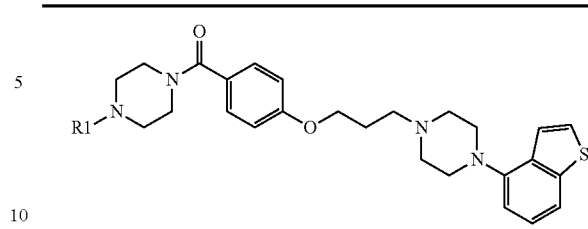

| Example | R1 | MS (M + 1) |
|---|---|---|
| 694 | (1-methyl-3-ethylpiperidine) | 576 |
| 695 | (1-methyl-4-ethylpiperidine) | 576 |
| 696 | (N-propionylpyrrolidine) | 576 |
| 697 | (2-ethylpyridine) | 556 |
| 698 | (3-ethylpyridine) | 556 |

TABLE 89

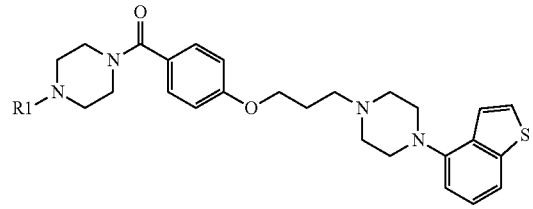

| Example | R1 | MS (M + 1) |
|---|---|---|
| 699 | (4-ethylpyridine) | 556 |
| 700 | (4-propylpyridine) | 570 |
| 701 | (2-propylpyridine) | 570 |

TABLE 89-continued

[Structure: R1-N(piperazine)-C(=O)-phenyl-O-CH2CH2CH2-N(piperazine)-N-benzothiophene]

| Example | R1 | MS (M + 1) |
|---|---|---|
| 702 | [phenyl-CH(CH3)-4-pyridyl] | 632 |
| 703 | [N-propyl imidazole] | 559 |
| 704 | [3-ethyl furan] | 545 |
| 705 | [1-methyl-4-methyl-piperidine] | 561 |
| 706 | -4-PYRIDYL | 542 |
| 707 | -3-PYRIDYL | 542 |
| 708 | -2-PYRIDYL | 542 |
| 709 | [2-methyl-3-cyano-pyridyl] | 567 |
| 710 | [2,3-dimethylpyridyl] | 556 |
| 711 | [2,4-dimethylpyridyl] | 556 |

TABLE 90

[Structure: R1-N(piperazine)-C(=O)-phenyl-O-CH2CH2CH2-N(piperazine)-N-benzothiophene]

| Example | R1 | MS (M + 1) |
|---|---|---|
| 712 | [2-methyl-3-CF3-pyridyl] | 610 |
| 713 | [5-methyl-thieno[2,3-c]pyridine] | 598 |

TABLE 91

[Structure: R1-C(=O)-phenyl-O-CH2CH2CH2-N(piperazine)-N-benzothiophene]

| Example | R1 | MS (M + 1) |
|---|---|---|
| 714 | [1-methyl-pyrrolidinyl] | 450 |
| 715 | [2-(hydroxymethyl)-1-methyl-pyrrolidinyl] | 480 |
| 716 | [2-carbamoyl-1-methyl-pyrrolidinyl] | 493 |
| 717 | [3-hydroxy-1-methyl-pyrrolidinyl] | 466 |
| 718 | [3-acetamido-1-methyl-pyrrolidinyl] | 507 |

TABLE 91-continued

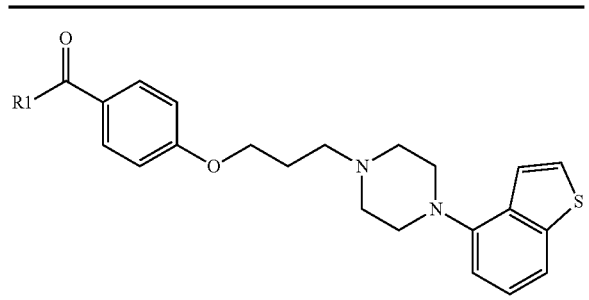

| Example | R1 | MS (M + 1) |
|---|---|---|
| 719 | morpholinylmethyl-N-methylpyrrolidine | 549 |
| 720 | (dimethylamino)methyl-N-methylpyrrolidine | 507 |
| 721 | pyrrolidinylmethyl-N-methylpyrrolidine | 533 |
| 722 | piperidinylmethyl-N-methylpyrrolidine | 547 |
| 723 | (4-methylpiperazinyl)methyl-N-methylpyrrolidine | 562 |
| 724 | (diethylamino)methyl-N-methylpyrrolidine | 535 |

TABLE 92

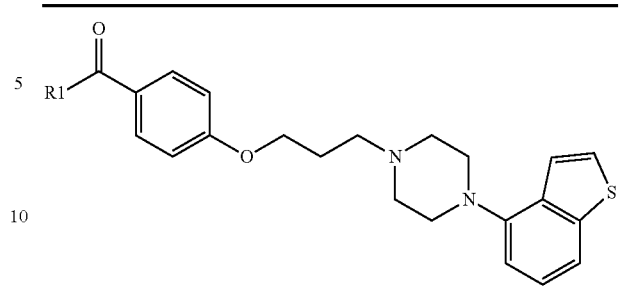

| Example | R1 | MS (M + 1) |
|---|---|---|
| 725 | 1-methylpiperidine | 464 |
| 726 | 1,3,5-trimethylpiperidine | 492 |
| 727 | 4-hydroxy-1-methylpiperidine | 480 |
| 728 | 3-hydroxy-1-methylpiperidine | 480 |
| 729 | (1-methylpiperidin-4-yl)methanol | 494 |
| 730 | (1-methylpiperidin-2-yl)methanol | 494 |
| 731 | N-ethyl-2-(1-methylpiperidin-4-yl)acetamide | 549 |
| 732 | 1-methylpiperidine-4-carboxamide | 507 |
| 733 | 4-methoxy-1-methylpiperidine | 494 |

TABLE 92-continued

R1-C(=O)-C6H4-O-(CH2)3-N(piperazine)N-benzothiophen-4-yl

| Example | R1 | MS (M + 1) |
|---|---|---|
| 734 | tert-butyl 1-methylpiperidine-4-carboxylate | 564 |

TABLE 93

R1-C(=O)-C6H4-O-(CH2)3-N(piperazine)N-benzothiophen-4-yl

| Example | R1 | MS (M + 1) |
|---|---|---|
| 735 | ethyl 1-methylpiperidine-3-carboxylate | 536 |
| 736 | ethyl 1-methylpiperidine-4-carboxylate | 536 |
| 737 | ethyl 1-methylpiperidine-2-carboxylate | 536 |
| 738 | N-(1-methylpiperidin-4-yl)acetamide | 521 |
| 739 | tert-butyl (1-methylpiperidin-4-yl)carbamate | 579 |

TABLE 93-continued

R1-C(=O)-C6H4-O-(CH2)3-N(piperazine)N-benzothiophen-4-yl

| Example | R1 | MS (M + 1) |
|---|---|---|
| 740 | 1'-methyl-1,4'-bipiperidine | 547 |
| 741 | 3-methyl-4-(1-methylpiperidin-4-yl)-1-methylpiperazine | 576 |
| 742 | 1-methyl-4-(1-methylpiperidin-4-yl)piperazine | 562 |
| 743 | 4-(1-methylpiperidin-4-yl)morpholine | 549 |
| 744 | 1-methyl-4-(1-methylpiperidin-4-yl)-1,4-diazepane | 576 |
| 745 | 8-methyl-1,4-dioxa-8-azaspiro[4.5]decane derivative | 522 |

TABLE 94

R1-C(=O)-C6H4-O-(CH2)3-N(piperazine)N-benzothiophen-4-yl

| Example | R1 | MS (M + 1) |
|---|---|---|
| 746 | 1-methylazepane | 478 |
| 747 | 4-methylthiomorpholine | 482 |

TABLE 94-continued
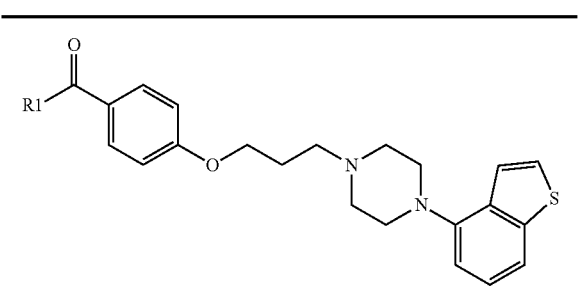
| Example | R1 | MS (M + 1) |
|---|---|---|
| 748 | 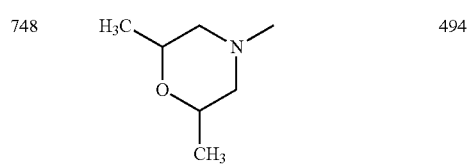 | 494 |
| 749 | 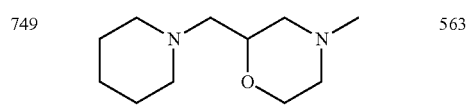 | 563 |
| 750 | 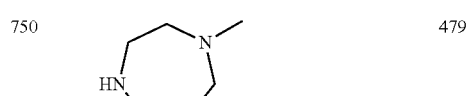 | 479 |
| 751 | 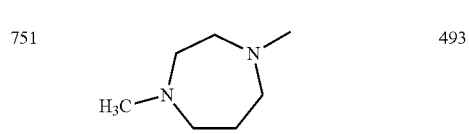 | 493 |
| 752 | 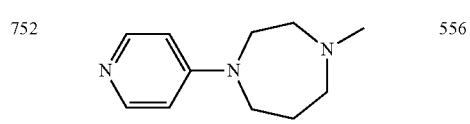 | 556 |
| 753 | 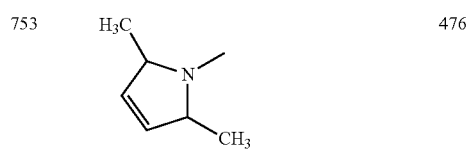 | 476 |
| 754 | 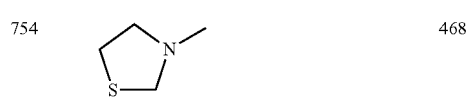 | 468 |
| 755 | 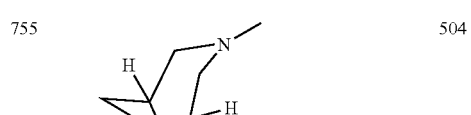 | 504 |
TABLE 95
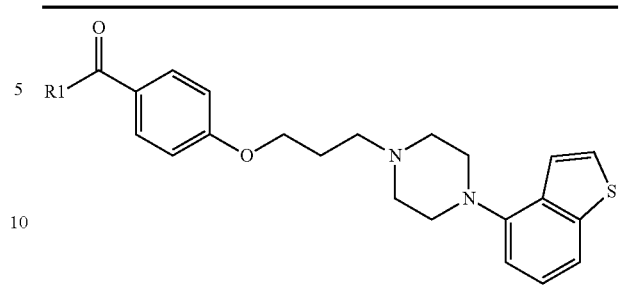
| Example | R1 | MS (M + 1) |
|---|---|---|
| 756 | 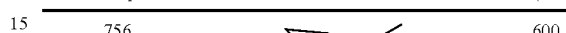 | 600 |
| 757 |  | 498 |
| 758 |  | 512 |
| 759 | 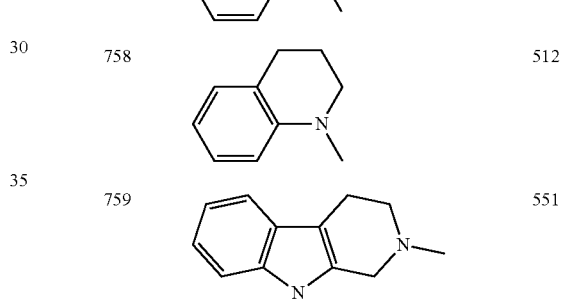 | 551 |
TABLE 96
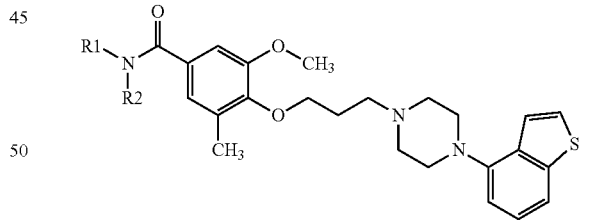
| Example | R1 | R2 | MS (M + 1) |
|---|---|---|---|
| 760 | —H | -cyclo-$C_6H_{11}$ | 522 |
| 761 | —H | —$CH(CH_3)_2$ | 482 |
| 762 | —H | —$C_4H_9$ | 496 |
| 763 | —H | -cyclo-$C_3H_5$ | 480 |
| 764 | —H | -cyclo-$C_7H_{13}$ | 536 |
| 765 | —H | —$CH_2C_6H_5$ | 530 |
| 766 | —H | —$C_3H_7$ | 482 |
| 767 | —H | —$CH_2CH(CH_3)_2$ | 496 |
| 768 | —H | —$CH_2CH_2OCH_3$ | 498 |
| 769 | —H | —$CH_2CH_2OC_2H_5$ | 512 |
| 770 | —H | —$(CH_2)_3OC_2H_5$ | 526 |
| 771 | —H | -1-CH3-CYCLOHEXYL | 536 |
| 772 | —H | —$(CH_2)_2OC_6H_5$ | 560 |
| 773 | —H | -cyclo-$C_5H_9$ | 508 |

TABLE 96-continued

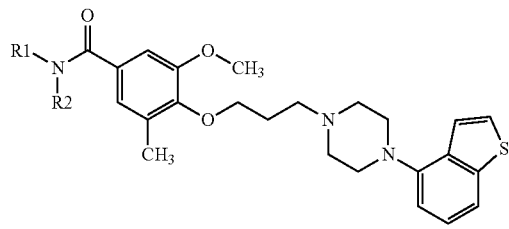

| Example | R1 | R2 | MS (M + 1) |
|---|---|---|---|
| 774 | —H | —CH$_2$-cyclo-C$_3$H$_6$ | 494 |
| 775 | —H | —CH$_2$-cyclo-C$_6$H$_{11}$ | 536 |
| 776 | —H | —CH(CH$_3$)C$_6$H$_5$ | 544 |
| 777 | —H | —(CH$_2$)$_2$C$_6$H$_5$ | 544 |
| 778 | —H | —CH$_2$CO$_2$CH$_3$ | 512 |
| 779 | —H | —CH$_2$CONH$_2$ | 497 |
| 780 | —H | —CH$_2$CCH | 478 |
| 781 | —H | —(CH$_2$)$_2$CH(CH$_3$)$_2$ | 510 |
| 782 | —H | —CH(CH$_3$)C(CH$_3$)$_3$ | 524 |
| 783 | —H | —CH$_2$C(CH$_3$)$_3$ | 510 |
| 784 | —CH$_3$ | -cyclo-C$_6$H$_{11}$ | 536 |
| 785 | —C$_2$H$_5$ | —C$_2$H$_5$ | 496 |
| 786 | —H | —C(CH$_3$)$_3$ | 496 |
| 787 | —CH$_3$ | —CH$_2$C$_6$H$_5$ | 544 |
| 788 | —C$_2$H$_5$ | —CH(CH$_3$)$_2$ | 510 |
| 789 | —CH$_3$ | —CH$_2$CO$_2$CH$_3$ | 526 |
| 790 | —CH$_3$ | —CH(CH$_3$)$_2$ | 496 |
| 791 | —CH$_3$ | —CH$_2$-cyclo-C$_3$H$_5$ | 508 |
| 792 | —H | —CH$_2$CF$_3$ | 522 |
| 793 | —H | —CH(C$_2$H$_5$)$_2$ | 510 |

TABLE 97

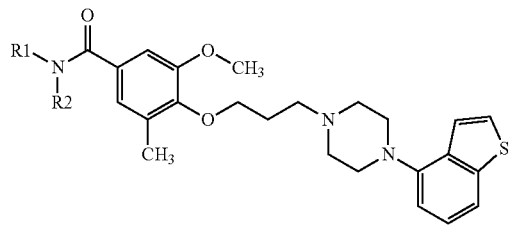

| Example | R1 | R2 | MS (M + 1) |
|---|---|---|---|
| 794 | —H | —(CH$_2$)$_3$OCH$_3$ | 512 |
| 795 | —H | —CH$_2$CH$_2$OH | 484 |
| 796 | —H | —CH$_2$CN | 479 |
| 797 | —C$_2$H$_5$ | -2-PYRIDYL | 545 |
| 798 | —H | -3-PYRIDYL | 517 |
| 799 | —H | —C$_6$H$_5$ | 516 |
| 800 | —H | —(CH$_2$)$_2$NHCOCH$_3$ | 525 |
| 801 | —H | —CH$_2$CH(C$_2$H$_5$)$_2$ | 524 |
| 802 | —H | —CH$_2$CH(OCH$_3$)$_2$ | 528 |
| 803 | —H | —(CH$_2$)$_3$OCH(CH$_3$)$_2$ | 540 |
| 804 | —H | —(CH$_2$)$_2$OCH(CH$_3$)$_2$ | 526 |
| 805 | —H | —CH$_2$CH$_2$F | 486 |
| 806 | —H | —CH$_2$CONHCH$_3$ | 511 |
| 807 | —H | —CH$_2$CH$_2$SCH$_3$ | 514 |
| 808 | —H | —CH$_2$CHF$_2$ | 504 |

TABLE 98

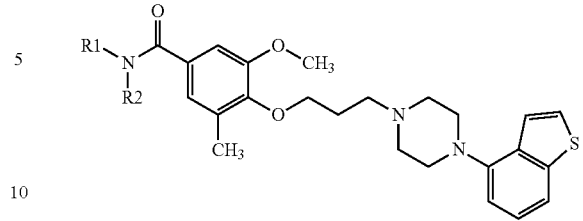

| Example | R1 | R2 | MS (M + 1) |
|---|---|---|---|
| 809 | —H | MeO$_2$C–CH(i-Pr)– | 554 |
| 810 | —H | i-Pr-CH$_2$-CH(CO$_2$Me)– | 568 |
| 811 | —H | H$_2$N-CO-CH(i-Pr)– | 539 |
| 812 | —H | EtO$_2$C-CH$_2$-CH(CO$_2$Et)– | 598 |
| 813 | —H | H$_3$C-CH(i-Pr?)-CO$_2$Et | 540 |
| 814 | —H | H$_3$C-CH(i-Pr?)-CO$_2$Me | 526 |
| 815 | —H | H$_3$C-CH(CH$_3$)-CONH$_2$ | 511 |
| 816 | —H | H$_3$C-C(=CH$_2$)-CH$_2$CH$_3$ | 494 |
| 817 | —H | H$_2$NOC-CH(CH$_3$)-CONH$_2$ | 540 |
| 818 | —H | EtO$_2$C-CH$_2$-CH(CH$_3$)-CO$_2$Et | 612 |
| 819 | —C$_2$H$_5$ | H$_3$C-C(=CH$_2$)-CH$_2$CH$_3$ | 522 |

TABLE 99

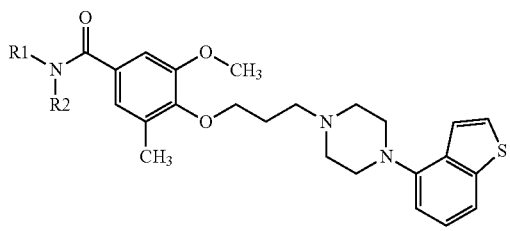

| Example | R1 | R2 | MS (M + 1) |
|---|---|---|---|
| 820 | —H | (2-methyl-1-methoxymethyl)propyl-like: CH3OCH2CH(CH3)CH2CH3 | 526 |
| 821 | —H | CH3OCH2CH(CH3)2 | 512 |
| 822 | —H | HOCH2CH(OH)CH2CH3 | 514 |
| 823 | —H | H2N-C(=NH)-CH2CH3 | 496 |
| 824 | —H | 1-methylcyclopropyl | 494 |
| 825 | —H | 1-methylcyclopentyl | 522 |
| 826 | —H | trans-4-hydroxycyclohexyl | 538 |
| 827 | —H | 2-methylcyclohexyl (with CH3) | 536 |
| 828 | —H | 4-(methoxycarbonyl)cyclohexyl | 580 |
| 829 | —CH3 | 2-methoxyphenyl | 560 |
| 830 | —CH3 | 4-methylphenyl | 544 |

TABLE 100

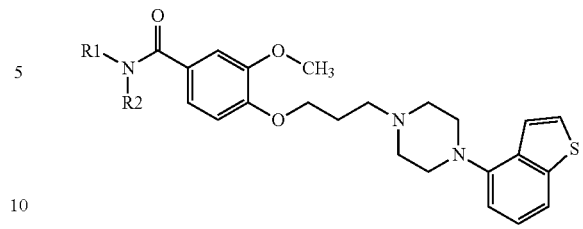

| Example | R1 | R2 | MS (M + 1) |
|---|---|---|---|
| 831 | —CH3 | 4-chlorophenyl | 564 |
| 832 | —H | 3-(methylthio)phenyl | 562 |
| 833 | —H | 2-(methylthio)phenyl | 562 |
| 834 | —H | 3,4-dichlorophenyl | 584 |
| 835 | —H | 4-(trifluoromethoxy)phenyl | 600 |
| 836 | —H | 4-butylphenyl | 572 |
| 837 | —H | 4-chlorophenyl | 550 |
| 838 | —H | 4-methoxyphenyl | 546 |
| 839 | —H | 2-methoxyphenyl | 546 |
| 840 | —H | 3-methoxyphenyl | 546 |
| 841 | —H | 2-chlorophenyl | 550 |

TABLE 101

Common structure: R1R2N-C(=O)- attached to benzene ring with OCH3, CH3, and O-(CH2)3-piperazine-benzothiophene substituents

| Example | R1 | R2 | MS (M + 1) |
|---|---|---|---|
| 842 | —H | 3-chlorophenyl | 550 |
| 843 | —H | 4-methylphenyl (H3C-) | 530 |
| 844 | —H | 4-acetylphenyl (CH3C(=O)-) | 558 |
| 845 | —H | 2-(methoxycarbonyl)phenyl (CO2CH3) | 574 |
| 846 | —H | 3,4-dimethoxyphenyl | 576 |
| 847 | —H | 2-biphenyl | 592 |
| 848 | —H | 2-(pyrrol-1-yl)phenyl | 581 |
| 849 | —H | 4-chloro-2-methoxyphenyl | 580 |
| 850 | —H | 2,5-dimethoxyphenyl | 576 |

TABLE 101-continued

| Example | R1 | R2 | MS (M + 1) |
|---|---|---|---|
| 851 | —H | 3,5-dimethoxyphenyl | 576 |

TABLE 102

Common structure: R1R2N-C(=O)- attached to benzene ring with OCH3, CH3, and O-(CH2)3-piperazine-benzothiophene substituents

| Example | R1 | R2 | MS (M + 1) |
|---|---|---|---|
| 852 | —H | 4-methoxy-2-methylphenyl | 560 |
| 853 | —H | 4-methoxy-3-methyl-acetamidophenyl | 603 |
| 854 | —H | 2,3-dimethoxy-5-methylphenyl | 576 |
| 855 | —H | 2-(prop-1-en-2-yl)phenyl | 556 |
| 856 | —H | 2-(2-phenylpropan-2-yl) / cumyl | 558 |
| 857 | —H | 2-chlorobenzyl | 564 |

TABLE 102-continued
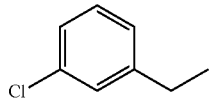
| Example | R1 | R2 | MS (M + 1) |
|---|---|---|---|
| 858 | —H | 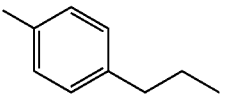 | 564 |
| 859 | —H | 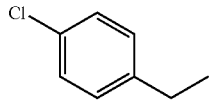 | 564 |
| 860 | —H | 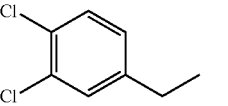 | 572 |
| 861 | —H | 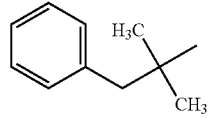 | 560 |
| 862 | —H | 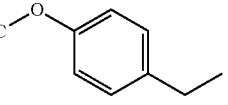 | 560 |
TABLE 103
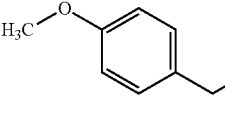
| Example | R1 | R2 | MS (M + 1) |
|---|---|---|---|
| 863 | —H | 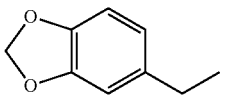 | 574 |
| 864 | —H | 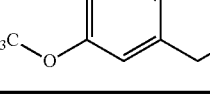 | 574 |
TABLE 103-continued
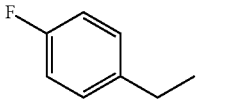
| Example | R1 | R2 | MS (M + 1) |
|---|---|---|---|
| 865 | —H | 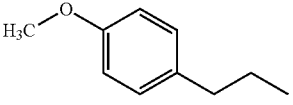 | 578 |
| 866 | —H | 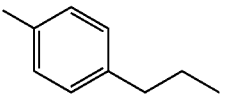 | 598 |
| 867 | —H | 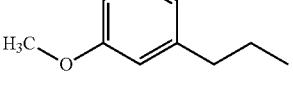 | 614 |
| 868 | —H | 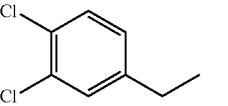 | 574 |
| 869 | —H | 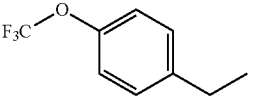 | 548 |
| 870 | —H | 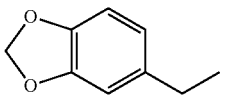 | 590 |
| 871 | —H | 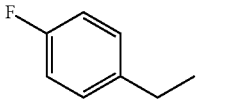 | 544 |
| 872 | —H | 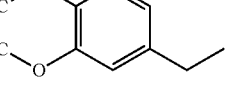 | 562 |
| 873 | —H | 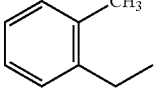 | 602 |

249

TABLE 104

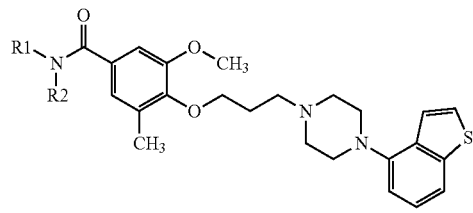

| Example | R1 | R2 | MS (M + 1) |
|---|---|---|---|
| 874 | —H | 2-phenyl-propanoic acid methyl ester (CH(CH3)CO2CH3, Ph) | 588 |
| 875 | —H | 2-benzyl-propanamide (CH(CH3)C(O)NH2, CH2Ph) | 587 |
| 876 | —H | 2-methoxybenzyl (CH2-C6H4-OCH3) | 560 |
| 877 | —H | 2-fluorophenylpropyl | 562 |
| 878 | —H | 2-methoxyphenylpropyl | 574 |
| 879 | —H | 2-chlorophenylpropyl | 578 |
| 880 | —H | 2-methylphenylpropyl | 558 |
| 881 | —H | 3-methylphenylpropyl | 558 |
| 882 | —H | 3-chlorophenylpropyl | 578 |
| 883 | —H | 3-fluorophenylpropyl | 562 |

250

TABLE 105

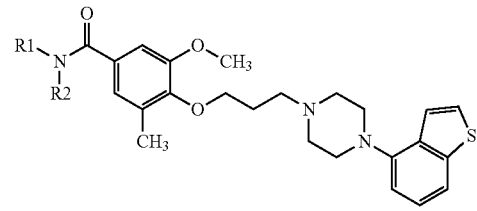

| Example | R1 | R2 | MS (M + 1) |
|---|---|---|---|
| 884 | —H | 3,5-dimethoxyphenylethyl | 590 |
| 885 | —H | 2-ethoxyphenylethyl | 574 |
| 886 | —H | 3-chloro-4-(difluoromethoxy)phenylethyl | 630 |
| 887 | —CH3 | 4-methylphenylethyl | 558 |
| 888 | —CH3 | benzo[1,3]dioxol-5-ylethyl | 588 |
| 889 | —CH3 | 2-methoxyphenylethyl | 574 |
| 890 | —H | 3-(trifluoromethyl)phenylethyl | 598 |
| 891 | —H | 2-fluorophenylethyl | 548 |
| 892 | —H | 2-(trifluoromethyl)phenylethyl | 598 |
| 893 | —H | 3-fluorophenylethyl | 548 |

TABLE 106

[Structure: R1R2N-C(O)-phenyl with OCH3, O-(CH2)3-piperazine-benzothiophene, and CH2 substituents]

| Example | R1 | R2 | MS (M+1) |
|---------|----|----|----------|
| 894 | —H | 3,5-difluorophenyl-ethyl | 566 |
| 895 | —H | 3-(trifluoromethoxy)phenyl-ethyl | 614 |
| 896 | —H | 2-fluorophenyl-isopropyl (CH(CH3)2) | 562 |
| 897 | —H | 3-fluorophenyl-isopropyl | 562 |
| 898 | —H | 4-fluorophenyl-isopropyl | 562 |
| 899 | —H | 3,5-difluorophenyl-isopropyl | 580 |
| 900 | —H | 2-(trifluoromethyl)phenyl-isopropyl | 612 |
| 901 | —H | 3-(trifluoromethyl)phenyl-isopropyl | 612 |

TABLE 106-continued

| Example | R1 | R2 | MS (M+1) |
|---------|----|----|----------|
| 902 | —H | 4-(trifluoromethyl)phenyl-isopropyl | 612 |

TABLE 107

[Structure: R1R2N-C(O)-phenyl with OCH3, O-(CH2)3-piperazine-benzothiophene, and CH3 substituents]

| Example | R1 | R2 | MS (M+1) |
|---------|----|----|----------|
| 903 | —H | 2-fluorophenyl-sec-butyl | 576 |
| 904 | —H | 3-fluorophenyl-sec-butyl | 576 |
| 905 | —H | 4-fluorophenyl-sec-butyl | 576 |
| 906 | —H | 3,5-difluorophenyl-sec-butyl | 594 |

TABLE 107-continued

| Example | R1 | R2 | MS (M + 1) |
|---|---|---|---|
| 907 | —H | 2-(CF3)-phenyl-CH(CH3)CH2CH3 | 626 |
| 908 | —H | 3-(CF3)-phenyl-CH(CH3)CH2CH3 | 626 |
| 909 | —H | 4-(CF3)-phenyl-CH(CH3)CH2CH3 | 626 |
| 910 | —H | 2,6-difluorophenyl-CH2CH3 | 566 |
| 911 | —H | 4-(OCF3)-phenyl-CH(CH3)2 | 628 |

TABLE 108

| Example | R1 | R2 | MS (M + 1) |
|---|---|---|---|
| 912 | —H | 4-(OCH3)-phenyl-CH(CH3)CH2CH3 | 602 |
| 913 | —H | 4-Cl-phenyl-CH(CH3)CH2CH3 | 606 |
| 914 | —H | phenyl-CH=CH-CH3 | 584 |
| 915 | —C2H5 | 1-methylnaphthalenyl | 566 |
| 916 | —H | 2-ethylnaphthalenyl | 580 |
| 917 | —H | 2-ethylpyridinyl | 531 |
| 918 | —H | 3-ethylpyridinyl | 531 |
| 919 | —H | 4-ethylpyridinyl | 531 |
| 920 | —H | 2-propylpyridinyl | 545 |
| 921 | —C2H5 | 2-propylpyridinyl | 573 |

TABLE 109
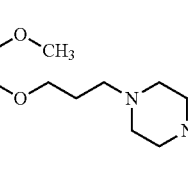
| Example | R1 | R2 | MS (M + 1) |
|---|---|---|---|
| 922 | —C₂H₅ | 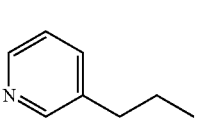 | 559 |
| 923 | —H | 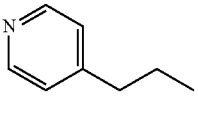 | 545 |
| 924 | —H | 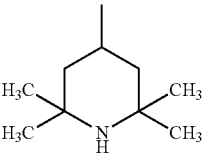 | 545 |
| 925 | —H | 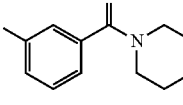 | 579 |
| 926 | —CH₃ | 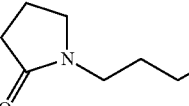 | 675 |
| 927 | —H | 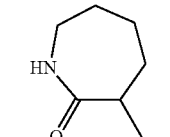 | 565 |
| 928 | —H | 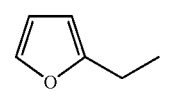 | 551 |
| 929 | —H | 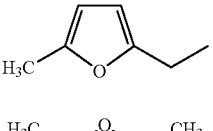 | 520 |
| 930 | —H | 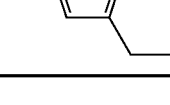 | 534 |
| 931 | —H |  | 548 |
TABLE 110
| Example | R1 | R2 | MS (M + 1) |
|---|---|---|---|
| 932 | —H |  | 520 |
| 933 | —H |  | 524 |
| 934 | —H |  | 524 |
| 935 | —H |  | 538 |
| 936 | —H |  | 526 |
| 937 | —H |  | 540 |
| 938 | —H |  | 536 |
| 939 | —H | 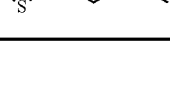 | 550 |
| 940 | —H |  | 536 |
| 941 | —H |  | 550 |

TABLE 111

| Example | R1 | R2 | MS (M + 1) |
|---|---|---|---|
| 942 | —H | 1-methyl-2-ethylpyrrole | 533 |
| 943 | —H | 1-propylpyrrole | 533 |
| 944 | —H | 5-methyl-4-butyl-1H-pyrazole | 562 |
| 945 | —H | 1,5-dimethyl-3-ethylpyrazole | 548 |
| 946 | —H | 1-butylimidazole | 548 |
| 947 | —H | imidazolyl-methyl-CH(CH3)-C(O)NH2 | 577 |
| 948 | —H | imidazolyl-CH2-CH(CH3)-CO2CH3 | 592 |
| 949 | —H | 4-propyl-1H-imidazole | 534 |
| 950 | —H | 2-ethylthiazole | 537 |
| 951 | —H | 2-methyl-5-ethylpyrazine | 546 |
| 952 | —H | 6-methyl-1H-indazole | 556 |

TABLE 112

| Example | R1 | R2 | MS (M + 1) |
|---|---|---|---|
| 953 | —H | 3-propyl-1H-indole | 583 |
| 954 | —H | 1-butylbenzimidazole | 598 |
| 955 | —H | 2-ethyl-1H-benzimidazole | 570 |
| 956 | —H | 5-ethyl-2,3-dihydrobenzofuran | 572 |
| 957 | —H | 8-methyl-3-methyl-3,4-dihydroquinolin-2(1H)-one | 599 |
| 958 | —H | 8-methoxy-3-methyl-3,4-dihydroquinolin-2(1H)-one | 615 |
| 959 | —H | 2-ethyl-4H-chromen-4-one | 598 |

TABLE 113

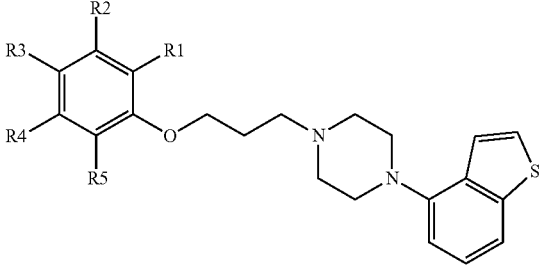

| Example | R1 | R2 | R3 | R4 | R5 | MS (M + 1) |
|---|---|---|---|---|---|---|
| 960 | —H | —H | —NHCOCH$_3$ | —H | —H | 410 |
| 961 | —H | —NHCOCH$_3$ | —H | —H | —H | 410 |
| 962 | —H | —H | —OCH$_3$ | —H | —H | 383 |
| 963 | —H | —H | —Cl | —H | —H | 387 |
| 964 | —H | —H | —CH$_3$ | —H | —H | 367 |
| 965 | —H | —H | —CF$_3$ | —H | —H | 421 |
| 966 | —H | —H | —OCF$_3$ | —H | —H | 437 |
| 967 | —H | —H | —SCH$_3$ | —H | —H | 399 |
| 968 | —H | —H | —C$_6$H$_5$ | —H | —H | 429 |
| 969 | —H | —H | —OCH$_2$C$_6$H$_5$ | —H | —H | 459 |
| 970 | —H | —H | —NO$_2$ | —H | —H | 398 |
| 971 | —H | —H | —COCH$_3$ | —H | —H | 395 |
| 972 | —OCH$_3$ | —OCH$_3$ | —H | —H | —H | 413 |
| 973 | —OCH$_3$ | —H | —H | —H | —OCH$_3$ | 413 |
| 974 | —H | —OCH$_3$ | —OCH$_3$ | —H | —H | 413 |
| 975 | —H | —CH$_3$ | —H | —H | —H | 367 |
| 976 | —CH$_3$ | —H | —H | —H | —CH$_3$ | 381 |
| 977 | —F | —H | —H | —H | —H | 371 |
| 978 | —H | —F | —H | —H | —H | 371 |
| 979 | —H | —H | —F | —H | —H | 371 |
| 980 | —F | —H | —F | —H | —H | 389 |
| 981 | —H | —F | —H | —H | —F | 389 |
| 982 | —F | —H | —H | —H | —F | 389 |
| 983 | —F | —H | —H | —CH$_3$ | —H | 385 |
| 984 | —H | —H | —CH$_2$CO2CH$_3$ | —H | —H | 425 |
| 985 | —CH$_3$ | —H | —COCH$_3$ | —H | —H | 409 |
| 986 | —H | —OC$_6$H$_5$ | —H | —H | —H | 445 |
| 987 | 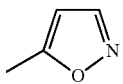 | —H | —H | —H | —H | 420 |
| 988 | —H | —H | 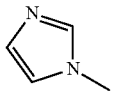 | —H | —H | 419 |

TABLE 114

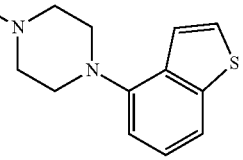

| Example | R1 | MS (M + 1) |
|---|---|---|
| 989 | -3-PYRIDYL | 354 |
| 990 | 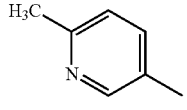 | 368 |

TABLE 114-continued

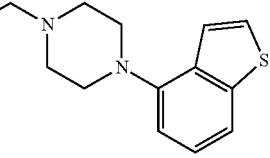

| Example | R1 | MS (M + 1) |
|---|---|---|
| 991 | 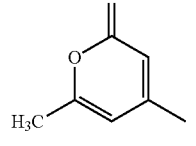 | 385 |

TABLE 114-continued

[Structure: R1—O—(CH2)3—N(piperazine)N—benzothiophen-4-yl]

| Example | R1 | MS (M + 1) |
|---|---|---|
| 992 | 4-methyl-2,3-dihydro-1H-inden-1-one-4-yl | 407 |
| 993 | 5-methyl-2,3-dihydro-1H-inden-yl | 393 |
| 994 | 5-methyl-2,3-dihydro-1H-inden-1-one-yl | 407 |
| 995 | 4,7-dimethyl-2,3-dihydro-1H-inden-yl | 407 |
| 996 | 6-methyl-3,4-dihydronaphthalen-1(2H)-one-yl | 421 |
| 997 | 5-methyl-3,4-dihydronaphthalen-1(2H)-one-yl | 421 |
| 998 | 5-methylnaphthalen-1-ol-yl | 419 |
| 999 | 6-methylnaphthalen-2-ol-yl | 419 |
| 1000 | 6-methyl-2-naphthonitrile-yl | 428 |

TABLE 115

[Structure: R1—O—(CH2)3—N(piperazine)N—benzothiophen-4-yl]

| Example | R1 | MS (M + 1) |
|---|---|---|
| 1001 | 7-methoxy-3-methylnaphthalen-yl | 433 |
| 1002 | 6-methoxy-2-methylnaphthalen-yl | 433 |
| 1003 | 8-chloro-5-methylnaphthalen-yl | 437 |
| 1004 | 6-methylbenzofuran-3(2H)-one-yl | 409 |
| 1005 | 2,2,7-trimethyl-2,3-dihydrobenzofuran-yl | 423 |
| 1006 | 5-methylbenzofuran-2(3H)-one-yl | 409 |
| 1007 | 7-methyl-2H-chromen-2-one-yl | 421 |
| 1008 | 4,6-dimethyl-2H-chromen-2-one-yl | 435 |
| 1009 | 7-methoxy-4-methyl-2H-chromen-2-one-yl | 451 |
| 1010 | 6-methylbenzo[d][1,3]oxathiol-2-one-yl | 427 |

TABLE 115-continued

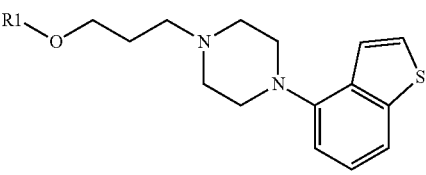

| Example | R1 | MS (M +1) |
|---|---|---|
| 1011 | 3-methyl-benzo[d]isoxazole | 394 |

TABLE 116

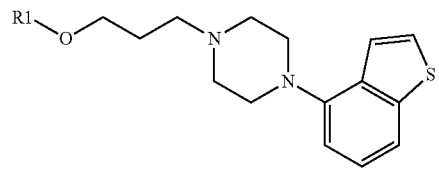

| Example | R1 | MS (M + 1) |
|---|---|---|
| 1012 | 5-methyl-benzo[c][1,2,5]oxadiazole | 395 |
| 1013 | 1,3,3-trimethyl-5-methyl-indolin-2-one | 450 |
| 1014 | 3,3-dimethyl-5-methyl-indolin-2-one | 436 |
| 1015 | 6-methyl-benzo[d]oxazol-2(3H)-one | 410 |
| 1016 | 3-methyl-6-methyl-benzo[d]oxazol-2(3H)-one | 424 |
| 1017 | 2-methyl-6-methyl-benzo[d]thiazole | 424 |
| 1018 | -2-BENZTHIAZOLYL | 410 |

TABLE 116-continued

| Example | R1 | MS (M + 1) |
|---|---|---|
| 1019 | 4-methyl-7-methyl-2H-benzo[b][1,4]oxazin-3(4H)-one | 438 |
| 1020 | 7-methyl-2H-benzo[b][1,4]thiazin-3(4H)-one | 440 |
| 1021 | 1,3-dimethyl-6-methyl-3,4-dihydroquinazolin-2(1H)-one | 451 |
| 1022 | 1,3-dimethyl-6-methyl-quinazoline-2,4(1H,3H)-dione | 465 |

TABLE 117

| Example | R1 | Ms (M + 1) |
|---|---|---|
| 1023 | 1,4-dimethyl-7-methyl-quinoxaline-2,3(1H,4H)-dione | 465 |
| 1024 | 7-methyl-4,5-dihydro-1H-benzo[b]azepin-2(3H)-one | 436 |

TABLE 117-continued

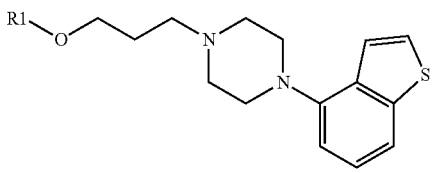

| Example | R1 | Ms (M + 1) |
|---|---|---|
| 1025 | 1-methyl-7-methyl-2,3,4,5-tetrahydro-1H-benzo[b]azepin-2-one | 450 |
| 1026 | 8-methyl-1,3,4,5-tetrahydro-2H-benzo[b]azepin-2-one | 436 |
| 1027 | 8-methyl-2,3-dihydrobenzo[b][1,4]oxazepin-4(5H)-one | 438 |
| 1028 | 5-methyl-8-methyl-2,3-dihydrobenzo[b][1,4]oxazepin-4(5H)-one | 452 |
| 1029 | 7-methyl-2,3-dihydrobenzo[b][1,4]oxazepin-4(5H)-one | 438 |
| 1030 | 7-methyl-3,4-dihydrobenzo[f][1,4]oxazepin-5(2H)-one | 438 |
| 1031 | 1,5-dimethyl-7-methyl-1H-benzo[e][1,4]diazepine-2,4(3H,5H)-dione | 479 |
| 1032 | 8-methyl-1H-benzo[e][1,4]diazepine-2,4(3H,5H)-dione | 451 |

TABLE 118

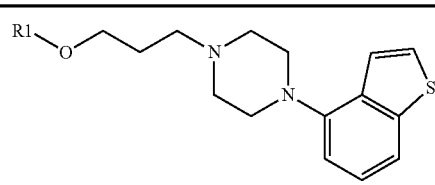

| Example | R1 | Ms (M + 1) |
|---|---|---|
| 1033 | 4-methyl-7-methyl-4,5-dihydro-1H-benzo[b]azepine-2,5(3H)-dione | 465 |
| 1034 | 1,4-dimethyl-7-methyl-1H-benzo[e][1,4]diazepine-2,5(3H,4H)-dione | 479 |
| 1035 | 7-methyl-4,5-dihydro-1H-benzo[b]azepin-2(3H)-one | 450 |
| 1036 | 8-methyldibenzofuran | 443 |

TABLE 119

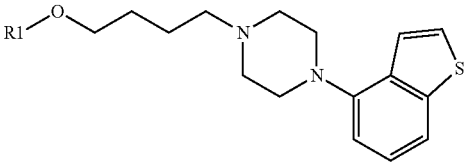

| Example | R1 | Ms (M + 1) |
|---|---|---|
| 1037 | 1,3,3,5-tetramethyl-1,3-dihydro-2H-indol-2-one | 464 |
| 1038 | 3,3,5-trimethyl-1,3-dihydro-2H-indol-2-one | 450 |

TABLE 119-continued
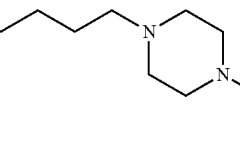
| Example | R1 | Ms (M + 1) |
|---|---|---|
| 1039 | 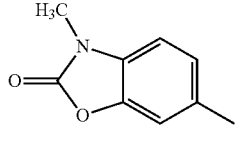 | 424 |
| 1040 | 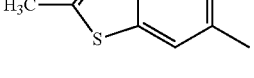 | 438 |
| 1041 | 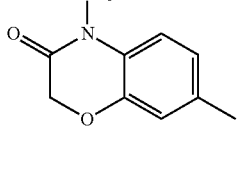 | 438 |
| 1042 | 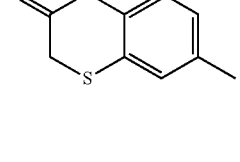 | 452 |
| 1043 | 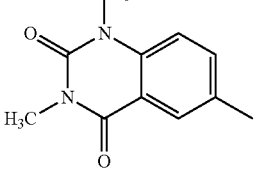 | 454 |
| 1044 | 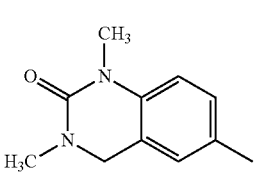 | 479 |
| 1045 | 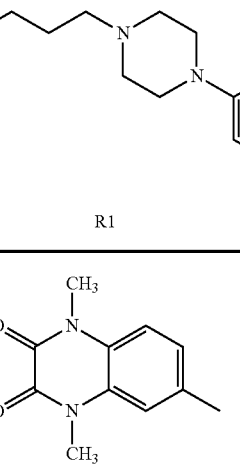 | 465 |
TABLE 120
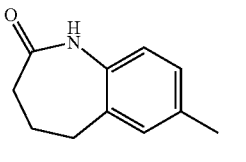
| Example | R1 | Ms (M + 1) |
|---|---|---|
| 1046 | 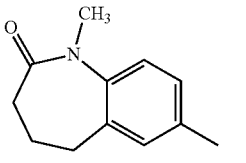 | 479 |
| 1047 | 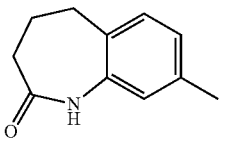 | 450 |
| 1048 | 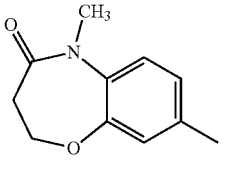 | 464 |
| 1049 | 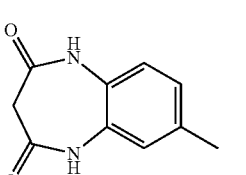 | 450 |
| 1050 | | 466 |
| 1051 | | 465 |

TABLE 120-continued

| Example | R1 | Ms (M + 1) |
|---|---|---|
| 1052 | (1,5-dimethyl-2,4-dioxo-benzodiazepin-7-yl, 7-CH3) | 493 |
| 1053 | (4-methyl-3,5-dioxo-benzodiazepin-7-yl, 7-CH3) | 479 |
| 1054 | (1,4-dimethyl-2,5-dioxo-benzodiazepin-7-yl, 7-CH3) | 493 |
| 1055 | (2-oxo-benzazocin-7-yl, 7-CH3) | 464 |

TABLE 121

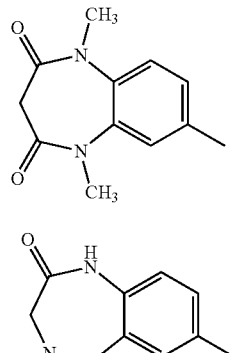

| Example | R1 | R2 | R3 | R4 | R5 | Crystal form (Recrystalization solvent) | Melting point (° C.) | salt |
|---|---|---|---|---|---|---|---|---|
| 1056 | —OCH₃ | —H | —NHSO₂C₂H₅ | —H | —CH₃ | White powder (Ethyl acetate) | 235.5-237.5 | Hydrochloride |
| 1057 | —CH₃ | —H | —CONHCH₃ | —H | —OH | White powder (Ethyl acetate) | 246.5 (dec) | Hydrochloride |
| 1058 | —CH₃ | —H | —Br | —H | —OCH₃ | White powder (Ethanol/ethyl acetate) | 265.0 (dec) | Hydrochloride |
| 1059 | —OCH₃ | —H | —NHCOCH₂NHCO₂C(CH₃)₃ | —H | —CH₃ | White powder (Ethyl acetate/isopropyl ether) | 140.5-142.5 | — |
| 1060 | —CH₃ | —H | —NHCOCH₂NH₂ | —H | —OCH₃ | White powder (Methanol/water) | 268.0 (dec) | Dihydrochloride |
| 1061 | —OCH₃ | —H | —NHCOCH₂NHCOCH₃ | —H | —CH₃ | White powder (Ethyl acetate/isopropyl ether) | 167.5-170.5 | — |
| 1062 | —OCH₃ | —H | —NHCOCH₂NHCO₂CH₃ | —H | —CH₃ | White powder (Ethyl acetate/isopropyl ether) | 157.0-159.5 | — |
| 1063 | —CH₃ | —H | —NHCOCH₂NHCHO | —H | —OCH₃ | White powder (Dichloromethane/water) | 235.5 (dec) | Hydrochloride |

TABLE 122

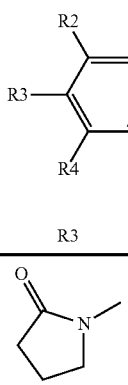

| Example | R1 | R2 | R3 | R4 | R5 | Crystal form (Recrystalization solvent) | Melting point (° C.) | salt |
|---|---|---|---|---|---|---|---|---|
| 1064 | —CH₃ | —H | —CONHCH₃ | —H | —O(CH₂)₂N(CH₃)₂ | White powder (Ethyl acetate) | 235.5-240.5 (dec) | Dihydrochloride |
| 1065 | —CH₃ | —H | —CONHCH₃ | —H | —O(CH₂)₂OCH₃ | White powder (Isopropyl alcohol/ isopropyl ether) | 194.0-197.5 | Hydrochloride |
| 1066 | —CH₃ | —H | —CONHCH₃ | —H | —OCH₂CF₃ | Light yellow powder (Ethyl acetate/ isopropyl ether) | 156.0-157.5 | Hydrochloride |

TABLE 123

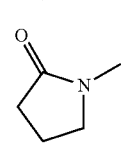

| Example | R1 | R2 | R3 | R4 | R5 | Crystal form (Recrystalization solvent) | Melting point (° C.) | Salt |
|---|---|---|---|---|---|---|---|---|
| 1067 | —H | —H | 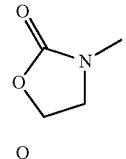 | —H | —H | White powder (Ethyl acetate/ isopropyl ether) | 114.0-115.5 | — |
| 1068 | —OCH₃ | —H | 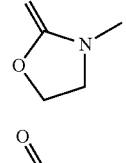 | —H | —CH₃ | White powder (Ethanol/ ethyl acetate) | 245.0 (dec) | Hydrochloride |
| 1069 | —H | —H | 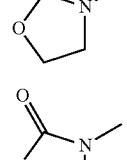 | —H | —H | White powder (Ethyl acetate) | 217.0-224.5 (dec) | Hydrochloride |
| 1070 | —OCH₃ | —H | 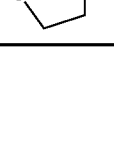 | —H | —CHO | White powder (Ethanol) | 218.0 (dec) | Hydrochloride |
| 1071 | —OCH₃ | —H | | —H | —CH₂OH | White powder (Ethanol) | 224.0-226.5 (dec) | Hydrochloride |
| 1072 | —OCH₃ | —H | | —H | —CH₂OCH₃ | White powder (Ethanol) | 224.0-226.0 | Hydrochloride |

TABLE 124

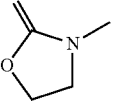

| Example | R1 | R2 | R3 | R4 | R5 | Crystal form (Recrystalization solvent) | Melting point (° C.) | Salt |
|---|---|---|---|---|---|---|---|---|
| 1073 | —OCH$_3$ | —H | 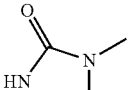 | —H | —CH$_2$N(CH$_3$)$_2$ | White powder (Ethanol/ether) | 151.0-152.0 | Difumarate |
| 1074 | —OCH$_3$ | —H | 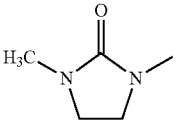 | —H | —CH$_3$ | Light yellow powder (Ethanol/water) | 264.0 (dec) | Hydrochloride |
| 1075 | —OCH$_3$ | —H | 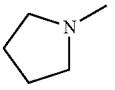 | —H | —CH$_3$ | Light yellow powder (Ehyl acetate/ isopropyl ether) | 143.5-151.0 | — |
| 1076 | —OCH$_3$ | —H |  | —H | —CH$_3$ | White powder (Ethyl acetate) | 246.5-249.0 (dec) | Hydrochloride |
| 1077 | —OCH$_3$ | —H | 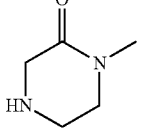 | —H | —CH$_3$ | Light yellow powder (Ethyl acetate) | 234.0-240.0 (dec) | Dihydrochloride |
| 1078 | —OCH$_3$ | —H | 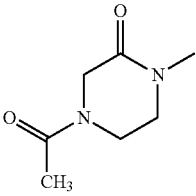 | —H | —CH$_3$ | White powder (Methanol/water) | 286.5 (dec) | Dihydrochloride |

TABLE 125

| Example | R1 | R2 | R3 | R4 | R5 | Crystal form (Recrystalization solvent) | Melting point (° C.) | Salt |
|---|---|---|---|---|---|---|---|---|
| 1079 | —OCH$_3$ | —H |  | —H | —CH$_3$ | White powder (Ethanol/water) | 218.0-221.5 | Hydrochloride |

TABLE 125-continued

[Structure: R2, R1 on benzene ring with R3, R4, R5; O—(CH₂)₃—N(piperazine)—N—benzothiophene]

| Example | R1 | R2 | R3 | R4 | R5 | Crystal form (Recrystalization solvent) | Melting point (° C.) | Salt |
|---|---|---|---|---|---|---|---|---|
| 1080 | —OCH₃ | —H | [4-methyl-3-oxo-piperazine-1-carboxylic acid methyl ester group] | —H | —CH₃ | White powder (Ethanol/ethyl acetate) | 223.0-228.0 | Hydrochloride |
| 1081 | —OCH₃ | —H | [4-methyl-3-oxopiperazinyl] | —H | —CH₃ | White powder (Ethyl acetate/ isopropyl ether) | 139.5-142.0 | — |
| 1082 | —OCH₃ | —H | [4-methylpiperazinyl with N-CH₃] | —H | —CH₃ | White powder (Ethyl acetate) | 270.0 (dec) | Trihydrochloride |
| 1083 | —OCH₃ | —H | [1-acetyl-4-methylpiperazinyl] | —H | —CH₃ | White powder (Ethyl acetate) | 257.0-261.0 (dec) | Hydrochloride |
| 1084 | —OCH₃ | —H | [1-acetyl-4-methylpiperazinyl] | —H | —CH₂OH | White powder (Ethyl acetate) | 217.5-221.0 | Hydrochloride |

TABLE 126

[Structure: R2, R1 on benzene ring with R3, R4, R5; O—(CH₂)₃—N(piperazine)—N—benzothiophene]

| Example | R1 | R2 | R3 | R4 | R5 | Crystal form (Recrystalization solvent) | Melting point (° C.) | Salt |
|---|---|---|---|---|---|---|---|---|
| 1085 | —OCH₃ | —H | [4-methylpiperazine-1-carboxylic acid methyl ester] | —H | —CH₃ | White powder (Ethyl acetate) | 250.0 (dec) | Hydrochloride |

TABLE 126-continued

Structure: R1,R2,R3,R4,R5-substituted phenyl-O-(CH₂)₃-piperazine-benzothiophene

| Example | R1 | R2 | R3 | R4 | R5 | Crystal form (Recrystalization solvent) | Melting point (° C.) | Salt |
|---|---|---|---|---|---|---|---|---|
| 1086 | —OCH₃ | —H | 4-(methoxycarbonyl)piperazin-1-yl (CH₃-O-C(O)-N-piperazine) | —H | —CHO | Light yellow powder (Ethyl acetate) | 225.0 (dec) | Hydrochloride |
| 1087 | —OCH₃ | —H | 4-(methoxycarbonyl)piperazin-1-yl | —H | —CH₂OH | White powder (Ethyl acetate/ isopropyl ether) | 128.0-130.0 | — |
| 1088 | —OCH₃ | —H | morpholin-4-yl | —H | —CH₃ | White powder (Ethyl acetate) | 246.0 (dec) | Hydrochloride |
| 1089 | —OCH₃ | —H | piperidin-1-yl | —H | —CH₃ | White powder (Ethyl acetate) | 248.0-251.0 (dec) | Dihydrochloride |

TABLE 127

Structure: R1,R2,R3,R4,R5-substituted phenyl-O-(CH₂)₃-piperazine-benzothiophene

| Example | R1 | R2 | R3 | R4 | R5 | NMR | Salt |
|---|---|---|---|---|---|---|---|
| 1090 | —NH₂ | —H | —CONHC₂H₅ | —H | —H | $^1$H-NMR (CDCl₃) δ ppm: 1.23 (3H, t, J = 7.4 Hz), 2.00-2.15 (2H, m), 2.67 (2H, t, J = 7.3 Hz), 2.75 (4H, brs), 3.21 (4H, brs), 3.40-3.50 (2H, m), 3.50-4.30 (2H, br), 4.13 (2H, t, J = 6.5 Hz), 5.99 (1H, brs), 6.80 (1H, d, J = 8.4 Hz), 6.90 (1H, d, J = 7.6 Hz), 7.08 (1H, dd, J = 2.1, 8.3 Hz), 7.19 (1H, d, J = 2.1 Hz), 7.25-7.30 (1H, m), 7.35-7.45 (2H, m), 7.55 (1H, d, J = 8.0 Hz). | — |

TABLE 128

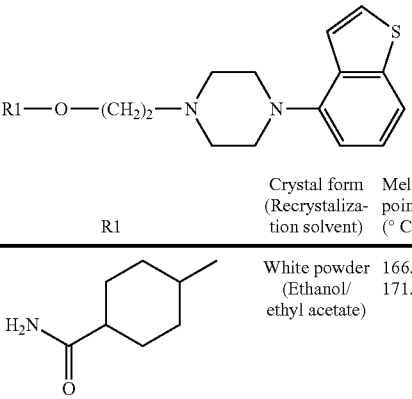

| Example | R1 | Crystal form (Recrystalization solvent) | Melting point (° C.) | Salt |
|---|---|---|---|---|
| 1091 | (4-methylcyclohexyl)carboxamide, H2N-C(=O)- | White powder (Ethanol/ ethyl acetate) | 166.0-171.0 | — |

TABLE 128-continued

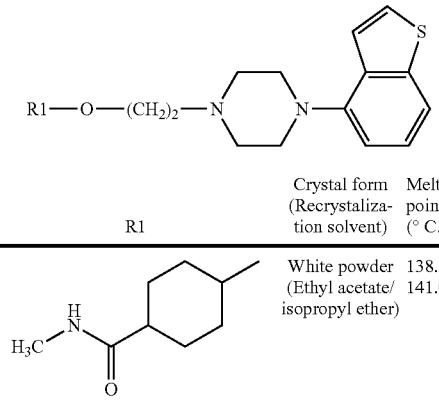

| Example | R1 | Crystal form (Recrystalization solvent) | Melting point (° C.) | Salt |
|---|---|---|---|---|
| 1092 | N-methyl (4-methylcyclohexyl)carboxamide | White powder (Ethyl acetate/ isopropyl ether) | 138.5-141.0 | — |

TABLE 129

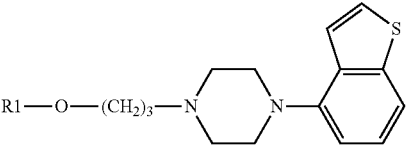

| Example | R1 | Crystal form (Recrystalization solvent) | Melting point (° C.) | Salt |
|---|---|---|---|---|
| 1093 | 1-allyl-5-methyl-N-methyl-pyrazole-3-carboxamide | White powder (Ethyl acetate/ isopropyl ether) | 138.5-140.5 | — |
| 1094 | 1-allyl-5-methyl-pyrazole-3-carboxylic acid | White powder (Ethanol) | 233.5 (dec) | Hydrochloride |
| 1095 | 1-propyl-5-methyl-N-methyl-pyrazole-3-carboxamide | White powder (Ethyl acetate/ isopropyl ether) | 147.0-148.5 | — |

TABLE 129-continued

R1—O—(CH₂)₃—N(piperazine)N—(benzothiophen-4-yl)

| Example | R1 | Crystal form (Recrystalization solvent) | Melting point (° C.) | Salt |
|---|---|---|---|---|
| 1096 | [1-(propyl)-5-methyl-1H-pyrazole-3-carboxylic acid] | White powder (water) | 115.0-121.0 | — |
| 1097 | [1-allyl-5-methyl-1H-pyrazole-3-carboxamide] | White powder (Ethyl acetate/ isopropyl ether) | 129.0-130.5 | — |
| 1098 | [1-propyl-5-methyl-1H-pyrazole-3-carboxamide] | White powder (Ethyl acetate/ isopropyl ether) | 139.0-140.5 | — |

TABLE 130

R1—O—(CH₂)₃—N(piperazine)N—(benzothiophen-4-yl)

| Example | R1 | Crystal form (Recrystalization solvent) | Melting point (° C.) | Salt |
|---|---|---|---|---|
| 1099 | [1,5-dimethyl-N,N-dimethyl-1H-pyrazole-3-carboxamide] | White powder (Ethyl acetate/ isopropyl ether) | 128.5-131.5 | — |

TABLE 130-continued

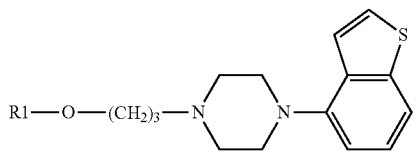

| Example | R1 | Crystal form (Recrystalization solvent) | Melting point (° C.) | Salt |
|---|---|---|---|---|
| 1100 | (1-methyl-5-methyl-pyrazol-3-yl)-C(=O)-NH-cyclopropyl | White powder (Isopropyl alcohol/ ethyl acetate) | 227.0 (dec) | Hydrochloride |
| 1101 | (1-methyl-5-methyl-pyrazol-3-yl)-C(=O)-N(CH3)(OCH3) | White powder (Ethanol/ ethyl acetate) | 211.0-213.5 | Hydrochloride |
| 1102 | (1-methyl-5-methyl-pyrazol-3-yl)-C(=O)-CH3 | White powder (Ethanol/water) | 245.0 (dec) | Hydrochloride |
| 1103 | 3-amino-1-methyl-5-methyl-pyrazole | White powder (Ethyl acetate/ isopropyl ether) | 112.0-113.0 | — |
| 1104 | (1-methyl-5-methyl-pyrazol-3-yl)-CH2OH | White powder (Ethyl acetate/ isopropyl ether) | 123.5-126.0 | — |
| 1105 | (1-methyl-5-methyl-pyrazol-3-yl)-NH-C(=O)-N(CH3)2 | Light yellow powder (Ethyl acetate) | 174.0-176.5 | Hydrochloride |

TABLE 130-continued

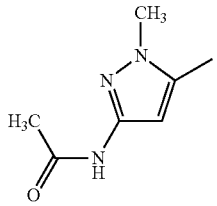

| Example | R1 | Crystal form (Recrystalization solvent) | Melting point (° C.) | Salt |
|---|---|---|---|---|
| 1106 | (1,5-dimethylpyrazol-3-yl with NHC(O)CH3) | White powder (Ethyl acetate/ isopropyl ether) | 137.0-139.0 | — |

TABLE 131

| Example | R1 | Crystal form (Recrystalization solvent) | Melting point (° C.) | Salt |
|---|---|---|---|---|
| 1107 | (1,5-dimethylpyrazol-3-yl with CH2OCH3) | White powder (Ethyl acetate) | 194.0-196.0 | Hydrochloride |
| 1108 | (1,5-dimethylpyrazol-3-yl with N(CH3)2) | White powder (Ethyl acetate) | 173.0-177.0 | Dihydrochloride |
| 1109 | (1,5-dimethylpyrazol-3-yl with NHC(O)OCH3) | White powder (Ethyl acetate/ isopropyl ether) | 162.5-165.0 | — |
| 1110 | ((CH3)2N-C(O)-(4-methylpiperidin-1-yl)) | White powder (Methanol) | 202-205 | Hydrochloride |

TABLE 131-continued

R1—O—(CH₂)₃—[piperazine]—[benzothiophene]

| Example | R1 | Crystal form (Recrystalization solvent) | Melting point (° C.) | Salt |
|---|---|---|---|---|
| 1111 | [1-acetyl-4-methylpiperidine group] | White powder (Methanol) | 208-210 | Hydrochloride |
| 1112 | [N-methylsuccinimide group] | White powder (Ethanol) | 255.0-257.0 | Hydrochloride |
| 1113 | [N,N-dimethyl-2-methylthiazole-4-carboxamide group] | White powder (Methanol) | 178-182 | Hydrochloride |

TABLE 132

R1—O—(CH₂)₃—[piperazine]—[benzothiophene]

| Example | R1 | Crystal form (Recrystalization solvent) | Melting point (° C.) | Salt |
|---|---|---|---|---|
| 1114 | [isobutyl 4-methylcyclohexanecarboxylate group] | White powder (Ethyl acetate) | 199.0-201.5 | Hydrochloride |
| 1115 | [4-methylcyclohexanecarboxamide group] | White powder (Ethyl acetate/ isopropyl ether) | 107.5-108.5 | — |
| 1116 | [N-methyl-4-methylcyclohexanecarboxamide group] | White powder (Ethyl acetate/ isopropyl ether) | 110.0-112.0 | — |

TABLE 132-continued


| Example | R1 | Crystal form (Recrystalization solvent) | Melting point (° C.) | Salt |
|---|---|---|---|---|
| 1117 |  | White powder (water) | 203.0-210.0 | — |
| 1118 | 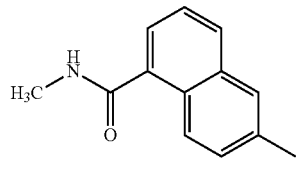 | White powder (Ethyl acetate/ isopropyl ether) | 167.0-169.0 | — |
| 1119 | 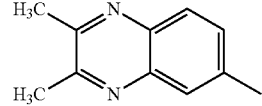 | White powder (Ethyl acetate) | 138.0-140.0 | — |
| 1120 | 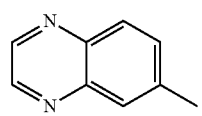 | White powder (Ethyl acetate/hexane) | 115 | — |
| 1121 | 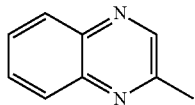 | Light brown powder (Ethanol) | 134.7 | — |

TABLE 133

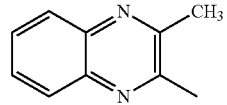

| Example | R1 | Crystal form (Recrystalization solvent) | Melting point (° C.) | Salt |
|---|---|---|---|---|
| 1122 |  | White powder (Ethanol) | 131.3 | — |
| 1123 |  | White powder (Ethanol) | 107.1 | — |

TABLE 133-continued

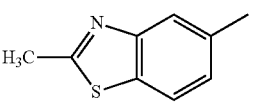

| Example | R1 | Crystal form (Recrystalization solvent) | Melting point (° C.) | Salt |
|---|---|---|---|---|
| 1124 | 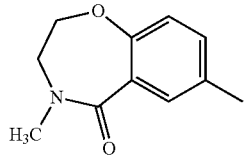 | White powder (Ethyl acetate) | 231.3-232.8 | Hydrochloride |
| 1125 | 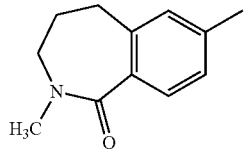 | White powder (Ethyl acetate) | 218.9-221.0 | Hydrochloride |
| 1126 | 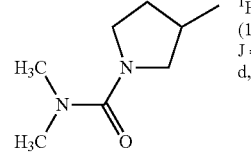 | White powder (Ethyl acetate) | 259.0-260.2 | Hydrochloride |

TABLE 134

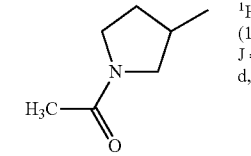

| Example | R1 | Melting point (° C.) | Salt |
|---|---|---|---|
| 1127 | 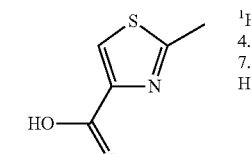 | $^1$H-NMR (DMSO-d$_6$) δ ppm: : 1.80-2.10 (4H, m), 2.74 (6H, s), 3.10-3.70 (16H, m), 4.00-4.10 (1H, m), 6.97 (1H, d, J = 7.5 Hz), 7.32 (1H, t, J = 7.9 Hz), 7.49 (1H, d, J = 5.6 Hz), 7.71 (1H, d, J = 8.0 Hz), 7.77 (1H, d, J = 5.5 Hz), 10.91 (1H, brs). | Hydrochloride |
| 1128 |  | $^1$H-NMR (DMSO-d$_6$) δ ppm: 1.80-2.10 (4H, m), 1.93 (3H, s), 3.10-3.60 (16H, m), 3.90-4.10 (1H, m), 6.95 (1H, d, J = 7.5 Hz), 7.30 (1H, t, J = 7.9 Hz), 7.47 (1H, d, J = 5.5 Hz), 7.68 (1H, d, J = 8.0 Hz), 7.75 (1H, d, J = 5.5 Hz), 11.30 (1H, brs). | Hydrochloride |
| 1129 |  | $^1$H-NMR (DMSO-d$_6$) δ ppm: 2.20-2.40 (2H, m), 2.70-3.70 (10H, m), 4.55 (2H, t, J = 5.9 Hz), 6.98 (1H, d, J = 7.5 Hz), 7.32 (1H, t, J = 7.9 Hz), 7.50 (1H, d, J = 5.5 Hz), 7.71 (1H, d, J = 8.0 Hz), 7.77 (1H, d, J = 5.5 Hz), 7.89 (1H, s), 10.97 (1H, brs), 12.93 (1H, brs). | Hydrochloride |

TABLE 134-continued

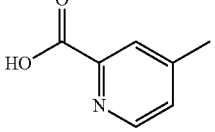

| Example | R1 | Melting point (° C.) | | Salt |
|---|---|---|---|---|
| 1130 | 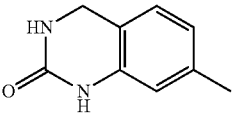 | ¹H-NMR (DMSO-d₆) δ ppm: 2.25-2.35 (2H, m), 3.20-4.00 (10H, m), 4.30 (2H, t, J = 5.8 Hz), 6.97 (1H, d, J = 7.5 Hz), 7.24 (1H, dd, J = 5.5, 2.8 Hz), 7.31 (1H, t, J = 7.8 Hz), 7.49 (1H, d, J = 5.4 Hz), 7.59 (1H, d, J = 2.5 Hz), 7.70 (1H, d, J = 8.1 Hz), 7.76 (1H, d, J = 5.5 Hz), 8.53 (1H, d, J = 5.7 Hz), 10.99 (1H, brs). | | Hydrochloride |
| 1131 | 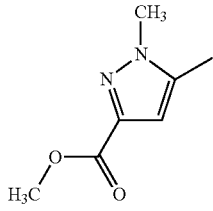 | ¹H-NMR (CDCl₃) δ ppm: 1.89-2.13 (2H, m), 2.52-2.83 (6H, m), 3.03-3.3- (4H, m), 4.01 (2H, t, J = 6.3 Hz), 4.46 (2H, brs), 5.30 (1H, brs), 6.51 (1H, dd, J = 8.3, 2.3 Hz), 6.83-6.96 (2H, m), 7.19-7.45 (3H, m), 7.48 (1H, brs), 7.55 (1H, d, J = 8.0 Hz). | | fumarate |

TABLE 135


| Example | R1 | Crystal form (Recrystalization solvent) | Melting point (° C.) | Salt |
|---|---|---|---|---|
| 1132 |  | Light brown powder (Ethanol/ethyl acetate) | 103.5-106.0 | — |
| 1133 | | Light brown powder (Dichloromethane/water) | 140.5-144.0 | — |
| 1134 | | White powder (Ethyl acetate/ isopropyl ether) | 143.0-144.5 | — |

TABLE 135-continued

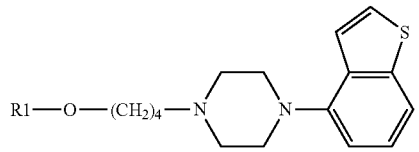

| Example | R1 | Crystal form (Recrystalization solvent) | Melting point (° C.) | Salt |
|---|---|---|---|---|
| 1135 | (1,5-dimethyl-1H-pyrazol-3-yl)-N-methylcarboxamide group | White powder (Ethanol/ethyl acetate) | 211.0-213.5 | Hydrochloride |
| 1136 | (1,5-dimethyl-1H-pyrazol-3-yl)methanol group | White powder (Ethyl acetate) | 207.5-209.5 | Hydrochloride |
| 1137 | 3-(methoxymethyl)-1,5-dimethyl-1H-pyrazole group | White powder (Ethanol) | 167.0-168.5 | Hydrochloride |
| 1138 | N,N,1,5-tetramethyl-1H-pyrazol-3-amine group | White powder (Ethyl acetate) | 156.5-158.5 | Hydrochloride |
| 1139 | methyl (1,5-dimethyl-1H-pyrazol-3-yl)carbamate group | White powder (Ethyl acetate/ isopropyl ether) | 157.5-161.5 | — |

TABLE 136

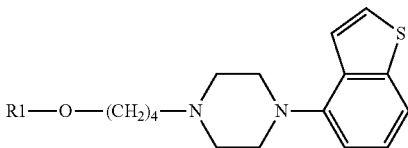

| Example | R1 | Crystal form (Recrystalization solvent) | Melting point (° C.) | Salt |
|---|---|---|---|---|
| 1140 | 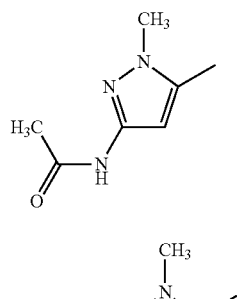 | White powder (Ethyl acetate) | 203.5-206.0 | Hydrochloride |
| 1141 | 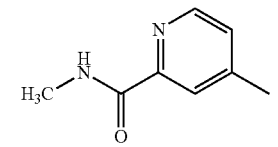 | White powder (Ethyl acetate) | 186.0-187.5 | Hydrochloride |
| 1142 | 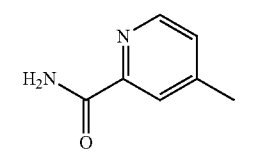 | White powder (Ethyl acetate) | 203.0-207.0 | Hydrochloride |
| 1143 | 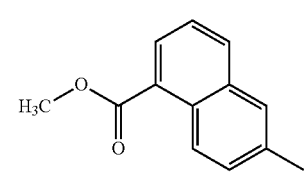 | White powder (Ethyl acetate/ isopropyl ether) | 146.5-148.0 | — |
| 1144 | 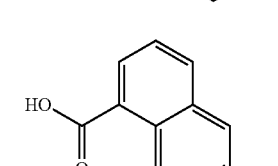 | White powder (Ethyl acetate/ isopropyl ether) | 96.5-97.0 | — |
| 1145 | 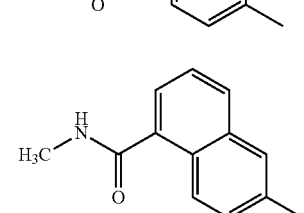 | White powder (acetic acid) | 254.0 (dec) | Dihydrochloride |
| 1146 |  | White powder (Ethyl acetate/ isopropyl ether) | 124.0-126.5 | — |

TABLE 136-continued

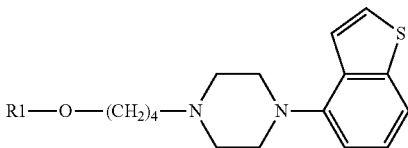

| Example | R1 | Crystal form (Recrystalization solvent) | Melting point (° C.) | Salt |
|---|---|---|---|---|
| 1147 | 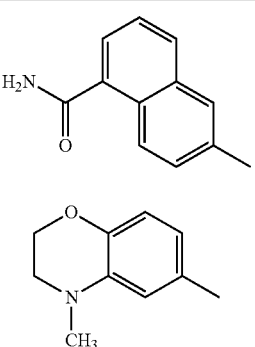 | White powder (Ethanol/ethyl acetate) | 181.5-183.5 | — |
| 1148 | 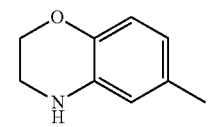 | White powder (Ethyl acetate) | 230.2-231.5 | Hydrochloride |
| 1149 | 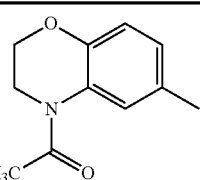 | White powder (Ethyl acetate) | 207.4-209.6 | Hydrochloride |

TABLE 137

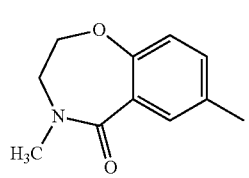

| Example | R1 | Crystal form (Recrystalization solvent) | Melting point (° C.) | Salt |
|---|---|---|---|---|
| 1150 | 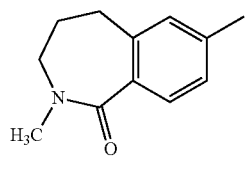 | White powder (Ethyl acetate) | 213.8-215.2 | Hydrochloride |
| 1151 | | White powder (Ethyl acetate) | 217.0-218.0 | Hydrochloride |
| 1152 | | White powder (Ethyl acetate) | 231.6-232.9 | Hydrochloride |

TABLE 137-continued
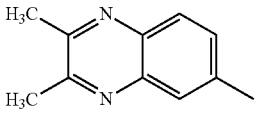
| Example | R1 | Crystal form (Recrystalization solvent) | Melting point (° C.) | Salt |
|---|---|---|---|---|
| 1153 | 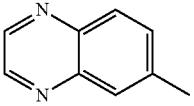 | Light yellow powder (Ethanol) | 135.7 | — |
| 1154 | 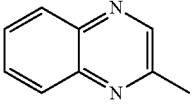 | Light brown powder (Ethanol) | 238.1-240.1 | Hydrochloride |
| 1155 | 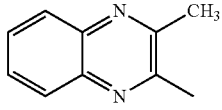 | White powder (Ethanol) | 210.4 | Hydrochloride |
| 1156 | 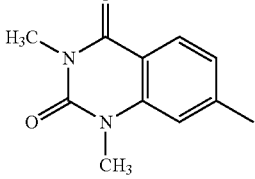 | White powder (Ethanol) | 94.1 | — |
TABLE 138
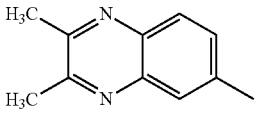
| Example | R1 | NMR | Salt |
|---|---|---|---|
| 1157 | 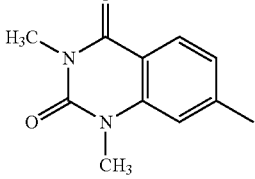 | $^1$H-NMR (CDCl$_3$) δ ppm: 1.72-1.83 (2H, m), 1.83-1.98 (2H, m), 2.48-2.59 (2H, m), 2.64-2.81 (4H, m), 3.12-3.28 (4H, m), 3.46 (3H, s), 3.58 (3H, s), 4.13 (2H, t, J = 6.3 Hz), 6.62 (1H, d, J = 2.1 Hz), 6.80 (1H, dd, J = 8.8, 2.1 Hz), 6.90 (1H, d, J = 7.6 Hz), 7.20-7.31 (1H, m), 7.35-7.43 (2H, m), 7.55 (1H, d, J = 8.0 Hz), 8.15 (1H, d, J = 8.8 Hz). | — |

TABLE 139

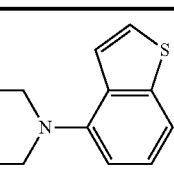

| Example | R1 | Crystal form (Recrystalization solvent) | Melting point (° C.) | Salt |
|---|---|---|---|---|
| 1158 | (1,5-dimethyl-pyrazol-3-yl)-C(O)OCH₃ | White powder (Ethyl acetate) | 200.5-201.5 | Hydrochloride |
| 1159 | (1,5-dimethyl-pyrazol-3-yl)-C(O)NHCH₃ | White powder (Ethanol/ethyl acetate) | 225.0-230.0 | Hydrochloride |
| 1160 | (1,5-dimethyl-pyrazol-3-yl)-C(O)OH | White powder (Dichloromethane/water) | 156.0-158.5 | — |
| 1161 | (1,5-dimethyl-pyrazol-3-yl)-C(O)NH₂ | White powder (Ethanol/ethyl acetate) | 169.0-171.5 | — |

TABLE 140

| Example | R1 | R2 | R3 | R4 | R5 | NMR |
|---|---|---|---|---|---|---|
| 1162 | —OCH₃ | —H | —NHCO2C(CH₃)₃ | —H | —CH₃ | $^1$H-NMR (CDCl₃) δ ppm: 1.51 (9H, s), 1.95-2.10 (2H, m), 2.24 (3H, s), 2.66-2.81 (6H, m), 3.14-3.31 (2H, m), 3.84 (3H, s), 3.95 (2H, t, J = 6.3 Hz), 6.36 (1H, br), 6.60 (1H, d, J = 2.5 Hz), 6.87-6.92 (1H, m), 7.01 (1H, d, J = 2.0 Hz), 7.24-7.31 (1H, m), 7.37-7.44 (2H, m), 7.55 (1H, d, J = 8.0 Hz) |
| 1163 | —OCH₃ | —H | —I | —H | —CH₃ | $^1$H-NMR (CDCl₃) δ ppm: 1.92-2.10 (2H, m), 2.23 (3H, s), 2.57-2.86 (6H, m), 3.11-3.31 (4H, m), 3.82 (3H, s), 3.98 (2H, t, J = 6.4 Hz), 6.90 (1H, d, J = 7.6 Hz), 7.03 (1H, d, J = 2.0 Hz), 7.13 (1H, d, J = 1.6 Hz), 7.22-7.34 (1H, m), 7.40 (1H, dd, J = 4.5 Hz, 9.3 Hz), 7.55 (1H, d, J = 8.0 Hz). |

TABLE 140-continued

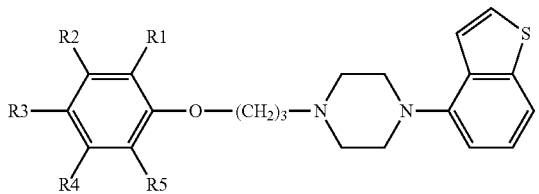

| Example | R1 | R2 | R3 | R4 | R5 | NMR |
|---|---|---|---|---|---|---|
| 1164 | —OCH$_3$ | —H | —NHCONH(CH$_2$)$_2$Cl | —H | —CH$_3$ | $^1$H-NMR (CDCl$_3$) δ ppm: 1.94-2.13 (2H, m), 2.28 (3H, s), 2.60-2.90 (6H, m), 3.12-3.33 (4H, m), 3.49-3.75 (4H, m), 3.83 (3H, s), 3.97 (2H, t, J = 6.4 Hz), 5.22 (1H, br), 6.25 (1H, br), 6.59 (1H, d, J = 2.3 Hz), 6.86 (1H, d, J = 2.3 Hz), 6.91 (1H, d, J = 7.4 Hz), 7.21-7.33 (1H, m), 7.41 (1H, dd, J = 5.6 Hz, 7.6 Hz), 7.56 (1H, d, J = 8.0 Hz). |
| 1165 | —OCH$_3$ | —H | —NH(CH$_2$)$_2$NH$_2$ | —H | —CH$_3$ | $^1$H-NMR (CDCl$_3$) δ ppm: 1.91-2.08 (2H, m), 2.22 (3H, s), 2.62-2.81 (6H, m), 2.95 (2H, t, J = 5.7 Hz), 3.08-3.27 (6H, m), 3.80 (3H, s), 3.91 (2H, t, J = 6.4 Hz), 6.05 (1H, d, J = 2.6 Hz), 6.10 (1H, d, J = 2.6 Hz), 6.90 (1H, d, J = 7.5 Hz), 7.20-7.32 (1H, m), 7.34-7.46 (2H, m), 7.55 (1H, d, J = 8.0 Hz). |
| 1166 | —OCH$_3$ | —H | —NH(CH$_2$)$_2$NHCOCH$_2$Cl | —H | —CH$_3$ | $^1$H-NMR (CDCl$_3$) δ ppm: 1.91-2.11 (2H, m), 2.23 (3H, s), 2.60-2.84 (6H, m), 3.11-3.26 (4H, m), 3.26-3.36 (2H, m), 3.45-3.63 (2H, m), 3.81 (3H, s), 3.91 (2H, t, J = 6.4 Hz), 4.06 (2H, s), 6.04 (1H, d, J = 2.5 Hz), 6.10 (1H, d, J = 2.5 Hz), 6.78-6.96 (2H, m), 7.21-7.33 (1H, m), 7.35-7.47 (2H, m), 7.55 (1H, d, J = 8.1 Hz). |

TABLE 141

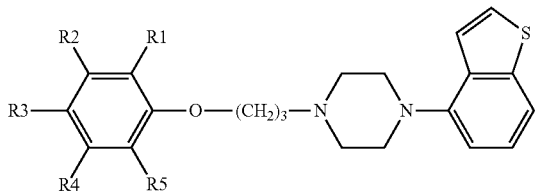

| Example | R1 | R2 | R3 | R4 | R5 | NMR |
|---|---|---|---|---|---|---|
| 1167 | —OCH$_3$ | —H | 3-methyl-oxazolidin-2-one | —H | —CH$_2$Cl | $^1$H-NMR (CDCl$_3$) δ ppm: 2.00-2.17 (2H, m), 2.63-2.83 (6H, m), 3.14-3.28 (2H, m), 3.89 (3H, s), 3.98-4.17 (4H, m), 4.40-4.54 (2H, m), 4.69 (2H, m), 6.77 (1H, d, J = 2.5 Hz), 6.91 (1H, d, J = 2.5 Hz), 7.21-7.32 (1H, m), 7.35-7.46 (2H, m), 7.55 (1H, d, J = 9.3 Hz) |
| 1168 | —OCH$_3$ | —H | tert-butyl piperazine-1-carboxylate | —H | —CH$_3$ | $^1$H-NMR (CDCl$_3$) δ ppm: 1.48 (9H, s), 1.93-2.12 (2H, m), 2.26 (3H, s), 2.60-2.86 (6H, m), 2.95-3.12 (4H, m), 3.14-3.31 (4H, m), 3.50-3.67 (4H, m), 3.83 (3H, s), 3.94 (2H, t, J = 6.3 Hz), 6.33 (1H, d, J = 2.5 Hz), 6.38 (1H, d, J = 2.5 Hz), 6.90 (1H, d, J = 7.5 Hz), 7.19-7.33 (1H, m), 7.41 (2H, dd, J = 5.5 Hz, 9.3 Hz), 7.55 (1H, d, J = 8.0 Hz). |
| 1169 | —OCH$_3$ | —H | piperazinyl | —H | —CH$_3$ | $^1$H-NMR (CDCl$_3$) δ ppm: 1.92-2.09 (2H, m), 2.26 (3H, s), 2.61-2.81 (6H, m), 2.98-3.12 (8H, m), 3.14-3.25 (4H, m), 3.83 (3H, s), 3.94 (2H, t, J = 6.4 Hz), 6.33 (1H, d, J = 2.5 Hz), 6.38 (1H, d, J = 2.5 Hz), 6.90 (1H, d, J = 7.0 Hz), 7.20-7.33 (1H, m), 7.34-7.45 (2H, m), 7.55 (1H, d, J = 8.0 Hz). |
| 1170 | —OCH$_3$ | —H | tert-butyl 3-oxopiperazine-1-carboxylate | —H | —CH$_3$ | $^1$H-NMR (CDCl$_3$) δ ppm: 1.50 (9H, s), 1.95-2.11 (2H, m), 2.27 (3H, s), 2.59-2.82 (6H, m), 3.12-3.27 (4H, m), 3.63-3.81 (4H, m), 3.83 (3H, s), 4.01 (2H, t, J = 6.4 Hz), 4.24 (2H, s), 6.61-6.71 (2H, m), 6.90 (1H, d, J = 7.6 Hz), 7.21-7.33 (1H, m), 7.41 (2H, dd, J = 5.5 Hz, 9.8 Hz), 7.55 (1H, d, J = 8.1 Hz). |
| 1171 | —OCH$_3$ | —H | tert-butyl piperazine-1-carboxylate | —H | —CHO | $^1$H-NMR (CDCl$_3$) δ ppm: 1.49 (9H, s), 1.96-2.12 (2H, m), 2.60-2.82 (6H, m), 3.04-3.16 (4H, m), 3.16-3.28 (4H, m), 3.52-3.64 (4H, m), 3.89 (3H, s), 4.14 (2H, t, J = 6.3 Hz), 6.78 (1H, d, J = 2.8 Hz), 6.86-6.96 (2H, m), 7.20-7.33 (1H, m), 7.35-7.46 (2H, m), 7.55 (1H, d, J = 8.0 Hz), 10.44 (1H, s). |

TABLE 141-continued

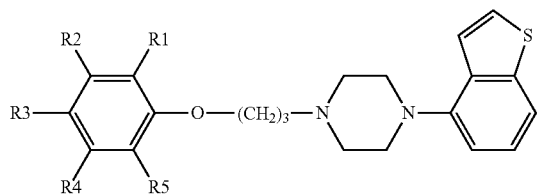

| Example | R1 | R2 | R3 | R4 | R5 | NMR |
|---|---|---|---|---|---|---|
| 1172 | —OCH₃ | —H | (piperazine, N-methyl) | —H | —CHO | ¹H-NMR (CDCl₃) δ ppm: 1.97-2.13 (2H, m), 2.59-2.83 (6H, m), 2.96-3.09 (4H, m), 3.09-3.17 (4H, m), 3.17-3.28 (4H, m), 3.89 (3H, s), 4.13 (2H, t, J = 6.5 Hz), 6.79 (1H, d, J = 2.7 Hz), 6.86-6.96 (2H, m), 7.20-7.34 (1H, m), 7.36-7.45 (2H, m), 7.55 (1H, d, J = 8.1 Hz), 10.44 (1H, s). |

TABLE 142

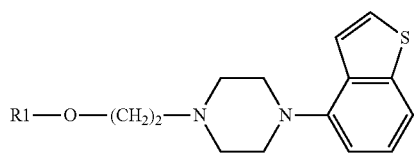

| Example | R1 | NMR |
|---|---|---|
| 1173 | (N-methylphthalimide) | ¹H-NMR (CDCl₃) δ ppm: 2.70-2.87 (4H, m), 2.95 (2H, t, J = 5.1 Hz), 2.99-3.14 (4H, m), 4.42 (2H, t, J = 5.1 Hz), 6.78 (1H, dd, J = 6 Hz, 7.6 Hz), 7.18-7.30 (1H, m), 7.38 (2H, s), 7.54 (1H, d, J = 8.0 Hz), 7.69-7.80 (2H, m), 7.80-7.89 (2H, m). |
| 1174 | (isobutyl 4-methylcyclohexanecarboxylate) | ¹H-NMR (CDCl₃) δ ppm: 0.93 (6H, d, J = 6.7 Hz), 1.41-1.75 (5H, m), 1.75-2.02 (4H, m), 2.23-2.48 (1H, m), 2.65-2.87 (6H, m), 3.06-3.25 (4H, m), 3.42-3.54 (1H, m), 3.62 (2H, t, J = 6.2 Hz), 3.85 (2H, d, J = 6.5 Hz), 6.89 (1H, d, J = 7.6 Hz), 7.20-7.34 (1H, m), 7.34-7.46 (2H, m), 7.54 (1H, d, J = 8.0 Hz). |
| 1175 | (4-methylcyclohexanecarboxylic acid) | ¹H-NMR (CDCl₃) δ ppm: 1.41-1.75 (4H, m), 1.75-2.01 (4H, m), 2.18-2.44 (1H, m), 2.72-3.04 (6H, m), 3.14-3.31 (4H, m), 3.44-3.54 (1H, m), 3.64 (2H, t, J = 6.0 Hz), 6.88 (1H, d, J = 7.6 Hz), 7.20-7.31 (1H, m), 7.31-7.44 (2H, m), 7.55 (1H, d, J = 8.0 Hz). |

TABLE 143

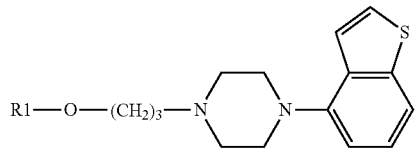

| Example | R1 | NMR |
|---|---|---|
| 1176 | (4-methylthiophene-2-carboxylic acid) | ¹H-NMR (DMSO-d₆) δ ppm: 1.85-1.95 (2H, m), 2.57 (2H, t, J = 7.1 Hz), 2.60-2.75 (4H, m), 3.05-3.15 (4H, m), 4.03 (2H, t, J = 6.3 Hz), 6.85-6.95 (2H, m), 7.20-7.31 (2H, m), 7.35-7.41 (1H, m), 7.60 (1H, d, J = 8.1 Hz), 7.68 (1H, d, J = 5.5 Hz). |

TABLE 143-continued

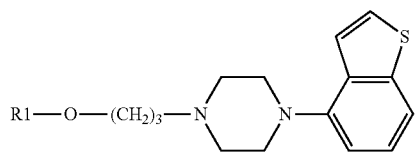

| Example | R1 | NMR |
|---|---|---|
| 1177 | (ethyl 1-(2,2-difluoro-2-propyl)-5-methyl-1H-pyrazole-3-carboxylate group) | $^1$H-NMR (CDCl$_3$) δ ppm: 1.39 (3H, t, J = 7.0 Hz), 2.00-2.11 (2H, m), 2.60 (2H, t, J = 7.0 Hz), 2.63-2.80 (4H, m), 3.09-3.25 (4H, m), 4.24 (2H, t, J = 6.3 Hz), 4.40 (2H, q, J = 7.0 Hz), 4.64 (2H, q, J = 8.3 Hz), 6.12 (1H, s), 6.90 (1H, dd, J = 0.5 Hz, 7.5 Hz), 7.25-7.31 (1H, m), 7.38-7.43 (2H, m), 7.56 (1H, d, J = 8.1 Hz). |
| 1178 | (ethyl 1-allyl-5-methyl-1H-pyrazole-3-carboxylate group) | $^1$H-NMR (CDCl$_3$) δ ppm: 1.39 (3H, t, J = 7.0 Hz), 2.00-2.06 (2H, m), 2.60 (2H, t, J = 7.5 Hz), 2.67-2.83 (4H, m), 3.13-3.28 (4H, m), 4.18 (2H, t, J = 6.3 Hz), 4.39 (2H, q, J = 7.0 Hz), 4.61 (2H, m), 5.08-5.23 (2H, m), 5.87-6.09 (1H, m), 6.11 (1H, s), 6.75 (1H, dd, J = 0.6 Hz, 7.5 Hz), 7.25-7.37 (1H, m), 7.40-7.43 (2H, m), 7.65 (1H, d, J = 8.0 Hz). |
| 1179 | (ethyl 1-propyl-5-methyl-1H-pyrazole-3-carboxylate group) | $^1$H-NMR (CDCl$_3$) δ ppm: 0.91 (3H, t, J = 7.5 Hz), 1.38 (3H, t, J = 7.0 Hz), 1.72-1.93 (2H, m), 1.98-2.13 (2H, m), 2.61 (2H, t, J = 7.3 Hz), 2.67-2.83 (4H, m), 3.09-3.28 (4H, m), 4.01 (2H, t, J = 7.0 Hz), 4.18 (2H, t, J = 6.3 Hz), 4.39 (2H, q, J = 7.0 Hz), 6.08 (1H, s), 6.90 (1H, dd, J = 0.7 Hz, 7.5 Hz), 7.25-7.30 (1H, m), 7.37-7.43 (2H, m), 7.56 (1H, d, J = 8.0 Hz). |

TABLE 144

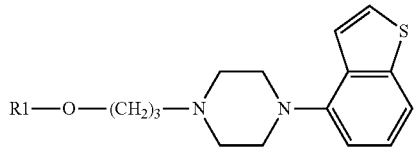

| Example | R1 | NMR |
|---|---|---|
| 1180 | (tert-butyl (2-methylthiazol-4-yl)carbamate group) | $^1$H-NMR (CDCl$_3$) δ ppm: 1.51 (9H, s), 1.97-2.12 (2H, m), 2.52-2.67 (2H, m), 2.67-2.80 (4H, m), 3.07-3.29 (4H, m), 4.38 (2H, t, J = 6.3 Hz), 6.52 (1H, br), 6.90 (1H, d, J = 7.6 Hz), 7.03 (1H, br), 7.21-7.33 (1H, m), 7.40 (2H, dd, J = 5.6 Hz, 7.3 Hz), 7.55 (1H, d, J = 8.0 Hz). |
| 1181 | (N-methylphthalimide group) | $^1$H-NMR (CDCl$_3$) δ ppm: 1.95-2.13 (2H, m), 2.65-2.83 (6H, m), 3.09-3.27 (4H, m), 4.33 (2H, t, J = 6.4 Hz), 6.89 (1H, d, J = 7.6 Hz), 7.20-7.32 (1H, m), 7.40 (1H, dd, J = 5.6 Hz, 9.0 Hz), 7.54 (1H, d, J = 8.0 Hz), 7.71-7.80 (2H, m), 7.80-7.90 (2H, m). |

TABLE 144-continued

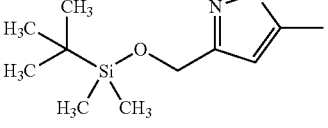

| Example | R1 | NMR |
|---------|----|----|
| 1182 | 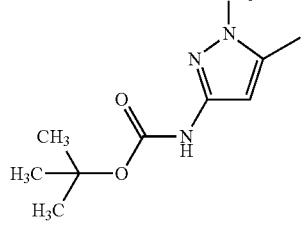 | ¹H-NMR (CDCl₃) δ ppm: 0.10 (6H, s), 0.92 (9H, s), 1.93-2.13 (2H, m), 2.62 (2H, t, J = 7.5 Hz), 2.70-2.83 (4H, m), 3.09-3.28 (4H, m), 3.59 (3H, s), 4.13 (2H, t, J = 6.3 Hz), 4.60 (2H, s), 5.54 (1H, s), 6.90 (1H, dd, J = 0.7 Hz, 7.5 Hz), 7.20-7.33 (1H, m), 7.35-7.48 (2H, m), 7.55 (1H, d, J = 8.0 Hz). |
| 1183 | 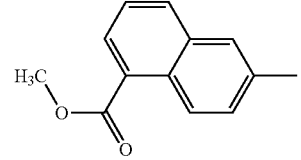 | ¹H-NMR (CDCl₃) δ ppm: 1.50 (9H, s), 1.94-2.12 (2H, m), 2.60 (2H, t, J = 7.0 Hz), 2.66-2.80 (4H, m), 3.10-3.27 (4H, m), 3.52 (3H, s), 4.15 (2H, t, J = 6.4 Hz), 5.85 (1H, s), 6.81-6.97 (2H, m), 7.20-7.33 (1H, m), 7.35-7.45 (2H, m), 7.55 (1H, d, J = 8.0 Hz). |

TABLE 145

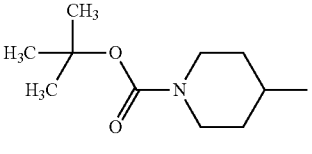

| Example | R1 | NMR |
|---------|----|----|
| 1184 | 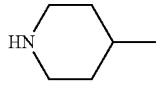 | ¹H-NMR (CDCl₃) δ ppm: 2.01-2.20 (2H, m), 2.62-2.87 (6H, m), 3.10-3.30 (4H, m), 3.99 (3H, s), 4.20 (2H, t, J = 6.3 Hz), 6.91 (1H, dd, J = 0.7 Hz, 7.6 Hz), 7.20 (1H, d, J = 2.6 Hz), 7.22-7.34 (2H, m), 7.35-7.50 (3H, m), 7.55 (1H, d, J = 8.1 Hz), 7.90 (1H, d, J = 8.1 Hz), 8.03 (1H, dd, J = 1.2 Hz, 7.3 Hz), 8.83 (1H, d, J = 9.4 Hz). |
| 1185 | 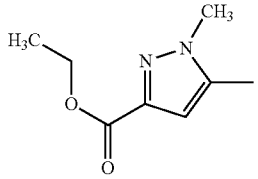 | ¹H-NMR (CDCl₃) δ ppm: 1.46 (9H, s) 1.45-1.60 (2H, m), 1.75-1.90 (4H, m), 2.50-2.60 (2H, m), 2.65-2.80 (4H, m), 3.05-3.25 (6H, m), 3.40-3.50 (1H, m), 3.53 (2H, t, J = 6.4 Hz), 3.70-3.80 (2H, m), 6.89 (1H, dd, J = 7.6, 0.7 Hz), 7.20-7.30 (1H, m), 7.35-7.45 (2H, m), 7.54 (1H, d, J = 8.0 Hz), 8.02 (1H, s). |
| 1186 |  | ¹H-NMR (CDCl₃) δ ppm: 1.30-1.60 (2H, m), 1.75-2.00 (4H, m), 2.50-2.75 (4H, m), 3.05-3.25 (6H, m), 3.30-3.40 (1H, m), 3.55 (2H, t, J = 6.5 Hz), 6.90 (1H, d, J = 7.6 Hz), 7.20-7.30 (1H, m), 7.35-7.45 (2H, m), 7.55 (1H, d, J = 8.1 Hz). |
| 1187 |  | ¹H-NMR (CDCl₃) δ ppm: 1.38 (3H, t, J = 7.1 Hz), 2.00-2.10 (2H, m), 2.60 (2H, t, J = 7.1 Hz), 2.65-2.75 (4H, m), 3.15-3.25 (4H, m), 3.72 (3H, s), 4.17 (2H, t, J = 4.4 Hz), 4.38 (2H, q, J = 7.1 Hz), 6.08 (1H, s), 6.89 (1H, d, J = 7.6 Hz), 7.20-7.30 (1H, m), 7.35-7.45 (2H, m), 7.54 (1H, d, J = 8.1 Hz). |

TABLE 145-continued

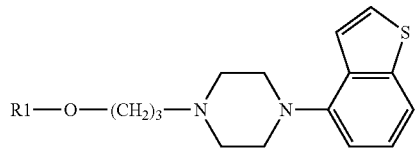

| Example | R1 | NMR |
|---|---|---|
| 1188 | ![phenyl carbamate pyrazole structure] | $^1$H-NMR (CDCl$_3$) δ ppm: 1.94-2.10 (2H, m), 2.60 (2H, t, J = 7.1 Hz), 2.65-2.78 (4H, m), 3.10-3.25 (4H, m), 3.57 (3H, s), 4.15 (2H, t, J = 6.3 Hz), 5.93 (1H, s), 6.89 (1H, d, J = 7.5 Hz), 7.12-7.32 (3H, m), 7.33-7.45 (4H, m), 7.55 (1H, d, J = 8.0 Hz), 7.93 (1H, br). |

TABLE 146

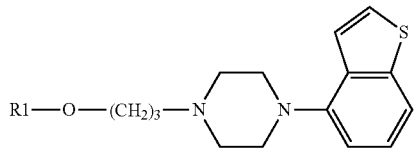

| Example | R1 | NMR |
|---|---|---|
| 1189 | ![Boc-pyrrolidine structure] | $^1$H-NMR (CDCl$_3$) δ ppm: 1.75-2.00 (4H, m), 2.50-2.60 (2H, m), 2.70-2.75 (4H, m), 3.15-3.25 (4H, m), 3.35-3.80 (6H, m), 4.00-4.05 (1H, m), 6.91 (1H, dd, J = 7.6, 0.5 Hz), 7.25-7.35 (1H, m), 7.35-7.45 (2H, m), 7.56 (1H, d, J = 4.0 Hz). |
| 1190 | ![pyrrolidine structure] | $^1$H-NMR (CDCl$_3$) δ ppm: 1.75-1.95 (4H, m), 2.51 (2H, t, J = 7.1 Hz), 2.50-2.75 (8H, m), 3.10-3.20 (4H, m), 3.46 (2H, t, J = 6.3 Hz), 4.00-4.10 (1H, m), 6.88 (1H, d, J = 7.1 Hz), 7.20-7.30 (1H, m), 7.30-7.45 (2H, m), 7.53 (1H, d, J = 8.0 Hz). |

TABLE 147

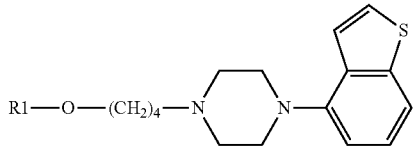

| Example | R1 | NMR |
|---|---|---|
| 1191 | ![Boc-pyrazole structure] | $^1$H-NMR (CDCl$_3$) δ ppm:: 1.50 (9H, s). 1.59-1.77(2H, m), 1.77-1.93 (2H, m), 2.50 (2H, t, J=7.3 Hz), 2.61-2.80 (4H, m), 3.11-3.27 (4H, m), 3.54(3H, s), 4.09 (2H, t, J=6.3 Hz), 5.85 (1H, s), 6.90 (1H, d, J=7.5 Hz), 7.23-7.32 (1H, m), 7.36-7.45 (2H, m), 7.55 (1H, d, J=8.0 Hz), 7.80(1H, br). |

TABLE 147-continued

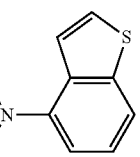

| Example | R1 | NMR |
|---|---|---|
| 1192 | (1,5-dimethyl-1H-pyrazol-3-amine) | ¹H-NMR (CDCl₃) δ ppm:: 1.64-1.93 (4H, m), 2.51 (2H, t, J=7.3 Hz), 2.61-2.79 (4H, m), 3.11-3.29 (4H, m), 3.46(3H, s), 3.49(2H, br), 4.02 (2H, t, J=6.2 Hz), 4.94 (1H, s), 6.90 (1H, dd, J=0, 7hz, 7.6 Hz), 7.22-7.33 (1H, m), 7.35-7.46 (2H, m), 7.55 (1H, d, J=8.0 Hz). |
| 1193 | (phenyl (1,5-dimethyl-1H-pyrazol-3-yl)carbamate) | ¹H-NMR (CDCl₃) δ ppm:: 1.64-1.78(2H, m), 1.78-1.94 (2H, m), 2.50 (2H, t, J=7.3 Hz), 2.61-2.81 (4H, m), 3.10-3.28 (4H, m), 3.57(3H, s), 4.09 (2H, t, J=6.3 Hz), 5.92 (1H, s), 6.77-6.98(4H, m), 7.11-7.32 (2H, m), 7.32-7.47 (4H, m), 7.55 (1H, d, J=8.0 Hz), 8.47(1H, br). |

TABLE 148

| Example | R1 | MS(M + 1) |
|---|---|---|
| 1194 | —CO₂OH₂C₆H₅ | 603 |
| 1195 | —O₂C₂H₅ | 541 |
| 1196 | —COCH₃ | 511 |
| 1197 | —CO₂C(CH₃)₃ | 569 |
| 1198 | —COC₆H₅ | 573 |
| 1199 | —COC₃H₇ | 539 |
| 1200 | (2-acetylfuran) | 563 |

TABLE 149

| Example | R1 | MS(M + 1) |
|---|---|---|
| 1201 | —CO₂CH₂C₆H₅ | 617 |
| 1202 | —CO₂C₂H₅ | 555 |
| 1203 | —COCH₃ | 525 |
| 1204 | —CO₂C(CH₃)₃ | 583 |
| 1205 | —COC₆H₅ | 587 |
| 1206 | —COC₃H₇ | 553 |
| 1207 | (2-acetylfuran) | 577 |

TABLE 150

| Example | R1 | R2 | R3 | R4 | R5 | MS(M + 1) |
|---|---|---|---|---|---|---|
| 1208 | —H | —H | —H | —Cl | —H | 608 |
| 1209 | —H | —H | —H | —H | —F | 592 |
| 1210 | —H | —H | —H | —H | —Cl | 608 |
| 1211 | —H | —H | —Cl | —Cl | —H | 642 |

TABLE 150-continued
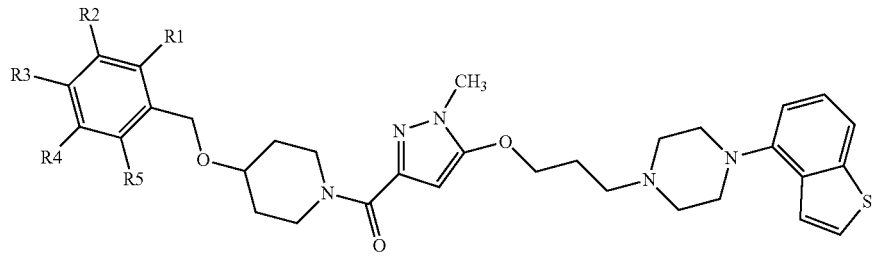
| Example | R1 | R2 | R3 | R4 | R5 | MS(M + 1) |
|---|---|---|---|---|---|---|
| 1212 | —H | —H | —H | —OCH₃ | —H | 604 |
| 1213 | —H | —OCH₃ | —H | —OCH₃ | —H | 634 |
| 1214 | —H | —H | —CH₃ | —H | —H | 588 |
| 1215 | —H | —H | —H | —CH₃ | —H | 588 |
| 1216 | —H | —H | —H | —H | —CH₃ | 588 |
| 1217 | —H | —H | —F | —H | —H | 592 |
| 1218 | —H | —H | —H | —F | —H | 592 |
| 1219 | —H | —H | —OCF₃ | —H | —H | 658 |
| 1220 | —H | —H | —H | —OCF₃ | —H | 658 |
| 1221 | —H | —H | —H | —H | —OCF₃ | 658 |
| 1222 | —H | —H | —OCH₃ | —Cl | —H | 638 |
| 1223 | —H | —H | —H | —Br | —H | 652 |
| 1224 | —H | —H | —OCH₃ | —H | —H | 604 |
| 1225 | —H | —H | —H | —H | —H | 574 |
TABLE 151
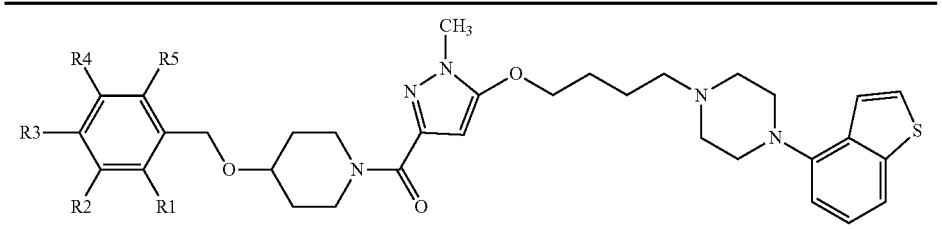
| Example | R1 | R2 | R3 | R4 | R5 | MS(M + 1) |
|---|---|---|---|---|---|---|
| 1226 | —H | —H | —H | —Cl | —H | 622 |
| 1227 | —H | —H | —H | —H | —F | 606 |
| 1228 | —H | —H | —H | —H | —Cl | 622 |
| 1229 | —H | —H | —Cl | —Cl | —H | 656 |
| 1230 | —H | —H | —H | —OCH₃ | —H | 618 |
| 1231 | —H | —OCH₃ | —H | —OCH₃ | —H | 648 |
| 1232 | —H | —H | —CH₃ | —H | —H | 602 |
| 1233 | —H | —H | —H | —CH₃ | —H | 602 |
| 1234 | —H | —H | —H | —H | —CH₃ | 602 |
| 1235 | —H | —H | —F | —H | —H | 606 |
| 1236 | —H | —H | —H | —F | —H | 606 |
| 1237 | —H | —H | —OCF₃ | —H | —H | 672 |
| 1238 | —H | —H | —H | —OCF₃ | —H | 672 |
| 1239 | —H | —H | —H | —H | —OCF₃ | 672 |
| 1240 | —H | —H | —OCH₃ | —Cl | —H | 852 |
| 1241 | —H | —H | —H | —Br | —H | 666 |
| 1242 | —H | —H | —OCH₃ | —H | —H | 618 |
| 1243 | —H | —H | —H | —H | —H | 588 |

TABLE 152
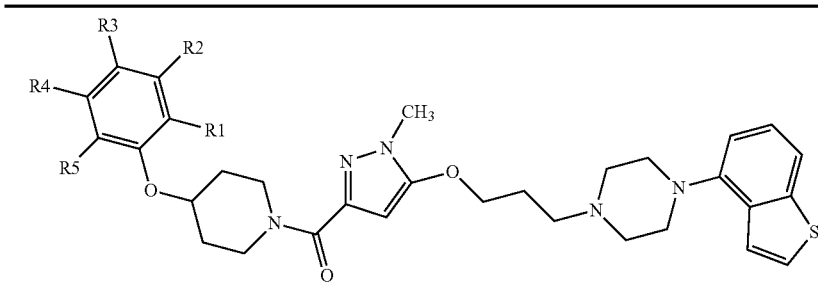
| Example | R1 | R2 | R3 | R4 | R5 | MS(M + 1) |
|---|---|---|---|---|---|---|
| 1244 | —H | —H | —CN | —H | —H | 585 |
| 1245 | —H | —H | —H | —H | —OCH₃ | 590 |
| 1246 | —H | —H | —H | —OCH₃ | —H | 590 |
| 1247 | —H | —H | —OCH₃ | —H | —H | 590 |
| 1248 | —H | —H | —H | —H | —H | 560 |
| 1249 | —H | —H | —H | —H | —Cl | 594 |
| 1250 | —H | —H | —H | —Cl | —H | 594 |
| 1251 | —H | —H | —Cl | —H | —H | 594 |
| 1252 | —H | —H | —H | —H | —CH₃ | 574 |
| 1253 | —H | —H | —CH₃ | —H | —H | 574 |
| 1254 | —H | —H | —F | —H | —H | 578 |
| 1255 | —H | —H | —CF₃ | —H | —H | 628 |
TABLE 153
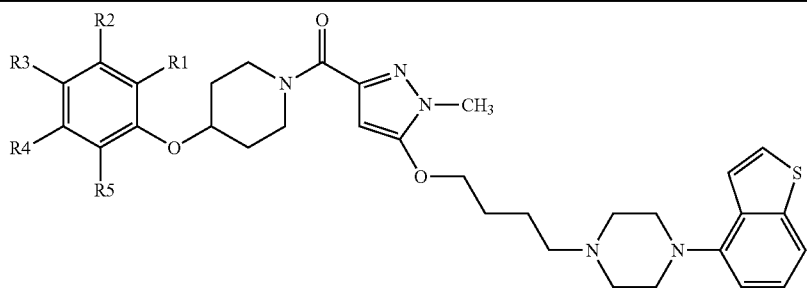
| Example | R1 | R2 | R3 | R4 | R5 | MS(M + 1) |
|---|---|---|---|---|---|---|
| 1256 | —H | —H | —CN | —H | —H | 599 |
| 1257 | —H | —H | —H | —H | —OCH₃ | 604 |
| 1258 | —H | —H | —H | —OCH₃ | —H | 604 |
| 1259 | —H | —H | —OCH₃ | —H | —H | 604 |
| 1260 | —H | —H | —H | —H | —H | 574 |
| 1261 | —H | —H | —H | —H | —Cl | 608 |
| 1262 | —H | —H | —H | —Cl | —H | 608 |
| 1263 | —H | —H | —Cl | —H | —H | 608 |
| 1264 | —H | —H | —H | —H | —CH₃ | 588 |
| 1265 | —H | —H | —CH₃ | —H | —H | 588 |
| 1266 | —H | —H | —F | —H | —H | 592 |
| 1267 | —H | —H | —CF₃ | —H | —H | 642 |
TABLE 154
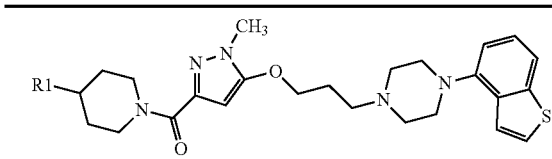
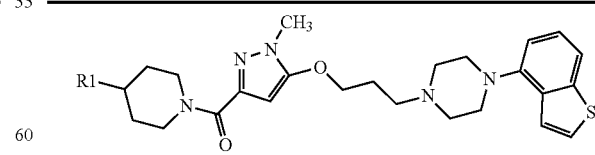
| Example | R1 | MS(M + 1) |
|---|---|---|
| 1268 | —OCH₃ | 498 |
| 1269 | —CH₂CONHC₂H₅ | 553 |
| 1270 | —OH | 484 |
| 1271 | —CO₂C₂H₅ | 540 |
| 1272 | —CONH₂ | 511 |
| 1273 | —CH₂OH | 498 |
| 1274 | —N(CH₃)CO₂C(CH₃)₃ | 597 |
| 1275 | —NHCO₂C(CH₃)₃ | 583 |

TABLE 154-continued

R1-[piperidine]-C(O)-[1-methyl-pyrazole]-O-(CH2)3-[piperazine]-N-[benzothiophen-4-yl]

| Example | R1 | MS(M + 1) |
|---|---|---|
| 1276 | —CO₂C(CH₃)₃ | 568 |
| 1277 | —NHCOCH₃ | 525 |
| 1278 | —N(CH₃)COCH₃ | 539 |
| 1279 | —COOH | 512 |
| 1280 | —N(CH₃)CO(CH₂)₂CH₃ | 567 |
| 1281 | —NHCO(CH₂)₂CH₃ | 553 |

TABLE 155

R1-[piperidine]-C(O)-[1-methyl-pyrazole]-O-(CH2)3-[piperazine]-N-[benzothiophen-4-yl]

| Example | R1 | MS(M + 1) |
|---|---|---|
| 1282 | 4-chlorophenyl | 578 |
| 1283 | 4-methoxyphenyl | 574 |
| 1284 | 3-hydroxyphenyl | 560 |
| 1285 | 4-chlorobenzyl | 592 |
| 1286 | 4-methylbenzyl | 572 |
| 1287 | benzyl | 558 |
| 1288 | (1,3-benzodioxol-5-yl)methyl | 602 |
| 1289 | 3-methoxybenzyl | 588 |

TABLE 155-continued

| Example | R1 | MS(M + 1) |
|---|---|---|
| 1290 | 3-(trifluoromethoxy)benzyl | 642 |
| 1291 | 4-chlorophenacyl (4-chlorobenzoylmethyl) | 606 |
| 1292 | 4-methoxyphenacyl | 602 |

TABLE 156

R1-[piperidine]-C(O)-[1-methyl-pyrazole]-O-(CH2)3-[piperazine]-N-[benzothiophen-4-yl]

| Example | R1 | MS(M + 1) |
|---|---|---|
| 1293 | 4-fluorophenacyl | 590 |
| 1294 | phenacyl | 572 |
| 1295 | (6-methylpyridin-2-yl) | 545 |
| 1296 | (6-methoxypyridin-2-yl) | 561 |
| 1297 | (2-methoxypyridin-4-yl) | 561 |

TABLE 156-continued

R1-[piperidine]-C(O)-[1-methyl-pyrazole]-O-(CH2)3-[piperazine]-[benzothiophene]

| Example | R1 | MS(M + 1) |
|---|---|---|
| 1298 | 3-(methoxymethyl)pyridine | 575 |
| 1299 | 4-(methoxymethyl)pyridine | 575 |
| 1300 | N-methylbenzamide | 587 |
| 1301 | N,N-dimethylbenzamide | 601 |

TABLE 157

R1-[piperidine]-C(O)-[1-methyl-pyrazole]-O-(CH2)3-[piperazine]-[benzothiophene]

| Example | R1 | MS(M + 1) |
|---|---|---|
| 1302 | tert-butyl 4-methylpiperidine-1-carboxylate | 651 |
| 1303 | (4-methylpiperidin-1-yl)(phenyl)methanone | 655 |
| 1304 | 1-(4-methylpiperidin-1-yl)ethanone | 593 |
| 1305 | 1-(4-methylpiperidin-1-yl)butan-1-one | 621 |

TABLE 158

R1-[piperidine]-C(O)-[1-methyl-pyrazole]-O-(CH2)4-[piperazine]-[benzothiophene]

| Example | R1 | MS(M + 1) |
|---|---|---|
| 1306 | 4-chlorobenzyl | 592 |
| 1307 | 4-methoxybenzyl | 588 |
| 1308 | 3-hydroxybenzyl | 574 |
| 1309 | 4-chlorophenethyl | 606 |
| 1310 | 4-methylphenethyl | 586 |
| 1311 | phenethyl | 572 |
| 1312 | benzo[d][1,3]dioxol-5-ylethyl | 616 |
| 1313 | 3-methoxyphenethyl | 602 |
| 1314 | 3-(trifluoromethoxy)phenethyl | 656 |
| 1315 | 1-(4-chlorophenyl)ethanone | 620 |
| 1316 | 1-(4-methoxyphenyl)ethanone | 616 |

TABLE 159

[Structure: R1-piperidine-C(O)-pyrazole(N-CH3)-O-(CH2)3-piperazine-benzothiophene]

| Example | R1 | MS(M + 1) |
|---|---|---|
| 1317 | —OCH₃ | 512 |
| 1318 | —CH₂CONHC₂H₅ | 567 |
| 1319 | —OH | 498 |
| 1320 | —CO₂C₂H₅ | 554 |
| 1321 | —CONH₂ | 525 |
| 1322 | —CH₂OH | 512 |
| 1323 | —N(CH₃)CO₂C(CH₃)₃ | 611 |
| 1324 | —NHCO₂C(CH₃)₃ | 597 |
| 1325 | —CO₂C(CH₃)₃ | 582 |
| 1326 | —NHCOCH₃ | 539 |
| 1327 | —N(CH₃)COCH₃ | 553 |
| 1328 | —N(CH₃)CO(CH₂)₂CH₃ | 581 |
| 1329 | —NHCO(CH₂)₂CH₃ | 567 |
| 1330 | —COOH | 526 |

TABLE 160

[Structure: R1-piperidine-C(O)-pyrazole(N-CH3)-O-(CH2)4-piperazine-benzothiophene]

| Example | R1 | MS(M + 1) |
|---|---|---|
| 1331 | 4-fluorobenzoyl | 604 |
| 1332 | benzoyl | 586 |
| 1333 | 2-methylpyridinyl | 559 |
| 1334 | 2-methoxypyridinyl | 575 |
| 1335 | 4-methoxypyridinyl | 575 |
| 1336 | 3-(methoxymethyl)pyridinyl | 589 |

TABLE 160-continued

| Example | R1 | MS(M + 1) |
|---|---|---|
| 1337 | 4-(methoxymethyl)pyridinyl | 589 |
| 1338 | PhC(O)NH— | 601 |
| 1339 | PhC(O)N(CH₃)— | 615 |

TABLE 161

[Structure: R1-piperidine-C(O)-pyrazole(N-CH3)-O-(CH2)4-piperazine-benzothiophene, with 4-methyl on R1 piperidine]

| Example | R1 | MS(M + 1) |
|---|---|---|
| 1340 | (CH₃)₃C-O-C(O)— (Boc) | 665 |
| 1341 | PhC(O)— | 669 |
| 1342 | CH₃C(O)— | 607 |
| 1343 | CH₃CH₂CH₂C(O)— | 635 |

TABLE 162
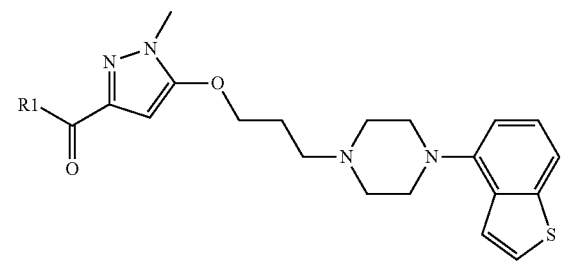
| Example | R1 | MS(M + 1) |
|---|---|---|
| 1344 | 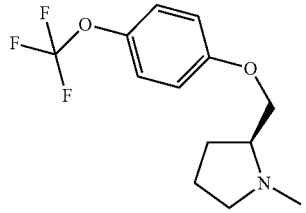 | 644 |
| 1345 | 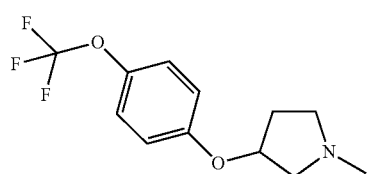 | 630 |
| 1346 | 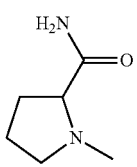 | 497 |
| 1347 | 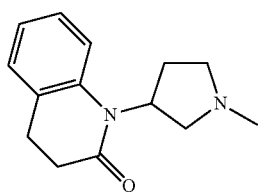 | 599 |
| 1348 | 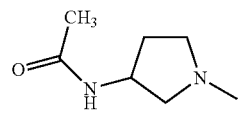 | 511 |
| 1349 | 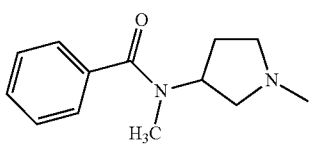 | 587 |
| 1350 | 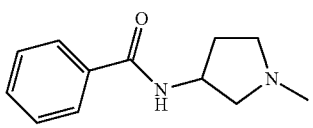 | 573 |
| 1351 | 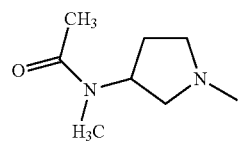 | 525 |
TABLE 162-continued
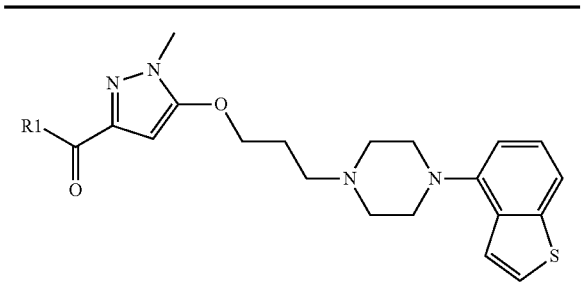
| Example | R1 | MS(M + 1) |
|---|---|---|
| 1352 | 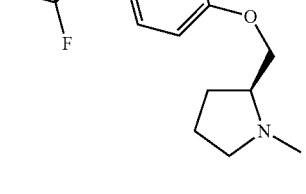 | 553 |
| 1353 | 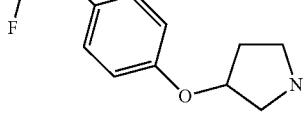 | 539 |
TABLE 163
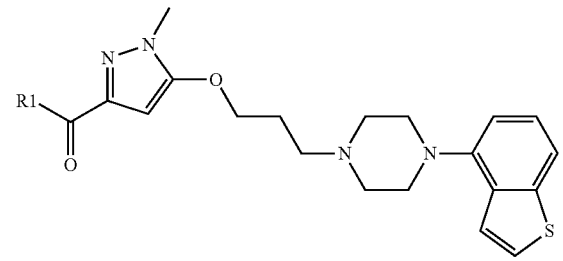
| Example | R1 | MS(M + 1) |
|---|---|---|
| 1354 | 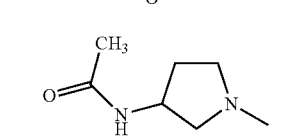 | 480 |
| 1355 | 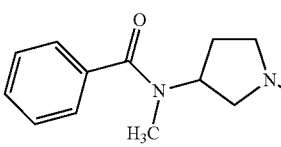 | 472 |
| 1356 | 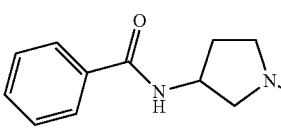 | 578 |

TABLE 163-continued
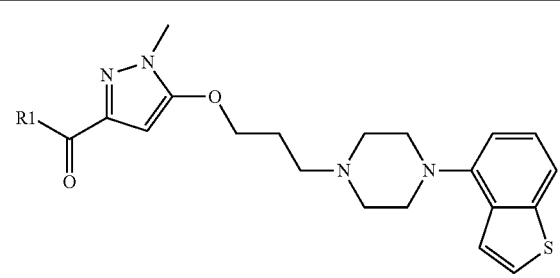
| Example | R1 | MS(M + 1) |
|---|---|---|
| 1357 | 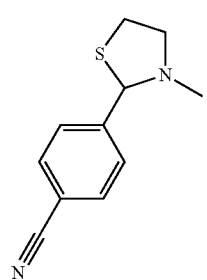 | 573 |
| 1358 | 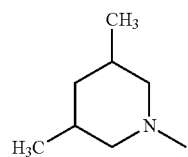 | 496 |
| 1359 | 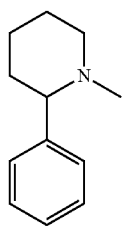 | 544 |
| 1360 | 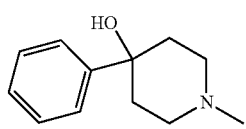 | 560 |
| 1361 | 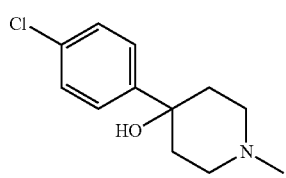 | 594 |
TABLE 164
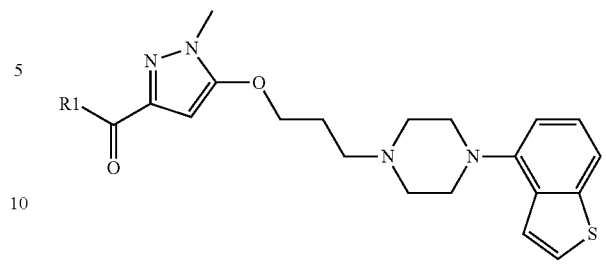
| Example | R1 | MS(M + 1) |
|---|---|---|
| 1362 | 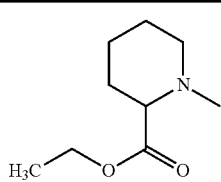 | 540 |
| 1363 | 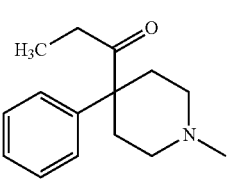 | 600 |
| 1364 | 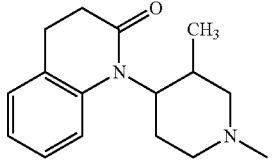 | 627 |
| 1365 | 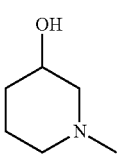 | 484 |
| 1366 | 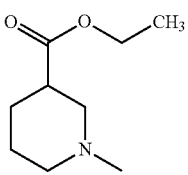 | 540 |
| 1367 | 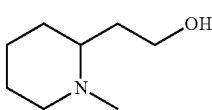 | 512 |
| 1368 | 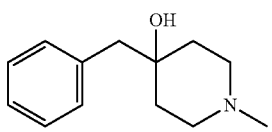 | 574 |
| 1369 | 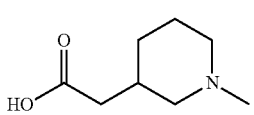 | 526 |

TABLE 164-continued
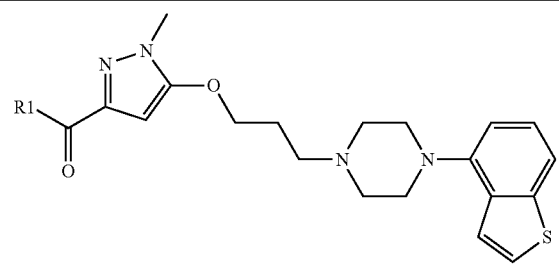
| Example | R1 | MS(M + 1) |
|---|---|---|
| 1370 | | 614 |
TABLE 165
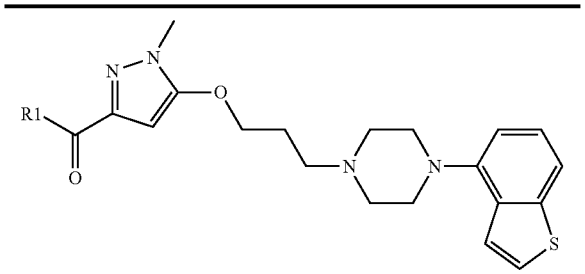
| Example | R1 | MS(M + 1) |
|---|---|---|
| 1371 | | 543 |
| 1372 | | 486 |
| 1373 | | 470 |
| 1374 | 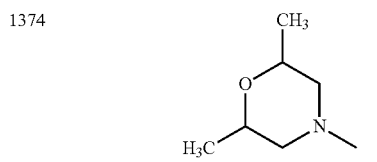 | 498 |
| 1375 | 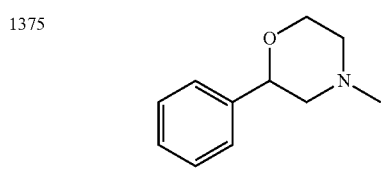 | 546 |
TABLE 165-continued
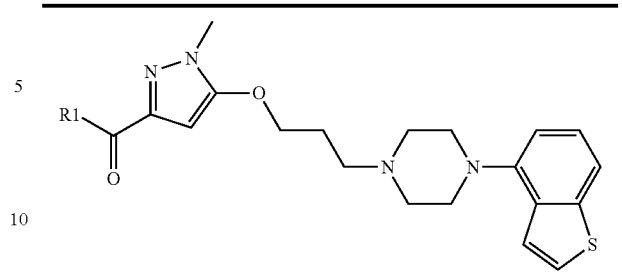
| Example | R1 | MS(M + 1) |
|---|---|---|
| 1376 | | 559 |
| 1377 | | 539 |
| 1378 | | 483 |
| 1379 | | 593 |
| 1380 | | 573 |
TABLE 166
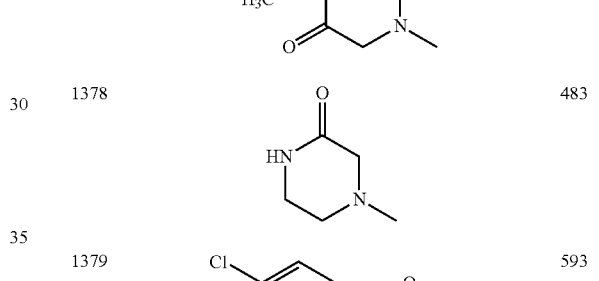
| Example | R1 | MS (M + 1) |
|---|---|---|
| 1381 | 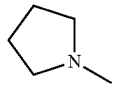 | 468 |

TABLE 166-continued
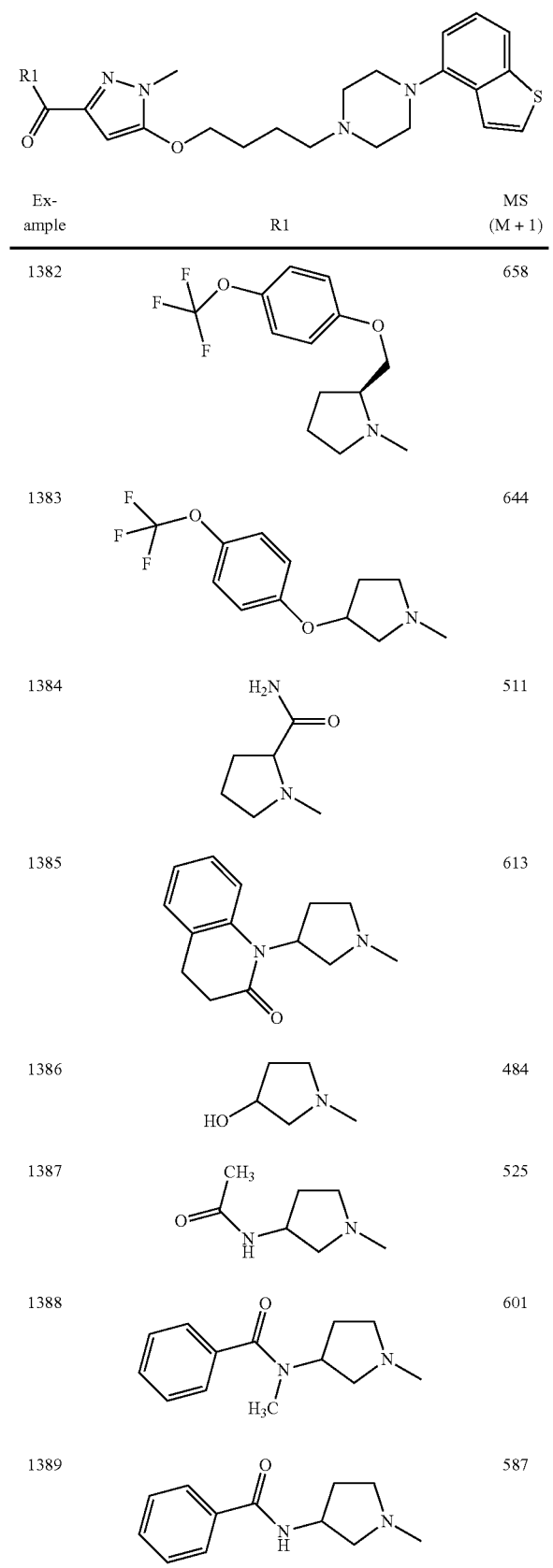
| Example | R1 | MS (M + 1) |
|---|---|---|
| 1382 | | 658 |
| 1383 | | 644 |
| 1384 | | 511 |
| 1385 | | 613 |
| 1386 | | 484 |
| 1387 | | 525 |
| 1388 | | 601 |
| 1389 | | 587 |
TABLE 166-continued
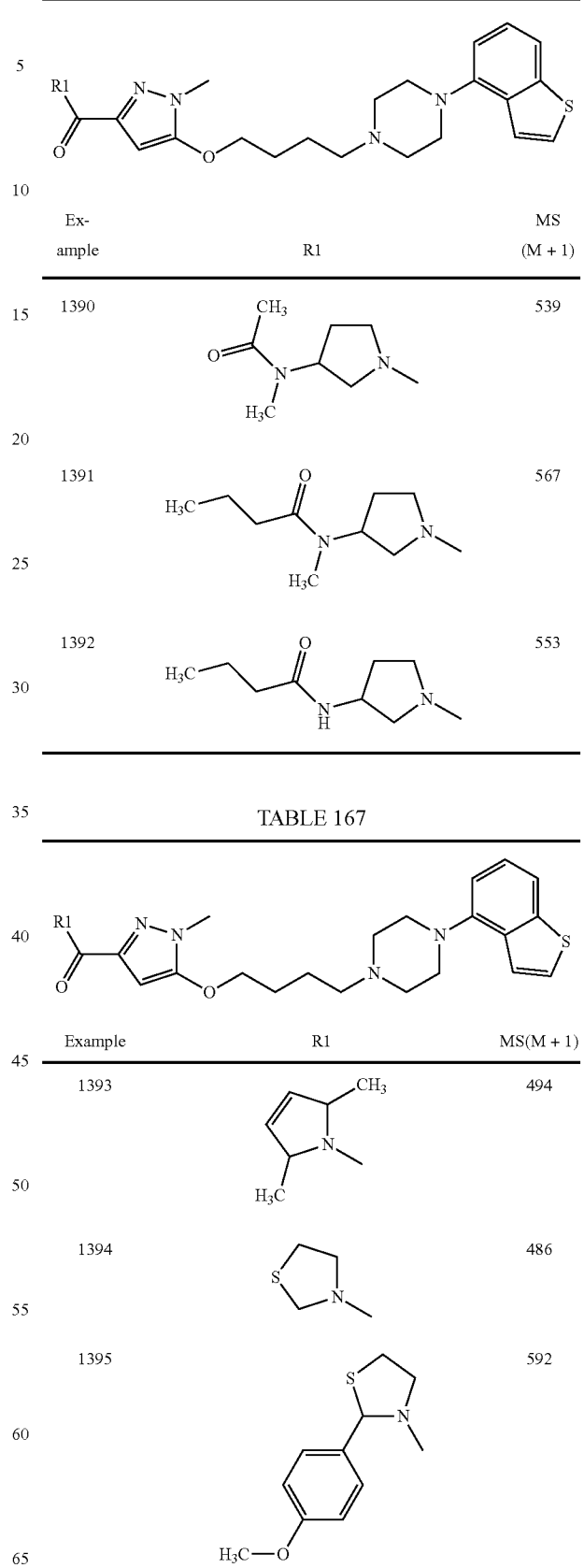
| Example | R1 | MS (M + 1) |
|---|---|---|
| 1390 | | 539 |
| 1391 | | 567 |
| 1392 | | 553 |
TABLE 167
| Example | R1 | MS(M + 1) |
|---|---|---|
| 1393 | | 494 |
| 1394 | | 486 |
| 1395 | | 592 |

TABLE 167-continued
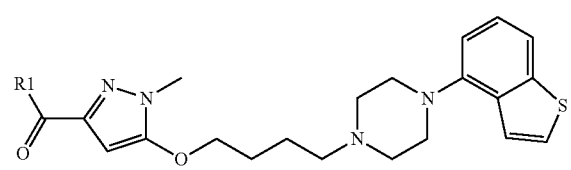
| Example | R1 | MS(M + 1) |
|---|---|---|
| 1396 | 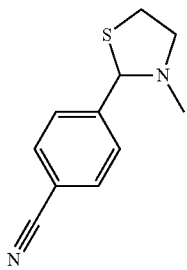 | 587 |
| 1397 | 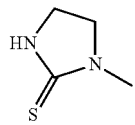 | 499 |
| 1398 | 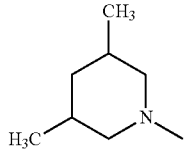 | 510 |
| 1399 | 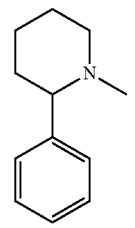 | 558 |
| 1400 | 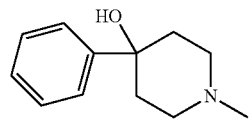 | 574 |
| 1401 | 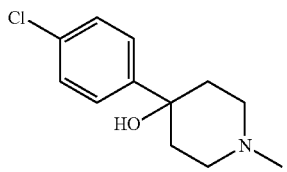 | 608 |
TABLE 168
| Example | R1 | MS(M + 1) |
|---|---|---|
| 1402 | 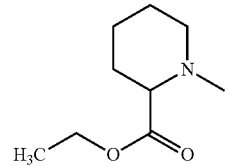 | 554 |
| 1403 | 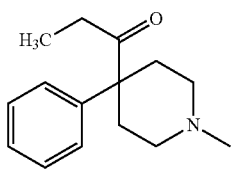 | 614 |
| 1404 | 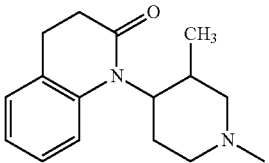 | 641 |
| 1405 | 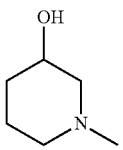 | 498 |
| 1406 | 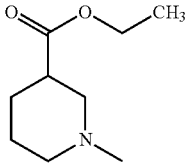 | 554 |
| 1407 | 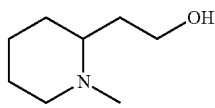 | 526 |
| 1408 | 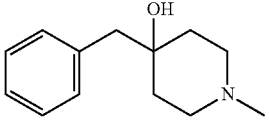 | 588 |
| 1409 | 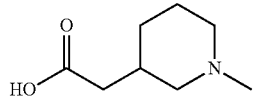 | 540 |

TABLE 168-continued

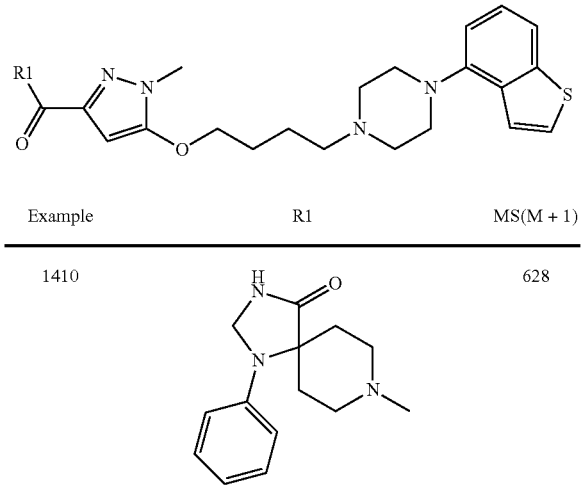

| Example | R1 | MS(M + 1) |
|---|---|---|
| 1410 | (1-phenyl-8-methyl-1,3,8-triazaspiro[4.5]decan-4-one-3-yl) | 628 |

TABLE 169

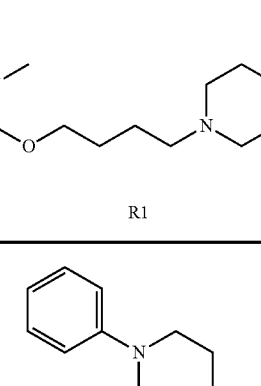

| Example | R1 | MS(M + 1) |
|---|---|---|
| 1411 | 1'-methyl-3',6'-dihydro-2H-[2,4'-bipyridin]-4'(5'H)-yl | 557 |
| 1412 | thiomorpholin-4-yl | 500 |
| 1413 | morpholin-4-yl | 484 |
| 1414 | 2,6-dimethylmorpholin-4-yl | 512 |
| 1415 | 2-phenylmorpholin-4-yl | 560 |
| 1416 | 4-methyl-2-oxo-1-phenylpiperazin-1-yl | 573 |
| 1417 | 1-tert-butyl-4-methyl-2-oxopiperazin-1-yl | 553 |
| 1418 | 4-methyl-2-oxopiperazin-1-yl | 497 |
| 1419 | 1-(4-chlorophenyl)-4-methyl-2-oxopiperazin-1-yl | 607 |
| 1420 | 4-methyl-1-(4-methylphenyl)-2-oxopiperazin-1-yl | 587 |

TABLE 170
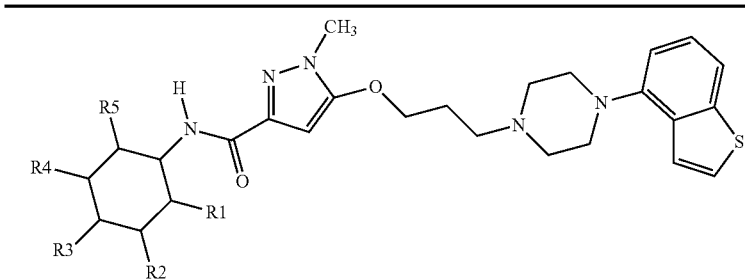
| Example | R1 | R2 | R3 | R4 | R5 | MS(M + 1) |
|---|---|---|---|---|---|---|
| 1421 | —H | —H | —OCF₃ | —H | —H | 560 |
| 1422 | —H | —H | —H | —H | —SO₂NH₂ | 555 |
| 1423 | —H | —H | —OCH₃ | —H | —H | 506 |
| 1424 | —H | —H | —H | —OCH₃ | —H | 506 |
| 1425 | —H | —H | —COCH₃ | —H | —H | 518 |
| 1426 | —H | —H | —H | —H | —CO₂CH₃ | 534 |
| 1427 | —H | —H | —OCH₃ | —H | —OCH₃ | 536 |
| 1428 | —OCH₃ | —H | —H | —OCH₃ | —H | 536 |
| 1429 | —H | —OCH₃ | —H | —OCH₃ | —H | 536 |
| 1430 | —OCH₃ | —H | —H | —NHCOCH₃ | —H | 563 |
| 1431 | —H | —H | —OCH₃ | —OCH₃ | —H | 536 |
| 1432 | —H | —H | —N(CH₃)₂ | —H | —H | 519 |
| 1433 | —H | —H | —H | —COCH₃ | —H | 518 |
| 1434 | —H | —H | —H | —NHCOCH₃ | —H | 533 |
| 1435 | —H | —H | —NHCOCH₃ | —H | —H | 533 |
| 1436 | —H | —CN | —H | —H | —H | 501 |
| 1437 | —OCH₃ | —H | —H | —CO₂CH₃ | —H | 564 |
| 1438 | —H | —H | —OC₆H₅ | —H | —H | 568 |
| 1439 | —H | —CO₂CH₃ | —H | —CO₂CH₃ | —H | 592 |
| 1440 | —H | —H | —OH | —Cl | —H | 526 |
| 1441 | —Cl | —H | —H | —NHCOCH₃ | —H | 567 |
| 1442 | —H | —CN | —H | —H | —Cl | 535 |
| 1443 | —Cl | —H | —H | —CONH₂ | —H | 553 |
| 1444 | —H | —H | —NO₂ | —H | —H | 521 |
| 1445 | —H | —H | —CN | —H | —H | 501 |
TABLE 171
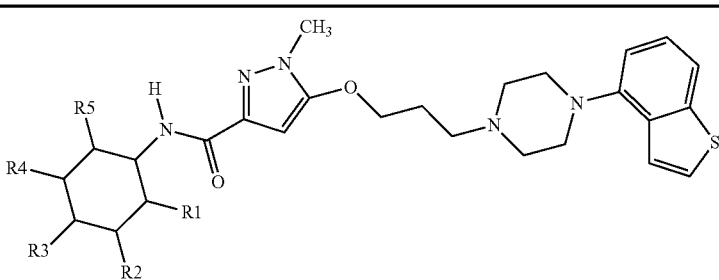
| Example | R1 | R2 | R3 | R4 | R5 | MS(M + 1) |
|---|---|---|---|---|---|---|
| 1446 | —H | —H | 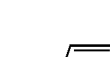 | —H | —H | 558 |
| 1447 | —H | —H | 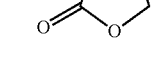 | —H | —H | 584 |
| 1448 | —H | —H | 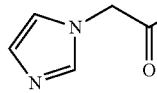 | —H | —H | 561 |

TABLE 171-continued
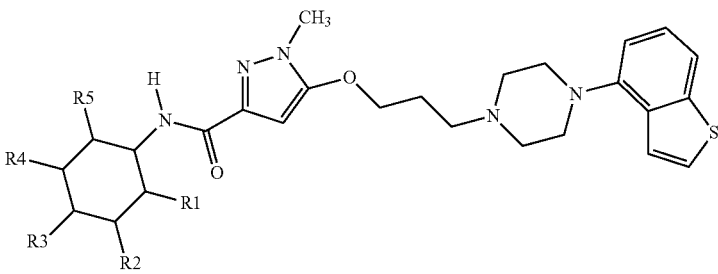
| Example | R1 | R2 | R3 | R4 | R5 | MS(M + 1) |
|---|---|---|---|---|---|---|
| 1449 | —H | —H | 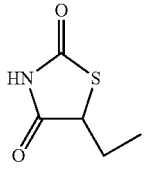 | —H | —H | 605 |
| 1450 | —H | —H | —H | 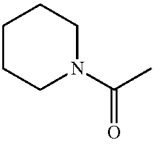 | —H | 587 |
| 1451 | —H | —H | —H | 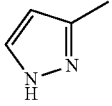 | —H | 542 |
TABLE 172
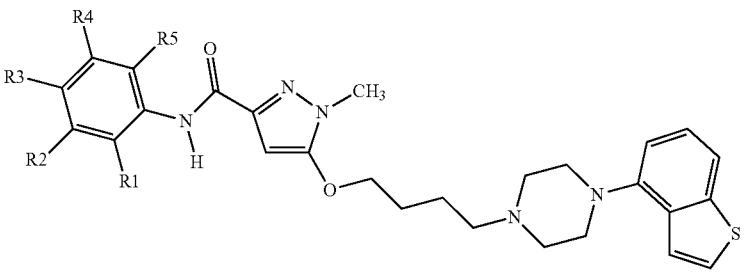
| Example | R1 | R2 | R3 | R4 | R5 | MS(M + 1) |
|---|---|---|---|---|---|---|
| 1452 | —H | —H | —OCF₃ | —H | —H | 574 |
| 1453 | —H | —H | —OCH₃ | —H | —H | 520 |
| 1454 | —H | —OCH₃ | —H | —H | —H | 520 |
| 1455 | —H | —H | —COCH₃ | —H | —H | 532 |
| 1456 | —CO₂CH₃ | —H | —H | —H | —H | 548 |
| 1457 | —OCH₃ | —H | —OCH₃ | —H | —H | 550 |
| 1458 | —H | —OCH₃ | —H | —H | —OCH₃ | 550 |
| 1459 | —H | —OCH₃ | —H | —OCH₃ | —H | 550 |
| 1460 | —H | —NHCOCH₃ | —H | —H | —OCH₃ | 577 |
| 1461 | —H | —OCH₃ | —OCH₃ | —H | —H | 550 |
| 1462 | —H | —H | —N(CH₃)₂ | —H | —H | 533 |
| 1463 | —H | —COCH₃ | —H | —H | —H | 532 |
| 1464 | —H | —NHCOCH₃ | —H | —H | —H | 547 |
| 1465 | —H | —H | —NHCOCH₃ | —H | —H | 547 |
| 1466 | —H | —CO₂CH₃ | —H | —H | —OCH₃ | 578 |
| 1467 | —H | —H | —OC₆H₅ | —H | —H | 582 |
| 1468 | —H | —CO₂CH₃ | —H | —CO₂CH₃ | —H | 606 |
| 1469 | —OCH₃ | —OCH₃ | —H | —H | —H | 550 |
| 1470 | —H | —Cl | —OH | —H | —H | 540 |
| 1471 | —H | —OCH₂C₆H₅ | —H | —H | —H | 596 |
| 1472 | —H | —H | —NHSO₂CH₃ | —H | —H | 583 |
| 1473 | —H | —H | —CONHC₆H₅ | —H | —H | 609 |

TABLE 172-continued
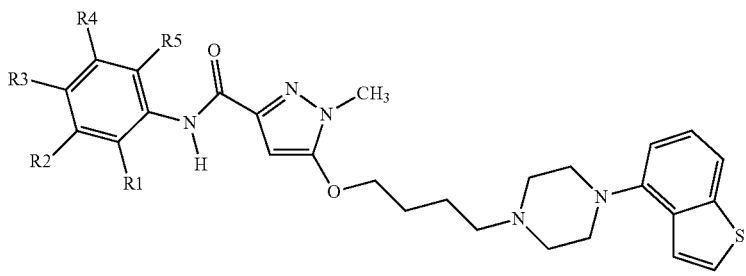
| Example | R1 | R2 | R3 | R4 | R5 | MS(M + 1) |
|---|---|---|---|---|---|---|
| 1474 | —H | —H | —CONHCH$_3$ | —H | —H | 547 |
| 1475 | —H | —H | —NHC$_6$H$_5$ | —H | —H | 581 |
| 1476 | —H | —H | —CH$_2$CH$_2$OH | —H | —H | 534 |
| 1477 | —H | —H | —CCH | —H | —H | 514 |
| 1478 | —H | —H | —COC$_3$H$_7$ | —H | —H | 560 |
| 1479 | —NHCOCH$_3$ | —H | —H | —H | —H | 547 |
| 1480 | —H | —CONHCH$_3$ | —H | —H | —H | 547 |
TABLE 173
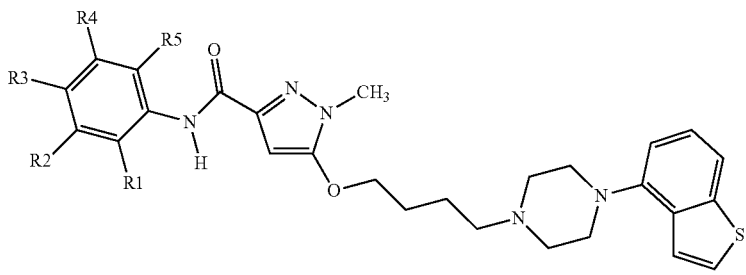
| Example | R1 | R2 | R3 | R4 | R5 | MS(M + 1) |
|---|---|---|---|---|---|---|
| 1481 | —H | —H | 1-(2-oxopyrrolidinyl) | —H | —H | 573 |
| 1482 | —H | —H | 4-methyl-2-oxo-2,5-dihydrofuran-3-yl | —H | —H | 572 |
| 1483 | —H | 1-piperidinyl-C(O)- | —H | —H | —H | 601 |
| 1484 | —H | 3-methyl-1H-pyrazol-5-yl | —H | —H | —H | 556 |
| 1485 | —H | 5-methyloxazol-2-yl | —H | —H | —H | 557 |

TABLE 174

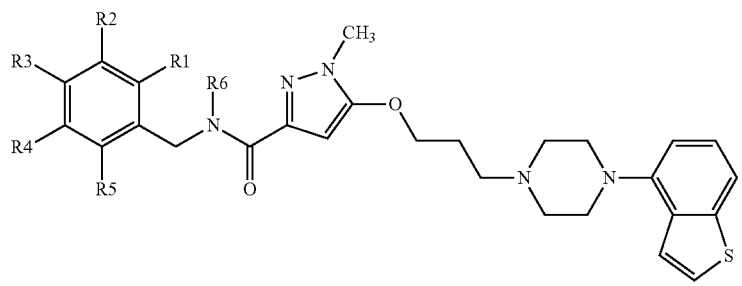

| Example | R1 | R2 | R3 | R4 | R5 | R6 | MS(M + 1) |
|---------|-----|-----|-----|-----|-----|-----|-----------|
| 1486 | —H | —H | —H | —H | —H | —H | 490 |
| 1487 | —Cl | —H | —H | —H | —H | —H | 524 |
| 1488 | —H | —Cl | —H | —H | —H | —H | 524 |
| 1489 | —H | —H | —Cl | —H | —H | —H | 524 |
| 1490 | —H | —H | —H | —H | —H | —CH$_2$CONHCH$_3$ | 561 |
| 1491 | —H | —H | —OC$_2$H$_5$ | —H | —H | —CH$_3$ | 548 |
| 1492 | —H | —OCH$_3$ | —OCH$_3$ | —H | —H | —CH$_3$ | 564 |
| 1493 | —H | —H | —OC$_2$H$_5$ | —H | —H | —C$_2$H$_5$ | 562 |
| 1494 | —H | —H | —OCH$_3$ | —H | —H | —H | 520 |
| 1495 | —H | —OCH$_3$ | —H | —H | —H | —H | 520 |
| 1496 | —H | —H | —OCF$_3$ | —H | —H | —CH$_3$ | 588 |
| 1497 | —H | —H | —OCF$_3$ | —H | —H | —H | 574 |
| 1498 | —H | —OCH$_3$ | —OCH$_3$ | —H | —H | —H | 550 |
| 1499 | —H | —OCH$_3$ | —OCH$_3$ | —H | —H | —C$_2$H$_5$ | 578 |
| 1500 | —OCH$_3$ | —H | —H | —H | —H | —H | 520 |
| 1501 | —H | —OCH$_3$ | —H | —OCH$_3$ | —H | —H | 550 |
| 1502 | —H | —OC$_4$H$_9$ | —H | —OC$_4$H$_9$ | —H | —H | 634 |
| 1503 | —OC$_2$H$_5$ | —H | —H | —H | —H | —H | 534 |
| 1504 | —H | —H | —H | —H | —H | —(CH$_2$)$_3$OH | 548 |
| 1505 | —H | —Cl | —OCHF$_2$ | —H | —H | —H | 590 |
| 1506 | —H | —OCF$_3$ | —H | —H | —H | —H | 574 |
| 1507 | —H | —H | —OCH$_3$ | —H | —H | —CH$_3$ | 534 |

TABLE 175

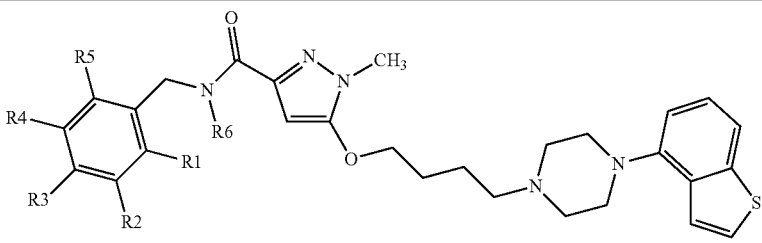

| Example | R1 | R2 | R3 | R4 | R5 | R6 | MS(M + 1) |
|---------|-----|-----|-----|-----|-----|-----|-----------|
| 1508 | —H | —H | —H | —H | —H | —H | 504 |
| 1509 | —Cl | —H | —H | —H | —H | —H | 538 |
| 1510 | —H | —Cl | —H | —H | —H | —H | 538 |
| 1511 | —H | —H | —Cl | —H | —H | —H | 538 |
| 1512 | —H | —H | —H | —H | —H | —CH$_2$CONHCH$_3$ | 575 |
| 1513 | —H | —H | —OC$_2$H$_5$ | —H | —H | —CH$_3$ | 562 |
| 1514 | —H | —OCH$_3$ | —OCH$_3$ | —H | —H | —CH$_3$ | 578 |
| 1515 | —H | —H | —OC$_2$H$_5$ | —H | —H | —C$_2$H$_5$ | 576 |
| 1516 | —H | —H | —OCH$_3$ | —H | —H | —H | 534 |
| 1517 | —H | —OCH$_3$ | —H | —H | —H | —H | 534 |
| 1518 | —H | —H | —OCF$_3$ | —H | —H | —CH$_3$ | 602 |
| 1519 | —H | —H | —OCF$_3$ | —H | —H | —H | 588 |
| 1520 | —H | —OCH$_3$ | —OCH$_3$ | —H | —H | —H | 584 |
| 1521 | —H | —OCH$_3$ | —OCH$_3$ | —H | —H | —C$_2$H$_5$ | 592 |
| 1522 | —OCH$_3$ | —H | —H | —H | —H | —H | 534 |
| 1523 | —H | —OCH$_3$ | —H | —OCH$_3$ | —H | —H | 564 |
| 1524 | —H | —OC$_4$H$_9$ | —H | —OC$_4$H$_9$ | —H | —H | 648 |
| 1525 | —OC$_2$H$_5$ | —H | —H | —H | —H | —H | 548 |
| 1526 | —H | —H | —H | —H | —H | —(CH$_2$)$_3$OH | 562 |

TABLE 175-continued

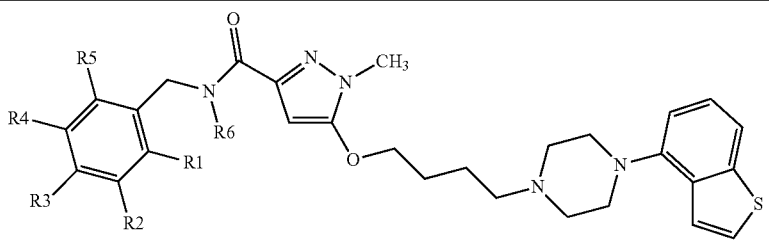

| Example | R1 | R2 | R3 | R4 | R5 | R6 | MS(M + 1) |
|---|---|---|---|---|---|---|---|
| 1527 | —H | —Cl | —OCHF₂ | —H | —H | —H | 604 |
| 1528 | —H | —OCF₃ | —H | —H | —H | —H | 588 |
| 1529 | —H | —H | —OCH₃ | —H | —H | —CH₃ | 548 |

TABLE 176

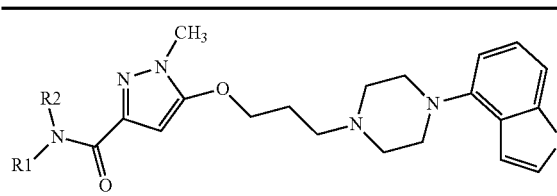

| Example | R1 | R2 | MS(M + 1) |
|---|---|---|---|
| 1530 | —cyclo-C₆H₁₁ | —CH₃ | 496 |
| 1531 | —cyclo-C₆H₁₁ | —H | 482 |
| 1532 | —CH₂CH(CH₃)₂ | —CH₂CH(CH₃)₂ | 512 |
| 1533 | —CH₂CH₂OH | —CH₂CH₂OH | 488 |
| 1534 | —CH₂CH₂OH | —C₂H₅ | 472 |
| 1535 | —cyclo-C₆H₁₁ | —CH₂CH₂OH | 526 |
| 1536 | —CH₂CH₂OCH₃ | —CH₂CH₂OCH₃ | 516 |
| 1537 | —C₂H₅ | —C₂H₅ | 456 |
| 1538 | —C₄H₉ | —H | 456 |
| 1539 | —C(CH₃)₃ | —H | 456 |
| 1540 | —cyclo-C₃H₅ | —H | 440 |
| 1541 | —CH₃ | —H | 414 |
| 1542 | —C₂H₅ | —H | 428 |
| 1543 | —CH₂CH(CH₃)₂ | —H | 456 |
| 1544 | —CH₂CH₂OCH₃ | —H | 458 |
| 1545 | —CH₂CH₂OC₂H₅ | —H | 472 |
| 1546 | —(CH₂)₃OC₂H₅ | —H | 486 |
| 1547 | —(CH₂)₂OC₆H₅ | —H | 520 |
| 1548 | —CH₂-cyclo-C₃H₅ | —H | 454 |
| 1549 | —(CH₂)₂NHCOCH₃ | —H | 485 |
| 1550 | —(CH₂)₅OH | —H | 486 |
| 1551 | —(CH₂)₂C₆H₅ | —H | 504 |
| 1552 | —CH₂CO₂CH₃ | —H | 472 |
| 1553 | —CH₂CONH₂ | —H | 457 |
| 1554 | —CH(CO₂C₂H₅)₂ | —H | 558 |
| 1555 | —CH(CH₃)CO₂C₂H₅ | —H | 500 |
| 1556 | —CH₂CO₂CH₃ | —CH₃ | 486 |
| 1557 | —CH₂CCH | —H | 438 |
| 1558 | —(CH₂)₂CH(CH₃)₂ | —H | 470 |
| 1559 | —(CH₂)₃CO₂C₂H₅ | —CH₃ | 528 |
| 1560 | —(CH₂)₄CO₂C₂H₅ | —H | 528 |
| 1561 | —CH(CONH₂)₂ | —H | 500 |
| 1562 | —CH₂CF₃ | —H | 482 |
| 1563 | —NHCH₂CF₃ | —H | 497 |
| 1564 | —CH₃ | —CH₃ | 428 |
| 1565 | —(CH₂)₃OCH(CH₃)₂ | —H | 500 |

TABLE 177

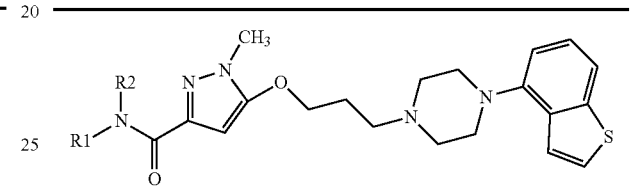

| Example | R1 | R2 | MS(M + 1) |
|---|---|---|---|
| 1566 | —CH₂CN | —H | 439 |
| 1567 | —(CH₂)₂OCH(CH₃)₂ | —H | 486 |
| 1568 | —CH(C₂H₅)CH₂OCH₃ | —H | 486 |
| 1569 | —CH(CH₃)CH₂OCH₃ | —H | 472 |
| 1570 | —CH₂CH₂F | —H | 446 |
| 1571 | —CH₂CH(OH)CH₂OH | —H | 474 |
| 1572 | —CH₂CONHCH₃ | —H | 471 |
| 1573 | —(CH₂)₂SCH₃ | —H | 474 |
| 1574 | —CH₂CH₂OH | —H | 444 |
| 1575 | —C₆H₁₃ | —H | 484 |
| 1576 | —CH₂CON(CH₃)₂ | —CH₃ | 499 |
| 1577 | —(CH₂)₂N(CH₃)COCH₃ | —H | 499 |
| 1578 | —(CH₂)₂N(CH₃)CO(CH₂)₂CH₃ | —H | 527 |

TABLE 178

| Example | R1 | R2 | MS (M + 1) |
|---|---|---|---|
| 1579 | ![pyridin-2-yl-propyl] | —CH₃ | 519 |
| 1580 | ![tetrahydropyran-2-yl-ethyl] | —C₂H₅ | 526 |

TABLE 178-continued

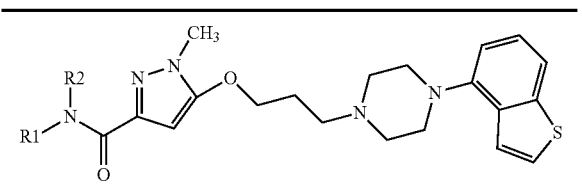

| Example | R1 | R2 | MS (M + 1) |
|---|---|---|---|
| 1581 | (2-methyl-2-phenylpropyl) | —H | 518 |
| 1582 | (pyridin-2-yl)ethyl | —H | 491 |
| 1583 | (pyridin-3-yl)ethyl | —H | 491 |
| 1584 | (pyridin-4-yl)ethyl | —H | 491 |
| 1585 | (furan-2-yl)ethyl | —H | 480 |
| 1586 | (pyridin-2-yl)propyl | —C$_2$H$_5$ | 533 |
| 1587 | (4-methoxyphenoxy)propyl | —C$_2$H$_5$ | 578 |
| 1588 | 1-phenyl-1-hydroxypropyl | —CH$_3$ | 534 |
| 1589 | (4-carbamoylphenoxy)propyl | —C$_2$H$_5$ | 591 |
| 1590 | N-methyl-N-(4-propoxyphenyl)propanamide | —C$_2$H$_5$ | 633 |

TABLE 179

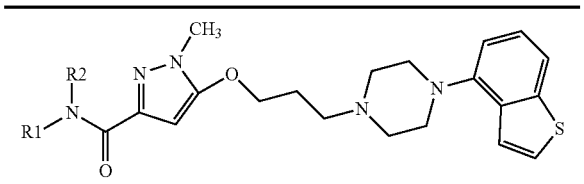

| Example | R1 | R2 | MS (M + 1) |
|---|---|---|---|
| 1591 | [2-(2-oxopyrrolidin-1-yl)phenoxy]propyl | —C$_2$H$_5$ | 631 |
| 1592 | (4-methylpiperidin-1-yl)(phenyl)methanone | —CH$_3$ | 601 |
| 1593 | 1-(4-methylpiperidin-1-yl)ethanone | —CH$_3$ | 539 |
| 1594 | (benzo[d][1,3]dioxol-5-yl)ethyl | —CH$_3$ | 548 |
| 1595 | (benzo[d][1,3]dioxol-5-yl)ethyl | —C$_2$H$_5$ | 562 |
| 1596 | (3,4-dimethoxyphenyl)propyl | —C$_2$H$_5$ | 592 |
| 1597 | 1-methylcyclopropyl | —H | 454 |
| 1598 | (4-methoxyphenyl)propyl | —H | 534 |
| 1599 | (3-methoxyphenyl)propyl | —H | 534 |
| 1600 | (4-chlorophenyl)propyl | —H | 538 |
| 1601 | (benzo[d][1,3]dioxol-5-yl)ethyl | —H | 534 |

TABLE 179-continued
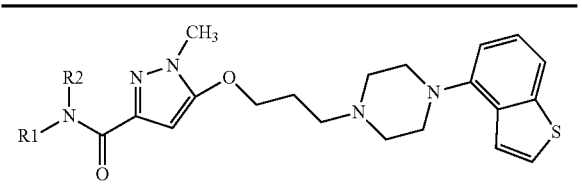
| Example | R1 | R2 | MS (M+1) |
|---|---|---|---|
| 1602 | 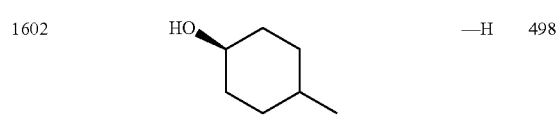 | —H | 498 |
| 1603 | 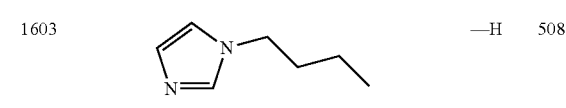 | —H | 508 |
TABLE 180
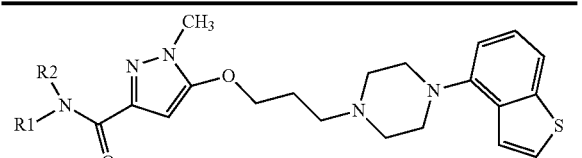
| Example | R1 | R2 | MS (M+1) |
|---|---|---|---|
| 1604 | 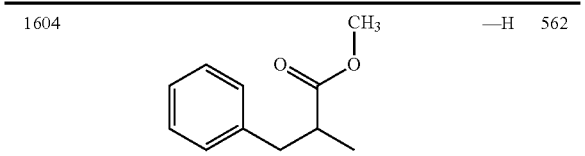 | —H | 562 |
| 1605 | 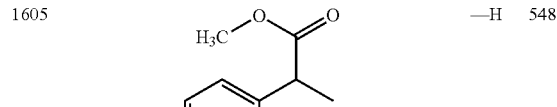 | —H | 548 |
| 1606 | 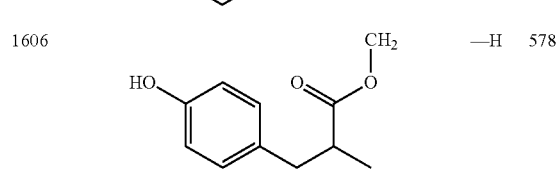 | —H | 578 |
| 1607 | 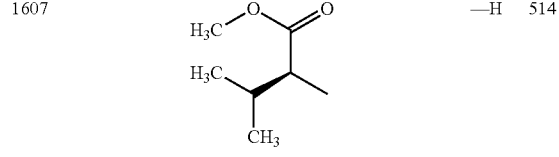 | —H | 514 |
| 1608 | 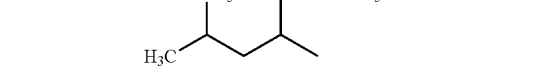 | —H | 528 |
TABLE 180-continued
| Example | R1 | R2 | MS (M+1) |
|---|---|---|---|
| 1609 | | —H | 537 |
| 1610 | | —H | 499 |
| 1611 | | —H | 547 |
| 1612 | | —H | 601 |
| 1613 | | —H | 552 |
| 1614 | | —H | 484 |
TABLE 181
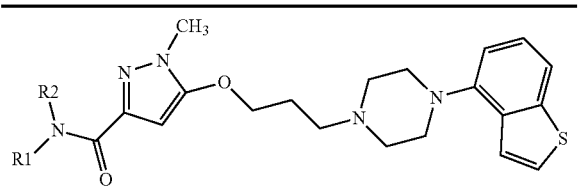
| Example | R1 | R2 | MS (M+1) |
|---|---|---|---|
| 1615 | 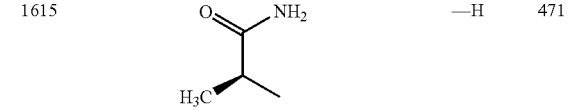 | —H | 471 |

TABLE 181-continued

| Example | R1 | R2 | MS (M+1) |
|---|---|---|---|
| 1616 | 4-methyl-isoxazolidin-3-one | —H | 485 |
| 1617 | 2-methoxy-N-phenyl propanamide | —CH₃ | 577 |
| 1618 | 4-methyl-N-phenyl propanamide | —CH₃ | 561 |
| 1619 | 2-methoxy propylbenzene | —H | 534 |
| 1620 | 2-methyl propylbenzene | —H | 518 |
| 1621 | 3-methyl propylbenzene | —H | 518 |
| 1622 | 1-methyl-3,4-dihydroquinolin-2(1H)-one | —H | 545 |
| 1623 | 3,8-dimethyl-3,4-dihydroquinolin-2(1H)-one | —H | 559 |
| 1624 | 2-propylpyridine | —H | 505 |
| 1625 | 2-propylpyridine | —CH(CH₃)₂ | 547 |

TABLE 181-continued

| Example | R1 | R2 | MS (M+1) |
|---|---|---|---|
| 1626 | (4-fluorophenyl)(4-methylpiperidin-1-yl)methanone | —CH₃ | 619 |

TABLE 182

| Example | R1 | R2 | MS (M+1) |
|---|---|---|---|
| 1627 | (2-methylphenyl)(4-methylpiperidin-1-yl)methanone | —CH₃ | 615 |
| 1628 | (3-methylphenyl)(4-methylpiperidin-1-yl)methanone | —CH₃ | 615 |
| 1629 | (4-methylphenyl)(4-methylpiperidin-1-yl)methanone | —CH₃ | 615 |
| 1630 | (2-chlorophenyl)(4-methylpiperidin-1-yl)methanone | —CH₃ | 635 |
| 1631 | (3-chlorophenyl)(4-methylpiperidin-1-yl)methanone | —CH₃ | 635 |

TABLE 182-continued
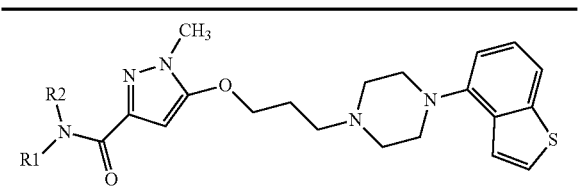
| Example | R1 | R2 | MS (M + 1) |
|---|---|---|---|
| 1632 | 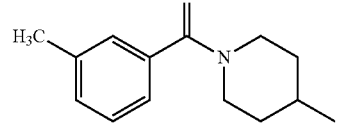 | —C₄H₉ | 657 |
| 1633 | 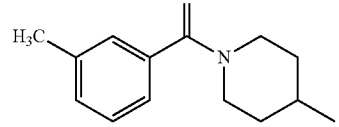 | —CH(CH₃)₂ | 643 |
| 1634 | 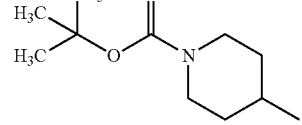 | —H | 583 |
| 1635 | 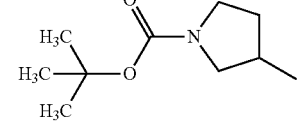 | —H | 569 |
| 1636 | 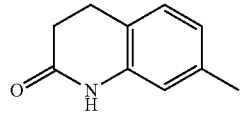 | —C₂H₅ | 573 |
| 1637 | 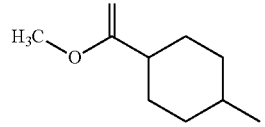 | —H | 540 |
TABLE 183
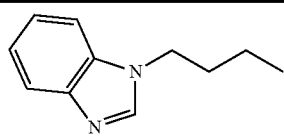
| Example | R1 | R2 | MS (M + 1) | MW |
|---|---|---|---|---|
| 1638 | (see structure) | —H | 558 | 557.72 |
TABLE 183-continued
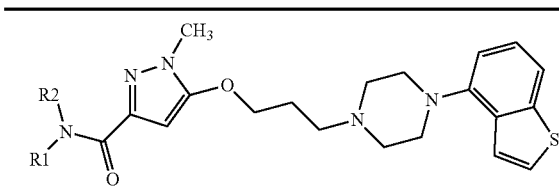
| Example | R1 | R2 | MS (M + 1) | MW |
|---|---|---|---|---|
| 1639 | 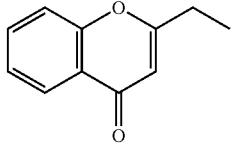 | —H | 558 | 557.68 |
| 1640 | 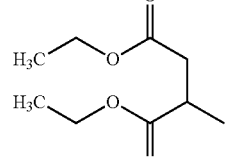 | —H | 572 | 571.70 |
| 1641 | 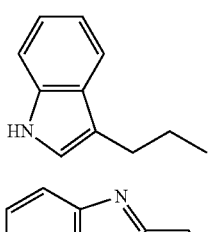 | —H | 543 | 542.71 |
| 1642 | 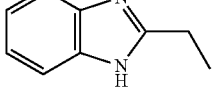 | —H | 530 | 529.67 |
| 1643 | 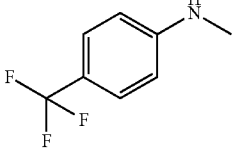 | —H | 559 | 558.63 |
| 1644 | 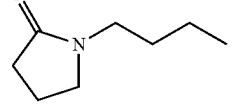 | —H | 525 | 524.69 |
| 1645 | 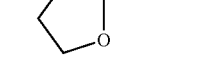 | —H | 484 | 483.64 |
| 1646 | 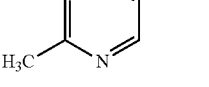 | —H | 506 | 505.65 |
| 1647 | 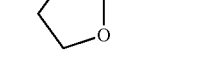 | —H | 486 | 485.61 |
| 1648 | 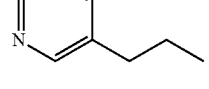 | —H | 505 | 504.66 |

TABLE 183-continued

Structure: N-methylpyrazole with R1R2N-C(O)- at 3-position and -O-(CH2)3-piperazinyl-benzothiophene at 5-position

| Example | R1 | R2 | MS (M+1) | MW |
|---------|----|----|----------|-----|
| 1649 | 4-(propyl)pyridin-yl | —H | 505 | 504.66 |

TABLE 184

Structure: N-methylpyrazole with R1R2N-C(O)- at 3-position and -O-(CH2)3-piperazinyl-benzothiophene at 5-position

| Example | R1 | R2 | MS(M+1) |
|---------|----|----|---------|
| 1650 | 5-methyl-2-(ethyl)furan-yl | —H | 494 |
| 1651 | 4-(propyl)-1H-imidazol-yl | —H | 494 |
| 1652 | 1-methyl-2-(ethyl)pyrrol-yl | —H | 493 |
| 1653 | 1,3-dimethyl-4-ethyl-pyrazol-5-yl | —H | 522 |
| 1654 | 2,5-dimethyl-3-ethyl-furan-yl | —H | 508 |
| 1655 | 1,5-dimethyl-3-ethyl-pyrazol-yl | —H | 508 |
| 1656 | 3-(ethyl)furan-yl | —H | 480 |

TABLE 184-continued

| Example | R1 | R2 | MS(M+1) |
|---------|----|----|---------|
| 1657 | 2-(ethyl)thiazol-yl | —H | 497 |
| 1658 | 4-(propyl)thiophen-yl | —H | 510 |
| 1659 | 5-(ethyl)-2,3-dihydrobenzofuran-yl | —H | 532 |
| 1660 | 2-methylbut-1-en-yl | —H | 454 |
| 1661 | 4-(butyl)-3-oxo-4,5-dihydro-1H-pyrazol-yl | —H | 524 |

TABLE 185

Structure: N-methylpyrazole with R1R2N-C(O)- at 3-position and -O-(CH2)3-piperazinyl-benzothiophene at 5-position

| Example | R1 | R2 | MS (M+1) |
|---------|----|----|----------|
| 1662 | 4-(ethyl)tetrahydropyran-yl | —H | 498 |
| 1663 | 4-(isopropyl)-1-(trifluoromethoxy)phenyl | —H | 588 |
| 1664 | 1-(4-chlorophenyl)butyl | —CH3 | 580 |

TABLE 185-continued
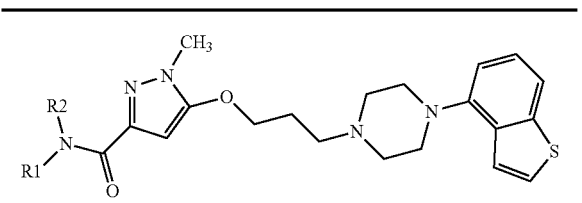
| Example | R1 | R2 | MS (M + 1) |
|---|---|---|---|
| 1665 | 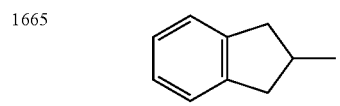 | —H | 516 |
| 1666 | 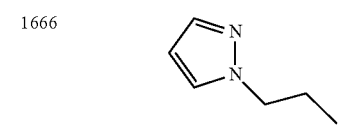 | —H | 494 |
| 1667 | 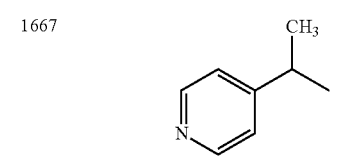 | —H | 505 |
| 1668 | 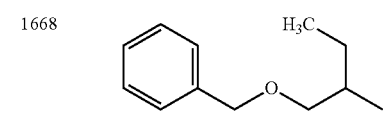 | —H | 562 |
| 1669 | 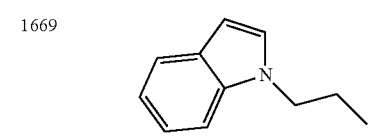 | —H | 543 |
| 1670 | 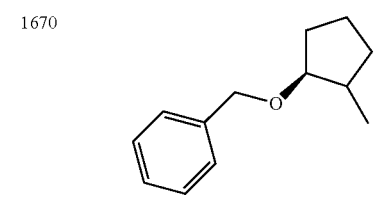 | —H | 574 |
| 1671 | 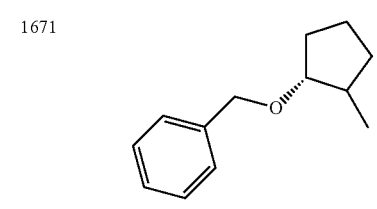 | —H | 574 |
TABLE 186
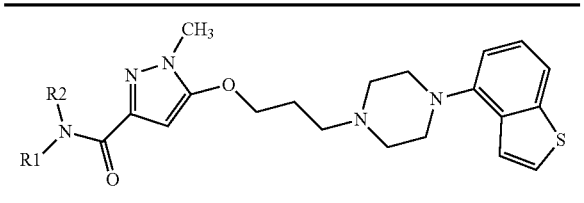
| Example | R1 | R2 | MS (M + 1) |
|---|---|---|---|
| 1672 | 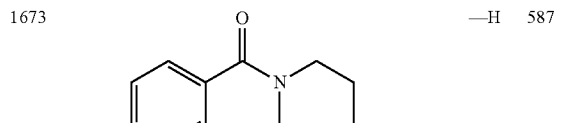 | —H | 484 |
| 1673 | 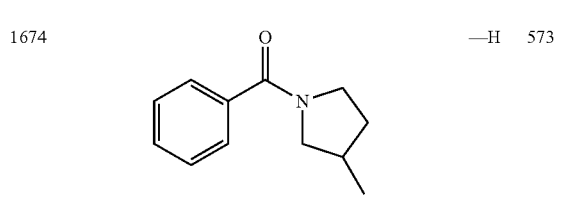 | —H | 587 |
| 1674 | 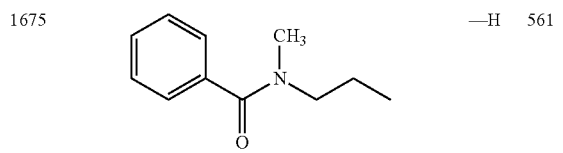 | —H | 573 |
| 1675 | 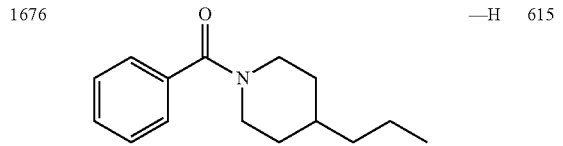 | —H | 561 |
| 1676 | 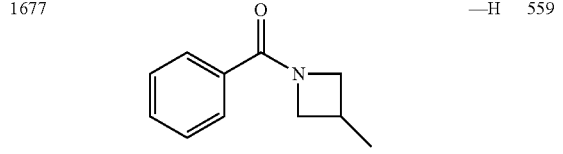 | —H | 615 |
| 1677 | 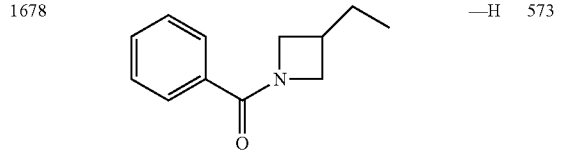 | —H | 559 |
| 1678 | 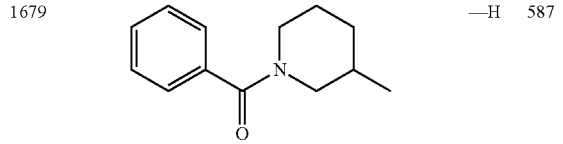 | —H | 573 |
| 1679 | | —H | 587 |

TABLE 186-continued

Structure: R1R2N-C(O)-[1-methyl-pyrazol-3-yl]-5-O-(CH2)3-[piperazin-N-yl]-benzothiophen-4-yl

| Example | R1 | R2 | MS (M + 1) |
|---|---|---|---|
| 1680 | 1-acetyl-4-methylpiperidin-4-yl | —H | 525 |
| 1681 | 1-acetyl-3-methylpyrrolidin-3-yl | —H | 511 |

TABLE 187

Structure: R1R2N-C(O)-[1-methyl-pyrazol-3-yl]-5-O-(CH2)3-[piperazin-N-yl]-benzothiophen-4-yl

| Example | R1 | R2 | MS (M + 1) |
|---|---|---|---|
| 1682 | 1-acetyl-4-propylpiperidin-4-yl | —H | 553 |
| 1683 | 1-acetyl-3-methylazetidin-3-yl | —H | 497 |
| 1684 | 1-acetyl-3-ethylazetidin-3-yl | —H | 511 |
| 1685 | 1-acetyl-3-methylpiperidin-3-yl | —H | 525 |
| 1686 | 1-butanoyl-4-methylpiperidin-4-yl | —H | 553 |
| 1687 | 1-butanoyl-3-methylpyrrolidin-3-yl | —H | 539 |
| 1688 | 1-butanoyl-4-propylpiperidin-4-yl | —H | 581 |
| 1689 | 1-butanoyl-3-methylazetidin-3-yl | —H | 525 |
| 1690 | 1-butanoyl-3-ethylazetidin-3-yl | —H | 539 |
| 1691 | 1-butanoyl-3-methylpiperidin-3-yl | —H | 553 |
| 1692 | 5-methylpyridin-3-yl | —H | 477 |

TABLE 188

Structure: R1R2N-C(O)-[1-methyl-pyrazol-3-yl]-5-O-(CH2)3-[piperazin-N-yl]-benzothiophen-4-yl

| Example | R1 | R2 | MS(M + 1) |
|---|---|---|---|
| 1693 | 6-methyl-1H-indazol-5-yl | —H | 516 |

TABLE 188-continued

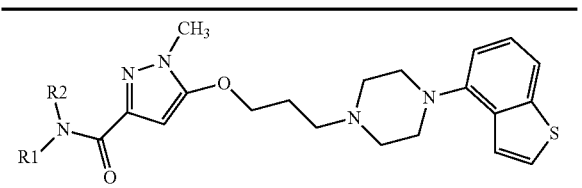

| Example | R1 | R2 | MS(M + 1) |
|---|---|---|---|
| 1694 | 4-methylpyridine | —H | 477 |
| 1695 | 3-methoxy-6-methylpyridine | —H | 507 |
| 1696 | 5-methoxy-6-methyl-3,4-dihydroquinolin-2(1H)-one | —H | 575 |
| 1697 | 5-methyl-1H-indole | —H | 515 |
| 1698 | 2-methylthiazole | —H | 483 |
| 1699 | methyl 2-methylthiophene-3-carboxylate | —H | 540 |
| 1700 | 3-methyl-1H-1,2,4-triazole | —H | 467 |
| 1701 | acetamidine | —H | 443 |
| 1702 | 3,5-dimethylisoxazole | —H | 481 |
| 1703 | 1-methyl-7-X₁-quinolin-2(1H)-one | —H | 557 |

TABLE 189

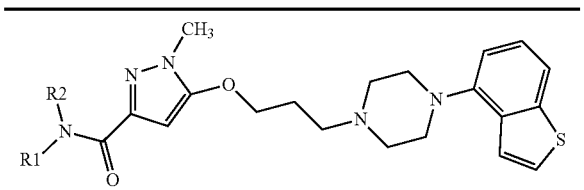

| Example | R1 | R2 | MS(M + 1) |
|---|---|---|---|
| 1704 | 6-methyl-2-oxoindoline | —H | 531 |
| 1705 | methyl 3-methylthiophene-2-carboxylate | —H | 540 |
| 1706 | 1,3-dimethyl-5-(methylthio)-1H-1,2,4-triazole | —H | 527 |
| 1707 | 2,5-dimethyl-1,3,4-thiadiazole | —H | 498 |
| 1708 | 5-methyl-1H-imidazole-4-carboxamide | —H | 509 |
| 1709 | 3-(furan-2-yl)-5-methyl-1H-pyrazole | —H | 532 |
| 1710 | 4-methoxy-2-methyloxazole | —H | 481 |
| 1711 | 1,5-dimethyl-1H-pyrazole | —H | 480 |
| 1712 | 3,5-dimethylisothiazole | —H | 497 |
| 1713 | 3-methylisoxazole | —H | 467 |

TABLE 190

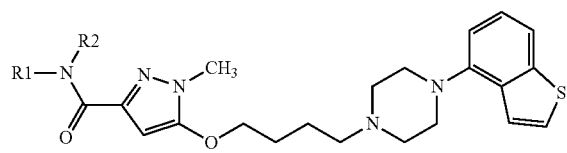

| Example | R1 | R2 | MS(M + 1) |
|---|---|---|---|
| 1714 | —CH₃ | -cyclo-C₆H₁₁ | 510 |
| 1715 | —H | -cyclo-C₆H₁₁ | 496 |
| 1716 | —H | —CH(CH₃)₂ | 456 |
| 1717 | —CH₂CH(CH₃)₂ | —CH₂CH(CH₃)₂ | 526 |
| 1718 | —CH₂CH₂OH | —CH₂CH₂OH | 502 |
| 1719 | —C₂H₅ | —CH₂CH₂OH | 486 |
| 1720 | —CH₂CH₂OH | -cyclo-C₆H₁₁ | 540 |
| 1721 | —CH₂CH₂OCH₃ | —CH₂CH₂OCH₃ | 530 |
| 1722 | —C₂H₅ | —C₂H₅ | 470 |
| 1723 | —H | —C₄H₉ | 470 |
| 1724 | —H | —C(CH₃)₃ | 470 |
| 1725 | —H | -cyclo-C₃H₅ | 454 |
| 1726 | —H | —CH₃ | 428 |
| 1727 | —H | —C₂H₅ | 442 |
| 1728 | —H | —C₃H₇ | 456 |
| 1729 | —H | —CH₂CH(CH₃)₂ | 470 |
| 1730 | —H | —CH₂CH₂OCH₃ | 472 |
| 1731 | —H | —CH₂CH₂OC₂H₅ | 486 |
| 1732 | —H | —(CH₂)₃OC₂H₅ | 500 |
| 1733 | —H | —(CH₂)₂OC₆H₅ | 534 |
| 1734 | —H | —CH₂-cyclo-C₃H₅ | 468 |
| 1735 | —H | —(CH₂)₂NHCOCH₃ | 499 |
| 1736 | —H | —(CH₂)₅OH | 500 |
| 1737 | —H | —(CH₂)₂C₆H₅ | 518 |
| 1738 | —H | —CH₂CO₂CH₃ | 486 |
| 1739 | —H | —CH₂CONH₂ | 471 |
| 1740 | —H | —CH(CO₂C₂H₅)₂ | 572 |
| 1741 | —H | —CH(CH₃)CO₂C₂H₅ | 514 |
| 1742 | —CH₃ | —CH₂CO₂CH₃ | 500 |
| 1743 | —H | —CH₂CCH | 452 |
| 1744 | —H | —(CH₂)₂CH(CH₃)₂ | 484 |
| 1745 | —CH₃ | —(CH₂)₃CO₂C₂H₅ | 542 |
| 1746 | —H | —(CH₂)₄CO₂C₂H₅ | 542 |
| 1747 | —H | —CH(CONH₂)₂ | 514 |
| 1748 | —H | —CH₂CF₃ | 496 |
| 1749 | —H | —NHCH₂CF₃ | 511 |

TABLE 191

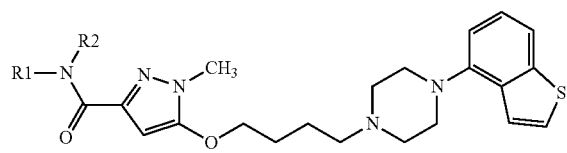

| Example | R1 | R2 | MS(M + 1) |
|---|---|---|---|
| 1750 | —CH₃ | —CH₃ | 442 |
| 1751 | —H | —CH₂CH(OCH₃)₂ | 502 |
| 1752 | —H | —(CH₂)₃OCH(CH₃)₂ | 514 |
| 1753 | —H | —CH₂CN | 453 |
| 1754 | —H | —(CH₂)₃OCH₃ | 486 |
| 1755 | —H | —(CH₂)₂OCH(CH₃)₂ | 500 |
| 1756 | —H | —CH(C₂H₅)CH₂OCH₃ | 500 |
| 1757 | —H | —CH(CH₃)CH₂OCH₃ | 486 |
| 1758 | —H | —CH₂CH₂F | 460 |
| 1759 | —H | —CH₂CH(OH)CH₂OH | 488 |
| 1760 | —H | —CH₂CONHCH₃ | 485 |
| 1761 | —H | —(CH₂)₂SCH₃ | 488 |
| 1762 | —H | —CH₂CH₂OH | 458 |
| 1763 | —H | —C₆H₁₃ | 498 |
| 1764 | —CH₃ | —CH₂CON(CH₃)₂ | 513 |
| 1765 | —H | —(CH₂)₂N(CH₃)COCH₃ | 513 |
| 1766 | —H | —(CH₂)₂N(CH₃)CO(CH₂)₂CH₃ | 541 |

TABLE 192

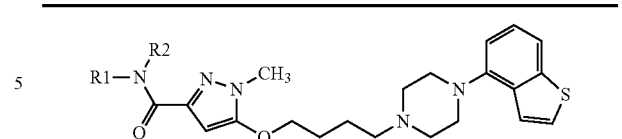

| Example | R1 | R2 | MS(M + 1) |
|---|---|---|---|
| 1767 | 2-propylpyridine | —CH₃ | 533 |
| 1768 | 2-ethyltetrahydropyran | —C₂H₅ | 540 |
| 1769 | α,α-dimethylbenzyl | —H | 532 |
| 1770 | 2-ethylpyridine | —H | 505 |
| 1771 | 3-ethylpyridine | —H | 505 |
| 1772 | 4-ethylpyridine | —H | 505 |
| 1773 | 2-ethylfuran | —H | 494 |
| 1774 | 2-propylpyridazine | —C₂H₅ | 547 |
| 1775 | 4-methoxyphenylpropyl | —C₂H₅ | 592 |
| 1776 | 1-hydroxy-1-phenylpropyl | —CH₃ | 548 |
| 1777 | 4-carbamoylphenoxypropyl | —C₂H₅ | 605 |

TABLE 192-continued

R1-N(R2)-C(=O)-[1-methyl-5-(4-(4-(benzothiophen-4-yl)piperazin-1-yl)butoxy)pyrazol-3-yl]

| Example | R1 | R2 | MS(M+1) |
|---|---|---|---|
| 1778 | N-methyl-N-(4-propoxyphenyl)propanamido | —C₂H₅ | 647 |

TABLE 193

R1-N(R2)-C(=O)-[1-methyl-5-(4-(4-(benzothiophen-4-yl)piperazin-1-yl)butoxy)pyrazol-3-yl]

| Example | R1 | R2 | MS(M+1) |
|---|---|---|---|
| 1779 | 1-(2-propoxyphenyl)-2-oxopyrrolidinyl | —C₂H₅ | 645 |
| 1780 | 1-benzoyl-4-methylpiperidinyl | —CH₃ | 615 |
| 1781 | 1-acetyl-4-methylpiperidinyl | —CH₃ | 553 |
| 1782 | 5-ethyl-benzo[1,3]dioxol-yl | —CH₃ | 562 |
| 1783 | 5-ethyl-benzo[1,3]dioxol-yl | —C₂H₅ | 576 |
| 1784 | 3,4-dimethoxyphenylpropyl | —C₂H₅ | 606 |
| 1785 | 1-methylcyclopropyl | —H | 468 |

TABLE 193-continued

| Example | R1 | R2 | MS(M+1) |
|---|---|---|---|
| 1786 | 4-methoxyphenylpropyl | —H | 548 |
| 1787 | 3-methoxyphenylpropyl | —H | 548 |
| 1788 | 4-chlorophenylpropyl | —H | 552 |
| 1789 | 5-ethyl-benzo[1,3]dioxol-yl | —H | 548 |
| 1790 | trans-4-hydroxycyclohexylmethyl | —H | 512 |
| 1791 | 1-butyl-imidazolyl | —H | 522 |

TABLE 194

R1-N(R2)-C(=O)-[1-methyl-5-(4-(4-(benzothiophen-4-yl)piperazin-1-yl)butoxy)pyrazol-3-yl]

| Example | R1 | R2 | MS(M+1) |
|---|---|---|---|
| 1792 | methyl 2-benzyl-propanoate | —H | 576 |
| 1793 | methyl 2-phenyl-propanoate | —H | 562 |
| 1794 | methyl 2-(4-hydroxybenzyl)-propanoate | —H | 592 |

TABLE 194-continued

Structure: R1-N(R2)-C(=O)-[pyrazole(N-CH3)]-O-(CH2)4-N(piperazine)N-[benzothiophene]

| Example | R1 | R2 | MS(M + 1) |
|---|---|---|---|
| 1795 | methyl 2,3-dimethylbutanoate | —H | 528 |
| 1796 | methyl 2,4-dimethylpentanoate | —H | 542 |
| 1797 | 2-methyl-3-(1H-imidazol-4-yl)propanamide | —H | 551 |
| 1798 | 2,3-dimethylbutanamide | —H | 513 |
| 1799 | 2-methyl-3-phenylpropanamide | —H | 561 |
| 1800 | methyl 2-methyl-3-(1H-indol-3-yl)propanoate | —H | 615 |
| 1801 | methyl 2-methyl-3-(1H-imidazol-4-yl)propanoate | —H | 566 |
| 1802 | 3-methyldihydrofuran-2(3H)-one | —H | 498 |

TABLE 195

Structure: R1-N(R2)-C(=O)-[pyrazole(N-CH3)]-O-(CH2)4-N(piperazine)N-[benzothiophene]

| Example | R1 | R2 | MS(M + 1) |
|---|---|---|---|
| 1803 | 2-methylpropanamide (alanine amide) | —H | 485 |
| 1804 | 4-methyl-isoxazolidin-3-one | —H | 499 |
| 1805 | N-(2-methoxyphenyl)propanamide | —CH3 | 591 |
| 1806 | N-(4-methylphenyl)propanamide | —CH3 | 575 |
| 1807 | 2-methoxyphenyl propyl | —H | 548 |
| 1808 | 2-methylphenyl propyl | —H | 532 |
| 1809 | 3-methylphenyl propyl | —H | 532 |
| 1810 | 1-methyl-3,4-dihydroquinolin-2(1H)-one | —H | 559 |
| 1811 | 3,8-dimethyl-3,4-dihydroquinolin-2(1H)-one | —H | 573 |
| 1812 | 2-propylpyridine | —H | 519 |
| 1813 | 2-propylpyridine | —CH(CH3)2 | 561 |

TABLE 195-continued

Structure: R1-N(R2)-C(=O)-[pyrazole(N-CH3)]-O-(CH2)4-N[piperazine]-N-(benzothiophen-4-yl)

| Example | R1 | R2 | MS(M + 1) |
|---|---|---|---|
| 1814 | HN=C(NH2)-CH2CH3 (propanimidamide) | —H | 470 |

TABLE 196

Structure: R1-N(R2)-C(=O)-[pyrazole(N-CH3)]-O-(CH2)4-N[piperazine]-N-(benzothiophen-4-yl)

| Example | R1 | R2 | MS(M + 1) |
|---|---|---|---|
| 1815 | 4-fluorobenzoyl-(4-methylpiperidin-1-yl) | —CH3 | 633 |
| 1816 | 2-methylbenzoyl-(4-methylpiperidin-1-yl) | —CH3 | 629 |
| 1817 | 3-methylbenzoyl-(4-methylpiperidin-1-yl) | —CH3 | 629 |
| 1818 | 4-methylbenzoyl-(4-methylpiperidin-1-yl) | —CH3 | 629 |
| 1819 | 2-chlorobenzoyl-(4-methylpiperidin-1-yl) | —CH3 | 649 |
| 1820 | 3-chlorobenzoyl-(4-methylpiperidin-1-yl) | —C4H9 | 649 |
| 1821 | 3-methylbenzoyl-(4-methylpiperidin-1-yl) | —C4H9 | 671 |

TABLE 196-continued

Structure: R1-N(R2)-C(=O)-[pyrazole(N-CH3)]-O-(CH2)4-N[piperazine]-N-(benzothiophen-4-yl)

| Example | R1 | R2 | MS(M + 1) |
|---|---|---|---|
| 1822 | 3-methylbenzoyl-(4-methylpiperidin-1-yl) | —CH(CH3)2 | 657 |
| 1823 | tert-butoxycarbonyl-(4-methylpiperidin-1-yl) | —H | 597 |
| 1824 | tert-butoxycarbonyl-(3-methylpyrrolidin-1-yl) | —H | 583 |
| 1825 | 7-methyl-2-oxo-1,2,3,4-tetrahydroquinolin-yl | —C2H5 | 587 |

TABLE 197

Structure: R1-N(R2)-C(=O)-[pyrazole(N-CH3)]-O-(CH2)4-N[piperazine]-N-(benzothiophen-4-yl)

| Example | R1 | R2 | MS(M + 1) |
|---|---|---|---|
| 1826 | methyl 4-methylcyclohexanecarboxylate | —H | 554 |
| 1827 | 1-butylbenzimidazol-yl | —H | 572 |
| 1828 | 2-ethyl-4-oxo-4H-chromen-yl | —H | 572 |
| 1829 | diethyl 2-methylsuccinate | —H | 586 |

TABLE 197-continued

| Example | R1 | R2 | MS(M + 1) |
|---|---|---|---|
| 1830 | 3-propyl-1H-indol-yl | —H | 557 |
| 1831 | 2-ethyl-1H-benzimidazol-yl | —H | 544 |
| 1832 | 4-(trifluoromethyl)-N-methylanilino | —H | 573 |
| 1833 | 1-butyl-2-oxopyrrolidin-yl | —H | 539 |
| 1834 | 2-ethyltetrahydrofuran-yl | —H | 498 |
| 1835 | 5-methyl-2-ethylpyrazin-yl | —H | 520 |
| 1836 | 2-ethyl-1,3-dioxolan-yl | —H | 500 |

TABLE 198

| Example | R1 | R2 | MS(M + 1) |
|---|---|---|---|
| 1837 | 3-propylpyridin-yl | —H | 519 |
| 1838 | 4-propylpyridin-yl | —H | 519 |

TABLE 198-continued

| Example | R1 | R2 | MS(M + 1) |
|---|---|---|---|
| 1839 | 5-ethyl-2-methylfuran-yl | —H | 508 |
| 1840 | 5-propyl-1H-imidazol-yl | —H | 508 |
| 1841 | 1-methyl-2-ethylpyrrol-yl | —H | 507 |
| 1842 | 1,3,5-trimethyl-4-ethylpyrazol-yl | —H | 536 |
| 1843 | 2,5-dimethyl-3-ethylfuran-yl | —H | 522 |
| 1844 | 1,5-dimethyl-3-ethylpyrazol-yl | —H | 522 |
| 1845 | 4-ethylisoxazol-yl | —H | 494 |
| 1846 | 2-ethylthiazol-yl | —H | 511 |
| 1847 | 2-propylthiophen-yl | —H | 524 |
| 1848 | 5-ethyl-2,3-dihydrobenzofuran-yl | —H | 546 |

TABLE 198-continued

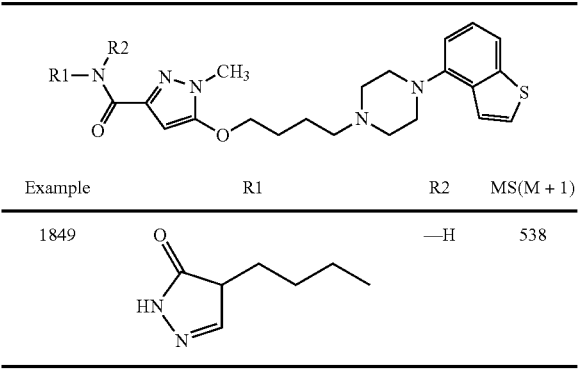

| Example | R1 | R2 | MS(M + 1) |
|---|---|---|---|
| 1849 | (3-oxo-4-butyl-pyrazoline) | —H | 538 |

TABLE 199

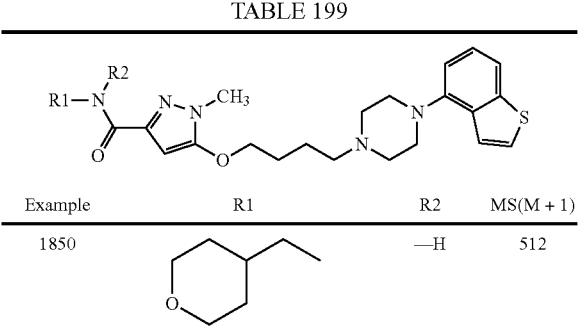

| Example | R1 | R2 | MS(M + 1) |
|---|---|---|---|
| 1850 | 4-ethyl-tetrahydropyran | —H | 512 |
| 1851 | 4-(1,1,1-trifluoro-2-methylpropan-2-yl)phenyl isopropyl | —H | 602 |
| 1852 | 1-(4-chlorophenyl)butyl | —CH₃ | 594 |
| 1853 | 2-methyl-indanyl | —H | 530 |
| 1854 | 1-propyl-pyrazolyl | —H | 508 |
| 1855 | 4-isopropyl-pyridinyl | —H | 519 |
| 1856 | 2-methyl-3-benzyloxy-propyl | —H | 576 |
| 1857 | 1-propyl-indolyl | —H | 557 |

TABLE 199-continued

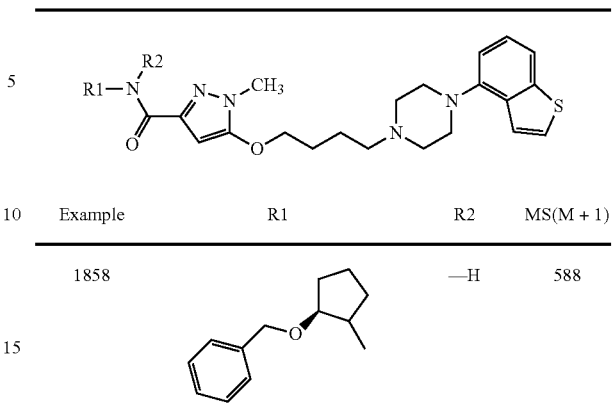

| Example | R1 | R2 | MS(M + 1) |
|---|---|---|---|
| 1858 | (benzyloxy-methylcyclopentyl, stereo) | —H | 588 |
| 1859 | (benzyloxy-methylcyclopentyl, stereo) | —H | 588 |
| 1860 | 4-methyl-tetrahydropyran | —H | 498 |

TABLE 200

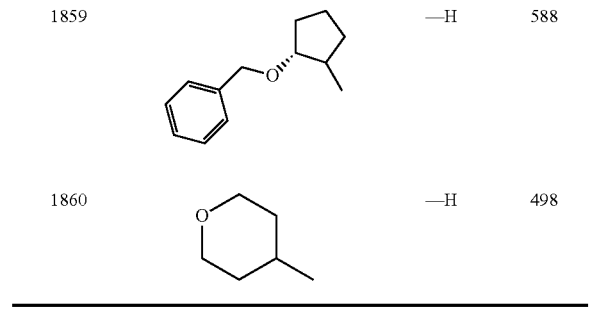

| Example | R1 | R2 | MS(M + 1) |
|---|---|---|---|
| 1861 | 4-methyl-1-benzoyl-piperidine | —H | 601 |
| 1862 | 3-methyl-1-benzoyl-pyrrolidine | —H | 587 |
| 1863 | N-methyl-N-propyl-benzamide | —H | 575 |
| 1864 | 4-propyl-1-benzoyl-piperidine | —H | 629 |

TABLE 200-continued

| Example | R1 | R2 | MS(M + 1) |
|---------|----|----|-----------|
| 1865 | phenyl-C(O)-azetidine-3-methyl | —H | 573 |
| 1866 | phenyl-C(O)-azetidine-3-ethyl | —H | 587 |
| 1867 | phenyl-C(O)-piperidine-3-methyl | —H | 601 |
| 1868 | H3C-C(O)-piperidine-4-methyl | —H | 539 |
| 1869 | H3C-C(O)-pyrrolidine-3-methyl | —H | 525 |
| 1870 | H3C-C(O)-piperidine-4-propyl | —H | 567 |

TABLE 201

| Example | R1 | R2 | MS(M + 1) |
|---------|----|----|-----------|
| 1871 | H3C-C(O)-azetidine-3-methyl | —H | 511 |
| 1872 | H3C-C(O)-azetidine-3-ethyl | —H | 525 |
| 1873 | H3C-C(O)-piperidine-3-methyl | —H | 539 |
| 1874 | H3C-CH2-C(O)-piperidine-4-methyl | —H | 567 |
| 1875 | H3C-CH2-C(O)-pyrrolidine-3-methyl | —H | 553 |
| 1876 | H3C-CH2-C(O)-piperidine-4-propyl | —H | 595 |
| 1877 | H3C-CH2-C(O)-azetidine-3-methyl | —H | 539 |
| 1878 | H3C-CH2-C(O)-azetidine-3-ethyl | —H | 553 |
| 1879 | H3C-CH2-C(O)-piperidine-3-methyl | —H | 567 |
| 1880 | 3-methylpyridine | —H | 491 |
| 1881 | 6-methyl-1H-indazole | —H | 530 |

TABLE 202

| Example | R1 | R2 | MS(M+1) |
|---|---|---|---|
| 1882 | 3-methylquinolin-yl | —H | 541 |
| 1883 | 3-methoxy-2-methylpyridinyl | —H | 505 |
| 1884 | 4-hydroxy-3-methylphenyl | —CH₃ | 520 |
| 1885 | 2-ethyl-4-methyl-1-(p-tolyl)imidazolyl | —CH₃ | 612 |
| 1886 | 3-methoxy-2-methylpyridinyl | —H | 521 |
| 1887 | 5-methoxy-6-methyl-2-oxo-1,2,3,4-tetrahydroquinolinyl | —H | 589 |
| 1888 | 5-methyl-1H-indolyl | —H | 529 |
| 1889 | 8-fluoro-5-methyl-2-oxo-1,2,3,4-tetrahydroquinolinyl | —H | 577 |
| 1890 | 2,5-dimethylpyridinyl | —H | 505 |
| 1891 | 2-methylthiazolyl | —H | 497 |

TABLE 202-continued

| Example | R1 | R2 | MS(M+1) |
|---|---|---|---|
| 1892 | 6-methylquinolinyl | —H | 541 |

TABLE 203

| Example | R1 | R2 | MS(M+1) |
|---|---|---|---|
| 1893 | acetamidine | —H | 456 |
| 1894 | 6-methyl-2-oxoindolinyl | —H | 545 |
| 1895 | 1,3,5-trimethyl-1H-pyrazolyl | —H | 508 |
| 1896 | 5-(furan-2-yl)-3-methyl-1H-pyrazolyl | —H | 546 |
| 1897 | 1,5-dimethyl-1H-pyrazolyl | —H | 494 |
| 1898 | 2,6-dimethylquinolinyl | —H | 555 |

TABLE 204

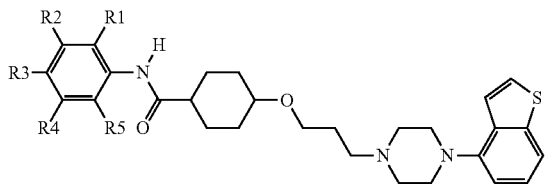

| Example | R1 | R2 | R3 | R4 | R5 | MS(M + 1) |
|---|---|---|---|---|---|---|
| 1899 | —H | —H | —OCF$_3$ | —H | —H | 562 |
| 1900 | —H | —H | —OCH$_3$ | —H | —H | 508 |
| 1901 | —H | —OCH$_3$ | —H | —H | —H | 508 |
| 1902 | —OCH$_3$ | —H | —OCH$_3$ | —H | —H | 538 |
| 1903 | —H | —OCH$_3$ | —H | —H | —OCH$_3$ | 538 |
| 1904 | —H | —OCH$_3$ | —H | —OCH$_3$ | —H | 538 |
| 1905 | —H | NHCOCH$_3$ | —H | —H | —OCH$_3$ | 565 |
| 1906 | —H | —OCH$_3$ | —OCH$_3$ | —H | —H | 538 |
| 1907 | —H | —H | —N(CH$_3$)$_2$ | —H | —H | 521 |
| 1908 | —H | —COCH$_3$ | —H | —H | —H | 520 |
| 1909 | —H | —NHCOCH$_3$ | —H | —H | —H | 535 |
| 1910 | —H | —H | —NHCOCH$_3$ | —H | —H | 535 |
| 1911 | —H | —H | —H | —CN | —H | 503 |
| 1912 | —H | —CO$_2$CH$_3$ | —H | —H | —OCH$_3$ | 566 |
| 1913 | —H | —H | —OC$_2$H$_6$ | —H | —H | 570 |
| 1914 | —H | —CO$_2$CH$_3$ | —H | —CO$_2$CH$_3$ | —H | 594 |
| 1915 | —OCH$_3$ | —OCH$_3$ | —H | —H | —H | 538 |
| 1916 | —H | —Cl | —OH | —H | —H | 528 |
| 1917 | —CO$_2$C$_2$H$_5$ | —H | —H | —H | —Cl | 584 |
| 1918 | —H | —CN | —H | —H | —H | 503 |
| 1919 | —H | —OCH$_2$C$_6$H$_5$ | —H | —H | —H | 584 |
| 1920 | —H | —H | —NHSO$_2$CH$_3$ | —H | —H | 571 |
| 1921 | —H | —H | —CONHC$_6$H$_5$ | —H | —H | 597 |
| 1922 | —H | —H | —CONHCH$_3$ | —H | —H | 535 |
| 1923 | —H | —H | —NHC$_6$H$_5$ | —H | —H | 569 |
| 1924 | —H | —H | —CH$_2$CH$_2$OH | —H | —H | 522 |
| 1925 | —H | —H | —C≡CH | —H | —H | 502 |
| 1926 | —NHCOCH$_3$ | —H | —H | —H | —H | 535 |
| 1927 | —H | —CONHCH$_3$ | —H | —H | —H | 535 |

TABLE 205

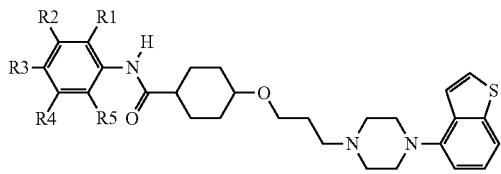

| Example | R1 | R2 | R3 | R4 | R5 | MS (M + 1) |
|---|---|---|---|---|---|---|
| 1928 | —H | —H | (1-methyl-2-oxopyrrolidinyl) | —H | —H | 561 |
| 1929 | —H | —H | (5-ethyl-2,4-dioxothiazolidinyl) | —H | —H | 607 |
| 1930 | —H | (1-acetylpiperidinyl) | —H | —H | —H | 589 |

TABLE 205-continued

| Example | R1 | R2 | R3 | R4 | R5 | MS (M + 1) |
|---|---|---|---|---|---|---|
| 1931 | —H | (5-methyloxazolyl) | —H | —H | —H | 545 |

TABLE 206

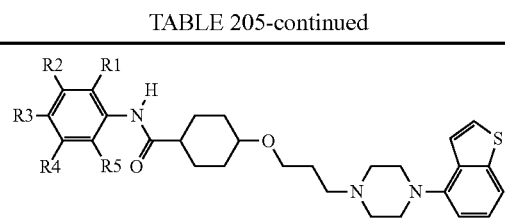

| Example | R1 | R2 | MS(M + 1) |
|---|---|---|---|
| 1932 | CH$_3$ | -cyclo-C$_6$H$_{11}$ | 498 |
| 1933 | -cyclo-C$_6$H$_{11}$ | H | 484 |

TABLE 206-continued

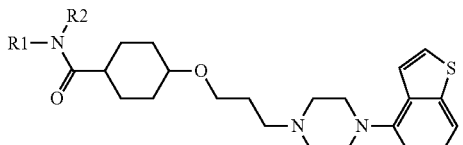

| Example | R1 | R2 | MS(M + 1) |
|---|---|---|---|
| 1934 | C₄H₉ | C₄H₉ | 514 |
| 1935 | CH₂CH(CH₃)₂ | CH₂CH(CH₃)₂ | 514 |
| 1936 | CH₂CH₂OH | CH₂CH₂OH | 490 |
| 1937 | C₂H₅ | CH₂CH₂OH | 474 |
| 1938 | CH₂CH₂OH | -cyclo-C₆H₁₁ | 528 |
| 1939 | CH₂CH₂OCH₃ | CH₂CH₂OCH₃ | 518 |
| 1940 | C₃H₇ | CH₂-cyclo-C₃H₅ | 498 |
| 1941 | -cyclo-C₄H₉ | CH₂CH=CH₂ | 510 |
| 1942 | C₂H₅ | C₂H₅ | 458 |
| 1943 | C₄H₉ | H | 458 |
| 1944 | C(CH₃)₃ | H | 458 |
| 1945 | -cyclo-C₃H₅ | H | 442 |
| 1946 | C₂H₅ | H | 430 |
| 1947 | CH₂CH₂OCH₃ | H | 460 |
| 1948 | C₄H₉ | C₂H₅ | 486 |
| 1949 | CH₂CH₂OC₂H₅ | H | 474 |
| 1950 | (CH₂)₃OC₂H₅ | H | 488 |
| 1951 | -cyclo-C₅H₉ | H | 470 |
| 1952 | CH-cyclo-CH | H | 456 |
| 1953 | CH₂-cyclo-C₆H₁₁ | H | 498 |
| 1954 | (CH₂)₂NHCOCH₃ | H | 487 |
| 1955 | (CH₂)₅OH | H | 488 |
| 1956 | CH₂CONH₂ | H | 459 |
| 1957 | CH₂C≡CH | H | 440 |
| 1958 | CH₃ | CH(CH₃)₂ | 458 |
| 1959 | (CH₂)₂CH(CH₃)₂ | H | 472 |
| 1960 | CH(CH₃)C(CH₃)₃ | H | 486 |
| 1961 | CH₂C(CH₃)₃ | H | 472 |
| 1962 | CH₂CH(C₂H₅)₂ | H | 486 |
| 1963 | CH(CONH₂)₂ | H | 502 |
| 1964 | CH₂-cyclo-C₃H₅ | CH₃ | 470 |
| 1965 | CH(CONH₂)₂ | H | 499 |

TABLE 207

| Example | R1 | R2 | MS(M + 1) |
|---|---|---|---|
| 1966 | —CH₃ | —CH₃ | 430 |
| 1967 | —(CH₂)₃OCH(CH₃)₂ | —H | 502 |
| 1968 | —CH₂CH₂C(CH₃)₃ | —H | 486 |
| 1969 | —CH(C₂H₅)₂ | —H | 472 |
| 1970 | —CH₂CN | —H | 441 |
| 1971 | —(CH₂)₃OCH₃ | —H | 474 |
| 1972 | —(CH₂)₂OCH(CH₃)₂ | —H | 488 |
| 1973 | —CH(C₂H₅)CH₂OCH₃ | —H | 488 |
| 1974 | —CH(CH₃)CH₂OCH₃ | —H | 474 |
| 1975 | —CH₂CH₂F | —H | 448 |
| 1976 | —CH₂CH(OH)CH₂OH | —H | 476 |
| 1977 | —CH₂CONHCH₃ | —H | 473 |
| 1978 | —(CH₂)₂SCH₃ | —H | 476 |
| 1979 | —CH₂CH₂OH | —H | 446 |
| 1980 | —CH₂CHF₂ | —H | 466 |
| 1981 | —C₆H₁₃ | —H | 486 |
| 1982 | —CH₂CH₂NHCONH₂ | —H | 488 |

TABLE 208

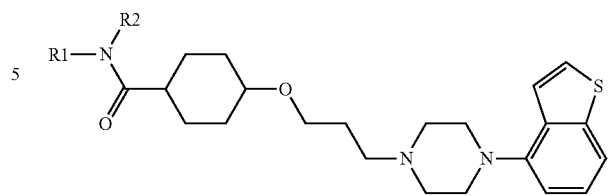

| Example | R1 | R2 | MS(M + 1) |
|---|---|---|---|
| 1983 | 4-hydroxyphenyl (HO-C₆H₄-) | —CH₃ | 508 |
| 1984 | 3-pyridyl | —H | 479 |
| 1985 | 2-pyridyl | —H | 479 |
| 1986 | 4-pyridyl | —H | 479 |
| 1987 | 3-methyl-2-pyridyl | —H | 493 |
| 1988 | 3-methoxy-2-pyridyl | —H | 509 |
| 1989 | 5-methyl-2-pyridyl | —H | 493 |
| 1990 | 2-thiazolyl | —H | 485 |
| 1991 | 1,3,4-thiadiazol-2-yl | —H | 486 |
| 1992 | 5-methyl-1,3,4-thiadiazol-2-yl | —H | 500 |
| 1993 | 1H-tetrazol-5-yl | —H | 470 |

TABLE 208-continued

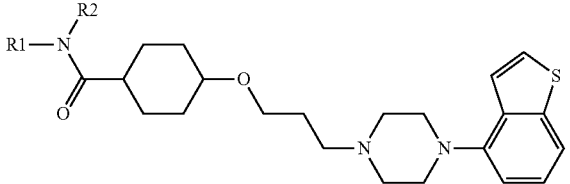

| Example | R1 | R2 | MS(M + 1) |
|---|---|---|---|
| 1994 | (3,5-dimethyl-1-methyl-pyrazol-4-yl) | —H | 496 |
| 1995 | (5-methylthio-1-methyl-3-methyl-1,2,4-triazol-yl) | —H | 529 |

TABLE 209

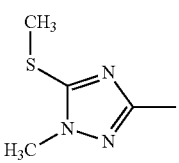

| Example | R1 | R2 | MS(M + 1) |
|---|---|---|---|
| 1996 | (4-methyl-1H-imidazole-5-carboxamide) | —H | 511 |
| 1997 | (3-methylisoxazol-5-yl) | —H | 469 |
| 1998 | (6-methyl-1H-indazol-5-yl) | —H | 518 |
| 1999 | (5-methyl-1H-indol-6-yl) | —H | 517 |
| 2000 | (6-methyl-2-oxoindolin-5-yl) | —H | 533 |

TABLE 209-continued

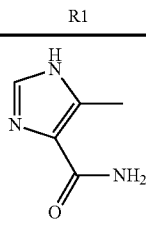

| Example | R1 | R2 | MS(M + 1) |
|---|---|---|---|
| 2001 | (2-methyl-1H-benzimidazol-5-yl) | —H | 518 |
| 2002 | (6-methyl-2-oxo-2,3-dihydrobenzothiazol-5-yl) | —H | 551 |
| 2003 | (3-methylquinolin-6-yl) | —H | 529 |
| 2004 | (6-methylquinolin-3-yl) | —H | 529 |
| 2005 | (2-methyl-6-methylquinolin-yl) | —H | 543 |
| 2006 | (5-methoxy-6-methyl-2-oxo-1,2,3,4-tetrahydroquinolin-yl) | —H | 577 |

TABLE 210

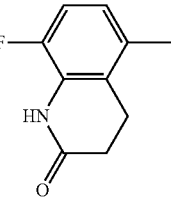

| Example | R1 | R2 | MS(M + 1) |
|---|---|---|---|
| 2007 | (8-fluoro-5-methyl-2-oxo-1,2,3,4-tetrahydroquinolin-yl) | —H | 565 |

TABLE 210-continued

R1-N(R2)-C(O)-[cyclohexyl]-O-(CH2)3-N(piperazine)N-benzothiophene

| Example | R1 | R2 | MS(M + 1) |
|---|---|---|---|
| 2008 | 6,8-dimethyl-2-oxo-1,2,3,4-tetrahydroquinolin-yl | —H | 561 |
| 2009 | H2N-C(=NH)-CH3 | —H | 444 |
| 2010 | 2-ethyl-tetrahydropyran | —C2H5 | 528 |
| 2011 | 2-ethyl-furan | —H | 482 |
| 2012 | 1-methyl-cyclopropyl | —H | 456 |
| 2013 | 1-methyl-cyclopentyl | —H | 484 |
| 2014 | trans-4-hydroxy-4-methyl-cyclohexyl | —H | 500 |
| 2015 | 1-butyl-imidazol-yl | —H | 510 |
| 2016 | (S)-CH(CH3)-C(O)NH2 | —H | 473 |
| 2017 | 4-methyl-3-oxo-isoxazolidin-yl | —H | 487 |
| 2018 | (CH3)2N-C(=NH)-CH3 | —H | 472 |

TABLE 210-continued

| Example | R1 | R2 | MS(M + 1) |
|---|---|---|---|
| 2019 | 2,3-dimethyl-cyclohexyl | —H | 498 |

TABLE 211

R1-N(R2)-C(O)-[cyclohexyl]-O-(CH2)3-N(piperazine)N-benzothiophene

| Example | R1 | R2 | MS(M + 1) |
|---|---|---|---|
| 2020 | 2-ethyl-thiophene | —H | 498 |
| 2021 | 2-methyl-but-1-en-yl | —C2H5 | 484 |
| 2022 | 1-butyl-2-oxo-pyrrolidin-yl | —H | 527 |
| 2023 | 2-ethyl-tetrahydrofuran | —H | 486 |
| 2024 | 2-ethyl-1,3-dioxolan-yl | —H | 488 |
| 2025 | 2-propyl-1,3-dioxolan-yl | —H | 502 |
| 2026 | 2-methyl-5-ethyl-furan | —H | 496 |
| 2027 | 4-propyl-imidazol-yl | —H | 496 |

TABLE 211-continued

| Example | R1 | R2 | MS(M + 1) |
|---|---|---|---|
| 2028 | 1-methyl-2-ethyl-pyrrole | —H | 495 |
| 2029 | 1,3,5-trimethyl-4-ethyl-pyrazole | —H | 524 |
| 2030 | 3-methyl-4-butyl-1H-pyrazole | —H | 524 |
| 2031 | 2,5-dimethyl-3-ethyl-furan | —H | 510 |
| 2032 | 1,5-dimethyl-3-ethyl-pyrazole | —H | 510 |

TABLE 212

| Example | R1 | R2 | MS(M + 1) |
|---|---|---|---|
| 2033 | 3-methyl-2-ethyl-thiophene | —H | 512 |
| 2034 | 3-ethyl-thiazole | —H | 498 |
| 2035 | 3-ethyl-furan | —H | 482 |
| 2036 | 2-ethyl-thiazole | —H | 499 |
| 2037 | 2-propyl-thiophene | —H | 512 |
| 2038 | 2-methylene-butane | —H | 456 |
| 2039 | 4-ethyl-tetrahydropyran | —H | 500 |
| 2040 | 1,5-dimethyl-pyrazole | —H | 482 |
| 2041 | 1-propyl-pyrazole | —H | 496 |
| 2042 | 4-methyl-tetrahydropyran | —H | 486 |
| 2043 | 1-methyl-2-ethyl-pyrrole | —CH3 | 510 |
| 2044 | 1,5-dimethyl-3-ethyl-pyrazole | —CH3 | 524 |
| 2045 | 2,5-dimethyl-4-ethyl-oxazole | —CH3 | 525 |

TABLE 212-continued

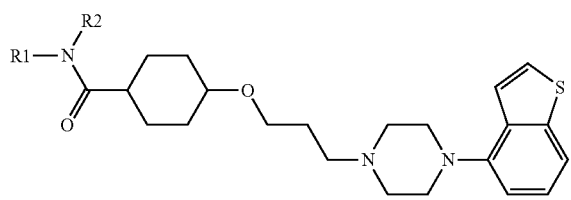

| Example | R1 | R2 | MS(M + 1) |
|---|---|---|---|
| 2046 | (3-methyl-1-methyl-5-ethyl-pyrazole) | —H | 510 |

TABLE 213

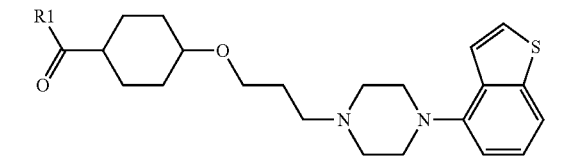

| Example | R1 | MS(M + 1) |
|---|---|---|
| 2047 | N-methylpyrrolidine | 458 |
| 2048 | 2-(hydroxymethyl)-1-methylpyrrolidine | 486 |
| 2049 | 1-methylpyrrolidine-2-carboxamide | 499 |
| 2050 | 3-hydroxy-1-methylpyrrolidine | 472 |
| 2051 | N-(1-methylpyrrolidin-3-yl)acetamide | 513 |
| 2052 | 1,2,5-trimethyl-2,5-dihydro-1H-pyrrole | 482 |
| 2053 | 3-methylthiazolidine | 474 |

TABLE 213-continued

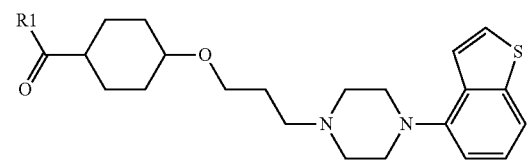

| Example | R1 | MS(M + 1) |
|---|---|---|
| 2054 | 4-methylthiomorpholine | 488 |
| 2055 | 4-methylmorpholine | 472 |
| 2056 | 2,6-dimethyl-4-methylmorpholine | 500 |
| 2057 | 3,5-dimethyl-1-methylpiperidine | 498 |
| 2058 | 1-methylpiperidine | 470 |

TABLE 214

(same core structure)

| Example | R1 | MS(M + 1) |
|---|---|---|
| 2059 | 4-hydroxy-1-methylpiperidine | 486 |
| 2060 | 1,2-dimethylpiperidine | 484 |
| 2061 | 1,3-dimethylpiperidine | 484 |

TABLE 214-continued

| Example | R1 | MS(M + 1) |
|---|---|---|
| 2062 | 2-ethyl-1-methylpiperidine | 498 |
| 2063 | 3-hydroxy-1-methylpiperidine | 486 |
| 2064 | 1-methylpiperidine-4-carboxamide | 513 |
| 2065 | (1-methylpiperidin-2-yl)methanol | 500 |
| 2066 | (1-methylpiperidin-4-yl)methanol | 500 |
| 2067 | N-(1-methylpiperidin-4-yl)acetamide | 527 |
| 2068 | 2-(1-methylpiperidin-2-yl)ethanol | 514 |
| 2069 | 8-methyl-1,4-dioxa-8-azaspiro[4.5]decane | 528 |
| 2070 | 1-acetyl-4-methylpiperazine | 513 |
| 2071 | 4-methylpiperazin-2-one | 485 |

TABLE 215

| Example | R1 | MS(M + 1) |
|---|---|---|
| 2072 | 8-methyl-1,4-dioxa-8-azaspiro[4.5]decane | 523 |
| 2073 | 4-methylthiomorpholine | 483 |
| 2074 | 1,2,5-trimethyl-2,5-dihydro-1H-pyrrole | 477 |
| 2075 | 3-methylthiazolidine | 469 |
| 2076 | 4-methylmorpholine | 467 |
| 2077 | 4-methoxy-1-methylpiperidine | 495 |
| 2078 | 4-methyl-1-phenylpiperazin-2-one | 556 |
| 2079 | 2-methyl-1,2,3,4-tetrahydroisoquinoline | 513 |
| 2080 | 2-methyl-2,3,4,9-tetrahydro-1H-β-carboline | 552 |
| 2081 | 1-methylpyrrolidine-2-carboxamide | 494 |

Table 216
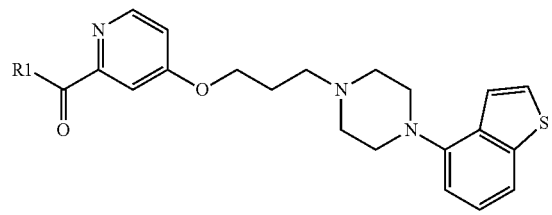
| Example | R1 | MS(M + 1) |
|---|---|---|
| 2082 | 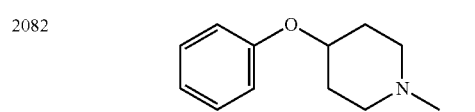 | 557 |
| 2083 | 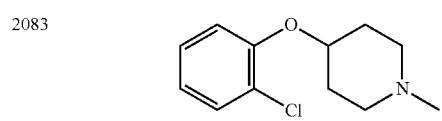 | 591 |
| 2084 | 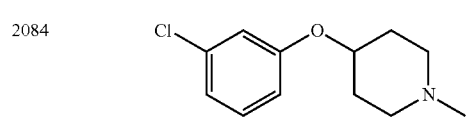 | 591 |
| 2085 | 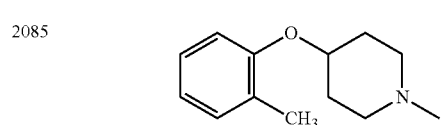 | 571 |
| 2086 | 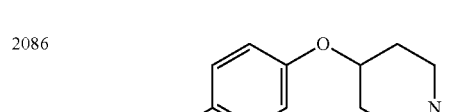 | 571 |
| 2087 | 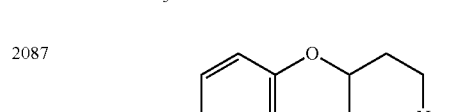 | 575 |
| 2088 | 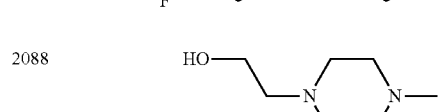 | 510 |
| 2089 | 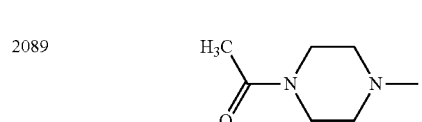 | 508 |
| 2090 | 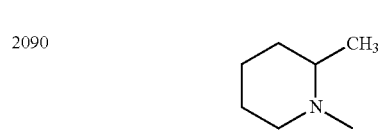 | 479 |
| 2091 |  | 479 |
TABLE 217
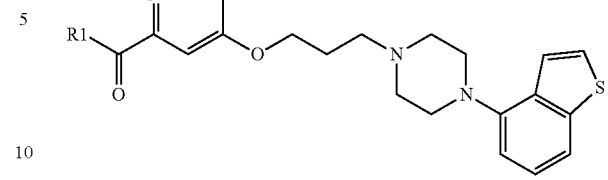
| Example | R1 | MS(M + 1) |
|---|---|---|
| 2092 | 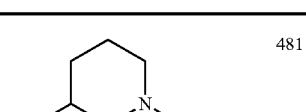 | 481 |
| 2093 | 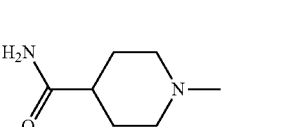 | 508 |
| 2094 | 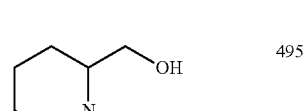 | 495 |
| 2095 | 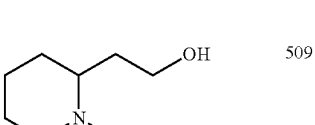 | 509 |
| 2096 | 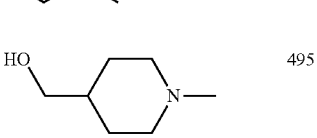 | 495 |
| 2097 | 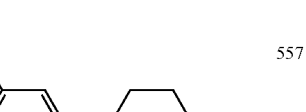 | 557 |
| 2098 | 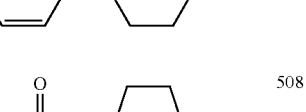 | 508 |
| 2099 | 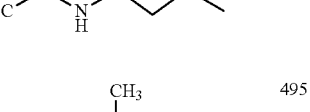 | 495 |
| 2100 | 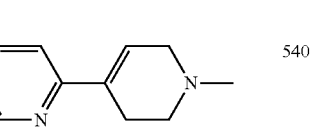 | 540 |

397
TABLE 218
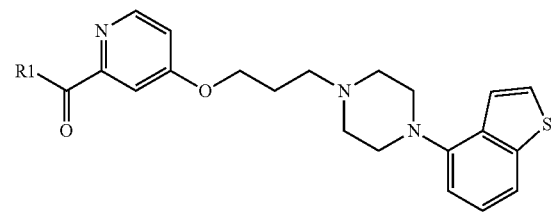
| Example | R1 | MS(M + 1) |
|---|---|---|
| 2101 | 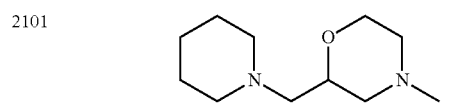 | 564 |
| 2102 | 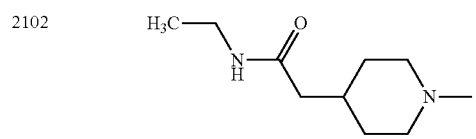 | 550 |
| 2103 | 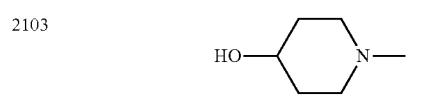 | 481 |
| 2104 | 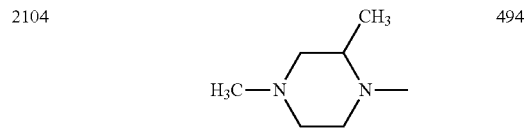 | 494 |
| 2105 | 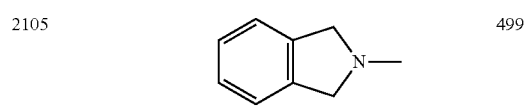 | 499 |
| 2106 | 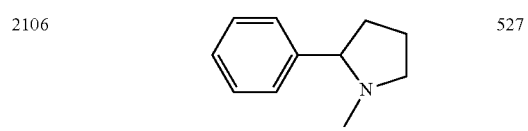 | 527 |
| 2107 | 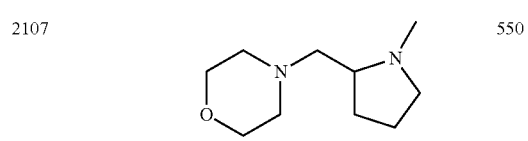 | 550 |
| 2108 | 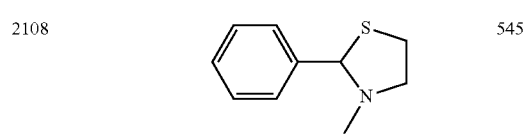 | 545 |
| 2109 | 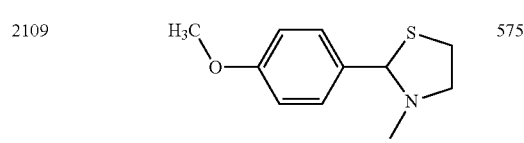 | 575 |
398
TABLE 219
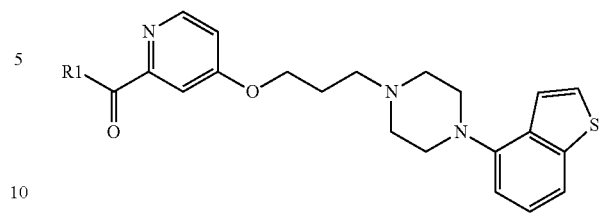
| Example | R1 | MS(M + 1) |
|---|---|---|
| 2110 | 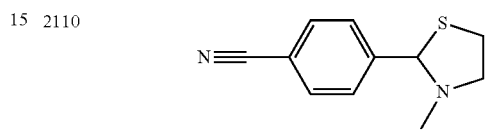 | 570 |
| 2111 | 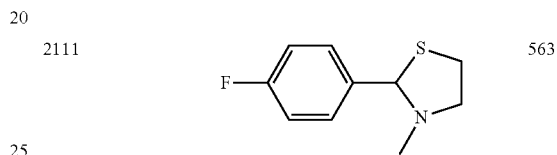 | 563 |
| 2112 | 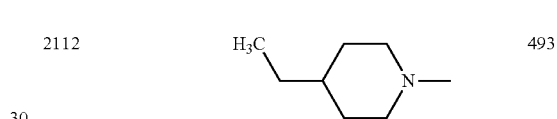 | 493 |
| 2113 | 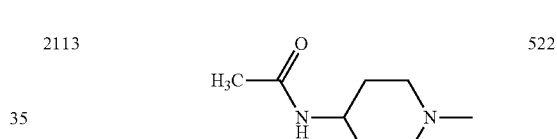 | 522 |
| 2114 | 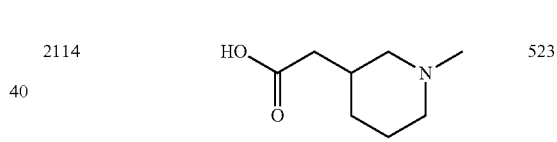 | 523 |
| 2115 | 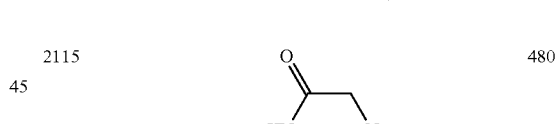 | 480 |
| 2116 | 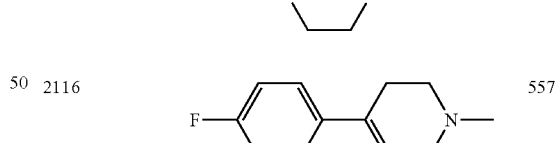 | 557 |
| 2117 | 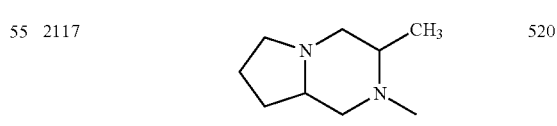 | 520 |
| 2118 | 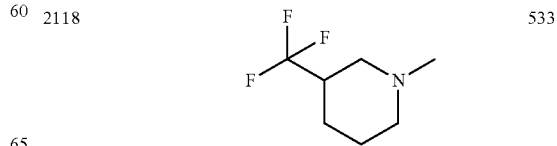 | 533 |

TABLE 220

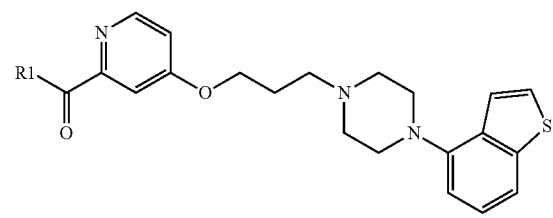

| Example | R1 | MS(M + 1) |
|---|---|---|
| 2119 | (furan-2-carbonyl)-4-methylpiperazine | 560 |
| 2120 | 4-methyl-1,4-oxazepane | 481 |
| 2121 | 2-phenyl-4-methylmorpholine | 543 |
| 2122 | 2-(1-methylpiperidin-4-yl)pyridine | 542 |
| 2123 | 2-(1-methylpiperidin-3-yl)pyridine | 542 |

TABLE 221

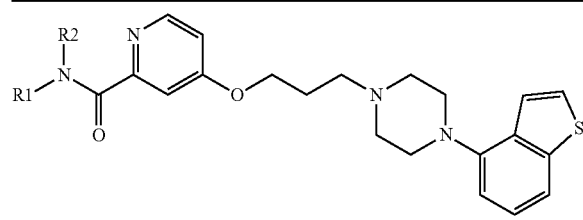

| Example | R1 | R2 | MS(M + 1) |
|---|---|---|---|
| 2124 | —CH₃ | -cyclo-C₆H₁₁ | 493 |
| 2125 | —H | -cyclo-C₆H₁₁ | 479 |
| 2126 | —CH₂CH₂OH | —CH₂CH₂OH | 485 |
| 2127 | —CH₃ | —CH₂CH₂N(CH₃)₂ | 482 |
| 2128 | —H | —C₄H₉ | 453 |
| 2129 | —H | -cyclo-C₃H₅ | 437 |
| 2130 | —H | —CH₂C₆H₅ | 487 |
| 2131 | —CH₃ | —CH₂C₆H₅ | 501 |
| 2132 | —C₂H₅ | —CH(CH₃)₂ | 467 |
| 2133 | —H | —CH₃ | 411 |
| 2134 | —H | —C₂H₅ | 425 |
| 2135 | —H | —C₃H₇ | 439 |
| 2136 | —H | —CH₂CH(CH₈)₂ | 453 |
| 2137 | —H | —CH₂CH₂OCH₃ | 455 |
| 2138 | —H | —CH₂CH₂OC₂H₅ | 469 |
| 2139 | —H | —(CH₂)₂OC₆H₅ | 517 |
| 2140 | —H | -cyclo-C₅H₆ | 465 |

TABLE 221-continued

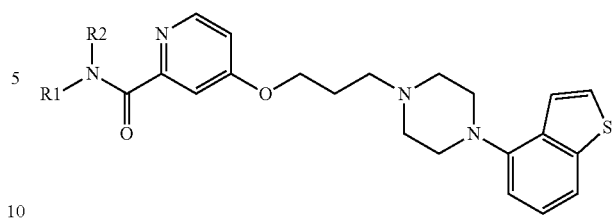

| Example | R1 | R2 | MS(M + 1) |
|---|---|---|---|
| 2141 | —H | —CH₂-cyclo-C₆H₁₁ | 493 |
| 2142 | —H | —CH(CH₃)C₅H₅ | 501 |
| 2143 | —H | —CH₂CONH₂ | 454 |

TABLE 222

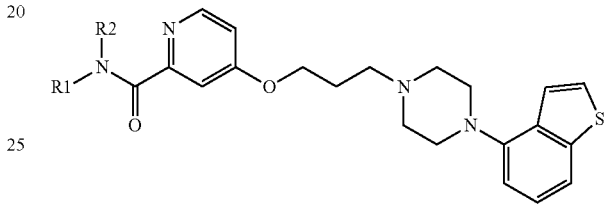

| Example | R1 | R2 | MS(M + 1) |
|---|---|---|---|
| 2144 | —H | —CH(CH₃)₂ | 439 |
| 2145 | —C₂H₅ | —C₂H₅ | 453 |
| 2146 | —H | —(CH₂)₅OH | 483 |
| 2147 | —H | —CH₂CCH | 435 |
| 2148 | —CH₃ | —CH(CH₃)₂ | 453 |
| 2149 | —H | —CH₂C(CH₃)₃ | 467 |
| 2150 | —H | —CH₂CH₂N(CH₃)₂ | 468 |
| 2151 | —H | —CH(CONH₂)₂ | 497 |
| 2152 | —CH₃ | —CH₂-cyclo-C₃H₅ | 465 |
| 2153 | —CH₃ | —(CH₂)₂N(C₂H₅)₂ | 510 |
| 2154 | —H | —CH₂CF₃ | 479 |
| 2155 | —H | —NHCH₂CF₃ | 494 |
| 2156 | —CH₃ | —CH₃ | 425 |
| 2157 | —H | —CH₂CH(OCH₃)₂ | 485 |
| 2158 | —H | —(CH₂)₃OCH(CH₃)₂ | 497 |
| 2159 | —H | —CH(C₂H₅)₂ | 467 |
| 2160 | —H | —CH₂CN | 436 |
| 2161 | —H | —(CH₂)₂OCH(CH₃)₂ | 483 |
| 2162 | —H | —CH(C₂H₅)CH₂OCH₃ | 483 |
| 2163 | —H | —CH₂CH₂F | 443 |
| 2164 | —H | —CH₂CONHCH₃ | 468 |
| 2165 | —H | —(CH₂)₂SCH₃ | 471 |
| 2166 | —H | —CH₂CHF₂ | 461 |
| 2167 | —CH₃ | —(CH₂)₂O(CH₂)₂NHCH₃ | 512 |

TABLE 223

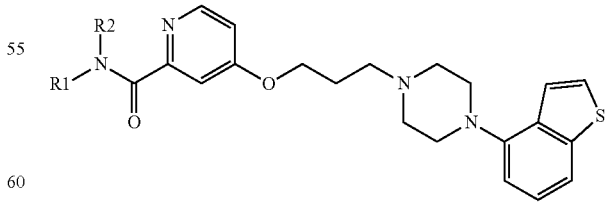

| Example | R1 | R2 | MS(M + 1) |
|---|---|---|---|
| 2168 | —CH₃ | 1-methyl-4-methylpiperidin-4-yl | 508 |

401

TABLE 223-continued

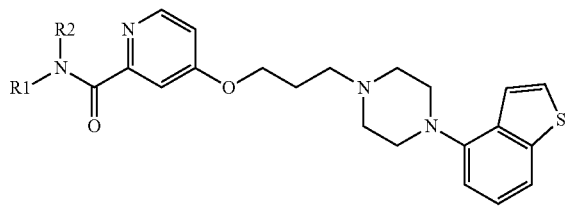

| Example | R1 | R2 | MS(M + 1) |
|---|---|---|---|
| 2169 | —H | phenyl-C(CH3)3 | 515 |
| 2170 | —H | 2-Cl,1-ethyl-phenyl | 521 |
| 2171 | —H | 3-Cl,1-ethyl-phenyl | 521 |
| 2172 | —H | 4-Cl,1-ethyl-phenyl | 521 |
| 2173 | —H | 2-ethyl-pyridine | 488 |
| 2174 | —H | 3-ethyl-pyridine | 488 |
| 2175 | —H | 4-ethyl-pyridine | 488 |
| 2176 | —H | 2-ethyl-furan | 477 |
| 2177 | —CH3 | 4-methyl-piperidine-C(O)CH3 | 536 |

402

TABLE 224

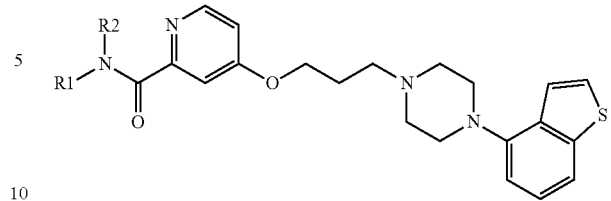

| Example | R1 | R2 | MS (M + 1) |
|---|---|---|---|
| 2178 | —CH3 | 2-OCH3,1-ethyl-phenyl | 531 |
| 2179 | —H | 1-methyl-cyclopropyl | 451 |
| 2180 | —H | 4-OCH3,1-ethyl-phenyl | 517 |
| 2181 | —H | 3-OCH3,1-ethyl-phenyl | 517 |
| 2182 | —H | 3,4-diCl,1-ethyl-phenyl | 555 |
| 2183 | —H | 4-OCF3,1-ethyl-phenyl | 571 |
| 2184 | —H | benzo[1,3]dioxole-ethyl | 531 |
| 2185 | —H | 2-methyl,1-SO2NH2-phenyl | 552 |
| 2186 | —H | trans-4-methyl-cyclohexanol | 495 |
| 2187 | —H | 4-F,1-ethyl-phenyl | 505 |

TABLE 225

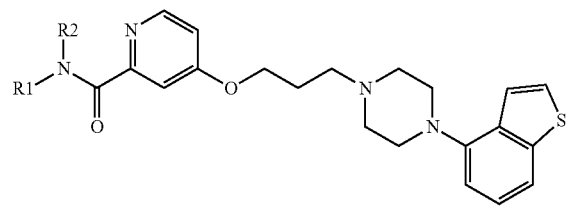

| Example | R1 | R2 | MS(M + 1) |
|---|---|---|---|
| 2188 | —H | 3,4-dimethoxyphenethyl | 547 |
| 2189 | —H | 2-methylphenethyl | 501 |
| 2190 | —H | 4-(1H-imidazol-1-yl)butyl | 505 |
| 2191 | —H | 1-carbamoyl-2,3-dimethylbutyl | 496 |
| 2192 | —H | 1-carbamoyl-2-phenylethyl | 544 |
| 2193 | —H | (3-methyl-2-oxotetrahydrofuran-3-yl) | 481 |
| 2194 | —H | 1-carbamoyl-2-methylpropyl | 468 |
| 2195 | —H | 2-ethyl-6-methoxyphenyl | 517 |
| 2196 | —H | 3-(piperidin-1-yl)propyl | 508 |

TABLE 226

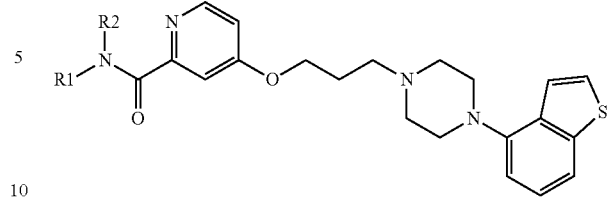

| Example | R1 | R2 | MS(M + 1) |
|---|---|---|---|
| 2197 | —H | (1-methylpyrrolidin-2-yl)methyl | 508 |
| 2198 | —H | 3-(pyrrolidin-1-yl)propyl | 494 |
| 2199 | —H | 3-morpholinopropyl | 510 |
| 2200 | —H | 1-amidinoethyl | 453 |
| 2201 | —H | N,N-dimethylacetamidinyl | 467 |
| 2202 | —H | 2-(4-oxo-4H-chromen-2-yl)ethyl | 555 |
| 2203 | —H | 2-(naphthalen-2-yl)ethyl | 537 |
| 2204 | —H | 2-(6-methyl-1-oxo-2,3-dihydro-1H-inden-5-yl)ethyl | 527 |
| 2205 | —H | 2-(1H-benzimidazol-2-yl)ethyl | 527 |
| 2206 | —H | 2-(thiophen-2-yl)ethyl | 493 |

405
TABLE 227
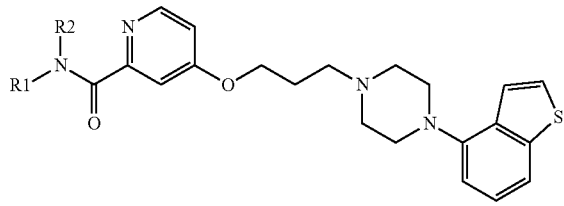
| Example | R1 | R2 | MS(M + 1) |
|---|---|---|---|
| 2207 | —H |  | 556 |
| 2208 | —H | 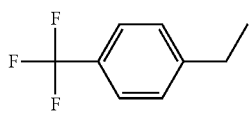 | 555 |
| 2209 | —H | 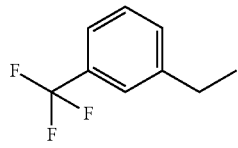 | 555 |
| 2210 | —C₂H₅ | 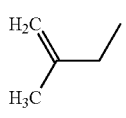 | 479 |
| 2211 | —H | 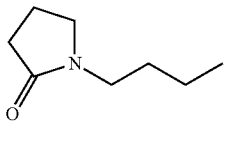 | 522 |
| 2212 | —H | 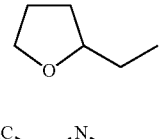 | 481 |
| 2213 | —H | 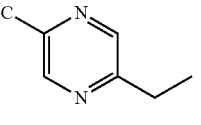 | 503 |
| 2214 | —H | 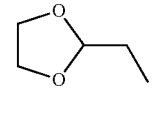 | 483 |
| 2215 | —H | 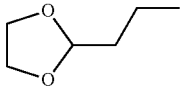 | 497 |
406
TABLE 228
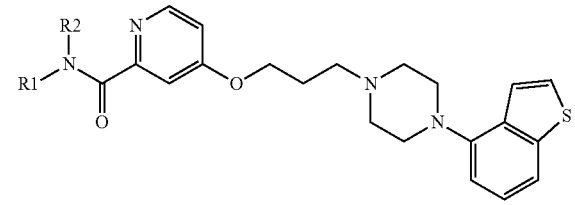
| Example | R1 | R2 | MS(M + 1) |
|---|---|---|---|
| 2216 | —H | 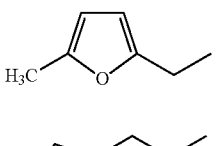 | 491 |
| 2217 | —H | 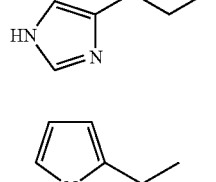 | 491 |
| 2218 | —H | 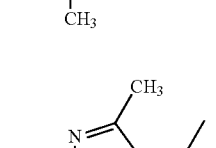 | 490 |
| 2219 | —H | 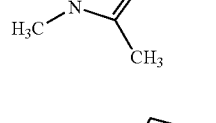 | 519 |
| 2220 | —H | 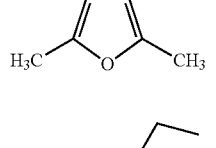 | 505 |
| 2221 | —H | 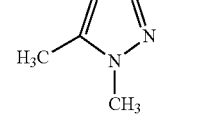 | 505 |
| 2222 | —H | 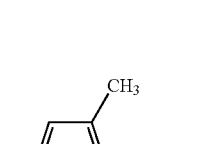 | 507 |
| 2223 | —H | 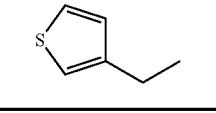 | 493 |

TABLE 229

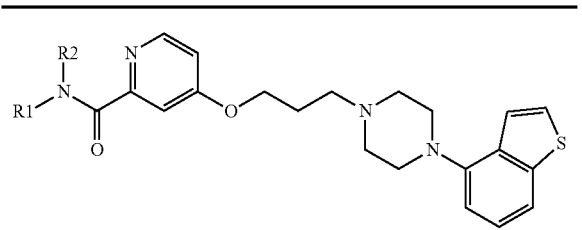

| Example | R1 | R2 | MS(M + 1) |
|---|---|---|---|
| 2224 | —H | 3-ethylfuran | 477 |
| 2225 | —H | 2-ethylthiazole | 494 |
| 2226 | —H | 5-ethyl-2,3-dihydrobenzofuran | 529 |
| 2227 | —H | 2-methylbut-1-ene | 451 |
| 2228 | —H | 4-ethyltetrahydropyran | 495 |
| 2229 | —H | 3-fluorophenethyl | 505 |
| 2230 | —H | 1-(2-fluorophenyl)ethyl | 519 |
| 2231 | —H | 1-(3-fluorophenyl)ethyl | 519 |
| 2232 | —H | 1-(4-fluorophenyl)ethyl | 519 |

TABLE 230

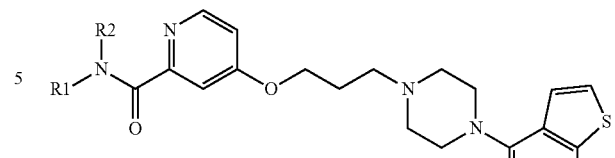

| Example | R1 | R2 | MS(M + 1) |
|---|---|---|---|
| 2233 | —H | 1-(3,5-difluorophenyl)ethyl | 537 |
| 2234 | —H | 2-ethylbenzothiophene | 543 |
| 2235 | —H | 2-methylindane | 513 |
| 2236 | —H | 1-methylindane | 513 |
| 2237 | —H | 1-(pyridin-4-yl)ethyl | 502 |
| 2238 | —H | 2-methylquinuclidine | 506 |

TABLE 231

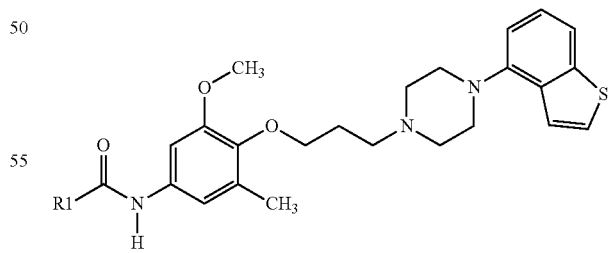

| Example | R1 | MS(M + 1) |
|---|---|---|
| 2239 | -2-PYRIDYL | 517 |
| 2240 | -3-PYRIDYL | 517 |
| 2241 | -4-PYRIDYL | 517 |
| 2242 | -2-FURYL | 506 |
| 2243 | -2-THIENYL | 522 |
| 2244 | -3-FURYL | 506 |
| 2245 | -3-THIENYL | 522 |

TABLE 231-continued

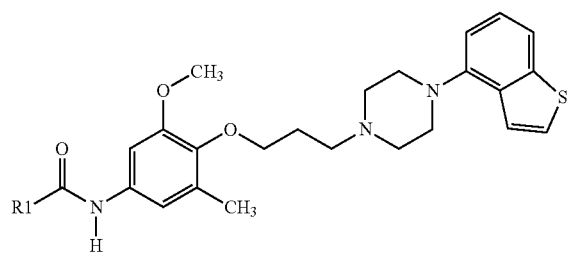

| Example | R1 | MS(M + 1) |
|---|---|---|
| 2246 | —CH₃ | 454 |
| 2247 | —C₂H₅ | 468 |
| 2248 | —C₃H₇ | 482 |
| 2249 | —CH(CH₃)₂ | 482 |
| 2250 | -cyclo-C₃H₅ | 480 |
| 2251 | -cyclo-C₅H₉ | 508 |
| 2252 | -cyclo-C₆H₁₁ | 522 |
| 2253 | —CH₂-cyclo-C₃H₅ | 494 |
| 2254 | —CH₂-cyclo-C₆H₁₁ | 536 |
| 2255 | —CH₂OCH₃ | 484 |
| 2256 | —CH₂N(CH₃)₂ | 497 |
| 2257 | —(CH₂)₃N(CH₃)₂ | 525 |
| 2258 | —(CH₂)₂N(C₂H₅)₂ | 539 |
| 2259 | —CH₂NHCHO | 497 |
| 2260 | —CH₂N(CH₂CH₂OH)₂ | 557 |
| 2261 | —CH₂N(CH₃)CO₂C(CH₃)₃ | 583 |
| 2262 | —(CH₂)₃NHCO₂C(CH₃)₃ | 597 |
| 2263 | —CH₂NHCH₃ | 483 |
| 2264 | —(CH₂)₃NH₂ | 497 |
| 2265 | —CH₂NHCOCH₃ | 511 |

TABLE 232

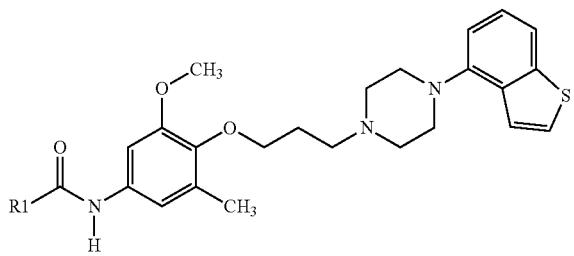

| Example | R1 | MS(M + 1) |
|---|---|---|
| 2266 | (3-methyl-2-methoxypyridin-yl) | 547 |
| 2267 | (6-chloro-3-methylpyridin-yl) | 551 |
| 2268 | (2,3-dichloro-5-methylpyridin-yl) | 585 |
| 2269 | (3-methyl-2-methylthiopyridin-yl) | 563 |

TABLE 232-continued

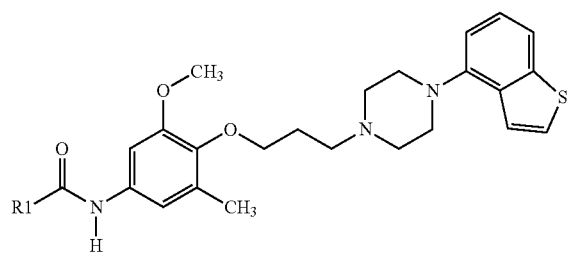

| Example | R1 | MS(M + 1) |
|---|---|---|
| 2270 | (2-chloro-4-methylpyridin-yl) | 551 |
| 2271 | (3-methyl-2-hydroxypyridin-yl) | 533 |
| 2272 | (3-chloro-5-methyl-2-hydroxypyridin-yl) | 567 |
| 2273 | (2-chloro-3-methylpyridin-yl) | 551 |
| 2274 | (5-methyl-1H-pyrrol-2-yl) | 505 |

TABLE 233

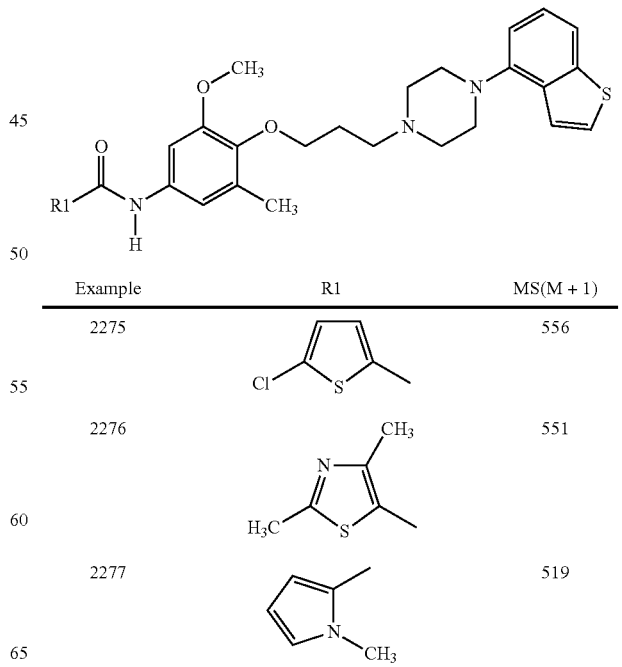

| Example | R1 | MS(M + 1) |
|---|---|---|
| 2275 | (5-chloro-2-methylthiophen-yl) | 556 |
| 2276 | (2,4-dimethylthiazol-5-yl) | 551 |
| 2277 | (1,5-dimethyl-1H-pyrrol-2-yl) | 519 |

TABLE 233-continued

Structure: R1-C(=O)-NH-phenyl(OCH3, CH3)-O-(CH2)3-piperazine-benzothiophene

| Example | R1 | MS(M + 1) |
|---------|----|-----------|
| 2278 | 3,4,5-trimethylisoxazol-yl | 535 |
| 2279 | 3-methylpyrazin-2-yl | 518 |
| 2280 | 3,6-dimethylpyrazin-2-yl | 532 |
| 2281 | 4-methylthiazol-5-yl | 523 |
| 2282 | 2,5-dimethylfuran-3-yl | 534 |
| 2283 | 2,5-dichloro-4-methylthiophen-3-yl | 590 |

TABLE 234

Structure: R1-C(=O)-NH-phenyl(OCH3, CH3)-O-(CH2)3-piperazine-benzothiophene

| Example | R1 | MS(M + 1) |
|---------|----|-----------|
| 2284 | 5-chloro-4-methylthiophen-2-yl | 556 |

TABLE 234-continued

| Example | R1 | MS(M + 1) |
|---------|----|-----------|
| 2285 | 2-methyl-4-methyl-5-trifluoromethyloxazol-yl | 589 |
| 2286 | 2-methyl-4-methyloxazol-5-yl | 521 |
| 2287 | 5-methylthiazol-4-yl | 523 |
| 2288 | 2,4,5-trimethyloxazol-yl | 535 |
| 2289 | 3-methyl-5-isopropylisoxazol-yl | 549 |
| 2290 | 1,5-dimethylimidazol-4-yl | 520 |
| 2291 | 1,4-dimethylimidazol-5-yl | 520 |

413
TABLE 235
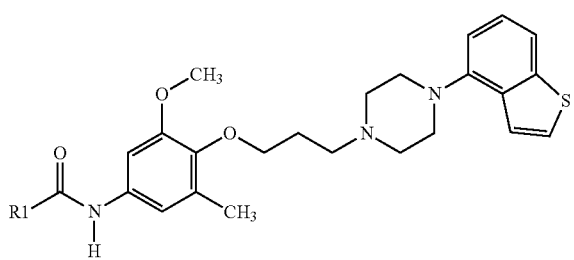
| Example | R1 | MS(M + 1) |
|---|---|---|
| 2292 | 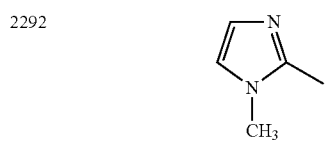 | 520 |
| 2293 | 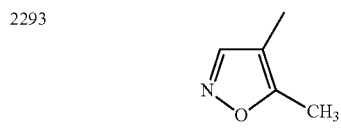 | 521 |
| 2294 | 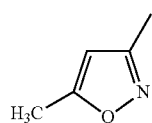 | 521 |
| 2295 | 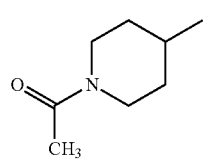 | 565 |
| 2296 | 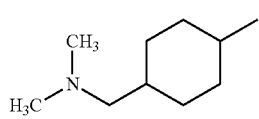 | 579 |
| 2297 | 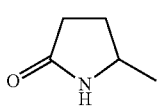 | 523 |
| 2298 | 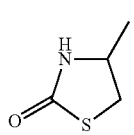 | 541 |
| 2299 | 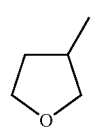 | 510 |
| 2300 | 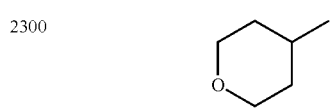 | 524 |
414
TABLE 236
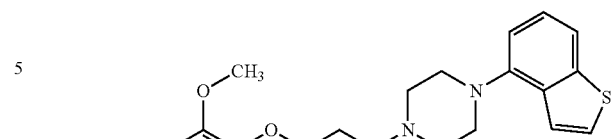
| Example | R1 | MS(M + 1) |
|---|---|---|
| 2301 | 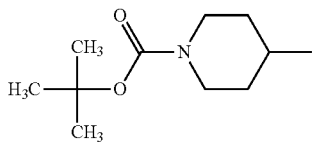 | 623 |
| 2302 | 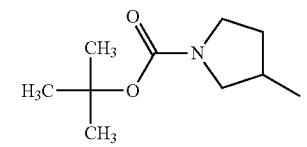 | 609 |
| 2303 | 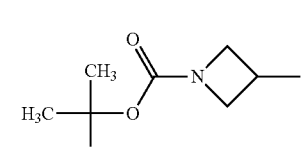 | 595 |
| 2304 | 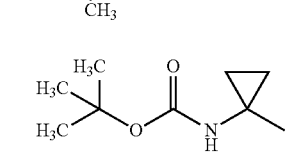 | 595 |
| 2305 | 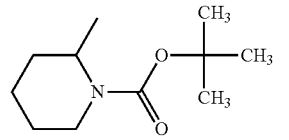 | 623 |
| 2306 | 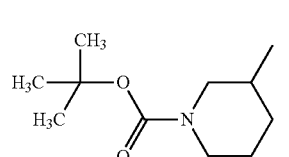 | 623 |
| 2307 | 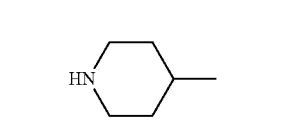 | 523 |
| 2308 | 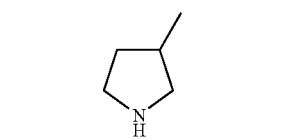 | 509 |
| 2309 | 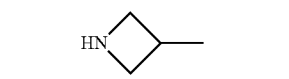 | 495 |

TABLE 237

| Example | R1 | MS(M + 1) |
|---|---|---|
| 2310 | 1-aminocyclopropyl | 495 |
| 2311 | 2-methylpiperidinyl | 523 |
| 2312 | 3-methylpiperidinyl | 523 |

TABLE 238

| Example | R1 | MS(M + 1) |
|---|---|---|
| 2313 | 3-propylpyridinyl | 545 |
| 2314 | 2-ethylpyridinyl | 531 |
| 2315 | 3-ethylpyridinyl | 531 |
| 2316 | 4-ethylpyridinyl | 531 |
| 2317 | 2-ethylthienyl | 536 |

TABLE 238-continued

| Example | R1 | MS(M + 1) |
|---|---|---|
| 2318 | 3-ethylthienyl | 536 |
| 2319 | ethylcyclopentyl | 522 |
| 2320 | 1-propylpiperidinyl | 551 |
| 2321 | 3-propenylpyridinyl | 543 |

TABLE 239

| Example | R1 | MS(M + 1) |
|---|---|---|
| 2322 | 4-propenylpyridinyl | 543 |
| 2323 | 4-(ethylthio)pyridinyl | 563 |
| 2324 | 2-propenylpyridinyl | 543 |
| 2325 | (2-hydroxybutyl)trimethylammonium | 556 |

TABLE 239-continued
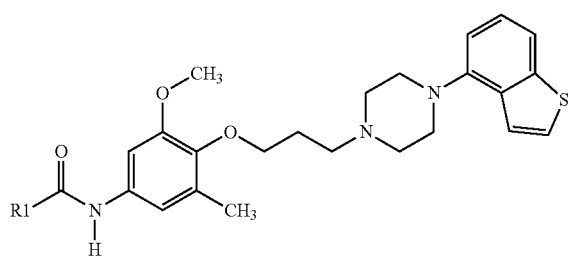
| Example | R1 | MS(M + 1) |
|---|---|---|
| 2326 | 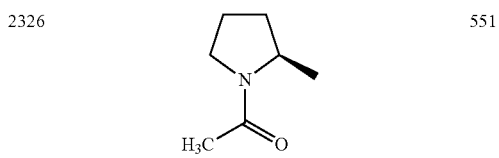 | 551 |
| 2327 | 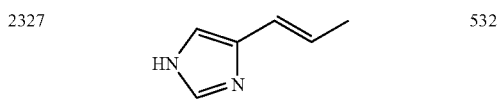 | 532 |
| 2328 | 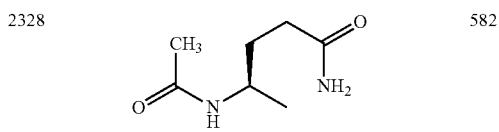 | 582 |
| 2329 | 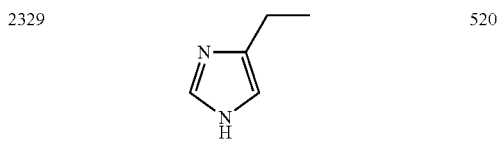 | 520 |
| 2330 | 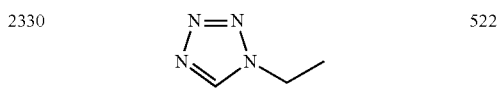 | 522 |
TABLE 240
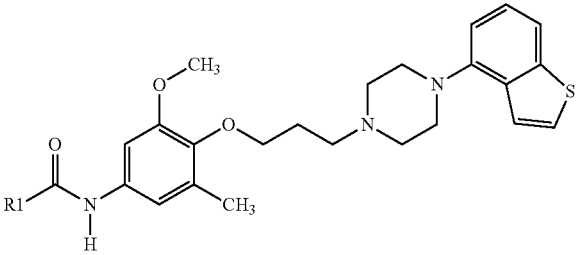
| Example | R1 | MS(M + 1) |
|---|---|---|
| 2331 | 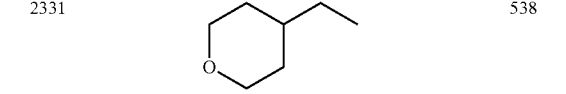 | 538 |
| 2332 | 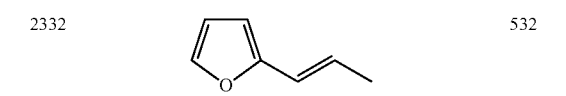 | 532 |
TABLE 240-continued
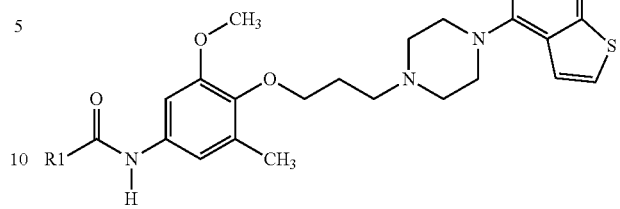
| Example | R1 | MS(M + 1) |
|---|---|---|
| 2333 | 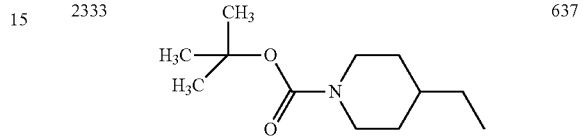 | 637 |
| 2334 | 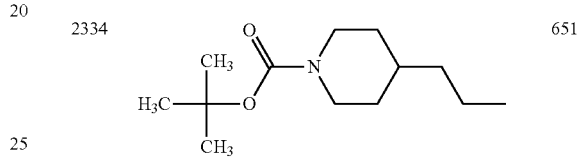 | 651 |
| 2335 | 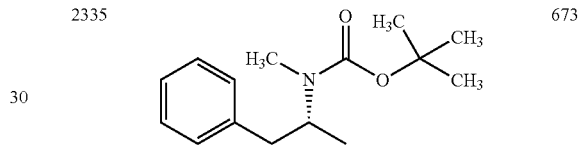 | 673 |
| 2336 | 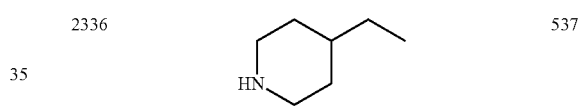 | 537 |
| 2337 | 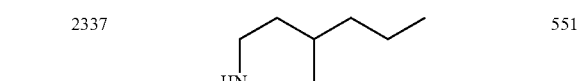 | 551 |
| 2338 | 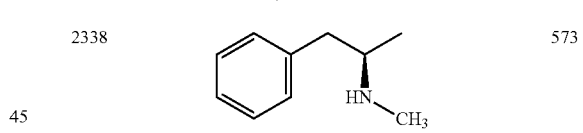 | 573 |
TABLE 241
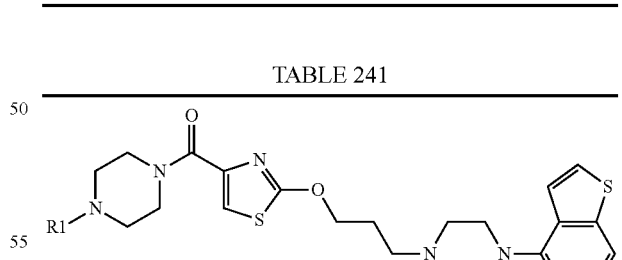
| Example | R1 | MS(M + 1) |
|---|---|---|
| 2339 | -2-PYRIDYL | 549 |
| 2340 | —C$_4$H$_9$ | 528 |
| 2341 | —CH(CH$_3$)$_2$ | 514 |
| 2342 | —CH$_2$CH$_2$N(CH$_3$)$_2$ | 543 |
| 2343 | -4-PYRIDYL | 549 |
| 2344 | —C$_6$H$_5$ | 548 |
| 2345 | —C$_3$H$_7$ | 514 |
| 2346 | —CH$_3$ | 486 |
| 2347 | -3-PYRIDYL | 549 |

TABLE 241-continued

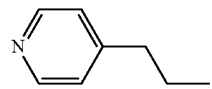

| Example | R1 | MS(M + 1) |
|---|---|---|
| 2348 | —C₅H₁₃ | 556 |
| 2349 | —C₂H₅ | 500 |
| 2350 | —CH₂CH₂OH | 516 |
| 2351 | —COCH₃ | 514 |
| 2352 | -cyclo-C₅H₁₁ | 554 |
| 2353 | —SO₂C₂H₅ | 564 |

TABLE 242

| Example | R1 | MS(M + 1) |
|---|---|---|
| 2354 | 2-ethylpyridine | 563 |
| 2355 | 3-ethylpyridine | 563 |
| 2356 | 4-ethylpyridine | 563 |
| 2357 | 2-methylpyrimidine | 550 |
| 2358 | 1-methyl-4-methylpiperidine | 569 |
| 2359 | ethyl-benzodioxepine | 634 |
| 2360 | methylpyrazine | 550 |
| 2361 | 1-propylimidazole | 566 |

TABLE 242-continued

| Example | R1 | MS(M + 1) |
|---|---|---|
| 2362 | 4-propylpyridine | 577 |

TABLE 243

| Example | R1 | MS(M + 1) |
|---|---|---|
| 2363 | 2-propylpyridine | 577 |
| 2364 | 1-propanoylpyrrolidine | 583 |
| 2365 | 2-methylthiazole | 555 |
| 2366 | 1-cyclopropylethanone | 540 |

| Example | R1 | MS(M + 1) |
|---|---|---|
| 2367 | —OCH₃ | 501 |
| 2368 | -cyclo-C₆H₁₁ | 553 |
| 2369 | —C₆H₅ | 547 |
| 2370 | —OCH₂C₆H₅ | 577 |
| 2371 | —OC₆H₅ | 563 |
| 2372 | —OH | 487 |
| 2373 | —CONH₂ | 514 |
| 2374 | —CH₂OH | 501 |

-continued
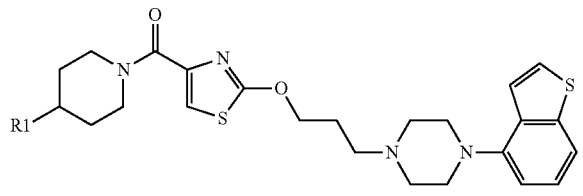
| Example | R1 | MS(M + 1) |
|---|---|---|
| 2375 | —C₂H₅ | 499 |
| 2376 | —NHCOCH₃ | 528 |
| 2377 | —COC₆H₅ | 575 |
| 2378 | -2-PYRIDYL | 548 |
TABLE 245
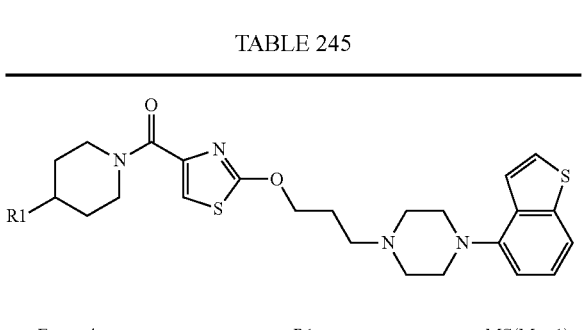
| Example | R1 | MS(M + 1) |
|---|---|---|
| 2379 | 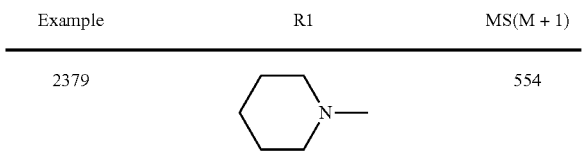 | 554 |
| 2380 | 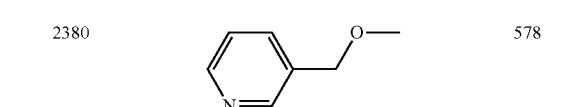 | 578 |
| 2381 | 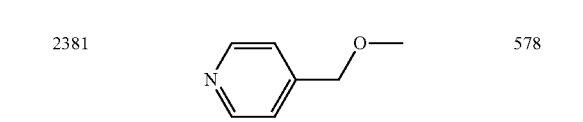 | 578 |
| 2382 | 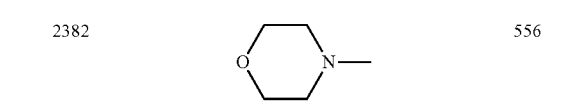 | 556 |
| 2383 | | 584 |
| 2384 | | 564 |
TABLE 246
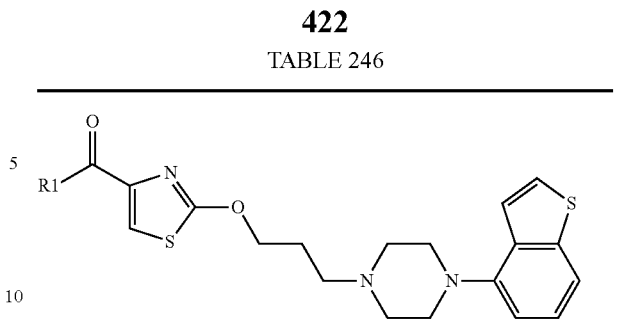
| Example | R1 | MS(M + 1) |
|---|---|---|
| 2385 | | 485 |
| 2386 | | 502 |
| 2387 | | 525 |
| 2388 | | 489 |
| 2389 | | 475 |
| 2390 | | 511 |
| 2391 | | 539 |
| 2392 | | 547 |
| 2393 | | 576 |

TABLE 247
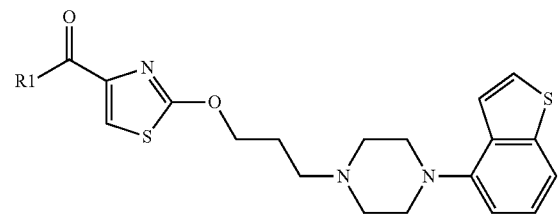
| Example | R1 | MS(M + 1) |
|---|---|---|
| 2394 | 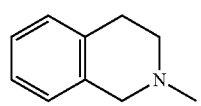 | 519 |
| 2395 | 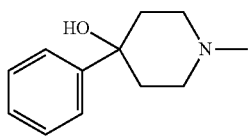 | 563 |
| 2396 | 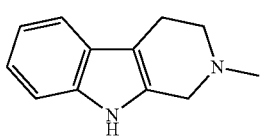 | 558 |
| 2397 | 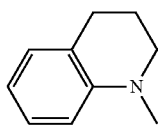 | 519 |
| 2398 | 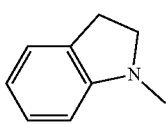 | 505 |
| 2399 | 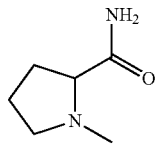 | 500 |
| 2400 | 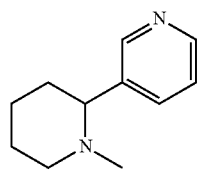 | 548 |
| 2401 | 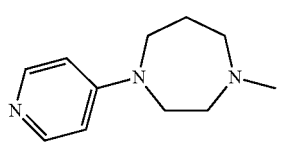 | 563 |
| 2402 | 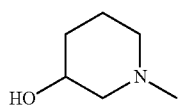 | 487 |
TABLE 248
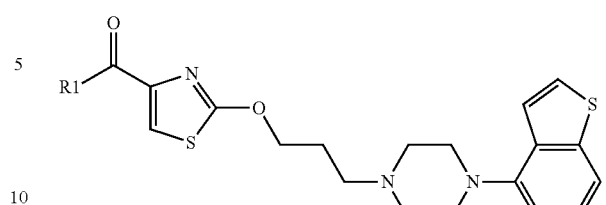
| Example | R1 | MS(M + 1) |
|---|---|---|
| 2403 | 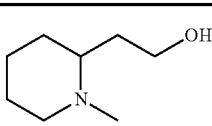 | 515 |
| 2404 | 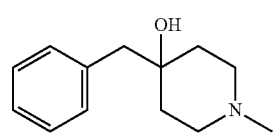 | 577 |
| 2405 | 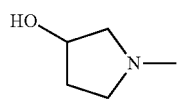 | 473 |
| 2406 | 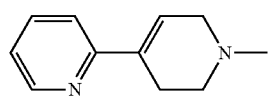 | 546 |
| 2407 | 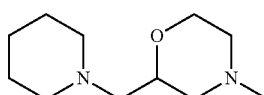 | 570 |
| 2408 | 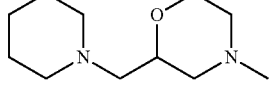 | 505 |
| 2409 | 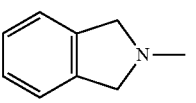 | 533 |
| 2410 | 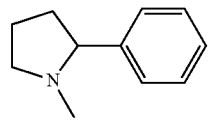 | 486 |
| 2411 | 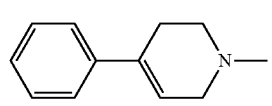 | |

TABLE 249

[Structure: R1-C(=O)-thiazole-O-(CH2)3-piperazine-benzothiophene]

| Example | R1 | MS(M + 1) |
|---------|----|-----------| 
| 2412 | (N-methyl piperazine with isobutyl substituent) | 542 |
| 2413 | (methyl-pyrrolopiperazine) | 528 |
| 2414 | (methyl-pyrrolopiperazine with isobutyl) | 568 |
| 2415 | (N-methyl-3-trifluoromethylpiperidine) | 539 |
| 2416 | (trifluoromethyl-triazolopiperazine, N-methyl) | 578 |
| 2417 | (N-methyl-1,4-oxazepane) | 487 |
| 2418 | (N-methyl piperidine with two butyl groups) | 583 |
| 2419 | (4-methyl-2-phenyl morpholine) | 549 |
| 2420 | (N-methyl diazaspiro compound with lactam) | 554 |

TABLE 250

[Structure: R1-C(=O)-thiazole-O-(CH2)3-piperazine-benzothiophene]

| Example | R1 | MS(M + 1) |
|---------|----|-----------| 
| 2421 | (1-methyl-3-(pyridin-2-yl)piperidine) | 548 |
| 2422 | (1-methyl-3-(pyridin-2-yl)tetrahydropyridine) | 545 |
| 2423 | (7-chloro-2-methyl-tetrahydroisoquinoline) | 553 |
| 2424 | (1-methyl-3-benzyl piperidine) | 561 |
| 2425 | (methyl tetrahydro-isoxazolo-pyridinone) | 526 |
| 2426 | (N-methyl azetidine) | 443 |

TABLE 251

[Structure: R1R2N-C(=O)-thiazole-O-(CH2)3-piperazine-benzothiophene]

| Example | R1 | R2 | MS(M + 1) |
|---------|-----|-----|-----------|
| 2427 | -cyclo-C₆H₁₁ | —CH₃ | 499 |
| 2428 | —H | -cyclo-C₆H₁₁ | 485 |
| 2429 | —H | —CH(CH₃)₂ | 445 |
| 2430 | —C₄M₈ | —C₄H₉ | 515 |
| 2431 | —CH₂CH(CH₃)₂ | —CH₂CH(CH₃)₂ | 515 |
| 2432 | —CH₂CH₂OH | —CH₂CH₂OH | 491 |
| 2433 | —CH₂CH₂OH | —C₂H₅ | 475 |
| 2434 | —C₆H₁₃ | —C₆H₁₃ | 571 |
| 2435 | —CH₂CH₂N(CH₃)₂ | —CH₃ | 488 |

TABLE 251-continued

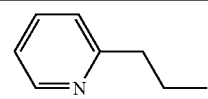

| Example | R1 | R2 | MS(M + 1) |
|---|---|---|---|
| 2436 | -cyclo-$C_6H_{11}$ | —$CH_2CH_2OH$ | 529 |
| 2437 | —$CH_2CH_2OCH_3$ | —$CH_2CH_2OCH_3$ | 519 |
| 2438 | —$(CH_2)_3N(CH_3)_2$ | —$(CH_2)_3N(CH_3)_2$ | 573 |
| 2439 | —$(CH_2)_3N(C_2H_5)_2$ | —$CH_3$ | 530 |
| 2440 | —$CH_2CH=CH_2$ | -cyclo-$C_5H_9$ | 511 |
| 2441 | —$C_2H_5$ | —$C_2H_5$ | 459 |
| 2442 | —H | —$C(CH_3)_3$ | 459 |
| 2443 | —H | -cyclo-$C_3H_5$ | 443 |
| 2444 | —H | -cyclo-$C_7H_{13}$ | 499 |
| 2445 | —H | —$CH_2C_6H_5$ | 493 |
| 2446 | —$C_3H_7$ | —$(CH_2)_3C_6H_5$ | 563 |
| 2447 | —$CH_2CONHCH_3$ | —$CH_2C_6H_5$ | 564 |
| 2448 | —$CH_2C_6H_5$ | -cyclo-$C_6H_{11}$ | 575 |
| 2449 | —$(CH_2)2C_6H_5$ | —$CH_3$ | 521 |
| 2450 | —$CH_2C_6H_5$ | —$CH_3$ | 507 |
| 2451 | —$CH_2CH_2N(CH_3)_2$ | —$CH_2C_6H_5$ | 564 |
| 2452 | —$CH_2C_6H_5$ | —$C_5H_{11}$ | 563 |

TABLE 252

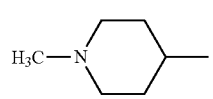

| Example | R1 | R2 | MS(M + 1) |
|---|---|---|---|
| 2453 | —$CH_2C_6H_5$ | —$CH_2C_6H_5$ | 583 |
| 2454 | —$CH_2C_6H_5$ | —$C_2H_5$ | 521 |
| 2455 | —$CH_2C_6H_5$ | —$CH(CH_3)_2$ | 535 |
| 2456 | —$CH_2CH_2CN$ | —$CH_2C_6H_5$ | 546 |
| 2457 | —$(CH_2)_2OC_6H_5$ | —$CH_3$ | 537 |
| 2458 | -cyclo-$C_6H_{11}$ | —$C_2H_5$ | 513 |
| 2459 | —$CH(CH_3)_2$ | —$C_2H_5$ | 473 |
| 2460 | —H | —$C_2H_5$ | 431 |
| 2461 | —H | —$CH_2CH(CH_3)_2$ | 459 |
| 2462 | —H | —$CH_2CH_2OCH_3$ | 461 |
| 2463 | —$C_2H_5$ | —$C_4H_9$ | 487 |
| 2464 | —H | —$CH_2CH_2OC_2H_5$ | 475 |
| 2465 | —H | —$(CH_2)_3OC_2H_5$ | 489 |
| 2466 | —$CH_2C_6H_5$ | —$C_6H_5$ | 569 |
| 2467 | —$C_6H_5$ | —$C_2H_5$ | 507 |
| 2468 | —$C_6H_5$ | -cyclo-$C_6H_{11}$ | 561 |
| 2469 | —$CH_2CH_2CN$ | —$C_6H_5$ | 532 |
| 2470 | -2-PYRIDYL | —$C_2H_5$ | 508 |
| 2471 | —H | —$C_6H_5$ | 479 |
| 2472 | —H | -3-PYRIDYL | 480 |
| 2473 | —H | -2-PYRIDYL | 480 |
| 2474 | —H | -4-PYRIDYL | 480 |
| 2475 | —$C_6H_5$ | —$CH_3$ | 493 |
| 2476 | —H | —$CH_2$-cyclo-$C_6H_{11}$ | 499 |
| 2477 | —H | —$(CH_2)_3C_6H_5$ | 521 |
| 2478 | —H | —$(CH_2)_2NHCOCH_3$ | 488 |
| 2479 | —H | —$(CH_2)_5OH$ | 489 |

TABLE 253

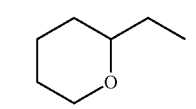

| Example | R1 | R2 | MS(M + 1) |
|---|---|---|---|
| 2480 | —H | —$(CH_2)_2C_6H_5$ | 507 |
| 2481 | —H | —$CH_2CONH_2$ | 460 |
| 2482 | —H | —$CH_2CCH$ | 441 |
| 2483 | —$C_5H_{11}$ | —$CH_3$ | 487 |
| 2484 | —H | —$(CH_2)_2CH(CH_3)_2$ | 473 |
| 2485 | —H | —$CH_2C(CH_3)_3$ | 473 |
| 2486 | —H | —$CH_2CH_2N(CH_3)_2$ | 474 |
| 2487 | —$CH_2C_6H_5$ | —$(CH_2)_3OH$ | 551 |
| 2488 | —$CH_3$ | —$CH_2$-cyclo-$C_3H_5$ | 471 |
| 2489 | —H | —$CH_2CF_3$ | 485 |
| 2490 | —H | —$NHCH_2CF_3$ | 500 |
| 2491 | —$CH_3$ | —$CH_3$ | 431 |
| 2492 | —H | —$(CH_2)_3OCH(CH_3)_2$ | 503 |
| 2493 | —H | —$CH_2CH_2C(CH_3)_3$ | 487 |
| 2494 | —H | —$CH_2CN$ | 442 |
| 2495 | —H | —$(CH_2)_3OCH_3$ | 475 |
| 2496 | —H | —$(CH_2)_2OCH(CH_3)_2$ | 489 |
| 2497 | —H | —$CH_2CH_2CN$ | 456 |
| 2498 | —H | —$CH_2CONHCH_3$ | 474 |
| 2499 | —H | —$(CH_2)SCH_3$ | 477 |
| 2500 | —H | —$CH_2CHF_2$ | 467 |
| 2501 | —H | —$CH_2CH_2OH$ | 447 |
| 2502 | —H | —$C_6H_{13}$ | 487 |
| 2503 | —$CH_2CON(CH_3)_2$ | —$CH_3$ | 502 |
| 2504 | —$CH_2C_6H_5$ | —$CH_2CH_2OCH_3$ | 551 |
| 2505 | —H | —$(CH_2)_2NHCONH_2$ | 489 |

TABLE 254

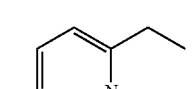

| Example | R1 | R2 | MS(M + 1) |
|---|---|---|---|
| 2506 | 2-pyridyl-ethyl | —$CH_3$ | 522 |
| 2507 | 1-methyl-4-piperidyl | —$CH_3$ | 514 |
| 2508 | 2-ethyl-tetrahydropyran | —$C_2H_5$ | 529 |
| 2509 | 2-pyridyl-ethyl | —H | 494 |

TABLE 254-continued

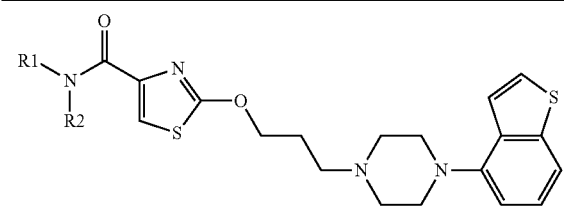

| Example | R1 | R2 | MS(M + 1) |
|---|---|---|---|
| 2510 | 3-pyridyl-ethyl | —H | 494 |
| 2511 | 4-pyridyl-ethyl | —H | 494 |
| 2512 | 2-furyl-ethyl | —H | 483 |
| 2513 | 2-pyridyl-propyl | —C₂H₅ | 536 |
| 2514 | 1-acetyl-4-methylpiperidinyl | —CH₃ | 542 |
| 2515 | cinnamyl (phenyl-butenyl) | —C₂H₅ | 547 |

TABLE 255

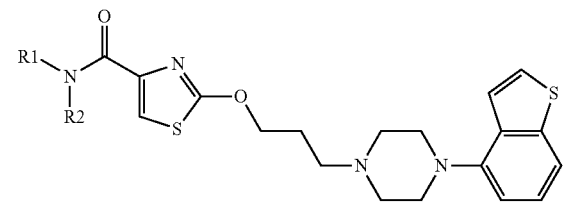

| Example | R1 | R2 | MS(M + 1) |
|---|---|---|---|
| 2516 | N-methyl-N-butyl-anilino | —CH₃ | 564 |
| 2517 | 4-pyridyl-ethyl | —C₂H₅ | 522 |
| 2518 | 1-methylcyclopropyl | —H | 457 |

TABLE 255-continued

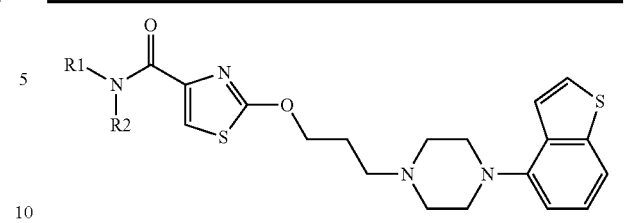

| Example | R1 | R2 | MS(M + 1) |
|---|---|---|---|
| 2519 | 1-methylcyclopentyl | —H | 485 |
| 2520 | p-tolyl | —CH₃ | 507 |
| 2521 | 4-methoxyphenyl-methyl | —H | 509 |
| 2522 | 4-acetylphenyl-methyl | —H | 521 |
| 2523 | 1-naphthyl-methyl | —H | 529 |
| 2524 | 2-(pyrrol-1-yl)phenyl-methyl | —H | 544 |
| 2525 | 6-methyl-1H-indazol-yl | —H | 519 |

TABLE 256

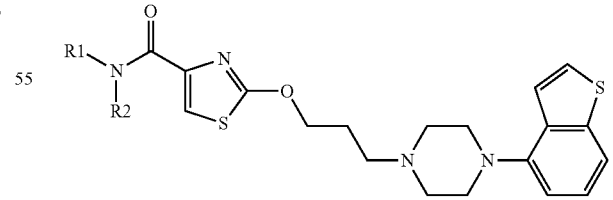

| Example | R1 | R2 | MS(M + 1) |
|---|---|---|---|
| 2526 | 2-methylquinolinyl | —H | 530 |

TABLE 256-continued
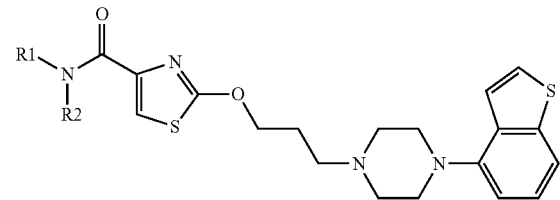
| Example | R1 | R2 | MS(M + 1) |
|---|---|---|---|
| 2527 | 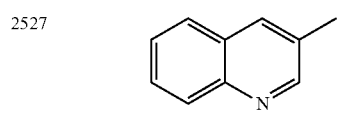 | —H | 530 |
| 2528 | 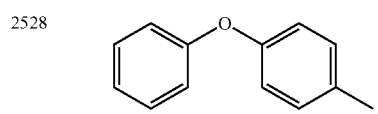 | —H | 571 |
| 2529 | 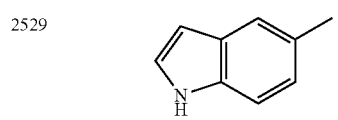 | —H | 518 |
| 2530 | 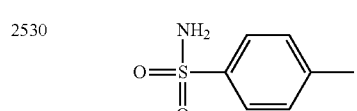 | —H | 558 |
| 2531 |  | —H | 486 |
| 2532 | 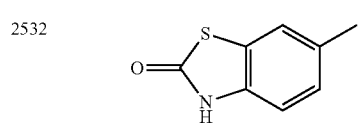 | —H | 552 |
| 2533 | 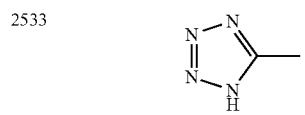 | —H | 471 |
| 2534 | 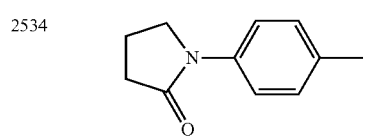 | —H | 562 |
TABLE 257
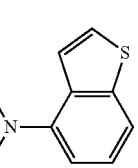
| Example | R1 | R2 | MS(M + 1) |
|---|---|---|---|
| 2535 | 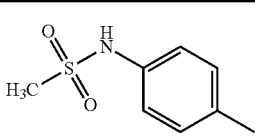 | —H | 572 |
| 2536 | 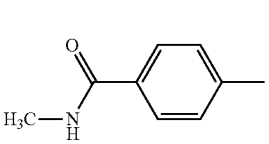 | —H | 536 |
| 2537 | 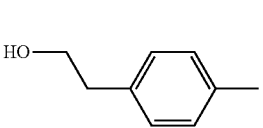 | —H | 523 |
| 2538 | 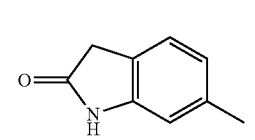 | —H | 534 |
| 2539 | 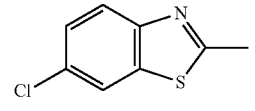 | —H | 570 |
| 2540 | 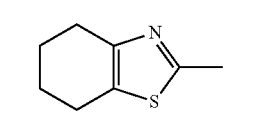 | —H | 540 |
| 2541 | 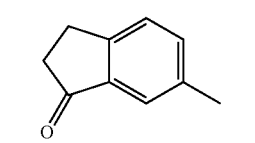 | —H | 533 |
| 2542 | 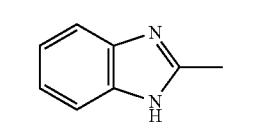 | —H | 519 |
| 2543 | 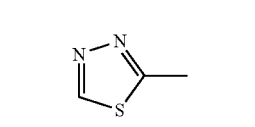 | —H | 487 |

TABLE 258
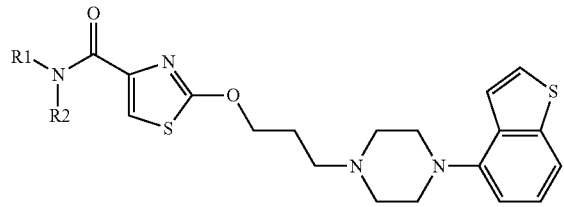
| Example | R1 | R2 | MS(M + 1) |
|---|---|---|---|
| 2544 | 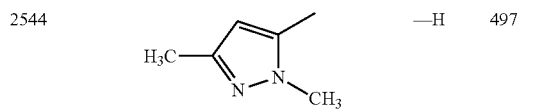 | —H | 497 |
| 2545 | 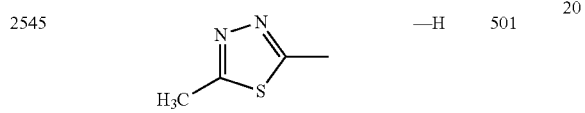 | —H | 501 |
| 2546 | 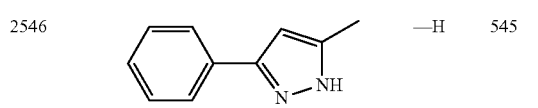 | —H | 545 |
| 2547 | 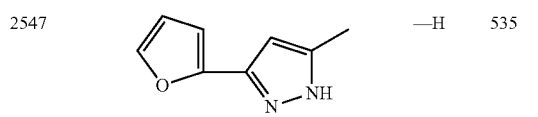 | —H | 535 |
| 2548 | 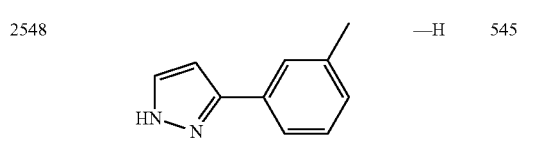 | —H | 545 |
| 2549 | 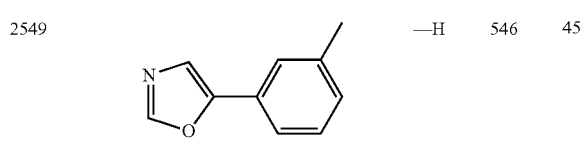 | —H | 546 |
| 2550 | 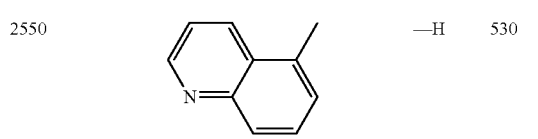 | —H | 530 |
| 2551 | 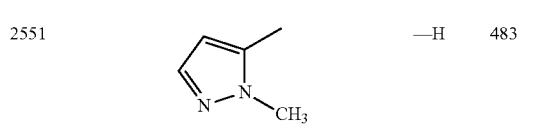 | —H | 483 |
TABLE 259
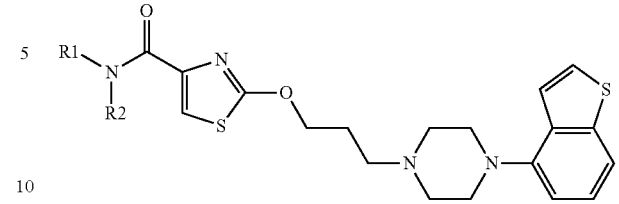
| Example | R1 | R2 | MS(M + 1) |
|---|---|---|---|
| 2552 | 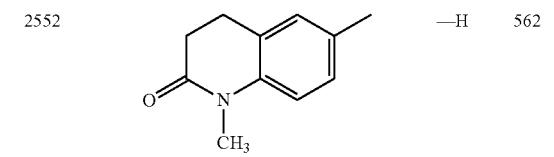 | —H | 562 |
| 2553 | 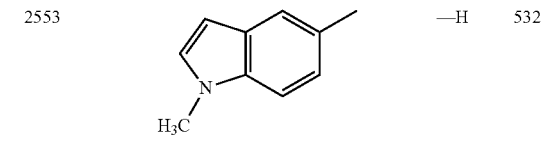 | —H | 532 |
| 2554 | 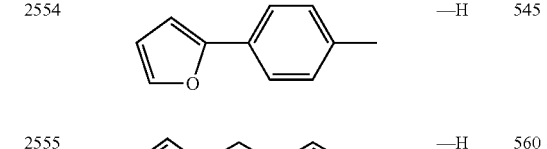 | —H | 545 |
| 2555 | 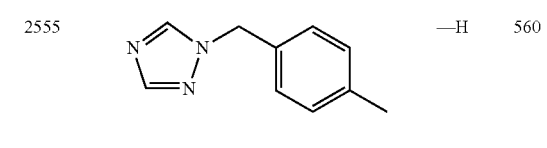 | —H | 560 |
| 2556 | 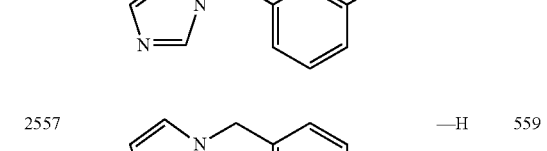 | —H | 559 |
| 2557 | 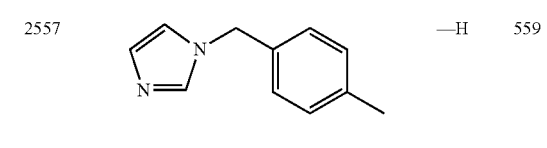 | —H | 559 |
| 2558 | 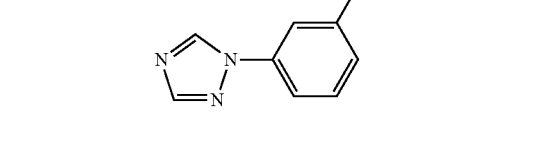 | —H | 546 |
| 2559 | 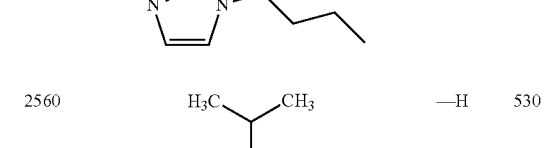 | —H | 511 |
| 2560 | 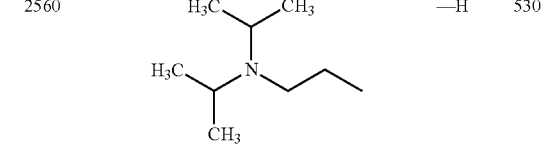 | —H | 530 |

TABLE 260

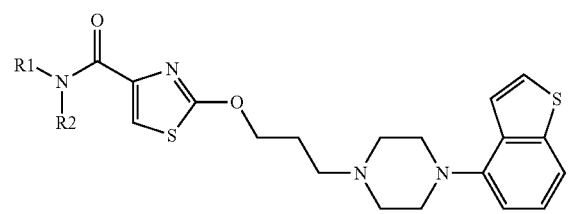

| Example | R1 | R2 | MS(M + 1) |
|---|---|---|---|
| 2561 | 2-propylpyridine | —H | 508 |
| 2562 | 1-propylpiperidine | —H | 514 |
| 2563 | 1-ethyl-2-ethylpyrrolidine | —H | 514 |
| 2564 | 1-propylpyrrolidine | —H | 500 |
| 2565 | 1-butylpyrrolidine | —H | 514 |
| 2566 | 4-propylmorpholine | —H | 516 |
| 2567 | 4-butylmorpholine | —H | 530 |
| 2568 | 1-butylbenzimidazole | —H | 561 |
| 2569 | 2-ethylnaphthalene | —H | 543 |
| 2570 | 3-propyl-1H-indole | —H | 546 |

TABLE 261

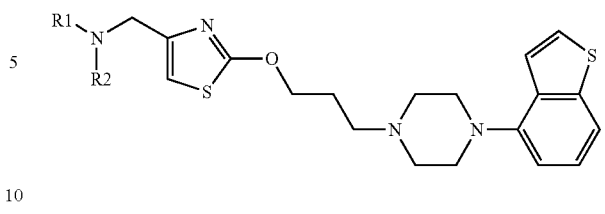

| Example | R1 | R2 | MS(M + 1) |
|---|---|---|---|
| 2571 | 2-ethyl-1H-benzimidazole | —H | 533 |
| 2572 | 2-ethylthiophene | —H | 499 |
| 2573 | 1-butyl-2-pyrrolidinone | —H | 528 |
| 2574 | 2-ethyltetrahydrofuran | —H | 487 |
| 2575 | 2-ethyl-5-methylpyrazine | —H | 509 |
| 2576 | 3-propylpyridine | —H | 508 |
| 2577 | 4-propylpyridine | —H | 508 |
| 2578 | 2-ethyl-5-methylfuran | —H | 497 |
| 2579 | 4-propyl-1H-imidazole | —H | 497 |
| 2580 | 2-ethyl-1-methylpyrrole | —H | 496 |

TABLE 262

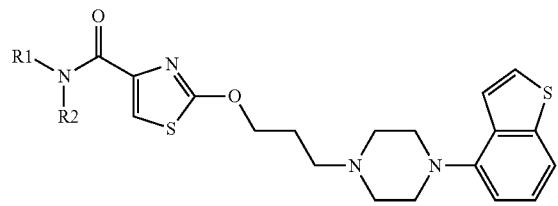

| Example | R1 | R2 | MS(M + 1) |
|---|---|---|---|
| 2581 | 1,3,5-trimethyl-4-ethylpyrazole | —H | 525 |
| 2582 | 2,5-dimethyl-3-ethylfuran | —H | 511 |
| 2583 | 1,5-dimethyl-3-ethylpyrazole | —H | 511 |
| 2584 | 3-methyl-2-ethylthiophene | —H | 513 |
| 2585 | 3-ethylthiophene | —H | 499 |
| 2586 | 3-ethylfuran | —H | 483 |
| 2587 | 2-ethylthiazole | —H | 500 |
| 2588 | 2-propylthiophene | —H | 513 |
| 2589 | 5-ethyl-2,3-dihydrobenzofuran | —H | 535 |
| 2590 | 2-methylbut-1-enyl | —H | 457 |

TABLE 263

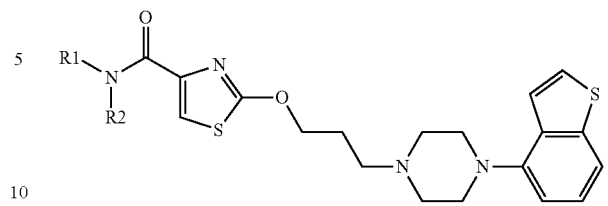

| Example | R1 | R2 | MS(M + 1) |
|---|---|---|---|
| 2591 | 4-butyl-5-oxo-4,5-dihydro-1H-pyrazole | —H | 527 |
| 2592 | 4-(pyrrolidin-1-yl)cyclohexyl | —H | 554 |
| 2593 | 2-ethylbenzothiophene | —H | 549 |
| 2594 | 2-methylindane | —H | 519 |
| 2595 | 1-methylindane | —H | 519 |
| 2596 | 1-propylpyrazole | —H | 497 |
| 2597 | 1-propylindole | —H | 546 |
| 2598 | 2-propylfuran | —H | 497 |
| 2599 | 1-pentylpyrrolidine | —H | 528 |
| 2600 | 4-methyltetrahydropyran | —H | 487 |

TABLE 264
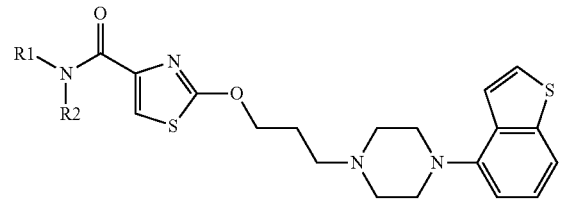
| Example | R1 | R2 | MS(M + 1) |
|---|---|---|---|
| 2601 | 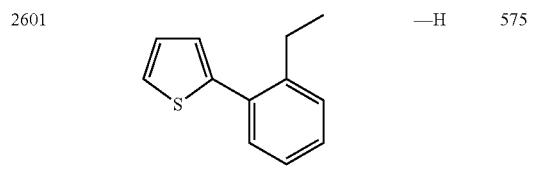 | —H | 575 |
| 2602 | 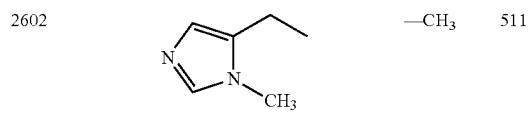 | —CH₃ | 511 |
| 2603 | 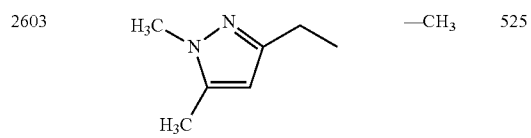 | —CH₃ | 525 |
| 2604 | 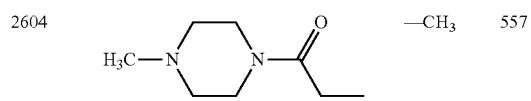 | —CH₃ | 557 |
| 2605 | 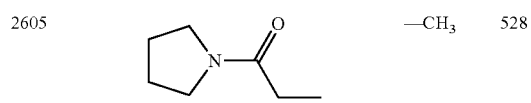 | —CH₃ | 528 |
| 2606 | 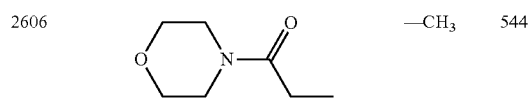 | —CH₃ | 544 |
| 2607 | 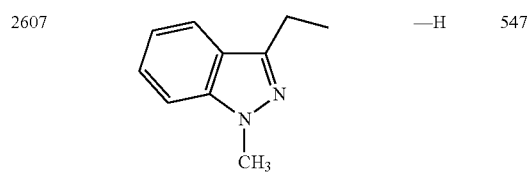 | —H | 547 |
| 2608 | 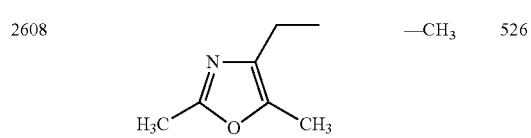 | —CH₃ | 526 |
| 2609 | 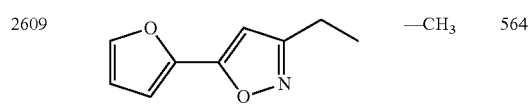 | —CH₃ | 564 |
TABLE 265
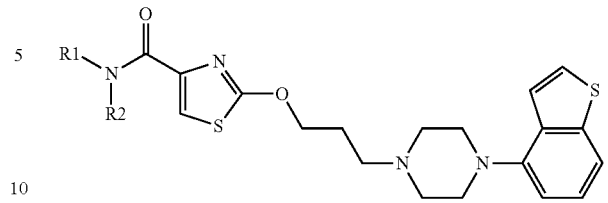
| Example | R1 | R2 | MS(M + 1) |
|---|---|---|---|
| 2610 | 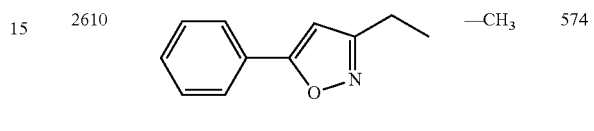 | —CH₃ | 574 |
| 2611 | 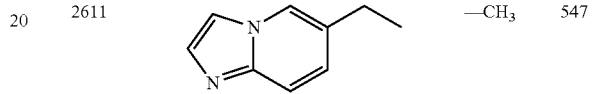 | —CH₃ | 547 |
| 2612 | 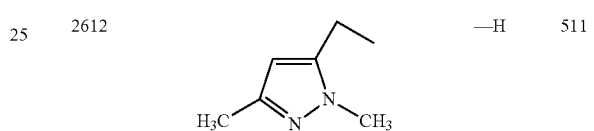 | —H | 511 |
| 2613 | 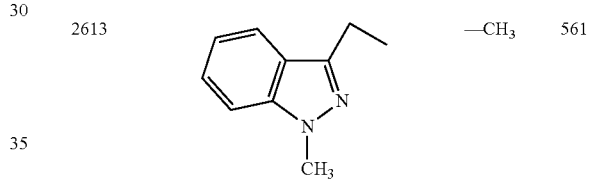 | —CH₃ | 561 |
| 2614 | 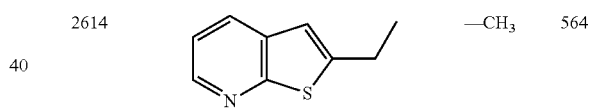 | —CH₃ | 564 |
| 2615 | 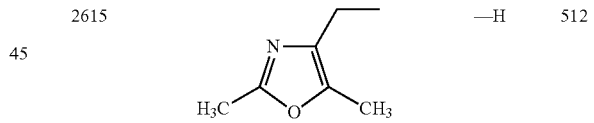 | —H | 512 |
| 2616 | 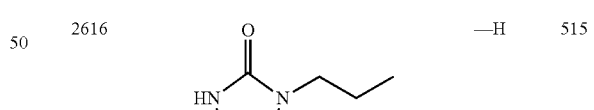 | —H | 515 |
| 2617 | 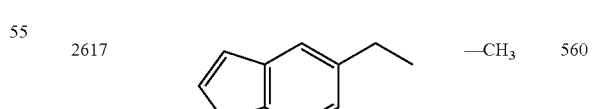 | —CH₃ | 560 |
| 2618 | 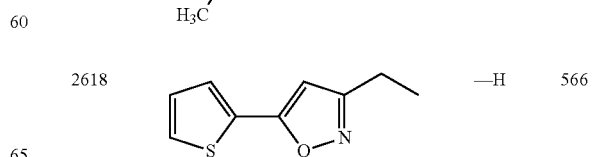 | —H | 566 |

TABLE 266
| Example | R1 | R2 | MS (M + 1) |
|---|---|---|---|
| 2619 | phenyl-pyrazole (N-CH3, 3-ethyl) | —H | 573 |
| 2620 | ethylenedioxythiophene-ethyl | —CH3 | 571 |
| 2621 | 2-(4-ethylphenyl)pyridine | —CH3 | 584 |
| 2622 | phenyl-pyrazole (N-CH3, 5-ethyl) | —CH3 | 587 |
TABLE 266-continued
| Example | R1 | R2 | MS (M + 1) |
|---|---|---|---|
| 2623 | 1-(3-ethylphenyl)-1,2,4-triazole | —H | 560 |
| 2624 | 3-propylbenzofuran | —H | 547 |
| 2625 | 7-propyl-2,3-dihydrobenzofuran | —H | 549 |
TABLE 267
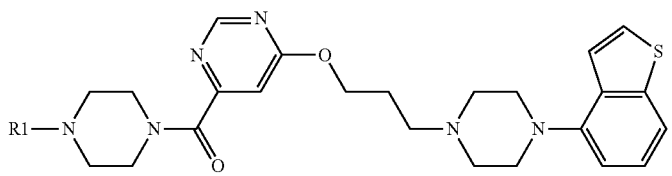
| Example | R1 | MS(M + 1) |
|---|---|---|
| 2626 | -2-PYRIDYL | 544 |
| 2627 | —C4H9 | 523 |
| 2628 | —CH(CH3)2 | 509 |
| 2629 | —CH2CH2N(CH3)2 | 538 |
| 2630 | -4-PYRIDYL | 544 |
| 2631 | —C6H5 | 543 |
| 2632 | —C3H7 | 509 |
| 2633 | —CH2CH2OCH3 | 525 |
| 2634 | —CH3 | 481 |
| 2635 | -3-PYRIDYL | 544 |
| 2636 | —C6H13 | 551 |
| 2837 | —C2H5 | 495 |
| 2638 | —CH2CH2OH | 511 |
| 2839 | —COCH3 | 509 |
| 2640 | -cyclo-C6H11 | 549 |
| 2641 | —SO2C2H5 | 559 |

TABLE 268

| Example | R1 | MS(M + 1) |
|---|---|---|
| 2642 | 2-ethylpyridine | 558 |
| 2643 | 3-ethylpyridine | 558 |
| 2644 | 4-ethylpyridine | 558 |
| 2645 | 2-methylpyrimidine | 545 |
| 2646 | 1,4-dimethylpiperidine | 564 |
| 2647 | 7-ethyl-3,4-dihydro-2H-1,5-benzodioxepine | 629 |
| 2648 | 2-methylpyrazine | 545 |
| 2649 | 2-ethyltetrahydrofuran | 551 |
| 2650 | 1-propylimidazole | 561 |

TABLE 269

| Example | R1 | MS(M + 1) |
|---|---|---|
| 2651 | 4-propylpyridine | 572 |

TABLE 269-continued
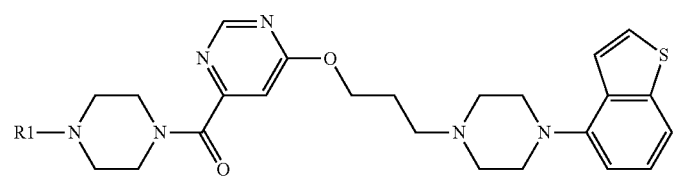
| Example | R1 | MS(M + 1) |
|---|---|---|
| 2652 | 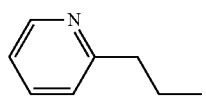 | 572 |
| 2653 | 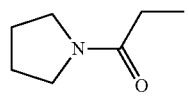 | 578 |
| 2654 | 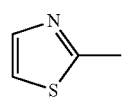 | 550 |
| 2655 | 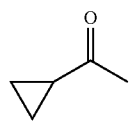 | 535 |
TABLE 270
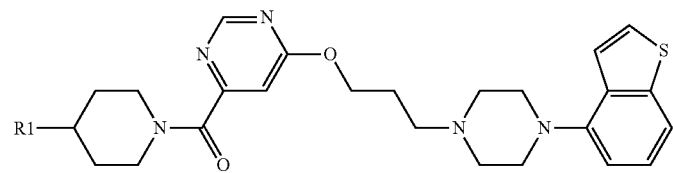
| Example | R1 | MS(M + 1) |
|---|---|---|
| 2656 | —OCH$_3$ | 496 |
| 2657 | -cyclo-C$_6$H$_{11}$ | 548 |
| 2658 | —C$_6$H$_5$ | 542 |
| 2659 | —OCH$_2$C$_6$H$_5$ | 572 |
| 2660 | —OC$_6$H$_5$ | 558 |
| 2661 | —OH | 482 |
| 2662 | —CONH$_2$ | 509 |
| 2663 | —C$_2$H$_5$ | 494 |
| 2664 | —NHCOCH$_3$ | 523 |
| 2665 | —COC$_6$H$_5$ | 570 |
| 2666 | -2-PYRIDYL | 543 |

TABLE 271
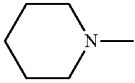
| Example | R1 | MS(M + 1) |
|---|---|---|
| 2667 | 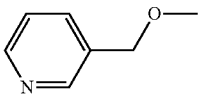 | 549 |
| 2668 | 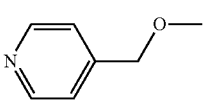 | 573 |
| 2669 | 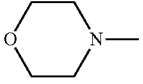 | 573 |
| 2670 | 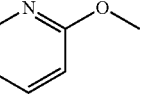 | 551 |
| 2671 | 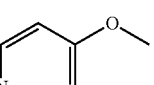 | 559 |
| 2672 | 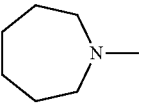 | 559 |
TABLE 272
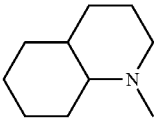
| Example | R1 | MS(M + 1) |
|---|---|---|
| 2673 | 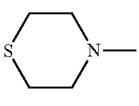 | 480 |
| 2874 | 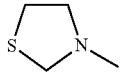 | 520 |
| 2675 | 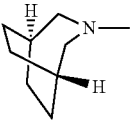 | 484 |
| 2676 |  | 470 |
| 2677 | 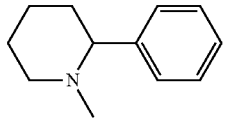 | 506 |
| 2678 | | 534 |
| 2679 | | 542 |

TABLE 272-continued

[Core structure: pyrimidine-O-(CH2)3-piperazine-benzothiophene with R1-C(O)- substituent]

| Example | R1 | MS(M + 1) |
|---|---|---|
| 2680 | 3-benzyl-1,4-dimethylpiperazin-2-yl | 571 |
| 2681 | 2-methyl-1,2,3,4-tetrahydroisoquinolin-3-yl | 514 |
| 2682 | 4-hydroxy-1-methyl-4-phenylpiperidin-3-yl | 558 |

TABLE 273

[Core structure: pyrimidine-O-(CH2)3-piperazine-benzothiophene with R1-C(O)- substituent]

| Example | R1 | MS(M + 1) |
|---|---|---|
| 2683 | 2-methyl-2,3,4,9-tetrahydro-1H-β-carbolin-3-yl | 553 |
| 2684 | 1-methyl-1,2,3,4-tetrahydroquinolin-2-yl | 514 |
| 2685 | 1-methylindolin-2-yl | 500 |
| 2686 | 1-methylpyrrolidine-2-carboxamide | 495 |

TABLE 273-continued

| Example | R1 | MS(M + 1) |
|---|---|---|
| 2687 | 1-methyl-2-(pyridin-3-yl)piperidin-2-yl | 543 |
| 2688 | 4-methyl-1-(pyridin-4-yl)-1,4-diazepan-2-yl | 558 |
| 2689 | 2-(2-hydroxyethyl)-1-methylpiperidin-2-yl | 510 |
| 2690 | 4-benzyl-4-hydroxy-1-methylpiperidin-3-yl | 572 |
| 2691 | 3-hydroxy-1-methylpyrrolidin-2-yl | 468 |

TABLE 274

[Core structure: pyrimidine-O-(CH2)3-piperazine-benzothiophene with R1-C(O)- substituent]

| Example | R1 | MS(M + 1) |
|---|---|---|
| 2692 | 1'-methyl-1',2',3',6'-tetrahydro-[2,4'-bipyridin]-3'-yl | 541 |
| 2693 | 4-methyl-2-(piperidin-1-ylmethyl)morpholin-3-yl | 565 |
| 2694 | 2-methylisoindolin-1-yl | 500 |

TABLE 274-continued

| Example | R1 | MS(M + 1) |
|---|---|---|
| 2695 | | 528 |
| 2696 | | 481 |
| 2697 | | 540 |
| 2698 | | 537 |
| 2699 | | 521 |
| 2700 | | 583 |
| 2701 | | 534 |

TABLE 275

| Example | R1 | MS(M + 1) |
|---|---|---|
| 2702 | | 573 |
| 2703 | | 482 |
| 2704 | | 578 |
| 2705 | | 544 |
| 2706 | | 549 |
| 2707 | | 543 |
| 2708 | | 541 |
| 2709 | | 548 |

TABLE 276

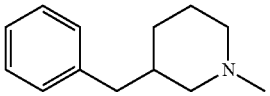

| Example | R1 | MS(M + 1) |
|---|---|---|
| 2710 | (benzyl-N-methylpiperidinyl) | 556 |
| 2711 | (5-methyl-tetrahydroisoxazolo-pyridin-3-one) | 521 |
| 2712 | (N-methylazetidinyl) | 438 |

TABLE 277

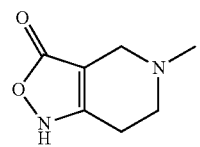

| Example | R1 | R2 | MS(M + 1) |
|---|---|---|---|
| 2713 | -cyclo-C$_6$H$_{11}$ | —CH$_3$ | 494 |
| 2714 | —H | —CH(CH$_3$)$_2$ | 440 |
| 2715 | —C$_4$H$_9$ | —C$_4$H$_9$ | 510 |
| 2716 | —CH$_2$CH(CH$_3$)$_2$ | —CH$_2$CH(CH$_3$)$_2$ | 510 |
| 2717 | —CH$_2$CH$_2$OH | —CH$_2$CH$_2$OH | 486 |
| 2718 | —C$_6$H$_{13}$ | —C$_6$H$_{13}$ | 566 |
| 2719 | —CH$_2$CH$_2$N(CH$_3$)$_2$ | —CH$_3$ | 483 |
| 2720 | —CH$_2$CH$_2$OCH$_3$ | —CH$_2$CH$_2$OCH$_3$ | 514 |
| 2721 | —CH$_2$CH(CH$_3$)$_2$ | —CH$_2$CH(CH$_3$)$_2$ | 568 |
| 2722 | —(CH$_2$)$_3$N(C$_2$H$_5$)$_2$ | —CH$_3$ | 525 |
| 2723 | —CH$_2$CH=CH$_2$ | -cyclo-C$_5$H$_6$ | 506 |
| 2724 | —H | —C$_4$H$_9$ | 454 |
| 2725 | —H | -cyclo-C$_3$H$_5$ | 438 |
| 2726 | —H | -cyclo-C$_7$H$_{13}$ | 494 |
| 2727 | —H | —CH$_2$C$_6$H$_5$ | 488 |
| 2728 | —C$_3$H$_7$ | —(CH$_2$)$_3$C$_6$H$_5$ | 558 |
| 2729 | —CH$_2$CONHCH$_3$ | —CH$_2$C$_6$H$_5$ | 559 |
| 2730 | —CH$_2$C$_6$H$_5$ | -cyclo-C$_5$H$_{11}$ | 570 |
| 2731 | —(CH$_2$)$_2$C$_6$H$_5$ | —CH$_3$ | 516 |
| 2732 | —CH$_2$C$_6$H$_5$ | —CH$_3$ | 502 |
| 2733 | —CH$_2$CH$_2$N(CH$_3$)$_2$ | —CH$_2$C$_6$H$_5$ | 559 |
| 2734 | —CH$_2$C$_6$H$_5$ | —C$_5$H$_{11}$ | 558 |
| 2735 | —CH$_2$C$_6$H$_5$ | —CH$_2$C$_6$H$_5$ | 578 |
| 2736 | —CH$_2$C$_6$H$_5$ | —C$_2$H$_5$ | 516 |
| 2737 | —CH$_2$C$_6$H$_5$ | —CH(CH$_3$)$_2$ | 530 |
| 2738 | —CH$_2$CH$_2$CN | —CH$_2$C$_6$H$_5$ | 541 |
| 2739 | —(CH$_2$)$_2$OC$_6$H$_5$ | —CH$_3$ | 532 |
| 2740 | -cyclo-C$_6$H$_{11}$ | —C$_2$H$_5$ | 508 |

TABLE 178

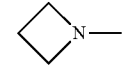

| Example | R1 | R2 | MS(M + 1) |
|---|---|---|---|
| 2741 | —CH(CH$_3$)$_2$ | —C$_2$H$_5$ | 468 |
| 2742 | —H | —C$_2$H$_5$ | 426 |
| 2743 | —H | —C$_3$H$_7$ | 440 |
| 2744 | —H | —CH$_2$CH$_2$OCH$_3$ | 456 |
| 2745 | —CH$_2$-cyclo-C$_6$H$_{11}$ | —C$_2$H$_5$ | 522 |
| 2746 | —C$_2$H$_5$ | —C$_4$H$_9$ | 482 |
| 2747 | —H | -1-CH$_3$-CYCLOHEXYL | 494 |
| 2748 | —H | —(CH$_2$)$_2$OC$_6$H$_5$ | 518 |
| 2749 | —CH$_2$C$_6$H$_5$ | —C$_6$H$_5$ | 564 |
| 2750 | —C$_6$H$_5$ | —CH$_2$CH$_2$OH | 518 |
| 2751 | —C$_6$H$_5$ | —C$_2$H$_5$ | 502 |
| 2752 | —CH$_2$CH$_2$CN | —C$_6$H$_5$ | 527 |
| 2753 | -2-PYRIDYL | —C$_2$H$_5$ | 503 |
| 2754 | —H | —C$_6$H$_5$ | 474 |
| 2755 | —H | -3-PYRIDYL | 475 |
| 2756 | —H | -2-PYRIDYL | 475 |
| 2757 | —H | -4-PYRIDYL | 475 |
| 2758 | —C$_6$H$_5$ | —CH$_3$ | 488 |
| 2759 | —H | —CH$_2$-cyclo-C$_6$H$_{11}$ | 494 |
| 2760 | —H | —(CH$_2$)$_3$C$_6$H$_5$ | 516 |
| 2761 | —H | —(CH$_2$)$_2$C$_6$H$_5$ | 502 |
| 2762 | —H | —CH$_2$CONH$_2$ | 455 |
| 2763 | —H | —CH$_2$CCH | 436 |
| 2764 | —C$_5$H$_{11}$ | —CH$_3$ | 482 |
| 2765 | —CH(CH$_3$)$_2$ | —CH$_3$ | 454 |
| 2766 | —H | —(CH$_2$)$_2$CH(CH$_3$)$_2$ | 468 |
| 2767 | —H | —CH$_2$C(CH$_3$)$_3$ | 468 |
| 2768 | —H | —CH$_2$CH$_2$N(CH$_3$)$_2$ | 469 |

TABLE 279

| Example | R1 | R2 | MS(M + 1) |
|---|---|---|---|
| 2769 | —CH$_2$C$_6$H$_5$ | —(CH$_2$)$_3$OH | 546 |
| 2770 | —CH$_3$ | —CH$_2$-cyclo-C$_3$H$_5$ | 466 |
| 2771 | —H | —CH$_2$CF$_3$ | 480 |
| 2772 | —H | —NHCH$_2$CF$_3$ | 495 |
| 2773 | —CH$_3$ | —CH$_3$ | 426 |
| 2774 | —H | —(CH$_2$)$_3$OCH(CH$_3$)$_2$ | 498 |
| 2775 | —H | —CH$_2$CH$_2$C(CH$_3$)$_3$ | 482 |
| 2776 | —H | —CH$_2$CN | 437 |
| 2777 | —H | —(CH$_2$)$_3$OCH$_3$ | 470 |
| 2778 | —H | —(CH$_2$)$_2$OCH(CH$_3$)$_2$ | 484 |
| 2779 | —H | —CH$_2$CH$_2$CN | 451 |
| 2780 | —H | —CH$_2$CONHCH$_3$ | 469 |
| 2781 | —H | —(CH$_2$)SCH$_3$ | 472 |
| 2782 | —H | —CH$_2$CHF$_2$ | 462 |
| 2783 | —H | —C$_6$H$_{13}$ | 482 |
| 2784 | —CH$_2$CON(CH$_3$)$_2$ | —CH$_3$ | 497 |
| 2785 | —CH$_2$C$_6$H$_5$ | —CH$_2$CH$_2$OCH$_3$ | 546 |
| 2786 | —H | —(CH$_2$)$_2$NHCONH$_2$ | 484 |

TABLE 280

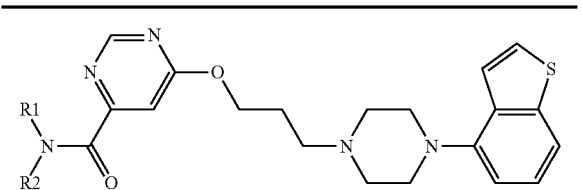

| Example | R1 | R2 | MS(M + 1) |
|---|---|---|---|
| 2787 | 2-propylpyridine | —CH₃ | 517 |
| 2788 | 1-methyl-4-methylpiperidine | —CH₃ | 509 |
| 2789 | 2-ethyltetrahydropyran | —C₂H₅ | 524 |
| 2790 | 2-ethylpyridine | —H | 489 |
| 2791 | 3-ethylpyridine | —H | 489 |
| 2792 | 4-ethylpyridine | —H | 489 |
| 2793 | 2-ethylfuran | —H | 478 |
| 2794 | 2-propylpyridine | —C₂H₅ | 531 |
| 2795 | 1-acetyl-4-methylpiperidine | —CH₃ | 537 |
| 2796 | cinnamyl | —C₂H₅ | 542 |

TABLE 281

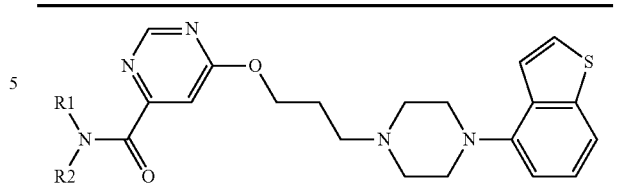

| Example | R1 | R2 | MS(M + 1) |
|---|---|---|---|
| 2797 | N-methyl-N-butylaniline | —CH₃ | 559 |
| 2798 | 4-ethylpyridine | —C₂H₅ | 517 |
| 2799 | 1,1-dimethylcyclopropyl | —H | 452 |
| 2800 | 1,1-dimethylcyclopentyl | —H | 480 |
| 2801 | 4-chlorophenethyl | —CH₃ | 536 |
| 2802 | 4-methylbenzyl | —CH₃ | 502 |
| 2803 | 4-chlorobenzyl | —H | 508 |
| 2804 | 4-methoxybenzyl | —H | 504 |
| 2805 | 4-acetylbenzyl | —H | 516 |
| 2806 | 1-methylnaphthyl | —H | 524 |
| 2807 | 2-methyl-3-pyrrolylpyridine | —H | 539 |

TABLE 282

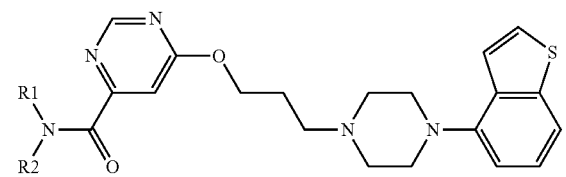

| Example | R1 | R2 | MS(M + 1) |
|---|---|---|---|
| 2808 | 6-methyl-1H-indazol-3-yl | —H | 514 |
| 2809 | 2-methylquinolin-8-yl | —H | 525 |
| 2810 | 3-methylquinolin-6-yl | —H | 525 |
| 2811 | 4-phenoxy-p-tolyl | —H | 566 |
| 2812 | 5-methyl-1H-indol-3-yl | —H | 513 |
| 2813 | 4-sulfamoyl-p-tolyl | —H | 553 |
| 2814 | 2-methylthiazol-4-yl | —H | 481 |
| 2815 | 2-methylpyrimidin-5-yl | —H | 476 |
| 2816 | 4-nitro-p-tolyl | —H | 519 |
| 2817 | 6-methyl-2-oxo-2,3-dihydrobenzothiazol-5-yl | —H | 547 |

TABLE 283

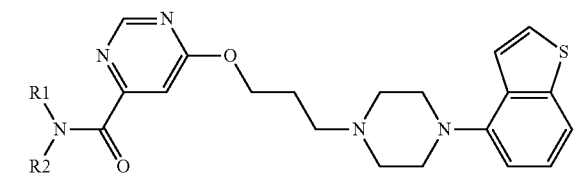

| Example | R1 | R2 | MS(M + 1) |
|---|---|---|---|
| 2818 | 5-methyl-1H-1,2,4-triazol-3-yl | —H | 465 |
| 2819 | 5-methyl-1H-tetrazol-2-yl | —H | 466 |
| 2820 | 3,5-dimethylisoxazol-4-yl | —H | 479 |
| 2821 | 4-(2-oxopyrrolidin-1-yl)-p-tolyl | —H | 557 |
| 2822 | 4-(methylsulfonamido)-p-tolyl | —H | 567 |
| 2823 | 4-(methylcarbamoyl)-p-tolyl | —H | 531 |
| 2824 | 4-(2-hydroxyethyl)-p-tolyl | —H | 518 |
| 2825 | 6-methyl-2-oxoindolin-5-yl | —H | 529 |
| 2826 | 6-chloro-2-methylbenzothiazol-5-yl | —H | 565 |

TABLE 284
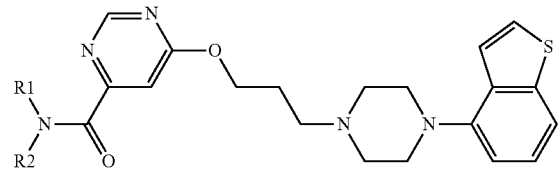
| Example | R1 | R2 | MS(M + 1) |
|---|---|---|---|
| 2827 | 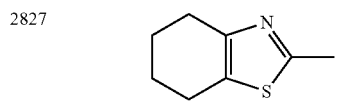 | —H | 535 |
| 2828 | 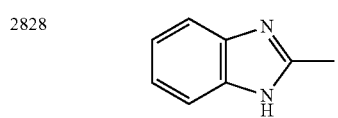 | —H | 514 |
| 2829 | 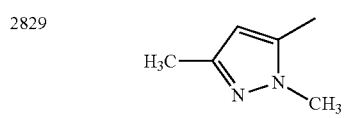 | —H | 492 |
| 2830 | 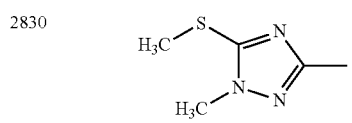 | —H | 525 |
| 2831 | 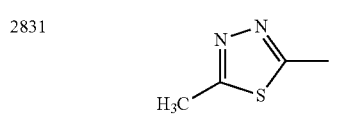 | —H | 496 |
| 2832 | 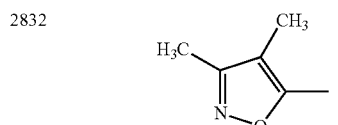 | —H | 493 |
| 2833 | 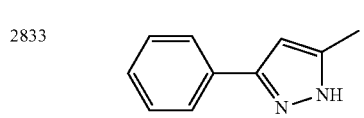 | —H | 540 |
| 2834 | 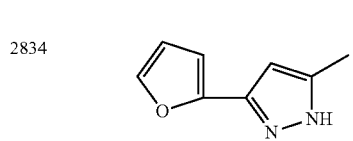 | —H | 530 |
| 2835 |  | —H | 540 |
TABLE 285
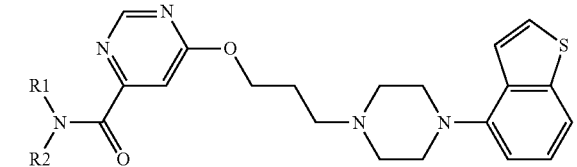
| Example | R1 | R2 | MS(M + 1) |
|---|---|---|---|
| 2836 | 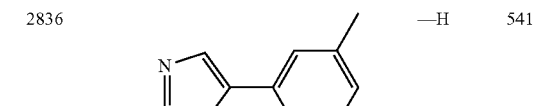 | —H | 541 |
| 2837 | 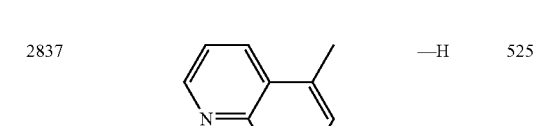 | —H | 525 |
| 2838 | 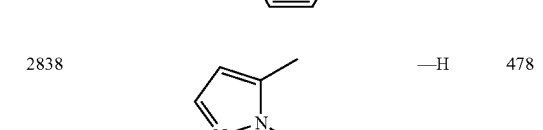 | —H | 478 |
| 2839 | 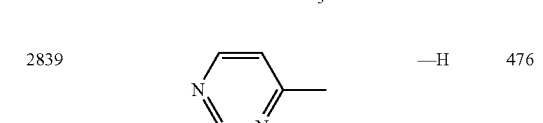 | —H | 476 |
| 2840 | 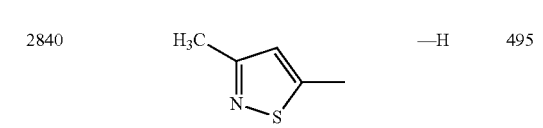 | —H | 495 |
| 2841 | 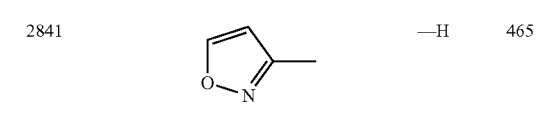 | —H | 465 |
| 2842 | 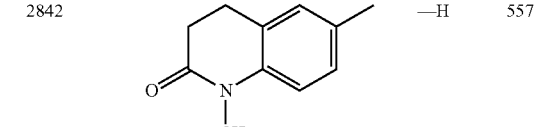 | —H | 557 |
| 2843 | 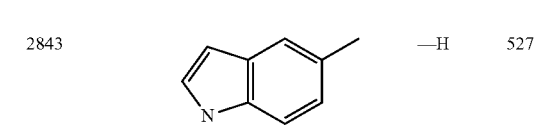 | —H | 527 |
| 2844 | 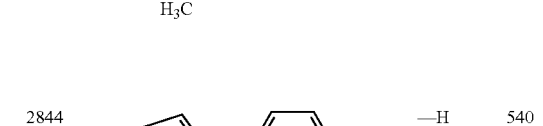 | —H | 540 |

461

TABLE 286

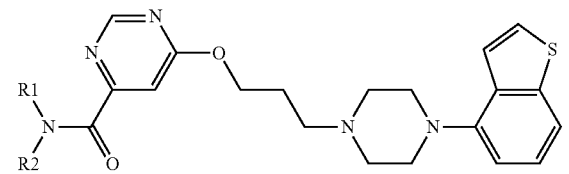

| Example | R1 | R2 | MS(M + 1) |
|---|---|---|---|
| 2845 | 4-methylbenzyl-1H-1,2,4-triazole | —H | 555 |
| 2846 | 3-methylbenzyl-1H-imidazole | —H | 554 |
| 2847 | 4-methylbenzyl-1H-imidazole | —H | 554 |
| 2848 | 3-methylphenyl-1H-1,2,4-triazole | —H | 541 |
| 2849 | butyl-1H-imidazole | —H | 506 |
| 2850 | N,N-diisopropylpropylamine | —H | 525 |
| 2851 | 2-propylpyridine | —H | 503 |
| 2852 | propylpiperidine | —H | 509 |
| 2853 | 1-ethyl-2-ethylpyrrolidine | —H | 509 |
| 2854 | propylpyrrolidine | —H | 495 |

462

TABLE 287

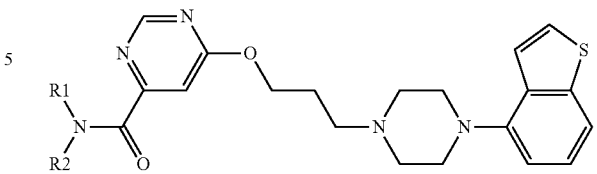

| Example | R1 | R2 | MS(M + 1) |
|---|---|---|---|
| 2855 | butylpyrrolidine | —H | 509 |
| 2856 | propylmorpholine | —H | 511 |
| 2857 | butylmorpholine | —H | 525 |
| 2858 | butyl-1H-benzimidazole | —H | 556 |
| 2859 | ethylnaphthalene | —H | 538 |
| 2860 | propyl-1H-indole | —H | 541 |
| 2861 | ethyl-1H-benzimidazole | —H | 528 |
| 2862 | ethylthiophene | —H | 494 |
| 2863 | butyl-2-oxopyrrolidine | —H | 523 |
| 2864 | ethyltetrahydrofuran | —H | 482 |

TABLE 288

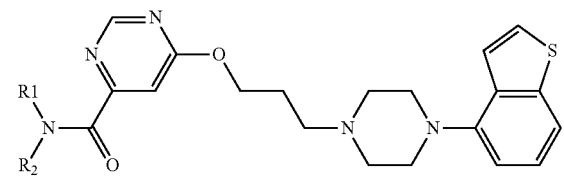

| Example | R1 | R2 | MS(M + 1) |
|---|---|---|---|
| 2865 | 5-methyl-pyrazin-2-yl ethyl | —H | 504 |
| 2866 | pyridin-3-yl propyl | —H | 503 |
| 2867 | pyridin-4-yl propyl | —H | 503 |
| 2868 | 5-methyl-furan-2-yl ethyl | —H | 492 |
| 2869 | 1H-imidazol-4-yl propyl | —H | 492 |
| 2870 | 1-methyl-pyrrol-2-yl ethyl | —H | 491 |
| 2871 | 1,3,5-trimethyl-pyrazol-4-yl ethyl | —H | 520 |
| 2872 | 2,5-dimethyl-furan-3-yl ethyl | —H | 506 |
| 2873 | 1,5-dimethyl-pyrazol-3-yl ethyl | —H | 506 |
| 2874 | 3-methyl-thiophen-2-yl ethyl | —H | 508 |

TABLE 289

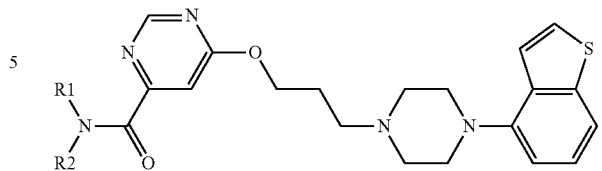

| Example | R1 | R2 | MS(M + 1) |
|---|---|---|---|
| 2875 | thiophen-3-yl ethyl | —H | 494 |
| 2876 | furan-3-yl ethyl | —H | 478 |
| 2877 | thiazol-2-yl ethyl | —H | 495 |
| 2878 | thiophen-2-yl propyl | —H | 508 |
| 2879 | 2,3-dihydrobenzofuran-5-yl ethyl | —H | 530 |
| 2880 | 2-methyl-but-1-enyl | —H | 452 |
| 2881 | 5-oxo-4,5-dihydro-1H-pyrazol-4-yl butyl | —H | 522 |
| 2882 | 1-methyl-piperidin-4-yl methyl | —H | 495 |
| 2883 | 4-pyrrolidin-1-yl-cyclohexyl methyl | —H | 549 |
| 2884 | benzothiophen-2-yl ethyl | —H | 544 |
| 2885 | indan-2-yl methyl | —H | 514 |

TABLE 290

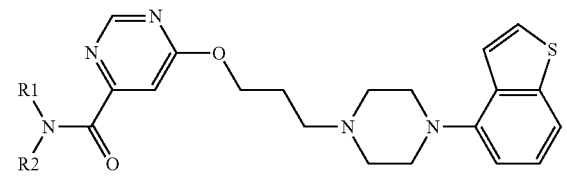

| Example | R1 | R2 | MS(M + 1) |
|---|---|---|---|
| 2886 | 2,3-dihydro-1H-inden-1-yl-methyl | —H | 514 |
| 2887 | (1H-pyrazol-1-yl)ethyl | —H | 492 |
| 2888 | 1-propyl-1H-indol-3-yl-methyl | —H | 541 |
| 2889 | furan-2-yl-propyl | —H | 492 |
| 2890 | tetrahydro-2H-pyran-4-yl-methyl | —H | 482 |
| 2891 | 2-(thiophen-2-yl)phenyl-ethyl | —H | 570 |
| 2892 | 5-ethyl-1-methyl-1H-imidazol-4-yl | —CH₃ | 506 |
| 2893 | 1,5-dimethyl-3-ethyl-1H-pyrazol-4-yl | —CH₃ | 520 |
| 2894 | 1-(4-methylpiperazin-1-yl)propan-1-one | —CH₃ | 552 |
| 2895 | 1-(pyrrolidin-1-yl)propan-1-one | —CH₃ | 523 |
| 2896 | 1-(morpholin-4-yl)propan-1-one | —CH₃ | 539 |

TABLE 291

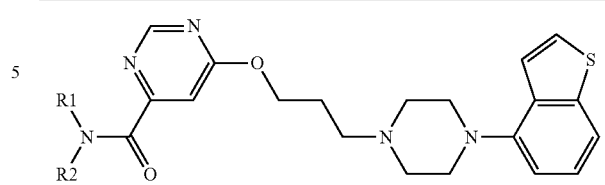

| Example | R1 | R2 | MS(M + 1) |
|---|---|---|---|
| 2897 | 3-ethyl-1-methyl-1H-indazol-? | —H | 542 |
| 2898 | 2,5-dimethyl-4-ethyl-oxazol-? | —CH₃ | 521 |
| 2899 | 5-(furan-2-yl)-3-ethyl-isoxazol-? | —CH₃ | 559 |
| 2900 | 5-phenyl-3-ethyl-isoxazol-? | —CH₃ | 569 |
| 2901 | 6-ethyl-imidazo[1,2-a]pyridin-? | —CH₃ | 542 |
| 2902 | 5-ethyl-1,3-dimethyl-1H-pyrazol-? | —H | 506 |
| 2903 | 3-ethyl-1-methyl-1H-indazol-? | —CH₃ | 556 |
| 2904 | 2-ethyl-thieno[3,2-b]pyridin-? | —CH₃ | 559 |
| 2905 | 2,5-dimethyl-4-ethyl-oxazol-? | —H | 507 |

TABLE 292

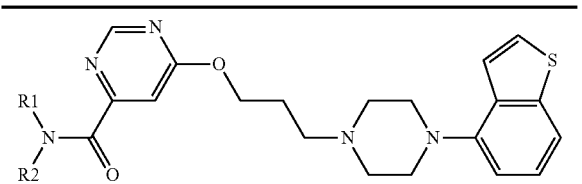

| Example | R1 | R2 | MS(M + 1) |
|---|---|---|---|
| 2906 | (1-propyl-imidazolidin-2-one) | —H | 510 |
| 2907 | (1-methyl-5-ethyl-indole) | —CH₃ | 555 |
| 2908 | (5-(thiophen-2-yl)-3-ethyl-isoxazole) | —H | 561 |
| 2909 | (1-methyl-5-phenyl-3-ethyl-pyrazole) | —H | 568 |

TABLE 292-continued

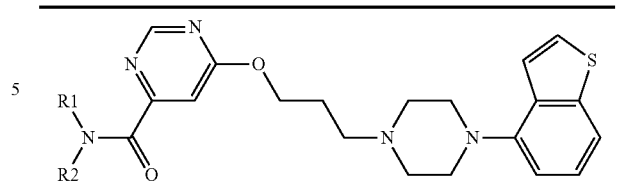

| Example | R1 | R2 | MS(M + 1) |
|---|---|---|---|
| 2910 | (2,3-dihydro-7-ethyl-thieno[3,4-b][1,4]dioxine) | —CH₃ | 566 |
| 2911 | (4-(pyridin-2-yl)phenyl ethyl) | —CH₃ | 579 |
| 2912 | (1-methyl-3-phenyl-5-ethyl-pyrazole) | —CH₃ | 582 |
| 2913 | (7-propyl-2,3-dihydrobenzofuran) | —H | 544 |

TABLE 293

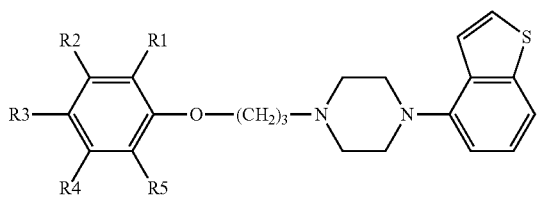

| Example | R1 | R2 | R3 | R4 | R5 | Crystal form (Recrystalization solvent) | Melting Point (° C.) | Salt |
|---|---|---|---|---|---|---|---|---|
| 2914 | —CH₃ | —H | (1-methyl-4-hydroxy-piperidine) | —H | —OCH₃ | White powder (Ethyl acetate) | 230.0 (dec) | Hydrochloride |
| 2915 | —CH₃ | —H | (N-(1-methylpiperidin-4-yl)acetamide) | —H | —OCH₃ | | | |
| 2916 | —CH₃ | —H | (N-methyl-N-(1-methylpiperidin-4-yl)acetamide) | —H | —OCH₃ | White powder (Ethyl acetate) | 235.0 (dec) | Hydrochloride |

TABLE 293-continued

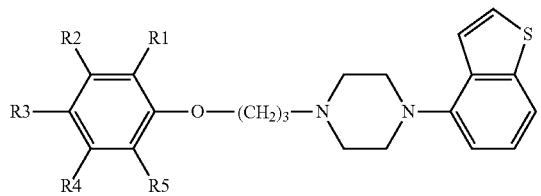

| Example | R1 | R2 | R3 | R4 | R5 | Crystal form (Recrystalization solvent) | Melting Point (° C.) | Salt |
|---|---|---|---|---|---|---|---|---|
| 2917 | —CH₃ | —H | ![structure] | —H | —OCH₃ | White powder (Ethyl acetate) | 227.0 (dec) | Hydrochloride |
| 2918 | —CH₃ | —H | ![structure] | —H | —OCH₃ | White powder (Ethyl acetate) | 240.0 (dec) | Hydrochloride |
| 2919 | —OCH₃ | —H | ![structure] | —H | —CH₃ | White powder (Ethyl acetate) | 211.0-213.5 | Hydrochloride |

TABLE 294

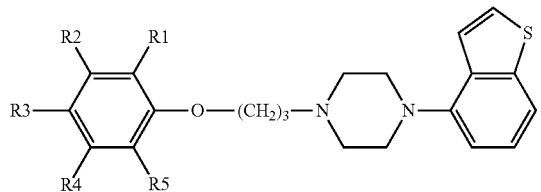

| Example | R1 | R2 | R3 | R4 | R5 | Crystal form (Recrystalization solvent) | Melting Point (° C.) | Salt |
|---|---|---|---|---|---|---|---|---|
| 2920 | —OCH₃ | —H | ![structure] | —H | —CH₃ | White powder (Ethyl acetate) | 207.5-210.0 | Hydrochloride |
| 2921 | —OCH₃ | —H | ![structure] | —H | —CH₃ | White powder (Ethanol/ethyl acetate) | 247.0 (dec) | — |
| 2922 | —CH₃ | —H | —CONHCH₃ | —H | —OC₃H₇ | White powder (Ethanol) | 178.5-179.5 | Hydrochloride |

TABLE 294-continued

[Structure: R1, R2, R3, R4, R5 substituted phenyl-O-(CH2)3-N(piperazine)-N-benzothiophen-4-yl]

| Example | R1 | R2 | R3 | R4 | R5 | Crystal form (Recrystalization solvent) | Melting Point (°C.) | Salt |
|---|---|---|---|---|---|---|---|---|
| 2923 | —OCH₃ | —H | H₃C-O-C(=O)-N(piperidin-4-yl)-NH— | —H | —CH₃ | | | Hydrochloride |
| 2924 | —OCH₃ | —H | H₃C-C(=O)-NH-CH₂-C(=O)-N(piperidin-4-yl)-N(CH₃)— | —H | —CH₃ | White powder (Ethyl acetate) | 248.5-257.5 | Hydrochloride |

TABLE 295

[Structure: R1, R2, R3, R4, R5 substituted phenyl-O-(CH2)3-N(piperazine)-N-benzothiophen-4-yl]

| Example | R1 | R2 | R3 | R4 | R5 | NMR | Salt |
|---|---|---|---|---|---|---|---|
| 2925 | —CH₃ | —H | H₃C-NH-(1-methylpiperidin-4-yl) | —H | —OCH₃ | ¹H-NMR(CDCl3) δ ppm: 1.36-1.65 (4H, m), 1.88-2.11(3H, m), 2.25(3H, s), 2.47(3H, s), 2.60-2.82(8H, m), 3.12-3.29(4H, m), 3.47-3.63(2H, m), 3.82 (3H, s), 3.93(2H, t, J = 6.4 Hz), 6.34 (1H, d, J = 2.7 Hz), 6.40(1H, d, J = 2.7 Hz), 6.90(1H, d, J = 7.1 Hz), 7.21-7.34(1H, m), 7.40(2H, dd, J = 5.5 Hz, 9.9 Hz), 7.55(1H, d, J = 8.0 Hz). | — |
| 2926 | —CH₃ | —H | (CH₃)₃C-O-C(=O)-N(CH₃)-(1-methylpiperidin-4-yl) | —H | —OCH₃ | ¹H-NMR(CDCl3) δ ppm: 1.48(9H, s), 1.67-1.92(4H, m), 1.95-2.11(2H, m), 2.25(3H, s), 2.61-2.87(12H, m), 3.11-3.28(4H, m), 3.54-3.70(2H, m), 3.83 (3H, s), 3.94(2H, t, J = 6.3 Hz), 6.34 (1H, d, J = 2.6 Hz), 6.39(1H, d, J = 2.6 Hz), 6.90(1H, d, J = 6.9 Hz), 7.17-7.34(1H, m), 7.35-7.47(2H, m), 7.55 (1H, d, J = 8.0 Hz). | — |
| 2927 | —CH₃ | —H | 1-methyl-4-oxopiperidine | —H | —OCH₃ | ¹H-NMR(CDCl3) δ ppm: 1.96-2.11 (2H, m), 2.27(3H, s), 2.57(4H, t, J = 6.0 Hz), 2.64-2.84(6H, m), 3.13-3.27 (14H, m), 3.51(4H, t, J = 6.0 Hz), 3.84(3H, s), 3.96(2H, t, J = 6.4 Hz), 6.38(1H, d, J = 2.7 Hz), 6.20(1H, d, J = 2.7 Hz), 6.90(1H, d, J = 7.5 Hz), 7.21-7.32(1H, m), 7.40(2H, dd, J = 5.5 Hz, 10.0 Hz), 7.55(1H, d, J = 8.1 Hz). | — |

TABLE 295-continued

| Example | R1 | R2 | R3 | R4 | R5 | NMR | Salt |
|---------|-----|-----|-----|-----|------|-----|------|
| 2928 | —CH₃ | —H | H₃C—O, H₃C—O (4,4-dimethoxypiperidin-1-yl) | —H | —OCH₃ | ¹H-NMR(CDCl3) δ ppm: 1.83-1.95 (4H, m), 1.95-2.10(2H, m), 2.25 (3H, s), 2.61-2.81(6H, m), 3.07-3.28(14H, m), 3.82(3H, s), 3.93 (2H, t, J = 6.5 Hz), 6.30-6.43 (2H, m), 6.90(1H, d, J = 7.5 Hz), 7.29-7.34(1H, m), 7.41(2H, dd, J = 6.0 Hz, 10.0 Hz), 7.55(1H, d, J = 7.9 Hz). | — |

TABLE 296

| Example | R1 | R2 | R3 | R4 | R5 | Crystal form (Recrystalization solvent) | Melting Point (° C.) | Salt |
|---------|------|-----|---------|-----|------|-----------------------------------------|----------------------|------|
| 2929 | —OCH₃ | —H | —CONH₂ | —H | —CH₃ | White powder (Ethanol) | 189.0-192.5 | Hydrochloride |
| 2930 | —OCH₃ | —H | —CONHCH₃ | —H | —CH₃ | White powder (Isopropyl/alcohol/water) | 165.5-167.0 | — |

TABLE 297

| Example | R1 | Crystal form (Recrystalization solvent) | Melting Point (° C.) | Salt |
|---------|----|------------------------------------------|----------------------|------|
| 2931 | H₃C—O—C(O)—N(piperidin-4-yl-methyl)— | White powder (Ethyl acetate/methanol) | 214-217 | Hydrochloride |
| 2932 | H₂N—C(O)—N(piperidin-4-yl-methyl)— | White powder (Ethyl acetate/methanol) | 218-222 | ½ fumarate |
| 2933 | H₂N-(2-amino-4-methylpyridinyl)— | Colorless needle-form crystal (Ethanol) | 195-196 | — |

TABLE 297-continued

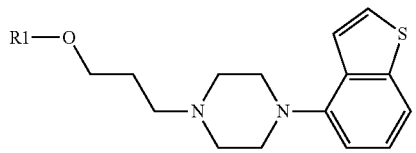

| Example | R1 | Crystal form (Recrystalization solvent) | Melting Point (° C.) | Salt |
|---|---|---|---|---|
| 2934 | ![structure] | White powder (Ethyl acetate) | 145-146 | — |
| 2935 | ![structure] | White powder (Ethanol/ ethyl acetate) | 219-221 | Dihydrochloride |
| 2936 | ![structure] | White powder (Ethyl acetate) | 162-164 | — |
| 2937 | ![structure] | White powder (Ethanol/ether) | 208.5-209.5 | Dihydrochloride |
| 2938 | ![structure] | White powder (n-hexane/ ethyl acetate) | 137-139 | — |
| 2939 | ![structure] | White powder (Ethanol) | 137-139 | — |
| 2940 | ![structure] | White powder (Ethyl acetate) | 163-165 | — |
| 2941 | ![structure] | White powder (Ethyl acetate) | 196-199 | — |

TABLE 298

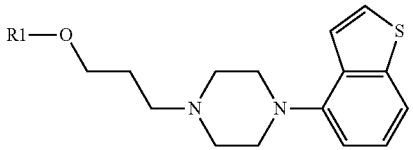

| Example | R1 | Crystal form (Recrystalization solvent) | Melting Point (° C.) | Salt |
|---|---|---|---|---|
| 2942 | 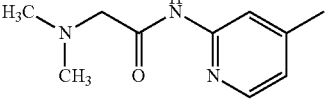 | White powder (Ethyl acetate) | 197-199 | — |
| 2943 | 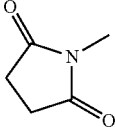 | White powder (Ethanol) | 232-233 | Dihydrochloride |
| 2944 | 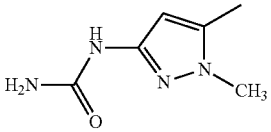 | White powder (Ethanol/ether) | 255-257 | Hydrochloride |
| 2945 | 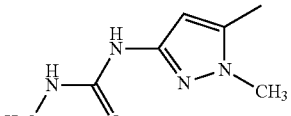 | White powder (Ethanol) | 169.5-172.5 | — |
| 2946 | 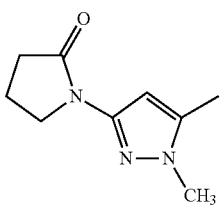 | White powder (Ethanol) | 195.0-196.5 | — |
| 2947 | 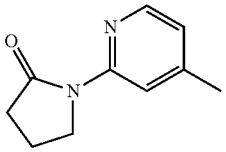 | White powder (Ethyl acetate/ isopropyl ether) | 151.5-153.5 | — |
| 2948 | 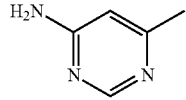 | White powder (Ethyl acetate) | 235.0 (dec) | Hydrochloride |
| 2949 | 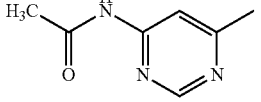 | | | |
| 2950 |  | White powder (Ethyl acetate) | 224.0-227.5 | Hydrochloride |

TABLE 298-continued

[Structure: R1—O—(CH₂)₃—N(piperazine)N—benzothiophen-4-yl]

| Example | R1 | Crystal form (Recrystalization solvent) | Melting Point (° C.) | Salt |
|---------|----|----|----|----|
| 2951 | H₃C-O-C(=O)-NH-(6-methylpyrimidin-4-yl) | White powder (Ethyl acetate/ isopropyl ether) | 175.0-178.5 | — |

TABLE 299

[Structure: R1—O—(CH₂)₃—N(piperazine)N—benzothiophen-4-yl]

| Example | R1 | Crystal form (Recrystalization solvent) | Melting Point (° C.) | Salt |
|---------|----|----|----|----|
| 2952 | 1-acetyl-4-(6-methylpyrimidin-4-yl)piperazinyl | White powder (Ethyl acetate) | 169.0-173.0 | Trihydrochloride |
| 2953 | 1-(6-methylpyrimidin-4-yl)-2-oxopyrrolidinyl | | | |
| 2954 | 1-(6-methylpyrimidin-4-yl)pyrrolidinyl | White powder (Ethyl acetate) | 210.0-217.0 | Dihydrochloride |
| 2955 | N,N-dimethyl-6-methylpyrimidin-4-amine | White powder (Ethyl acetate) | 181.0-188.0 | Dihydrochloride |
| 2956 | (2S,4R)-1-acetyl-4-methyl-N-methylpyrrolidine-2-carboxamide | White powder (Ethanol/ethyl acetate) | 163.5-167.0 | Hydrochloride |

TABLE 299-continued

| Example | R1 | Crystal form (Recrystalization solvent) | Melting Point (° C.) | Salt |
|---|---|---|---|---|
| 2957 | (structure) | White powder (Ethyl acetate/ether) | 172.5-176.5 | Hydrochloride |
| 2958 | (structure) | White powder (Ethyl acetate/ether) | 145.0-151.0 | Dihydrochloride |
| 2959 | (structure) | White powder (Ethanol/ethyl acetate) | 144.0-150.0 | Dihydrochloride |

TABLE 300

| Example | R1 | Crystal form (Recrystalization solvent) | Melting Point (° C.) | Salt |
|---|---|---|---|---|
| 2960 | (structure) | White powder (Ethyl acetate/ether) | 177-182 | Dihydrochloride |
| 2961 | (structure) | White powder (Ethyl acetate/ether) | 198-201 | Hydrochloride |
| 2962 | (structure) | White powder (Ethyl acetate/ether) | 195-200 | Hydrochloride |

TABLE 300-continued

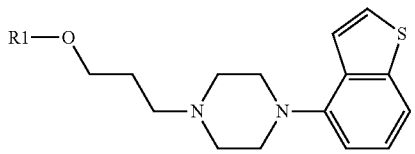

| Example | R1 | Crystal form (Recrystalization solvent) | Melting Point (° C.) | Salt |
|---|---|---|---|---|
| 2963 | morpholine-4-carbonyl-(4-methylpiperidine) | White powder (Ethyl acetate/ether) | 215-218 | Hydrochloride |
| 2964 | ethyl-NH-C(O)-(4-methylpiperidine) | White powder (Ethyl acetate/ether) | 152-157 | Hydrochloride |
| 2965 | cyclopropyl-NH-C(O)-(4-methylpiperidine) | White powder (Ethyl acetate/ether) | 158-161 | Hydrochloride |
| 2966 | isopropyl-NH-C(O)-(4-methylpiperidine) | White powder (Ethyl acetate/ether) | 168-172 | Hydrochloride |
| 2967 | 5-methylpyrazine-2-carboxamide | White powder (Ethyl acetate) | 178.5-181.5 | — |
| 2968 | 1-(2,2,2-trifluoroethyl)-5-methyl-N-methyl-pyrazole-3-carboxamide | White powder (Ethyl acetate) | 228.0 (dec) | Hydrochloride |

TABLE 301

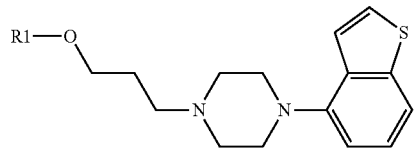

| Example | R1 | NMR | Salt |
|---|---|---|---|
| 2969 | (structure: 6-methylpyrimidine-4-carboxylic acid) | ¹H-NMR (DMSO-d6) δ ppm: 1.95-2.10 (2H, m), 2.85-2.95 (2H, m), 3.00-3.15 (4H, m), 3.15-3.30 (4H, m), 4.41 (2H, t, J = 5.8 Hz), 6.89 (1H, d, J = 5.0 Hz), 7.15 (1H, s), 7.26 (1H, t, J = 7.9 Hz), 7.43 (1H, d, J = 5.5 Hz), 7.63 (1H, d, J = 8.0 Hz), 7.71 (1H, d, J = 5.5 Hz), 8.73 (1H, s). | — |
| 2970 | (structure: N-methyl-4-methylprolinamide) | ¹H-NMR (CDCl₃) δ ppm: 1.72-1.98 (4H, m), 2.30-2.46 (1H, m), 2.46-2.58 (2H, m), 2.62-2.77 (5H, m), 2.80 (3H, d, J = 5.1 Hz), 3.04-3.29 (5H, m), 3.38-3.55 (2H, m), 3.83-4.04 (2H, m), 6.90 (1H, dd, J = 0.5 Hz, 7.6 Hz), 7.22-7.34 (1H, m), 7.34-7.47 (2H, m), 7.55 (1H, d, J = 8.0 Hz), 7.63 (1H, br). | |
| 2971 | (structure: N-Boc N-methyl-4-methylprolinamide) | ¹H-NMR (CDCl₃) δ ppm: 1.46 (9H, s), 1.70-1.89 (2H, m), 1.90-2.17 (1H, m), 2.44-2.60 (2H, m), 2.62-2.75 (4H, m), 2.81 (3H, d, J = 4.7 Hz), 3.09-3.26 (4H, m), 3.39-3.57 (4H, m), 3.93-4.21 (1H, m), 4.21-4.46 (1H, m), 6.65-6.95 (1H, br), 6.90 (1H, d, J = 7.0 Hz), 7.20-7.34 (1H, m), 7.35-7.45 (2H, m), 7.55 (1H, d, J = 8.0 Hz). | |

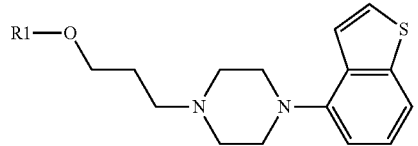

| Example | R1 | MS(M + 1) | Salt |
|---|---|---|---|
| 2972 | (structure: 1,1-dimethyl-3-(4-methylpyridin-2-yl)urea) | 440 | Hydrochloride |
| 2973 | (structure: 1-methylpyrrolidin-2-one) | 360 | Maleate |

TABLE 302

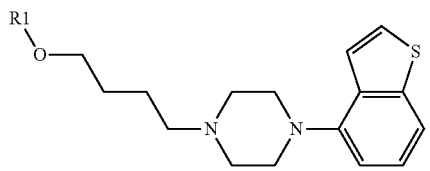

| Example | R1 | Crystal form (Recrystalization solvent) | Melting Point (° C.) | Salt |
|---|---|---|---|---|
| 2974 | ![pyrrolidine-2,5-dione N-methyl] | White powder (Ethyl acetate/ether) | 215.5-216.5 | Hydrochloride |
| 2975 | ![1-methylpyrrolidin-2-one] | | | |
| 2976 | ![H2N-C(O)-NH-pyrazole-1,5-dimethyl] | White powder (Ethyl acetate/ isopropyl ether) | 132.5-135.0 | — |
| 2977 | ![H3C-NH-C(O)-NH-pyrazole] | White powder (2-proparol water) | 180.0-182.0 | — |
| 2978 | ![pyrrolidinone-pyrazole] | White powder (Ethyl acetate) | 216.0-220.2 | Hydrochloride |
| 2979 | ![H3C-NH-C(O)-pyridine-methyl] | White powder (Ethyl acetate) | 203.0-207.0 | Hydrochloride |
| 2980 | ![H2N-C(O)-pyridine-methyl] | White powder (Ethyl acetate/ isopropyl ether) | 146.5-148.0 | — |
| 2981 | ![H3C-NH-C(O)-pyrimidine-methyl] | White powder (Ethyl acetate) | 197.0-201.0 | Hydrochloride |

TABLE 302-continued

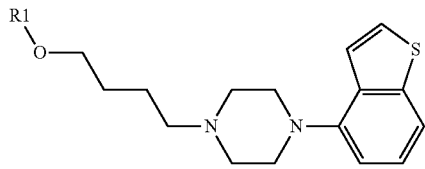

| Example | R1 | Crystal form (Recrystalization solvent) | Melting Point (° C.) | Salt |
|---|---|---|---|---|
| 2982 | 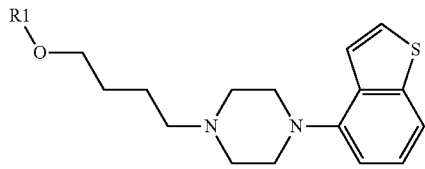 | White powder (Ethyl acetate/ isopropyl ether) | 133.0-134.5 | — |

TABLE 303

| Example | R1 | R2 | R3 | R4 | R5 | R6 | MS(M + 1) |
|---|---|---|---|---|---|---|---|
| 2983 | —OCH₃ | —H | —H | —H | —H | —CH₃ | 517 |
| 2984 | —H | —H | —CH₃ | —H | —H | —CH₃ | 501 |
| 2985 | —H | —H | —Cl | —H | —H | —CH₃ | 521 |
| 2986 | —H | —SCH₃ | —H | —H | —H | —H | 519 |
| 2987 | —SCH₃ | —H | —H | —H | —H | —H | 519 |
| 2988 | —H | —Cl | —Cl | —H | —H | —H | 541 |
| 2989 | —H | —H | —OCF₃ | —H | —H | —H | 557 |
| 2990 | —H | —H | —H | —H | —H | —H | 473 |
| 2991 | —H | —H | —Cl | —H | —H | —H | 507 |
| 2992 | —H | —H | —OCH₃ | —H | —H | —H | 503 |
| 2993 | —OCH₃ | —H | —H | —H | —H | —H | 503 |
| 2994 | —H | —OCH₃ | —H | —H | —H | —H | 503 |
| 2995 | —Cl | —H | —H | —H | —H | —H | 507 |
| 2996 | —H | —Cl | —H | —H | —H | —H | 507 |
| 2997 | —H | —H | —CH₃ | —H | —H | —H | 487 |
| 2998 | —OCH₃ | —H | —OCH₃ | —H | —H | —H | 533 |
| 2999 | —N(CH₃)₂ | —H | —H | —H | —H | —H | 516 |
| 3000 | -1-PYRRYL | —H | —H | —H | —H | —H | 538 |
| 3001 | —H | —Cl | —H | —H | —OCH₃ | —H | 537 |
| 3002 | —H | —OCH₃ | —H | —H | —OCH₃ | —H | 533 |
| 3003 | —H | —OCH₃ | —H | —OCH₃ | —H | —H | 533 |
| 3004 | —OCH₃ | —H | —H | —CH₃ | —H | —H | 517 |
| 3005 | —H | —OCH₃ | —OCH₃ | —H | —H | —H | 533 |
| 3006 | —C(CH₃)=CH₂ | —H | —H | —H | —H | —H | 513 |
| 3007 | —H | —OCF₃ | —H | —H | —H | —H | 557 |
| 3008 | —CH₃ | —H | —H | —H | —H | —H | 487 |
| 3009 | —H | —CH₃ | —H | —H | —H | —H | 487 |
| 3010 | —F | —H | —H | —H | —H | —H | 491 |

TABLE 304

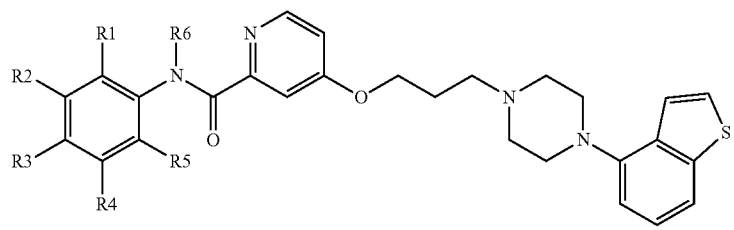

| Example | R1 | R2 | R3 | R4 | R5 | R6 | MS(M + 1) |
|---|---|---|---|---|---|---|---|
| 3011 | —H | —H | —F | —H | —H | —H | 491 |
| 3012 | —H | —N(CH$_3$)$_2$ | —H | —H | —H | —H | 516 |
| 3013 | —H | —H | —N(CH$_3$)$_2$ | —H | —H | —H | 516 |
| 3014 | —CF$_3$ | —H | —H | —H | —H | —H | 541 |
| 3015 | —H | —CF$_3$ | —H | —H | —H | —H | 541 |
| 3016 | —H | —NHCOCH$_3$ | —H | —H | —H | —H | 530 |
| 3017 | —H | —H | —NHCOCH$_3$ | —H | —H | —H | 530 |
| 3018 | —H | —H | —H | —H | —CN | —H | 498 |
| 3019 | —H | —H | —H | —CN | —H | —H | 498 |
| 3020 | —CH$_3$ | —H | —H | —H | —H | —CH$_3$ | 501 |
| 3021 | —H | —CH$_3$ | —H | —H | —H | —CH$_3$ | 501 |
| 3022 | —H | —Cl | —H | —H | —H | —CH$_3$ | 521 |
| 3023 | —H | —H | —OH | —H | —H | —CH$_3$ | 503 |
| 3024 | —CH$_3$ | —CH$_3$ | —H | —H | —H | —H | 501 |
| 3025 | —CH$_3$ | —H | —CH$_3$ | —H | —H | —H | 501 |
| 3026 | —CH$_3$ | —H | —H | —H | —CH$_3$ | —H | 501 |
| 3027 | —H | —CH$_3$ | —CH$_3$ | —H | —H | —H | 501 |
| 3028 | —H | —CH$_3$ | —H | —CH$_3$ | —H | —H | 501 |
| 3029 | —F | —F | —H | —H | —H | —H | 509 |
| 3030 | —H | —F | —F | —H | —H | —H | 509 |
| 3031 | —H | —F | —H | —F | —H | —H | 509 |
| 3032 | —H | —F | —OCH$_3$ | —H | —H | —H | 521 |
| 3033 | —H | —OCH$_3$ | —CH$_3$ | —H | —H | —H | 517 |
| 3034 | —H | —Cl | —OCH$_3$ | —H | —H | —H | 537 |
| 3035 | —H | —Cl | —CH$_3$ | —H | —H | —H | 521 |
| 3036 | —OCH$_3$ | —OCH$_3$ | —H | —H | —H | —H | 533 |
| 3037 | —H | —Cl | —OH | —H | —H | —H | 523 |
| 3038 | —Cl | —H | —H | —CH$_3$ | —H | —H | 521 |

TABLE 305

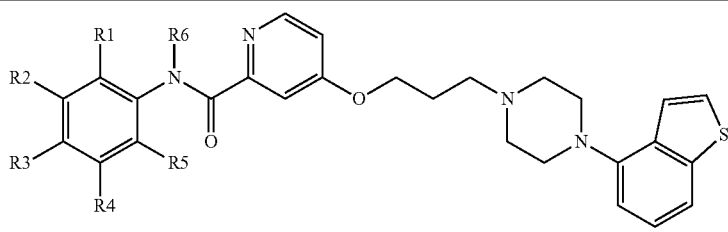

| Example | R1 | R2 | R3 | R4 | R5 | R6 | MS(M + 1) |
|---|---|---|---|---|---|---|---|
| 3039 | —H | —CONH$_2$ | —H | —H | —Cl | —H | 550 |
| 3040 | —CH$_3$ | —H | —Br | —H | —CH$_3$ | —H | 579 |
| 3041 | —H | —H | —CN | —H | —H | —H | 498 |
| 3042 | —H | —H | —SCH$_3$ | —H | —H | —H | 519 |
| 3043 | —H | —H | —CH(CH$_3$)$_2$ | —H | —H | —H | 515 |
| 3044 | —H | —H | -2-FURYL | —H | —H | —H | 539 |

TABLE 306
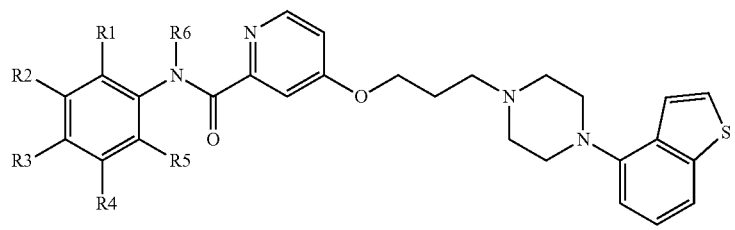
| Example | R1 | R2 | R3 | R4 | R5 | R6 | MS(M + 1) |
|---|---|---|---|---|---|---|---|
| 3045 | —H | 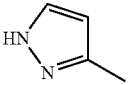 | —H | —H | —H | —H | 539 |
| 3046 | —H | 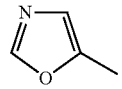 | —H | —H | —H | —H | 540 |
| 3047 | —H | 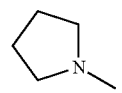 | —H | —H | —H | —H | 542 |
| 3048 | —H | —H | 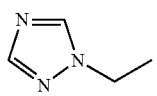 | —H | —H | —H | 554 |
| 3049 | —H | 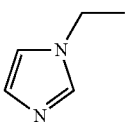 | —H | —H | —H | —H | 553 |
| 3050 | —H | —H | 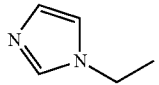 | —H | —H | —H | 553 |
| 3051 | —H | 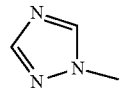 | —H | —H | —H | —H | 540 |
TABLE 307
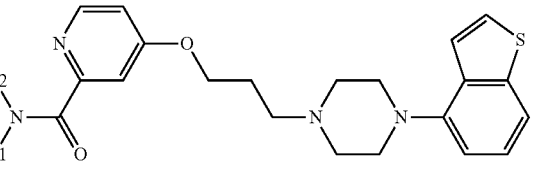
| Example | R1 | R2 | MS(M + 1) |
|---|---|---|---|
| 3052 | 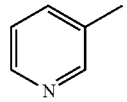 | —H | 474 |
| 3053 | 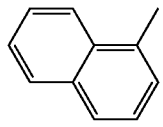 | —H | 523 |
| 3054 | 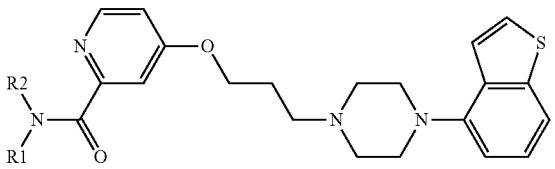 | —H | 513 |
| 3055 | 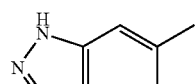 | —H | 474 |
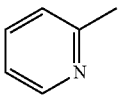

TABLE 307-continued

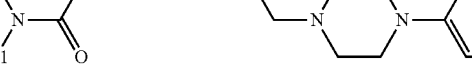

| Example | R1 | R2 | MS(M + 1) |
|---|---|---|---|
| 3056 | 4-methylpyridin-3-yl | —H | 474 |
| 3057 | 3-methylquinolin-? | —H | 524 |
| 3058 | 3-methoxy-2-methylpyridinyl | —H | 504 |
| 3059 | 5-methyl-1H-indol-? | —H | 512 |
| 3060 | 8-fluoro-5-methyl-3,4-dihydroquinolin-2(1H)-one | —H | 560 |

TABLE 308

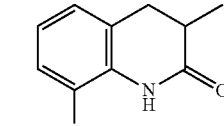

| Example | R1 | R2 | MS(M + 1) |
|---|---|---|---|
| 3061 | 5,8-dimethyl-3,4-dihydroquinolin-2(1H)-one | —H | 556 |
| 3062 | 6,8-dimethyl-3,4-dihydroquinolin-2(1H)-one | —H | 556 |

TABLE 308-continued

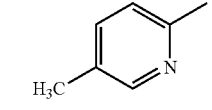

| Example | R1 | R2 | MS(M + 1) |
|---|---|---|---|
| 3063 | 8-methoxy-3-methyl-3,4-dihydroquinolin-2(1H)-one | —H | 572 |
| 3064 | 2,5-dimethylpyridinyl | —H | 488 |
| 3065 | 2-methylthiazol-? | —H | 480 |
| 3066 | 6-methylquinolin-? | —H | 524 |
| 3067 | 6-methylbenzothiazol-2(3H)-one | —H | 546 |
| 3068 | 3,5-dimethylisoxazol-? | —H | 478 |

TABLE 309

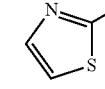

| Example | R1 | R2 | MS(M + 1) |
|---|---|---|---|
| 3069 | 4-methyl-6-(2-oxopyrrolidin-1-yl)pyridin-? | —H | 556 |
| 3070 | 6-methyl-1,3-dihydro-2H-indol-2-one | —H | 528 |

TABLE 309-continued

Structure: pyridine with R2-N(R1)-C(=O) at 2-position and O-CH2CH2CH2-N(piperazine)-N-benzothiophen-4-yl at 4-position.

| Example | R1 | R2 | MS(M + 1) |
|---|---|---|---|
| 3071 | 6-chloro-2-methyl-benzothiazol-yl | —H | 564 |
| 3072 | 2-methyl-4,5,6,7-tetrahydrobenzothiazol-yl | —H | 534 |
| 3073 | 2-methyl-1H-benzimidazol-yl | —H | 513 |
| 3074 | 1,3-dimethyl-1H-pyrazol-5-yl (H3C, CH3) | —H | 491 |
| 3075 | 5-methyl-1H-imidazole-4-carboxamide-yl | —H | 506 |
| 3076 | 3,4-dimethyl-isoxazol-5-yl | —H | 492 |
| 3077 | 5-(furan-2-yl)-1H-pyrazol-3-yl methyl | —H | 529 |

TABLE 310

Structure: pyridine with R2-N(R1)-C(=O) at 2-position and O-CH2CH2CH2-N(piperazine)-N-benzothiophen-4-yl at 4-position.

| Example | R1 | R2 | MS(M + 1) |
|---|---|---|---|
| 3078 | CH3-C(=N-CH2-CHO) | —H | 480 |
| 3079 | 1,5-dimethyl-1H-pyrazol-yl | —H | 477 |
| 3080 | 3,5-dimethyl-isothiazol-yl | —H | 494 |
| 3081 | 3-methyl-isoxazol-yl | —H | 464 |
| 3082 | 3,5-dimethyl-isoxazol-yl | —H | 478 |
| 3083 | 5-bromo-2,4-dimethyl-pyridin-yl | —H | 566 |
| 3084 | 1,6-dimethyl-2-oxo-1,2,3,4-tetrahydroquinolin-yl | —H | 556 |
| 3085 | 1,5-dimethyl-1H-indol-yl | —H | 526 |

TABLE 311

[Structure: core compound with R1-NH-C(=O)- attached to benzene ring bearing OCH3, CH3, and O-(CH2)3-piperazine-benzo[b]thiophen-4-yl]

| Example | R1 | MS(M + 1) |
|---|---|---|
| 3086 | H3C-C(=O)-NH-CH(CH3)-CH(CH3)2 type group | 553 |
| 3087 | O=C(CH3)-NH-CH(CH3)2 | 525 |
| 3088 | H3C-O-piperidine-N-ethyl | 567 |
| 3089 | HO-CH2-CH(NH2)-CH3 | 499 |
| 3090 | H2N-C(CH3)2-C(=O)- | 497 |
| 3091 | H3C-S-CH2-CH(NH2)-CH3 | 543 |
| 3092 | imidazolyl-CH2-CH(NH2)-CH3 | 549 |
| 3093 | phenyl-CH2-CH(NH2)-CH3 | 559 |

Example 3094

Synthesis of 3-amino-4-[3-(4-benzo[b]thiophen-4-yl-piperazin-1-yl)propoxy]-N-ethyl-benzamide 5% palladium carbon (0.8 g) was added to an ethanol solution (30 ml) of 4-[3-(4-benzo[b]thiophen-4-yl-piperazin-1-yl)propoxy]-N-ethyl-3-nitrobenzamide (1.0 g, 2.1 mmol) and the mixture was subjected to catalytic reduction at room temperature under normal pressure. The catalyst was removed by filtration and the filtrate was concentrated under reduced pressure. Water was added to the residue and the solution was extracted with ethyl acetate. The organic layer was dried over anhydrous sodium sulfate and thereafter concentrated under reduced pressure. The residue was purified by silica gel column chromatography (dichloromethane:methanol=30:1→20:1). The purified product was concentrated under reduced pressure to obtain 3-amino-4-[3-(4-benzo[b]thiophen-4-yl-piperazin-1-yl)propoxy]-N-ethyl-benzamide (0.78 g, 83% yield) as yellow amorphous solid.

$^1$H-NMR (CDCl$_3$) δppm: 1.23 (3H, t, J=7.4 Hz), 2.00-2.15 (2H, m), 2.67 (2H, t, J=7.3 Hz), 2.75 (4H, brs), 3.21 (4H, brs), 3.40-3.50 (2H, m), 3.50-4.30 (2H, br), 4.13 (2H, t, J=6.5 Hz), 5.99 (1H, brs), 6.80 (1H, d, J=8.4 Hz), 6.90 (1H, d, J=7.6 Hz), 7.08 (1H, dd, J=2.1, 8.3 Hz), 7.19 (1H, d, J=2.1 Hz), 7.25-7.30 (1H, m), 7.35-7.45 (2H, m), 7.55 (1H, d, J=8.0 Hz).

Example 3095

Synthesis of 1-benzo[b]thiophen-4-yl-4-[3-(1-acetylpiperidin-4-yloxy)propyl]piperazine hydrochloride Triethylamine (0.28 ml, 2.0 mmol) was added to a dichloromethane solution (15 ml) of 1-benzo[b]thiophen-4-yl-4-[3-(piperidin-4-yloxy)-propyl]-piperazine (0.45 g, 1.25 mmol) and the mixture was cooled in an ice bath. To this, acetyl chloride (0.1 ml, 1.4 mmol) was added and the mixture was stirred at room temperature overnight. Water was added to the reaction solution, which was then extracted with dichloromethane. The organic layer was dried over anhydrous sodium sulfate and thereafter concentrated under reduced pressure. The residue was purified by silica gel column chromatography (dichloromethane:methanol=30:1). The purified product was concentrated under reduced pressure. To the residue, 0.5 N hydrochloride-methanol solution (3 ml) was added. The crystal produced was obtained by filtration and dried to obtain 1-benzo[b]thiophen-4-yl-4-[3-(1-acetylpiperidin-4-yloxy)propyl]piperazine hydrochloride as white powder (0.36 g, 66% yield).

Melting point: 208-210° C.

Example 3096

Synthesis of 1-[3-(4-Benzo[b]thiophen-4-yl-piperazin-1-yl)propoxy]pyrrolidine-2,5-dione hydrochloride PS-triphenylphosphine (3 mmol/g, 1.80 g), ditert-butylazodicarboxylate (1.27 g, 5.4 mmol) and N-hydroxysuccinimide (510 mg, 4.3 mmol) were added to a THF solution (50 ml) of 3-(4-benzo[b]thiophen-4-ylpiperazin-1-yl)propanol (1.00 g, 3.6 mmol) and the mixture was stirred at room temperature for 4 hours. The resin was removed by filtration and the filtrate was concentrated under reduced pressure. The residue was purified by basic silica gel column chromatography (n-hexane:ethyl acetate=1:2). The purified product was concentrated under reduced pressure to obtain white amorphous solid (762 mg, 47% yield). 157 mg of the white amorphous solid was dissolved in ethanol. To the solution, 1N hydrochloric acid-ethanol solution (0.42 ml) was added and further ether was added. The solution was stand still in a refrigerator. The crystal produced was filtrated and dried to obtain 1-[3-(4-Benzo[b]thiophen-4-yl-piperazin-1-yl)propoxy]-pyrrolidine-2,5-dione hydrochloride (158 mg) as a white powder.

Melting point: 255.0-257.0° C.

Example 3097

Synthesis of 6-[3-(4-benzo[b]thiophen-4-yl-piperazin-1-yl)propoxy]naphthalene-1-carboxylic acid amide Triethylamine (0.24 ml, 1.7 mmol) and isobutyl chloroformate (0.19 ml, 1.4 mmol) were added to an acetonitrile solution (10 ml) of 6-[3-(4-benzo[b]thiophen-4-yl-piperazin-1-yl)-propoxy]-naphthalene-1-carboxylic acid (0.52 g, 1.2 mmol) under ice cooling and the mixture was stirred for 20 minutes. To the reaction solution, 28% ammonia water (0.5 ml) was added and the mixture was stirred at room temperature for 20 minutes. To the reaction solution, ethyl acetate was added and the solution was washed with water. The organic layer was dried over anhydrous magnesium sulfate and thereafter concentrated under reduced pressure. The residue was purified by basic silica gel column chromatography (n-hexane:ethyl acetate=2:1→0:1). The purified product was concentrated under reduced pressure and the residue was recrystallized from a solvent mixture of ethyl acetate-diisopropylether to obtain 6-[3-(4-benzo[b]thiophen-4-yl-piperazin-1-yl)propoxy]-1-naphthalene-1-carboxylic acid amide (0.27 g, 53% yield) as white powder.
Melting point 167.0-169.0° C.

Example 3098

Synthesis of 1-allyl-5-[3-(4-benzo[b]thiophen-4-yl-piperazin-1-yl)propoxy]-1H-pyrazole-3-carboxylic acid methylamide 40% methylamine methanol solution (5 ml) was added to a methanol solution (5 ml) of 1-allyl-5-[3-(4-benzo[b]thiophen-4-yl-piperazin-1-yl)propoxy]-1H-pyrazole-3-carboxylic acid ethyl ester (0.5 g, 1.1 mmol) and the mixture was stirred at room temperature for 3 days. The solution was concentrated under reduced pressure and the residue was purified by basic silica gel column chromatography (n-hexane:ethyl acetate=5:1→0:1). The purified product was concentrated under reduced pressure and the residue was recrystallized from a solvent mixture of ethyl acetate-diisopropylether to obtain 1-allyl-5-[3-(4-benzo[b]thiophen-4-yl-piperazin-1-yl)propoxy]-1H-pyrazole-3-carboxylic acid methylamide (0.32 µg, 67% yield) as white powder.
Melting point 138.5-140.5° C.

Example 3099

Synthesis of 4-[3-(4-benzo[b]thiophen-4-yl-piperazin-1-yl)propoxy]-cyclohexanecarboxylic acid amide Ammonia water (28%, 0.5 ml), 1-(3-dimethylaminopropyl)-3-ethylcarbodiimide hydrochloride (WSC)(0.36 g, 1.9 mmol) and 4-dimethylaminopyridine (DMAP) (0.05 g, 0.4 mmol) were added to a dichloromethane solution (10 ml) of 4-[3-(4-benzo[b]thiophen-4-yl-piperazin-1-yl)propoxy]-cyclohexanecarboxylic acid (0.5 g, 1.2 mmol) and the mixture was stirred at room temperature for 19 hours. To the reaction solution, dichloromethane was added and the mixture was washed with water. The organic layer was dried over anhydrous magnesium sulfate and thereafter concentrated under reduced pressure. The residue was purified by basic silica gel column chromatography (n-hexane:ethyl acetate=3:1→0:1). The purified product was concentrated under reduced pressure and the residue was recrystallized from a solvent mixture of ethyl acetate-diisopropylether to obtain 4-[3-(4-benzo[b]thiophen-4-yl-piperazin-1-yl)-propoxy]-cyclohexanecarboxylic acid amide (0.1 g, 22% yield), as white powder.
Melting point 107.5-108.5° C.

Example 3100

Synthesis of ethanesulfonic acid {4-[3-(4-benzo[b]thiophen-4-yl-piperazin-1-yl)propoxy]-3-methoxy-5-methyl-phenyl}amide hydrochloride A dichloromethane solution (4 ml) of 4-[3-(4-benzo[b]thiophen-4-yl-piperazin-1-yl)propoxy]-3-methoxy-5-methylphenylamine (0.2 g, 0.49 mmol) was cooled on ice. To this, N-ethyldiisopropylamine (0.15 ml, 0.87 mmol) and ethane sulfonylchloride (0.07 ml, 0.73 mmol) were added and the mixture was stirred at room temperature for one hour. Further, N-ethyldiisopropylamine (0.15 ml, 0.87 mmol) and ethane sulfonylchloride (0.07 ml, 0.73 mmol) were added and the mixture was stirred at room temperature for 19 hours. To this, an aqueous 6N-sodium hydroxide solution (0.5 ml) and ethanol (2 ml) were added and the mixture was stirred at room temperature overnight. Dichloromethane was added to the reaction solution, which was then washed with water. The organic layer was dried over anhydrous magnesium sulfate and thereafter concentrated under reduced pressure. The residue was purified by basic silica gel column chromatography (n-hexane:ethyl acetate=2:1→0:1). The purified product was concentrated under reduced pressure. 4N-hydrochloride/ethyl acetate solution was added to the residue. The crystal generated was filtrated and dried to obtain ethanesulfonic acid {4-[3-(4-benzo[b]thiophen-4-yl-piperazin-1-yl)propoxy]-3-methoxy-5-methyl-phenyl}amide hydrochloride (222 mg, 85% yield) as white powder.
Melting point: 235.5-237.5° C.

Example 3101

Synthesis of 5-[3-(4-benzo[b]thiophen-4-yl-piperazin-1-yl)propoxy]-1-methyl-1H-pyrazol-3-yl}-carbamic acid methyl ester A dichloromethane solution (2 ml) of 5-[3-(4-benzo[b]thiophen-4-yl-piperazin-1-yl)propoxy]-1-methyl-1H-pyrazol-3-yl-amine (0.17 g, 0.47 mmol) was cooled on ice. To this, pyridine (0.08 ml, 0.94 mmol) and methyl chloroformate (0.04 ml, 0.52 mmol) were added and the mixture was stirred at room temperature for 17 hours. To the reaction solution, ethyl acetate was added and the reaction mixture was washed with water. The water layer was extracted with ethyl acetate. The organic layers were combined, dried over anhydrous magnesium sulfate, and thereafter, concentrated under reduced pressure. The residue was purified by basic silica gel column chromatography (n-hexane:ethyl acetate=2:1→1:1). The purified product was concentrated under reduced pressure and the residue was recrystallized from a solvent mixture of ethyl acetate-diisopropylether to obtain 5-[3-(4-benzo[b]thiophen-4-yl-piperazin-1-yl)propoxy]-1-methyl-1H-pyrazol-3-yl}carbamic acid methyl ester (0.10 g, 51% yield) as white powder.
Melting point: 162.5-165.0° C.

Example 3102

Synthesis of 3-{5-[3-(4-benzo[b]thiophen-4-yl-piperazin-1-yl)propoxy]-1-methyl-1H-pyrazol-3-yl}-1,1-dimethyl-urea hydrochloride A dichloromethane solution (5 ml) of 5-[3-(4-benzo[b]thiophen-4-yl-piperazin-1-yl)propoxy]-1-methyl-1H-pyrazol-3-yl-amine (0.27 g, 0.73 mmol) was cooled on ice. To this, triethylamine (0.36 ml, 2.5 mmol), dimethylcarbamoyl chloride (0.20 ml, 2.1 mmol) and pyridine (0.06 ml, 0.73 mmol) were added and the mixture was stirred at room temperature overnight. To the reaction solution, water was added and the reaction solution was extracted with ethyl acetate. The organic layer was dried over anhydrous magnesium sulfate and thereafter concentrated under reduced pressure. The residue was purified by basic silica gel column chromatography (n-hexane:ethyl acetate=3:1→0:1). The purified product was concentrated under reduced pressure and the residue was dissolved in ethyl acetate and a 4N-hydrochloride/ethyl acetate solution was added thereto. The crystal produced was filtrated and dried to obtain 3-{5-[3-(4-benzo[b]thiophen-4-yl-piperazin-1-yl)propoxy]-1-methyl-1H-pyrazol-3-yl}-1,1-dimethyl-urea hydrochloride (0.10 g, 30% yield), as light yellow powder.

Melting point: 174.0-176.5° C.

Example 3103

Synthesis of 3-{5-[4-(4-benzo[b]thiophen-4-yl-piperazin-1-yl)butoxy]-1-methyl-1H-pyrazol-3-yl}-1,1-dimethyl-urea hydrochloride An aqueous dimethylamine solution (50%, 0.16 ml, 1.6 mmol) was added to a DMF solution (3 ml) of 5-[4-(4-Benzo[b]thiophen-4-yl-piperazin-1-yl)butoxy]-1-methyl-1H-pyrazol-3-yl carbamic acid phenyl ester (0.26 g, 0.52 mmol) and the mixture was stirred at room temperature for 16-hours. Water was added to the reaction solution, which was then extracted with ethyl acetate. The organic layer was dried over anhydrous magnesium sulfate and thereafter concentrated under reduced pressure. The residue was purified by basic silica gel column chromatography (n-hexane:ethyl acetate=7:3→0:1). The purified product was concentrated under reduced pressure and the residue was dissolved in ethyl acetate. A 1N-hydrochloric acid/ethanol solution was added and the crystal produced was filtrated and dried to obtain 3-{5-[4-(4-benzo[b]thiophen-4-yl-piperazin-1-yl)butoxy]-1-methyl-1H-pyrazol-3-yl}-1,1-dimethyl-urea hydrochloride (95 mg, 37% yield) as white powder.

Melting point: 186.0-187.5° C.

Example 3104

Synthesis of N-{5-[3-(4-benzo[b]thiophen-4-yl-piperazin-1-yl)propoxy]-1-methyl-1H-pyrazol-3-yl}-acetamide Acetic anhydride (1 ml) and triethylamine (0.09 ml, 0.65 mmol) were added to a dichloromethane solution (4 ml) of 5-[3-(4-benzo[b]thiophen-4-yl-piperazin-1-yl)propoxy]-1-methyl-1H-pyrazol-3-yl-amine (0.20 g, 0.54 mmol) and the mixture was stirred at room temperature for 6 hours. An aqueous potassium carbonate solution was added to the reaction solution, which was then extracted with ethyl acetate. The organic layer was dried over anhydrous magnesium sulfate and thereafter concentrated under reduced pressure. The residue was purified by basic silica gel column chromatography (n-hexane:ethyl acetate=2:1→0:1). The purified product was concentrated under reduced pressure and the residue was recrystallized from a solvent mixture of ethyl acetate-diisopropylether to obtain N-{5-[3-(4-benzo[b]thiophen-4-yl-piperazin-1-yl)propoxy]-1-methyl-1H-pyrazol-3-yl}acetamide (0.19 g, 89% yield) as white powder.

Melting point: 137.0-139.0° C.

Example 3105

Synthesis of 3-{4-[3-(4-benzo[b]thiophen-4-yl-piperazin-1-yl)propoxy]-3-hydroxymethyl-5-methoxyphenyl}oxazolidin-2-one hydrochloride First, 2-[3-(4-benzo[b]thiophen-4-yl-piperazin-1-yl)propoxy]-3-methoxy-5-(2-oxo-oxazolidin-3-yl)benzaldehyde hydrochloride (1.28 g. 2.4 mmol)) was added to an aqueous potassium hydrochloride solution. The mixture was extracted with dichloromethane. The extracted solution was concentrated under reduced pressure and the residue was dissolved in THF (15 ml). To the solution, sodium borohydride (0.05 g, 1.2 mmol) was added under ice cooling and the mixture was stirred at room temperature for 3 hours. Then, 10% hydrochloric acid was added to the mixture under ice cooling to decompose the reagent excessively present. After an aqueous 6N sodium hydroxide solution was added to the solution to make it an alkaline solution, which was then extracted with ethyl acetate. The organic layer was dried over anhydrous magnesium sulfate and thereafter concentrated under reduced pressure. The residue was purified by silica gel column chromatography (dichloromethane:ethyl acetate=3:7→dichloromethane:methanol=100:3). The purified product was concentrated under reduced pressure and the residue was dissolved in ethanol. A 1N hydrochloric acid/ethanol solution was added to this. The crystal produced was recrystallized from ethanol to obtain 3-{4-[3-(4-benzo[b]thiophen-4-yl-piperazin-1-yl)-propoxy]-3-hydroxymethyl-5-methoxyphenyl}oxazolidin-2-one hydrochloride (0.52 g, 41% yield) as white powder.

Melting point: 224.0-226.5° C. (decomposed)

Example 3106

Synthesis of 1-acetyl-4-{4-[3-(4-benzo[b]thiophen-4-yl-piperazin-1-yl)propoxy]-3-methoxy-5-methylphenyl}piperazin hydrochloride 1-benzo[b]thiophen-4-yl-4-[3-(4-bromo-2-methoxy-6-methylphenoxy)propyl]piperazine hydrochloride (0.5 g, 0.98 mmol), 1-acetyl piperazine (0.15 g, 1.2 mmol), palladium acetate (11 mg, 0.048 mmol), 2,2'-bis(diphenylphosphino)-1,1'-binaphtyl (BINAP)(63 mg, 0.098 mmol) and sodium t-butoxide (0.23 g, 2.3 mmol) were added to toluene (10 ml) and the mixture was stirred under an argon atmosphere at 90° C. for 22 hours. The reaction mixture was cooled to room temperature and filtrated by cerite. The filter cake was washed with ethyl acetate. The filtrate and wash liquid were combined and thereafter concentrated under reduced pressure. The residue was purified by basic silica gel column chromatography (n-hexane:ethyl acetate=11:1→1:1). The purified product was concentrated under reduced pressure and the residue was dissolved in ethyl acetate. A 1N hydrochloric acid/ethanol solution was added to this and the crystal produced was filtrated and dried to obtain 1-acetyl-4-{4-[3-(4-benzo[b]thiophen-4-yl-piperazin-1-yl)propoxy]-3-methoxy-5-methylphenyl}-piperazin hydrochloride (75 mg, 14% yield) as white powder.

Melting point: 257.0-261.0° C. (decomposed)

Example 3107

Synthesis of 1-benzo[b]thiophen-4-yl-4-[3-(4-imidazol-1-yl-2-methoxy-6-methyl-phenoxy)-propyl]-piperazine dihydrochloride 1-benzo[b]thiophen-4-yl-4-[3-(4-iodo-2-methoxy-6-methyl-phenoxy)-propyl]-piperazine (0.6 g, 0.69 mmol), imidazole (0.07 g, 1.03 mmol), copper iodide (I) (13 mg, 0.069 mmol), trans-N,N'-dimethyl-1,2-cyclohexanedimaine (0.02 ml, 0.14 mmol) and cesium carbonate (0.47 g, 1.38 mmol) were added to 1,4-dioxane (6 ml) and the mixture was refluxed with heating under an argon atmosphere for 50 hours. After the resultant reaction mixture was cooled to room temperature, water was added to the reaction solution, which was then extracted with ethyl acetate. The organic layer was dried over anhydrous magnesium sulfate and thereafter concentrated under reduced pressure. The residue was purified by basic silica gel column chromatography (n-hexane:ethyl acetate=5:1→1:1). The purified product was concentrated under reduced pressure and the residue was dissolved in ethyl acetate. A 1N-hydrochloric acid/ethanol solution was added to this and the crystal produced was filtrated and dried to obtain 1-benzo[b]thiophen-4-yl-4-[3-(4-imidazol-1-yl-2-methoxy-6-methylphenoxy)propyl]-piperazine dihydrochloride (60 mg, 17% yield) as light yellow powder.

Melting point: 234.0-240.0° C. (decomposed).

Example 3108

Synthesis of 4-[3-(4-benzo[b]thiophen-4-yl-piperazin-1-yl)propoxy]-3,N-dimethyl-5-(2,2,2-trifluoro-ethoxy)benzamide hydrochloride Cesium carbonate (0.34 g, 0.99 mmol) and 1,1,1-trifluoro-2-iodoethane (0.05 ml, 0.47 mmol) were added to a DMF solution (2 ml) of 4-[3-(4-Benzo[b]thiophen-4-yl-piperazin-1-yl)propoxy]-3-hydroxy-5,N-dimethylbenzamide (188 mg, 0.39 mmol), and the mixture was stirred at 40° C. for 2 hours. Then, 1,1,1-trifluoro-2-iodoethane (0.1 ml, 0.94 mmol) was further added and the mixture was stirred at 40° C. for 5 hours. After the reaction mixture was cooled to room temperature, water was added to the reaction solution, which was then extracted with ethyl acetate. The organic layer was dried over anhydrous magnesium sulfate and thereafter concentrated under reduced pressure. The residue was purified by basic silica gel column chromatography (n-hexane:ethyl acetate=3:1→0:1). The purified product was concentrated under reduced pressure and the residue was dissolved in isopropyl alcohol. A 1N-hydrochloric acid/ethanol solution was added to this and thereafter concentrated under reduced pressure. The residue was recrystallized from a solvent mixture of isopropyl alcohol/ethyl acetate to obtain 4-[3-(4-benzo[b]thiophen-4-yl-piperazin-1-yl)propoxy]-3,N-dimethyl-5-(2,2,2-trifluoro-ethoxy)benzamide hydrochloride (88 mg, 40% yield) as light yellow powder.

Melting point: 156.0-157.5° C.

Example 3109

Synthesis of 1-{5-[3-(4-benzo[b]thiophen-4-yl-piperazin-1-yl)propoxy]-1-methyl-1H-pyrazol-3-yl}-ethanone hydrochloride 5-[3-(4-Benzo[b]thiophen-4-yl-piperazin-1-yl)-propoxy]-1-methyl-1H-pyrazol-3-carboxylic acid methoxy methylamide hydrochloride (0.61 g, 1.3 mmol) was added to an aqueous sodium hydroxide solution and the solution mixture was extracted with dichloromethane. The extracted solution was concentrated under reduced pressure and the residue was dissolved in THF (12 ml). The solution was cooled to −78° C. and 1N-methyllithium ether solution (1.2 ml) was added thereto and the mixture was stirred at the same temperature for 2 hours. To the reaction solution, an aqueous ammonium chloride solution was added and the solution was heated to room temperature. Potassium chloride was added to the solution, which was then extracted with ethyl acetate. The organic layer was dried over anhydrous magnesium sulfate and thereafter concentrated under reduced pressure. The residue was purified by silica gel column chromatography (dichloromethane:ethyl acetate=3:1→0:1). The purified product was concentrated under reduced pressure and the residue was dissolved in ethanol. A 1N hydrochloric acid/ethanol solution was added to this and the crystal produced was recrystallized from water-containing ethanol to obtain 1-{5-[3-(4-benzo[b]thiophen-4-yl-piperazin-1-yl)propoxy]-1-methyl-1H-pyrazol-3-yl}ethanone hydrochloride (0.22 g, 40% yield) as white powder.

Melting point: 245.0° C. (decomposed)

Example 3110

Synthesis of 5-[3-(4-benzo[b]thiophen-4-yl-piperazin-1-yl)propoxy]-3-hydroxymethyl-1-methyl-1H pyrazole.

A THF solution (8 ml) of 5-[3-(4-benzo[b]thiophen-4-yl-piperazin-1-yl)propoxy]-3-(tert-butyl-dimethylsilanyloxymethyl)-1-methyl-1H-pyrazole (0.75 g, 1.5 mmol) was cooled on ice and a 1M THF solution of tetrabutyl ammonium fluoride (1.7 ml) was added thereto. The mixture was stirred at room temperature for 16 hours. Ethyl acetate was added to the reaction solution, which was washed with water. The organic layer was dried over anhydrous magnesium sulfate and thereafter concentrated under reduced pressure. The residue was purified by silica gel column chromatography (dichloromethane: methanol=1:0→30:1→15:1). The purified product was concentrated under reduced pressure and the residue was recrystallized from a solvent mixture of ethyl acetate and diisopropyl ether to obtain 5-[3-(4-benzo[b]thiophen-4-yl-piperazin-1-yl)-propoxy]-3-hydroxymethyl-1-methyl-1H-pyrazole (0.46 g, 79% yield) as white powder.

Melting temperature: 123.5-126.0° C.

Pharmacological Test 1

1) Dopamine $D_2$ Receptor Binding Assay

The assay was performed according to the method by Kohler et al. (Kohler C, Hall H, Ogren S O and Gawell L, Specific in vitro and in vivo binding of 3H-raclopride. A potent substituted benzamide drug with high affinity for dopamine D-2 receptors in the rat brain. Biochem. Pharmacol., 1985; 34: 2251-2259).

Wistar male rats were decapitated, the brain was retrieved immediately and corpus striatum was taken out. It was homogenized in 50 mM tris(hydroxymethyl)aminomethane (Tris)-hydrochloric acid buffer (pH 7.4) of a volume 50 times of the weight of the tissue using a homogenizer with a high-speed rotating blade, and centrifuged at 4° C., 48,000×g for 10 minutes. The obtained precipitate was suspended again in the above-described buffer of a volume 50 times of the weight of the tissue and after incubated at 37° C. for 10 minutes, centrifuged in the above-described condition. The obtained precipitate was suspended in 50 mM (Tris)-hydrochloric acid buffer (containing 120 mM NaCl, 5 mM KCl, 2 mM $CaCl_2$, 1 mM $MgCl_2$, pH 7.4) of a volume 25 times of the weight of the tissue and preserved by freezing at −85° C. till it was used for binding assay as a membrane specimen.

The binding assay was performed using 40 μl of the membrane specimen, 20 μl of [$^3$H]-raclopride (final concentration 1 to 2 nM), 20 μl of a test drug and 50 mM Tris-hydrochloric acid buffer (containing 120 mM NaCl, 5 mM KCl, 2 mM $CaCl_2$, 1 mM $MgCl_2$, pH 7.4) so that the total amount was 200 μl (final dimethylsulfoxide concentration 1%). The reaction was performed at room temperature for 1 hour and terminated by conducting suction filtration with a cell harvester on a glass fiber filter plate. The filter plate made of glass fiber was washed with 50 mM Tris-hydrochloric acid buffer (pH 7.4), and after dried, a microplate liquid scintillation cocktail was added and the radioactivity was measured with a microplate scintillation counter. Radioactivity in the presence of 10 μM (+)-butaclamol hydrochloride was assumed as nonspecific binding.

$IC_{50}$ value was calculated from concentration-dependent reaction using a non-linear analysis program. Ki value was calculated from $IC_{50}$ value using Cheng-Prussoff formula. The results are shown in the following Table 312.

TABLE 312

Dopamine D2 receptor binding test

| Test compound | Ki (nM) |
|---|---|
| Compound of Example 3 | 1.5 |
| Compound of Example 4 | 1.9 |
| Compound of Example 6 | 0.7 |
| Compound of Example 7 | 0.8 |
| Compound of Example 11 | 0.2 |
| Compound of Example 14 | 0.3 |
| Compound of Example 15 | 0.4 |
| Compound of Example 17 | 0.6 |
| Compound of Example 26 | 2.6 |
| Compound of Example 27 | 1.5 |
| Compound of Example 32 | 2.5 |
| Compound of Example 40 | 3.1 |
| Compound of Example 48 | 2.3 |
| Compound of Example 58 | 2.0 |
| Compound of Example 61 | 5.0 |
| Compound of Example 62 | 1.6 |
| Compound of Example 72 | 3.4 |
| Compound of Example 73 | 1.3 |
| Compound of Example 76 | 2.5 |
| Compound of Example 80 | 1.6 |
| Compound of Example 94 | 2.4 |
| Compound of Example 95 | 1.9 |
| Compound of Example 112 | 1.0 |
| Compound of Example 115 | 1.6 |
| Compound of Example 121 | 1.1 |
| Compound of Example 123 | 0.7 |
| Compound of Example 125 | 2.0 |
| Compound of Example 127 | 0.4 |
| Compound of Example 133 | 0.3 |
| Compound of Example 144 | 0.4 |
| Compound of Example 146 | 0.1 |
| Compound of Example 160 | 0.4 |
| Compound of Example 169 | 0.9 |
| Compound of Example 170 | 1.0 |
| Compound of Example 186 | 1.3 |
| Compound of Example 190 | 1.2 |
| Compound of Example 232 | 1.1 |
| Compound of Example 241 | 0.4 |
| Compound of Example 243 | 0.2 |
| Compound of Example 252 | 0.3 |
| Compound of Example 271 | 1.2 |
| Compound of Example 281 | 0.3 |
| Compound of Example 286 | 0.2 |
| Compound of Example 301 | 0.2 |
| Compound of Example 303 | 1.0 |
| Compound of Example 307 | 0.3 |
| Compound of Example 313 | 0.7 |
| Compound of Example 314 | 0.8 |

TABLE 312-continued

Dopamine D2 receptor binding test

| Test compound | Ki (nM) |
|---|---|
| Compound of Example 323 | 1.5 |
| Compound of Example 340 | 1.9 |
| Compound of Example 343 | 0.9 |
| Compound of Example 345 | 1.6 |
| Compound of Example 354 | 0.2 |
| Compound of Example 358 | 0.2 |
| Compound of Example 359 | 0.2 |
| Compound of Example 363 | 2.0 |
| Compound of Example 368 | 0.4 |
| Compound of Example 382 | 0.5 |
| Compound of Example 394 | 3.8 |
| Compound of Example 453 | 0.9 |
| Compound of Example 462 | 0.4 |
| Compound of Example 546 | 0.6 |
| Compound of Example 650 | 1.2 |
| Compound of Example 706 | 1.0 |
| Compound of Example 802 | 0.6 |
| Compound of Example 1014 | 3.3 |
| Compound of Example 1016 | 2.2 |
| Compound of Example 1026 | 1.9 |
| Compound of Example 1027 | 1.9 |
| Compound of Example 1034 | 2.1 |
| Compound of Example 1059 | 0.4 |
| Compound of Example 1060 | 0.1 |
| Compound of Example 1061 | 0.1 |
| Compound of Example 1071 | 0.1 |
| Compound of Example 1076 | 1.2 |
| Compound of Example 1079 | 0.4 |
| Compound of Example 1080 | 0.6 |
| Compound of Example 1083 | 0.3 |
| Compound of Example 1084 | 0.1 |
| Compound of Example 1086 | 1.0 |
| Compound of Example 1087 | 0.3 |
| Compound of Example 1089 | 1.0 |
| Compound of Example 1106 | 1.0 |
| Compound of Example 1110 | 1.2 |
| Compound of Example 1113 | 0.7 |
| Compound of Example 1138 | 1.4 |

2) Serotonin 5-$HT_{2A}$ Receptor Binding Assay

The assay was performed according to the method by Leysen J E et al. (Leysen J E, Niemegeers C J E, Van Nueten J M and Laduron P M. [3H] Ketanserin (R 41 468), a selective 3H-ligand for serotonin 2 receptor binding sites. Mol. Pharmacol., 1982, 21: 301-314).

Wistar male rats were decapitated, the brain was retrieved immediately and frontal cortex was taken out. It was homogenized in 0.25 M sucrose of a volume 10 times of the weight of the tissue using a Teflon glass homogenizer, and centrifuged at 4° C., 1,000×g for 10 minutes. The obtained supernatant was transferred to another centrifuge tube and suspended in 0.25 M sucrose of a volume 5 times of the weight of the tissue and the precipitate was centrifuged in the above-described condition. The obtained supernatant was combined with the supernatant obtained above and adjusted to a volume 40 times of the weight of the tissue with 50 mM Tris-hydrochloric acid buffer (pH 7.4), and centrifuged at 4° C., 35,000×g for 10 minutes. The obtained precipitate was suspended again in the above-described buffer of a volume 40 times of the weight of the tissue and centrifuged in the above-described condition. The obtained precipitate was suspended in the above-described buffer of a volume 20 times of the weight of the tissue and preserved by freezing at −85° C. till it was used for binding assay as a membrane specimen.

The binding assay was performed using 40 μl of the membrane specimen, 20 μl of [$^3$H]-Ketanserin (final concentration 1 to 3 nM), 20 μl of a test drug and 50 mM Tris-hydrochloric acid buffer (pH 7.4) so that the total amount was 200 μl (final dimethylsulfoxide concentration 1%). The reaction was performed at 37° C. for 20 minutes and terminated by conducting suction filtration with a cell harvester on a glass fiber filter plate.

The filter plate made of glass fiber was washed with 50 mM Tris-hydrochloric acid buffer (pH 7.4), and after dried, a microplate liquid scintillation cocktail was added and the radioactivity was measured with a microplate scintillation counter. Radioactivity in the presence of 10 μM spiperone was assumed as nonspecific binding.

$IC_{50}$ value was calculated from concentration-dependent reaction using a non-linear analysis program. Ki value was calculated from $IC_{50}$ value using Cheng-Prussoff formula. The results are shown in the following Table 313

TABLE 313

Serotonion 5-$HT_{2A}$ receptor binding test

| Test compound | Ki (nM) |
| --- | --- |
| Compound of Example 3 | 6.0 |
| Compound of Example 4 | 7.7 |
| Compound of Example 6 | 3.3 |
| Compound of Example 7 | 2.9 |
| Compound of Example 11 | 4.4 |
| Compound of Example 14 | 2.4 |
| Compound of Example 15 | 5.9 |
| Compound of Example 17 | 3.4 |
| Compound of Example 26 | 0.8 |
| Compound of Example 27 | 1.0 |
| Compound of Example 32 | 1.4 |
| Compound of Example 40 | 0.6 |
| Compound of Example 48 | 3.8 |
| Compound of Example 58 | 4.9 |
| Compound of Example 61 | 4.9 |
| Compound of Example 62 | 4.7 |
| Compound of Example 72 | 3.4 |
| Compound of Example 73 | 5.6 |
| Compound of Example 76 | 1.7 |
| Compound of Example 80 | 3.3 |
| Compound of Example 94 | 2.0 |
| Compound of Example 95 | 2.3 |
| Compound of Example 112 | 0.7 |
| Compound of Example 115 | 3.7 |
| Compound of Example 121 | 1.5 |
| Compound of Example 123 | 1.4 |
| Compound of Example 125 | 3.9 |
| Compound of Example 127 | 2.4 |
| Compound of Example 133 | 4.7 |
| Compound of Example 144 | 1.4 |
| Compound of Example 146 | 2.4 |
| Compound of Example 160 | 0.6 |
| Compound of Example 169 | 2.6 |
| Compound of Example 170 | 3.3 |
| Compound of Example 186 | 2.0 |
| Compound of Example 190 | 0.6 |
| Compound of Example 232 | 2.7 |
| Compound of Example 241 | 0.7 |
| Compound of Example 243 | 0.5 |
| Compound of Example 252 | 0.3 |
| Compound of Example 271 | 0.6 |
| Compound of Example 281 | 0.6 |
| Compound of Example 286 | 0.8 |
| Compound of Example 301 | 0.4 |
| Compound of Example 303 | 2.5 |
| Compound of Example 307 | 0.7 |
| Compound of Example 313 | 1.1 |
| Compound of Example 314 | 0.8 |
| Compound of Example 323 | 0.7 |
| Compound of Example 340 | 4.8 |
| Compound of Example 343 | 0.5 |
| Compound of Example 345 | 1.9 |
| Compound of Example 354 | 0.6 |
| Compound of Example 358 | 1.1 |
| Compound of Example 359 | 1.1 |
| Compound of Example 363 | 1.1 |
| Compound of Example 368 | 0.7 |
| Compound of Example 382 | 0.6 |

TABLE 313-continued

Serotonion 5-$HT_{2A}$ receptor binding test

| Test compound | Ki (nM) |
| --- | --- |
| Compound of Example 394 | 4.7 |
| Compound of Example 453 | 1.2 |
| Compound of Example 462 | 1.7 |
| Compound of Example 546 | 0.7 |
| Compound of Example 650 | 0.6 |
| Compound of Example 706 | 0.9 |
| Compound of Example 802 | 1.4 |
| Compound of Example 1014 | 4.2 |
| Compound of Example 1016 | 2.3 |
| Compound of Example 1026 | 3.5 |
| Compound of Example 1027 | 2.0 |
| Compound of Example 1034 | 3.1 |
| Compound of Example 1059 | 3.8 |
| Compound of Example 1060 | 1.2 |
| Compound of Example 1061 | 1.2 |
| Compound of Example 1071 | 1.3 |
| Compound of Example 1076 | 12.4 |
| Compound of Example 1079 | 2.8 |
| Compound of Example 1080 | 3.4 |
| Compound of Example 1083 | 1.5 |
| Compound of Example 1084 | 1.4 |
| Compound of Example 1086 | 5.8 |
| Compound of Example 1087 | 2.6 |
| Compound of Example 1089 | 13.9 |
| Compound of Example 1106 | 7.1 |
| Compound of Example 1110 | 4.9 |
| Compound of Example 1113 | 5.0 |
| Compound of Example 1138 | 19.7 |

3) Adrenalin α1 Receptor Binding Assay

The assay was performed according to the method by Groβ G et al. (Groβ G, Hanft G and Kolassa N. Urapidil and some analogues with hypotensive properties show high affinities for 5-hydroxytryptamine (5-HT) binding sites of the 5-HT1A subtype and for α1-adrenoceptor binding sites. Naunyn-Schmiedeberg's Arch Pharmacol., 1987, 336: 597-601).

Wistar male rats were decapitated, the brain was retrieved immediately and cerebral cortex was taken out. It was homogenized in 50 mM Tris-hydrochloric acid buffer (100 mM NaCl, containing 2 mM dihydrogen disodium ethylene diamine tetraacetate, pH 7.4) of a volume 20 times of the weight of the tissue using a homogenizer with a high-speed rotating blade, and centrifuged at 4° C., 80,000×g for 20 minutes. The obtained precipitate was suspended in the above-described buffer of a volume 20 times of the weight of the tissue and after incubated at 37° C. for 10 minutes, centrifuged in the above-described condition. The obtained precipitate was suspended again in the above-described buffer of a volume 20 times of the weight of the tissue and centrifuged in the above-described condition. The obtained precipitate was suspended in 50 mM (Tris)-hydrochloric acid buffer (containing 1 mM dihydrogen disodium ethylene diamine tetraacetate, pH 7.4) of a volume 20 times of the weight of the tissue and preserved by freezing at −85° C. till it was used for binding assay as a membrane specimen.

The binding assay was performed using 40 μl of the membrane specimen, 20 μl of [$^3$H]-prazosin (final concentration 0.2 to 0.5 nM), 20 μl of a test drug and 50 mM Tris-hydrochloric acid buffer (containing 1 mM EDTA, pH 7.4) so that the total amount was 200 μl (final dimethylsulfoxide concentration 1%). The reaction was performed at 30° C. for 45 minutes and terminated by conducting suction filtration with a cell harvester on a glass fiber filter plate.

The filter plate made of glass fiber was washed with 50 mM Tris-hydrochloric acid buffer (pH 7.4), and after dried, a microplate liquid scintillation cocktail was added and the radioactivity was measured with a microplate scintillation counter. Radioactivity in the presence of 10 μM phentolamine hydrochloride was assumed as nonspecific binding.

$IC_{50}$ value was calculated from concentration-dependent reaction using a non-linear analysis program. Ki value was calculated from $IC_{50}$ value using Cheng-Prussoff formula.

Pharmacological Test 2

Partial agonistic activity on dopamine $D_2$ receptor using $D_2$ receptor expression cells Partial agonistic activity on dopamine $D_2$ receptor was evaluated by quantitatively determining cyclic AMP production inhibitory effect of a test compound in dopamine $D_2$ receptor expression cells in which adenosine 3',5'-cyclic monophosphate (cyclic AMP) production was induced by forskolin stimulation.

Human recombinant dopamine $D_2$ receptor expressing Chinese hamster ovary/DHFR(−) cells were cultured in a culture medium (Iscove's Modified Dulbecco's Medium (IMDM culture medium), 10% fetal bovine serum, 50 I.U./ml penicillin, 50 μg/ml streptomycin, 200 μg/ml geneticin, 0.1 mM sodium hypoxanthine, 16 μM thymidine) at 37° C. and 5% carbon dioxide condition. Cells were seeded at $10^4$ cells/well on a 96-well microtiter plate coated with poly-L-lysine and grown under the same condition for 2 days. Each well was washed with 100 μl of a culture medium (IMDM culture medium, 0.1 mM sodium hypoxanthine, 16 μM thymidine). The culture medium was replaced with 50 μl of culture medium (IMDM culture medium, 0.1% sodium ascorbate, 0.1 mM sodium hypoxanthine, 16 μM thymidine) having dissolved therein 3 μM of a test compound. After allowed to incubate at 37° C., 5% carbon dioxide condition for 20 minutes, the culture medium was replaced with 100 μl of forskolin stimulative culture medium (IMDM culture medium, 0.1% sodium ascorbate, 0.1 mM sodium hypoxanthine, 16 μM thymidine, 10 μM forskolin, 500 μM 3-isobutyl-1-methylxanthine) having 3 μM of the test compound dissolved therein and allowed to incubate at 37° C., 5% carbon dioxide condition for 10 minutes. After the culture medium was removed, 200 μl of Lysis 1B aqueous solution (Amersham Bioscience, reagent attached to cyclic AMP biotrack enzyme immunoassay system) was dispensed and shaken for 10 minutes. The aqueous solution of each well was used as a sample for measurement. Samples for measurement quadruply diluted were subjected to measurement of the quantity of cyclic AMP using the above-described enzyme immunoassay system. Inhibition ratio of the respective test compound was calculated assuming that the quantity of cyclic AMP of the well to which no test compound was added was 100%. In this empiric test system, dopamine which was used as a control drug suppressed the quantity of cyclic AMP to about 10% as the maximum activity.

It was confirmed that test compounds had partial agonistic activity for dopamine $D_2$ receptor in the above-described test.

Since the test compounds has partial agonistic activity for dopamine $D_2$ receptor, they can stabilize dopamine neurotransmission to a normal condition in a schizophrenia patient and as a result, exhibit, for example, positive and negative condition improving effect, cognitive impairment improving effect and the other symptom improving effects without causing side effects.

Pharmacological Test 3

Inhibitory Effect on Apomorphine-Induced Stereotyped Behavior in Rats

Wistar rats (male, six-seven weeks old, Japan SLC, Inc.) were used as test animals. A test compound was suspended in 5% gum arabic/(physiological saline or water) using an agate mortar and was diluted with the same solvent if necessary.

Test animals were fasted overnight from the day before. Apomorphine (0.7 mg/kg) was subcutaneously administered (1 ml/kg) 1 hour after each test compound was orally administered (5 ml/kg). Stereotyped behavior was observed for 1 minute respectively 20, 30 and 40 minutes after apomorphine injection.

The stereotyped behavior of each animal was quantified according to the following condition and score made at three points were summed up and the anti-apomorphine effect was evaluated. Six test animals were used for each group.

0: The appearance of the animals is the same as saline treated rats;
1: Discontinuous sniffing, constant exploratory activity;
2: Continuous sniffing, periodic exploratory activity;
3: Continuous sniffing, discontinuous biting, gnawing or licking. Very brief periods of locomotor activity;
4: Continuous biting, gnawing or licking; no exploratory activity.

Non-clinical statistical analysis system was used for all statistical processing. When the significance probability value was lower than 0.05, it was judged that a significant difference existed. The difference of the score between the solvent administration group and each test compound administration group was analyzed using Wilcoxon rank-sum test or Steel test. In addition, linear regression analysis was used for calculating 50% effective dose (95% confidence interval).

Since the test compounds showed inhibitory effect for apomorphine-induced stereotyped behavior, it was confirmed that the test compounds have $D_2$ receptor antagonistic effect.

Pharmacological Test 4

Inhibitory Effect on (±) D-2,5-dimethoxy-4-iodoamphetamine (DOI) Induced Head Twitch in Rats Wistar rats (male, six-seven weeks old, Japan SLC, Inc.) were used as test animals. A test compound was suspended in 5% gum arabic/(physiological saline or water) using an agate mortar and was diluted with the same solvent if necessary.

Test animals were fasted overnight from the day before. DOI (5.0 mg/kg) was subcutaneously administered (1 ml/kg) 1 hour after each test compound was orally administered (5 ml/kg). The number of head twitches was counted for 10 minutes immediately after DOI injection. Six test animals were used for each group.

Non-clinical statistical analysis was used for all statistical processing. When the significance probability value was lower than 0.05, it was judged that a significant difference existed. The difference of the number of head twitches between the solvent administration group and each test compound administration group was analyzed using t-test or Dunnett's test. In addition, linear regression analysis was used for calculating 50% effective dose (95% confidence interval).

Since the test compounds showed inhibitory effect for DOI-induced head twitch, it was confirmed that the test compounds have serotonin $5HT_{2A}$ receptor antagonistic effect.

Pharmacological Test 5

Catalepsy inducing effect in rats

Wistar rats (male, six-seven weeks old, Japan SLC, Inc.) were used as test animals. A test compound was suspended in 5% gum arabic/(physiological saline or water) using an agate mortar and was diluted with the same solvent if necessary.

Test animals were fasted overnight from the day before observation on catalepsy and ptosis was performed 1, 2, 4, 6 and 8 hours after each test compound was orally administered (5 ml/kg). Six test animals were used for each group.

One forepaw of a rat was placed on an edge of a steel small box (width: 6.5 cm, depth: 4.0 cm, height: 7.2 cm) (an unnatural pose) and when the rat maintained the pose for more than 30 seconds, it was judged that the case was catalepsy positive.

This observation was performed three times at each point, and if there was at least one positive case, it was judged that catalepsy occurred in the individual.

As a result, catalepsy induction effect of a test compound was dissociated from inhibitory effect on apomorphine-induced stereotyped behavior, therefore it was suggested that apprehension for extrapyramidal side effect in clinic would be low.

Pharmacological Test 6

Measurement of serotonin (5-HT) uptake inhibitory activity of a test compound by rat brain synaptosome Wistar male rats were decapitated, the brain was retrieved and frontal cortex was dissected out, and it was homogenized in 0.32 M sucrose solution of a weight 20 times of the weight of the tissue using a Potter type homogenizer. The homogenate was centrifuged at 4° C., 1,000×g for 10 minutes, the obtained supernatant was further centrifuged at 4° C., 20,000×g for 20 minutes, and the pellet was suspended in an incubation buffer (20 mM Hepes buffer (pH 7.4) containing 10 mM glucose, 145 mM sodium chloride, 4.5 mM potassium chloride, 1.2 mM magnesium chloride, 1.5 mM calcium chloride), which was used as crude synaptosome fraction.

5-HT uptake reaction was performed in a volume of 200 μl using a 96-well round bottom plate and pargyline (final concentration 10 μM) and sodium ascorbate (final concentration 0.2 mg/ml) were contained in the incubation buffer upon reaction and used.

Incubation buffer (total counting), non-labeled 5-HT (final concentration 10 μM, non-specific counting) and the diluted test compound (final concentration 300 nM) were added to each well. One-tenth quantity of the final volume of the synaptosome fraction was added and after preincubated at 37° C. for 10 minutes, tritium labeled 5-HT solution (final concentration 8 nM) was added and uptake reaction was started at 37° C. The uptake time was 10 minutes and the reaction was terminated by vacuum filtration through a 96-well fiber glass filter paper plate, and after the filter paper was washed with cold normal saline, it was dried enough and Microscint0 (Perkin-Elmer) was added to the filter and remaining radioactivity on the filter was measured.

Serotonin uptake inhibitory activity (%) was calculated from the radioactivity of total counting as 100%, of non-specific counting as 0%, and of counting obtained with test compound.

% of inhibition of 5-HT(%)=100−[(Count obtained with test compound−Nonspecific count (0% Uptake))/(Total count (100% Uptake)−Nonspecific count (0% Uptake))]×100

The results are shown in the next Table 314.

TABLE 314

| Test compound | Serotonin uptake inhibitory ratio (%) (300 nM) |
|---|---|
| Compound of Example 11 | 95.2 |
| Compound of Example 15 | 95.3 |
| Compound of Example 802 | 96.6 |
| Compound of Example 1071 | 94.4 |
| Compound of Example 1076 | 87.8 |
| Compound of Example 1089 | 85.0 |
| Compound of Example 1083 | 96.3 |
| Compound of Example 1106 | 69.9 |
| Compound of Example 1079 | 82.3 |
| Compound of Example 1080 | 95.6 |
| Compound of Example 1138 | 67.2 |
| Compound of Example 1059 | 97.2 |
| Compound of Example 1060 | 97.5 |
| Compound of Example 1061 | 97.5 |

TABLE 314-continued

| Test compound | Serotonin uptake inhibitory ratio (%) (300 nM) |
|---|---|
| Compound of Example 1110 | 38.5 |
| Compound of Example 1086 | 98.6 |
| Compound of Example 1087 | 97.1 |
| Compound of Example 1113 | 59.3 |

Preparation Examples 100 g of a compound of the present invention, 40 g of Avicel (trade name, product of Asahi Chemical Industry Co., Ltd.), 30 μg of corn starch and 2 g of magnesium stearate was mixed and polished and tableted with a pestle for glycocalyx R10 mm.

The obtained tablet was coated with a film using a film coating agent made up of 10 g of TC-5 (trade name, product of Shin-Etsu Chemical Co., Ltd., hydroxypropyl methylcellulose), 3 g of polyethylene glycol 6000, 40 g of castor oil and an appropriate amount of ethanol to produce a film coated tablet of the above composition.

The invention claimed is:

1. A heterocyclic compound or a salt thereof represented by the formula (1):

[Formula 1]

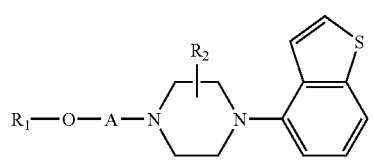

(1)

where $R^2$ represents a hydrogen atom or a lower alkyl group;

A represents a lower alkylene group or a lower alkenylene group; and $R^1$ represents a cyclo C3-C8 alkyl group or an aromatic group selected from the group consisting of (I) to (II) below:

(I) a cyclo C3-C8 alkyl group; and (II) an aromatic group selected from a phenyl group, a naphthyl group, a dihydroindenyl group and a tetrahydronaphthyl group;

wherein at least one group selected from the group consisting of the groups (1) to (65) below may be present as a substituent on the cyclo C3-C8 alkyl group and the aromatic group represented by $R^1$:

(1) a lower alkyl group, (2) a lower alkenyl group, (3) a halogen substituted lower alkyl group, (4) a lower alkoxy group, (5) an aryloxy group, (6) a lower alkylthio group, (7) a halogen substituted lower alkoxy group, (8) a hydroxy group, (9) a protected hydroxy group,

(10) a hydroxy lower alkyl group,

(11) a protected hydroxy lower alkyl group,

(12) a cyano group,

(13) an aryl group,

(14) a nitro group,

(15) an amino group,

(16) an amino group having a group(s) selected from the group consisting of a lower alkyl group, a lower alkanoyl group, a lower alkoxycarbonyl group, a lower alkylsulfonyl group, a carbamoyl group, a lower alkyl carbamoyl group, an amino lower alkanoyl group, a lower alkanoylamino lower alkanoyl group and a lower alkoxy carbonylamino lower alkanoyl group as a substituent,
(17) a lower alkanoyl group,
(18) an arylsulfonyl group that may have a lower alkyl group(s) on the aryl group,
(19) a carboxy group,
(20) a lower alkoxycarbonyl group,
(21) a carboxy lower alkyl group,
(22) a lower alkoxycarbonyl lower alkyl group,
(23) a lower alkanoylamino lower alkanoyl group,
(24) a carboxy lower alkenyl group,
(25) a lower alkoxycarbonyl lower alkenyl group,
(26) a carbamoyl lower alkenyl group that may have a group(s) selected from the group consisting of a lower alkyl group and a halogen substituted lower alkyl group as a substituent,
(27) a carbamoyl group that may have a group(s) selected from the group consisting of the groups (i) to (lxxviii) below as a substituent:
(i) a lower alkyl group,
(ii) a lower alkoxy group,
(iii) a hydroxy lower alkyl group,
(iv) a lower alkoxy lower alkyl group,
(v) an aryloxy lower alkyl group,
(vi) a halogen substituted lower alkyl group,
(vii) an amino lower alkyl group that may have a group(s) selected from the group consisting of a lower alkyl group, a lower alkanoyl group, an aroyl group and a carbamoyl group,
(viii) a cyclo C3-C8 alkyl group that may have a group(s) selected from the group consisting of a lower alkyl group, a hydroxy group, a lower alkoxycarbonyl group and a phenyl lower alkoxy group as a substituent,
(ix) a cyclo C3-C8 alkyl substituted lower alkyl group,
(x) a lower alkenyl group,
(xi) a carbamoyl lower alkyl group that may have a group(s) selected from the group consisting of a lower alkyl group, phenyl group that may have a lower alkyl group(s) and a phenyl group(s) that may have a lower alkoxy group(s) as a substituent,
(xii) a lower alkoxycarbonyl lower alkyl group,
(xiii) a furyl lower alkyl group (that may have a lower alkyl group(s) as a substituent) on the furyl group,
(xiv) a tetrahydrofuryl lower alkyl group,
(xv) a 1,3-dioxolanyl lower alkyl group,
(xvi) a tetrahydropyranyl lower alkyl group,
(xvii) a pyrrolyl lower alkyl group (that may have a lower alkyl group(s) as a substituent on the pyrrolyl group),
(xviii) a lower alkyl group substituted with a dihydropyrazolyl group that may have an oxo group(s),
(xix) a pyrazolyl lower alkyl group (that may have a lower alkyl group(s) as a substituent on the pyrazolyl group),
(xx) an imidazolyl lower alkyl group,
(xxi) a pyridyl lower alkyl group,
(xxii) a pyrazinyl lower alkyl group (that may have a lower alkyl group(s) as a substituent on the pyrazinyl group),
(xxiii) a pyrrolidinyl lower alkyl group (that may have a group(s) selected from the group consisting of an oxo group(s) and a lower alkyl group as a substituent on the pyrrolidinyl group),
(xxiv) a piperidyl lower alkyl group (that may have a group(s) selected from the group consisting of a benzoyl group and a lower alkanoyl group as a substituent on the piperidyl group),
(xxv) a piperazinyl lower alkyl group (that may have a lower alkyl group(s) as a substituent on the piperazinyl group),
(xxvi) a morpholinyl lower alkyl group,
(xxvii) a thienyl lower alkyl group (that may have a lower alkyl group(s) as a substituent on the thienyl group),
(xxviii) a thiazolyl lower alkyl group,
(xxix) a dihydrobenzofuryl lower alkyl group,
(xxx) a benzopyranyl lower alkyl group (that may have an oxo group(s) as a substituent on the benzopyranyl group),
(xxxi) a benzimidazolyl lower alkyl group,
(xxxii) an indolyl lower alkyl group that may have a lower alkoxycarbonyl group(s) on the lower alkyl group),
(xxxiii) an imidazolyl lower alkyl group that has a substituent(s) selected from the group consisting of a carbamoyl group and a lower alkoxycarbonyl group on the lower alkyl group,
(xxxiv) a pyridyl group that may have a group(s) selected from the group consisting of a lower alkyl group, a lower alkoxy group and a lower alkylthio lower alkyl group as a substituent,
(xxxv) a pyrrolidinyl group that may have a group(s) selected from the group consisting of a lower alkyl group, a lower alkoxycarbonyl group, a lower alkanoyl group and an aroyl group as a substituent,
(xxxvi) a piperidyl group that may have a group(s) selected from the group consisting of a lower alkyl group, a lower alkoxycarbonyl group, a lower alkanoyl group and an aroyl group that may have a group(s) selected from the group consisting of a lower alkyl group and a halogen atom as a substituent,
(xxxvii) a tetrahydrofuryl group that may have an oxo group(s),
(xxxviii) a hexahydroazepinyl group that may have an oxo group(s),
(xxxix) a pyrazolyl group that may have a group(s) selected from the group consisting of a lower alkyl group, an aryl group and a furyl group as a substituent,
(xl) a thiazolyl group,
(xli) a thiadiazolyl group that may have a lower alkyl group(s),
(xlii) an isoxazolyl group that may have a lower alkyl group(s),
(xliii) an indazolyl group,
(xliv) an indolyl group,
(xlv) a tetrahydrobenzothiazolyl group,
(xlvi) a tetrahydroquinolyl group that may have a group(s) selected from the group consisting of a lower alkyl group, a lower alkoxy group, a halogen atom and an oxo group as a substituent,
(xlvii) a quinolyl group that may have a lower alkyl group(s),
(xlviii) a benzodioxolyl lower alkyl group, (xlix) an aryl group that may have a group(s) as a substituent, selected from the group consisting of
a halogen atom; a lower alkyl group; a lower alkoxy group; a halogen substituted lower alkyl group; a halogen substituted lower alkoxy group; a lower alkenyl group; an amino group that may have a group selected from the group consisting of a lower alkanoyl group, a lower alkyl sulfonyl group, a lower alkyl group and an aryl group; a sulfamoyl group; a lower alkylthio group; a lower alkanoyl group; a lower alkoxycarbonyl group; a pyrrolyl group; a lower alkynyl group; a cyano group; a nitro group; an aryloxy group; an aryl lower alkoxy group; a hydroxy group; a hydroxy lower alkyl group; a carbamoyl group that may have a group(s) selected from the group consisting of a lower alkyl group and an aryl group; a pyrazolyl group; a pyrrolidinyl group that may have an oxo group(s); an oxazolyl group; an imidazolyl group that may have a lower alkyl group(s); a dihydrofuryl group that may have an oxo group(s); a thiazolidinyl lower alkyl group that may have an oxo group(s); an imidazolyl lower alkanoyl group and a piperidinylcarbonyl group, (l) a cyano lower alkyl group, (li) a dihydroquinolyl group that may have a group(s) selected from the group consisting of a lower alkyl group and an oxo group, (lii) a halogen substituted lower alkylamino group, (liii) a lower alkylthio lower alkyl group, (liv) an amidino group that may have a lower alkyl group(s), (lv) an amidino lower alkyl group, (lvi) a lower alkenyloxy lower alkyl group, (lvii) an arylamino group that may have a substituent(s) selected from the group consisting of a lower alkyl group, a lower alkoxy group, a halogen substituted lower alkyl group and a halogen substituted lower alkoxy group, on the aryl group, (lviii) an aryl lower alkenyl group, (lix) a pyridylamino group that may have a lower alkyl group(s), (lx) an aryl lower alkyl group (that may have on the aryl group and/or the lower alkyl group a group(s) selected from the group consisting of a halogen atom, a lower alkyl group, a halogen substituted lower alkyl group, a halogen substituted lower alkoxy group, a lower alkoxy group, a carbamoyl group and a lower alkoxycarbonyl group as a substituent), (lxi) a lower alkynyl group, (lxii) an aryloxy lower alkyl group (that may have as a substituent on the aryl group a group(s) selected from the group consisting of a lower alkoxy group; a carbamoyl group that may have a group(s) selected from the group consisting of a lower alkoxy group and a lower alkyl group; and a pyrrolidinyl group that may have an oxo group(s)), (lxiii) an isoxazolidinyl group that may have an oxo group(s), (lxiv) a dihydroindenyl group, (lxv) an aryl lower alkoxy lower alkyl group, (lxvi) a tetrahydropyranyl group, (lxvii) an azetidinyl group that may have a group(s) selected from the group consisting of a lower alkanoyl group and an aroyl group, (lxviii) an azetidinyl lower alkyl group that may have a group(s) selected from the group consisting of a lower alkanoyl group and aroyl group, (lxix) a tetrazolyl group, (lxx) an indolinyl group that may have an oxo group(s), (lxxi) a triazolyl group that may have a group(s) selected from the group consisting of a lower alkyl group and a lower alkylthio group, (lxxii) an imidazolyl group that may have a carbamoyl group(s), (lxxiii) an oxazolyl group that may have a lower alkyl group(s), (lxxiv) an isothiazolyl group that may have a lower alkyl group(s), (lxxv) a benzimidazolyl group, (lxxvi) a dihydrobenzothiazolyl group that may have an oxo group(s), (lxxvii) a thienyl group that may have a lower alkoxycarbonyl group(s), and (lxxviii) an oxazolyl lower alkyl group that may have a lower alkyl group(s)

(28) an amino lower alkyl group that may have a group(s) selected from the group consisting of a lower alkyl group, a halogen substituted lower alkyl group, a lower alkoxycarbonyl group, a lower alkanoyl group, an aryl group, an aryl lower alkyl group, an aroyl group and an amino substituted alkyl group (that may have a lower alkyl group(s) as a substituent on the amino group) on the amino group,

(29) a lower alkyl group substituted with a carbamoyl group that may have a group(s) selected from the group consisting of a lower alkyl group and a halogen substituted lower alkyl group,

(30) a thiocarbamoyl group that may have a lower alkyl group(s),

(31) a sulfamoyl group,

(32) an oxazolidinyl group that may have an oxo group(s),

(33) an imidazolidinyl group that may have a substituent(s) selected from the group consisting of an oxo group and a lower alkyl group,

(34) a pyrrolidinyl group that may have an oxo group(s),

(35) an imidazolyl group,

(36) a triazolyl group,

(37) an isoxazolyl group,

(38) a piperidyl group that may have a substituent(s) selected from the group consisting of a lower alkyl group, a lower alkanoyl group, an arylsulfonyl group, an oxo group, a hydroxy group, and an amino group that may have a group(s) selected from the group consisting of a lower alkyl group, a lower alkanoyl group, a lower alkoxycarbonyl group and lower alkanoylamino lower alkanoyl group,

(39) a piperidylcarbonyl group that may have a substituent(s) selected from the group consisting of a lower alkyl group, a hydroxy group, a hydroxy lower alkyl group, a lower alkanoyl group, a carboxy lower alkyl group, a lower alkyl carbamoyl lower alkyl group, a carbamoyl group, a lower alkoxy group, a carboxy group, a lower alkoxycarbonyl group, an amino group (on which 1 to 2 groups selected from the group consisting of a lower alkyl group, a lower alkanoyl group, a lower alkoxycarbonyl group and an aroyl group may be present), a piperidyl group (on which a group(s) selected from the group consisting of a lower alkanoyl group, a lower alkoxycarbonyl group and an aroyl group may be present), piperazinyl group (on which a lower alkyl group(s) may be present as a substituent), a 1,4-dioxa-8-azaspiro[4.5]decyl group, a morpholinyl group, a hexahydro-1,4-diazepinyl group (on which a lower alkyl group(s) may be present as a substituent), a pyridyl group, a pyridyloxy group, a pyridyl lower alkoxy group, a tetrahydroquinolyl group (on which an oxo group(s) may be present), a benzodioxolyl group, an aryl lower alkoxy group (that may have a group(s) selected from the group consisting of a halogen atom, a lower alkyl group, a lower alkoxy group and a halogen substituted lower alkoxy group on the aryl group), an aryl group (on which a group(s) selected from the group consisting of a halogen atom, a lower alkoxy group, hydroxy group may be present), an aryloxy group (that may have on the aryl group a group(s) selected from the group consisting of a cyano group, a halogen atom, lower alkyl group, a lower alkoxy group and a halogen substituted lower alkyl group), an aryl lower alkyl group (that may have on the aryl group a group(s) selected from the group consisting of a halogen atom, a lower alkyl group, a lower alkoxy group and a halogen substituted lower alkyl group), and an aroyl group (that may have on the aryl group a group(s) selected from the group consisting of a halogen atom and a lower alkoxy group),

(40) a pyrrolidinylcarbonyl group that may have a group as a substituent, selected from the group consisting of a hydroxy lower alkyl group, a carbamoyl group, a hydroxy group, an amino group (that may have on the amino group a group(s) selected from the group consisting of a lower alkyl group, a lower alkanoyl group and an aroyl group), a morpholinyl lower alkyl group, a pyrrolidinyl lower alkyl group, a piperidyl lower alkyl group, a piperazinyl lower alkyl group (that may have a lower alkyl group(s) as a substituent on the piperazinyl group), an amino lower alkyl group (that may have a lower alkyl group(s) as a substituent on the amino group), an aryloxy group (that may have a halogen substituted lower alkoxy group(s) on the aryl group), an aryloxy lower alkyl group (that may have a halogen substituted lower alkoxy group(s) on the aryl group) and a tetrahydroquinolyl group (on which an oxo group(s) may be present),

(41) a piperazinylcarbonyl group that may have a group(s) as a substituent, selected from the group consisting of a lower alkyl group, a cyclo C3-C8 alkyl group, a lower alkanoyl group, a hydroxy lower alkyl group, a lower alkoxy lower alkyl group, a lower alkoxycarbonyl group, an amino lower alkyl group (that may have a lower alkyl group(s) as a substituent on the amino group), a piperidyl lower alkyl group (that may have a lower alkyl group(s) as a substituent on the piperidyl group), a morpholinyl lower alkyl group, a pyrrolidinyl lower alkyl group, a 1,3-dioxolanyl lower alkyl group, a tetrahydrofuryl lower alkyl group, a pyridyl lower alkyl group (that may have a phenyl group(s) as a substituent on the lower alkyl group), a imidazolyl lower alkyl group, a furyl lower alkyl group, a pyrrolidinylcarbonyl lower alkyl group, a piperidyl group that may have a lower alkyl group(s) as a substituent, pyridyl group (that may have on the pyridyl group a group(s) selected from the group consisting of a lower alkyl group, a cyano group and a halogen substituted lower alkyl group as a substituent), a thieno[2,3-b]pyridyl group, an aryl group (on which a group(s) selected from the group consisting of a halogen atom and a lower alkyl group may be present), an aroyl group, a furyl carbonyl group, an aryl lower alkoxycarbonyl group and an oxo group,

(42) a hexahydroazepinylcarbonyl group,
(43) a hexahydro-1,4-diazepinylcarbonyl group that may have a substituent(s) selected from the group consisting of a lower alkyl group and a pyridyl group,
(44) a dihydropyrrolylcarbonyl group that may have a lower alkyl group(s),
(45) a thiomorpholinylcarbonyl group,
(46) a morpholinylcarbonyl group that may have a group(s) selected from the group consisting of a lower alkyl group, a piperidyl lower alkyl group and an aryl group,
(47) a thiazolidinyl carbonyl group that may have an aryl group(s) that may have a group(s) selected from the group consisting of a lower alkoxy group and a cyano group,
(48) an azabicyclo[3.2.2]nonylcarbonyl group,
(49) an 8-azabicyclo[3.2.1]octylcarbonyl group that may have a halogen substituted or unsubstituted aryloxy group(s),
(50) an indolinylcarbonyl group,
(51) a tetrahydroquinolylcarbonyl group,
(52) a tetrahydropyrido[3.4-b]indolylcarbonyl group,
(53) a morpholinyl lower alkyl group,
(54) a piperazinyl lower alkyl group that may have a lower alkyl group(s) on the piperazinyl group,
(55) a morpholinylcarbonyl lower alkyl group,
(56) a piperazinylcarbonyl lower alkyl group that may have a lower alkyl group(s) on the piperazinyl group,
(57) an oxo group,
(58) an amino lower alkoxy group (that may have a lower alkyl group(s) on the amino group),
(59) a lower alkoxy lower alkoxy group,
(60) a piperazinyl group that may have a group(s) selected from the group consisting of an oxo group, a lower alkyl group, a lower alkanoyl group and a lower alkoxycarbonyl group,
(61) a morpholinyl group,
(62) a 1,3,8-triazaspiro[4.5]decanylcarbonyl group that may have a group(s) selected from the group consisting of an oxo group and an aryl group,
(63) a tetrahydropyridylcarbonyl group that may have a pyridyl group(s),
(64) an imidazolidinylcarbonyl group that may have a thioxo group(s), and
(65) a 1,4-dioxa-8-azaspiro[4.5]decanyl group.

2. The compound according to claim 1, wherein
$R^1$ represents a cyclo C5-C6 alkyl group or an aromatic group selected from the group consisting of (I) to (II) below:
(I) a cyclo C5-C6 alkyl group; and
(II) an aromatic group selected from a phenyl group, naphthyl group, dihydroindenyl group and tetrahydronaphthyl group;
wherein, on the aromatic group and the cyclo $C_5$-$C_6$ group represented by $R^1$, 1 to 5 groups selected from the group consisting of the groups (1) to (65) below may be present as a substituent(s):
(1) a lower alkyl group,
(2) a lower alkenyl group,
(3) a halogen substituted lower alkyl group,
(4) a lower alkoxy group,
(5) a phenoxy group,
(6) a lower alkylthio group,
(7) a halogen substituted lower alkoxy group,
(8) a hydroxy group,
(9) a phenyl lower alkoxy group,
(10) a hydroxy lower alkyl group,

(11) a lower alkoxy lower alkyl group,
(12) a cyano group,
(13) a phenyl group,
(14) a nitro group,
(15) an amino group,
(16) an amino group having 1 to 2 groups selected from the group consisting of a lower alkyl group, a lower alkanoyl group, a lower alkoxycarbonyl group, a lower alkylsulfonyl group, a carbamoyl group, a lower alkyl carbamoyl group, an amino lower alkanoyl group, a lower alkanoylamino lower alkanoyl group and a lower alkoxycarbonylamino lower alkanoyl group as a substituent(s),
(17) a lower alkanoyl group,
(18) a phenylsulfonyl group that may have a single lower alkyl group on the phenyl group,
(19) a carboxy group,
(20) a lower alkoxycarbonyl group,
(21) a carboxy lower alkyl group,
(22) a lower alkoxycarbonyl lower alkyl group,
(23) a lower alkanoylamino lower alkanoyl group,
(24) a carboxy lower alkenyl group,
(25) a lower alkoxycarbonyl lower alkenyl group,
(26) a carbamoyl lower alkenyl group that may have 1 to 2 groups selected from the group consisting of a lower alkyl group and a lower alkyl group substituted with 1 to 3 halogen atoms as a substituent(s),
(27) a carbamoyl group that may have 1 to 2 groups selected from the group consisting of the groups (i) to (lxxviii) below as a substituent(s):
(i) a lower alkyl group,
(ii) a lower alkoxy group,
(iii) a hydroxy lower alkyl group,
(iv) a lower alkoxy lower alkyl group,
(v) an phenoxy lower alkyl group,
(vi) a halogen substituted lower alkyl group,
(vii) an amino lower alkyl group that may have 1 to 2 groups selected from the group consisting of a lower alkyl group, a lower alkanoyl group, a benzoyl group and a carbamoyl group,
(viii) a cyclo C3-C8 alkyl group that may have 1 to 3 groups selected from the group consisting of a lower alkyl group, a hydroxy group, a lower alkoxycarbonyl group and a phenyl lower alkoxy group as a substituent(s),
(ix) a cyclo C3-C8 alkyl substituted lower alkyl group,
(x) a lower alkenyl group,
(xi) a lower alkyl group having 1 to 2 carbamoyl groups that may have 1 to 2 groups as a substituent(s) selected from the group consisting of a lower alkyl group, a phenyl group that may have a single lower alkyl group and a phenyl group that may have a single lower alkoxy group,
(xii) a lower alkyl group having 1 to 2 lower alkoxy carbonyl groups,
(xiii) a furyl lower alkyl group (that may have 1 to 2 lower alkyl groups as a substituent(s) on the furyl group),
(xiv) a tetrahydrofuryl lower alkyl group,
(xv) a 1,3-dioxolanyl lower alkyl group,
(xvi) a tetrahydropyranyl lower alkyl group,
(xvii) a pyrrolyl lower alkyl group (that may have 1 to 2 lower alkyl groups on the pyrrolyl group as a substituent(s)),
(xviii) a lower alkyl group substituted with a dihydropyrazolyl group that may have a single oxo group,
(xix) a pyrazolyl lower alkyl group (that may have 1 to 3 lower alkyl groups as a substituent(s) on the pyrazolyl group),
(xx) an imidazolyl lower alkyl group,
(xxi) a pyridyl lower alkyl group,
(xxii) a pyrazinyl lower alkyl group (that may have 1 to 3 (preferably 1) lower alkyl groups as a substituent(s) on the pyrazinyl group),
(xxiii) a pyrrolidinyl lower alkyl group (that may have 1 to 2 groups selected from the group consisting of an oxo group and a lower alkyl group as a substituent(s) on the pyrrolidinyl group),
(xxiv) a piperidyl lower alkyl group (that may have 1 to 3 groups selected from the group consisting of a benzoyl group and a lower alkanoyl group as a substituent(s) on the piperidyl group),
(xxv) a piperazinyl lower alkyl group (that may have 1 to 3 lower alkyl groups as a substituent(s) on the piperazinyl group),
(xxvi) a morpholinyl lower alkyl group,
(xxvii) a thienyl lower alkyl group (that may have 1 to 3 lower alkyl groups as a substituent(s) on the thienyl group),
(xxviii) a thiazolyl lower alkyl group,
(xxix) a dihydrobenzofuryl lower alkyl group,
(xxx) a benzopyranyl lower alkyl group (that may have a single oxo group as a substituent on the benzopyranyl group),
(xxxi) a benzimidazolyl lower alkyl group,
(xxxii) an indolyl lower alkyl group that may have 1 to 3 lower alkoxycarbonyl groups on the lower alkyl group),
(xxxiii) an imidazolyl lower alkyl group that has 1 to 3 substituents selected from the group consisting of a carbamoyl group and a lower alkoxycarbonyl group, on the lower alkyl group,
(xxxiv) a pyridyl group that may have 1 to 3 groups selected from the group consisting of a lower alkyl group, a lower alkoxy group and a lower alkylthio lower alkyl group as a substituent(s),
(xxxv) a pyrrolidinyl group that may have 1 to 3 groups selected from the group consisting of a lower alkyl group, a lower alkoxycarbonyl group, a lower alkanoyl group and a benzoyl group as a substituent(s),
(xxxvi) a piperidyl group that may have 1 to 3 groups selected from the group consisting of a lower alkyl group, a lower alkoxycarbonyl group, a lower alkanoyl group and a benzoyl group (that may have 1 to 3 groups selected from the group consisting of a lower alkyl group and a halogen atom as a substituent(s) on the phenyl group),
(xxxvii) a tetrahydrofuryl group that may have a single oxo group
(xxxviii) a hexahydroazepinyl group that may have a single oxo group,
(xxxix) a pyrazolyl group that may have 1 to 3 groups selected from the group consisting of a lower alkyl group, a phenyl group and a furyl group as a substituent(s),
(xl) a thiazolyl group,
(xli) a thiadiazolyl group that may have 1 to 3 lower alkyl groups,
(xlii) an isoxazolyl group that may have 1 to 3 lower alkyl groups,
(xliii) an indazolyl group,
(xliv) an indolyl group, (xlv) a tetrahydrobenzothiazolyl group,
(xlvi) a tetrahydroquinolyl group that may have 1 to 3 groups selected from the group consisting of a lower alkyl group, a lower alkoxy group, a halogen atom and an oxo group as a substituent(s),
(xlvii) a quinolyl group that may have 1 to 3 lower alkyl groups,
(xlviii) a benzodioxolyl lower alkyl group,
(xlix) a phenyl group or naphthyl group that may have 1 to 3 groups as a substituent(s), selected from the group consisting of
a halogen atom; a lower alkyl group; a lower alkoxy group; a halogen substituted lower alkyl group; a halogen substituted lower alkoxy group; a lower alkenyl group; an amino group that may have 1 to 2 groups selected from the group consisting of a lower alkanoyl group, a lower alkyl sulfonyl group, a lower alkyl group and an aryl group; a sulfamoyl group; a lower alkylthio group; a lower alkanoyl group; a lower alkoxycarbonyl group; pyrrolyl group; a lower alkynyl group; a cyano group; a nitro group; a phenyloxy group; a phenyl lower alkoxy group; a hydroxy group; a hydroxy lower alkyl group; a carbamoyl group that may have 1 to 2 groups selected from the group consisting of a lower alkyl group and a phenyl group; a pyrazolyl group; a pyrrolidinyl group that may have a single oxo group; oxazolyl group; an imidazolyl group that may have 1 to 3 lower alkyl groups; a dihydrofuryl group that may have a single oxo group; thiazolidinyl lower alkyl group that may have two oxo groups; imidazolyl lower alkanoyl group and piperidinylcarbonyl group,
(l) a cyano lower alkyl group,
(li) a dihydroquinolyl group that may have 1 to 3 group(s) selected from the group consisting of a lower alkyl group and an oxo group,
(lii) a halogen substituted lower alkylamino group,
(liii) a lower alkylthio lower alkyl group,
(liv) an amidino group that may have a lower alkyl group,
(lv) an amidino lower alkyl group,
(lvi) a lower alkenyloxy lower alkyl group,
(lvii) a phenylamino group that may have 1 to 3 substituents selected from the group consisting of a lower alkyl group, a lower alkoxy group, a halogen substituted lower alkyl group and a halogen substituted lower alkoxy group on the phenyl group,
(lviii) a phenyl lower alkenyl group,
(lix) a pyridylamino group that may have 1 to 3 lower alkyl groups,
(lx) a phenyl lower alkyl group (that may have as a substituent(s) on the phenyl group and/or the lower alkyl group 1 to 3 groups selected from the group consisting of a halogen atom, a lower alkyl group, a halogen substituted lower alkyl group, a halogen substituted lower alkoxy group, a lower alkoxy group, carbamoyl group and a lower alkoxycarbonyl group),
(lxi) a lower alkynyl group,
(lxii) a phenyloxy lower alkyl group (that may have 1 to 3 groups selected from the group consisting of a lower alkoxy group, N-lower alkoxy-N-lower alkylcarbamoyl group and oxopyrrolidinyl group as a substituent(s) on the phenyl group),
(lxiii) an isoxazolidinyl group that may have a single oxo group,
(lxiv) a dihydroindenyl group,
(lxv) a phenyl lower alkoxy lower alkyl group,
(lxvi) a tetrahydropyranyl group,
(lxvii) an azetidinyl group that may have 1 to 3 groups selected from the group consisting of a lower alkanoyl group and benzoyl group,
(lxviii) an azetidinyl lower alkyl group that may have 1 to 3 groups selected from the group consisting of a lower alkanoyl group and benzoyl group,
(lxix) a tetrazolyl group,
(lxx) an indolinyl group that may have a single oxo group,
(lxxi) a triazolyl group that may have 1 to 3 groups selected from the group consisting of a lower alkyl group and a lower alkylthio group,
(lxxii) an imidazolyl group that may have 1 to 3 carbamoyl groups,
(lxxiii) an oxazolyl group that may have 1 to 3 lower alkyl groups,
(lxxiv) an isothiazolyl group that may have 1 to 3 lower alkyl groups,
(lxxv) a benzimidazolyl group,
(lxxvi) a dihydrobenzothiazolyl group that may have a single oxo group,
(lxxvii) a thienyl group that may have 1 to 3 lower alkoxycarbonyl groups, and
(lxxviii) an oxazolyl lower alkyl group that may have 1 to 3 lower alkyl groups,
(28) an amino lower alkyl group that may have 1 to 2 groups selected from the group consisting of a lower alkyl group, a halogen substituted lower alkyl group, a lower alkoxycarbonyl group, a lower alkanoyl group, a phenyl group, a phenyl lower alkyl group, a benzoyl group and an amino substituted alkyl group (that may have 1 to 2 lower alkyl groups as a substituent(s) on the amino group), on the amino group,
(29) a lower alkyl group substituted with a single carbamoyl group that may have 1 to 2 groups selected from the group consisting of a lower alkyl group and a halogen substituted lower alkyl group,
(30) a thiocarbamoyl group that may have 1 to 2 lower alkyl groups,
(31) a sulfamoyl group,
(32) an oxazolidinyl group that may have a single oxo group,
(33) an imidazolidinyl group that may have 1 to 2 substituents selected from the group consisting of an oxo group and a lower alkyl group,
(34) a pyrrolidinyl group that may have a single oxo group,
(35) an imidazolyl group,
(36) a triazolyl group,
(37) an isoxazolyl group,
(38) a piperidyl group that may have 1 to 3 substituents selected from the group consisting of a lower alkyl group, a lower alkanoyl group, a lower alkylphenylsulfonyl group, an oxo group, a hydroxy group, and an amino group that may have 1 to 2 groups selected from the group consisting of a lower alkyl group, a lower alkanoyl group, a lower alkoxycarbonyl group and a lower alkanoylamino lower alkanoyl group,
(39) a piperidylcarbonyl group that may have 1 to 3 substituent(s) selected from the group consisting of a lower alkyl group, a hydroxy group, a hydroxy lower alkyl group, a lower alkanoyl group, a carboxy lower alkyl group, a lower alkyl carbamoyl lower alkyl group, a carbamoyl group, a lower alkoxy group, a carboxy group, a lower alkoxycarbonyl group, an amino group (on which 1 to 2 groups selected from the group consisting of a lower alkyl group, a lower alkanoyl group, a lower alkoxycarbonyl group and a benzoyl group may be present), a piperidyl group (on which 1 to 3 groups selected from the group consisting of a lower alkanoyl group, a lower alkoxycarbonyl group and a benzoyl group may be present), a piperazinyl group (on which 1 to 3 lower alkyl groups may be present as a substituent(s)), a 1,4-dioxa-8-azaspiro[4.5]decyl group, a morpholinyl group, a hexahydro-1,4-diazepynyl group (on which a single lower alkyl group may be present as a substituent), a pyridyl group, a pyridyloxy group, a pyridyl lower alkoxy group, a tetrahydroquinolyl group (on which a single oxo group may be present), a benzodioxolyl group, a phenyl lower alkoxy group (that may have on the phenyl group 1 to 3 groups selected from the group consisting of a halogen atom, a lower alkyl group, a lower alkoxy group and a halogen substituted lower alkoxy group), a phenyl group (on which 1 to 3 groups selected from the group consisting of a halogen atom, a lower alkoxy group and a hydroxy group may be present), phenyloxy group (that may have on the phenyl group 1 to 3 groups selected from the group consisting of a cyano group, a halogen atom, a lower alkyl group, a lower alkoxy group and a halogen substituted lower alkyl group), a phenyl lower alkyl group (on the phenyl group, 1 to 3 groups selected from the group consisting of a halogen atom, a lower alkyl group, a lower alkoxy group and a halogen substituted lower alkyl group may be present), and a benzoyl group (that may have 1 to 3 groups selected from the group consisting of a halogen atom and a lower alkoxy group on the phenyl group),

(40) a pyrrolidinylcarbonyl group that may have 1 to 3 groups as a substituent(s) selected from the group consisting of a hydroxy lower alkyl group, carbamoyl group, a hydroxy group, an amino group (that may have 1 to 2 groups selected from the group consisting of a lower alkyl group, a lower alkanoyl group and a benzoyl group on the amino group), a morpholinyl lower alkyl group, a pyrrolidinyl lower alkyl group, a piperidyl lower alkyl group, a piperazinyl lower alkyl group (that may have a single lower alkyl group as a substituent on the piperazinyl group), an amino lower alkyl group (that may have 1 to 2 lower alkyl groups may be present as a substituent on the amino group), phenyloxy group (that may have 1 to 3 halogen substituted lower alkoxy groups on the phenyl group), a phenyloxy lower alkyl group (that may have 1 to 3 halogen substituted lower alkoxy groups on the phenyl group) and a tetrahydroquinolyl group (on which an oxo group may be present),

(41) a piperazinylcarbonyl group that may have 1 to 3 groups as a substituent(s) selected from the group consisting of a lower alkyl group, a cyclo C3-C8 alkyl group, a lower alkanoyl group, a hydroxy lower alkyl group, a lower alkoxy lower alkyl group, a lower alkoxycarbonyl group, an amino lower alkyl group (that may have 1 to 2 lower alkyl groups as a substituent(s) on the amino group), a piperidyl lower alkyl group (that may have 1 to 2 lower alkyl groups as a substituent(s) on the piperidyl group), a morpholinyl lower alkyl group, a pyrrolidinyl lower alkyl group, a 1,3-dioxoranyl lower alkyl group, a tetrahydrofuryl lower alkyl group, a pyridyl lower alkyl group (that may have 1 to 2 phenyl groups as a substituent(s) on the lower alkyl group), an imidazolyl lower alkyl group, a furyl lower alkyl group, a pyrrolidinylcarbonyl lower alkyl group, a piperidyl group that may have 1 to 2 lower alkyl groups as a substituent(s)), a pyridyl group (that may have 1 to 3 groups selected from the group consisting of a lower alkyl group, a cyano group and a halogen substituted lower alkyl group as a substituent(s) on the pyridyl group), a thieno[2,3-b]pyridyl group, a phenyl group (on which 1 to 3 groups selected from the group consisting of a halogen atom and a lower alkyl group may be present), a benzoyl group, a furyl carbonyl group, a phenyl lower alkoxycarbonyl group and an oxo group,

(42) a hexahydroazepinylcarbonyl group,

(43) a hexahydro-1,4-diazepinylcarbonyl group that may have 1 to 3 substituents selected from the group consisting of a lower alkyl group and a pyridyl group,

(44) a dihydropyrrolylcarbonyl group that may have 1 to 3 lower alkyl groups,

(45) a thiomorpholinylcarbonyl group,

(46) a morpholinylcarbonyl group that may have 1 to 3 groups selected from the group consisting of a lower alkyl group, a piperidyl lower alkyl group and a phenyl group,

(47) a thiazolidinyl cabonyl group that may have 1 to 3 phenyl groups that may have 1 to 3 groups selected from the group consisting of a lower alkoxy group and a cyano group,

(48) an azabicyclo[3.2.2]nonylcarbonyl group,

(49) an 8-azabicyclo[3.2.1]octylcarbonyl group that may have 1 to 3 halogen substituted or unsubstituted phenyloxy groups,

(50) an indolinylcarbonyl group,

(51) a tetrahydroquinolylcarbonyl group,

(52) a tetrahydropyrido[3.4-b]indolylcarbonyl group,

(53) a morpholinyl lower alkyl group,

(54) a piperazinyl lower alkyl group that may have 1 to 3 lower alkyl groups on the piperazinyl group,

(55) a morpholinylcarbonyl lower alkyl group,

(56) a piperazinylcarbonyl lower alkyl group that may have 1 to 3 lower alkyl groups on the piperazinyl group,

(57) an oxo group,

(58) an amino lower alkoxy group (that may have 1 to 2 lower alkyl groups on the amino group),

(59) a lower alkoxy lower alkoxy group,

(60) a piperazinyl group that may have 1 to 3 groups selected from the group consisting of an oxo group, a lower alkyl group, a lower alkanoyl group and a lower alkoxycarbonyl group,

(61) a morpholinyl group,

(62) a 1,3,8-triazaspiro[4.5]decanylcarbonyl group that may have 1 to 3 groups selected from the group consisting of an oxo group and a phenyl group,

(63) a tetrahydropyridylcarbonyl group that may have 1 to 3 pyridyl groups,

(64) an imidazolidinylcarbonyl group that may have a single thioxo group, and

(65) a 1,4-dioxa-8-azaspiro[4.5]decanyl group.

3. The compound according to claim 1, wherein A is a lower alkylene group.

4. The compound according to claim 3, wherein R¹ represents a cyclo C5-C6 alkyl group or an aromatic group selected from the group consisting of (I) to (II) shown below:
- (I) a cyclo C5-C6 alkyl group;
- (II) a phenyl group; and
- on the cyclo C5-C6 alkyl group and the phenly group represented by $R^1$, 1 to 5 groups selected from the group consisting of (1) to (65) below may be present as a substituent(s):
    - (1) a lower alkyl group,
    - (2) a lower alkenyl group,
    - (3) a halogen substituted lower alkyl group,
    - (4) a lower alkoxy group,
    - (5) a phenoxy group,
    - (6) a lower alkylthio group,
    - (7) a halogen substituted lower alkoxy group,
    - (8) a hydroxy group,
    - (9) a phenyl lower alkoxy group,
    - (10) a hydroxy lower alkyl group,
    - (11) a lower alkoxy lower alkyl group,
    - (12) a cyano group,
    - (13) a phenyl group,
    - (14) a nitro group,
    - (15) an amino group,
    - (16) an amino group having 1 to 2 groups selected from the group consisting of a lower alkyl group, a lower alkanoyl group, a lower alkoxycarbonyl group, a lower alkylsulfonyl group, a carbamoyl group, a lower alkyl carbamoyl group, an amino lower alkanoyl group, a lower alkanoylamino lower alkanoyl group and a lower alkoxycarbonylamino lower alkanoyl group as a substituent(s),
    - (17) a lower alkanoyl group,
    - (18) a phenylsulfonyl group that may have a single lower alkyl group on the phenyl group,
    - (19) a carboxy group,
    - (20) a lower alkoxycarbonyl group,
    - (21) a carboxy lower alkyl group,
    - (22) a lower alkoxycarbonyl lower alkyl group,
    - (23) a lower alkanoylamino lower alkanoyl group,
    - (24) a carboxy lower alkenyl group,
    - (25) a lower alkoxycarbonyl lower alkenyl group,
    - (26) a carbamoyl lower alkenyl group that may have 1 to 2 groups selected from the group consisting of a lower alkyl group and a lower alkyl group substituted with 1 to 3 halogen atoms as a substituent(s),
    - (27), a carbamoyl group that may have 1 to 2 groups selected from the group consisting of the groups (i) to (lxxviii) below as a substituent(s):
        - (i) a lower alkyl group,
        - (ii) a lower alkoxy group,
        - (iii) a hydroxy lower alkyl group,
        - (iv) a lower alkoxy lower alkyl group,
        - (v) an phenoxy lower alkyl group,
        - (vi) a halogen substituted lower alkyl group,
        - (vii) an amino lower alkyl group that may have 1 to 2 groups selected from the group consisting of a lower alkyl group, a lower alkanoyl group, a benzoyl group and a carbamoyl group,
        - (viii) a cyclo C3-C8 alkyl group that may have 1 to 3 groups selected from the group consisting of a lower alkyl group, a hydroxy group, a lower alkoxycarbonyl group and a phenyl lower alkoxy group as a substituent(s),
        - (ix) a cyclo C3-C8 alkyl substituted lower alkyl group,
        - (x) a lower alkenyl group,
        - (xi) a lower alkyl group having 1 to 2 carbamoyl groups that may have 1 to 2 groups as a substituent(s) selected from the group consisting of a lower alkyl group, a phenyl group that may have a single lower alkyl group and a phenyl group that may have a single lower alkoxy group,
        - (xii) a lower alkyl group having 1 to 2 lower alkoxy carbonyl groups,
        - (xiii) a furyl lower alkyl group (that may have 1 to 2 lower alkyl groups as a substituent(s) on the furyl group),
        - (xiv) a tetrahydrofuryl lower alkyl group,
        - (xv) a 1,3-dioxolanyl lower alkyl group,
        - (xvi) a tetrahydropyranyl lower alkyl group,
        - (xvii) a pyrrolyl lower alkyl group (that may have 1 to 2 lower alkyl groups on the pyrrolyl group as a substituent(s)),
        - (xviii) a lower alkyl group substituted with a dihydropyrazolyl group that may have a single oxo group,
        - (xix) a pyrazolyl lower alkyl group (that may have 1 to 3 lower alkyl groups as a substituent(s) on the pyrazolyl group),
        - (xx) an imidazolyl lower alkyl group,
        - (xxi) a pyridyl lower alkyl group,
        - (xxii) a pyrazinyl lower alkyl group (that may have 1 to 3 (preferably 1) lower alkyl groups as a substituent(s) on the pyrazinyl group),
        - (xxiii) a pyrrolidinyl lower alkyl group (that may have 1 to 2 groups selected from the group consisting of an oxo group and a lower alkyl group as a substituent(s) on the pyrrolidinyl group),
        - (xxiv) a piperidyl lower alkyl group (that may have 1 to 3 groups selected from the group consisting of a benzoyl group and a lower alkanoyl group as a substituent(s) on the piperidyl group),
        - (xxv) a piperazinyl lower alkyl group (that may have 1 to 3 lower alkyl groups as a substituent(s) on the piperazinyl group),
        - (xxvi) a morpholinyl lower alkyl group,
        - (xxvii) a thienyl lower alkyl group (that may have 1 to 3 lower alkyl groups as a substituent(s) on the thienyl group),
        - (xxviii) a thiazolyl lower alkyl group,
        - (xxix) a dihydrobenzofuryl lower alkyl group,
        - (xxx) a benzopyranyl lower alkyl group (that may have a single oxo group as a substituent on the benzopyranyl group),
        - (xxxi) a benzimidazolyl lower alkyl group,
        - (xxxii) an indolyl lower alkyl group (that may have 1 to 3 lower alkoxycarbonyl groups on the lower alkyl group),
        - (xxxiii) an imidazolyl lower alkyl group that has 1 to 3 substituents selected from the group consisting of a carbamoyl group and a lower alkoxycarbonyl group, on the lower alkyl group,
        - (xxxiv) a pyridyl group that may have 1 to 3 groups selected from the group consisting of a lower alkyl group, a lower alkoxy group and a lower alkylthio lower alkyl group as a substituent(s),
        - (xxxv) a pyrrolidinyl group that may have 1 to 3 groups selected from the group consisting of a lower alkyl group, a lower alkoxycarbonyl group, a lower alkanoyl group and a benzoyl group as a substituent(s),
        - (xxxvi) a piperidyl group that may have 1 to 3 groups selected from the group consisting of a lower alkyl group, a lower alkoxycarbonyl group, a lower alkanoyl group and a benzoyl group (that may have 1 to 3 groups selected from the group consisting of a lower alkyl group and a halogen atom as a substituent(s) on the phenyl group), (xxxvii) a tetrahydrofuryl group that may have a single oxo group
(xxxviii) a hexahydroazepinyl group that may have a single oxo group,
(xxxix) a pyrazolyl group that may have 1 to 3 groups selected from the group consisting of a lower alkyl group, a phenyl group and a furyl group as a substituent(s),
(xl) a thiazolyl group,
(xli) a thiadiazolyl group that may have 1 to 3 lower alkyl groups,
(xlii) an isoxazolyl group that may have 1 to 3 lower alkyl groups,
(xliii) an indazolyl group,
(xliv) an indolyl group,
(xlv) a tetrahydrobenzothiazolyl group,
(xlvi) a tetrahydroquinolyl group that may have 1 to 3 groups selected from the group consisting of a lower alkyl group, a lower alkoxy group, a halogen atom and an oxo group as a substituent(s),
(xlvii) a quinolyl group that may have 1 to 3 lower alkyl groups,
(xlviii) a benzodioxolyl lower alkyl group,
(xlix) a phenyl group or naphthyl group that may have 1 to 3 groups as a substituent(s), selected from the group consisting of
a halogen atom; a lower alkyl group; a lower alkoxy group; a halogen substituted lower alkyl group; a halogen substituted lower alkoxy group; a lower alkenyl group; an amino group that may have 1 to 2 groups selected from the group consisting of a lower alkanoyl group, a lower alkyl sulfonyl group, a lower alkyl group and an aryl group; a sulfamoyl group; a lower alkylthio group; a lower alkanoyl group; a lower alkoxycarbonyl group; pyrrolyl group; a lower alkynyl group; a cyano group; a nitro group; a phenyloxy group; a phenyl lower alkoxy group; a hydroxy group; a hydroxy lower alkyl group; a carbamoyl group that may have 1 to 2 groups selected from the group consisting of a lower alkyl group and a phenyl group; a pyrazolyl group; a pyrrolidinyl group that may have a single oxo group; oxazolyl group; an imidazolyl group that may have 1 to 3 lower alkyl groups; a dihydrofuryl group that may have a single oxo group; thiazolidinyl lower alkyl group that may have two oxo groups; imidazolyl lower alkanoyl group and piperidinylcarbonyl group,
(l) a cyano lower alkyl group,
(li) a dihydroquinolyl group that may have 1 to 3 group(s) selected from the group consisting of a lower alkyl group and an oxo group,
(lii) a halogen substituted lower alkylamino group,
(liii) a lower alkylthio lower alkyl group,
(liv) an amidino group that may have a lower alkyl group,
(lv) an amidino lower alkyl group,
(lvi) a lower alkenyloxy lower alkyl group,
(lvii) a phenylamino group that may have 1 to 3 substituents selected from the group consisting of a lower alkyl group, a lower alkoxy group, a halogen substituted lower alkyl group and a halogen substituted lower alkoxy group on the phenyl group,
(lviii) a phenyl lower alkenyl group,
(lix) a pyridylamino group that may have 1 to 3 lower alkyl groups,
(lx) a phenyl lower alkyl group (that may have as a substituent(s) on the phenyl group and/or the lower alkyl group 1 to 3 groups selected from the group consisting of a halogen atom, a lower alkyl group, a halogen substituted lower alkyl group, a halogen substituted lower alkoxy group, a lower alkoxy group, carbamoyl group and a lower alkoxycarbonyl group),
(lxi) a lower alkynyl group,
(lxii) a phenyloxy lower alkyl group (that may have 1 to 3 groups selected from the group consisting of a lower alkoxy group, N-lower alkoxy-N-lower alkylcarbamoyl group and oxopyrrolidinyl group as a substituent(s) on the phenyl group),
(lxiii) an isoxazolidinyl group that may have a single oxo group,
(lxiv) a dihydroindenyl group,
(lxv) a phenyl lower alkoxy lower alkyl group,
(lxvi) a tetrahydropyranyl group,
(lxvii) an azetidinyl group that may have 1 to 3 groups selected from the group consisting of a lower alkanoyl group and benzoyl group,
(lxviii) an azetidinyl lower alkyl group that may have 1 to 3 groups selected from the group consisting of a lower alkanoyl group and benzoyl group,
(lxix) a tetrazolyl group,
(lxx) an indolinyl group that may have a single oxo group,
(lxxi) a triazolyl group that may have 1 to 3 groups selected from the group consisting of a lower alkyl group and a lower alkylthio group,
(lxxii) an imidazolyl group that may have 1 to 3 carbamoyl groups,
(lxxiii) an oxazolyl group that may have 1 to 3 lower alkyl groups,
(lxxiv) an isothiazolyl group that may have 1 to 3 lower alkyl groups,
(lxxv) a benzimidazolyl group,
(lxxvi) a dihydrobenzothiazolyl group that may have a single oxo group,
(lxxvii) a thienyl group that may have 1 to 3 lower alkoxycarbonyl groups, and
(lxxviii) an oxazolyl lower alkyl group that may have 1 to 3 lower alkyl groups,
(28) an amino lower alkyl group that may have 1 to 2 groups selected from the group consisting of a lower alkyl group, a halogen substituted lower alkyl group, a lower alkoxycarbonyl group, a lower alkanoyl group, a phenyl group, a phenyl lower alkyl group, a benzoyl group and an amino substituted alkyl group (that may have 1 to 2 lower alkyl groups as a substituent(s) on the amino group), on the amino group,
(29) a lower alkyl group substituted with a single carbamoyl group that may have 1 to 2 groups selected from the group consisting of a lower alkyl group and a halogen substituted lower alkyl group,
(30) a thiocarbamoyl group that may have 1 to 2 lower alkyl groups,
(31), a sulfamoyl group,
(32) an oxazolidinyl group that may have a single oxo group,
(33) an imidazolidinyl group that may have 1 to 2 substituents selected from the group consisting of an oxo group and a lower alkyl group,
(34) a pyrrolidinyl group that may have a single oxo group,
(35) an imidazolyl group,
(36) a triazolyl group,
(37) an isoxazolyl group,
(38) a piperidyl group that may have 1 to 3 substituents selected from the group consisting of a lower alkyl group, a lower alkanoyl group, a lower alkylphenylsulfonyl group, an oxo group, a hydroxy group, and an amino group that may have 1 to 2 groups selected from the group consisting of a lower alkyl group, a lower alkanoyl group, a lower alkoxycarbonyl group and a lower alkanoylamino lower alkanoyl group,

(39) a piperidylcarbonyl group that may have 1 to 3 substituent(s) selected from the group consisting of a lower alkyl group, a hydroxy group, a hydroxy lower alkyl group, a lower alkanoyl group, a carboxy lower alkyl group, a lower alkyl carbamoyl lower alkyl group, a carbamoyl group, a lower alkoxy group, a carboxy group, a lower alkoxycarbonyl group, an amino group (on which 1 to 2 groups selected from the group consisting of a lower alkyl group, a lower alkanoyl group, a lower alkoxycarbonyl group and a benzoyl group may be present), a piperidyl group (on which 1 to 3 groups selected from the group consisting of a lower alkanoyl group, a lower alkoxycarbonyl group and a benzoyl group may be present), a piperazinyl group (on which 1 to 3 lower alkyl groups may be present as a substituent(s)), a 1,4-dioxa-8-azaspiro[4.5]decyl group, a morpholinyl group, a hexahydro-1,4-diazepynyl group (on which a single lower alkyl group may be present as a substituent), a pyridyl group, a pyridyloxy group, a pyridyl lower alkoxy group, a tetrahydroquinolyl group (on which a single oxo group may be present), a benzodioxolyl group, a phenyl lower alkoxy group (that may have on the phenyl group 1 to 3 groups selected from the group consisting of a halogen atom, a lower alkyl group, a lower alkoxy group and a halogen substituted lower alkoxy group), a phenyl group (on which 1 to 3 groups selected from the group consisting of a halogen atom, a lower alkoxy group and a hydroxy group may be present), phenyloxy group (that may have on the phenyl group 1 to 3 groups selected from the group consisting of a cyano group, a halogen atom, a lower alkyl group, a lower alkoxy group and a halogen substituted lower alkyl group), a phenyl lower alkyl group (on the phenyl group, 1 to 3 groups selected from the group consisting of a halogen atom, a lower alkyl group, a lower alkoxy group and a halogen substituted lower alkyl group may be present), and a benzoyl group (that may have 1 to 3 groups selected from the group consisting of a halogen atom and a lower alkoxy group on the phenyl group),

(40) a pyrrolidinylcarbonyl group that may have 1 to 3 groups as a substituent(s) selected from the group consisting of a hydroxy lower alkyl group, carbamoyl group, a hydroxy group, an amino group (that may have 1 to 2 groups selected from the group consisting of a lower alkyl group, a lower alkanoyl group and a benzoyl group on the amino group), a morpholinyl lower alkyl group, a pyrrolidinyl lower alkyl group, a piperidyl lower alkyl group, a piperazinyl lower alkyl group (that may have a single lower alkyl group as a substituent on the piperazinyl group), an amino lower alkyl group (that may have 1 to 2 lower alkyl groups may be present as a substituent on the amino group), phenyloxy group (that may have 1 to 3 halogen substituted lower alkoxy groups on the phenyl group), a phenyloxy lower alkyl group (that may have 1 to 3 halogen substituted lower alkoxy groups on the phenyl group) and a tetrahydroquinolyl group (on which an oxo group may be present),

(41) a piperazinylcarbonyl group that may have 1 to 3 groups as a substituent(s) selected from the group consisting of a lower alkyl group, a cyclo C3-C8 alkyl group, a lower alkanoyl group, a hydroxy lower alkyl group, a lower alkoxy lower alkyl group, a lower alkoxycarbonyl group, an amino lower alkyl group (that may have 1 to 2 lower alkyl groups as a substituent(s) on the amino group), a piperidyl lower alkyl group (that may have 1 to 2 lower alkyl groups as a substituent(s) on the piperidyl group), a morpholinyl lower alkyl group, a pyrrolidinyl lower alkyl group, a 1,3-dioxoranyl lower alkyl group, a tetrahydrofuryl lower alkyl group, a pyridyl lower alkyl group (that may have 1 to 2 phenyl groups as a substituent(s) on the lower alkyl group), an imidazolyl lower alkyl group, a furyl lower alkyl group, a pyrrolidinylcarbonyl lower alkyl group, a piperidyl group that may have 1 to 2 lower alkyl groups as a substituent(s)), a pyridyl group (that may have 1 to 3 groups selected from the group consisting of a lower alkyl group, a cyano group and a halogen substituted lower alkyl group as a substituent(s) on the pyridyl group), a thieno[2,3-b]pyridyl group, a phenyl group (on which 1 to 3 groups selected from the group consisting of a halogen atom and a lower alkyl group may be present), a benzoyl group, a fury carbonyl group, a phenyl lower alkoxycarbonyl group and an oxo group,

(42) a hexahydroazepinylcarbonyl group,

(43) a hexahydro-1,4-diazepinylcarbonyl group that may have 1 to 3 substituents selected from the group consisting of a lower alkyl group and a pyridyl group,

(44) a dihydropyrrolylcarbonyl group that may have 1 to 3 lower alkyl groups,

(45) a thiomorpholinylcarbonyl group,

(46) a morpholinylcarbonyl group that may have 1 to 3 groups selected from the group consisting of a lower alkyl group, a piperidyl lower alkyl group and a phenyl group,

(47) a thiazolidinyl cabonyl group that may have 1 to 3 phenyl groups that may have 1 to 3 groups selected from the group consisting of a lower alkoxy group and a cyano group,

(48) an azabicyclo[3.2.2]nonylcarbonyl group,

(49) an 8-azabicyclo[3.2.1]octylcarbonyl group that may have 1 to 3 halogen substituted or unsubstituted phenyloxy groups,

(50) an indolinylcarbonyl group,

(51) a tetrahydroquinolylcarbonyl group,

(52) a tetrahydropyrido[3.4-b]indolylcarbonyl group,

(53) a morpholinyl lower alkyl group,

(54) a piperazinyl lower alkyl group that may have 1 to 3 lower alkyl groups on the piperazinyl group,

(55) a morpholinylcarbonyl lower alkyl group,

(56) a piperazinylcarbonyl lower alkyl group that may have 1 to 3 lower alkyl groups on the piperazinyl group,

(57) an oxo group,

(58) an amino lower alkoxy group (that may have 1 to 2 lower alkyl groups on the amino group),

(59) a lower alkoxy lower alkoxy group,

(60) a piperazinyl group that may have 1 to 3 groups selected from the group consisting of an oxo group, a lower alkyl group, a lower alkanoyl group and a lower alkoxycarbonyl group,

(61) a morpholinyl group,

(62) a 1,3,8-triazaspiro[4.5]decanylcarbonyl group that may have 1 to 3 groups selected from the group consisting of an oxo group and a phenyl group,

(63) a tetrahydropyridylcarbonyl group that may have 1 to 3 pyridyl groups,

(64) an imidazolidinylcarbonyl group that may have a single thioxo group, and

(65) a 1,4-dioxa-8-azaspiro[4.5]decanyl group.

5. The compound according to claim 4, wherein $R^1$ represents (I) a cyclo C5-C6 alkyl group, and, on the cyclo C5-C6 alkyl group represented by R¹, 1 to 5 groups selected from the group consisting of (1) to (65) below may be present as a substituent(s):

(1) a lower alkyl group,
(2) a lower alkenyl group,
(3) a halogen substituted lower alkyl group,
(4) a lower alkoxy group,
(5) a phenoxy group,
(6) a lower alkylthio group,
(7) a halogen substituted lower alkoxy group,
(8) a hydroxy group,
(9) a phenyl lower alkoxy group,
(10) a hydroxy lower alkyl group,
(11) a lower alkoxy lower alkyl group,
(12) a cyano group,
(13) a phenyl group,
(14) a nitro group,
(15) an amino group,
(16) an amino group having 1 to 2 groups selected from the group consisting of a lower alkyl group, a lower alkanoyl group, a lower alkoxycarbonyl group, a lower alkylsulfonyl group, a carbamoyl group, a lower alkyl carbamoyl group, an amino lower alkanoyl group, a lower alkanoylamino lower alkanoyl group and a lower alkoxycarbonylamino lower alkanoyl group as a substituent(s),
(17) a lower alkanoyl group,
(18) a phenylsulfonyl group that may have a single lower alkyl group on the phenyl group,
(19) a carboxy group,
(20) a lower alkoxycarbonyl group,
(21) a carboxy lower alkyl group,
(22) a lower alkoxycarbonyl lower alkyl group,
(23) a lower alkanoylamino lower alkanoyl group,
(24) a carboxy lower alkenyl group,
(25) a lower alkoxycarbonyl lower alkenyl group,
(26) a carbamoyl lower alkenyl group that may have 1 to 2 groups selected from the group consisting of a lower alkyl group and a lower alkyl group substituted with 1 to 3 halogen atoms as a substituent(s),
(27) a carbamoyl group that may have 1 to 2 groups selected from the group consisting of the groups (i) to (lxxviii) below as a substituent(s):

(i) a lower alkyl group,
(ii) a lower alkoxy group,
(iii) a hydroxy lower alkyl group,
(iv) a lower alkoxy lower alkyl group,
(v) an phenoxy lower alkyl group,
(vi) a halogen substituted lower alkyl group,
(vii) an amino lower alkyl group that may have 1 to 2 groups selected from the group consisting of a lower alkyl group, a lower alkanoyl group, a benzoyl group and a carbamoyl group,
(viii) a cyclo C3-C8 alkyl group that may have 1 to 3 groups selected from the group consisting of a lower alkyl group, a hydroxy group, a lower alkoxycarbonyl group and a phenyl lower alkoxy group as a substituent(s),
(ix) a cyclo C3-C8 alkyl substituted lower alkyl group,
(x) a lower alkenyl group,
(xi) a lower alkyl group having 1 to 2 carbamoyl groups that may have 1 to 2 groups as a substituent(s) selected from the group consisting of a lower alkyl group, a phenyl group that may have a single lower alkyl group and a phenyl group that may have a single lower alkoxy group,
(xii) a lower alkyl group having 1 to 2 lower alkoxy carbonyl groups,
(xiii) a furyl lower alkyl group (that may have 1 to 2 lower alkyl groups as a substituent(s) on the furyl group),
(xiv) a tetrahydrofuryl lower alkyl group,
(xv) a 1,3-dioxolanyl lower alkyl group,
(xvi) a tetrahydropyranyl lower alkyl group,
(xvii) a pyrrolyl lower alkyl group (that may have 1 to 2 lower alkyl groups on the pyrrolyl group as a substituent(s)),
(xviii) a lower alkyl group substituted with a dihydropyrazolyl group that may have a single oxo group,
(xix) a pyrazolyl lower alkyl group (that may have 1 to 3 lower alkyl groups as a substituent(s) on the pyrazolyl group),
(xx) an imidazolyl lower alkyl group,
(xxi) a pyridyl lower alkyl group,
(xxii) a pyrazinyl lower alkyl group (that may have 1 to 3 (preferably 1) lower alkyl groups as a substituent(s) on the pyrazinyl group),
(xxiii) a pyrrolidinyl lower alkyl group (that may have 1 to 2 groups selected from the group consisting of an oxo group and a lower alkyl group as a substituent(s) on the pyrrolidinyl group),
(xxiv) a piperidyl lower alkyl group (that may have 1 to 3 groups selected from the group consisting of a benzoyl group and a lower alkanoyl group as a substituent(s) on the piperidyl group),
(xxv) a piperazinyl lower alkyl group (that may have 1 to 3 lower alkyl groups as a substituent(s) on the piperazinyl group),
(xxvi) a morpholinyl lower alkyl group,
(xxvii) a thienyl lower alkyl group (that may have 1 to 3 lower alkyl groups as a substituent(s) on the thienyl group),
(xxviii) a thiazolyl lower alkyl group,
(xxix) a dihydrobenzofuryl lower alkyl group,
(XXX) a benzopyranyl lower alkyl group (that may have a single oxo group as a substituent on the benzopyranyl group),
(xxxi) a benzimidazolyl lower alkyl group,
(xxxii) an indolyl lower alkyl group that may have 1 to 3 lower alkoxycarbonyl groups on the lower alkyl group),
(xxxiii) an imidazolyl lower alkyl group that has 1 to 3 substituents selected from the group consisting of a carbamoyl group and a lower alkoxycarbonyl group, on the lower alkyl group,
(xxxiv) a pyridyl group that may have 1 to 3 groups selected from the group consisting of a lower alkyl group, a lower alkoxy group and a lower alkylthio lower alkyl group as a substituent(s),
(xxxv) a pyrrolidinyl group that may have 1 to 3 groups selected from the group consisting of a lower alkyl group, a lower alkoxycarbonyl group, a lower alkanoyl group and a benzoyl group as a substituent(s),
(xxxvi) a piperidyl group that may have 1 to 3 groups selected from the group consisting of a lower alkyl group, a lower alkoxycarbonyl group, a lower alkanoyl group and a benzoyl group (that may have 1 to 3 groups selected from the group consisting of a lower alkyl group and a halogen atom as a substituent(s) on the phenyl group),
(xxxvii) a tetrahydrofuryl group that may have a single oxo group
(xxxviii) a hexahydroazepinyl group that may have a single oxo group, (xxxix) a pyrazolyl group that may have 1 to 3 groups selected from the group consisting of a lower alkyl group, a phenyl group and a furyl group as a substituent(s),
(xl) a thiazolyl group,
(xli) a thiadiazolyl group that may have 1 to 3 lower alkyl groups,
(xlii) an isoxazolyl group that may have 1 to 3 lower alkyl groups,
(xliii) an indazolyl group,
(xliv) an indolyl group,
(xlv) a tetrahydrobenzothiazolyl group,
(xlvi) a tetrahydroquinolyl group that may have 1 to 3 groups selected from the group consisting of a lower alkyl group, a lower alkoxy group, a halogen atom and an oxo group as a substituent(s),
(xlvii) a quinolyl group that may have 1 to 3 lower alkyl groups,
(xlviii) a benzodioxolyl lower alkyl group,
(xlix) a phenyl group or naphthyl group that may have 1 to 3 groups as a substituent(s), selected from the group consisting of
a halogen atom; a lower alkyl group; a lower alkoxy group; a halogen substituted lower alkyl group; a halogen substituted lower alkoxy group; a lower alkenyl group; an amino group that may have 1 to 2 groups selected from the group consisting of a lower alkanoyl group, a lower alkyl sulfonyl group, a lower alkyl group and an aryl group; a sulfamoyl group; a lower alkylthio group; a lower alkanoyl group; a lower alkoxycarbonyl group; a pyrrolyl group; a lower alkynyl group; a cyano group; a nitro group; a phenyloxy group; a phenyl lower alkoxy group; a hydroxy group; a hydroxy lower alkyl group; a carbamoyl group that may have 1 to 2 groups selected from the group consisting of a lower alkyl group and a phenyl group; a pyrazolyl group; a pyrrolidinyl group that may have a single oxo group; oxazolyl group; an imidazolyl group that may have 1 to 3 lower alkyl groups; a dihydrofuryl group that may have a single oxo group; thiazolidinyl lower alkyl group that may have two oxo groups; imidazolyl lower alkanoyl group and piperidinylcarbonyl group,
(l) a cyano lower alkyl group,
(li) a dihydroquinolyl group that may have 1 to 3 group(s) selected from the group consisting of a lower alkyl group and an oxo group,
(lii) a halogen substituted lower alkylamino group,
(liii) a lower alkylthio lower alkyl group,
(liv) an amidino group that may have a lower alkyl group,
(lv) an amidino lower alkyl group,
(lvi) a lower alkenyloxy lower alkyl group,
(lvii) a phenylamino group that may have 1 to 3 substituents selected from the group consisting of a lower alkyl group, a lower alkoxy group, a halogen substituted lower alkyl group and a halogen substituted lower alkoxy group on the phenyl group,
(lviii) a phenyl lower alkenyl group,
(lix) a pyridylamino group that may have 1 to 3 lower alkyl groups,
(lx) a phenyl lower alkyl group (that may have as a substituent(s) on the phenyl group and/or the lower alkyl group 1 to 3 groups selected from the group consisting of a halogen atom, a lower alkyl group, a halogen substituted lower alkyl group, a halogen substituted lower alkoxy group, a lower alkoxy group, carbamoyl group and a lower alkoxycarbonyl group),
(lxi) a lower alkynyl group,
(lxii) a phenyloxy lower alkyl group (that may have 1 to 3 groups selected from the group consisting of a lower alkoxy group, N-lower alkoxy-N-lower alkylcarbamoyl group and oxopyrrolidinyl group as a substituent(s) on the phenyl group),
(lxiii) an isoxazolidinyl group that may have a single oxo group,
(lxiv) a dihydroindenyl group,
(lxv) a phenyl lower alkoxy lower alkyl group,
(lxvi) a tetrahydropyranyl group,
(lxvii) an azetidinyl group that may have 1 to 3 groups selected from the group consisting of a lower alkanoyl group and benzoyl group,
(lxviii) an azetidinyl lower alkyl group that may have 1 to 3 groups selected from the group consisting of a lower alkanoyl group and benzoyl group,
(lxix) a tetrazolyl group,
(lxx) an indolinyl group that may have a single oxo group,
(lxxi) a triazolyl group that may have 1 to 3 groups selected from the group consisting of a lower alkyl group and a lower alkylthio group,
(lxxii) an imidazolyl group that may have 1 to 3 carbamoyl groups,
(lxxiii) an oxazolyl group that may have 1 to 3 lower alkyl groups,
(lxxiv) an isothiazolyl group that may have 1 to 3 lower alkyl groups,
(lxxv) a benzimidazolyl group,
(lxxvi) a dihydrobenzothiazolyl group that may have a single oxo group,
(lxxvii) a thienyl group that may have 1 to 3 lower alkoxycarbonyl groups, and
(lxxviii) an oxazolyl lower alkyl group that may have 1 to 3 lower alkyl groups,
(28) an amino lower alkyl group that may have 1 to 2 groups selected from the group consisting of a lower alkyl group, a halogen substituted lower alkyl group, a lower alkoxycarbonyl group, a lower alkanoyl group, a phenyl group, a phenyl lower alkyl group, a benzoyl group and an amino substituted alkyl group (that may have 1 to 2 lower alkyl groups as a substituent(s) on the amino group), on the amino group,
(29) a lower alkyl group substituted with a single carbamoyl group that may have 1 to 2 groups selected from the group consisting of a lower alkyl group and a halogen substituted lower alkyl group,
(30) a thiocarbamoyl group that may have 1 to 2 lower alkyl groups,
(31) a sulfamoyl group,
(32) an oxazolidinyl group that may have a single oxo group,
(33) an imidazolidinyl group that may have 1 to 2 substituents selected from the group consisting of an oxo group and a lower alkyl group,
(34) a pyrrolidinyl group that may have a single oxo group,
(35) an imidazolyl group,
(36) a triazolyl group,
(37) an isoxazolyl group,
(38) a piperidyl group that may have 1 to 3 substituents selected from the group consisting of a lower alkyl group, a lower alkanoyl group, a lower alkylphenylsulfonyl group, an oxo group, a hydroxy group, and an amino group that may have 1 to 2 groups selected from the group consisting of a lower alkyl group, a lower alkanoyl group, a lower alkoxycarbonyl group and a lower alkanoylamino lower alkanoyl group,

(39) a piperidylcarbonyl group that may have 1 to 3 substituent(s) selected from the group consisting of a lower alkyl group, a hydroxy group, a hydroxy lower alkyl group, a lower alkanoyl group, a carboxy lower alkyl group, a lower alkyl carbamoyl lower alkyl group, a carbamoyl group, a lower alkoxy group, a carboxy group, a lower alkoxycarbonyl group, an amino group (on which 1 to 2 groups selected from the group consisting of a lower alkyl group, a lower alkanoyl group, a lower alkoxycarbonyl group and a benzoyl group may be present), a piperidyl group (on which 1 to 3 groups selected from the group consisting of a lower alkanoyl group, a lower alkoxycarbonyl group and a benzoyl group may be present), a piperazinyl group (on which 1 to 3 lower alkyl groups may be present as a substituent(s)), a 1,4-dioxa-8-azaspiro[4.5]decyl group, a morpholinyl group, a hexahydro-1,4-diazepynyl group (on which a single lower alkyl group may be present as a substituent), a pyridyl group, a pyridyloxy group, a pyridyl lower alkoxy group, a tetrahydroquinolyl group (on which a single oxo group may be present), a benzodioxolyl group, a phenyl lower alkoxy group (that may have on the phenyl group 1 to 3 groups selected from the group consisting of a halogen atom, a lower alkyl group, a lower alkoxy group and a halogen substituted lower alkoxy group), a phenyl group (on which 1 to 3 groups selected from the group consisting of a halogen atom, a lower alkoxy group and a hydroxy group may be present), phenyloxy group (that may have on the phenyl group 1 to 3 groups selected from the group consisting of a cyano group, a halogen atom, a lower alkyl group, a lower alkoxy group and a halogen substituted lower alkyl group), a phenyl lower alkyl group (on the phenyl group, 1 to 3 groups selected from the group consisting of a halogen atom, a lower alkyl group, a lower alkoxy group and a halogen substituted lower alkyl group may be present), and a benzoyl group (that may have 1 to 3 groups selected from the group consisting of a halogen atom and a lower alkoxy group on the phenyl group),

(40) a pyrrolidinylcarbonyl group that may have 1 to 3 groups as a substituent(s) selected from the group consisting of a hydroxy lower alkyl group, carbamoyl group, a hydroxy group, an amino group (that may have 1 to 2 groups selected from the group consisting of a lower alkyl group, a lower alkanoyl group and a benzoyl group on the amino group), a morpholinyl lower alkyl group, a pyrrolidinyl lower alkyl group, a piperidyl lower alkyl group, a piperazinyl lower alkyl group (that may have a single lower alkyl group as a substituent on the piperazinyl group), an amino lower alkyl group (that may have 1 to 2 lower alkyl groups may be present as a substituent on the amino group), phenyloxy group (that may have 1 to 3 halogen substituted lower alkoxy groups on the phenyl group), a phenyloxy lower alkyl group (that may have 1 to 3 halogen substituted lower alkoxy groups on the phenyl group) and a tetrahydroquinolyl group (on which an oxo group may be present),

(41) a piperazinylcarbonyl group that may have 1 to 3 groups as a substituent(s) selected from the group consisting of a lower alkyl group, a cyclo C3-C8 alkyl group, a lower alkanoyl group, a hydroxy lower alkyl group, a lower alkoxy lower alkyl group, a lower alkoxycarbonyl group, an amino lower alkyl group (that may have 1 to 2 lower alkyl groups as a substituent(s) on the amino group), a piperidyl lower alkyl group (that may have 1 to 2 lower alkyl groups as a substituent(s) on the piperidyl group), a morpholinyl lower alkyl group, a pyrrolidinyl lower alkyl group, a 1,3-dioxaranyl lower alkyl group, a tetrahydrofuryl lower alkyl group, a pyridyl lower alkyl group (that may have 1 to 2 phenyl groups as a substituent(s) on the lower alkyl group), an imidazolyl lower alkyl group, a furyl lower alkyl group, a pyrrolidinylcarbonyl lower alkyl group, a piperidyl group that may have 1 to 2 lower alkyl groups as a substituent(s)), a pyridyl group (that may have 1 to 3 groups selected from the group consisting of a lower alkyl group, a cyano group and a halogen substituted lower alkyl group as a substituent(s) on the pyridyl group), a thieno[2,3-b]pyridyl group, a phenyl group (on which 1 to 3 groups selected from the group consisting of a halogen atom and a lower alkyl group may be present), a benzoyl group, a furyl carbonyl group, a phenyl lower alkoxycarbonyl group and an oxo group,

(42) a hexahydroazepinylcarbonyl group,

(43) a hexahydro-1,4-diazepinylcarbonyl group that may have 1 to 3 substituents selected from the group consisting of a lower alkyl group and a pyridyl group,

(44) a dihydropyrrolylcarbonyl group that may have 1 to 3 lower alkyl groups,

(45) a thiomorpholinylcarbonyl group,

(46) a morpholinylcarbonyl group that may have 1 to 3 groups selected from the group consisting of a lower alkyl group, a piperidyl lower alkyl group and a phenyl group,

(47) a thiazolidinyl cabonyl group that may have 1 to 3 phenyl groups that may have 1 to 3 groups selected from the group consisting of a lower alkoxy group and a cyano group,

(48) an azabicyclo[3.2.2]nonylcarbonyl group,

(49) an 8-azabicyclo[3.2.1]octylcarbonyl group that may have 1 to 3 halogen substituted or unsubstituted phenyloxy groups,

(50) an indolinylcarbonyl group,

(51) a tetrahydroquinolylcarbonyl group,

(52) a tetrahydropyrido[3.4-b]indolylcarbonyl group,

(53) a morpholinyl lower alkyl group,

(54) a piperazinyl lower alkyl group that may have 1 to 3 lower alkyl groups on the piperazinyl group,

(55) a morpholinylcarbonyl lower alkyl group,

(56) a piperazinylcarbonyl lower alkyl group that may have 1 to 3 lower alkyl groups on the piperazinyl group,

(57) an oxo group,

(58) an amino lower alkoxy group (that may have 1 to 2 lower alkyl groups on the amino group),

(59) a lower alkoxy lower alkoxy group,

(60) a piperazinyl group that may have 1 to 3 groups selected from the group consisting of an oxo group, a lower alkyl group, a lower alkanoyl group and a lower alkoxycarbonyl group,

(61) a morpholinyl group,

(62) a 1,3,8-triazaspiro[4.5]decanylcarbonyl group that may have 1 to 3 groups selected from the group consisting of an oxo group and a phenyl group,

(63) a tetrahydropyridylcarbonyl group that may have 1 to 3 pyridyl groups,

(64) an imidazolidinylcarbonyl group that may have a single thioxo group, and

(65) a 1,4-dioxa-8-azaspiro[4.5]decanyl group.

6. The compound according to claim 4, wherein $R^1$ represents (II) a phenyl group, and, on the phenyl group represented by $R^1$, 1 to 5 groups selected from the group consisting of (1) to (65) below may be present as a substituent(s);

(1) a lower alkyl group, (2) a lower alkenyl group, (3) a halogen substituted lower alkyl group,
(4) a lower alkoxy group,
(5) a phenoxy group,
(6) a lower alkylthio group,
(7) a halogen substituted lower alkoxy group,
(8) a hydroxy group,
(9) a phenyl lower alkoxy group,
(10) a hydroxy lower alkyl group,
(11) a lower alkoxy lower alkyl group,
(12) a cyano group,
(13) a phenyl group,
(14) a nitro group,
(15) an amino group,
(16) an amino group having 1 to 2 groups selected from the group consisting of a lower alkyl group, a lower alkanoyl group, a lower alkoxycarbonyl group, a lower alkylsulfonyl group, a carbamoyl group, a lower alkyl carbamoyl group, an amino lower alkanoyl group, a lower alkanoylamino lower alkanoyl group and a lower alkoxycarbonylamino lower alkanoyl group as a substituent(s),
(17) a lower alkanoyl group,
(18) a phenylsulfonyl group that may have a single lower alkyl group on the phenyl group,
(19) a carboxy group,
(20) a lower alkoxycarbonyl group,
(21) a carboxy lower alkyl group,
(22) a lower alkoxycarbonyl lower alkyl group,
(23) a lower alkanoylamino lower alkanoyl group,
(24) a carboxy lower alkenyl group,
(25) a lower alkoxycarbonyl lower alkenyl group,
(26) a carbamoyl lower alkenyl group that may have 1 to 2 groups selected from the group consisting of a lower alkyl group and a lower alkyl group substituted with 1 to 3 halogen atoms as a substituent(s),
(27) a carbamoyl group that may have 1 to 2 groups selected from the group consisting of the groups (i) to (lxxviii) below as a substituent(s):
(i) a lower alkyl group,
(ii) a lower alkoxy group,
(iii) a hydroxy lower alkyl group,
(iv) a lower alkoxy lower alkyl group,
(v) an phenoxy lower alkyl group,
(vi) a halogen substituted lower alkyl group,
(vii) an amino lower alkyl group that may have 1 to 2 groups selected from the group consisting of a lower alkyl group, a lower alkanoyl group, a benzoyl group and a carbamoyl group,
(viii) a cyclo C3-C8 alkyl group that may have 1 to 3 groups selected from the group consisting of a lower alkyl group, a hydroxy group, a lower alkoxycarbonyl group and a phenyl lower alkoxy group as a substituent(s),
(ix) a cyclo C3-C8 alkyl substituted lower alkyl group,
(x) a lower alkenyl group,
(xi) a lower alkyl group having 1 to 2 carbamoyl groups that may have 1 to 2 groups as a substituent(s) selected from the group consisting of a lower alkyl group, a phenyl group that may have a single lower alkyl group and a phenyl group that may have a single lower alkoxy group,
(xii) a lower alkyl group having 1 to 2 lower alkoxy carbonyl groups,
(xiii) a furyl lower alkyl group (that may have 1 to 2 lower alkyl groups as a substituent(s) on the furyl group),
(xiv) a tetrahydrofuryl lower alkyl group,
(xv) a 1,3-dioxolanyl lower alkyl group,
(xvi) a tetrahydropyranyl lower alkyl group,
(xvii) a pyrrolyl lower alkyl group (that may have 1 to 2 lower alkyl groups on the pyrrolyl group as a substituent(s)),
(xviii) a lower alkyl group substituted with a dihydropyrazolyl group that may have a single oxo group,
(xix) a pyrazolyl lower alkyl group (that may have 1 to 3 lower alkyl groups as a substituent(s) on the pyrazolyl group),
(xx) an imidazolyl lower alkyl group,
(xxi) a pyridyl lower alkyl group,
(xxii) a pyrazinyl lower alkyl group (that may have 1 to 3 (preferably 1) lower alkyl groups as a substituent(s) on the pyrazinyl group),
(xxiii) a pyrrolidinyl lower alkyl group (that may have 1 to 2 groups selected from the group consisting of an oxo group and a lower alkyl group as a substituent(s) on the pyrrolidinyl group),
(xxiv) a piperidyl lower alkyl group (that may have 1 to 3 groups selected from the group consisting of a benzoyl group and a lower alkanoyl group as a substituent(s) on the piperidyl group),
(xxv) a piperazinyl lower alkyl group (that may have 1 to 3 lower alkyl groups as a substituent(s) on the piperazinyl group),
(xxvi) a morpholinyl lower alkyl group,
(xxvii) a thienyl lower alkyl group (that may have 1 to 3 lower alkyl groups as a substituent(s) on the thienyl group),
(xxviii) a thiazolyl lower alkyl group,
(xxix) a dihydrobenzofuryl lower alkyl group,
(xxx) a benzopyranyl lower alkyl group (that may have a single oxo group as a substituent on the benzopyranyl group),
(xxxi) a benzimidazolyl lower alkyl group,
(xxxii) an indolyl lower alkyl group that may have 1 to 3 lower alkoxycarbonyl groups on the lower alkyl group),
(xxxiii) an imidazolyl lower alkyl group that has 1 to 3 substituents selected from the group consisting of a carbamoyl group and a lower alkoxycarbonyl group, on the lower alkyl group,
(xxxiv) a pyridyl group that may have 1 to 3 groups selected from the group consisting of a lower alkyl group, a lower alkoxy group and a lower alkylthio lower alkyl group as a substituent(s),
(xxxv) a pyrrolidinyl group that may have 1 to 3 groups selected from the group consisting of a lower alkyl group, a lower alkoxycarbonyl group, a lower alkanoyl group and a benzoyl group as a substituent(s),
(xxxvi) a piperidyl group that may have 1 to 3 groups selected from the group consisting of a lower alkyl group, a lower alkoxycarbonyl group, a lower alkanoyl group and a benzoyl group (that may have 1 to 3 groups selected from the group consisting of a lower alkyl group and a halogen atom as a substituent(s) on the phenyl group),
(xxxvii) a tetrahydrofuryl group that may have a single oxo group
(xxxviii) a hexahydroazepinyl group that may have a single oxo group,
(xxxix) a pyrazolyl group that may have 1 to 3 groups selected from the group consisting of a lower alkyl group, a phenyl group and a furyl group as a substituent(s),
(xl) a thiazolyl group,
(xli) a thiadiazolyl group that may have 1 to 3 lower alkyl groups, (xlii) an isoxazolyl group that may have 1 to 3 lower alkyl groups,
(xliii) an indazolyl group,
(xliv) an indolyl group,
(xlv) a tetrahydrobenzothiazolyl group,
(xlvi) a tetrahydroquinolyl group that may have 1 to 3 groups selected from the group consisting of a lower alkyl group, a lower alkoxy group, a halogen atom and an oxo group as a substituent(s),
(xlvii) a quinolyl group that may have 1 to 3 lower alkyl groups,
(xlviii) a benzodioxolyl lower alkyl group,
(xlix) a phenyl group or naphthyl group that may have 1 to 3 groups as a substituent(s), selected from the group consisting of
a halogen atom; a lower alkyl group; a lower alkoxy group; a halogen substituted lower alkyl group; a halogen substituted lower alkoxy group; a lower alkenyl group; an amino group that may have 1 to 2 groups selected from the group consisting of a lower alkanoyl group, a lower alkyl sulfonyl group, a lower alkyl group and an aryl group; a sulfamoyl group; a lower alkylthio group; a lower alkanoyl group; a lower alkoxycarbonyl group; pyrrolyl group; a lower alkynyl group; a cyano group; a nitro group; a phenyloxy group; a phenyl lower alkoxy group; a hydroxy group; a hydroxy lower alkyl group; a carbamoyl group that may have 1 to 2 groups selected from the group consisting of a lower alkyl group and a phenyl group; a pyrazolyl group; a pyrrolidinyl group that may have a single oxo group; oxazolyl group; an imidazolyl group that may have 1 to 3 lower alkyl groups; a dihydrofuryl group that may have a single oxo group; thiazolidinyl lower alkyl group that may have two oxo groups; imidazolyl lower alkanoyl group and piperidinylcarbonyl group,
(l) a cyano lower alkyl group,
(li) a dihydroquinolyl group that may have 1 to 3 group(s) selected from the group consisting of a lower alkyl group and an oxo group,
(lii) a halogen substituted lower alkylamino group,
(liii) a lower alkylthio lower alkyl group,
(liv) an amidino group that may have a lower alkyl group,
(lv) an amidino lower alkyl group,
(lvi) a lower alkenyloxy lower alkyl group,
(lvii) a phenylamino group that may have 1 to 3 substituents selected from the group consisting of a lower alkyl group, a lower alkoxy group, a halogen substituted lower alkyl group and a halogen substituted lower alkoxy group on the phenyl group,
(lviii) a phenyl lower alkenyl group,
(lix) a pyridylamino group that may have 1 to 3 lower alkyl groups,
(lx) a phenyl lower alkyl group (that may have as a substituent(s) on the phenyl group and/or the lower alkyl group 1 to 3 groups selected from the group consisting of a halogen atom, a lower alkyl group, a halogen substituted lower alkyl group, a halogen substituted lower alkoxy group, a lower alkoxy group, carbamoyl group and a lower alkoxycarbonyl group),
(lxi) a lower alkynyl group,
(lxii) a phenyloxy lower alkyl group (that may have 1 to 3 groups selected from the group consisting of a lower alkoxy group, N-lower alkoxy-N-lower alkylcarbamoyl group and oxopyrrolidinyl group as a substituent(s) on the phenyl group),
(lxiii) an isoxazolidinyl group that may have a single oxo group,
(lxiv) a dihydroindenyl group,
(lxv) a phenyl lower alkoxy lower alkyl group,
(lxvi) a tetrahydropyranyl group,
(lxvii) an azetidinyl group that may have 1 to 3 groups selected from the group consisting of a lower alkanoyl group and benzoyl group,
(lxviii) an azetidinyl lower alkyl group that may have 1 to 3 groups selected from the group consisting of a lower alkanoyl group and benzoyl group,
(lxix) a tetrazolyl group,
(lxx) an indolinyl group that may have a single oxo group,
(lxxi) a triazolyl group that may have 1 to 3 groups selected from the group consisting of a lower alkyl group and a lower alkylthio group,
(lxxii) an imidazolyl group that may have 1 to 3 carbamoyl groups,
(lxxiii) an oxazolyl group that may have 1 to 3 lower alkyl groups,
(lxxiv) an isothiazolyl group that may have 1 to 3 lower alkyl groups,
(lxxv) a benzimidazolyl group,
(lxxvi) a dihydrobenzothiazolyl group that may have a single oxo group,
(lxxvii) a thienyl group that may have 1 to 3 lower alkoxycarbonyl groups, and
(lxxviii) an oxazolyl lower alkyl group that may have 1 to 3 lower alkyl groups,
(28) an amino lower alkyl group that may have 1 to 2 groups selected from the group consisting of a lower alkyl group, a halogen substituted lower alkyl group, a lower alkoxycarbonyl group, a lower alkanoyl group, a phenyl group, a phenyl lower alkyl group, a benzoyl group and an amino substituted alkyl group (that may have 1 to 2 lower alkyl groups as a substituent(s) on the amino group), on the amino group,
(29) a lower alkyl group substituted with a single carbamoyl group that may have 1 to 2 groups selected from the group consisting of a lower alkyl group and a halogen substituted lower alkyl group,
(30) a thiocarbamoyl group that may have 1 to 2 lower alkyl groups,
(31) a sulfamoyl group,
(32) an oxazolidinyl group that may have a single oxo group,
(33) an imidazolidinyl group that may have 1 to 2 substituents selected from the group consisting of an oxo group and a lower alkyl group,
(34) a pyrrolidinyl group that may have a single oxo group,
(35) an imidazolyl group,
(36) a triazolyl group,
(37) an isoxazolyl group,
(38) a piperidyl group that may have 1 to 3 substituents selected from the group consisting of a lower alkyl group, a lower alkanoyl group, a lower alkylphenylsulfonyl group, an oxo group, a hydroxy group, and an amino group that may have 1 to 2 groups selected from the group consisting of a lower alkyl group, a lower alkanoyl group, a lower alkoxycarbonyl group and a lower alkanoylamino lower alkanoyl group,
(39) a piperidylcarbonyl group that may have 1 to 3 substituent(s) selected from the group consisting of a lower alkyl group, a hydroxy group, a hydroxy lower alkyl group, a lower alkanoyl group, a carboxy lower alkyl group, a lower alkyl carbamoyl lower alkyl group, a carbamoyl group, a lower alkoxy group, a carboxy group, a lower alkoxycarbonyl group, an amino group (on which 1 to 2 groups selected from the group consisting of a lower alkyl group, a lower alkanoyl group, a lower alkoxycarbonyl group and a benzoyl group may be present), a piperidyl group (on which 1 to 3 groups selected from the group consisting of a lower alkanoyl group, a lower alkoxycarbonyl group and a benzoyl group may be present), a piperazinyl group (on which 1 to 3 lower alkyl groups may be present as a substituent(s)), a 1,4-dioxa-8-azaspiro [4.5]decyl group, a morpholinyl group, a hexahydro-1,4-diazepynyl group (on which a single lower alkyl group may be present as a substituent), a pyridyl group, a pyridyloxy group, a pyridyl lower alkoxy group, a tetrahydroquinolyl group (on which a single oxo group may be present), a benzodioxolyl group, a phenyl lower alkoxy group (that may have on the phenyl group 1 to 3 groups selected from the group consisting of a halogen atom, a lower alkyl group, a lower alkoxy group and a halogen substituted lower alkoxy group), a phenyl group (on which 1 to 3 groups selected from the group consisting of a halogen atom, a lower alkoxy group and a hydroxy group may be present), phenyloxy group (that may have on the phenyl group 1 to 3 groups selected from the group consisting of a cyano group, a halogen atom, a lower alkyl group, a lower alkoxy group and a halogen substituted lower alkyl group), a phenyl lower alkyl group (on the phenyl group, 1 to 3 groups selected from the group consisting of a halogen atom, a lower alkyl group, a lower alkoxy group and a halogen substituted lower alkyl group may be present), and a benzoyl group (that may have 1 to 3 groups selected from the group consisting of a halogen atom and a lower alkoxy group on the phenyl group),

(40) a pyrrolidinylcarbonyl group that may have 1 to 3 groups as a substituent(s) selected from the group consisting of a hydroxy lower alkyl group, carbamoyl group, a hydroxy group, an amino group (that may have 1 to 2 groups selected from the group consisting of a lower alkyl group, a lower alkanoyl group and a benzoyl group on the amino group), a morpholinyl lower alkyl group, a pyrrolidinyl lower alkyl group, a piperidyl lower alkyl group, a piperazinyl lower alkyl group (that may have a single lower alkyl group as a substituent on the piperazinyl group), an amino lower alkyl group (that may have 1 to 2 lower alkyl groups may be present as a substituent on the amino group), phenyloxy group (that may have 1 to 3 halogen substituted lower alkoxy groups on the phenyl group), a phenyloxy lower alkyl group (that may have 1 to 3 halogen substituted lower alkoxy groups on the phenyl group) and a tetrahydroquinolyl group (on which an oxo group may be present),

(41) a piperazinylcarbonyl group that may have 1 to 3 groups as a substituent(s) selected from the group consisting of a lower alkyl group, a cyclo C3-C8 alkyl group, a lower alkanoyl group, a hydroxy lower alkyl group, a lower alkoxy lower alkyl group, a lower alkoxycarbonyl group, an amino lower alkyl group (that may have 1 to 2 lower alkyl groups as a substituent(s) on the amino group), a piperidyl lower alkyl group (that may have 1 to 2 lower alkyl groups as a substituent(s) on the piperidyl group), a morpholinyl lower alkyl group, a pyrrolidinyl lower alkyl group, a 1,3-dioxoranyl lower alkyl group, a tetrahydrofuryl lower alkyl group, a pyridyl lower alkyl group (that may have 1 to 2 phenyl groups as a substituent(s) on the lower alkyl group), an imidazolyl lower alkyl group, a furyl lower alkyl group, a pyrrolidinylcarbonyl lower alkyl group, a piperidyl group that may have 1 to 2 lower alkyl groups as a substituent(s)), a pyridyl group (that may have 1 to 3 groups selected from the group consisting of a lower alkyl group, a cyano group and a halogen substituted lower alkyl group as a substituent(s) on the pyridyl group), a thieno[2,3-b]pyridyl group, a phenyl group (on which 1 to 3 groups selected from the group consisting of a halogen atom and a lower alkyl group may be present), a benzoyl group, a furyl carbonyl group, a phenyl lower alkoxycarbonyl group and an oxo group,

(42) a hexahydroazepinylcarbonyl group,

(43) a hexahydro-1,4-diazepinylcarbonyl group that may have 1 to 3 substituents selected from the group consisting of a lower alkyl group and a pyridyl group,

(44) a dihydropyrrolylcarbonyl group that may have 1 to 3 lower alkyl groups,

(45) a thiomorpholinylcarbonyl group,

(46) a morpholinylcarbonyl group that may have 1 to 3 groups selected from the group consisting of a lower alkyl group, a piperidyl lower alkyl group and a phenyl group,

(47) a thiazolidinyl cabonyl group that may have 1 to 3 phenyl groups that may have 1 to 3 groups selected from the group consisting of a lower alkoxy group and a cyano group, (48), an azabicyclo[3.2.2]nonylcarbonyl group,

(49) an 8-azabicyclo[3.2.1]octylcarbonyl group that may have 1 to 3 halogen substituted or unsubstituted phenyloxy groups,

(50) an indolinylcarbonyl group,

(51) a tetrahydroquinolylcarbonyl group,

(52) a tetrahydropyrido[3.4-b]indolylcarbonyl group,

(53) a morpholinyl lower alkyl group,

(54) a piperazinyl lower alkyl group that may have 1 to 3 lower alkyl groups on the piperazinyl group,

(55) a morpholinylcarbonyl lower alkyl group,

(56) a piperazinylcarbonyl lower alkyl group that may have 1 to 3 lower alkyl groups on the piperazinyl group,

(57) an oxo group,

(58) an amino lower alkoxy group (that may have 1 to 2 lower alkyl groups on the amino group),

(59) a lower alkoxy lower alkoxy group,

(60) a piperazinyl group that may have 1 to 3 groups selected from the group consisting of an oxo group, a lower alkyl group, a lower alkanoyl group and a lower alkoxycarbonyl group,

(61) a morpholinyl group,

(62) a 1,3,8-triazaspiro[4.5]decanylcarbonyl group that may have 1 to 3 groups selected from the group consisting of an oxo group and a phenyl group,

(63) a tetrahydropyridylcarbonyl group that may have 1 to 3 pyridyl groups,

(64) an imidazolidinylcarbonyl group that may have a single thioxo group, and

(65) a 1,4-dioxa-8-azaspiro[4.5]decanyl group.

7. The compound according to claim 4, wherein $R^1$ represents a cyclo C5-C6 alkyl group or an aromatic group selected from the group consisting of (I) to (II) shown below:

(I) a cyclo C5-C6 alkyl group; and (II) a phenyl group; and on the cyclo C5-C6 alkyl group and the phenyl group represented by $R^1$, 1 to 5 groups selected from the group consisting of (1), (4), (10), (17), (18), (21), (28), (29), (30), (33), (34), (35), (36), (39), (61) and (62) shown below may be present as a substituent(s):

(1) a lower alkyl group, (4) a lower alkoxy group,

(10) a hydroxy lower alkyl group,

(17) an amino group having 1 to 2 groups selected from the group consisting of a lower alkyl group, a lower alkanoyl group, a lower alkoxycarbonyl group, a lower alkylsulfonyl group, a carbamoyl group, a lower alkyl carbamoyl group, an amino lower alkanoyl group, a lower alkanoylamino lower alkanoyl group and a lower alkoxycarbonylamino lower alkanoyl group, as a substituent(s),
(18) a lower alkanoyl group,
(21) a lower alkoxycarbonyl group,
(28) a carbamoyl group that may have 1 to 2 groups selected from the group consisting of the groups (i), (ii), (iv), (xii) and (xxi) below as a substituent(s):
(i) a lower alkyl group,
(ii) a lower alkoxy group,
(iv) a lower alkoxy lower alkyl group,
(xii) a lower alkyl group having 1 to 2 lower alkoxy carbonyl groups,
(xxi) a pyridyl lower alkyl group,
(29) an amino lower alkyl group that may have, on the amino group, 1 to 2 groups selected from the group consisting of a lower alkyl group, a halogen substituted lower alkyl group, a lower alkoxycarbonyl group, a lower alkanoyl group, a phenyl group, a phenyl lower alkyl group, a benzoyl group and an amino substituted lower alkyl group (which may have 1 to 2 lower alkyl groups may be present as a substituent(s) on the amino group),
(30) a lower alkyl group substituted with a single carbamoyl group that may have 1 to 2 groups selected from the group consisting of a lower alkyl group and a halogen substituted lower alkyl group,
(33) an oxazolidinyl group that may have a single oxo group,
(34) an imidazolidinyl group that may have 1 to 2 substituents selected from the group consisting of an oxo group and a lower alkyl group,
(35) a pyrrolidinyl group that may have a single oxo group,
(36) an imidazolyl group,
(39) a piperidyl group that may have 1 to 3 substituents selected from the group consisting of a lower alkyl group, a lower alkanoyl group, a lower alkyl phenylsulfonyl group, an oxo group, hydroxy group, and an amino group that may have 1 to 2 groups selected from the group consisting of a lower alkyl group, a lower alkanoyl group, a lower alkoxycarbonyl group and a lower alkanoylamino lower alkanoyl group,
(61) a piperazinyl group that may have 1 to 3 groups selected from the group consisting of an oxo group, a lower alkyl group, a lower alkanoyl group and a lower alkoxycarbonyl group, and
(62) a morpholinyl group.

8. The compound according to claim 7, wherein $R^1$ represents (I) a cyclohexyl group, and, on the cyclo C5-C6 alkyl group represented by $R^1$, 1 to 3 groups selected from the group consisting of (1), (4), (10), (17), (18), (21), (28), (29), (30), (33), (34), (35), (36), (39), (61) and (62) defined in claim 8 may be present as a substituent(s).

9. The compound according to claim 7, wherein $R^1$ represents (II) a phenyl group, and, on the phenyl group represented by $R^1$, 1 to 3 groups selected from the group consisting of (1), (4), (10), (17), (18) (21), (28), (29), (30), (33), (34), (35), (36), (39), (61) and (62) defined in claim 8 may be present as a substituent(s).

10. The compound according to claim 9, wherein $R^1$ represents (II) a phenyl group, and, on the phenyl group represented by $R^1$, 1 to 3 groups selected from the group consisting of (1), (4), (10), (17), (18), (28), (33), (35), (39) and (61) shown below may be present as a substituent(s):
(1) a lower alkyl group,
(4) a lower alkoxy group,
(10) a hydroxy lower alkyl group,
(17) an amino group having 1 to 2 groups selected from the group consisting of a lower alkyl group, an amino lower alkanoyl group, a lower alkanoylamino lower alkanoyl group and a lower alkoxy carbonylamino lower alkanoyl group, as a substituent(s),
(18) a lower alkanoyl group,
(28) a carbamoyl group having a single lower alkoxy lower alkyl group,
(33) an oxazolidinyl group that may have a single oxo group,
(35) a pyrrolidinyl group that may have a single oxo group,
(39) a piperidyl group, and
(61) a piperazinyl group that may have 1 to 2 groups selected from the group consisting of an oxo group, a lower alkanoyl group and a lower alkoxycarbonyl group.

11. The compound according to claim 10, wherein $R^1$ is a phenyl group substituted with a single lower alkyl group, a single lower alkoxy group and a single amino group having 1 or 2 lower alkyl groups on the amino group;
a phenyl group substituted with a single lower alkyl group, a single lower alkoxy group and a single carbamoyl group having a single lower alkyl group, which has two lower alkoxy groups on the lower alkyl group;
a phenyl group substituted with a single hydroxy lower alkyl group, a single lower alkoxy group and a single oxazolidinyl group having a single oxo group on the oxazolidinyl group;
a phenyl group substituted with a single lower alkyl group, a single lower alkoxy group and a single pyrrolidinyl group;
a phenyl group substituted with a single lower alkyl group, a single lower alkoxy group and a single piperidyl group;
a phenyl group substituted with a single lower alkyl group, a single lower alkoxy group and a single piperazyl group having a single lower alkanoyl group on the piperazyl group;
a phenyl group substituted with a single lower alkyl group, a single lower alkoxy group and a single piperazyl group having a single lower alkanoyl group and a single oxo group on the piperazyl group;
a phenyl group substituted with a single lower alkyl group, a single lower alkoxy group and a single piperazyl group having a single lower alkoxycarbonyl group and a single oxo group on the piperazyl group;
a phenyl group substituted with a single lower alkyl group, a single lower alkoxy group and a single N-[(N-lower alkoxy-carbonylamino)lower alkanoyl]amino group;
a phenyl group substituted with a single lower alkyl group, a single lower alkoxy group and a single N-(amino lower alkanoyl)amino group;
a phenyl group substituted with a single lower alkyl group, a single lower alkoxy group and a single N-[(N-lower alkanoyl amino)lower alkanoyl]amino group;
a phenyl group substituted with a single lower alkoxy group, a single lower alkanoyl group and a single piperazyl group having a single lower alkoxycarbonyl group on the piperazyl group; or
a phenyl group substituted with a single lower alkoxy group, a single hydroxy lower alkyl group and a single piperazyl group having a single lower alkoxycarbonyl group on the piperazyl group.

12. The compound according to claim 11 selected from the group consisting of:
- (1) N-methyl-4-[3-{4-(benzo[b]thiophen-4-yl)piperazin -1-yl}propoxy]-3-methoxy-5-methylaniline;
- (2) 4-[3-{4-(Benzo[b]thiophen-4-yl)piperazin-1-yl}propoxy]-N,N-dimethyl-3-methoxy-5-methylaniline;
- (3) 4-[3-{4-(Benzo[b]thiophen-4-yl)piperazin-1-yl}propoxy]-N-(2,2-dimethoxyethyl)-3-methoxy-5-methylbenzamide;
- (4) 1-(Benzo[b]thiophen-4-yl)-4[3-{2-methoxy-6-methyl-4-(pyrrolidin-1-yl)phenoxy}propyl]piperazine;
- (5) 1-(Benzo[b]thiophen-4-yl)-4-[3-{2-methoxy-6-methyl-4-(piperidin-1-yl)phenoxy}propyl]piperazine;
- (6) 1-Acetyl-4-{4-[3-{4-(Benzo[b]thiophen-4-yl)piperazin-1-yl}propoxy]-3-methoxy-5-methylphenyl}piperazine;
- (7) 4-Acetyl-1-{4-[3-{4-(benzo[b]thiophen-4-yl)piperazin-1-yl}propoxy]-3-methoxy-5-methylphenyl}piperazin-2-one;
- (8) 4-{4-[3-{4-(Benzo[b]thiophen-4-yl)piperazin-1-yl}propoxy]-3-methoxy-5-methylphenyl}-3-oxo-1-methoxycarbonylpiperazine;
- (9) Tert-Butyl N-(N-{4-[3-{4-(benzo[b]thiophen-4-yl)piperazin-1-yl}propoxy]-3-methoxy-5-methylphenyl}carbamoylmethyl)carbamate;
- (10) 2-Amino-N-{4-[3-{4-(benzo[b]thiophen-4-yl)piperazin-1-yl}propoxy]-3-methoxy-5-methylphenyl}acetamide;
- (11) 2-Acetylamino-N-{4-[3-{4-(benzo[b]thiophen-4-yl)piperazin-1 -yl}propoxy]-3-methoxy-5-methylphenyl}acetamide;
- (12) 4-{4-[3-{4-(Benzo[b]thiophen-4-yl)piperazin-1-yl}propoxy]-3-formyl-5-methoxyphenyl}-1-methoxycarbonylpiperazine; and
- (13) 4-{4-[3-{4-(Benzo[b]thiophen-4-yl)piperazin-1-yl}propoxy]-3-hydroxymethyl-5-methoxyphenyl}-1-methoxycarbonylpiperazine, or a salt thereof.

13. A pharmaceutical composition comprising a heterocylic compound of formula (1) or a salt thereof according to any one of claims 1 to 6, 7 to 11, and 12 and a pharmaceutically acceptable carrier for treating a central nervous system disorder selected from the group consisting of schizophrenia; refractory, intractable or chronic schizophrenia; bipolar I type disorder; bipolar II type disorder; depression; endogenous depression; major depression; melancholy and refractory depression; autism disorder (autism); and attention-deficit/hyperactivity disorder.

14. A process for producing a pharmaceutical composition comprising mixing a heterocyclic compound of formula (1) or a salt thereof according to any one of claims 1 to 6, 7 to 11, and 12 with a pharmaceutically acceptable carrier.

* * * * *

UNITED STATES PATENT AND TRADEMARK OFFICE
CERTIFICATE OF CORRECTION

PATENT NO. : 8,071,600 B2
APPLICATION NO. : 11/991146
DATED : December 6, 2011
INVENTOR(S) : Yamashita et al.

Page 1 of 2

It is certified that error appears in the above-identified patent and that said Letters Patent is hereby corrected as shown below:

In the Claims

Claim 1, column 514, line 26, before "formula" delete "the".

Claim 1, column 519, line 56, "a imidazolyl" should read --an imidazolyl--.

Claim 2, column 520, line 55, "$C_5$-$C_6$group" should read --C5-C6 group--.

Claim 2, column 521, line 36, "an phenoxy" should read --a phenoxy--.

Claim 2, column 522, line 54, after "group", insert --,--.

Claim 2, column 526, line 25, "cabonyl" should read --carbonyl--.

Claim 4, column 527, line 6, "phenly" should read --phenyl--.

Claim 4, column 527, line 49, "(lxxviii)" should read --lxxvii--.

Claim 4, column 527, line 54, "an phenoxy" should read --a phenoxy--.

Claim 4, column 529, line 2, after "group", insert --,--.

Claim 4, column 530, line 22, "(1xx)an indolynl" should read --(1xx) an indolinyl--.

Claim 4, column 530, line 53, "(31), a sulfamoyl" should read --(31) a sulfamoyl--.

Claim 4, column 532, line 19, "fury" should read --furyl--.

Claim 4, column 532, line 32, "cabonyl" should read --carbonyl--.

Signed and Sealed this
Eleventh Day of March, 2014

Michelle K. Lee
*Deputy Director of the United States Patent and Trademark Office*

CERTIFICATE OF CORRECTION (continued)
U.S. Pat. No. 8,071,600 B2

Claim 5, column 533, line 43, "(Ixxvii)" should read --(1xxvii)--.

Claim 5, column 533, line 48, "an phenoxy" should read --a phenoxy--.

Claim 5, column 534, line 38, "(XXX)a benzopyranyl" should read --(xxx) a benzopyranyl--.

Claim 5, column 534, line 65, after "group", insert --,--.

Claim 5, column 538, line 28, "cabonyl" should read --carbonyl--.

Claim 6, column 539, line 43, "an phenoxy" should read --a phenoxy--.

Claim 6, column 540, line 58, after "group", insert --,--.

Claim 6, column 544, line 21, "carbonyl" should read --nonylcarbonyl--.

Claim 6, column 544, line 25, "(48), an azabicyclo[3.2.2]nonylcarbonyl" should read --(48) an azabicyclo[3.2.2]noncarbonyl--.

Claim 8, column 545, lines 57-58, "claim 8" should read --claim 7--.

Claim 9, column 545, line 62, "(18) (21)," should read --(18), (21),--.

Claim 9, column 545, line 63, "claim 8" should read --claim 7--.